United States Patent
Gibson et al.

(10) Patent No.: US 10,683,269 B2
(45) Date of Patent: Jun. 16, 2020

(54) 2-CYANOISOINDOLINE DERIVATIVES FOR TREATING CANCER

(71) Applicant: MISSION THERAPEUTICS LIMITED, Cambridge (GB)

(72) Inventors: Karl Richard Gibson, Sandwich Kent (GB); Alison Jones, Cambridge (GB); Mark Ian Kemp, Cambridge (GB); Andrew Madin, Cambridge (GB); Martin Lee Stockley, Cambridge (GB); Gavin Alistair Whitlock, Sandwich Kent (GB); Michael D Woodrow, Cambridge (GB); Keith Allan Menear, Storrington (GB)

(73) Assignee: MISSION THERAPEUTICS LIMITED, Cambridge (GB)

( * ) Notice: Subject to any disclaimer, the term of this patent is extended or adjusted under 35 U.S.C. 154(b) by 0 days.

(21) Appl. No.: 16/080,506

(22) PCT Filed: Mar. 17, 2017

(86) PCT No.: PCT/GB2017/050763
§ 371 (c)(1),
(2) Date: Aug. 28, 2018

(87) PCT Pub. No.: WO2017/158388
PCT Pub. Date: Sep. 21, 2017

(65) Prior Publication Data
US 2019/0010122 A1    Jan. 10, 2019

(30) Foreign Application Priority Data

Mar. 18, 2016 (GB) .................... 1604647.6

(51) Int. Cl.
| | | |
|---|---|---|
| C07D 209/44 | (2006.01) |
| C07D 403/10 | (2006.01) |
| C07D 403/04 | (2006.01) |
| C07D 401/04 | (2006.01) |
| C07D 471/04 | (2006.01) |
| C07D 413/04 | (2006.01) |
| C07D 401/12 | (2006.01) |
| C07D 413/12 | (2006.01) |
| C07D 409/12 | (2006.01) |
| A61P 35/00 | (2006.01) |
| C07D 519/00 | (2006.01) |
| C07D 403/14 | (2006.01) |
| C07D 487/04 | (2006.01) |
| C07D 401/06 | (2006.01) |

(Continued)

(52) U.S. Cl.
CPC ............ *C07D 209/44* (2013.01); *A61P 35/00* (2018.01); *C07D 401/04* (2013.01); *C07D 401/06* (2013.01); *C07D 401/12* (2013.01); *C07D 401/14* (2013.01); *C07D 403/04* (2013.01); *C07D 403/10* (2013.01); *C07D 403/12* (2013.01); *C07D 403/14* (2013.01); *C07D 405/12* (2013.01); *C07D 409/12* (2013.01); *C07D 413/04* (2013.01); *C07D 413/10* (2013.01); *C07D 413/12* (2013.01); *C07D 413/14* (2013.01); *C07D 417/12* (2013.01); *C07D 471/04* (2013.01); *C07D 487/04* (2013.01); *C07D 519/00* (2013.01)

(58) Field of Classification Search
CPC .. C07D 209/44; C07D 401/04; C07D 401/06; C07D 401/12; C07D 401/14; C07D 403/04; C07D 403/10; C07D 403/12; C07D 403/14; C07D 405/12; C07D 409/12; C07D 413/04; C07D 413/10; C07D 413/12; C07D 413/14; C07D 417/12; C07D 471/04; C07D 487/04; C07D 519/00; A61P 35/00
USPC ................................................ 514/210.18
See application file for complete search history.

(56) References Cited

U.S. PATENT DOCUMENTS

| | | |
|---|---|---|
| 5,478,357 A | 12/1995 | Madison et al. |
| 2003/0191143 A1 | 10/2003 | Pitts et al. |

(Continued)

FOREIGN PATENT DOCUMENTS

| | | |
|---|---|---|
| WO | 0177073 A1 | 10/2001 |
| WO | 02087513 A2 | 11/2002 |

(Continued)

OTHER PUBLICATIONS

Cancer [online], [retrieved on Jul. 6, 2007] Retrieved from the Internet, URL: http://www.nlm.nih.gov/medlineplus/cancer.html (Year: 2007).*

(Continued)

*Primary Examiner* — Kristin A Vajda

(57) ABSTRACT

The invention relates to novel compounds of formula I which are inhibitors of deubiquitylating enzymes (DUBs) and/or desumoylating enzymes. In particular, the invention relates to the inhibition of ubiquitin C-terminal hydrolase 7 or ubiquitin specific peptidase 7 (USP7). The invention further relates to methods for the preparation of these compounds and to their use in the treatment of cancer.

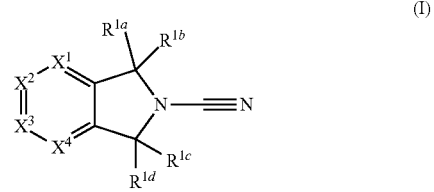

(I)

15 Claims, 1 Drawing Sheet

(51) Int. Cl.

| | | |
|---|---|---|
| *C07D 405/12* | (2006.01) | |
| *C07D 401/14* | (2006.01) | |
| *C07D 413/14* | (2006.01) | |
| *C07D 413/10* | (2006.01) | |
| *C07D 403/12* | (2006.01) | |
| *C07D 417/12* | (2006.01) | |

(56) References Cited

U.S. PATENT DOCUMENTS

| | | |
|---|---|---|
| 2006/0264457 A1 | 11/2006 | Devasthale et al. |
| 2014/0243288 A1 | 8/2014 | Zhang et al. |

FOREIGN PATENT DOCUMENTS

| | | |
|---|---|---|
| WO | 2007125405 A2 | 11/2007 |
| WO | 2012040527 A2 | 3/2012 |
| WO | 2012115480 A2 | 8/2012 |
| WO | 2013030218 A1 | 3/2013 |
| WO | 2015143692 A1 | 10/2015 |
| WO | 2016005878 A1 | 1/2016 |
| WO | 2016/046530 A1 | 3/2016 |
| WO | 2016156816 A1 | 10/2016 |
| WO | 2017/009650 A1 | 1/2017 |
| WO | 2017/093718 A1 | 6/2017 |
| WO | 2017/109488 A1 | 6/2017 |
| WO | 2017103614 A1 | 6/2017 |
| WO | 2017/141036 A1 | 8/2017 |
| WO | 2017/149313 A1 | 9/2017 |
| WO | 2017/163078 A1 | 9/2017 |
| WO | 2017158381 A1 | 9/2017 |
| WO | 2018060689 A1 | 4/2018 |
| WO | 2018060691 A1 | 4/2018 |
| WO | 2018060742 A1 | 4/2018 |
| WO | 2018065768 A1 | 4/2018 |

OTHER PUBLICATIONS

Lala et al., Role of nitric oxide in tumor progression: Lessons from experimental tumors, Cancer and Metastasis Reviews (1998), 17, 91-106 (Year: 1998).*

Golub et al., Molecular Classification of Cancer: Class Discovery and Class Prediction by Gene Expression Monitoring, Science (1999), vol. 286, 531-537 (Year: 1999).*

The International Search Report and Written Opinion, dated May 8, 2017, in the corresponding PCT Appl. No. PCT/GB2017/050763.

Falgueyret et al., "Novel, Nonpeptidic Cyanamides as Potent and Reversible Inhibitors of Human Cathepsins K and L," J. Med. Chem. 2001, 44, 94-104.

Laine et al., "Discovery of Novel Cyanamide-Based Inhibitors of Cathepsin C," ACS Med. Chem. Lett. 2011, 2, 142-147.

Komander et al, "Breaking the chains: structure and function of the deubiquitinases", Nature Reviews Molecular Cell Biology, 10, 550-563, 2009.

Rydzewski et al, "Peptidic 1-Cyanopyrrolidines: Synthesis and SAR of a Series of Potent, Selective Cathepsin Inhibitors", Bioorganic & Medicinal Chemistry 10 (2002) 3277-3284.

Deaton et al, "Novel and potent cyclic cyanamide-based cathepsin K inhibitors", Bioorganic & Medicinal Chemistry Letters 15 (2005) 1815-1819.

Oballa et al, "A generally applicable method for assessing the electrophilicity and reactivity of diverse nitrile-containing compounds", Bioorganic & Medicinal Chemistry Letters 17 (2007) 998-1002.

Zapf et al, "Covalent Inhibitors of Interleukin-2 Inducible T Cell Kinase (Itk) with Nanomolar Potency in a Whole-Blood Assay", J. Med. Chem. 2012, 55, 10047-10063.

Nakamura et al, "Regulation of Mitochondrial Morphology by USP30, a Deubiquitinating Enzyme Present in the Mitochondrial Outer Membrane", Molecular Biology of the Cell, vol. 19, 1903-1911, May 2008.

Bingol et al, "The mitochondrial deubiquitinase USP30 opposes parkin-mediated mitophagy", Nature vol. 510, 370-375, 2014.

Liang et al, "USP30 deubiquitylates mitochondrial Parkin substrates and restricts apoptotic cell death", EMBO Reports, 1-10, 2015; DOI 10.15252/embr.201439820.

Wolfgang Sippl et al, "Ubiquitin-specific proteases as cancer drug targets", Future Oncology, 7(5), 2011, 619-632.

Nicholson et al, "The Multifaceted Roles of USP7: New Therapeutic Opportunities", Cell Biochem Biophys, 2011, 60, 61-68.

Van Loosdregt et al, "Stabilization of the Transcription Factor Foxp3 by the Deubiquitinase USP7 Increases Treg-Cell-Suppressive Capacity", Immunity, Aug. 22, 2013; 39, 259-271.

Laurence et al, "A Degrading View of Regulatory T Cells", Immunity, Aug. 22, 2013, 39, 201-203.

Nudubaku et al, "Inhibiting the Deubiquitinating Enzymes (DUBs)", J.Med.Chem., Feb. 26, 2015, 59(4), 1581-95.

Kemp et al, "Recent Advances in the Discovery of Deubiquitinating Enzyme Inhibitors", Progress in Medicinal Chemistry, 2016, 55, 149-192.

Ward et al., "Quantitative Chemical Proteomic Profiling of Ubiquitin Specific Proteases in Intact Cancer Cells," ACS Chem. Biol. 2016, 11, 3268-3272.

* cited by examiner

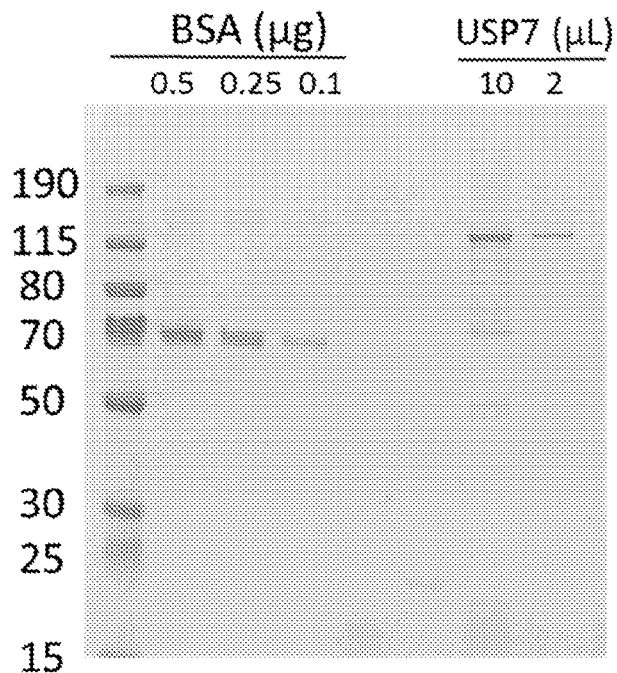
Figure 1 – Expression and Purification of FLAG-USP7 from mammalian cells
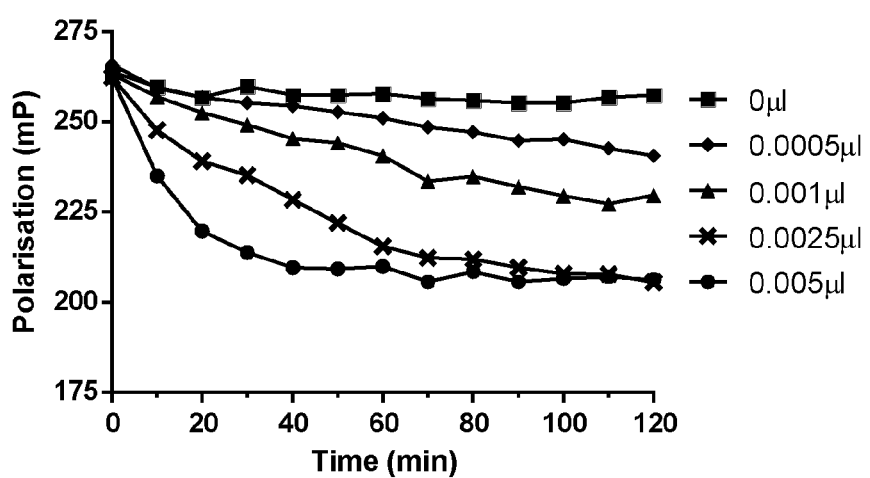
Figure 2 – USP7 assay for high throughput screening of compounds using an isopeptide linked substrate

2-CYANOISOINDOLINE DERIVATIVES FOR TREATING CANCER

CROSS-REFERENCE TO RELATED APPLICATIONS

This application is a National Stage Application of PCT/GB2017/050763 filed Mar. 17, 2017, which claims priority from UK Patent Application. No. 1604647.6, filed on Mar. 18, 2016. The priority of said PCT and UK Patent Application are claimed. Each of the prior mentioned applications is hereby incorporated by reference herein in its entirety, The present invention relates to novel compounds and methods for the manufacture of inhibitors of deubiquitylating enzymes (DUBs) and/or desumoylating enzymes. In particular, the invention relates to the inhibition of ubiquitin C-terminal hydrolase 7 or ubiquitin specific peptidase 7 (USP7). The invention further relates to the use of DUB or desumoylating enzyme inhibitors in the treatment of cancer.

BACKGROUND TO THE INVENTION

The listing or discussion of an apparently prior-published document in this specification should not necessarily be taken as an acknowledgement that the document is part of the state of the art or is common general knowledge.

Ubiquitin is a small protein consisting of 76 amino acids that is important for the regulation of protein function in the cell (Lill J R et al., Pharmacological Sciences 2014 April; 35(4): 187-207). In addition to ubiquitin, there are a growing number of structurally related ubiquitin-like molecules (UBLs) that modify substrates in parallel but distinct cellular pathways. These proteins include but are not restricted to small ubiquitin-like modifier (SUMO), interferon-stimulated gene 15 (ISG15), ubiquitin-related modifier-1 (URM1), neuronal-precursor-cell-expressed developmentally downregulated protein-8 (NEDD8), human leukocyte antigen F-associated (FAT10), autophagy-8 (ATG8) and -12 (ATG12), few ubiquitin-like protein (FUB1), membrane-anchored UBL (MUB), ubiquitin fold-modifier-1 (UFM1) and ubiquitin-like protein-5 (UBL5). Ubiquitylation and deubiquitylation of ubiquitin and UBLs are enzymatically mediated processes by which ubiquitin or UBLs are covalently bound or cleaved from a target protein by ubiquitylating enzymes and deubiquitylating enzymes (DUBs). Including the Sentrin specific proteases (SENPs), there are approximately 95 DUBs in human cells, divided into subfamilies based on sequence homology, the largest of these being the USP family that is characterised by a common Cys and His box containing Cys and His residues critical for DUB activity. The ubiquitylation and deubiquitylation processes have been implicated in the regulation of many cellular functions including cell cycle progression, apoptosis, modification of cell surface receptors, regulation of DNA transcription and DNA repair. Thus, the ubiquitin system has been implicated in the pathogenesis of numerous disease states including inflammation, viral infection, metabolic dysfunction, CNS disorders, and oncogenesis.

USP7 is a DUB with strong oncology links and is an established anti-cancer target. The rationale behind targeting USP7 is principally due to its well validated role in regulating multiple oncogenes, tumour suppressors, viral proteins and epigenetic regulators including Phosphatase and tensin homolog (PTEN), Forkhead box protein O4 (FOXO4), the p53:HDM2 axis and DNA (cytosine-5)-methyltransferase 1 (DNMT1) (Nicholson B et al., Cell Biochem. Biophys. 2011; 60:61-68). Inhibition of USP7 causes degradation of Human double minute 2 homolog (HDM2), stabilisation of p53 and activation of apoptosis in tumour cells meaning it is a potential target for cancers where there is deregulated HDM2 expression (~7% of all cancers) and/or wild-type p53 (~50% of all cancers). In addition, USP7 inhibition has also been shown to reduce the immune-suppressive capacity of regulatory T-cells (Van Loosdregt J et al., Immunity 2013 Aug. 22; 39:259-271, Laurence A et al., Immunity 2013 Aug. 22; 39:201-203). Thus, USP7 inhibitors may have synergistic anti-cancer effects by boosting surveillance and killing of cancer cells by the host immune system.

The ubiquitin-proteasome system has gained interest as a target for the treatment of cancer following the approval of the proteasome inhibitor bortezomib for the treatment of multiple myeloma. Extended treatment with bortezomib is limited by its associated toxicity and drug resistance. However, therapeutic strategies that target specific aspects of the ubiquitin-proteasome pathway upstream of the proteasome, such as DUBs, are predicted to be better tolerated (Ndubaku C et al., J. Med. Chem. 2015 Feb. 26; 59(4):1581-95). Although there is strong interest in this field, DUB inhibitors have yet to enter the market (Kemp M, Progress in Medicinal Chemistry 2016; 55:140-192). Thus, there is a need for compounds and pharmaceutical compositions to inhibit DUBs such as USP7 for the treatment of indications where DUB activity is observed, including, although not limited to, cancer.

SUMMARY OF THE INVENTION

In accordance with a first aspect of the invention there is provided a compound of formula (I)

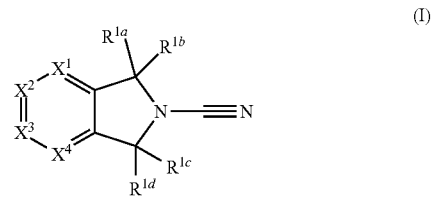

(I)

or a pharmaceutically acceptable salt thereof, wherein:
$R^{1a}$, $R^{1b}$, $R^{1c}$ and $R^{1d}$ each independently represent hydrogen or optionally substituted $C_1$-$C_6$ alkyl, or
$R^{1a}$ and $R^{1b}$ together form an optionally substituted $C_3$-$C_6$ cycloalkyl ring, or $R^{1c}$ and $R^{1d}$ together form an optionally substituted $C_3$-$C_6$ cycloalkyl ring;
$X^1$, $X^3$ and $X^4$ each independently represent N, C-$Q^1$-$R^2$ or C-$Q^2$-$(R^6)_n$, and $X^2$ represents N or CH, wherein one of $X^1$, $X^3$ and $X^4$ represents C-$Q^1$-$R^2$ and no more than two of $X^1$, $X^2$, $X^3$ and $X^4$ represent N;
$Q^1$ represents a covalent bond, an oxygen atom, a sulphur atom, —$OR^5$—, —SO—, —$SO_2$—, —CO—, —C(O)O—, —$C_0$-$C_3$ alkylene-$CONR^3$—$C_0$-$C_3$ alkylene-, —$C_0$-$C_3$ alkylene-$NR^3$—$C_0$-$C_3$ alkylene, —$C_0$-$C_3$ alkylene-$NR^3$CO— $C_0$-$C_3$ alkylene, —$NR^3CONR^4$—, —$SO_2NR^3$—, $NR^3SO_2$—, —$NR^3SO_2NR^4$—, —$NR^3C(O)O$—, —$NR^3C(O)OR^5$—, optionally substituted —$C_1$-$C_6$ alkylene or optionally substituted —$C_2$-$C_6$ alkenylene;
$R^2$ is an optionally substituted 3 to 10 membered monocyclic or bicyclic heteroaryl, aryl or heterocyclyl ring;
$R^3$ and $R^4$ each independently represent hydrogen or optionally substituted $C_1$-$C_6$ alkyl;

$R^5$ represents optionally substituted $C_1$-$C_6$ alkylene or optionally substituted $C_3$-$C_4$ cycloalkylene;

n is 0 or 1;

$Q^2$ represents hydrogen, halogen, cyano, nitro, hydroxyl, —$SR^7$, —$NR^7R^8$, —$CONR^7R^8$, —$NR^7COR^8$, —$NR^7CONR^8R^{8a}$, —$COR^7$, —$C(O)OR^7$, —$SO_2R^7$, —$SO_2NR^7R^8$, —$NR^7SO_2R^8$, —$NR^7SO_2NR^8R^{8a}$, —$NR^7C(O)OR^8$, optionally substituted —$C_1$-$C_6$ alkyl, optionally substituted —$C_1$-$C_6$ alkoxy, optionally substituted $C_2$-$C_6$ alkenyl, a covalent bond, an oxygen atom, a sulphur atom, —$OR^9$—, —SO—, —$SO_2$—, —CO—, —C(O)O—, —$C_0$-$C_3$ alkylene-$CONR^7$—$C_0$-$C_3$ alkylene, —$C_0$-$C_3$ alkylene-$NR^7$—$C_0$-$C_3$ alkylene, —$C_0$-$C_3$ alkylene-$NR^7CO$—$C_0$-$C_3$ alkylene, —$NR^7CONR^8$—, —$SO_2NR^7$—, $NR^7SO_2$—, —$NR^7SO_2NR^8$—, —$NR^7C(O)O$—, —$NR^7C(O)OR^9$—, optionally substituted $C_1$-$C_6$ alkylene, or optionally substituted —$C_2$-$C_6$ alkenylene;

$R^6$ is an optionally substituted 3 to 10 membered monocyclic or bicyclic heteroaryl, aryl, heterocyclyl or cycloalkyl ring;

$R^7$, $R^8$ and $R^{8a}$ each independently represent hydrogen or optionally substituted $C_1$-$C_6$ alkyl;

$R^9$ represents optionally substituted $C_1$-$C_6$ alkylene.

In one embodiment, $X^4$ is N or C-$Q^2$-$(R^6)$, wherein n is 0 and $Q^2$ is hydrogen.

$R^2$ may be unsubstituted or substituted with one or more substituents selected from halogen, cyano, oxo, nitro, hydroxyl, —$SR^{10}$, —$C_1$-$C_6$ alkyl, —$C_1$-$C_6$ alkoxy, —$C_2$-$C_6$ alkenyl, —$C_2$-$C_6$ alkynyl, -$Q^{3a}$-$R^{12}$, -$Q^{3a}$-O-$Q^{3b}$-$R^{12}$, -$Q^{3a}$-S-$Q^{3b}$-$R^{12}$, -$Q^{3a}$-SO-$Q^{3b}$-$R^{12}$, -$Q^{3a}$-$NR^{10}CONR^{11}R^{11a}$, -$Q^{3a}$-$NR^{10}CONR^{11}$-$Q^{3b}$-$R^{12}$, -$Q^{3a}$-$NR^{10}R^{11}$, -$Q^{3a}$-$NR^{10}$-$Q^{3b}$-$R^{12}$, -$Q^{3a}$-$COR^{10}$, -$Q^{3a}$-CO-$Q^{3b}$-$R^{12}$, -$Q^{3a}$-$NR^{10}COR^{11}$, -$Q^{3a}NR^{10}CO$-$Q^{3b}$-$R^{12}$, -$Q^{3a}$-$NR^{10}C(O)OR^{11}$, -$Q^{3a}$-$NR^{10}C(O)O$-$Q^{3a}$-$R^{12}$, -$Q^{3a}$-$SO_2R^{10}$, -$Q^{3a}$-$SO_2$-$Q^{3b}$-$R^{12}$, -$Q^{3a}$-$CONR^{10}R^{11}$, -$Q^{3a}$-$CONR^{10}$-$Q^{3b}$-$R^{12}$, -$Q^{3a}$-$CO_2R^{10}$, -$Q^{3a}$-$CO_2$-$Q^{3c}$-$R^{12}$, -$Q^{3a}$-$SO_2NR^{10}R^{11}$, -$Q^{3a}$-$SO_2NR^{10}$-$Q^{3b}$-$R^{12}$, -$Q^{3a}$-$NR^{10}$—$SO_2R^{11}$, -$Q^{3a}$-$NR^{10}SO_2$-$Q^{3b}$-$R^{12}$, -$Q^{3a}$-$NR^{10}SO_2NR^{11}R^{11a}$, and -$Q^{3a}$-$NR^{10}SO_2NR^{11}$-$Q^{3b}$-$R^{12}$; wherein $Q^{3a}$ and $Q^{3b}$ independently represent a covalent bond optionally substituted $C_1$-$C_6$ alkylene or optionally substituted $C_2$-$C_6$ alkenylene;

$R^{10}$, $R^{11}$ and $R^{11a}$ each independently represent hydrogen or optionally substituted $C_1$-$C_6$ alkyl; and $R^{12}$ represents optionally substituted heterocyclyl, optionally substituted heteroaryl, optionally substituted aryl, or an optionally substituted cycloalkyl.

$R^6$ may be unsubstituted or substituted with one or more substituents selected from halogen, cyano, oxo, nitro, hydroxyl, —$SR^{13}$, —$C_1$-$C_6$ alkyl, —$C_1$-$C_6$ alkoxy, —$C_2$-$C_6$ alkenyl, —$C_2$-$C_6$ alkynyl, -$Q^{4a}$-$R^{15}$, -$Q^{4a}$-O-$Q^{4b}$-$R^{15}$, -$Q^{4a}$-S-$Q^{4b}$-$R^{15}$, -$Q^{4a}$-SO-$Q^{4b}$-$R^{15}$, -$Q^{4a}$-$NR^{13}CONR^{14}R^{14b}$, -$Q^{4a}$-$NR^{13}CONR^{14}$-$Q^{4b}$-$R^{15}$, -$Q^{4a}$-$NR^{13}R^{14}$, -$Q^{4a}$-$NR^{13}$-$Q^{4b}$-$R^{15}$—, -$Q^{4a}$-$COR^{13}$, -$Q^{4a}$-CO-$Q^{4b}$-$R^{15}$—, -$Q^{4a}$-$NR^{13}COR^{14}$, -$Q^{4a}$-$NR^{13}CO$-$Q^{4b}$-$R^{15}$, -$Q^{4a}NR^{13}C(O)OR^{14}$, -$Q^{4a}$-$NR^{13}C(O)O$-$Q^{4b}$-$R^{14}$—, -$Q^{4a}$-$SO_2R^{13}$, -$Q^{4a}$-$SO_2$-$Q^{4b}$-$R^{15}$, -$Q^{4a}$-$CONR^{13}R^{14}$, -$Q^{4a}$-$CONR^{13}$-$Q^{4b}$-$R^{15}$, -$Q^{4a}$-$CO_2R^{13}$, -$Q^{4a}$-$CO_2$-$Q^{4b}$-$R^{15}$, -$Q^{4a}SO_2NR^{13}R^{14}$, -$Q^{4a}$-$SO_2NR^{13}$-$Q^{4b}$-$R^{15}$, -$Q^{4a}$-$NR^{13}SO_2R^{14}$, -$Q^{4a}NR^{13}SO_2$-$Q^{4b}$-$R^{15}$, -$Q^{4a}$-$NR^{13}SO_2NR^{14}R^{14b}$ and -$Q^{4a}$-$NR^{13}SO_2NR^{14}$-$Q^{4b}$-$R^{15}$; wherein $Q^{4a}$ and $Q^{4b}$ independently represent a covalent bond optionally substituted $C_1$-$C_6$ alkylene or optionally substituted $C_2$-$C_6$ alkenylene;

$R^{13}$, $R^{14}$, and $R^{14a}$ each independently represent hydrogen or optionally substituted $C_1$-$C_6$ alkyl; and $R^{15}$ represents optionally substituted heterocyclyl, optionally substituted heteroaryl, optionally substituted aryl, or an optionally substituted cycloalkyl.

In one aspect, the invention also relates to pharmaceutical compositions comprising the compounds of the present invention and one or more pharmaceutically acceptable excipients.

In another aspect, the compounds of the invention are useful for the treatment of cancer.

BRIEF DESCRIPTION OF THE FIGURES

FIG. 1 provides an image of FLAG-USP7 purified from mammalian cells. FLAG-purified protein or the indicated concentrations of BSA were separated by SDS-PAGE and stained with Imperial Protein Stain (Pierce Biotechnology).

FIG. 2 is a graph showing proteolytic activity of purified FLAG-USP7 using a fluorescence polarisation assay. Various volumes of purified USP7 as indicated were incubated with a TAMRA labelled peptide linked to ubiquitin via an isopeptide bond.

DETAILED DESCRIPTION OF THE INVENTION

The definitions and explanations below are for the terms as used throughout this entire document including both the specification and the claims. Reference to compounds as described herein (e.g. a compound of Formula I), includes reference to Formula I including any sub-generic embodiments thereof.

Where any group of the compounds of formula I have been referred to as optionally substituted, this group may be substituted or unsubstituted. Substitution may be by one or more of the specified substituents which may be the same or different. It will be appreciated that the number and nature of substituents will be selected to avoid any sterically undesirable combinations.

In the context of the present specification, unless otherwise stated an alkyl, alkylene, alkoxy, alkenyl, or alkynyl substituent (or linker) group or an alkyl, alkenyl moiety in a substituent group may be linear or branched. Alkyl, alkylene, alkenyl and alkenylene chains may also include intervening heteroatoms such as oxygen.

$C_x$-$C_y$ alkyl refers to a saturated aliphatic hydrocarbon group having x-y carbon atoms which may be linear or branched. For example $C_1$-$C_6$ alkyl contains from 1 to 6 carbon atoms and includes $C_1$, $C_2$, $C_3$, $C_4$, $C_5$ and $C_6$. "Branched" means that at least one carbon branch point is present in the group. For example, tert-butyl and isopropyl are both branched groups. Examples of $C_1$-$C_6$ alkyl groups include methyl, ethyl, propyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, tert-butyl, n-pentyl, isopentyl, neopentyl and n-hexyl. $C_1$-$C_6$ alkyl, $C_1$-$C_4$ alkyl and $C_1$-$C_3$ alkyl within the definitions of $R^{1a}$, $R^{1b}$, $R^{1c}$, $R^{1d}$, $R^3$, $R^4$, $R^7$, $R^8$, $R^{8a}$, $R^{10}$, $R^{11}$, $R^{11a}$, $R^{13}$, $R^{14}$, $R^{14a}$, $Q^2$, and within the definition of substituents for $R^2$ and $R^6$, may be unsubstituted or substituted with one or more of the substituents defined herein. Examples of substituted $C_1$-$C_6$ alkyl therefore include $CF_3$, $CH_2CF_3$, $CH_2CN$, $CH_2OH$ and $CH_2CH_2OH$.

A $C_x$-$C_y$ alkylene group or moiety may be linear or branched and refers to a divalent hydrocarbon group having one less hydrogen atom from $C_x$-$C_y$ alkyl as defined above. $C_1$-$C_6$ alkylene may include intervening heteroatoms such as oxygen, and therefore includes alkyleneoxy groups. Alkyleneoxy as employed herein also extends to embodiments in which the or an oxygen atom (e.g. a single oxygen atom) is located within the alkylene chain, for example $CH_2CH_2OCH_2$ or $CH_2OCH_2$. Examples of $C_1$-$C_6$ alkylene groups include methylene, methyleneoxy, ethylene, ethyleneoxy, n-propylene, n-propyleneoxy, n-butylene, n-butyleneoxy, methylmethylene and dimethylmethylene. Unless stated otherwise, $C_1$-$C_6$ alkylene, $C_1$-$C_4$ alkylene and $C_1$-$C_3$ alkylene within the definitions of $R^5$, $R^9$, $R^{12}$, $R^{15}$, $Q^1$, $Q^2$, $Q^{3a}$, $Q^{4a}$, $Q^{4b}$ may be unsubstituted or substituted with one or more of the substituents defined herein.

$C_2$-$C_6$ alkenyl refers to a linear or branched hydrocarbon chain radical containing at least two carbon atoms and at least one double bond and includes $C_2$-$C_4$ alkenyl. Examples of alkenyl groups include ethenyl, propenyl, 2-propenyl, 1-butenyl, 2-butenyl, 1-hexenyl, 2-methyl-1-propenyl, 1,2-butadienyl, 1,3-pentadienyl, 1,4-pentadienyl and 1-hexadienyl. Unless stated otherwise, $C_2$-$C_6$ alkenyl and $C_2$-$C_4$ alkenyl within the definition of $Q^2$ and within the definition of substituents for $R^2$ and $R^6$, may be unsubstituted or substituted with one or more of the substituents defined herein.

$C_2$-$C_6$ alkenylene refers to linear or branched hydrocarbon group having one less hydrogen atom from $C_2$-$C_6$ alkenyl as defined above. Examples of $C_2$-$C_6$ alkenylene include ethenylene, propenylene and butenylene. Unless stated otherwise, $C_2$-$C_6$ alkenylene and $C_2$-$C_4$ alkenylene within the definition of substituents for $Q^1$, $Q^2$, $Q^{3a}$, $Q^{3b}$ and $Q^{4a}$, $Q^{4b}$ may be unsubstituted or substituted with one or more of the substituents defined herein.

$C_2$-$C_6$ alkynyl refers to a linear or branched hydrocarbon chain radical containing at least two carbon atoms and at least one triple bond. Examples of alkenyl groups include ethynyl, propynyl, 2-propynyl, 1-butynyl, 2-butynyl and 1-hexynyl. Unless specified otherwise, $C_2$-$C_6$ alkynyl, within the definition of substituents for $R^2$ and $R^6$, may be unsubstituted or substituted with one or more of the substituents defined herein.

$C_1$-$C_6$ alkoxy refers to a group or part of a group having an —O—$C_x$-$C_y$ alkyl group according to the definition of $C_x$, $C_y$ alkyl above. $C_1$-$C_6$ alkoxy contains from 1 to 6 carbon atoms and includes $C_1$, $C_2$, $C_3$, $C_4$, $C_5$ and $C_6$. Examples of $C_1$-$C_6$ alkoxy include methoxy, ethoxy, propoxy, isopropoxy, butoxy, pentoxy and hexoxy. Alkoxy as employed herein also extends to embodiments in which the or an oxygen atom (e.g. a single oxygen atom) is located within the alkyl chain, for example $CH_2CH_2OCH_3$ or $CH_2OCH_3$. Thus the alkoxy may be linked through carbon to the remainder of the molecule, for example, —$CH_2CH_2OCH_3$, or alternatively, the alkoxy is linked through oxygen to the remainder of the molecule, for example —$OC_{1-6}$ alkyl. In certain instances, the alkoxy may be linked through oxygen to the remainder of the molecule but the alkoxy group contains a further oxygen atom, for example $OCH_2CH_2OCH_3$. Unless specified otherwise, $C_1$-$C_6$ alkoxy and $C_1$-$C_3$ alkoxy within the definitions $Q^2$ and within the definition of substituents for $R^2$ and $R^6$, may be unsubstituted or substituted with one or more of the substituents defined herein. Examples of substituted $C_1$-$C_6$ alkoxy therefore include $OCF_3$, $OCHF_2$, $OCH_2CF_3$, $CH_2CH_2OCH_3$ and $CH_2CH_2OCH_3$.

The term "halogen" or "halo" refers to chlorine, bromine, fluorine or iodine atoms, in particular chlorine or fluorine atoms.

The term "oxo" means =O.

For the avoidance of doubt it will be understood that the cycloalkyl, heterocyclyl, aryl and heteroaryl rings disclosed herein and within the definitions of $R^{1a}$, $R^{1b}$, $R^{1c}$, $R^{1d}$, $R^2$, $R^6$, $R^{12}$, $R^{15}$, do not include any unstable ring structures or, in the case of heteroaryl and heterocyclic ring systems, any O—O, O—S or S—S bonds. The ring systems may be monocyclic or bicyclic. Bicyclic ring systems include bridged, fused and spiro ring systems. A substituent if present may be attached to any suitable ring atom which may be a carbon atom or, in the case of heteroaryl and heterocyclic ring systems, a heteroatom. Substitution on a ring may also include a change in the ring atom at the position of the substitution. For example, substitution on a phenyl ring may include a change in the ring atom at the position of substitution from carbon to nitrogen, resulting in a pyridine ring.

"cycloalkyl" refers to a monocyclic saturated or partially unsaturated, non-aromatic ring, wherein all of the ring atoms are carbon, and having the number of ring atoms as indicated. For example $C_3$-$C_{10}$ cycloalkyl refers to a monocyclic or bicyclic hydrocarbon ring containing 3 to 10 carbon atoms. Examples of $C_3$-$C_{10}$ cycloalkyl are cyclopropyl, cyclobutyl, cyclopentyl, cyclohexyl, cycloheptyl, cyclooctyl and decahydronaphthalenyl. Bicyclic cycloalkyl groups include bridged ring systems such as bicycloheptane and bicyclooctane. Unless specified otherwise, cycloalkyl within the definitions of $R^{1a}$, $R^{1b}$, $R^{1c}$, $R^{1d}$, $R^6$, $R^{12}$, $R^{15}$, may be unsubstituted or substituted with one or more of the substituents defined herein.

An "aryl" group/moiety refers to any monocyclic or bicyclic hydrocarbon group comprising at least one aromatic group and having from 5 to 10 carbon atom ring members. Examples of aryl groups include phenyl, naphthyl and tetrahydronaphthalenyl. Bicyclic rings may be fused aromatic rings where both rings are aromatic, for example, naphthalenyl, or where only one ring is aromatic, for example tetrahydronaphthalenyl. Preferred aryl groups are phenyl, naphthyl and tetrahydronaphthalenyl, more preferably phenyl and tetrahydronaphthalenyl, even more preferably phenyl. Unless specified otherwise, aryl within the definitions of $R^2$, $R^6$, $R^{12}$, $R^{15}$, may be unsubstituted or substituted with one or more of the substituents defined herein.

"Heteroaryl" as used herein means a polyunsaturated, monocyclic or bicyclic 5 to 10 membered aromatic moiety containing at least one and up to 5 heteroatoms, particularly 1, 2 or 3 heteroatoms selected from N, O and S, and the remaining ring atoms are carbon atoms, in stable combinations known to the skilled person. Heteroaryl ring nitrogen and sulphur atoms are optionally oxidised, and the nitrogen atom(s) are optionally quaternized. A heteroaryl ring can be a single aromatic ring or a fused bicyclic ring where the bicyclic ring system can be aromatic, or one of the fused rings is aromatic and the other is at least partially saturated. In one example, a bicyclic heteroaryl is one in which the entire fused ring system is aromatic. A bicyclic heteroaryl can have the at least one heteroatom in either of the fused rings. For example, a bicyclic ring with an aromatic ring fused to a partially saturated ring may contain the at least one heteroatom in the aromatic ring or the partially saturated ring. Attachment of the bicyclic ring to the group it is a substituent of may be via either a heteroatom containing ring or a carbon only containing ring. The point of attachment of heteroaryl to the group it is a substituent of can be via a carbon atom or a heteroatom (e.g. nitrogen). Examples of heteroaryl rings include pyridinyl, pyrazinyl, pyrimidinyl, pyridazinyl, furanyl, thiophenyl, pyrrolyl, oxazolyl, thiazolyl, pyrazolyl, triazolyl, tetrazolyl, indolyl, indolizinyl, isoindolyl, purinyl, furazanyl, imidazolyl, indazolyl, isothiazolyl, isoxazolyl, oxadiazolyl, tetrazolyl, thiadiazolyl, benzofuranyl, isobenzofuranyl, benzothiophenyl, isobenzothiophenyl, benzimidazolyl, benzothiazolyl, benzoxazolyl, napthyridinyl, pteridinyl, pyrazinyl, quinolinyl, isoquinolinyl, cinnolinyl, phthalazinyl, quinazolinyl, imidazopyridinyl, pyrazolopyridinyl, thiazolopyridinyl, triazinyl, dihydrophyridinyl, dihydropyrrolopyridinyl, quinoxalinyl and dihydrobenzoxazinyl. Unless specified otherwise, heteroaryl within the definitions of $R^2$, $R^6$, $R^{12}$, $R^{15}$, may be unsubstituted or substituted with one or more of the substituents defined herein.

"Heterocyclyl" or "heterocyclic" as used herein in describing a ring means, unless otherwise stated, a monocyclic saturated or partially unsaturated, non-aromatic ring or a bicyclic saturated or partially unsaturated ring, wherein the bicyclic ring system is non-aromatic, the mono- or bicyclic ring having, for example, 3 to 10 members, where at least one member and up to 5 members, particularly 1, 2 or 3 members of the ring are heteroatoms selected from N, O and S, and the remaining ring atoms are carbon atoms, in stable combinations known to those of skill in the art. Heterocyclic ring nitrogen and sulphur atoms are optionally oxidised, and the nitrogen atoms(s) are optionally quaternized. As used herein, the heterocyclic ring may be a fused ring to another ring system to form a bicycle, i.e. one or two of the heterocyclic ring carbons is common to an additional ring system. In instances where the heterocyclyl is a bicyclic ring, the second ring can be aromatic, e.g. a fused phenyl, pyridyl, pyrazolyl, or the like. The heterocyclyl may be linked through carbon or a heteroatom to the remainder of the molecule and in instances where the heterocyclyl is a bicyclic ring, the link may be via the heteroatom containing ring or the fused ring. Examples of heterocyclyl groups include azetidinyl, pyrrolidinyl, piperidinyl, azepanyl, diazepanyl, dihydrofuranyl (e.g. 2,3-dihydrofuranyl, 2,5-dihydrofuranyl), dioxolanyl, morpholinyl, oxazolidinyl, oxazinanyl, indolinyl, isoindolinyl, piperazinyl, tetrahydrofuranyl, thiomorpholinyl, dihydropyranyl (e.g. 3,4-dihydropyranyl, 3,6-dihydropyranyl), homopiperazinyl, dioxanyl, hexahydropyrimidinyl, pyrazolinyl, pyrazolidinyl, 4H-quinolizinyl, quinuclidinyl, tetrahydropyranyl, tetrahydropyridinyl, tetrahydropyrimidinyl, tetrahydrothiophenyl, thiazolidinyl, benzopyranyl, tetrahydroquinolinyl, dihydropyrrolopyranyl, dihydrobenzoxazinyl, pyrrolopyridinyl, dihydronaphthyridinyl, dihydroisoquinolinyl and tetrahydroisoquinolinyl. Unless specified otherwise, heterocyclyl within the definitions of $R^2$, $R^6$, $R^{12}$, $R^{15}$ and within the definition of substituents for $R^2$ and $R^6$, may be unsubstituted or substituted with one or more of the substituents defined herein. Examples of substituted heterocyclyl rings include for example 4,5-dihydro-1H-maleimido, tetramethylenesulfoxide and hydantoinyl.

"Optionally substituted" as applied to any group means that the said group may if desired be substituted with one or more substituents (e.g., 1, 2, 3 or 4 substituents) which may be the same or different.

Examples of suitable substituents for "substituted" and "optionally substituted" $C_1$-$C_6$ alkyl (including $C_1$-$C_4$ alkyl, $C_1$-$C_3$ alkyl and $C_1$-$C_2$ alkyl) and $C_1$-$C_6$ alkoxy (including $C_1$-$C_4$ alkoxy, $C_1$-$C_3$ alkoxy and $C_1$-$C_2$ alkoxy) and $C_2$-$C_6$ alkenyl (including $C_2$-$C_4$ alkenyl) and $C_2$-$C_6$ alkynyl (including $C_2$-$C_4$ alkynyl), for example within the definitions of $R^{1a}$, $R^{1b}$, $R^{1c}$, $R^{1d}$, $R^3$, $R^4$, $R^7$, $R^8$, $R^{8a}$, $R^{10}$, $R^{11}$, $R^{11a}$, $R^{13}$, $R^{14}$, $R^{14a}$, $Q^2$, and within the definition of substituents for $R^2$ and $R^6$, and $C_1$-$C_6$ alkylene (including $C_1$-$C_3$ alkylene) and $C_2$-$C_6$ alkenylene, for example within the definitions of $R^5$, $R^9$, $R^{12}$, $R^{15}$, $Q^1$, $Q^2$, $Q^{3a}$, $Q^{3b}$, $Q^{4a}$, $Q^{4b}$ include halogen, cyano, oxo, nitro, amino, amido, hydroxy, $C_1$-$C_6$ alkyl or $C_1$-$C_3$ alkyl, $C_1$-$C_6$ alkoxy or $C_1$-$C_3$ alkoxy, aryl, heteroaryl, heterocyclyl, $C_3$-$C_6$ cycloalkyl, $C_{1-3}$ alkylamino, $C_{2-6}$ alkenylamino, di-$C_1$-$C_3$ alkylamino, $C_1$-$C_3$ acylamino, di-$C_1$-$C_3$ acylamino, carboxy, $C_1$-$C_3$ alkoxycarbonyl, carboxamidyl, carbamoyl, mono-$C_{1-3}$ carbamoyl, di-$C_{1-3}$ carbamoyl or any of the above in which a hydrocarbyl moiety is itself substituted by halogen, e.g. fluorine, hydroxyl, cyano, amino, nitro or $SF_5$ (a known mimetic of nitro). In particular, suitable substituents may be selected from halogen, hydroxyl, thiol, cyano, amino, amido, nitro and $SF_5$ (a known mimetic of nitro), in particular, halogen (preferably fluorine or chlorine), hydroxyl and cyano.

Examples of suitable substituents for all remaining "substituted" and "optionally substituted" moieties, including the cycloalkyl, heterocyclyl, aryl and heteroaryl rings within the definitions of $R^{1a}$, $R^{1b}$, $R^{1c}$, $R^{1d}$, $R^2$, $R^6$, $R^{12}$, $R^{15}$, include halogen, cyano, oxo, nitro, amino, amido, hydroxy, amido, $C_1$-$C_6$ alkyl or $C_1$-$C_3$ alkyl, $C_1$-$C_6$ alkoxy or $C_1$-$C_3$ alkoxy, aryl, heteroaryl, heterocyclyl, $C_3$-$C_6$ cycloalkyl, $C_{1-3}$ alkylamino, $C_{2-6}$ alkenylamino, di-$C_1$-$C_3$ alkylamino, $C_1$-$C_3$ acylamino, di-$C_1$-$C_3$ acylamino, carboxy, $C_1$-$C_3$ alkoxycarbonyl, carboxamidyl, carbamoyl, mono-$C_{1-3}$ carbamoyl, di-$C_{1-3}$ carbamoyl or any of the above in which a hydrocarbyl moiety is itself substituted by halogen, e.g. fluorine, hydroxyl, cyano, amino, amido, nitro or $SF_5$ (a known mimetic of nitro).

Examples of suitable substituents for "substituted" and "optionally substituted" rings include in particular, fluorine, chlorine, oxo, cyano, $C_1$-$C_3$ alkyl, $C_1$-$C_3$ alkoxy, heterocyclyl, cycloalkyl, heteroaryl or aryl, wherein the alkyl or alkoxy is optionally substituted with one or more (e.g. one, two or three) substituents selected from halogen, hydroxyl, thiol, cyano, amino, amido, nitro and $SF_5$.

Substituted groups thus include for example Br, Cl, F, CN, Me, Et, Pr, t-Bu, OMe, OEt, OPr, $C(CH_3)_3$, $CH(CH_3)_2$, $CF_3$, $OCF_3$, $C(O)NHCH_3$, cyclopropyl, phenyl, etc. In the case of aryl groups, the substitutions may be in the form of rings from adjacent carbon atoms in the aryl ring, for example cyclic acetals such as O—$CH_2$—O.

In substituted groups containing an oxygen atom such as hydroxy and alkoxy, the oxygen atom can be replaced with sulphur to make groups such as thio (SH) and thio-alkyl (S-alkyl). Optional substituents therefore include groups such as S-methyl. In thio-alkyl groups, the sulphur atom may be further oxidised to make a sulfoxide or sulfone, and thus optional substituents therefore includes groups such as S(O)-alkyl and $S(O)_2$-alkyl.

The term "treat" or "treating" or "treatment" includes prophylaxis and means to ameliorate, alleviate symptoms, eliminate the causation of the symptoms either on a temporary or permanent basis, or to prevent or slow the appearance of symptoms of the named disorder or condition. The compounds of the invention are useful in the treatment of humans and non-human animals.

The dose of the compound is that amount effective to prevent occurrence of the symptoms of the disorder or to treat some symptoms of the disorder from which the patient suffers. By "effective amount" or "therapeutically effective amount" or "effective dose" is meant that amount sufficient to elicit the desired pharmacological or therapeutic effects, thus resulting in effective prevention or treatment of the disorder. Prevention of the disorder is manifested by delaying the onset of the symptoms of the disorder to a medically significant extent. Treatment of the disorder is manifested by a decrease in the symptoms associated with the disorder or an amelioration of the reoccurrence of the symptoms of the disorder.

Pharmaceutically acceptable salts of the compounds of the invention include but are not limited to addition salts (for example phosphates, nitrates, sulphates, borates, acetates, maleates, citrates, fumarates, succinates, methanesulphonates, benzoates, salicylates and hydrohalides), salts derived from organic bases (such as lithium, potassium and sodium), salts of amino acids (such as glycine, alanine, valine, leucine, isoleucine, cysteine, methionine and proline), inorganic bases (such as triethylamine, hydroxide, choline, thiamine and N—N'-diacetylethylenediamine). Other pharmaceutically acceptable salts include ammonium salts, substituted ammonium salts and aluminium salts. Further pharmaceutically acceptable salts include quaternary ammonium salts of the compounds of the invention.

General methods for the production of salts are well known to the person skilled in the art. Such salts may be formed by conventional means, for example by reaction of a free acid or a free base form of a compound with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound in the form of a salt with another counter-ion, for example using a suitable ion exchange resin.

Where compounds of the invention exist in different enantiomeric and/or diastereoisomeric forms, the invention relates to these compounds prepared as isomeric mixtures or racemates whether present in an optically pure form or as mixtures with other isomers. Enantiomers differ only in their ability to rotate plane-polarized light by equal amounts in opposite directions and are denoted as the (+)/(S) or (−)/(R) forms respectively. Individual enantiomers or isomers may be prepared by methods known in the art, such as optical resolution of products or intermediates (for example chiral chromatographic separation e.g. chiral HPLC, or an asymmetric synthesis approach). Similarly where compounds of the invention exist as alternative tautomeric forms e.g. keto/enol, amide/imidic acid, the invention relates to the individual tautomers in isolation, and to mixtures of the tautomers in all proportions.

Isotopes

The compounds described herein may contain one or more isotopic substitutions, and a reference to a particular element includes within its scope all isotopes of the element. For example, a reference to hydrogen includes within its scope $^1H$, $^2H$ (D), and $^3H$ (T). Similarly, references to carbon and oxygen include within their scope respectively $^{12}C$, $^{13}C$ and $^{14}C$ and $^{16}O$ and $^{18}O$. Examples of isotopes include $^2H$, $^3H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$ and $^{35}S$.

In an analogous manner, a reference to a particular functional group also includes within its scope isotopic variations, unless the context indicates otherwise. For example, a reference to an alkyl group such as an ethyl group also covers variations in which one or more of the hydrogen atoms in the group is in the form of a deuterium or tritium isotope, e.g. as in an ethyl group in which all five hydrogen atoms are in the deuterium isotopic form (a perdeuteroethyl group). Deuterium may be referred to throughout as "deutero".

The isotopes may be radioactive or non-radioactive. In one embodiment, the compounds contain no radioactive isotopes. Such compounds are preferred for therapeutic use. In another embodiment, however, the compounds may contain one or more radioisotopes. Compounds containing such radioisotopes may be useful in a diagnostic context.

Certain isotopically labelled compounds of formula (I), for example, those incorporating a radioactive isotope, are useful in drug and/or substrate tissue distribution studies. The radioactive isotopes i.e. $^3H$ and $^{14}C$ are particularly useful for this purpose in view of their ease of incorporation and ready means of detection. Substitution with heavier isotopes i.e. $^2H$, may afford certain therapeutic advantages resulting from greater metabolic stability, for example, increased in vivo half-life or reduced dosage requirements, and hence may be preferred in some circumstances. Substitution with positron emitting isotopes, such as $^{11}C$, $^{18}F$, $^{15}O$ and $^{13}N$, can be useful in Positron Emission Topography (PET) studies for examining receptor occupancy. Isotopically labelled compounds of formula (I) can generally be prepared by conventional techniques known to those skilled in the art or by processes analogous to those described in the accompanying examples and preparations using an appropriate isotopically labelled reagent in place of the non-labelled reagent previously employed.

Crystalline and Amorphous Forms

The compounds of formula (I) may exist in crystalline or amorphous form and some of the crystalline forms may exist as polymorphs, which are included within the scope of the present invention. Polymorphic forms of compounds of formula (I) may be characterised and differentiated using a number of conventional analytical techniques, including, but not limited to, infra-red spectra, Raman spectra, X-ray powder diffraction, differential scanning calorimetry, thermogravimetric analysis and solid state nuclear magnetic resonance.

Accordingly, in further embodiments, the invention provides a compound according to any described embodiments in a crystalline form. The compound may be from 50% to 100% crystalline, and more particularly is at least 50% crystalline, or at least 60% crystalline, or at least 70% crystalline, or at least 80% crystalline, or at least 90% crystalline, or at least 95% crystalline, or at least 98% crystalline, or at least 99% crystalline, or at least 99.5% crystalline, or at least 99.9% crystalline, for example 100% crystalline. The compound may alternatively be in an amorphous form.

The invention described herein relates to all crystal forms, solvates and hydrates of any of the disclosed compounds however so prepared. To the extent that any of the compounds disclosed herein have acid or basic centres such as carboxylates or amino groups, then all salt forms of said compounds are included herein. In the case of pharmaceutical uses, the salt should be seen as being a pharmaceutically acceptable salt.

The invention relates to any solvates of the compounds and their salts. Preferred solvates are solvates formed by the incorporation into the solid state structure (e.g. crystal structure) of the compounds of the invention of molecules of a non-toxic pharmaceutically acceptable solvent (referred to below as the solvating solvent). Examples of such solvents include water, alcohols (such as ethanol, isopropanol and butanol) and dimethylsulfoxide. Solvates can be prepared by recrystallising the compounds of the invention with a solvent or mixture of solvents containing the solvating solvent. Whether or not a solvate has been formed in any given instance can be determined by subjecting crystals of the compound to analysis using well known and standard techniques such as thermogravimetric analysis (TGE), differential scanning calorimetry (DSC) and X-ray crystallography.

The solvates can be stoichiometric or non-stoichiometric solvates. Particular solvates may be hydrates, and examples of hydrates include hemihydrates, monohydrates and dihydrates. For a more detailed discussion of solvates and the methods used to make and characterise them, see Bryn et al., Solid-State Chemistry of Drugs, Second Edition, published by SSCI, Inc of West Lafayette, Ind., USA, 1999, ISBN 0-967-06710-3.

The invention relates to pharmaceutically functional derivatives of compounds as defined herein including ester derivatives and/or derivatives that have, or provide for, the same biological function and/or activity as any relevant compound of the invention. Thus, for the purposes of this invention, the term also includes prodrugs of compounds as defined herein.

The term "prodrug" of a relevant compound includes any compound that, following oral or parenteral administration, is metabolised in vivo to form that compound in an experimentally-detectable amount, and within a predetermined time (e.g. within a dosing interval of between 6 and 24 hours (i.e. once to four times daily).

Prodrugs of compounds may be prepared by modifying functional groups present on the compound in such a way that the modifications are cleaved, in vivo when such prodrug is administered to a mammalian subject. The modifications typically are achieved by synthesizing the parent compound with a prodrug substituent. Prodrugs include compounds wherein a hydroxyl, amino, sulfhydryl, carboxyl or carbonyl group in a compound is bonded to any group that may be cleaved in vivo to regenerate the free hydroxyl, amino, sulfhydryl, carboxyl or carbonyl group, respectively.

Examples of prodrugs include, but are not limited to, esters and carbamates of hydroxyl functional groups, ester groups of carboxyl functional groups, N-acyl derivatives and N-Mannich bases. General information on prodrugs may be found e.g. in Bundegaard, H. "Design of Prodrugs" p. 1-92, Elsevier, New York-Oxford (1985).

Compounds of the invention may be metabolised in vivo. Metabolites of compounds of formula (I) are also within the scope of the present invention. The term 'metabolites' refers to all molecules derived from any of the compounds according to the present invention in a cell or organism, preferably mammal. Preferably the term relates to molecules which differ from any molecule which is present in any such cell or organism under physiological conditions.

A treatment defined herein may be applied as a sole therapy of may involve, in addition to the compounds of the invention, conventional surgery or radiotherapy or chemotherapy. Furthermore, compounds of formula (I) can also be used in combination with existing therapeutic agents for the treatment of conditions associated with cancer, including small molecule therapeutics or antibody based therapeutics.

In accordance with a first aspect of the invention there is provided a compound of formula I:

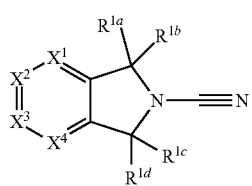

(I)

or a pharmaceutically acceptable salt thereof, wherein:
$R^{1a}$, $R^{1b}$, $R^{1c}$ and $R^{1d}$ each independently represent hydrogen or optionally substituted $C_1$-$C_6$ alkyl, or $R^{1a}$ and $R^{1b}$ together form an optionally substituted $C_3$-$C_6$ cycloalkyl ring, or $R^{1c}$ and $R^{1d}$ together form an optionally substituted $C_3$-$C_6$ cycloalkyl ring;

$X^1$, $X^3$ and $X^4$ each independently represent N, C-$Q^1$-$R^2$ or C-$Q^2$-$(R^6)_n$ and $X^2$ represents N or CH, wherein one of $X^1$, $X^3$ and $X^4$ represents C-$Q^1$-$R^2$ and no more than two of $X^1$, $X^2$, $X^3$ and $X^4$ represent N;

$Q^1$ represents a covalent bond, an oxygen atom, a sulphur atom, —$OR^5$—, —SO—, —$SO_2$—, —CO—, —C(O)O—, —$C_0$-$C_3$ alkylene-CONR$^3$—$C_0$-$C_3$ alkylene-, —$C_0$-$C_3$ alkylene-NR$^3$—$C_0$-$C_3$ alkylene, —$C_0$-$C_3$ alkylene-NR$^3$CO—$C_0$-$C_3$ alkylene, —NR$^3$CONR$^4$—, —$SO_2$NR$^3$—, NR$^3$SO$_2$—, —NR$^3$SO$_2$NR$^4$—, —NR$^3$C(O)O—, —NR$^3$C(O)OR$^5$—, optionally substituted —$C_1$-$C_6$ alkylene or optionally substituted —$C_2$-$C_6$ alkenylene;

$R^2$ is an optionally substituted 3 to 10 membered monocyclic or bicyclic heteroaryl, aryl or heterocyclyl ring;

$R^3$ and $R^4$ each independently represent hydrogen or optionally substituted $C_1$-$C_6$ alkyl;

$R^5$ represents optionally substituted $C_1$-$C_6$ alkylene or optionally substituted $C_3$-$C_4$ cycloalkylene;

n is 0 or 1;

$Q^2$ represents hydrogen, halogen, cyano, nitro, hydroxyl, —SR$^7$, —NR$^7$R$^8$, —CONR$^7$R$^8$, —NR$^7$COR$^8$, —NR$^7$CONR$^8$R$^{8a}$, —COR$^7$, —C(O)OR$^7$, —SO$_2$R$^7$, —SO$_2$NR$^7$R$^8$, —NR$^7$SO$_2$R$^8$, —NR$^7$SO$_2$NR$^8$R$^{8a}$, —NR$^7$C(O)OR$^8$, optionally substituted —$C_1$-$C_6$ alkyl, optionally substituted —$C_1$-$C_6$ alkoxy, optionally substituted $C_2$-$C_6$ alkenyl, a covalent bond, an oxygen atom, a sulphur atom, —OR$^9$—, —SO—, —SO$_2$—, —CO—, —C(O)O—, —$C_0$-$C_3$ alkylene-CONR$^7$—$C_0$-$C_3$ alkylene, —$C_0$-$C_3$ alkylene-NR$^7$—$C_0$-$C_3$ alkylene, —$C_0$-$C_3$ alkylene-NR$^7$CO—$C_0$-$C_3$ alkylene, —NR$^7$CONR$^8$—, —SO$_2$NR$^7$—, NR$^7$SO$_2$—, —NR$^7$SO$_2$NR$^8$—, —NR$^7$C(O)O—, —NR$^7$C(O)OR$^9$—, optionally substituted $C_1$-$C_6$ alkylene, or optionally substituted —$C_2$-$C_6$ alkenylene;

$R^6$ is an optionally substituted 3 to 10 membered monocyclic or bicyclic heteroaryl, aryl, heterocyclyl or cycloalkyl ring;

$R^7$, $R^8$ and $R^{8a}$ each independently represent hydrogen or optionally substituted $C_1$-$C_6$ alkyl;

$R^9$ represents optionally substituted $C_1$-$C_6$ alkylene.

The compounds of the invention are characterised by a 9 membered bicyclic ring structure which is formed from a cyanopyrrolidine core fused to an aromatic ring, wherein the aromatic ring may contain up to two, i.e. 0, 1 or 2, nitrogen ring atoms.

In all cases described herein, $R^{1a}$, $R^{1b}$, $R^{1c}$ and $R^{1d}$ may each independently represent hydrogen, optionally substituted $C_1$-$C_6$ alkyl, or $R^{1a}$ together with e forms an optionally substituted $C_3$-$C_6$ cycloalkyl, or $R^{1c}$ and together with $R^{1d}$ form an optionally substituted $C_3$-$C_6$ cycloalkyl. In particular, $R^{1a}$, $R^{1b}$, $R^{1c}$ and $R^{1d}$ may each independently represent hydrogen or $C_1$-$C_3$ alkyl (e.g. methyl or ethyl). $R^{1a}$ may be hydrogen or $C_1$-$C_3$ alkyl and $R^{1b}$ may be hydrogen. $R^{1c}$ may be hydrogen or $C_1$-$C_3$ alkyl and $R^{1d}$ may be hydrogen. In particular, $R^{1a}$, $R^{1b}$, $R^{1c}$ and $R^{1d}$ each represent hydrogen. The alkyl within the definitions of $R^{1a}$, $R^{1b}$, $R^{1c}$ and $R^{1d}$ may be unsubstituted or substituted with one or more substituents selected from halogen, hydroxyl, thiol, cyano, amino, amido, nitro and SF$_5$. In particular, the alkyl may be substituted with fluorine.

$R^{1a}$ represent hydrogen. $R^{1a}$ may represent $C_1$-$C_6$ alkyl. $R^{1a}$ may represent $C_1$-$C_3$ alkyl, for example, methyl or ethyl.

When $R^{1a}$ represents $C_1$-$C_6$ alkyl, $R^{1b}$, $R^{1c}$ and $R^{1d}$ may each represent hydrogen. The alkyl within the definition of $R^{1a}$ may be unsubstituted or substituted with one or more substituents selected from halogen, hydroxyl, thiol, cyano, amino, amido, nitro and $SF_5$. In particular, the alkyl may be substituted with fluorine.

$R^{1b}$ may represent hydrogen. $R^{1b}$ may represent $C_1$-$C_6$ alkyl. $R^{1b}$ may represent $C_1$-$C_3$ alkyl, for example, methyl or ethyl. When $R^{1b}$ represents $C_1$-$C_6$ alkyl, $R^{1a}$, $R^{1c}$ and $R^{1d}$ may each represent hydrogen. The alkyl within the definition of $R^{1b}$ may be unsubstituted or substituted with one or more substituents selected from halogen, hydroxyl, thiol, cyano, amino, amido, nitro and $SF_5$. In particular, the alkyl may be substituted with fluorine.

$R^{1c}$ represent hydrogen. $R^{1c}$ may represent $C_1$-$C_6$ alkyl. $R^{1c}$ may represent $C_1$-$C_3$ alkyl, for example, methyl or ethyl. When $R^{1c}$ represents $C_1$-$C_6$ alkyl, $R^{1a}$, $R^{1b}$ and $R^{1d}$ may each represent hydrogen. The alkyl within the definition of $R^{1c}$ may be unsubstituted or substituted with one or more substituents selected from halogen, hydroxyl, thiol, cyano, amino, amido, nitro and $SF_5$. In particular, the alkyl may be substituted with fluorine.

$R^{1d}$ may represent hydrogen. $R^{1d}$ may represent $C_1$-$C_6$ alkyl. $R^{1d}$ may represent $C_1$-$C_3$ alkyl, for example, methyl or ethyl. When $R^{1d}$ represents $C_1$-$C_6$ alkyl, $R^{1a}$, $R^{1b}$ and $R^{1c}$ may each represent hydrogen. The alkyl within the definition of $R^{1d}$ may be unsubstituted or substituted with one or more substituents selected from halogen, hydroxyl, thiol, cyano, amino, amido, nitro and $SF_5$. In particular, the alkyl may be substituted with fluorine.

Alternatively, $R^{1a}$ and $R^{1c}$ may together form a cycloalkyl ring. In addition, or alternatively, $R^{1c}$ and $R^{1d}$ may together form a cycloalkyl ring. When $R^{1a}$ and $R^{1b}$ together form a cycloalkyl ring, $R^{1c}$ and $R^{1d}$ may each independently represent hydrogen or optionally substituted $C_1$-$C_6$ alkyl. When $R^{1c}$ and $R^{1d}$ together form a cycloalkyl ring, $R^{1a}$ and $R^{1b}$ may each independently represent hydrogen or optionally substituted $C_1$-$C_6$ alkyl. The cycloalkyl ring within the definitions of $R^{1a}$, $R^{1b}$, $R^{1c}$ and $R^{1d}$ can contain 3, 4, 5, or 6 carbon ring atoms, in particular 3 or 4 carbon ring atoms. The cycloalkyl ring is attached to the cyanopyrrolidine core as a spiro ring, i.e. they share one ring atom. The cycloalkyl ring may be unsubstituted or substituted with a substituent selected from $C_1$-$C_3$ alkyl, $C_1$-$C_3$ alkoxy, halogen, hydroxyl, thiol, cyano, amino, amido, nitro and $SF_5$, wherein the alkyl and alkoxy may be optionally substituted with halogen.

The compounds may be in the form where $R^{1a}$, $R^{1b}$, $R^{1c}$ and $R^{1d}$ are each hydrogen. In such cases the compounds may be of the formula:

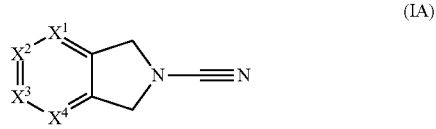

(IA)

or a pharmaceutically acceptable salt thereof, wherein $X^1$, $X^3$ and $X^4$ each independently represent N, C-$Q^1$-$R^2$ or C-$Q^2$-$(R^6)_n$ and $X^2$ represents N or CH, wherein one of $X^1$, $X^3$ and $X^4$ represents C-$Q^1$-$R^2$ and no more than two of $X^1$, $X^2$, $X^3$ and $X^4$ represent N;

$Q^1$ represents a covalent bond, an oxygen atom, a sulphur atom, —$OR^5$—, —SO—, —$SO_2$—, —CO—, —C(O)O—, —$C_0$-$C_3$ alkylene-$CONR^3$—$C_0$-$C_3$ alkylene-, —$C_0$-$C_3$ alkylene-$NR^3$—$C_0$-$C_3$ alkylene, —$C_0$-$C_3$ alkylene-$NR^3$CO—$C_0$-$C_3$ alkylene, —$NR^3CONR^4$—, —$SO_2NR^3$—, $NR^3SO_2$—, —$NR^3SO_2NR^4$—, —$NR^3C(O)O$—, —$NR^3C(O)OR^5$—, optionally substituted —$C_1$-$C_6$ alkylene or optionally substituted —$C_2$-$C_6$ alkenylene;

$R^2$ is an optionally substituted 3 to 10 membered monocyclic or bicyclic heteroaryl, aryl or heterocyclyl ring;

$R^3$ and $R^4$ each independently represent hydrogen or optionally substituted $C_1$-$C_6$ alkyl;

$R^5$ represents optionally substituted $C_1$-$C_0$ alkylene or optionally substituted $C_3$-$C_4$ cycloalkylene;

n is 0 or 1;

$Q^2$ represents hydrogen, halogen, cyano, nitro, hydroxyl, —$SR^7$, —$NR^7R^8$, —$CONR^7R^8$, —$NR^7COR^8$, —$NR^7CONR^8R^{8a}$, —$COR^7$, —$C(O)OR^7$, —$SO_2R^7$, —$SO_2NR^7R^8$, —$NR^7SO_2R^8$, —$NR^7SO_2NR^8R^{8a}$, —$NR^7C(O)OR^8$, optionally substituted —$C_1$-$C_6$ alkyl, optionally substituted —$C_1$-$C_6$ alkoxy, optionally substituted —$C_2$-$C_6$ alkenyl, a covalent bond, an oxygen atom, a sulphur atom, —$OR^9$—, —SO—, —$SO_2$—, —CO—, —C(O)O—, —$C_0$-$C_3$ alkylene-$CONR^7$—$C_0$-$C_3$ alkylene, —$C_0$-$C_3$ alkylene-$NR^7$—$C_0$-$C_3$ alkylene, —$C_0$-$C_3$ alkylene-$NR^7CO$—$C_0$-$C_3$ alkylene, —$NR^7CONR^8$—, —$SO_2NR^7$—, $NR^7SO_2$—, —$NR^7SO_2NR^8$—, —$NR^7C(O)O$—, —$NR^7C(O)OR^9$—, optionally substituted $C_1$-$C_6$ alkylene, or optionally substituted —$C_2$-$C_6$ alkenylene;

$R^6$ is an optionally substituted 3 to 10 membered monocyclic or bicyclic heteroaryl, aryl, heterocyclyl or cycloalkyl ring;

$R^7$, $R^8$ and $R^{8a}$ each independently represent hydrogen or optionally substituted $C_1$-$C_6$ alkyl;

$R^9$ represents optionally substituted $C_1$-$C_6$ alkylene.

In all cases described herein, $X^1$, $X^3$ and $X^4$ each independently represent N, C-$Q^1$-$R^2$ or C-$Q^2$-$(R^6)_n$ and $X^2$ represents N or CH, wherein one of $X^1$, $X^3$ and $X^4$ represents C-$Q^1$-$R^2$ and no more than two of $X^1$, $X^2$, $X^3$ and $X^4$ represent N. The aromatic ring fused to the cyanopyrrolidine core contains no more than two nitrogen ring atoms.

In one embodiment, $X^1$, $X^3$ and $X^4$ each independently represent C-$Q^1$-$R^2$ or C-$Q^2$-$(R^6)_n$ and $X^2$ represents CH, wherein one of $X^1$, $X^3$ and $X^4$ represents C-$Q^1$-$R^2$, i.e. the fused aromatic ring is a substituted phenyl.

In one embodiment, $X^1$ is nitrogen and $X^3$ and $X^4$ each independently represent C-$Q^1$-$R^2$ or C-$Q^2$-$(R^6)_n$ and $X^2$ represents CH, wherein one of $X^3$ and $X^4$ represents C-$Q^1$-$R^2$, i.e. the fused ring is a substituted pyridinyl.

In one embodiment, $X^2$ is nitrogen and $X^1$, $X^3$ and $X^4$ each independently represent C-$Q^1$-$R^2$ or C-$Q^2$-$(R^6)_n$, wherein one of $X^1$, $X^3$ and $X^4$ represents C-$Q^1$-$R^2$, i.e. the fused ring is a substituted pyridinyl.

In one embodiment, $X^1$ and $X^2$ each represent nitrogen and $X^3$ and $X^4$ each independently represent C-$Q^1$-$R^2$ or C-$Q^2$-$(R^6)_n$, wherein one of $X^3$ and $X^4$ represents C-$Q^1$-$R^2$, i.e. the fused ring is a substituted pyridazinyl.

In one embodiment, $X^2$ and $X^3$ each represent nitrogen and $X^1$ and $X^4$ each independently represent C-$Q^1$-$R^2$ or C-$Q^2$-$(R^6)_n$, wherein one of $X^1$ and $X^4$ represents C-$Q^1$-$R^2$, i.e. the fused ring is a substituted pyridazinyl.

In one embodiment, $X^1$ and $X^3$ each represent nitrogen, $X^2$ represents CH and $X^4$ represents C-$Q^1$-$R^2$, i.e. the fused ring is a substituted pyrimidinyl.

In one embodiment, $X^1$ and $X^4$ each represent nitrogen, $X^2$ represents CH and $X^3$ represents C-Q-$R^2$, i.e. the fused ring is a substituted pyrazinyl.

In one embodiment, $X^1$ and $X^3$ each independently represent C-$Q^1$-$R^2$ or C-$Q^2$-$(R^6)_n$ and $X^2$ and $X^4$ are either both N or both CH (i.e. $X^4$ represents N or C-$Q^2(R^6)_n$ where n is 0 and $Q^2$ is hydrogen), wherein one of $X^1$ and $X^3$ represents C-Q$^1$-R$^2$. In a further embodiment, X$^1$ represents C-Q$^1$-R$^2$, X$^3$ represents C-Q$^2$-(R$^6$)$_n$ and X$^4$ are either both N or both CH.

The fused aromatic ring may therefore be selected from:

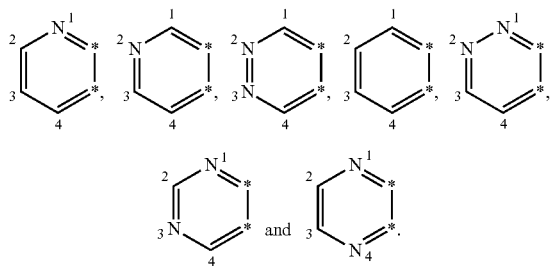

In particular, the fused aromatic ring is selected from:

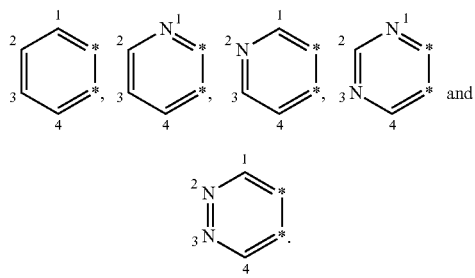

More particularly, the fused aromatic ring is selected from:

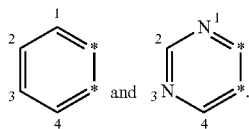

Wherein * represents the ring atoms shared with the cyanopyrrolidine core to form a 9 membered bicyclic ring, wherein the ring is substituted according to the definitions of X$^1$, X$^2$, X$^3$, X$^4$ above. The numbering on the aromatic rings corresponds to the positioning of the X$^1$, X$^2$, X$^3$, X$^4$ groups, i.e. numbers 1, 2, 3 and 4 relate to X$^1$, X$^2$, X$^3$ and X$^4$ respectively, wherein the nitrogen or carbon ring atoms are substituted according to the definitions of X$^1$, X$^2$, X$^3$ and X$^4$ provided herein.

One of X$^1$, X$^3$ and X$^4$ must represent C-Q$^1$-R$^2$, i.e. the fused aromatic ring must be substituted with at least one heteroaryl, aryl or heterocyclyl ring at a carbon ring atom. In certain embodiments, X$^1$ represents C-Q$^1$-R$^2$.

In all cases described herein, Q$^1$ may be selected from a covalent bond, an oxygen atom, a sulphur atom, —OR$^5$—, —SO—, —SO$_2$—, —CO—, —C(O)O—, —C$_0$-C$_3$ alkylene-CONR$^3$—C$_0$-C$_3$ alkylene, C$_0$-C$_3$ alkylene-NR$^3$—C$_0$-C$_3$ alkylene (e.g. methylamino), —C$_0$-C$_3$ alkylene-NR$^3$C(O)—C$_0$-C$_3$ alkylene, —NR$^3$C(O)NR$^4$—, —SO$_2$NR$^3$—, NR$^3$SO$_2$—, —NR$^3$SO$_2$NR$^4$—, —NR$^3$C(O)O—, —NR$^3$C(O)OR$^5$—, optionally substituted —C$_1$-C$_6$ alkylene (e.g. methylene or ethylene) or optionally substituted —C$_2$-C$_6$ alkenylene (e.g. vinyl).

R$^3$ and R$^4$ each independently represent hydrogen or optionally substituted C$_1$-C$_6$ alkyl. For example, R$^3$ and R$^4$ may each independently represent hydrogen, C$_1$-C$_6$ alkyl, C$_1$-C$_4$ alkyl or C$_1$-C$_2$ alkyl. The alkyl may be optionally substituted with halogen, hydroxyl, thiol, cyano, amino, amido, nitro and SF$_5$.

R$^5$ represents optionally substituted C$_1$-C$_6$ alkylene or optionally substituted C$_3$-C$_4$ cycloalkylene. For example, R$^5$ may represent C$_1$-C$_6$ alkylene, C$_1$-C$_4$ alkylene, C$_1$-C$_2$ alkylene or C$_3$-C$_4$ cycloalkylene. The alkyl and cycloalkylene may be optionally substituted with halogen, hydroxyl, thiol, cyano, amino, amido, nitro and SF$_5$.

In particular, Q$^1$ may be selected from a covalent bond, —C$_0$-C$_3$ alkylene-CONR$^3$—C$_0$-C$_3$ alkylene, —C$_0$-C$_3$ alkylene-NR$^3$C(O)—C$_0$-C$_3$ alkylene, C$_0$-C$_3$ alkylene-NR$^3$—C$_0$-C$_3$ alkylene, —NR$^3$C(O)R$^5$—, wherein R$^3$ and R$^4$ are each independently selected from hydrogen and C$_1$-C$_3$ alkyl, and R$^5$ represents C$_1$-C$_3$ alkylene or C$_3$-C$_4$ cycloalkyl. The alkyl, alkylene and cycloalkyl may be unsubstituted or substituted with halogen, hydroxyl, thiol, cyano, amino, amido, nitro and SF$_5$. In one embodiment, Q$^1$ is a covalent bond. More particularly, Q$^1$ is a covalent bond.

In all cases described herein, R$^2$ represents an optionally substituted monocyclic or bicyclic 5 to 10 membered (e.g. 5, 6, 7, 8, 9 or 10 membered) heterocyclyl, heteroaryl or aryl ring.

R$^2$ may represent an optionally substituted 5 or 6 membered monocyclic heterocyclyl, heteroaryl or aryl ring.

Alternatively, R$^2$ may represent an optionally substituted 9 or 10 membered bicyclic heterocyclyl, heteroaryl or aryl ring.

R$^2$ may be selected from phenyl, naphthyl, naphthalenyl, tetrahydronaphthalenyl, pyridinyl, pyrazinyl, pyrimidinyl, pyridazinyl, furanyl, thiophenyl, pyrrolyl, oxazolyl, thiazolyl, pyrazolyl, tetrazolyl, indolyl, indolizinyl, isoindolyl, indolinyl, purinyl, furazanyl, imidazolyl, indazolyl, isothiazolyl, isoxazolyl, oxadiazolyl, tetrazolyl, thiadiazolyl, benzofuranyl, isobenzofuranyl, benzothiophenyl, isobenzothiophenyl, benzimidazolyl, benzothiazolyl, benzoxazolyl, napthyridinyl, pteridinyl, pyrazinyl, quinolinyl, isoquinolinyl, cinnolinyl, phthalazinyl, quinazolinyl, imidazopyridinyl, pyrazolopyridinyl, thiazolopyridinyl, isoindolinyl, triazinyl, dihydrophyridinyl, quinoxalinyl, dihydrobenzoxazinyl, dihydropyrrolopyridinyl, azetidinyl, pyrrolidinyl, piperidinyl, azepanyl, diazepanyl, dihydrofuranyl (e.g. 2,3-dihydrofuranyl, 2,5-dihydrofuranyl), dioxolanyl, morpholinyl, oxazolidinyl, oxazinanyl, indolinyl, isoindolinyl, piperazinyl, tetrahydrofuranyl, thiomorpholinyl, dihydropyranyl (e.g. 3,4-dihydropyranyl, 3,6-dihydropyranyl), homopiperazinyl, dioxanyl, hexahydropyrimidinyl, pyrazolinyl, pyrazolidinyl, 4H-quinolizinyl, quinuclidinyl, tetrahydropyranyl, tetrahydropyridinyl, tetrahydropyrimidinyl, tetrahydrothiophenyl, thiazolidinyl, benzopyranyl, tetrahydroquinolinyl, dihydrobenzoxazinyl, pyrrolopyridinyl, dihydroisoquinolinyl, dihydronaphthyridinyl, tetrahydroisoquinolinyl, dihydroindenyl, tetrahydroisoquinolinyl, and tetrahydronaphthyridinyl.

In particular, R$^2$ is selected from pyrrolidinyl, phenyl, quinazolinyl, pyrazolyl, quinolinyl, pyrrolopyridinyl, oxadiazolyl, isoquinolinyl, dihydroisoquinolinyl, tetrahydroisoquinolinyl, pyridinyl, pyrimidinyl, isoxazolyl, indazolyl, thiazolyl, dihydronaphthyridinyl, piperazinyl, isoindolyl, tetrahydronaphthalenyl, benzoxazolyl, morpholinyl, tetrahydropyranyl, thiophenyl, furanyl, imidazolyl, piperidinyl, indolinyl, dihydroindenyl, tetrahydroisoquinolinyl, and tetrahydronaphthyridinyl. More particularly, $R^2$ is phenyl, benzoxazolyl or benzopiperidinyl. Even more particularly, $R^2$ may be phenyl.

In all cases described herein, $R^2$ may be unsubstituted or substituted with one or more non-ring substituents and/or ring substituents.

Therefore, $R^2$ may be unsubstituted or substituted with one or more substituents selected from halogen, cyano, oxo, nitro, hydroxyl, —$CF_3$, —$SR^{10}$, —$C_1$-$C_6$ alkyl, —$C_1$-$C_6$ alkoxy, —$C_2$-$C_6$ alkenyl, —$C_2$-$C_6$ alkynyl, -$Q^{3a}$-$R^{12}$, -$Q^{3a}$-O-$Q^{3b}$-$R^{12}$, -$Q^{3a}$-S-$Q^{3b}$-$R^{12}$, -$Q^{3a}$-SO-$Q^{3b}$-$R^{12}$, -$Q^{3a}$-$NR^{10}CONR^{11}R^{11a}$, -$Q^{3a}$-$NR^{10}CONR^{11}$-$Q^{3b}$-$R^{12}$, -$Q^{3a}$-$NR^{10}R^{11}$, -$Q^{3a}NR^{10}$-$Q^{3b}$-$R^{12}$, -$Q^{3a}$-$COR^{10}$, -$Q^{3a}$-CO-$Q^{3b}$-$R^{12}$, -$Q^{3a}$-$NR^{10}COR^{11}$, -$Q^{3a}$-$NR^{10}CO$-$Q^{3b}$-$R^{12}$, -$Q^{3a}$-$NR^{10}C(O)OR^{11}$, -$Q^{3a}$-$NR^{10}C(O)O$-$Q^{3b}$-$R^{12}$, -$Q^{3a}$-$SO_2R^{10}$, -$Q^{3a}$-$SO_2$-$Q^{3b}$-$R^{12}$, -$Q^{3a}$-$CONR^{10}R^{11}$, -$Q^{3a}$-$CONR^{10}$-$Q^{3b}$-$R^{12}$, -$Q^{3a}$-$CO_2R^{10}$, -$Q^{3a}$-$CO_2$-$Q^{3b}$-$R^{12}$, -$Q^{3a}$-$SO_2NR^{10}R^{11}$, -$Q^{3a}$-$SO_2NR^{10}$-$Q^{3b}$-$R^{12}$, -$Q^{3a}$-$NR^{10}SO_2R^{11}$, -$Q^{3a}$-$NR^{10}SO_2$-$Q^{3b}$-$R^{12}$, -$Q^{3a}$-$NR^{10}SO_2NR^{11}R^{11a}$, and -$Q^{3a}$-$NR^{10}SO_2NR^{11}$-$Q^{3b}$-$R^{12}$.

$Q^{3a}$ and $Q^{3b}$ each independently represent a covalent bond, optionally substituted $C_1$-$C_6$ alkylene or optionally substituted $C_2$-$C_6$ alkenylene. For example, $Q^{3a}$ and $Q^{3b}$ may each independently represent a covalent bond, $C_1$-$C_6$ alkylene, $C_1$-$C_4$ alkylene, $C_1$-$C_2$ alkylene, $C_2$-$C_6$ alkenylene or $C_2$-$C_4$ alkenylene. The alkylene and alkenylene may be optionally substituted with halogen, hydroxyl, thiol, cyano, amino, amido, nitro and $SF_5$.

$R^{10}$, $R^{11}$ and $R^{11a}$ each independently represent hydrogen or optionally substituted $C_1$-$C_6$ alkyl. For example, $R^{10}$, $R^{11}$ and $R^{11a}$ may each independently represent $C_1$-$C_6$ alkyl, $C_1$-$C_4$ alkyl or $C_1$-$C_2$ alkyl. The alkyl may be optionally substituted with halogen, hydroxyl, thiol, cyano, amino, amido, nitro and $SF_5$.

$R^{12}$ represents optionally substituted heterocyclyl, optionally substituted heteroaryl, optionally substituted aryl, or an optionally substituted cycloalkyl.

The non-ring substituents may be selected from halogen, cyano, oxo, nitro, hydroxyl, —$SR^{10}$, —$C_1$-$C_6$ alkyl, —$C_1$-$C_6$ alkoxy, —$C_2$-$C_6$ alkenyl, —$C_2$-$C_6$ alkynyl, -$Q^{3a}$-$NR^{10}CONR^{11}R^{11a}$, -$Q^{3a}$-$NR^{10}R^{11}$, -$Q^{3a}$-$COR^{10}$, -$Q^{3a}$-$NR^{10}COR^{11}$, -$Q^{3a}$-$NR^{10}C(O)OR^{11}$, -$Q^{3a}$-$SO_2R^{10}$, -$Q^{3a}$-$CONR^{10}R^{11}$, -$Q^{3a}$-$CO_2R^{10}$, -$Q^{3a}$-$SO_2NR^{10}R^{11}$, -$Q^{3a}$-$NR^{10}SO_2R^{11}$ and -$Q^{3a}$-$NR^{10}SO_2NR^{11}R^{11a}$, wherein $Q^{3a}$, $R^{10}$, $R^{11}$, $R^{11a}$ and $R^{12}$ are as defined above.

In addition to the non-ring substituents, or alternatively, $R^2$ may be substituted with one or more, in particular only one, ring substituents which may be selected from -$Q^{3a}$-$R^{12}$, -$Q^{3a}$-O-$Q^{3b}$-$R^{12}$, -$Q^{3a}$-S-$Q^{3b}$-$R^{12}$, -$Q^{3a}$-SO-$Q^{3b}$-$R^{12}$, -$Q^{3a}$-$NR^{10}CONR^{11}$-$Q^{3b}$-$R^{12}$, -$Q^{3a}$-$NR^{10}$-$Q^{3b}$-$R^{12}$, -$Q^{3a}$-CO-$Q^{3b}$-$R^{12}$, -$Q^{3a}$-$NR^{10}CO$-$Q^{3b}$-$R^{12}$, -$Q^{3a}$-$NR^{10}C(O)O$-$Q^{3b}$-$R^{12}$, -$Q^{3a}$-$SO_2$-$Q^{3b}$-$R^{12}$, -$Q^{3a}$-$CONR^{10}$-$Q^{3b}$-$R^{12}$, -$Q^{3a}$-$CO_2$-$Q^{3b}$-$R^{12}$, -$Q^{3a}$-$SO_2NR^{10}$-$Q^{3b}$-$R^{12}$, -$Q^{3a}$-$NR^{10}SO_2$-$Q^{3b}$-$R^{12}$, and -$Q^{3a}$-$NR^{10}SO_2NR^{11}$-$Q^{3b}$-$R^{12}$, wherein $Q^{3a}$, $Q^{3b}$, $R^{10}$, $R^{11}$ and $R^{12}$ are as defined above.

$R^2$ may be substituted with one or more substituents selected from halogen (e.g. chlorine or fluorine), cyano, oxo, hydroxyl, $C_1$-$C_6$ alkyl (e.g. propyl, isobutyl or tert butyl) or $C_1$-$C_2$ alkyl (e.g. methyl or ethyl), $C_1$-$C_6$ alkoxy (e.g. propoxy) or $C_1$-$C_2$ alkoxy (e.g. methoxy or ethoxy), -$Q^{3a}$-$C(O)NR^{10}R^{11}$, -$Q^{3a}$-$NR^{10}C(O)OR^{11}$, -$Q^{3a}$-$COR^{10}$, -$Q^{3a}$-$NR^{10}SO_2R^{11}$, -$Q^{3a}$-$R^{12}$, -$Q^{3a}$-O-$Q^{3b}$-$R^{12}$, -$Q^{3a}$-CO-$Q^{3b}$-$R^{12}$, -$Q^{3a}$-$CONR^{10}$-$Q^{3b}$-$R^{12}$, -$Q^{3a}$-$NR^{10}CO$-$Q^{3b}$-$R^{12}$, -$Q^{3a}$-$SO_2NR^{10}$-$Q^{3b}$-$R^{12}$ and -$Q^{3a}$-$NR^{10}C(O)O$-$Q^{3b}$-$R^{12}$ wherein $Q^{3a}$, $Q^{3b}$, $R^{10}$, $R^{11}$ and $R^{12}$ are as defined herein.

In particular, $Q^{3a}$ is selected from a covalent bond or optionally substituted $C_1$-$C_3$ alkylene.

In particular, $Q^{3b}$ is selected from a covalent bond or optionally substituted $C_1$-$C_3$ alkylene. For example, $Q^{3b}$ is selected from a covalent bond, $C_1$-$C_3$ alkylene or $C_1$-$C_2$ alkylene, e.g. methylene or ethylene. The alkylene may be optionally substituted with halogen, hydroxyl, thiol, cyano, amino, amido, nitro and $SF_5$.

In particular $R^{10}$, $R^{11}$ and $R^{11a}$ each independently represent hydrogen or optionally substituted $C_1$-$C_3$ alkyl (e.g. methylene or ethylene). The optional substituents for the alkyl may be selected from halogen, hydroxyl, thiol, cyano, amino, amido, nitro and $SF_5$. In particular, the optional substituents are selected from fluorine and hydroxyl.

More particularly, $R^2$ is unsubstituted or substituted with halogen, cyano, amido, $C_1$-$C_6$ alkyl or $C_1$-$C_6$ alkoxy wherein the alkyl or alkoxy is optionally substituted with fluorine.

$R^{12}$ may be an optionally substituted 3 to 10 membered (e.g. 3, 4, 5, 6, 7, 8, 9 or 10 membered) monocyclic or bicyclic heterocyclyl, heteroaryl, cycloalkyl or aryl ring. $R^{12}$ may be a 3 to 6 membered ring. Alternatively, $R^{12}$ may be a 9 or 10 membered ring.

The optional substituents may be selected from halogen, cyano, oxo, nitro, amino, hydroxy, amido, $C_1$-$C_6$ alkyl or $C_1$-$C_3$ alkyl, $C_1$-$C_6$ alkoxy or $C_1$-$C_3$ alkoxy. In particular, $R^{12}$ may be unsubstituted or substituted with halogen, amido, $C_1$-$C_3$ alkyl or $C_1$-$C_3$ alkoxy, wherein the alkyl or alkoxy is optionally substituted with halogen.

In particular, $R^{12}$ may be an optionally substituted 3 to 6 membered monocyclic heterocyclyl, heteroaryl, cycloalkyl or aryl ring.

$R^{12}$ may be selected from phenyl, pyrazinyl, pyridinyl, cyclopropyl, piperazinyl, azetidinyl, morpholinyl, pyrimidinyl, imidazolyl, pyrrolidinyl, oxazolidinyl, pyrazoyl, and imidazolidinyl, all optionally substituted.

In one embodiment, $R^2$ is unsubstituted, mono-substituted, bi-substituted or tri-substituted. In particular, $R^2$ is unsubstituted, mono-substituted or bi-substituted.

In certain instances, $R^2$ is selected from phenyl, naphthyl, naphthalenyl, tetrahydronaphthalenyl, pyridinyl, pyrazinyl, pyrimidinyl, pyridazinyl, furanyl, thiophenyl, pyrrolyl, oxazolyl, thiazolyl, pyrazolyl, tetrazolyl, indolyl, indolizinyl, isoindolyl, indolinyl, purinyl, furazanyl, imidazolyl, indazolyl, isothiazolyl, isoxazolyl, oxadiazolyl, tetrazolyl, thiadiazolyl, benzofuranyl, isobenzofuranyl, benzothiophenyl, isobenzothiophenyl, benzimidazolyl, benzothiazolyl, benzoxazolyl, napthyridinyl, pteridinyl, pyrazinyl, quinolinyl, isoquinolinyl, cinnolinyl, phthalazinyl, quinazolinyl, imidazopyridinyl, pyrazolopyridinyl, thiazolopyridinyl, isoindolinyl, triazinyl, dihydrophyridinyl, quinoxalinyl, dihydrobenzoxazinyl, dihydropyrrolopyridinyl, azetidinyl, pyrrolidinyl, piperidinyl, azepanyl, diazepanyl, dihydrofuranyl (e.g. 2,3-dihydrofuranyl, 2,5-dihydrofuranyl), dioxolanyl, morpholinyl, oxazolidinyl, oxazinanyl, indolinyl, isoindolinyl, piperazinyl, tetrahydrofuranyl, thiomorpholinyl, dihydropyranyl (e.g. 3,4-dihydropyranyl, 3,6-dihydropyranyl), homopiperazinyl, dioxanyl, hexahydropyrimidinyl, pyrazolinyl, pyrazolidinyl, 4H-quinolizinyl, quinuclidinyl, tetrahydropyranyl, tetrahydropyridinyl, tetrahydropyrimidinyl, tetrahydrothiophenyl, thiazolidinyl, benzopyranyl, tetrahydroquinolinyl, dihydrobenzoxazinyl, pyrrolopyridinyl, dihydronaphthyridinyl, dihydroisoquinolinyl and tetrahydroisoquinolinyl which is either unsubstituted or substituted with one or more substituents selected from halogen, cyano, oxo, nitro, hydroxyl, —$SR^{10}$, —$C_1$-$C_6$ alkyl, —$C_1$-$C_6$ alkoxy, —$C_2$-$C_6$ alkenyl, —$C_2$-$C_6$ alkynyl, -$Q^{3a}$-$R^{12}$, -$Q^{3a}$-O-$Q^{3b}$-$R^{12}$, -$Q^{3a}$-S-$Q^{3b}$-$R^{12}$, -$Q^{3a}$-SO-$Q^{3b}$-$R^{12}$, -$Q^{3a}$-$NR^{10}CONR^{11}R^{11a}$, -$Q^{3a}$-$NR^{10}CONR^{11}$-$Q^{3b}$-$R^{12}$, -$Q^{3a}$-$NR^{10}R^{11}$, -$Q^{3a}$-$NR^{10}$-$Q^{3b}$-$R^{12}$, -$Q^{3a}$-$COR^{10}$, -$Q^{3a}$-CO-$Q^{3b}$-

$R^{12}$, -$Q^{3a}$-$NR^{10}COR^{11}$, -$Q^{3a}$-$NR^{10}CO$-$Q^{3b}$-$R^{12}$, -$Q^{3a}$-$NR^{10}C(O)OR^{11}$, -$Q^{3a}$-$NR^{10}C(O)O$-$Q^{3b}$-$R^{12}$, -$Q^{3a}$-$SO_2R^{10}$, -$Q^{3a}$-$SO_2$-$Q^{3b}$-$R^{12}$, -$Q^{3a}$-$CONR^{10}R^{11}$, -$Q^{3a}$-$CONR^{10}$-$Q^{3b}$-$R^{12}$, -$Q^{3a}$-$CO_2R^{10}$, -$Q^{3a}$-$CO_2$-$Q^{3b}$-$R^{12}$, -$Q^{3a}$-$SO_2NR^{10}R^{11}$, -$Q^{3a}$-$SO_2NR^{10}$-$Q^{3b}$-$R^{12}$, $Q^{3a}$-$NR^{10}SO_2R^{11}$, -$Q^{3a}$-$NR^{10}SO_2$-$Q^{3b}$-$R^{12}$, -$Q^{3a}$-$NR^{10}SO_2NR^{11}R^{11a}$, and -$Q^{3a}$-$NR^{10}SO_2NR^{11}$-$Q^{3b}$-$R^{12}$; wherein $Q^{3a}$ and $Q^{3b}$ independently represent a covalent bond, optionally substituted $C_1$-$C_6$ alkylene or optionally substituted $C_2$-$C_6$ alkenylene; $R^{10}$, $R^{11}$ and $R^{12}$ each independently represent hydrogen or optionally substituted $C_1$-$C_6$ alkyl; and $R^{12}$ represents optionally substituted heterocyclyl, optionally substituted heteroaryl, optionally substituted aryl, or an optionally substituted cycloalkyl.

$R^2$ may represent a ring selected from pyrrolidinyl, phenyl, quinazolinyl, pyrazolyl, quinolinyl, pyrrolopyridinyl, oxadiazolyl, isoquinolinyl, dihydroisoquinolinyl, tetrahydroisoquinolinyl, pyridinyl, pyrimidinyl, isoxazolyl, indazolyl, thiazolyl, dihydronaphthyridinyl, piperazinyl, isoindolyl, tetrahydronaphthalenyl, benzoxazolyl, morpholinyl, tetrahydropyranyl, thiophenyl, furanyl, imidazolyl and piperidinyl, which may be unsubstituted or substituted with one or more substituents selected from halogen, cyano, oxo, nitro, hydroxyl, —$SR^{10}$, —$C_1$-$C_6$ alkyl, —$C_1$-$C_6$ alkoxy, —$C_2$-$C_6$ alkenyl, —$C_2$-$C_6$ alkynyl, -$Q^{3a}$-$R^{12}$, -$Q^{3a}$-O-$Q^{3b}$-$R^{12}$, -$Q^{3a}$-S-$Q^{3b}$-$R^{12}$, -$Q^{3a}$-SO-$Q^{3b}$-$R^{12}$, -$Q^{3a}$-$NR^{10}CONR^{11}R^{11a}$, -$Q^{3a}$-$NR^{10}CONR^{11}$-$Q^{3b}$-$R^{12}$, -$Q^{3a}$-$NR^{10}R^{11}$, -$Q^{3a}$-$NR^{10}$-$Q^{3b}$-$R^{12}$, -$Q^{3a}$-$COR^{10}$, -$Q^{3a}$-CO-$Q^{3b}$-$R^{12}$, -$Q^{3a}$-$NR^{10}COR^{11}$, -$Q^{3a}$-$NR^{10}CO$-$Q^{3b}$-$R^{12}$, -$Q^{3a}$-$NR^{10}C(O)OR^{11}$, -$Q^{3a}$-$NR^{10}C(O)O$-$Q^{3b}$-$R^{12}$, -$Q^{3a}SO_2R^{10}$, -$Q^{3a}$-$SO_2$-$Q^{3b}$-$R^{12}$, -$Q^{3a}$-$CONR^{10}R^{11}$, -$Q^{3a}$-$CONR^{10}$-$Q^{3b}$-$R^{12}$, -$Q^{3a}$-$CO_2R^{10}$, -$Q^{3a}$-$CO_2$-$Q^{3b}$-$R^{12}$, -$Q^{3a}$-$SO_2NR^{10}R^{11}$, -$Q^{3a}$-$SO_2NR^{10}$-$Q^{3b}$-$R^{12}$, -$Q^{3a}$-$NR^{10}SO_2R^{11}$, -$Q^{3a}$-$NR^{10}SO_2$-$Q^{3b}$-$R^{12}$, -$Q^{3a}$-$NR^{10}SO_2NR^{11}R^{11a}$, -$Q^{3a}$-$NR^{10}SO_2NR^{11}$-$Q^{3b}$-$R^{12}$; wherein $Q^{3a}$ and $Q^{3b}$ independently represent a covalent bond, optionally substituted $C_1$-$C_6$ alkylene or optionally substituted $C_2$-$C_6$ alkenylene; $R^{10}$, $R^{11}$ and $R^{11a}$ each independently represent hydrogen or optionally substituted $C_1$-$C_6$ alkyl; and $R^{12}$ represents optionally substituted heterocyclyl, optionally substituted heteroaryl, optionally substituted aryl, or an optionally substituted cycloalkyl.

$R^2$ may represent a ring selected from pyrrolidinyl, phenyl, quinazolinyl, pyrazolyl, quinolinyl, pyrrolopyridinyl, oxadiazolyl, isoquinolinyl, dihydroisoquinolinyl, tetrahydroisoquinolinyl, pyridinyl, pyrimidinyl, isoxazolyl, indazolyl, thiazolyl, dihydronaphthyridinyl, thiophenyl, piperazinyl, isoindolyl, tetrahydronaphthalenyl, benzoxazolyl, morpholinyl, tetrahydropyranyl, furanyl, imidazolyl and piperidinyl, which may unsubstituted or substituted with one or more (e.g. one, two or three) substituents selected from halogen, cyano, oxo, hydroxyl, $C_1$-$C_6$ alkyl, $C_1$-$C_6$ alkoxy, -$Q^{3a}$-$C(O)NR^{10}R^{11}$, -$Q^{3a}$-$NR^{10}C(O)OR^{11}$, -$Q^{3a}$-$COR^{10}$, -$Q^{3a}$-$NR^{10}SO_2R^{11}$, -$Q^{3a}$-$R^{12}$, -$Q^{3a}$-O-$Q^{3b}$-$R^{12}$, -$Q^{3a}$-CO-$Q^{3b}$-$R^{12}$, -$Q^{3a}$-$CONR^{10}$-$Q^{3b}$-$R^{12}$, -$Q^{3a}$-$NR^{10}CO$-$Q^{3b}$-$R^{12}$, -$Q^{3a}$-$SO_2NR^{10}$-$Q^{3b}$-$R^{12}$ and -$Q^{3a}$-$NR^{10}C(O)O$-$Q^{3b}$-$R^{12}$ wherein $Q^{3a}$, $Q^{3b}$, $R^{10}$, $R^{11}$ and $R^{12}$ are as defined herein.

In all cases described herein, $Q^2$ represents hydrogen, halogen, cyano, nitro, hydroxyl, —$SR^7$, —$NR^7R^8$, —$CONR^7R^8$, —$NR^7COR^8$, —$NR^7CONR^8R^{8a}$, —$COR^7$, —$C(O)OR^7$, —$SO_2R^7$, —$SO_2NR^7R^8$, —$NR^7SO_2R^8$, —$NR^7SO_2NR^7R^{8a}$, —$NR^7C(O)OR^8$, optionally substituted —$C_1$-$C_6$ alkyl, optionally substituted —$C_1$-$C_6$ alkoxy, optionally substituted —$C_2$-$C_6$ alkenyl, a covalent bond, an oxygen atom, a sulphur atom, —$OR^9$—, —SO—, —$SO_2$—, —CO—, —C(O)O—, —$C_0$-$C_3$ alkylene-$CONR^7$—$C_0$-$C_3$ alkylene, —$C_0$-$C_3$ alkylene-$NR^7$—$C_0$-$C_3$ alkylene, —$C_0$-$C_3$ alkylene-$NR^7CO$—$C_0$-$C_3$ alkylene, —$NR^7CONR^8$—, —$SO_2NR^7$—, $NR^7SO_2$—, —$NR^7SO_2NR^8$—, —$NR^7C(O)O$—, —$NR^7C(O)OR^9$—, optionally substituted $C_1$-$C_6$ alkylene, or optionally substituted —$C_2$-$C_6$ alkenylene, wherein $R^7$, $R^8$ and $R^{8a}$ each independently represent hydrogen or optionally substituted $C_1$-$C_6$ alkyl, $R^9$ represents optionally substituted $C_1$-$C_6$ alkylene.

In particular, $Q^2$ represents halogen, optionally substituted —$C_1$-$C_6$ alkyl, —$C(O)OR^7$, —$NR^7COR^8$, —$NR^7SO_2R^8$, —$NR^7R^8$, a covalent bond, —$C_0$-$C_3$ alkylene-$NR^7$—$C_0$-$C_3$ alkylene and —$C_0$-$C_3$ alkylene-$NR^7CO$—$C_0$-$C_3$ alkylene, wherein $R^7$ and $R^8$ each independently represent hydrogen or optionally substituted $C_1$-$C_6$ alkyl.

In particular $R^7$ and $R^8$ each independently represent hydrogen or $C_1$-$C_3$ alkyl. The optional substituents for the alkyl may be selected from halogen, hydroxyl, thiol, cyano, amino, amido, nitro and $SF_5$ In particular, the optionally substituents may be selected from hydroxyl and amido.

When n is 1, $R^6$ represents an optionally substituted 3 to 10 membered (e.g. 3, 4, 5, 6, 7, 8, 9 or 10 membered) monocyclic or bicyclic heterocyclyl, cycloalkyl, heteroaryl or aryl ring (when n is 0, $Q^2$ is present and $R^6$ is absent).

$R^6$ may represent an optionally substituted 5 or 6 membered monocyclic heterocyclyl, heteroaryl or aryl ring.

Alternatively, $R^6$ may represent an optionally substituted 9 or 10 membered bicyclic heterocyclyl, heteroaryl or aryl ring.

$R^6$ may be selected from cyclopropyl, cyclobutyl, cyclopentyl, cyclohexyl, cycloheptyl, cyclooctyl, decahydronaphthalenyl, phenyl, naphthyl, naphthalenyl, tetrahydronaphthalenyl, pyridinyl, pyrazinyl, pyrimidinyl, pyridazinyl, furanyl, thiophenyl, pyrrolyl, oxazolyl, thiazolyl, pyrazolyl, tetrazolyl, indolyl, indolizinyl, isoindolyl, indolinyl, purinyl, furazanyl, imidazolyl, indazolyl, isothiazolyl, isoxazolyl, oxadiazolyl, tetrazolyl, thiadiazolyl, benzofuranyl, isobenzofuranyl, benzothiophenyl, isobenzothiophenyl, benzimidazolyl, benzothiazolyl, benzoxazolyl, napthyridinyl, pteridinyl, pyrazinyl, quinolinyl, isoquinolinyl, cinnolinyl, phthalazinyl, quinazolinyl, imidazopyridinyl, pyrazolopyridinyl, thiazolopyridinyl, isoindolinyl, triazinyl, dihydrophyridinyl, quinoxalinyl, dihydrobenzoxazinyl, dihydropyrrolopyridinyl, azetidinyl, pyrrolidinyl, piperidinyl, azepanyl, diazepanyl, dihydrofuranyl (e.g. 2,3-dihydrofuranyl, 2,5-dihydrofuranyl), dioxolanyl, morpholinyl, oxazolidinyl, oxazinanyl, indolinyl, isoindolinyl, piperazinyl, tetrahydrofuranyl, thiomorpholinyl, dihydropyranyl (e.g. 3,4-dihydropyranyl, 3,6-dihydropyranyl), homopiperazinyl, dioxanyl, hexahydropyrimidinyl, pyrazolinyl, pyrazolidinyl, 4H-quinolizinyl, quinuclidinyl, tetrahydropyranyl, tetrahydropyridinyl, tetrahydropyrimidinyl, tetrahydrothiophenyl, thiazolidinyl, benzopyranyl, tetrahydroquinolinyl, dihydrobenzoxazinyl, pyrrolopyridinyl, dihydronaphthyridinyl, dihydroisoquinolinyl and tetrahydroisoquinolinyl.

In particular, $R^6$ is selected from phenyl, oxadiazolyl, pyrazolyl, piperidinyl, morpholinyl, pyridinyl, pyrrolidinyl, tetrahydropyranyl, thiophenyl tetrahydroisoquinolinyl, dihydronaphthyridinyl, isoxazolyl, isoquinolinyl, pyrimidinyl, tetrahydronaphthalenyl, thiazolyl, cyclohexyl, furanyl and imidazolyl.

When $R^2$ is phenyl and n is 1, $R^6$ may be a 5 or 6 membered cycloalkyl, heterocyclyl, heteroaryl or aryl ring.

In particular, when $R^2$ is phenyl and n is 1, $R^6$ may be selected from oxadiazolyl, pyrazolyl, piperidinyl, morpholinyl, pyridinyl, pyrrolidinyl, tetrahydropyranyl, thiophenyl, tetrahydroisoquinolinyl, piperazinyl, pyrimidinyl, phenyl, thiazolyl, cyclohexyl, furanyl and imidazolyl.

In all cases described herein, $R^6$ may be a 5 or 6 membered heterocyclyl or heteroaryl ring. $R^6$ may be selected from pyrazolyl, piperidinyl, morpholinyl, pyrrolidinyl, tetrahydropyranyl and piperazinyl.

In all cases described herein, $R^6$ may be unsubstituted or substituted with one or more substituents selected from halogen, cyano, oxo, nitro, hydroxyl, —$SR^{13}$, —$C_1$-$C_6$ alkyl, —$C_1$-$C_6$ alkoxy, $C_2$-$C_6$ alkenyl, —$C_2$-$C_6$ alkynyl, -$Q^{4a}$-$R^{15}$, -$Q^{4a}$-O-$Q^{4b}$-$R^{15}$, -$Q^{4a}$-S-$Q^{4b}$-$R^{15}$, -$Q^{4a}$-SO-$Q^{4b}$-$R^{15}$, -$Q^{4a}$-$NR^{13}CONR^{14}R^{14b}$, -$Q^{4a}$-$NR^{13}CONR^{14}$-$Q^{4b}$-$R^{15}$, -$Q^{4a}$-$NR^{13}R^{14}$, -$Q^{4a}$-$NR^{13}$-$Q^{4b}$-$R^{15}$—, -$Q^{4a}COR^{13}$, -$Q^{4a}$-CO-$Q^{4b}$-$R^{15}$—, -$Q^{4a}$-$NR^{13}COR^{14}$, -$Q^{4a}$-$NR^{14}CO$-$Q^{4b}$-$R^{15}$, -$Q^{4a}$-$NR^{13}C(O)OR^{14}$, -$Q^{4a}$-$NR^{13}C(O)O$-$Q^{4b}$-$R^{14}$—, -$Q^{4a}$-$SO_2R^{13}$, -$Q^{4a}$-$SO_2$-$Q^{4b}$-$R^{15}$, $^-Q^{4a}$-$CONR^{13}R^{14}$, $^-Q^{4a}$-$CONR^{13}$-$Q^{4b}$-$R^{15}$, -$Q^{4a}$-$CO_2R^{13}$, -$Q^{4a}$-$CO_2$-$Q^{4b}$-$R^{15}$, -$Q^{4a}$-$SO_2NR^{13}R^{14}$, -$Q^{4a}$-$SO_2NR^{13}$-$Q^{4b}$-$R^{15}$, -$Q^{4a}$-$NR^{13}SO_2R^{14}$, -$Q^{4a}$-$NR^{13}SO_2$-$Q^{4b}$-$R^{15}$, -$Q^{4a}$-$NR^{13}SO_2NR^{14}R^{14b}$ and -$Q^{4a}$-$NR^{13}SO_2NR^{14}$-$Q^{4b}$-$R^{15}$.

$Q^{4a}$ and $Q^{4b}$ independently represent a covalent bond, optionally substituted $C_1$-$C_6$ alkylene or optionally substituted $C_2$-$C_6$ alkenylene. For example, $Q^{4a}$ and $Q^{4b}$ may independently represent a covalent bond, $C_1$-$C_6$ alkylene, $C_1$-$C_4$ alkylene, $C_1$-$C_2$ alkylene, $C_2$-$C_6$ alkenylene or $C_2$-$C_4$ alkenylene. The alkylene and alkenylene may be substituted with halogen, hydroxyl, thiol, cyano, amino, amido, nitro and $SF_5$.

$R^{13}$, $R^{14}$ and $R^{14a}$ each independently represent hydrogen or optionally substituted $C_1$-$C_6$ alkyl. For example, $R^{13}$, $R^{14}$ and $R^{14a}$ may each independently represent hydrogen, $C_1$-$C_6$ alkyl, $C_1$-$C_4$ alkyl or $C_1$-$C_2$ alkyl. The alkyl may be optionally substituted with halogen, hydroxyl, thiol, cyano, amino, amido, nitro and $SF_5$.

$R^{15}$ represents optionally substituted heterocyclyl, optionally substituted heteroaryl, optionally substituted aryl, or an optionally substituted cycloalkyl.

In particular, $R^6$ may be substituted with one or more substituents selected from halogen (e.g. chlorine or fluorine), cyano, oxo, hydroxyl, $C_1$-$C_6$ alkyl (e.g. propyl, isobutyl or tert butyl) or $C_1$-$C_2$ alkyl (e.g. methyl or ethyl), $C_1$-$C_6$ alkoxy (e.g. propoxy) or $C_1$-$C_2$ alkoxy (e.g. methoxy or ethoxy), -$Q^{4a}$-$CONR^{13}R^{14}$, -$Q^{4a}$-$COR^{13}$ and -$Q^{4a}R^{15}$ wherein $Q^{4a}$, $R^{13}$, $R^{14}$ and $R^{15}$ are as defined herein.

In particular, $Q^{4a}$ is a covalent bond.

In particular $R^{13}$, $R^{14}$ and $R^{14a}$ each independently represent hydrogen or optionally substituted $C_1$-$C_3$ alkyl. The optional substituents for the alkyl may be selected from halogen, hydroxyl, thiol, cyano, amino, nitro and $SF_5$.

$R^{15}$ may be an optionally substituted 3 to 10 membered (e.g. 3, 4, 5, 6, 7, 8, 9 or 10 membered) monocyclic or bicyclic heterocyclyl, heteroaryl, cycloalkyl or aryl ring. $R^{15}$ may be a 3 to 6 membered ring. Alternatively, $R^{15}$ may be a 9 or 10 membered ring.

The optional substituents may be selected from halogen, cyano, oxo, nitro, amino, hydroxy, amido, $C_1$-$C_6$ alkyl or $C_1$-$C_3$ alkyl, $C_1$-$C_6$ alkoxy or $C_1$-$C_3$ alkoxy. In particular, $R^{12}$ may be unsubstituted or substituted with halogen, amido, $C_1$-$C_3$ alkyl or $C_1$-$C_3$ alkoxy, wherein the alkyl or alkoxy is optionally substituted with halogen.

In particular, $R^{15}$ may be an optionally substituted 3 to 6 membered monocyclic heterocyclyl, heteroaryl, cycloalkyl or aryl ring.

$R^{12}$ may be unsubstituted or substituted phenyl.

In one embodiment, $R^6$ is unsubstituted, mono-substituted, bi-substituted or tri-substituted. In particular $R^6$ is unsubstituted, mono-substituted or bi-substituted.

In certain instances, $R^6$ is selected from cyclopropyl, cyclobutyl, cyclopentyl, cyclohexyl, cycloheptyl, cyclooctyl, decahydronaphthalenyl, phenyl, naphthyl, naphthalenyl, tetrahydronaphthalenyl, pyridinyl, pyrazinyl, pyrimidinyl, pyridazinyl, furanyl, thiophenyl, pyrrolyl, oxazolyl, thiazolyl, pyrazolyl, tetrazolyl, indolyl, indolizinyl, isoindolyl, indolinyl, purinyl, furazanyl, imidazolyl, indazolyl, isothiazolyl, isoxazolyl, oxadiazolyl, tetrazolyl, thiadiazolyl, benzofuranyl, isobenzofuranyl, benzothiophenyl, isobenzothiophenyl, benzimidazolyl, benzothiazolyl, benzoxazolyl, napthyridinyl, pteridinyl, pyrazinyl, quinolinyl, isoquinolinyl, cinnolinyl, phthalazinyl, quinazolinyl, imidazopyridinyl, pyrazolopyridinyl, thiazolopyridinyl, isoindolinyl, triazinyl, dihydrophyridinyl, quinoxalinyl, dihydrobenzoxazinyl, dihydropyrrolopyridinyl, azetidinyl, pyrrolidinyl, piperidinyl, azepanyl, diazepanyl, dihydrofuranyl (e.g. 2,3-dihydrofuranyl, 2,5-dihydrofuranyl), dioxolanyl, morpholinyl, oxazolidinyl, oxazinanyl, indolinyl, isoindolinyl, piperazinyl, tetrahydrofuranyl, thiomorpholinyl, dihydropyranyl (e.g. 3,4-dihydropyranyl, 3,6-dihydropyranyl), homopiperazinyl, dioxanyl, hexahydropyrimidinyl, pyrazolinyl, pyrazolidinyl, 4H-quinolizinyl, quinuclidinyl, tetrahydropyranyl, tetrahydropyridinyl, tetrahydropyrimidinyl, tetrahydrothiophenyl, thiazolidinyl, benzopyranyl, tetrahydroquinolinyl, dihydrobenzoxazinyl, pyrrolopyridinyl, dihydronaphthyridinyl, dihydroisoquinolinyl and tetrahydroisoquinolinyl which is either unsubstituted or substituted with one or more substituents selected from halogen, cyano, oxo, nitro, hydroxyl, —$SR^{13}$, —$C_1$-$C_6$ alkyl, —$C_1$-$C_6$ alkoxy, —$C_2$-$C_6$ alkenyl, —$C_2$-$C_6$ alkynyl, -$Q^{4a}$-$R^{15}$, -$Q^{4a}$-O-$Q^{4b}$-$R^{15}$, -$Q^{4a}$-S-$Q^{4b}$-$R^{15}$, -$Q^{4a}$-SO-$Q^{4b}$-$R^{15}$, -$Q^{4a}$-$NR^{13}CONR^{14}R^{14b}$, -$Q^{4a}$-$NR^{13}CONR^{14}$-$Q^{4b}$-$R^{15}$, -$Q^{4a}$-$NR^{13}R^{14}$, -$Q^{4a}$-$NR^{13}$-$Q^{4b}$-$R^{15}$—, -$Q^{4a}$-$COR^{13}$, -$Q^{4a}$-CO-$Q^{4b}$-$R^{15}$—, -$Q^{4a}$-$NR^{13}COR^{14}$, -$Q^{4a}$-$NR^{13}CO$-$Q^{4b}$-$R^{15}$, -$Q^{4a}$-$NR^{13}C(O)OR^{14}$, -$Q^{4a}$-$NR^{13}C(O)O$-$Q^{4b}$-$R^{14}$—, -$Q^{4a}$-$SO_2R^{13}$, -$Q^{4a}$-$SO_2$-$Q^{4b}$-$R^{15}$, $^-Q^{4a}$-$CONR^{13}R^{14}$, $^-Q^{4a}$-$CONR^{13}$-$Q^{4b}$-$R^{15}$, -$Q^{4a}$-$CO_2R^{13}$, -$Q^{4a}$-$CO_2$-$Q^{4b}$-$R^{15}$, -$Q^{4a}$-$SO_2NR^{13}R^{14}$, -$Q^{4a}$-$SO_2NR^{13}$-$Q^{4b}$-$R^{15}$, -$Q^{4a}$-$NR^{13}SO_2R^{14}$, -$Q^{4a}$-$NR^{13}SO_2$-$Q^{4b}$-$R^{15}$, -$Q^{4a}$-$NR^{13}SO_2NR^{14}R^{14b}$ and -$Q^{4a}$-$NR^{13}SO_2NR^{14}$-$Q^{4b}$-$R^{15}$; wherein $Q^{4a}$ and $Q^{4b}$ independently represent a covalent bond optionally substituted $C_1$-$C_6$ alkylene or optionally substituted $C_2$-$C_6$ alkenylene; $R^{13}$, $R^{14}$ and $R^{14a}$ each independently represent hydrogen or optionally substituted $C_1$-$C_6$ alkyl; and $R^{15}$ represents optionally substituted heterocyclyl, optionally substituted heteroaryl, optionally substituted aryl, or an optionally substituted cycloalkyl.

$R^6$ may represent a ring selected from phenyl, oxadiazolyl, pyrazolyl, piperidinyl, morpholinyl, pyridinyl, pyrrolidinyl, tetrahydropyranyl, thiophenyl, tetrahydroisoquinolinyl, dihydronaphthyridinyl, isoxazolyl, isoquinolinyl, pyrimidinyl, tetrahydronaphthalenyl, thiazolyl, cyclohexyl, furanyl and imidazolyl, which may be unsubstituted or substituted with one or more substituents selected from halogen, cyano, oxo, nitro, hydroxyl, —$SR^{13}$, —$C_1$-$C_6$ alkyl, —$C_1$-$C_6$ alkoxy, —$C_2$-$C_6$ alkenyl, —$C_2$-$C_6$ alkynyl, -$Q^{4a}$-$R^{15}$, -$Q^{4a}$-O-$Q^{4b}$-$R^{15}$, -$Q^{4a}$-S-$Q^{4b}$-$R^{15}$, -$Q^{4a}$-SO-$Q^{4b}$-$R^{15}$, -$Q^{4a}$-$NR^{13}CONR^{14}R^{14b}$, -$Q^{4a}$-$NR^{13}CONR^{14}$-$Q^{4b}$-$R^{15}$, -$Q^{4a}$-$NR^{13}R^{14}$, -$Q^{4a}$-$NR^{13}$-$Q^{4b}$-$R^{15}$, -$Q^{4a}$-$COR^{13}$, -$Q^{4a}$-CO-$Q^{4b}$-$R^{13}$—, -$Q^{4a}$-$NR^{13}COR^{14}$, -$Q^{4a}$-$NR^{13}CO$-$Q^{4b}$-$R^{15}$, -$Q^{4a}$-$NR^{13}C(O)OR^{14}$, -$Q^{4a}$-$NR^{13}C(O)O$-$Q^{4b}$-$R^{14}$—, -$Q^{4a}$-$SO_2R^{13}$, -$Q^{4a}$-$SO_2$-$Q^{4b}$-$R^{15}$, $^-Q^{4a}$-$CONR^{13}R^{14}$, $^-Q^{4a}$-$CONR^{13}$-$Q^{4b}$-$R^{15}$, -$Q^{4a}$-$CO_2R^{13}$, -$Q^{4a}$-$CO_2$-$Q^{4b}$-$R^{15}$, -$Q^{4a}$-$SO_2NR^{13}R^{14}$, -$Q^{4a}SO_2NR^{13}$-$Q^{4b}$-$R^{15}$, -$Q^{4a}NR^{13}SO_2R^{14}$, -$Q^{4a}$-$NR^{13}SO_2$-$Q^{4b}$-$R^{15}$, -$Q^{4a}$-$NR^{13}SO_2NR^{14}R^{14b}$ and -$Q^{4a}$-$NR^{13}SO_2NR^{14}$-$Q^{4b}$-$R^{15}$; wherein $Q^{4a}$ and $Q^{4b}$ independently represent a covalent bond optionally substituted $C_1$-$C_6$ alkylene or optionally substituted $C_2$-$C_6$ alkenylene; $R^{13}$, $R^{14}$ and $R^{14a}$ each independently represent hydrogen or optionally substituted $C_1$-$C_6$ alkyl; and $R^{15}$ represents optionally substituted heterocyclyl, optionally substituted heteroaryl, optionally substituted aryl, or an optionally substituted cycloalkyl.

$R^6$ may represent a ring selected from phenyl, oxadiazolyl, pyrazolyl, piperidinyl, morpholinyl, pyridinyl, pyrrolidinyl, tetrahydropyranyl, thiophenyl, tetrahydroisoquinolinyl, dihydronaphthyridinyl, isoxazolyl, isoquinolinyl, pyrimidinyl, tetrahydronaphthalenyl, thiazolyl, cyclohexyl, furanyl and imidazolyl, which may unsubstituted or substituted with one or more (e.g. one, two or three) substituents selected from halogen, cyano, oxo, hydroxyl, $C_1$-$C_6$ alkyl, $C_1$-$C_6$ alkoxy, -$Q^{4a}$-CONR$^{13}$R$^{14}$, -$Q^{4a}$-COR$^{13}$ and -$Q^{4a}$-R$^{15}$ wherein $Q^{4a}$ represents a covalent bond. $R^{13}$ and $R^{14}$ are each independently selected from hydrogen and optionally substituted $C_1$-$C_3$ alkyl and $R^{15}$ represents an optionally substituted 3 to 10 membered monocyclic or bicyclic heterocyclyl, heteroaryl, cycloalkyl or aryl ring.

The present invention further relates to compounds of formula I, or a pharmaceutically acceptable salt thereof, wherein:

$R^{1a}$, $R^{1b}$, $R^{1c}$ and $R^{1d}$ each independently represent hydrogen or optionally substituted $C_1$-$C_6$ alkyl;

$X^1$ and $X^3$ each independently represent C-$Q^1$-$R^2$ or C-$Q^2$-($R^6$)$_n$ and $X^2$ and $X^4$ are either both N or both CH, wherein one of $X^1$ and $X^3$ represents C-$Q^1$-$R^2$;

n is 0 or 1; and $Q^1$, $Q^2$, $R^2$ and $R^6$ are as defined herein.

In particular, $X^1$ represents C-$Q^1$-$R^2$, $X^3$ represents C-$Q^2$-($R^6$)$_n$ and $X^2$ and $X^4$ are either both N or both CH.

The present invention further relates to compounds of formula I, or a pharmaceutically acceptable salt thereof, wherein:

$R^{1a}$, $R^{1b}$, $R^{1c}$ and $R^{1d}$ each independently represent hydrogen;

$X^1$ and $X^3$ each independently represent C-$Q^1$-$R^2$ or C-$Q^2$-($R^6$)$_n$ and $X^2$ and $X^4$ are either both N or both CH, wherein one of $X^1$ and $X^3$ represents C-$Q^1$-$R^2$;

$Q^1$ represents a covalent bond;

$R^2$ is an optionally substituted 5 to 10 membered monocyclic or bicyclic heterocyclyl, heteroaryl or aryl ring;

n is 0 or 1; and $Q^2$ and $R^6$ are as defined herein.

In particular, $X^1$ represents C-$Q^1$-$R^2$, $X^3$ represents C-$Q^2$-($R^6$)$_n$ and $X^2$ and $X^4$ are either both N or both CH.

$R^2$ may be unsubstituted or substituted with a non-ring substituent.

The present invention further relates to compounds of formula I, or a pharmaceutical acceptable salt thereof, wherein:

$R^{1a}$, $R^{1b}$, $R^{1c}$ and $R^{1d}$ each independently represent hydrogen;

$X^1$ represents C-$Q^1$-$R^2$, $X^3$ represents C-$Q^2$-($R^6$)$_n$ and $X^2$ and $X^4$ are either both N or both CH;

$Q^1$ represents a covalent bond;

$R^2$ is an optionally substituted 5 to 10 membered monocyclic or bicyclic heterocyclyl, heteroaryl or aryl ring selected from phenyl, benzoxazolyl and piperidinyl;

n is 0 or 1;

$Q^2$ and $R^6$ are as defined herein.

$R^2$ may be unsubstituted or substituted with a non-ring substituent.

In particular, $Q^2$ represents hydrogen, halogen, —NRC(O)R$^7$, a covalent bond, —$C_0$-$C_3$—NH— or —NHC(O)—, wherein R represents hydrogen or $C_1$-$C_6$ alkyl optionally substituted with halogen, hydroxyl, thiol, cyano, amino, nitro or SF$_5$, in particular amino.

In particular, $R^6$ is a 5 or 6 membered heterocyclyl or heteroaryl ring. $R^6$ may be selected from pyrazolyl, piperidinyl, morpholinyl, pyrrolidinyl, tetrahydropyranyl and piperazinyl.

Examples of novel compounds of formula I include:
5-cyano-2-(2-cyanoisoindolin-4-yl)benzamide;
5-chloro-2-(2-cyanoisoindolin-4-yl)benzamide;
2-(2-cyanoisoindolin-4-yl)-5-methylbenzamide;
4-(2-(azetidine-1-carbonyl)-4-cyanophenyl)isoindoline-2-carbonitrile;
6-((1-methyl-1H-pyrazol-4-yl)amino)-4-phenylisoindoline-2-carbonitrile;
4-phenylisoindoline-2-carbonitrile;
4-(1-methyl-1H-pyrazol-4-yl)isoindoline-2-carbonitrile;
4-(quinolin-3-yl)isoindoline-2-carbonitrile;
4-(1H-pyrrolo[2,3-b]pyridin-5-yl)isoindoline-2-carbonitrile;
4-(1-methyl-1,2,3,6-tetrahydropyridin-4-yl)isoindoline-2-carbonitrile;
4-(2-methyl-2H-indazol-5-yl)isoindoline-2-carbonitrile;
4-(o-tolyl)isoindoline-2-carbonitrile;
4-(4-cyanophenyl)isoindoline-2-carbonitrile;
4-(1-methylpiperidin-4-yl)isoindoline-2-carbonitrile;
N-benzyl-3-(6-cyano-6,7-dihydro-5H-pyrrolo[3,4-b]pyridin-4-yl)benzamide;
4-(4-chlorophenyl)-5,7-dihydro-6H-pyrrolo[3,4-b]pyridine-6-carbonitrile;
4-(4-methoxyphenyl)-5,7-dihydro-6H-pyrrolo[3,4-b]pyridine-6-carbonitrile;
4-(3-chlorophenyl)-5,7-dihydro-6H-pyrrolo[3,4-b]pyridine-6-carbonitrile;
4-phenyl-1,3-dihydro-2H-pyrrolo[3,4-d]pyridine-2-carbonitrile;
6-(5-methyl-1,2,4-oxadiazol-3-yl)-4-phenylisoindoline-2-carbonitrile;
4-(quinazolin-2-ylamino)isoindoline-2-carbonitrile;
3-((2-cyanoisoindolin-4-yl)amino)-N-methylisoquinoline-6-carboxamide;
N-(2-cyano-7-phenylisoindolin-5-yl)nicotinamide;
2-(6-acetamido-2-cyanoisoindolin-4-yl)benzamide;
(R)—N-(2-cyano-7-(3-fluorophenyl)isoindolin-5-yl)-1-methylpiperidine-3-carboxamide;
(R)—N-(2-cyano-7-(4-cyanophenyl)isoindolin-5-yl)-1-methylpiperidine-3-carboxamide;
(R)—N-(2-cyano-7-(3-cyanophenyl)isoindolin-5-yl)-1-methylpiperidine-3-carboxamide;
(R)—N-(2-cyano-7-(4-fluorophenyl)isoindolin-5-yl)-1-methylpiperidine-3-carboxamide;
(R)—N-(2-cyano-7-(4-(methylcarbamoyl)phenyl)isoindolin-5-yl)-1-methylpiperidine-3-carboxamide;
(R)—N-(2-cyano-7-(3-(methylcarbamoyl)phenyl)isoindolin-5-yl)-1-methylpiperidine-3-carboxamide;
(R)—N-(2-cyano-7-(3-methoxyphenyl)isoindolin-5-yl)-1-methylpiperidine-3-carboxamide;
(R)—N-(2-cyano-7-(4-methoxyphenyl)isoindolin-5-yl)-1-methylpiperidine-3-carboxamide;
(R)—N-(7-(4-chlorophenyl)-2-cyanoisoindolin-5-yl)-1-methylpiperidine-3-carboxamide;
(R)—N-(7-(3-chlorophenyl)-2-cyanoisoindolin-5-yl)-1-methylpiperidine-3-carboxamide;
(R)—N-(2-cyano-7-(2-methylbenzo[d]oxazol-6-yl)isoindolin-5-yl)-1-methylpiperidine-3-carboxamide;
N-(2-cyano-7-phenylisoindolin-5-yl)-1-methylpiperidine-3-carboxamide;
(S)—N-(2-cyano-7-phenylisoindolin-5-yl)-1-methylpiperidine-3-carboxamide;

(R)—N-(2-cyano-7-phenylisoindolin-5-yl)-1-methylpiperidine-3-carboxamide;
N-(2-cyano-7-phenylisoindolin-5-yl)-1-methyl-1H-pyrazole-5-carboxamide;
4-benzyl-N-(2-cyano-7-phenylisoindolin-5-yl)morpholine-2-carboxamide;
N-(2-cyano-7-phenylisoindolin-5-yl)-3-(pyridin-3-yl)propanamide;
N-(2-cyano-7-phenylisoindolin-5-yl)-5-oxopyrrolidine-3-carboxamide;
N-(2-cyano-7-phenylisoindolin-5-yl)-1-methylpyrrolidine-3-carboxamide;
N-(2-cyano-7-phenylisoindolin-5-yl)-1-methyl-6-oxopiperidine-3-carboxamide;
1-acetyl-N-(2-cyano-7-phenylisoindolin-5-yl)piperidine-3-carboxamide;
N1-(2-cyano-7-phenylisoindolin-5-yl)-N4,N4-dimethylsuccinamide;
1-acetyl-N-(2-cyano-7-phenylisoindolin-5-yl)piperidine-4-carboxamide;
N-(2-cyano-7-phenylisoindolin-5-yl)-1-methylpiperidine-4-carboxamide;
N-(2-cyano-7-phenylisoindolin-5-yl)-2-(dimethylamino)acetamide;
N-(2-cyano-7-phenylisoindolin-5-yl)tetrahydro-2H-pyran-4-carboxamide;
N-(2-cyano-7-phenylisoindolin-5-yl)tetrahydro-2H-thiopyran-4-carboxamide 1,1-dioxide;
N-(2-cyano-7-phenylisoindolin-5-yl)-1-methyl-5-oxopyrrolidine-3-carboxamide;
N-(2-cyano-7-phenylisoindolin-5-yl)-4-methylmorpholine-2-carboxamide;
N-(2-cyano-7-phenylisoindolin-5-yl)-4-ethylmorpholine-2-carboxamide;
N-(2-cyano-7-phenylisoindolin-5-yl)-4-isopropylmorpholine-2-carboxamide;
N-(7-(2-carbamoylphenyl)-2-cyanoisoindolin-5-yl)-1-methylpiperidine-3-carboxamide;
N-(2-cyano-7-phenylisoindolin-5-yl)acetamide;
N-(2-cyano-7-phenylisoindolin-5-yl)-N-methylacetamide;
N-(2-cyano-7-phenylisoindolin-5-yl)-N,1-dimethylpiperidine-3-carboxamide;
N-(2-cyano-7-phenylisoindolin-5-yl)-4-methylpiperazine-1-carboxamide;
N-(2-cyano-7-phenylisoindolin-5-yl)methanesulfonamide;
N-(2-cyano-7-phenylisoindolin-5-yl)piperidine-3-carboxamide;
N-(2-cyano-7-phenylisoindolin-5-yl)piperidine-4-carboxamide;
6-(((1-methylpiperidin-3-yl)methyl)amino)-4-phenylisoindoline-2-carbonitrile;
4-(2-chloro-4-cyanophenyl)isoindoline-2-carbonitrile;
4-(4-cyano-2-methylphenyl)isoindoline-2-carbonitrile;
4-(4-cyano-2,6-dimethylphenyl)isoindoline-2-carbonitrile;
3-oxo-[4,4'-biisoindoline]-2'-carbonitrile;
4-(1-oxo-1,2,3,4-tetrahydroisoquinolin-8-yl)isoindoline-2-carbonitrile;
(R)-4-(2-(1-hydroxyethyl)phenyl)isoindoline-2-carbonitrile;
(S)-4-(2-(1-hydroxyethyl)phenyl)isoindoline-2-carbonitrile;
4-(2-cyanoisoindolin-4-yl)isophthalonitrile;
N-benzyl-3-(2-cyanoisoindolin-4-yl)benzamide;
3-(2-cyanoisoindolin-4-yl)-N-(1-phenylethyl)benzamide;
3-(2-cyanoisoindolin-4-yl)-N-phenylbenzamide;
(R)-3-(2-cyanoisoindolin-4-yl)-N-(1-phenylethyl)benzamide;
N-(2-aminoethyl)-2-(2-cyanoisoindolin-4-yl)benzamide;
4-(2-(piperazine-1-carbonyl)phenyl)isoindoline-2-carbonitrile;
N-benzyl-4-(2-cyanoisoindolin-4-yl)picolinamide;
N-(2-cyanoisoindolin-4-yl)-3-(cyclopropanecarboxamido)benzamide;
N-(2-cyanoisoindolin-4-yl)-4-(pyridin-3-yl)benzamide;
N-(2-cyanoisoindolin-4-yl)-4-(pyridin-4-yl)benzamide;
N-(2-cyanoisoindolin-4-yl)-3-(o-tolyl)-1H-pyrazole-5-carboxamide;
N-(2-cyanoisoindolin-4-yl)-2-phenylthiazole-4-carboxamide;
N-(2-cyanoisoindolin-4-yl)-5-methoxy-1H-pyrrolo[2,3-c]pyridine-2-carboxamide;
N-(2-cyanoisoindolin-4-yl)-5-(pyrazin-2-yl)-1H-pyrazole-3-carboxamide;
1-benzyl-N-(2-cyanoisoindolin-4-yl)-6-oxo-1,6-dihydropyridine-3-carboxamide
N-(2-cyanoisoindolin-4-yl)-4-(methoxymethyl)benzamide;
methyl (3-((2-cyanoisoindolin-4-yl)carbamoyl)phenyl)carbamate;
3-benzamido-N-(2-cyanoisoindolin-4-yl)benzamide;
benzyl (4-((2-cyanoisoindolin-4-yl)carbamoyl)benzyl)carbamate;
N-(2-cyanoisoindolin-4-yl)-4-(N-phenylsulfamoyl)benzamide;
N-(2-cyanoisoindolin-4-yl)-5-morpholinothiophene-2-carboxamide;
N-(2-cyanoisoindolin-5-yl)-1-methylpyrrolidine-3-carboxamide;
N-benzyl-2-cyanoisoindoline-4-carboxamide;
N-(2-cyano-4-phenylisoindolin-5-yl)acetamide;
1-(1-methyl-1H-pyrazol-4-yl)-4-phenyl-5,7-dihydro-6H-pyrrolo[3,4-d]pyridazine-6-carbonitrile;
methyl 2-cyano-7-phenylisoindoline-5-carboxylate;
4-(4-(2,4-difluorophenyl)piperazin-1-yl)-5,7-dihydro-6H-pyrrolo[3,4-d]pyrimidine-6-carbonitrile;
4-(isoindolin-2-yl)-5,7-dihydro-6H-pyrrolo[3,4-d]pyrimidine-6-carbonitrile;
4-(4-(pyridin-3-yloxy)piperidin-1-yl)-5,7-dihydro-6H-pyrrolo[3,4-d]pyrimidine-6-carbonitrile;
4-(4-(3-methoxyphenoxy)piperidin-1-yl)-5,7-dihydro-6H-pyrrolo[3,4-d]pyrimidine-6-carbonitrile;
2-((1-(6-cyano-6,7-dihydro-5H-pyrrolo[3,4-d]pyrimidin-4-yl)piperidin-4-yl)oxy)benzamide;
N-(6-cyano-4-phenyl-6,7-dihydro-5H-pyrrolo[3,4-d]pyrimidin-2-yl)acetamide;
N-(6-cyano-4-(3-cyanophenyl)-6,7-dihydro-5H-pyrrolo[3,4-d]pyrimidin-2-yl)acetamide;
N-(6-cyano-4-(3-(trifluoromethoxy)phenyl)-6,7-dihydro-5H-pyrrolo[3,4-d]pyrimidin-2-yl)acetamide;
N-(6-cyano-4-(1-methyl-1H-pyrazol-4-yl)-6,7-dihydro-5H-pyrrolo[3,4-d]pyrimidin-2-yl)acetamide;
N-(3-(2-acetamido-6-cyano-6,7-dihydro-5H-pyrrolo[3,4-d]pyrimidin-4-yl)phenyl)acetamide;
N-(6-cyano-4-(3-(methylsulfonamido)phenyl)-6,7-dihydro-5H-pyrrolo[3,4-d]pyrimidin-2-yl)acetamide;
2-(((1r,4r)-4-hydroxycyclohexyl)amino)-4-phenyl-5,7-dihydro-6H-pyrrolo[3,4-d]pyrimidine-6-carbonitrile;
4-phenyl-2-(((tetrahydro-2H-pyran-4-yl)methyl)amino)-5,7-dihydro-6H-pyrrolo[3,4-d]pyrimidine-6-carbonitrile;
2-((1-methyl-1H-pyrazol-4-yl)amino)-4-phenyl-5,7-dihydro-6H-pyrrolo[3,4-d]pyrimidine-6-carbonitrile;
4-phenyl-2-((pyrimidin-2-ylmethyl)amino)-5,7-dihydro-6H-pyrrolo[3,4-d]pyrimidine-6-carbonitrile;
4-phenyl-2-((2-(pyridin-2-yl)ethyl)amino)-5,7-dihydro-6H-pyrrolo[3,4-d]pyrimidine-6-carbonitrile;

4-phenyl-2-((1,2,3,4-tetrahydronaphthalen-1-yl)amino)-5,7-dihydro-6H-pyrrolo[3,4-d]pyrimidine-6-carbonitrile;
4-phenyl-2-(phenylamino)-5,7-dihydro-6H-pyrrolo[3,4-d]pyrimidine-6-carbonitrile;
4-phenyl-2-((pyridin-2-ylmethyl)amino)-5,7-dihydro-6H-pyrrolo[3,4-d]pyrimidine-6-carbonitrile;
4-phenyl-2-((pyridin-3-ylmethyl)amino)-5,7-dihydro-6H-pyrrolo[3,4-d]pyrimidine-6-carbonitrile;
4-phenyl-2-((thiazol-5-ylmethyl)amino)-5,7-dihydro-6H-pyrrolo[3,4-d]pyrimidine-6-carbonitrile;
2-((2-hydroxyethyl)amino)-4-phenyl-5,7-dihydro-6H-pyrrolo[3,4-d]pyrimidine-6-carbonitrile;
2-((furan-2-ylmethyl)amino)-4-phenyl-5,7-dihydro-6H-pyrrolo[3,4-d]pyrimidine-6-carbonitrile;
2-((3-(1H-imidazol-1-yl)propyl)amino)-4-phenyl-5,7-dihydro-6H-pyrrolo[3,4-d]pyrimidine-6-carbonitrile;
2-(6-cyano-2-(ethylamino)-6,7-dihydro-5H-pyrrolo[3,4-d]pyrimidin-4-yl)benzamide;
2-(((4-methylmorpholin-2-yl)methyl)amino)-4-phenyl-5,7-dihydro-6H-pyrrolo[3,4-d]pyrimidine-6-carbonitrile;
2-(((1-methylpiperidin-3-yl)methyl)amino)-4-phenyl-5,7-dihydro-6H-pyrrolo[3,4-d]pyrimidine-6-carbonitrile;
2-(((1-methyl-1H-pyrazol-5-yl)methyl)amino)-4-phenyl-5,7-dihydro-6H-pyrrolo[3,4-d]pyrimidine-6-carbonitrile;
2-(((1-methylpyrrolidin-3-yl)methyl)amino)-4-phenyl-5,7-dihydro-6H-pyrrolo[3,4-d]pyrimidine-6-carbonitrile;
N-(6-cyano-4-(3,4-dihydroisoquinolin-2(1H)-yl)-6,7-dihydro-5H-pyrrolo[3,4-d]pyrimidin-2-yl)acetamide;
N-(6-cyano-4-phenyl-6,7-dihydro-5H-pyrrolo[3,4-d]pyrimidin-2-yl)-5-oxopyrrolidine-3-carboxamide;
2-(4-methoxyphenyl)-4-(pyrrolidin-1-yl)-5,7-dihydro-6H-pyrrolo[3,4-d]pyrimidine-6-carbonitrile;
1-(6-cyano-2-phenyl-6,7-dihydro-5H-pyrrolo[3,4-d]pyrimidin-4-yl)pyrrolidine-2-carboxamide;
2-((6-cyano-2-phenyl-6,7-dihydro-5H-pyrrolo[3,4-d]pyrimidin-4-yl)amino)acetamide;
1-(6-cyano-2-phenyl-6,7-dihydro-5H-pyrrolo[3,4-d]pyrimidin-4-yl)-N-methylpyrrolidine-2-carboxamide;
2-(5-methyl-1H-pyrazol-4-yl)-4-(pyrrolidin-1-yl)-5,7-dihydro-6H-pyrrolo[3,4-d]pyrimidine-6-carbonitrile;
2-(2-methoxyphenyl)-4-(pyrrolidin-1-yl)-5,7-dihydro-6H-pyrrolo[3,4-d]pyrimidine-6-carbonitrile;
2-(3-methoxyphenyl)-4-(pyrrolidin-1-yl)-5,7-dihydro-6H-pyrrolo[3,4-d]pyrimidine-6-carbonitrile;
2-(pyridin-3-yl)-4-(pyrrolidin-1-yl)-5,7-dihydro-6H-pyrrolo[3,4-d]pyrimidine-6-carbonitrile;
2-(6-cyano-4-(3,4-dihydroisoquinolin-2(1H)-yl)-6,7-dihydro-5H-pyrrolo[3,4-d]pyrimidin-2-yl)benzamide;
4-(3,4-dihydroisoquinolin-2(1H)-yl)-2-(5-methyl-1H-pyrazol-4-yl)-5,7-dihydro-6H-pyrrolo[3,4-d]pyrimidine-6-carbonitrile;
4-(3,4-dihydroisoquinolin-2(1H)-yl)-2-(2-methoxyphenyl)-5,7-dihydro-6H-pyrrolo[3,4-d]pyrimidine-6-carbonitrile;
2-(3-cyanophenyl)-4-(3,4-dihydroisoquinolin-2(1H)-yl)-5,7-dihydro-6H-pyrrolo[3,4-d]pyrimidine-6-carbonitrile;
4-(3,4-dihydroisoquinolin-2(1H)-yl)-2-(1-methyl-1H-pyrazol-4-yl)-5,7-dihydro-6H-pyrrolo[3,4-d]pyrimidine-6-carbonitrile;
1-(6-cyano-2-(o-tolyl)-6,7-dihydro-5H-pyrrolo[3,4-d]pyrimidin-4-yl)pyrrolidine-2-carboxamide;
1-(6-cyano-2-(5-methyl-1H-pyrazol-4-yl)-6,7-dihydro-5H-pyrrolo[3,4-d]pyrimidin-4-yl)pyrrolidine-2-carboxamide;
4-(3,4-dihydroisoquinolin-2(1H)-yl)-2-(1H-pyrazol-4-yl)-5,7-dihydro-6H-pyrrolo[3,4-d]pyrimidine-6-carbonitrile;
4-(3,4-dihydroisoquinolin-2(1H)-yl)-2-(1-(2-methoxyethyl)-1H-pyrazol-4-yl)-5,7-dihydro-6H-pyrrolo[3,4-d]pyrimidine-6-carbonitrile;
4-(5,8-dihydro-1,7-naphthyridin-7(6H)-yl)-2-(5-methyl-1H-pyrazol-4-yl)-5,7-dihydro-6H-pyrrolo[3,4-d]pyrimidine-6-carbonitrile;
N-(6-cyano-4-(pyrrolidin-1-yl)-6,7-dihydro-5H-pyrrolo[3,4-d]pyrimidin-2-yl)acetamide;
2-chloro-4-(4-fluorophenyl)-5,7-dihydro-6H-pyrrolo[3,4-d]pyrimidine-6-carbonitrile;
2-chloro-4-(2-fluorophenyl)-5,7-dihydro-6H-pyrrolo[3,4-d]pyrimidine-6-carbonitrile;
4-(4-fluorophenyl)-2-methyl-5,7-dihydro-6H-pyrrolo[3,4-d]pyrimidine-6-carbonitrile;
(R)-2-(((4-methylmorpholin-2-yl)methyl)amino)-4-phenyl-5,7-dihydro-6H-pyrrolo[3,4-d]pyrimidine-6-carbonitrile;
(S)-2-(((4-methylmorpholin-2-yl)methyl)amino)-4-phenyl-5,7-dihydro-6H-pyrrolo[3,4-d]pyrimidine-6-carbonitrile;
2-chloro-6-(2-cyanoisoindolin-4-yl)benzamide;
4-(2-(pyrrolidine-1-carbonyl)phenyl)isoindoline-2-carbonitrile;
5-cyano-2-(2-cyanoisoindolin-4-yl)-4-methylbenzamide;
2-(2-cyanoisoindolin-4-yl)benzamide;
2-(2-cyanoisoindolin-4-yl)-5-fluorobenzamide;
4-(2-acetylphenyl)isoindoline-2-carbonitrile;
2-(2-cyanoisoindolin-4-yl)-N-methylbenzene sulfonamide;
2-(2-cyanoisoindolin-4-yl)benzene sulfonamide;
4-(2-(methylsulfonyl)phenyl)isoindoline-2-carbonitrile;
(R)—N-(2-cyano-7-(pyridin-4-yl)isoindolin-5-yl)-1-methylpiperidine-3-carboxamide;
(R)—N-(2-cyano-7-(pyridin-3-yl)isoindolin-5-yl)-1-methylpiperidine-3-carboxamide;
4-(2-oxoindolin-7-yl)isoindoline-2-carbonitrile;
4-(2-cyanophenyl)isoindoline-2-carbonitrile;
4-(2-cyano-4-fluorophenyl)isoindoline-2-carbonitrile;
4-(2-cyano-6-fluorophenyl)isoindoline-2-carbonitrile;
4-(4-chloro-2-cyanophenyl)isoindoline-2-carbonitrile;
4-(2-cyano-3-methoxyphenyl)isoindoline-2-carbonitrile;
4-(2-cyano-4-methoxyphenyl)isoindoline-2-carbonitrile;
4-(2-cyano-5-methoxyphenyl)isoindoline-2-carbonitrile;
4-(3-cyano-6-methoxypyridin-2-yl)isoindoline-2-carbonitrile;
2-(2-cyanoisoindolin-4-yl)-N,N-dimethylbenzene sulfonamide;
2-(2-cyanoisoindolin-4-yl)-N-ethylbenzene sulfonamide;
4-(7-cyano-3-oxo-2,3-dihydro-1H-inden-4-yl)isoindoline-2-carbonitrile;
4-(4-cyano-2-(trifluoromethyl)phenyl)isoindoline-2-carbonitrile;
4-(2-(azetidin-1-ylsulfonyl)phenyl)isoindoline-2-carbonitrile;
2-(2-cyanoisoindolin-4-yl)-N-(2-hydroxyethyl)benzene sulfonamide;
2-(2-cyanoisoindolin-4-yl)-N-(2-(6-oxopyrimidin-1(6H)-yl)ethyl)benzamide;
4-(2-cyano-4-(1H-imidazol-1-yl)phenyl)isoindoline-2-carbonitrile;
1-(3-methoxyphenyl)-4-(1-methyl-1H-pyrazol-4-yl)-5,7-dihydro-6H-pyrrolo[3,4-d]pyridazine-6-carbonitrile;
4-(3,4-dihydroisoquinolin-2(1H)-yl)-5,7-dihydro-6H-pyrrolo[3,4-d]pyrimidine-6-carbonitrile;
4-(4-(o-tolyloxy)piperidin-1-yl)-5,7-dihydro-6H-pyrrolo[3,4-d]pyrimidine-6-carbonitrile;
4-(4-(benzyloxy)piperidin-1-yl)-5,7-dihydro-6H-pyrrolo[3,4-d]pyrimidine-6-carbonitrile;
4-(4-(2-methoxyphenoxy)piperidin-1-yl)-5,7-dihydro-6H-pyrrolo[3,4-d]pyrimidine-6-carbonitrile;
N-(6-cyano-4-(4-fluorophenyl)-6,7-dihydro-5H-pyrrolo[3,4-d]pyrimidin-2-yl)acetamide;

2-((2-(methylsulfonyl)ethyl)amino)-4-phenyl-5,7-dihydro-6H-pyrrolo[3,4-d]pyrimidine-6-carbonitrile;
4-phenyl-2-((tetrahydro-2H-pyran-4-yl)amino)-5,7-dihydro-6H-pyrrolo[3,4-d]pyrimidine-6-carbonitrile;
2-((2-hydroxyethyl)(methyl)amino)-4-phenyl-5,7-dihydro-6H-pyrrolo[3,4-d]pyrimidine-6-carbonitrile;
2-(methyl((4-methylmorpholin-2-yl)methyl)amino)-4-phenyl-5,7-dihydro-6H-pyrrolo[3,4-d]pyrimidine-6-carbonitrile;
2-(((4-methylmorpholin-2-yl)methyl)amino)-4-(pyridin-3-yl)-5,7-dihydro-6H-pyrrolo[3,4-d]pyrimidine-6-carbonitrile;
4-(3-fluorophenyl)-2-(((4-methylmorpholin-2-yl)methyl)amino)-5,7-dihydro-6H-pyrrolo[3,4-d]pyrimidine-6-carbonitrile;
4-(4-fluorophenyl)-2-(((4-methylmorpholin-2-yl)methyl)amino)-5,7-dihydro-6H-pyrrolo[3,4-d]pyrimidine-6-carbonitrile;
N-(3-(6-cyano-2-(((4-methylmorpholin-2-yl)methyl)amino)-6,7-dihydro-5H-pyrrolo[3,4-d]pyrimidin-4-yl)phenyl)acetamide;
4-(3,4-dihydroisoquinolin-2(1H)-yl)-2-(((1-methylpiperidin-3-yl)methyl)amino)-5,7-dihydro-6H-pyrrolo[3,4-d]pyrimidine-6-carbonitrile;
4-(3,4-dihydroisoquinolin-2(1H)-yl)-2-(((4-methylmorpholin-2-yl)methyl)amino)-5,7-dihydro-6H-pyrrolo[3,4-d]pyrimidine-6-carbonitrile;
4-(3,4-dihydroisoquinolin-2(1H)-yl)-2-(((1-methyl-1H-pyrazol-5-yl)methyl)amino)-5,7-dihydro-6H-pyrrolo[3,4-d]pyrimidine-6-carbonitrile;
4-(3,4-dihydroisoquinolin-2(1H)-yl)-2-((trans)-4-hydroxycyclohexyl)amino)-5,7-dihydro-6H-pyrrolo[3,4-d]pyrimidine-6-carbonitrile;
4-(3,4-dihydroisoquinolin-2 (1H)-yl)-2-(((tetrahydro-2H-pyran-4-yl)methyl)amino)-5,7-dihydro-6H-pyrrolo[3,4-d]pyrimidine-6-carbonitrile;
4-(3,4-dihydroisoquinolin-2(1H)-yl)-2-(((1-methyl-1H-pyrazol-4-yl)methyl)amino)-5,7-dihydro-6H-pyrrolo[3,4-d]pyrimidine-6-carbonitrile;
4-(3,4-dihydroisoquinolin-2(1H)-yl)-2-((2-hydroxyethyl)amino)-5,7-dihydro-6H-pyrrolo[3,4-d]pyrimidine-6-carbonitrile;
4-(3,4-dihydroisoquinolin-2(1H)-yl)-2-(methyl((4-methylmorpholin-2-yl)methyl)amino)-5,7-dihydro-6H-pyrrolo[3,4-d]pyrimidine-6-carbonitrile;
2-(methylamino)-4-(4-phenoxypiperidin-1-yl)-5,7-dihydro-6H-pyrrolo[3,4-d]pyrimidine-6-carbonitrile;
2-(dimethylamino)-4-(4-phenoxypiperidin-1-yl)-5,7-dihydro-6H-pyrrolo[3,4-d]pyrimidine-6-carbonitrile;
2-((2-hydroxyethyl)amino)-4-(4-phenoxypiperidin-1-yl)-5,7-dihydro-6H-pyrrolo[3,4-d]pyrimidine-6-carbonitrile;
2-amino-4-(4-phenoxypiperidin-1-yl)-5,7-dihydro-6H-pyrrolo[3,4-d]pyrimidine-6-carbonitrile;
4-(4-cyanophenyl)-2-((2-hydroxyethyl)amino)-5,7-dihydro-6H-pyrrolo[3,4-d]pyrimidine-6-carbonitrile;
4-(3,4-difluorophenyl)-2-((2-hydroxyethyl)amino)-5,7-dihydro-6H-pyrrolo[3,4-d]pyrimidine-6-carbonitrile;
N-(3-(6-cyano-2-((2-hydroxyethyl)amino)-6,7-dihydro-5H-pyrrolo[3,4-d]pyrimidin-4-yl)phenyl)acetamide;
2-((2-hydroxyethyl)amino)-4-(4-methoxyphenyl)-5,7-dihydro-6H-pyrrolo[3,4-d]pyrimidine-6-carbonitrile;
2-((2-hydroxyethyl)amino)-4-(4-(4-methylpiperazin-1-yl)phenyl)-5,7-dihydro-6H-pyrrolo[3,4-d]pyrimidine-6-carbonitrile;
6-((dimethylamino)methyl)-4-phenylisoindoline-2-carbonitrile;
N-((2-cyano-7-phenylisoindolin-5-yl)methyl)acetamide;
6-(2-methoxyethyl)-4-phenylisoindoline-2-carbonitrile;
4-(4-cyanophenyl)-6-((methylsulfonyl)methyl)isoindoline-2-carbonitrile;
N-((2-cyano-7-(4-cyanophenyl)isoindolin-5-yl)methyl)acetamide;
N-((2-cyano-7-(4-cyanophenyl)isoindolin-5-yl)methyl)-N-methylacetamide;
N-((2-cyano-7-(4-cyanophenyl)isoindolin-5-yl)methyl)tetrahydro-2H-pyran-4-carboxamide;
N-((2-cyano-7-(4-cyanophenyl)isoindolin-5-yl)methyl)tetrahydro-2H-thiopyran-4-carboxamide-1,1-dioxide;
N-((2-cyano-7-(4-cyanophenyl)isoindolin-5-yl)methyl)-1-methyl-1H-pyrazole-4-carboxamide;
N-((2-cyano-7-(4-cyanophenyl)isoindolin-5-yl)methyl) methane sulfonamide;
3-((2-cyano-7-(4-cyanophenyl)isoindolin-5-yl)methyl)-1,1-dimethylurea;
isopropyl ((2-cyano-7-(4-cyanophenyl)isoindolin-5-yl)methyl)carbamate;
N-((2-cyano-7-(2-cyanophenyl)isoindolin-5-yl)methyl)acetamide;
N-((2-cyano-7-(2,4-dicyanophenyl)isoindolin-5-yl)methyl) acetamide;
1-((2-cyano-7-(4-cyanophenyl)isoindolin-5-yl)methyl)-3-methylurea;
1-((2-cyano-7-(2,4-dicyanophenyl)isoindolin-5-yl)methyl)-3-methylurea;
1-((2-cyano-7-(2-cyanophenyl)isoindolin-5-yl)methyl)-3-methylurea;
6-(((1H-pyrazol-5-yl)amino)methyl)-4-(4-cyanophenyl)isoindoline-2-carbonitrile;
2-(2,6-dicyanoisoindolin-4-yl)benzamide;
2-cyano-7-(4-cyanophenyl)-N,N-dimethylisoindoline-5-carboxamide;
2-cyano-7-(2,4-dicyanophenyl)isoindoline-5-carboxamide;
2-cyano-7-(2-cyano-5-methoxyphenyl)isoindoline-5-carboxamide;
2-cyano-7-(2-cyano-4-fluorophenyl)isoindoline-5-carboxamide;
4-(4-cyanophenyl)-6-(1,1-dioxidothiomorpholine-4-carbonyl)isoindoline-2-carbonitrile;
2-cyano-7-(4-cyanophenyl)-N-methylisoindoline-5-carboxamide;
2-cyano-7-(4-cyanophenyl)-N-(tetrahydro-2H-pyran-4-yl)isoindoline-5-carboxamide;
2-cyano-7-(2,4-dicyanophenyl)-N-methylisoindoline-5-carboxamide;
2-cyano-7-(4-fluorophenyl)-N-methylisoindoline-5-carboxamide;
2-cyano-7-(2-cyanophenyl)isoindoline-5-carboxamide;
N-(2-cyano-7-(2-cyanophenyl)isoindolin-5-yl)methane sulfonamide;
N-(2-cyano-7-(2,4-dicyanophenyl)isoindolin-5-yl)methane sulfonamide;
N-(2-cyano-7-(4-cyanophenyl)isoindolin-5-yl)methane sulfonamide;
N-(2-cyano-7-(2-cyano-5-methoxyphenyl)isoindolin-5-yl) methane sulfonamide;
4-(4-fluorophenyl)-2-(((tetrahydro-2H-pyran-4-yl)methyl)amino)-5,7-dihydro-6H-pyrrolo[3,4-b]pyridine-6-carbonitrile;
4-(4-fluorophenyl)-2-((pyridin-2-ylmethyl)amino)-5,7-dihydro-6H-pyrrolo[3,4-b]pyridine-6-carbonitrile;
4-(4-fluorophenyl)-2-(((1-methyl-1H-pyrazol-5-yl)methyl)amino)-5,7-dihydro-6H-pyrrolo[3,4-b]pyridine-6-carbonitrile;

N-(6-cyano-4-(4-fluorophenyl)-6,7-dihydro-5H-pyrrolo[3,4-b]pyridin-2-yl)acetamide;
2-((2,3-dihydroxypropyl)amino)-4-(4-fluorophenyl)-5,7-dihydro-6H-pyrrolo[3,4-b]pyridine-6-carbonitrile;
2-(2-cyano-7-phenylisoindolin-5-yl)-N,N-dimethylacetamide;
6-(2-(methylsulfonyl)ethyl)-4-phenylisoindoline-2-carbonitrile;
6-((methylsulfonyl)methyl)-4-phenylisoindoline-2-carbonitrile;
4-(4-cyanophenyl)-6-(2-methoxyethyl)isoindoline-2-carbonitrile;
2-(2-cyano-6-(2-methoxyethyl)isoindolin-4-yl)benzamide;
4-(4-cyanophenyl)-6-(2-(pyridin-3-yl)ethyl)isoindoline-2-carbonitrile;
6-(2-(1-acetylpiperidin-4-yl)ethyl)-4-(4-cyanophenyl)isoindoline-2-carbonitrile;
5-chloro-2-(2-cyano-1-methylisoindolin-4-yl)benzamide;
5-cyano-2-(2-cyano-1-methylisoindolin-4-yl)benzamide;
5-cyano-2-(2-cyano-5-fluoroisoindolin-4-yl)benzamide;
5-cyano-2-(2-cyano-7-fluoroisoindolin-4-yl)benzamide;
6-(1-methyl-6-oxopiperidin-3-yl)-4-phenylisoindoline-2-carbonitrile;
6-(1-methyl-6-oxo-1,6-dihydropyridin-3-yl)-4-phenylisoindoline-2-carbonitrile;
N-(2-cyano-7-(4-cyanophenyl)isoindolin-5-yl)tetrahydro-2H-pyran-4-carboxamide;
N-(2-cyano-7-(4-cyanophenyl)isoindolin-5-yl)-1-methyl-5-oxopyrrolidine-3-carboxamide;
N-(2-cyano-7-(4-cyanophenyl)isoindolin-5-yl)-1-methyl-6-oxopiperidine-3-carboxamide;
N-(2-cyano-7-(4-cyanophenyl)isoindolin-5-yl)-2-(dimethylamino)acetamide;
4-(2,6-dioxopiperidin-1-yl)isoindoline-2-carbonitrile;
4-(4-cyanophenyl)-6-(methylamino)isoindoline-2-carbonitrile;
4-(4-cyanophenyl)-6-(dimethylamino)isoindoline-2-carbonitrile;
4-(4-cyanophenyl)-6-((2-hydroxyethyl)amino)isoindoline-2-carbonitrile;
4-(4-cyanophenyl)-6-(isopropylamino)isoindoline-2-carbonitrile;
4-(4-cyanophenyl)-6-((1,1-dioxidotetrahydro-2H-thiopyran-4-yl)amino)isoindoline-2-carbonitrile;
4-(4-cyanophenyl)-6-((tetrahydro-2H-pyran-4-yl)amino)isoindoline-2-carbonitrile;
4-(4-cyanophenyl)-6-(((tetrahydro-2H-pyran-4-yl)methyl)amino)isoindoline-2-carbonitrile;
4-(4-cyanophenyl)-6-(((1-methyl-1H-pyrazol-5-yl)methyl)amino)isoindoline-2-carbonitrile;
4-(4-cyanophenyl)-6-(ethylamino)isoindoline-2-carbonitrile;
4-(4-cyanophenyl)-6-(1,1-dioxidothiomorpholino)isoindoline-2-carbonitrile;
4-(4-cyanophenyl)-6-(diethylamino)isoindoline-2-carbonitrile;
4-(4-cyanophenyl)-6-((2,3-dihydroxypropyl)amino)isoindoline-2-carbonitrile;
5-cyano-2-(2-cyano-6-(((tetrahydro-2H-pyran-4-yl)methyl)amino)isoindolin-4-yl)benzamide;
(S)-6-((2,3-dihydroxypropyl)amino)-4-(4-fluorophenyl)isoindoline-2-carbonitrile;
(S)-4-(2-cyanophenyl)-6-((2,3-dihydroxypropyl)amino)isoindoline-2-carbonitrile;
4-(4-cyanophenyl)-6-((3-hydroxy-2-methoxypropyl)amino)isoindoline-2-carbonitrile;
5-cyano-2-(2-cyano-6-(dimethylamino)isoindolin-4-yl)benzamide;
4-(4-cyanophenyl)-6-((2-hydroxypropyl)amino)isoindoline-2-carbonitrile;
4-(4-cyanophenyl)-6-((2-hydroxy-2-methylpropyl)amino)isoindoline-2-carbonitrile;
4-(4-cyanophenyl)-6-((2-hydroxy-3-methoxypropyl)amino)isoindoline-2-carbonitrile;
2-methyl-4-(3-(2-oxopyrrolidin-1-yl)phenyl)-5,7-dihydro-6H-pyrrolo[3,4-d]pyrimidine-6-carbonitrile;
2-(((1-methyl-1H-pyrazol-5-yl)methyl)amino)-4-(3-(2-oxopyrrolidin-1-yl)phenyl)-5,7-dihydro-6H-pyrrolo[3,4-d]pyrimidine-6-carbonitrile;
2-((2-hydroxyethyl)amino)-4-(3-(2-oxopyrrolidin-1-yl)phenyl)-5,7-dihydro-6H-pyrrolo[3,4-d]pyrimidine-6-carbonitrile;
2-((2-hydroxyethyl)amino)-4-(3-(2-oxooxazolidin-3-yl)phenyl)-5,7-dihydro-6H-pyrrolo[3,4-d]pyrimidine-6-carbonitrile;
2-cyano-7-(2-cyano-5-methoxypyridin-3-yl)-N-methylisoindoline-5-carboxamide;
4-(2-cyano-4-(1H-pyrazol-4-yl)phenyl)isoindoline-2-carbonitrile;
4-(5,8-dihydro-1,7-naphthyridin-7 (6H)-yl)-2-(methyl((1-methylpiperidin-3-yl)methyl)amino)-5,7-dihydro-6H-pyrrolo[3,4-d]pyrimidine-6-carbonitrile;
2-(2,6-dicyanoisoindolin-4-yl)-5-fluorobenzamide;
5-cyano-2-(2,6-dicyanoisoindolin-4-yl)-3-fluorobenzamide;
4-(2-cyano-5-(2-oxooxazolidin-3-yl)phenyl)isoindoline-2-carbonitrile;
4-(2-cyano-5-(2-oxopyrrolidin-1-yl)phenyl)isoindoline-2-carbonitrile;
4-(3-(2-oxoimidazolidin-1-yl)phenyl)-5,7-dihydro-6H-pyrrolo[3,4-d]pyrimidine-6-carbonitrile; and
5-cyano-2-(2-cyanoisoindolin-4-yl)-3-fluorobenzamide It should be noted that each of the chemical compounds listed above represents a particular and independent aspect of the invention.

According to a further aspect of the invention there is provided a process for the preparation of a compound of formula I or a pharmaceutically acceptable salt thereof comprising the steps of reacting an amine of formula (II) with cyanogen bromide to form N—CN compounds:

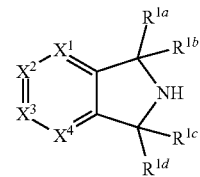

Where $R^{1a}$-$R^{1d}$ and $X^1$-$X^4$ are as defined elsewhere.

According to a further aspect of the invention there is provided a pharmaceutical composition comprising a compound of the invention.

The compounds of the invention may be used in the treatment of disorders and diseases related to DUB or desumoylation inhibition, particularly USP7.

According to a further aspect of the invention there is provided a compound of formula (I) or pharmaceutical composition thereof for use in therapy. In particular, the compounds of the invention have use in the treatment of cancer and more particularly in the treatment of cancer linked to DUB or desumoylation activity. Compounds of the invention may be useful against any DUB or desumoylating enzyme, including but not limited to USP7, USP30, USP47, SENP2 and SENP6.

The compounds described herein may be used in the manufacture of a medicament for the treatment of cancer linked to DUB or desumoylation activity.

In a further aspect of the invention there is provided a method of treatment or prevention of cancer, the method comprising administering a pharmaceutically effective amount of a compound of the invention or a pharmaceutical composition thereof to an individual suffering from cancer.

The compounds or compositions disclosed herein may be used to treat cancer. References to "cancer" or "tumour" include but are not limited to breast, ovarian, prostate, lung, kidney, gastric, colon, testicular, head and neck, pancreas, brain, melanoma, bone, liver, soft tissue or other cancers of tissue organs and cancers of the blood cells such as lymphomas and leukaemias. Particular cancers include lymphoma, multiple myeloma, CML, AML, mantle cell lymphoma, neuroblastoma, colorectal cancer, melanoma, soft tissue sarcomas including liposarcoma, fibroblastic sarcoma and leiomyosarcoma, hepatocellular carcinoma, osteosarcoma, oesophageal cancer and non-small cell lung cancer.

The compounds or compositions disclosed herein may be used to treat additional diseases linked to USP7 activity.

The compounds of the invention or pharmaceutical compositions thereof as described herein may be combined with one or more additional agents. The compounds may be combined with one or more additional anti-tumour therapeutic agents, for example chemotherapeutic drugs, immune checkpoint inhibitors or inhibitors of other regulatory proteins. In one embodiment the one or more anti-tumour agent is a chemotherapeutic agent. Chemotherapeutic agents may be selected from olaparib, mitomycin C, cisplatin, carboplatin, oxaliplatin, ionizing radiation (IR), camptothecin, irinotecan, topotecan, temozolomide, taxanes, 5-fluoropyrimidines, gemcitabine, and doxorubicin. In a further embodiment the additional anti-tumour therapeutic agent is a BH-3 mimetic. In a further embodiment BH-3 mimetics may be selected from but not limited to one or more of ABT-737, ABT-199, ABT-263, and Obatoclax.

As discussed above, the compounds of the invention may be useful in the treatment of disorders and diseases related to USP30 inhibition. The compounds of the invention may therefore be useful in the treatment of disorders or diseases having a component relating to mitochondrial dysfunction.

Mitochondria are specialized subcellular organelles required for energy production in the form of ATP. In the case of mitochondrial dysfunction, cells cannot produce sufficient ATP resulting in cell injury or death. Diseases of the mitochondria appear most often in organs that are very energy demanding such as the brain, heart, liver, skeletal muscles, kidney and the endocrine and respiratory system.

The condition involving mitochondrial dysfunction may be selected from a condition involving a mitophagy defect, a condition involving a mutation in mitochondrial DNA, a condition involving mitochondrial oxidative stress, a condition involving a defect in mitochondrial membrane potential, mitochondrial biogenesis, a condition involving a defect in mitochondrial shape or morphology, and a condition involving a lysosomal storage defect.

In particular, the condition involving mitochondrial dysfunction may be selected from a neurodegenerative disease; multiple sclerosis (MS), mitochondrial myopathy, encephalopathy, lactic acidosis, and stroke-like episodes (MELAS) syndrome; Leber's hereditary optic neuropathy (LHON); cancer; neuropathy, ataxia, retinitis pigmentosa-maternally inherited Leigh syndrome (NARP-MILS); Danon disease; diabetes; diabetic nephropathy; metabolic disorders; heart failure; ischemic heart disease leading to myocardial infarction; psychiatric diseases, for example schizophrenia; multiple sulfatase deficiency (MSD); mucolipidosis II (ML II); mucolipidosis III (ML III); mucolipidosis IV (ML IV); GM1-gangliosidosis (GM1); neuronal ceroid-lipofuscinoses (NCL1); Alpers disease; Barth syndrome; Beta-oxidation defects; carnitine-acyl-carnitine deficiency; carnitine deficiency; creatine deficiency syndromes; co-enzyme Q10 deficiency; complex I deficiency; complex II deficiency; complex III deficiency; complex IV deficiency; complex V deficiency; COX deficiency; chronic progressive external ophthalmoplegia syndrome (CPEO); CPT I deficiency; CPT II deficiency; glutaric aciduria type II; Kearns-Sayre syndrome; lactic acidosis; long-chain acyl-CoA dehydrogenase deficiency (LCHAD); Leigh disease or syndrome; lethal infantile cardiomyopathy (LIC); Luft disease; glutaric aciduria type II; medium-chain acyl-CoA dehydrogenase deficiency (MCAD); myoclonic epilepsy and ragged-red fiber (MERRF) syndrome; mitochondrial cytopathy; mitochondrial recessive ataxia syndrome; mitochondrial DNA depletion syndrome; myoneurogastointestinal disorder and encephalopathy; Pearson syndrome; pyruvate dehydrogenase deficiency; pyruvate carboxylase deficiency; POLG mutations; medium/short-chain 3-hydroxyacyl-CoA dehydrogenase (M/SCHAD) deficiency; and very long-chain acyl-CoA dehydrogenase (VLCAD) deficiency.

The condition involving mitochondrial dysfunction may be a CNS disorder, for example a neurodegenerative disease. Neurodegenerative diseases include, but are not limited to, Parkinson's disease, Alzheimer's disease, amyotrophic lateral sclerosis (ALS), Huntington's disease, ischemia, stroke, dementia with Lewy bodies, and frontotemporal dementia.

Dosage Forms

The pharmaceutical compositions of the invention may be designed for administration by the oral, parenteral or mucosal route and the choice or the specific form of composition is dependent on the administration route. Thus for oral administration the composition may be in the form, for example, of tablets, lozenges, dragees, films, powders, elixirs, syrups, liquid preparations including dispersions, suspensions, emulsions, solutions or sprays, cachets, granules, capsules, etc. For administration to mucosa the composition may be in the form of sprays, inhalants, dispersions, suspensions, emulsions, solutions, gels, patches, films, ointments, creams, lotions, suppositories etc. For parenteral administration the composition is in the form of a liquid preparation such as a solution, dispersion, emulsion or suspension including liposome compositions.

Preparations according to the invention for parenteral administration include sterile aqueous, aqueous-organic, and organic solutions, suspensions and emulsions.

Such dosage forms are prepared according to techniques known in the art of pharmaceutical formulation. When in the form of sprays or inhalants the pharmaceutical compositions may be administered nasally. Suitable formulations for this purpose are known to those skilled in the art.

The pharmaceutical compositions of the invention may be administered by injection and may be in the form of a sterile liquid preparation for injection, including liposome preparations. The pharmaceutical compositions of the invention may also be in the form of suppositories for rectal administration. These are formulated so that the pharmaceutical composition is solid at room temperature and liquid at body temperature to allow release of the active compound.

The dosages may be varied depending upon the requirements of the patient, the severity of the condition being treated, and the compound being employed. Determination of the proper dosage for a particular situation is within the remit of the person skilled in the skill of the art. Generally, treatment is initiated with smaller dosages which are less than the optimal dose of the compound. Thereafter the dosage is increased by small increments until the optimum effect under the circumstances is reached.

The magnitude of an effective dose of a compound will, of course, vary with the nature of the severity of the condition to be treated and with the particular compound and its route of administration. The selection of appropriate dosages is within the ability of one of ordinary skill in this art, without undue burden. The daily dose range is about 10 μg to about 100 mg per kg body weight of a human and non-human animal and in general may be around 10 μg to 30 mg per kg body weight per dose. The above dose may be given from one to three times per day.

Synthetic Methodologies

Compounds of the invention may be prepared via a variety of synthetic routes. Exemplary routes to certain compounds of the invention are shown below. Representative compounds of the present invention can be synthesized in accordance with the general synthetic methods described below and are illustrated more particularly in the schemes that follow. Since the schemes are an illustration, the invention should not be construed as being limited by the chemical reactions and conditions expressed. The preparation of the various starting materials used in the schemes is well within the skill of persons versed in the art. Those skilled in the art appreciate that, where appropriate, the individual transformations within a scheme can be completed in a different order. The following schemes describe general synthetic methods whereby intermediate and target compounds of the present invention may be prepared. Additional representative compounds and stereoisomers, racemic mixtures, diastereomers and enantiomers thereof can be synthesized using the intermediates prepared in accordance to the general schemes and other materials, compounds and reagents known to those skilled in the art. All such compounds, stereoisomers, racemic mixtures, diastereomers and enantiomers thereof are intended to be encompassed within the scope of the present invention.

All the compounds were characterised by either liquid chromatography-mass spectroscopy (LCMS) or $^1$H NMR or both.

Synthetic Schemes

Abbreviations:

AcOH Acetic acid
AIBN Azobisisobutyronitrile
Ar Aryl
BEH Ethylene Bridged Hybrid
Boc Tert-butoxycarbonyl
br Broad (NMR signal)
d Doublet (NMR signal)
dba dibenzylideneacetone
DCE 1,2-Dichloroethane
DCM Dichloromethane
DIPEA Diisopropylethylamine
DMAP 4-Dimethylaminopyridine
DMF N,N-Dimethylformamide
DMS Dimethylsulphide
DMSO Dimethylsulphoxide
Dppf 1,1'-Bis(diphenylphosphino)ferrocene
EDC 1-Ethyl-3-(3-dimethylaminopropyl)carbodiimide
ES Electrospray
EtOAc Ethyl acetate
EtOH Ethanol
Fmoc Fluorenylmethyloxycarbonyl
g gram(s)
h Hour(s)
HATU 1-[Bis(dimethylamino)methylene]-1H-1,2,3-triazolo[4,5-b]pyridinium 3-oxide hexafluorophosphate
HOBt Hydroxybenzotriazole
IPA Isopropanol
m Multiplet (NMR signal)
M Molar
m-CPBA meta-chloroperoxybenzoic acid
MeCN Acetonitrile
MeOH Methanol
min Minutes
NBS N-bromosuccinimide
NMP N-methyl-2-pyrrolidone
PE Petroleumether
RT Retention time
rt Room temperature
s Singlet (NMR signal)
SFC Supercritical Fluid Chromatography
t Triplet (NMR signal)
TEA Triethylamine
TFA Trifluoroacetic acid
TFAA Trifluoroacetic anhydride
THF Tetrahydrofuran
TLC Thin layer chromatography
Xantphos 4,5-Bis(diphenylphosphino)-9,9-dimethyxanthene Analytical Methods:

| Method A | |
|---|---|
| Column | BEH C18, 50 × 2.1 mm, 1.7 μm or equivalent |
| Mobile Phase | (A) 5 mM Ammonium Acetate + 0.1% Formic Acid in Water |
| | (B) 0.1% Formic Acid in MeCN |
| Flow Rate | 0.55 ml/min |

| Gradient | Time | % B |
|---|---|---|
| | 0.01 | 5 |
| | 0.40 | 5 |
| | 0.80 | 35 |
| | 1.20 | 55 |
| | 2.50 | 100 |
| | 3.30 | 100 |
| | 3.31 | 5 |
| | 4.00 | 5 |

| Method B | |
|---|---|
| Column | X-bridge C18, 150 × 4.6 mm, 5 μm or equivalent |
| Mobile Phase | (A) 0.1% Ammonia in Water; (B) 0.1% Ammonia in MeCN |
| Flow Rate | 1.0 ml/min |

| Gradient | Time | % B |
|---|---|---|
| | 0.01 | 10 |
| | 5.00 | 90 |
| | 7.00 | 100 |
| | 11.00 | 100 |
| | 11.01 | 10 |
| | 12.00 | 10 |

| Method C | |
|---|---|
| Column | YMC Triart C18 (150 × 4.6 mm), 5 µm or Equivalent |
| Mobile Phase | (A) 10 mM Ammonium Acetate in Water; (B) 100% MeCN |
| Flow Rate | 1.0 ml/min |

| Gradient | Time | % B |
|---|---|---|
| | 0.01 | 10 |
| | 5.00 | 90 |
| | 7.00 | 100 |
| | 11.00 | 100 |
| | 11.01 | 10 |
| | 12.00 | 10 |

| Method D | |
|---|---|
| Column | X-bridge C18, 50 × 4.6 mm, 3.5 µm or equivalent |
| Mobile Phase | (A) 0.1% Ammonia in Water; (B) 0.1% Ammonia in MeCN |
| Flow Rate | 1.0 ml/min |

| Gradient | Time | % B |
|---|---|---|
| | 0.01 | 5 |
| | 5.00 | 90 |
| | 5.80 | 95 |
| | 7.20 | 95 |
| | 7.21 | 5 |
| | 10.00 | 5 |

| Method E | |
|---|---|
| Column | BEH C18, 50 × 2.1 mm, 1.7 µm or equivalent |
| Mobile Phase | (A) 5 mM Ammonium Acetate + 0.1% Formic Acid in Water<br>(B) 0.1% Formic Acid in MeCN |
| Flow Rate | 0.45 ml/min |

| Gradient | Time | % B |
|---|---|---|
| | 0.01 | 2 |
| | 0.50 | 2 |
| | 5.00 | 90 |
| | 6.00 | 95 |
| | 7.00 | 95 |
| | 7.01 | 2 |
| | 8.00 | 2 |

| Method F | |
|---|---|
| Column | Agilent TC-C18, 2.1 × 50 mm, 5 µm or equivalent |
| Mobile Phase | (A) 0.04% TFA in water; (B) 0.02% TFA in MeCN |
| Flow Rate | 0.60 ml/min |

| Gradient | Time | % B |
|---|---|---|
| | 0.01 | 0 |
| | 3.40 | 100 |
| | 4.00 | 100 |
| | 4.01 | 0 |
| | 4.50 | 0 |

| Method G | |
|---|---|
| Column | Agilent TC-C18, 2.1 × 50 mm, 5 µm or equivalent |
| Mobile Phase | (A) 0.04% TFA in water; (B) 0.02% TFA in MeCN |
| Flow Rate | 0.80 ml/min |

| Gradient | Time | % B |
|---|---|---|
| | 0.01 | 1 |
| | 3.40 | 100 |
| | 4.00 | 100 |
| | 4.01 | 1 |
| | 4.50 | 1 |

| Method H | |
|---|---|
| Column | XBridge ShieldRP18, 2.1 × 50 mm, 5 µm or equivalent |
| Mobile Phase | (A) 0.05% Ammonia in water; (B) MeCN |
| Flow Rate | 0.80 ml/min |

| Gradient | Time | % B |
|---|---|---|
| | 0.01 | 5 |
| | 3.40 | 100 |
| | 4.00 | 100 |
| | 4.01 | 5 |
| | 4.50 | 5 |

| Method I | |
|---|---|
| Column | Agilent Poroshell 120 (SB-C18, 4.6 mm × 30 mm, 2.7 µm) or equivalent |
| Mobile Phase | (A) 0.1% v/v formic acid in water<br>(B) 0.1% v/v formic acid in MeCN |
| Flow Rate | 2.0 ml/min |

| Gradient | Time | % B |
|---|---|---|
| | 0.5 | 5 |
| | 1.5 | 100 |
| | 4.0 | 100 |
| | 4.3 | 5 |
| | 4.5 | 5 |

| Method J | |
|---|---|
| Column | Agilent Poroshell 120 (SB-C18, 4.6 mm × 30 mm, 2.7 µm) or equivalent |
| Mobile Phase | (A) 0.1% v/v formic acid in water<br>(B) 0.1% v/v formic acid in MeCN |
| Flow Rate | 2.0 ml/min |

| Gradient | Time | % B |
|---|---|---|
| | 0.5 | 5 |
| | 3.0 | 100 |
| | 5.0 | 100 |
| | 5.5 | 5 |
| | 6.5 | 5 |

| Method K | |
|---|---|
| Column | Agilent Poroshell 120 EC-C18 (3.0 mm × 50 mm, 2.7 µm) or equivalent |
| Mobile Phase | (A) 0.1% v/v formic acid in water<br>(B) 0.1% v/v formic acid in MeCN |
| Flow Rate | 0.8 ml/min |

Method K

| Gradient | Time | % B |
|---|---|---|
| | 1.0 | 5 |
| | 5.0 | 95 |
| | 7.0 | 95 |
| | 7.25 | 5 |
| | 8.0 | 5 |

Method L

| | |
|---|---|
| Column | Agilent Poroshell 120 EC-C18 (3.0 mm × 50 mm, 2.7 µm) or equivalent |
| Mobile Phase | (A) 0.1% v/v formic acid in water |
| | (B) 0.1% v/v formic acid in MeCN |
| Flow Rate | 0.8 ml/min |

| Gradient | Time | % B |
|---|---|---|
| | 0.2 | 5 |
| | 2.0 | 95 |
| | 3.0 | 95 |
| | 3.25 | 5 |
| | 3.5 | 5 |

Method M

| | |
|---|---|
| Column | Agilent Poroshell 120 (SB-C18, 4.6 mm × 30 mm, 2.7 µm) or equivalent |
| Mobile Phase | (A) 0.1% v/v formic acid in water |
| | (B) 0.1% v/v formic acid in MeCN |
| Flow Rate | 2.0 ml/min |

| Gradient | Time | % B |
|---|---|---|
| | 0.5 | 5 |
| | 3.0 | 100 |
| | 7.5 | 100 |
| | 8.0 | 5 |
| | 9.0 | 5 |

Method N

| | |
|---|---|
| Column | Agilent TC-C18, 2.1 × 50 mm, 5 µm or equivalent |
| Mobile Phase | (A) 0.04% TFA in water |
| | (B) 0.02% TFA in MeCN |
| Flow Rate | 0.80 ml/min |

| Gradient | Time | % B |
|---|---|---|
| | 0.01 | 10 |
| | 3.40 | 100 |
| | 4.00 | 100 |
| | 4.01 | 10 |
| | 4.50 | 10 |

Method O

| | |
|---|---|
| Column | CHIRALCEL OJ-H 250 × 4.6 mm 5 µm or equivalent |
| Mobile Phase | (A) 0.04% TFA in water; (B) 0.02% TFA in MeCN |
| Flow Rate | 0.80 ml/min |

| Gradient | Time | % B |
|---|---|---|
| | 0.01 | 10 |
| | 3.40 | 100 |
| | 4.00 | 100 |
| | 4.01 | 10 |
| | 4.50 | 10 |

Method P

| | |
|---|---|
| Column | Agilent Poroshell 120 (SB-C18, 4.6 mm × 30 mm, 2.7 µm) or equivalent |
| Mobile Phase | (A) 0.1% v/v formic acid in water |
| | (B) 0.1% v/v formic acid in MeCN |
| Flow Rate | 2.0 ml/min |

| Gradient | Time | % B |
|---|---|---|
| | 0.5 | 5 |
| | 1.5 | 100 |
| | 5.0 | 100 |
| | 5.3 | 5 |
| | 5.5 | 5 |

Method Q

| | |
|---|---|
| Column | Agilent Poroshell 120 (SB-C18, 4.6 mm × 30 mm, 2.7 µm) or equivalent |
| Mobile Phase | (A) 0.1% v/v formic acid in water |
| | (B) 0.1% v/v formic acid in MeCN |
| Flow Rate | 2.0 ml/min |

| Gradient | Time | % B |
|---|---|---|
| | 0.5 | 5 |
| | 1.5 | 100 |
| | 4.5 | 100 |
| | 4.8 | 5 |
| | 5.0 | 5 |

Method R

| | |
|---|---|
| Column | Agilent Poroshell 120 EC-C18 (3.0 mm × 50 mm, 2.7 µm) or equivalent |
| Mobile Phase | (A) 0.1% v/v formic acid in water |
| | (B) 0.1% v/v formic acid in MeCN |
| Flow Rate | 0.8 ml/min |

| Gradient | Time | % B |
|---|---|---|
| | 0.01 | 5 |
| | 1.25 | 95 |
| | 3.5 | 95 |
| | 3.75 | 5 |
| | 4.0 | 5 |

Method S

| | |
|---|---|
| Column | Agilent Poroshell 120 (SB-C18, 4.6 mm × 30 mm, 2.7 µm) or equivalent |

Method S

| Mobile Phase | (A) 0.1% v/v formic acid in water |
| | (B) 0.1% v/v formic acid in MeCN |
| Flow Rate | 2.0 ml/min |

| Gradient | Time | % B |
| --- | --- | --- |
| | 0.5 | 5 |
| | 1.5 | 100 |
| | 3.0 | 100 |
| | 3.3 | 5 |
| | 3.5 | 5 |

Method T

| Column | Chiralcel OJ-H (250 × 4.6 mm, 5 μm) |
| Mobile Phase | (A) liquid $CO_2$; (B) 0.1% $NH_3$ in IPA |
| Flow Rate | 4.0 ml/min, ABPR 150 bar |

| Gradient | Time | % B |
| --- | --- | --- |
| | 0 | 5 |
| | 5.0 | 50 |
| | 10.0 | 50 |

Method U

| Column | Chiralcel OX-H (250 × 4.6 mm, 5 μm) |
| Mobile Phase | (A) liquid $CO_2$; (B) IPA |
| Flow Rate | 4.0 ml/min, ABPR 150 bar |

| Gradient | Time | % B |
| --- | --- | --- |
| | 0 | 5 |
| | 5.0 | 50 |
| | 10.0 | 50 |

Method V

| Column | YMC Triart C18 ExRS 250 × 4.6 mm, 5 μm or equivalent |
| Mobile Phase | (A) 0.1% v/v formic acid in water; (B) MeCN |
| Flow Rate | 1.0 mL/min |

| Gradient | Time | % B |
| --- | --- | --- |
| | 0 | 0 |
| | 25 | 40 |
| | 30 | 100 |
| | 35 | 100 |
| | 35.01 | 0 |
| | 40 | 0 |

Intermediate 1 tert-butyl 4-bromoisoindoline-2-carboxylate

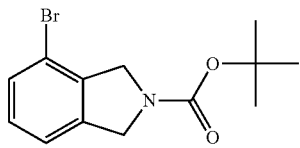 [SMILES: CC(C)(C)OC(=O)N1Cc2cccc(Br)c2C1]

To a solution of 4-bromoisoindoline hydrochloride (CAS Number 923590-95-8, available from Ark Pharma) (2.5 g, 10.6 mmol) in THF (30 ml) was added TEA (2.97 ml, 21.3 mmol) at 0° C. The resulting reaction mixture was stirred at 0° C. for 15 min. Boc anhydride (3.02 g, 13.859 mmol) was added to the reaction mixture at 0° C. The reaction mixture was stirred at rt for 2 h. The resulting reaction mixture was poured into water (100 ml) and extracted with EtOAc (2×100 ml). The combined organic phase was washed with brine (70 ml), dried over $Na_2SO_4$, filtered and concentrated under reduced pressure yielding tert-butyl 4-bromoisoindoline-2-carboxylate (3.1 g, 10.436 mmol). LCMS: Method A, 2.888 min, MS: ES+ 242.0 (M−56); $^1$H NMR (400 MHz, DMSO-d6) δ ppm 7.26-7.49 (m, 3H), 4.69 (d, J=9.6 Hz, 2H), 4.52 (d, J=9.2 Hz, 2H), 1.47 (s, 9H).

Intermediate 2 tert-butyl 4-(4,4,5,5-tetramethyl-1,3,2-dioxaborolan-2-yl)isoindoline-2-carboxylate

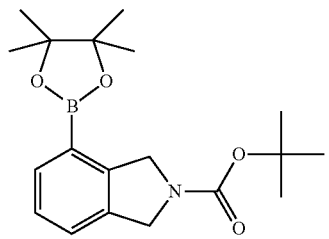 [SMILES: CC(C)(C)OC(=O)N1Cc2cccc(B3OC(C)(C)C(C)(C)O3)c2C1]

A mixture of tert-butyl 4-bromoisoindoline-2-carboxylate (Intermediate 1, 500 mg, 1.68 mmol), bis(pinacolato)diboron (512 mg, 2.02 mmol) and potassium acetate (495 mg, 5.04 mmol) in 1,4-dioxane (10 ml) was degassed by nitrogen bubbling for 10 min. Pd(dppf)$Cl_2$.DCM (140 mg, 0.17 mmol) was then added. The mixture was heated at reflux for 18 h, then cooled to rt. The mixture was filtered on a silica pad and washed with diethyl ether (150 ml). The filtrate was evaporated under reduced pressure, the residue (900 mg) was dissolved in DCM and purified by flash column chromatography (0-10% EtOAc in hexane) to give tert-butyl 4-(4,4,5,5-tetramethyl-1,3,2-dioxaborolan-2-yl)isoindoline-2-carboxylate (435 mg, 75%) as a white solid. LCMS: Method I, 3.87 min, MS: ES+ 346; $^1$H NMR (400 MHz, $CDCl_3$) δ ppm 7.71 (d, J=6.9 Hz, 1H), 7.25-7.37 (m, 2H), 4.79-4.88 (m, 2H), 4.65-4.69 (m, 2H), 1.54 (m, 9H), 1.33 (m, 12H).

Intermediate 3 tert-butyl 4-bromo-6-nitroisoindoline-2-carboxylate

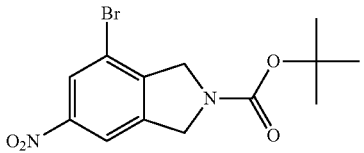 [SMILES: CC(C)(C)OC(=O)N1Cc2cc([N+](=O)[O-])cc(Br)c2C1]

Step a.
To a stirred solution of 1,2-dimethyl-4-nitrobenzene (CAS Number 99-51-4, available from TCI chemicals) (25 g, 165.4 mmol) in DCM (300 ml) was added portion wise $AlCl_3$ (55.13 g, 413.4 mmol) at 0° C. The reaction mixture was stirred at 0° C. for 50 min. Bromine (31.72 g, 198.4 mmol) was added drop wise to the reaction mixture at 0° C. The reaction mixture was stirred at 40° C. for 48 h. The resulting reaction mixture was cooled to rt and combined with 1 other batch prepared on the same scale by an identical method. The reaction mixture was quenched by careful and slow addition of saturated $NaS_2O_3.5H_2O$ solution until neutralization and extracted with DCM (3×500 ml). The combined organic phase was washed with brine (500 ml). The organic phase was separated, dried over $Na_2SO_4$, filtered and concentrated under reduced pressure. The residue was purified by column chromatography (100% hexane) yielding 1-bromo-2,3-dimethyl-5-nitrobenzene (56.0 g, 243.4 mmol). $^1$H NMR (400 MHz, DMSO-d6) δ ppm 8.23 (d, J=2.0 Hz, 1H), 7.99 (d, J=1.6 Hz, 1H), 2.44 (s, 3H), 2.42 (s, 3H).

Step b.

To a stirred solution of 1-bromo-2,3-dimethyl-5-nitrobenzene (27 g, 117.4 mmol) in $CCl_4$ (270 ml) was added AIBN (0.674 g, 4.11 mmol) at rt. The reaction mixture was stirred at rt for 10 min. NBS (52.22 g, 293.4 mmol) was portion wise added to the reaction mixture at rt. The reaction mixture was stirred at 75° C. for 18 h. The resulting reaction mixture was cooled to rt and combined with 1 other batch prepared on the same scale by an identical method. The reaction mixture was filtered off and residue was washed with $CCl_4$ (3×100 ml). The filtrate was concentrated under reduced pressure yielding 1-bromo-2,3-bis(bromomethyl)-5-nitrobenzene (100.5 g, quantitative). This material was used for the next step without further purification.

Step c.

To a stirred solution of benzylamine (13.81 g, 128.9 mmol) in THF (500 ml) was added $KHCO_3$ (32.26 g, 322.3 mmol) at rt. The reaction mixture was stirred at rt for 15 min. A solution of 1-bromo-2,3-bis(bromomethyl)-5-nitrobenzene (50 g, 128.9 mmol) in THF was added to the reaction mixture at rt. The resulting reaction mixture was stirred at rt for 18 h. The reaction mixture was combined with another batch prepared on the same scale by an identical method. The resulting reaction mixture was poured into water (500 ml) and extracted with EtOAc (3×500 ml). The combined organic phase was washed with brine (200 ml). The organic phase was separated, dried over $Na_2SO_4$, filtered and concentrated under reduced pressure. The resulting residue was purified by column chromatography (2.5% EtOAc in hexane), the obtained residue was re-purified by another round of column chromatography whereby the column was packed in 100% DCM and ran in the same mobile phase to elute an undesired impurity, and the required product was then eluted in 5% MeOH in DCM. The process yielded 2-benzyl-4-bromo-6-nitroisoindoline (17.5 g, 52.5 mmol). LCMS: Method A, 2.007 min, MS: ES+ 333.2, 335.2; $^1$H NMR (400 MHz, DMSO-d6) δ ppm 8.27 (s, 1H), 8.17 (s, 1H), 7.38 (s, 4H), 7.27-7.31 (m, 1H), 4.07 (s, 2H), 3.93 (s, 2H), 3.91 (s, 2H).

Step d.

To a stirred solution of 2-benzyl-4-bromo-6-nitroisoindoline (8.5 g, 25.5 mmol) in chlorobenzene (42.5 ml) was added 4 Å molecular sieves (oven dried) (4.25 g, 0.5 w/w) at rt. The reaction mixture was stirred at rt for 45 min. 1-Chloroethyl chloroformate (CAS Number 50893-53-3, available from Alfa Aesar) (7.29 g, 51.02 mmol) was added drop wise to the reaction mixture at rt. The resulting reaction mixture was stirred at 90° C. for 6 h. The resulting reaction mixture was cooled to rt and was filtered off. The residue was washed with MeOH (34 ml) and chlorobenzene (10 ml). The obtained filtrate was stirred at 70° C. for 2 h and was then cooled to rt and stirred for a further 18 h. The reaction mixture was combined with 1 other batch prepared on the same scale by an identical method. The resulting solids were collected by filtration and were washed with hexane (3×100 ml). The obtained solid mass was dried under vacuum yielding 4-bromo-6-nitroisoindoline hydrochloride (10.1 g, 36.1 mmol). LCMS: Method A, 1.507 min, MS: ES+ 243.03, 245.03; $^1$H NMR (400 MHz, DMSO-d6) δ ppm 10.32 (s, 2H), 8.42 (s, 1H), 8.34 (s, 1H), 4.72 (2, H), 4.59 (s, 2H).

Step e.

To a stirred solution of 4-bromo-6-nitroisoindoline hydrochloride (5.0 g, 17.89 mmol) in THF (100 ml) was added TEA (3.62 g, 35.77 mmol) at rt. The reaction mixture was stirred at rt for 10 min. Boc anhydride (5.86 g, 26.83 mmol) was added portion wise to the reaction mixture at rt. The reaction mixture was stirred at rt for 3 h. The reaction mixture was combined with another batch prepared on the same scale by an identical method. The resulting reaction mixture was poured into water (100 ml) and extracted with EtOAc (3×100 ml). The combined organic phase was washed with brine (100 ml). The organic phase was separated, dried over $Na_2SO_4$, filtered and concentrated under reduced pressure. The resulting residue was purified by flash chromatography (5% EtOAc in hexane) yielding tert-butyl 4-bromo-6-nitroisoindoline-2-carboxylate (12.1 g, 35.38 mmol). LCMS: Method E, 5.256 min, MS: ES+ 286.99 (M−56); $^1$H NMR (400 MHz, DMSO-d6) δ ppm 8.34 (d, J=2.0 Hz, 1H), 8.27 (d, J=6.0 Hz, 1H), 4.78 (d, J=10.0 Hz, 2H), 4.62 (d, J=8.8 Hz, 2H), 1.47 (s, 9H).

Intermediate 4 tert-butyl
6-amino-4-phenylisoindoline-2-carboxylate

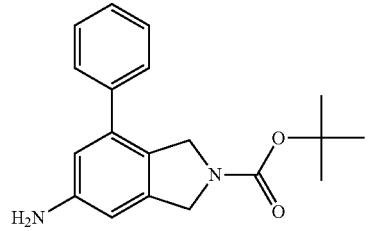 [SMILES: CC(C)(C)OC(=O)N1Cc2cc(N)cc(-c3ccccc3)c2C1]

Step a.

A solution of tert-butyl 4-bromo-6-nitroisoindoline-2-carboxylate (Intermediate 3, 0.4 g, 1.165 mmol), $Cs_2CO_3$ (0.76 g, 2.331 mmol) in 1,4-dioxane:water (8:2; 10 ml) was stirred at rt. The reaction mixture was degassed using nitrogen for 20 min before addition of $Pd(PPh_3)_4$ (0.13 g, 0.116 mmol) and phenylboronic acid (0.21 g, 1.748 mmol). The resulting reaction mixture was heated at 90° C. (external temperature) for 3 h. The resulting mixture was cooled to rt and poured into water (50 ml) and extracted with EtOAc (3×50 ml). The combined organic phase was wash with brine solution (20 ml) and dried over $Na_2SO_4$, filtered and concentrated under reduced pressure. The residue was purified by flash chromatography (5.5% EtOAc in hexane) yielding a tert-butyl 6-nitro-4-phenyl-isoindoline-2-carboxylate (0.385 g, 1.13). $^1$H NMR (400 MHz, DMSO-d6) δ ppm 8.26 (d, J=7.6 Hz, 1H), 8.10 (d, J=10.0 Hz, 1H), 7.47-7.63 (m, 5H), 7.74-7.76 (m, 4H), 1.44 (d, J=14.8 Hz, 9H).

Step b.

To a stirred solution of tert-butyl 6-nitro-4-phenylisoindoline-2-carboxylate (0.38 g, 1.116 mmol) in THF:water (1:1, 10 ml) were added Fe powder (0.31 g, 5.58 mmol) and NH₄Cl (0.29 g, 5.58 mmol) at rt. The reaction mixture was heated at 60° C. for 18 h. The resulting reaction mixture was cooled to rt. The reaction mixture was filtered off and evaporated to dryness under vacuum. The resulting residue was purified by flash chromatography (25% EtOAc in hexane) yielding tert-butyl 6-amino-4-phenylisoindoline-2-carboxylate (0.21 g, 0.767 mmol). This material was used for the next step without further purification. LCMS: Method A, 2.314 min, MS: ES+ 311.52; ¹H NMR (400 MHz, DMSO-d₆) δ ppm 7.34-7.44 (m, 5H), 6.49-6.53 (m, 2H), 5.20 (s, 2H), 4.46-4.51 (m, 4H), 1.25 (d, J=11.2 Hz, 9H).

Intermediate 5 6-(methylsulfonyl)-6,7-dihydro-5H-pyrrolo[3,4-b]pyridine 1-oxide

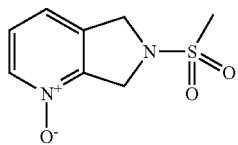

Step a.

A solution of 6,7-dihydro-5H-pyrrolo[3,4-b]pyridine dihydrochloride (CAS Number 147739-88-6, available from Tyger Scientific) (2.0 g, 10.38 mmol) in DCM (20 ml) was stirred at −10° C. DIPEA (4.02 g, 31.15 mmol) and methanesulphonyl chloride (1.43 g, 12.46 mmol) were added to the reaction mixture at −10° C. The reaction mixture was stirred at rt for 18 h. The resulting reaction mixture was poured into saturated NaHCO₃ solution (50 ml) and extracted with EtOAc (3×50 ml). The combined organic phase was washed with brine (50 ml). The organic phase was separated, dried over Na₂SO₄, filtered and concentrated under reduced pressure yielding 6-(methylsulfonyl)-6,7-dihydro-5H-pyrrolo[3,4-b]pyridine (2 g, 10.07 mmol). This material was used for the next step without further purification. LCMS: Method A, 1.479 min, MS: ES+ 199.24; ¹H NMR (400 MHz, DMSO-d6) δ ppm 8.48 (dd, J=0.8 Hz, 4.4 Hz, 1H), 7.79 (d, J=8.0 Hz, 1H), 7.34 (dd, J=5.2 Hz, 8.0 Hz, 1H), 4.69 (d, J=1.2 Hz, 2H), 4.63 (d, J=1.2 Hz, 2H), 3.03 (s, 3H).

Step b.

To a stirred solution of 6-(methylsulfonyl)-6,7-dihydro-5H-pyrrolo[3,4-b]pyridine (2 g, 10.07 mmol) in DCM (20 ml) was added meta-chloroperoxybenzoic acid (2.6 g, 15.10 mmol) portion wise at 0° C. The reaction mixture was stirred at rt for 4 h. The excess of solvent was evaporated to dryness under vacuum. The residue was washed with diethyl ether (3×50 ml). The resulting residue was dried under vacuum to yield 6-(methylsulfonyl)-6,7-dihydro-5H-pyrrolo[3,4-b]pyridine 1-oxide (1.9 g, 8.87 mmol). This material was used for the next step without further purification. LCMS: Method A, 0.581 min, MS: ES+ 214.9; ¹H NMR (400 MHz, DMSO-d6) δ ppm 8.21 (d, J=6.4 Hz, 1H), 7.383-7.419 (m, 1H), 7.33 (d, J=7.6 Hz, 1H), 4.76 (s, 2H), 4.68 (s, 2H), 3.07 (s, 3H).

Intermediate 6
3-amino-N-methylisoquinoline-6-carboxamide
Trifluoracetic Acid Salt

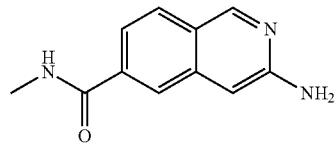

Step a.

LiHMDS (1M in hexane) (18 ml, 18 mmol) was added dropwise to a stirred solution of 6-bromoisoquinolin-3-amine (2.00 g, 9.01 mmol) in THF (40 ml) at −40° C. The resulting reaction mixture was stirred at 0° C. for 30 min. A solution of Boc anhydride (1.96 g, 9.01 mmol) in THF (10 ml) at 0° C. was added dropwise to the reaction mixture. The reaction mixture was stirred at rt for 1 h and then poured into NH₄Cl solution (80 ml) and extracted with EtOAc (3×80 ml). The combined organic phase was collected, dried over Na₂SO₄, filtered and concentrated under reduced pressure yielding tert-butyl (6-bromoisoquinolin-3-yl)carbamate (2.87 g, 8.91 mmol). LCMS: Method A, 2.64 min, MS: ES+ 323.19.

Step b.

A mixture of tert-butyl (6-bromoisoquinolin-3-yl)carbamate (2.80 g, 8.69 mmol), sodium acetate (3.56 g, 43.48 mmol) and Pd(dppf)Cl₂.DCM complex (3.55 g, 4.35 mmol) in MeOH (60 ml) was taken in a pressure vessel. The resulting reaction mixture was stirred at 85° C. under a pressure of CO (25 kg/cm²) for 48 h. The resulting reaction mixture was filtered and the filtrate was concentrated under reduced pressure. The residue was suspended in DCM and filtered. The filtrate was concentrated under reduced pressure and the resulting residue was purified by chromatography (1% MeOH in DCM) yielding methyl 3-((tert-butoxycarbonyl)amino)isoquinoline-6-carboxylate (2.40 g, 7.95 mmol). LCMS: Method A, 2.43 min, MS: ES+ 303.

Step c.

A solution of NaOH (0.70 g, 17.38 mmol) in 50 ml water was added to a solution of methyl 3-((tert-butoxycarbonyl)amino)isoquinoline-6-carboxylate (1.75 g, 5.79 mmol) in MeOH (50 ml) at rt. The reaction mixture was heated at 70° C. for 4 h. The resulting reaction mixture was cooled to rt and acidified by slow addition of citric acid solution under continuous stirring. The resulting mixture was extracted with EtOAc (3×100 ml). The combined organic phase was collected dried over Na₂SO₄, filtered and concentrated under reduced pressure yielding 3-((tert-butoxycarbonyl)amino)-isoquinoline-6-carboxylic acid (1.80 g, quantitative). LCMS: Method A, 2.12 min, MS: ES+ 289.33.

Step d.

A mixture of 3-((tert-butoxycarbonyl)amino)isoquinoline-6-carboxylic acid (1.80 g, 6.25 mmol), HATU (3.56 g, 9.37 mmol) and DIPEA (2.15 ml, 12.5 mmol) in THF (50 ml) was prepared at 0° C. The reaction mixture was stirred at rt for 0.5 h. Methylamine (2M in THF) (6.25 ml, 12.5 mmol) was added to the reaction mixture at rt. The reaction mixture was stirred at rt for 18 h. The resulting reaction mixture was poured into saturated NaHCO₃ solution (100 ml) and extracted with EtOAc (3×100 ml). The combined organic phase was collected, dried over Na₂SO₄, filtered and concentrated under reduced pressure. The resulting residue was purified by column chromatography (3% MeOH in DCM) yielding tert-butyl (6-(methylcarbamoyl)isoquinolin-3-yl)carbamate (1.35 g, 4.48 mmol). LCMS: Method A, 2.01 min, MS: ES+ 302.38.

Step e.

To a solution of tert-butyl (6-(methylcarbamoyl)isoquinolin-3-yl)carbamate (1.30 g, 4.32 mmol) in DCM (50 ml) was added TFA (13 ml) at 0° C. The reaction mixture was stirred at rt for 2 h. The resulting reaction mixture was concentrated under reduced pressure yielding 3-amino-N-methylisoquinoline-6-carboxamide TFA salt (2.0 g, quantitative). LCMS: Method A, 0.89 min, MS: ES+ 202.13.

Intermediate 7 2-(tert-butoxycarbonyl)isoindoline-4-carboxylic Acid

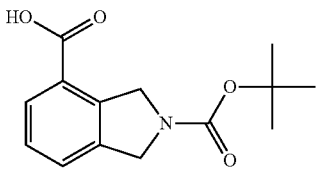 [SMILES: CC(C)(C)OC(=O)N1Cc2cccc(C(=O)O)c2C1]

Step a.

To a solution of methyl 2,3-dimethylbenzoate (CAS Number 15012-36-9, available from Accela Chembio) (5 g, 30.48 mmol) in CCl$_4$ (40 ml) were added NBS (10.8 g, 61 mmol) and AIBN (0.2 g, 0.91 mmol) at rt. The reaction mixture was heated at 80° C. for 16 h. The reaction mixture was filtered and evaporate to yield methyl 2,3-bis(bromomethyl)benzoate (10.1 g, quantitative). This material was used directly for the next step without further purification.

Step b.

To a solution of methyl 2,3-bis(bromomethyl)benzoate (5 g, 15.6 mmol) in THF (30 ml) was added TEA (4.57 ml, 32.9 mmol) and benzylamine (1.67 g, 15.6 mmol) at 0° C. The reaction mixture was stirred at rt for 4 h. The resulting mixture was poured into water (200 ml) and acidified with 50% aqueous HCl solution. The resulting mixture was extracted with EtOAc (150 ml). The aqueous layer was further basified by saturated aqueous NaHCO$_3$ solution and extracted with EtOAc (2×200 ml). The combined organic phase was washed with brine (100 ml) and dried over Na$_2$SO$_4$, filtered and concentrated under reduced pressure to yield methyl 2-benzylisoindoline-4-carboxylate (2.1 g, 7.86 mmol). LCMS: Method A, 1.693 min, MS: ES+ 268.48.

Step c.

To a solution of methyl 2-benzylisoindoline-4-carboxylate (2.1 g, 7.86 mmol) in EtOH (20 ml) were added polymethyl hydroxysilane (7 ml) and Boc anhydride (9 ml, 43 mmol) at 0° C. 20% Pd(OH)$_2$ on carbon (0.5 g) was added to the reaction mixture at rt. The reaction mixture was stirred at rt for 1 h. The resulting mixture was filtered off and evaporated under reduced pressure to yield 2-(tert-butyl) 4-methyl isoindoline-2,4-dicarboxylate (2.6 g, 9.38 mmol). LCMS: Method B, 7.038 min, MS: ES+ 222.03 (M−56).

Step d.

To a solution of 2-(tert-butyl) 4-methyl isoindoline-2,4-dicarboxylate (2.5 g, 9.02 mmol) in THF:water (1:1, 20 ml) was added NaOH (0.9 g, 22.56 mmol) at rt. The reaction mixture was refluxed for 4 h. The reaction mixture was cooled to rt and poured into ice water (50 ml). The resulting mixture was acidified with 50% aqueous HCl solution. The resulting mixture was extracted with EtOAc (2×300 ml). The combined organic phase was dried over Na$_2$SO$_4$, filtered and concentrated under reduced pressure to yield 2-(tert-butoxycarbonyl) isoindoline-4-carboxylic acid (1.67 g, 6.34 mmol). LCMS: Method A, 2.036 min, MS: ES+ 262.43.

Intermediate 8
7-cyano-3-oxo-2,3-dihydro-1H-inden-4-yl Trifluoromethanesulfonate

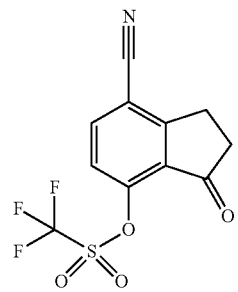

Step a.

A solution of 4-bromo-7-hydroxyindanone (0.95 g, 4 mmol) and copper(I) cyanide (0.47 g, 5.2 mmol) in DMF (8 mL) was heated for 5 h at 150° C. Further copper(I) cyanide (0.5 g, 5.5 mmol) and copper(I) iodide (0.1 g, 0.5 mmol) were added and heating continued at 150° C. overnight. The reaction mixture was cooled to rt and water and EtOAc were added. The mixture was filtered and phases separated. The aqueous phase was extracted twice with EtOAc, and the combined organics were washed with brine, dried over Na$_2$SO$_4$, filtered and concentrated to give 7-hydroxy-1-oxo-2,3-dihydro-1H-indene-4-carbonitrile as a brown solid (246 mg, 35%). LCMS (Method P): rt 2.5-3.0 min, m/z 172 [M−H]$^-$; $^1$H NMR (400 MHz, CDCl$_3$) δ ppm 9.47 (brs, 1H), 7.75 (d, J=8.2 Hz, 1H), 6.88 (d, J=8.2 Hz, 1H), 3.34-3.24 (m, 2H), 2.87-2.79 (m, 2H).

Step b.

To a solution of 7-hydroxy-1-oxo-2,3-dihydro-1H-indene-4-carbonitrile (246 mg, 1.42 mmol) and DIPEA (0.37 ml, 2.13 mmol) in DCM (7 mL) at 0° C. was added Trifluoromethanesulfonic anhydride (0.29 ml, 1.70 mmol) dropwise. The resulting mixture was stirred at 0° C. for 30 min, before being warmed to rt. The reaction mixture was diluted with DCM and washed sequentially with saturated aqueous NaHCO$_3$ solution, water and brine. The organic phase was dried over Na$_2$SO$_4$, filtered and concentrated to an oil. Purification by flash chromatography over silica gel eluting with 0 to 20% EtOAc in hexane gave 7-cyano-3-oxo-2,3-dihydro-1H-inden-4-yl trifluoromethanesulfonate as a brown solid (283 mg, 65%). LCMS (Method P): rt 3.58 min, m/z 306 [M+H]$^+$; NMR (400 MHz, CDCl$_3$) δ ppm 7.96 (d, J=8.4 Hz, 1H), 7.34 (d, J=8.4 Hz, 1H), 3.41-3.35 (m, 2H), 2.92-2.86 (m, 2H).

Intermediate 9 2-bromo-N-(2-(6-oxopyrimidin-1(6H)-yl)ethyl)benzamide

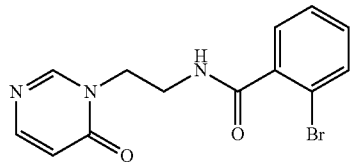 [SMILES: O=C(NCCn1cnccc1=O)c1ccccc1Br]

3-(2-Aminoethyl)pyrimidin-4(3H)-one bis HCl salt (200 mg, 0.91 mmol), DIPEA (0.2 ml, 1.37 mmol) and 2-bromobenzoyl chloride (219 mg, 1.0 mmol) were combined in DCM (5 ml). After 2 h, the reaction mixture was evaporated to a residue, which was purified on a prepacked silica column (12 g) eluting with 0 to 100% EtOAc in hexane, followed by 0 to 20% MeOH in DCM, to give 2-bromo-N-(2-(6-oxopyrimidin-1(6H)-yl)ethyl)benzamide, as a yellow glass (130 mg) that was used without further purification. LCMS (Method R): rt 2.09 min, m/z 322/324 [M+H]+; 1H NMR (400 MHz, CDCl3) δ ppm 9.77 (s, 1H), 7.73 (d, 1H), 7.40-7.50 (3H, m), 7.31 (t, 1H), 7.21 (t, 1H), 6.60 (d, 1H), 4.49 (br s, 2H), 3.90 (br s, 2H).

Intermediate 10
2-chloro-5-(1H-imidazol-1-yl)benzonitrile

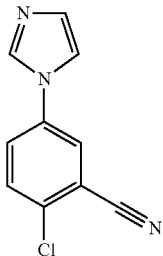 [SMILES: N#Cc1cc(-n2ccnc2)ccc1Cl]

(4-Chloro-3-cyanophenyl)boronic acid (287 mg, 1.58 mmol), 1H-imidazole (215 mg, 3.16 mmol), copper (II) acetate (632 mg, 3.48 mmol) and pyridine (0.64 ml, 7.90 mmol) were combined in DCM (16 ml) and heated open vessel at 40° C. for 18 h. The reaction mixture was cooled to rt and filtered through a celite pad, washing through with DCM. The filtrate was evaporated and purified by flash column chromatography (0-50% EtOAc in hexane) to give 2-chloro-5-(1H-imidazol-1-yl)benzonitrile (64 mg, 20%). LCMS (Method R): rt 2.00 min, m/z 204 [M+H]+; 1H NMR (400 MHz, CDCl3) δ ppm 7.88 (br s, 1H), 7.72 (d, 1H), 7.66 (d, 1H), 7.59 (dd, 1H), 7.25-7.30 (m, 2H).

Intermediate 11 tert-butyl
4-bromo-6-formylisoindoline-2-carboxylate

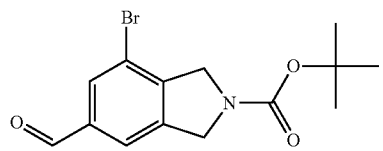 [SMILES: CC(C)(C)OC(=O)N1Cc2cc(C=O)cc(Br)c2C1]

To a solution of tert-butyl 4-bromo-6-(hydroxymethyl) isoindoline-2-carboxylate (Prepared as in step a of Example 216, 0.700 g, 2.140 mmol) in DCM (15 ml) was added Dess Martin periodinane (1.180 g, 2.78 mmol) at 0° C. The reaction mixture was stirred at rt for 2 h. The resulting mixture was poured into saturated NaHCO3 solution (25 ml) and extracted with EtOAc (3×25 ml). The combined organic phase was dried over Na2SO4, filtered and concentrated under reduced pressure yielding tert-butyl 4-bromo-6-formylisoindoline-2-carboxylate (0.600 g, 1.846 mmol). This material was used directly for next step without further purification. LCMS: Method A, 2.400 min, MS: ES+ 311.28, 313.28 [M−15]

Intermediate 12 tert-butyl 6-(aminomethyl)-4-(4-cyanophenyl)isoindoline-2-carboxylate

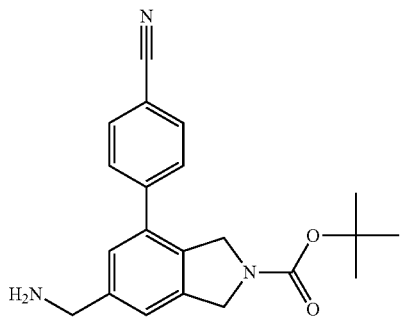 [SMILES: CC(C)(C)OC(=O)N1Cc2cc(CN)cc(-c3ccc(C#N)cc3)c2C1]

Step a.

To a stirred solution of Intermediate 11 (4.600 g, 14.153 mmol) in 1,4-dioxane:water (9:1, 10 ml) were added K3PO4 (9.000 g, 6.462 mmol) and 4-cyanophenylboronic Acid (2.479 g, 16.98 mmol) at rt. The reaction mixture was degassed with N2 gas for 30 min before addition of PdCl2(dppf) (0.220 g, 0.305 mmol). The resulting reaction mixture was heated at 90° C. for 5 h. The reaction mixture was cooled to rt, poured into water (250 ml) and extracted with EtOAc (3×70 ml). The combined organic phase was washed with brine solution (2×100 ml), dried over Na2SO4, filtered and concentrated under reduced pressure. The residue was purified by flash column chromatography (25% EtOAc in hexane) yielding tert-butyl 4-(4-cyanophenyl)-6-formylisoindoline-2-carboxylate (4.700 g, 13.505 mmol). LCMS: Method C, 6.930 min, MS: ES− 347.10

Step b.

To a stirred solution of tert-butyl 4-(4-cyanophenyl)-6-formylisoindoline-2-carboxylate (0.600 g, 1.724 mmol) in MeOH (25 ml) was added NH2OH.HCl (1.198 g, 17.24 mmol) at rt. The reaction mixture was stirred at rt for 4 h. The reaction mixture was evaporated under reduced pressure, poured into saturated NaHCO3 solution (50 ml) and extracted with EtOAc (3×50 ml). The combined organic phase was dried over Na2SO4, filtered and concentrated under reduced pressure. Then residue obtained was dissolved in AcOH (25 ml) and cooled to 0° C. Zinc dust (0.788 g, 12.060 mmol) was added to the reaction mixture at 0° C. The reaction mixture was stirred at rt for 40 h. The resulting reaction mixture was poured into saturated NaHCO3 solution (150 ml) and extracted with EtOAc (3×25 ml). The combined organic phase was dried over Na2SO4, filtered and concentrated under reduced pressure yielding tert-butyl 6-(aminomethyl)-4-(4-cyanophenyl)isoindoline-2-carboxylate (0.400 g, quantitative). This material was use directly for next step without further purification. LCMS: Method A, 1.627 min, MS: ES+ 350.49

51
Intermediate 13 2-(tert-butyl) 5-methyl 7-bromoisoindoline-2,5-dicarboxylate

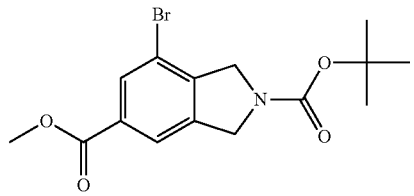 [SMILES: COC(=O)c1cc(Br)c2c(c1)CN(C(=O)OC(C)(C)C)C2]

Step a.

To a solution of methyl 7-bromoisoindoline-5-carboxylate HCl salt (prepared as in step e of Example 98, 20.00 g, 68.4 mmol) in DMF (200 ml) was added TEA (28.6 ml, 205 mmol) at 0° C. Boc anhydride (17.39 g, 82.05 mmol) was added to the reaction at 0° C. The reaction mixture was stirred at rt for 4 h. The resulting reaction mixture was poured into ice-cold water (200 ml) and extracted with EtOAc (3×200 ml). The combined organic layer was dried over $Na_2SO_4$, filtered and concentrated under reduced pressure. The resulting residue was triturated with n-hexane (2×5 ml) yielding 2-(tert-butyl) 5-methyl 7-bromoisoindoline-2,5-dicarboxylate (21.00 g, 58.95 mmol). This material was directly used for next step without any further purification. LCMS: Method A, 2.647 min, MS: ES+ 341.36, 343.36 (M−15); $^1$H NMR (400 MHz, DMSO-d6) δ ppm 7.99 (s, 1H), 7.93 (d, J=9.2 Hz, 1H), 4.74 (d, J=9.6 Hz, 2H), 4.58 (d, J=9.2 Hz, 2H), 3.87 (s, 3H), 1.46 (s, 9H).

52
Intermediate 14 3-(3-(4,4,5,5-tetramethyl-1,3,2-dioxaborolan-2-yl)phenyl)oxazolidin-2-one

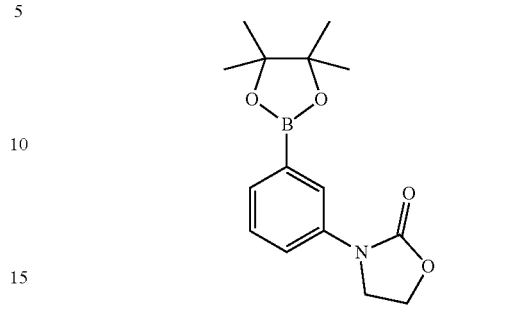

To a stirred solution of 3-(3-bromophenyl)oxazolidin-2-one (CAS Number 1086221-37-5; 0.600 g, 2.49 mmol) in 1,4-dioxane (10 ml) were added KOAc (0.488 g, 4.98 mmol) and bispinacolatodiboron (0.948 g, 3.73 mmol) at rt. The reaction mixture was degassed for 15 min before addition of $PdCl_2(dppf)$ (0.181 g, 0.248 mmol). The resulting reaction mixture was heated at 100° C. for 2 h. The resulting reaction mixture was combined with one other batch prepared on the same scale by an identical method. The reaction mixture was cooled to rt and poured into water (70 ml). The resulting mixture was extracted with EtOAc (3×50 ml). The combined organic phase was dried over $Na_2SO_4$, filtered and concentrated under reduced pressure yielding 3-(3-(4,4,5,5-tetramethyl-1,3,2-dioxaborolan-2-yl)phenyl)oxazolidin-2-one (1.500 g, Quantitative). This material was directly used for next step without any further purification.

Scheme A

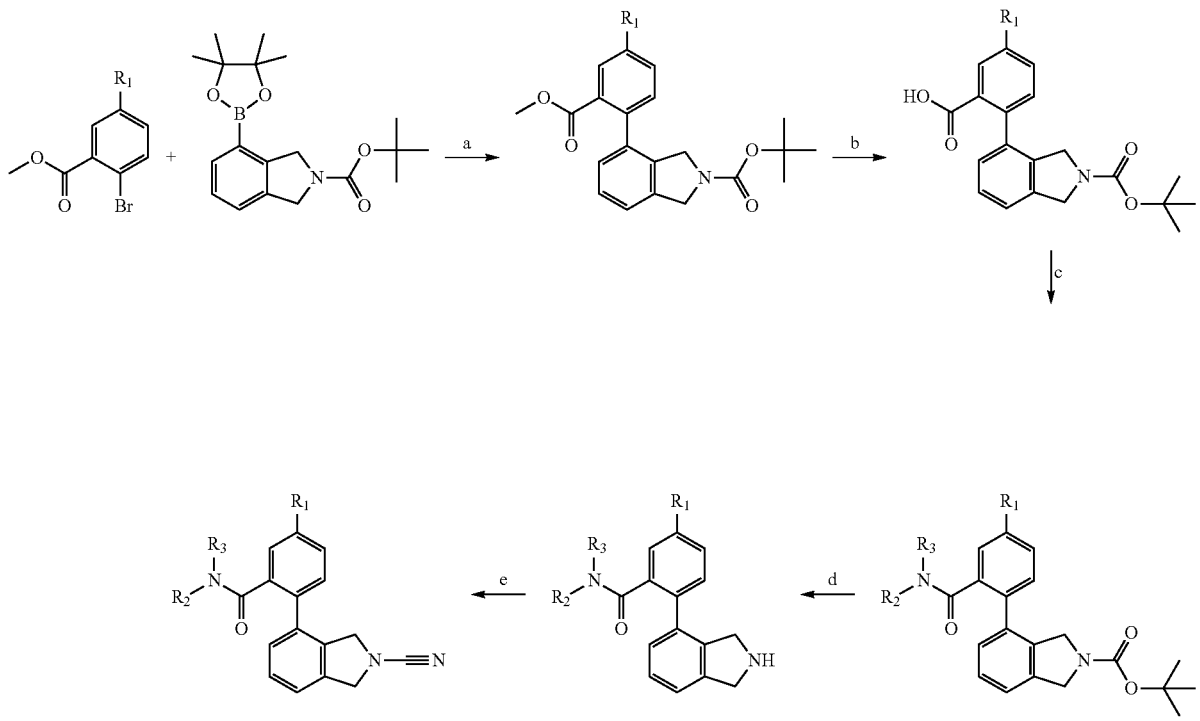

Reagents and conditions: a) $NaHCO_3$, $PdCl_2(dppf)$, DMF; b) $LiOH \cdot H_2O$, water, THF; c) EDC, HOBt, $R_2R_3NH$, DIPEA, THF; d) TFA, DCM; e) BrCN, $K_2CO_3$, THF

Example 1
5-cyano-2-(2-cyanoisoindolin-4-yl)benzamide (Prepared According to Scheme A)

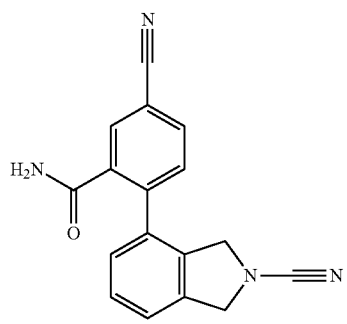 [SMILES: N#Cc1ccc(-c2cccc3c2CN(C#N)C3)c(C(N)=O)c1]

Step a.

A solution of methyl 2-bromo-5-cyanobenzoate (CAS Number 1031927-03-3, available from Combi blocks) (0.30 g, 1.250 mmol), tert-butyl 4-(4,4,5,5-tetramethyl-1,3,2-dioxaborolan-2-yl)isoindoline-2-carboxylate (Intermediate 2, 0.86 g, 2.500 mmol) and $NaHCO_3$ (0.21 g, 2.500 mmol) in DMF:water (8.5:1.5) (3.5 ml) was degassed with nitrogen for 20 min at rt. $PdCl_2$(dppf) (0.091 g, 0.125 mmol) was added to the reaction mixture at rt. The reaction mixture was heated at 100° C. for 5 h. The resulting reaction mixture was cooled to rt and was combined with 3 other batches prepared on the same scale by an identical method. The resulting reaction mixture was poured into water (100 ml) and extracted with EtOAc (2×100 ml). The combined organic phase was washed with brine (50 ml) and dried over $Na_2SO_4$, filtered and concentrated under reduced pressure. The resulting residue was purified by flash chromatography (10% EtOAc in hexane) yielding tert-butyl 4-(4-cyano-2-(methoxycarbonyl)phenyl)isoindoline-2-carboxylate (0.80 g, 2.115 mmol). LCMS: Method A, 2.583 min, MS: ES+ 323.18 (M−56); $^1$H NMR (400 MHz, DMSO-d6) δ ppm 8.31 (s, 1H), 8.12 (d, J=8 Hz, 1H), 7.65 (t, J=7.6 Hz, 1H), 7.34-7.40 (m, 2H), 7.052 (t, J=8 Hz, 1H), 4.67 (d, J=9.2 Hz, 2H), 4.33 (d, J=17.2 Hz, 2H), 3.60 (s, 3H) 1.42 (d, J=18 Hz, 9H).

Step b.

To a solution of tert-butyl 4-(4-cyano-2-(methoxycarbonyl)phenyl)isoindoline-2-carboxylate (0.8 g, 2.115 mmol) in THF (5 ml) was added a solution of $LiOH.H_2O$ (0.36 g, 8.462 mmol) in water (5 ml) at rt. The reaction mixture was stirred at rt for 15 h. The resulting reaction mixture was diluted by water and extracted with EtOAc (3×30 ml) to separate undesired impurities. The resulting aqueous layer was acidified by 1M HCl (40 ml) and extracted with EtOAc (3×50 ml). The combined organic phase was wash with brine (50 ml) and dried over $Na_2SO_4$, filtered and concentrated under reduced pressure yielding 2-(2-(tert-butoxycarbonyl)isoindolin-4-yl)-5-cyanobenzoic acid (0.65 g, 1.785 mmol). LCMS: Method A, 2.279 min, MS: ES− 363.23; $^1$H NMR (400 MHz, DMSO-d6) δ ppm 13.27 (br s, 1H), 8.25 (s, 1H), 8.06 (d, J=8 Hz, 1H), 7.59 (t, J=8 Hz, 1H), 7.33-7.37 (m, 2H), 7.07-7.11 (m, 1H), 4.65 (d, J=8.8 Hz, 2H), 4.34 (d, J=18 Hz, 2H), 1.41 (d, J=18 Hz, 9H).

Step c.

To a solution of 2-(2-(tert-butoxycarbonyl)isoindolin-4-yl)-5-cyanobenzoic acid (0.65 g, 1.785 mmol) in THF (8 ml) were added EDC.HCl (0.68 g, 3.571 mmol), HOBT (0.27 g, 1.785 mmol) and DIPEA (0.91 ml, 5.357 mmol) at rt. The reaction mixture was stirred for 15 min and then after $NH_4Cl$ (0.48 g, 8.928 mmol) was added in to the reaction mixture at rt. The reaction mixture was stirred at rt for 15 h. The resulting reaction mixture was poured into $NaHCO_3$ solution (50 ml) and extracted with EtOAc (3×50 ml). The combined organic phase was washed with brine (50 ml), dried over $Na_2SO_4$, filtered and concentrated under reduced pressure. The resulting residue was purified by flash chromatography (2% MeOH in DCM) yielding tert-butyl 4-(2-carbamoyl-4-cyanophenyl)isoindoline-2-carboxylate (0.51 g, 1.404 mmol). LCMS: Method A, 2.131 min, MS: ES− 362.13; $^1$H NMR (400 MHz, DMSO-d6) δ ppm 7.94-7.98 (m, 2H), 7.78 (d, J=9.6 Hz, 1H), 7.58 (t, J=7.2 Hz, 1H), 7.42 (d, J=12.4 Hz, 1H), 7.31-7.37 (m, 2H), 7.11-7.15 (m, 1H), 4.65 (d, J=9.6 Hz, 2H), 4.46 (d, J=13.6 Hz, 2H), 1.42 (d, J=14 Hz, 9H).

Step d.

To a solution of tert-butyl 4-(2-carbamoyl-4-cyanophenyl)isoindoline-2-carboxylate (0.51 g, 1.404 mmol) in DCM (10 ml) was added TFA (3.0 ml) at rt. The reaction mixture was stirred at rt for 1 h. The resulting reaction mixture was concentrated under reduced pressure. The obtained residue was azeotropically distilled with a with DCM (5 ml), triturated with diethyl ether (3 ml) and finally dried under high vacuum yielding 5-cyano-2-(isoindolin-4-yl)benzamide TFA salt (0.46 g, 1.22 mmol). LCMS: Method A, 1.390 min, MS: ES+ 264.13.

Step e.

To a solution of 5-cyano-2-(isoindolin-4-yl)benzamide TFA salt (0.46 g, 1.22 mmol) in THF (8 ml) was added $K_2CO_3$ (0.42 g, 3.050 mmol) at rt. Cyanogen bromide (0.13 g, 1.220 mmol) was added to the reaction mixture at rt. The reaction mixture was stirred at rt for 30 min. The resulting reaction mixture was poured into water (75 ml) and extracted with EtOAc (3×50 ml). The combined organic phase was dried over $Na_2SO_4$, filtered and concentrated under reduced pressure. The resulting residue was purified by flash chromatography (1.5% MeOH in DCM) yielding the title compound (0.32 g, 1.111 mmol). LCMS: Method D, 3.432 min, MS: ES+ 288.97; $^1$H NMR (400 MHz, DMSO-d6) δ ppm 7.98 (d, J=1.2 Hz, 1H), 7.93-7.96 (m, 1H), 7.77 (s, 1H), 7.56 (d, J=7.6 Hz, 1H), 7.44 (s, 1H), 7.34-7.40 (m, 2H), 7.17 (d, J=6.8 Hz, 1H), 4.85 (s, 2H), 4.66 (s, 2H).

Compounds in Table 1 were synthesised using a procedure similar to that described for Example 1, varying the aryl halide used in step c.

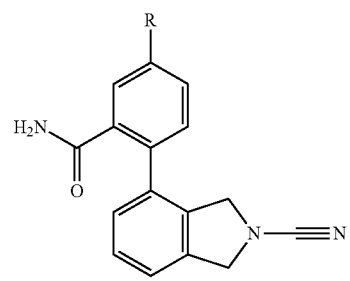

TABLE 1

| Example | R | Name | Aryl halide CAS Number | LCMS method | LCMS RT/ min | MS ES+ |
|---|---|---|---|---|---|---|
| Example 2 | Cl | 5-chloro-2-(2-cyanoisoindolin-4-yl)benzamide | 27007-53-0 | D | 3.838 | 298.02 |
| Example 3 | Me | 2-(2-cyanoisoindolin-4-yl)-5-methylbenzamide | 90971-88-3 | E | 3.536 | 278.45 |

Example 4 4-(2-(azetidine-1-carbonyl)-4-cyanophenyl)isoindoline-2-carbonitrile

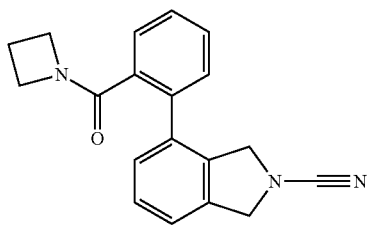 [SMILES: N#CN1Cc2cccc(-c3ccccc3C(=O)N3CCC3)c2C1]

This was synthesised using a procedure similar to that described for Example 1, using azetidine in step c. LCMS: Method J, 4.6 min, MS: ES+ 329.

Example 154
2-chloro-6-(2-cyanoisoindolin-4-yl)benzamide

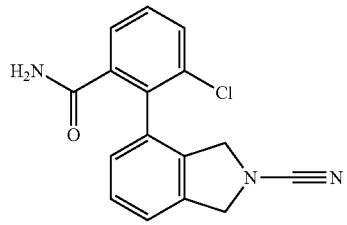 [SMILES: N#CN1Cc2cccc(-c3c(Cl)cccc3C(N)=O)c2C1]

This was synthesised using a procedure similar to that described for Example 1, using methyl 2-bromo-6-chlorobenzoate (CAS Number 685892-23-3) in step a. LCMS: Method J, 3.56 min, MS: ES+ 298.

Example 155 4-(2-(pyrrolidine-1-carbonyl)phenyl)isoindoline-2-carbonitrile

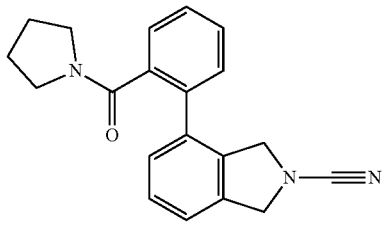 [SMILES: N#CN1Cc2cccc(-c3ccccc3C(=O)N3CCCC3)c2C1]

This was synthesised using a procedure similar to that described for Example 1, using pyrrolidine (CAS Number 123-75-1) in step c. LCMS: Method J, 3.95 min, MS: ES+ 318.

Example 156 5-cyano-2-(2-cyanoisoindolin-4-yl)-4-methylbenzamide

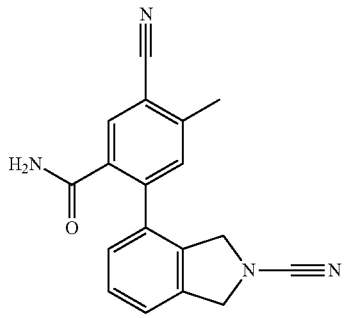 [SMILES: Cc1cc(-c2cccc3c2CN(C#N)C3)c(C(N)=O)cc1C#N]

This was synthesised using a procedure similar to that described for Example 1, using methyl 2-bromo-4-methyl-5-cyanobenzoate (CAS Number 1399182-23-0) in step a.

LCMS: Method J, 2.72 min, MS: ES+ 302.

Scheme B

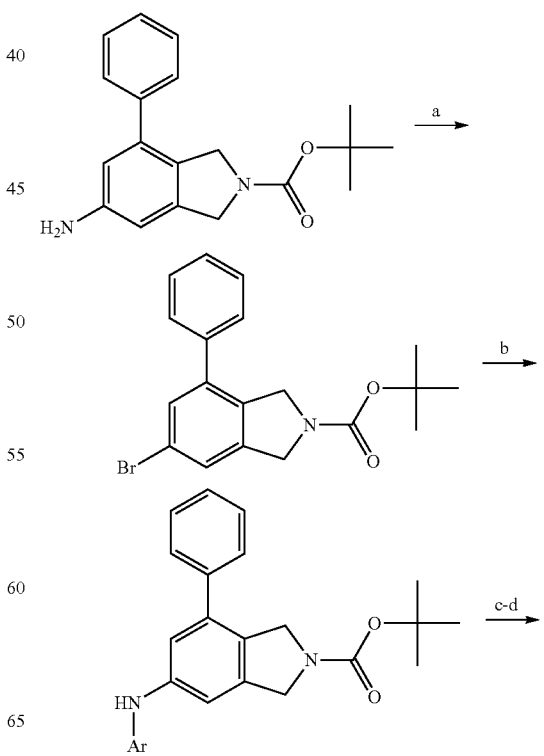

-continued

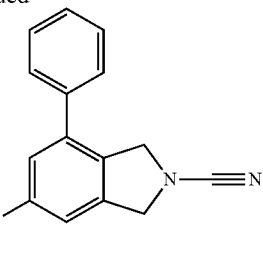

Reagents and conditions: a) isoamyl nitrite, Cu(II)Br, MeCN; b) ArNH$_2$, Cs$_2$CO$_3$, Xantphos, Pd$_2$(dba)$_3$, 1,4-dioxane; c) TFA, DCM; d) BrCN, K$_2$CO$_3$, THF Example 5 6-((1-methyl-1H-pyrazol-4-yl)amino)-4-phenylisoindoline-2-carbonitrile (Prepared According to Scheme B)

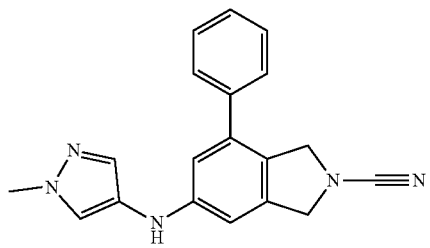 [SMILES: Cn1cc(Nc2cc3c(c(-c4ccccc4)c2)CN(C#N)C3)cn1]

Step a.

To a solution of tert-butyl 6-amino-4-phenylisoindoline-2-carboxylate (Intermediate 4, 0.25 g, 0.806 mmol) in MeCN (10 ml) was added copper (II)bromide (0.27 g, 1.200 mmol) at rt. Isoamyl nitrite (0.142 g, 1.200 mmol) was added rt. The reaction mixture was heated at 50° C. for 1 h. The resulting reaction mixture was poured into 2M HCl (15 ml) and extracted with EtOAc (3×10 ml). The combined organic phase was dried over Na$_2$SO$_4$, filtered and concentrated under reduced pressure. The resulting residue was purified by flash chromatography (2% EtOAc in hexane) yielding tert-butyl 6-bromo-4-phenylisoindoline-2-carboxylate (0.26 g, 0.696 mmol). LCMS: Method A, 3.012 min, MS: ES+ 318.1 (M−56).

Step b.

To a solution of tert-butyl 6-bromo-4-phenylisoindoline-2-carboxylate (0.25 g, 0.670 mmol) in 1,4-dioxane (10 ml) were added 1-methyl-1H-pyrazol-4-amine (CAS Number 69843-13-6, available from Combi blocks) (0.20 g, 2.010 mmol) and Cs$_2$CO$_3$ (0.44 g, 1.34 mmol) at rt. The reaction mixture was degassed with nitrogen at rt for 10 min. Xantphos (0.02 g, 0.033 mmol) and Pd$_2$(dba)$_3$ (0.03 g, 0.033 mmol) were added in to the reaction mixture at rt. The reaction mixture was heated at 95° C. for 6 h. The resulting reaction mixture was cooled to rt, poured into water (30 ml) and extracted with EtOAc (3×15 ml). The combined organic phase was dried over Na$_2$SO$_4$, filtered and concentrated under reduced pressure. The resulting residue was purified by flash chromatography (70% EtOAc in hexane) yielding tert-butyl 6-((1-methyl-1H-pyrazol-4-yl)amino)-4-phenylisoindoline-2-carboxylate (0.085 g, 0.217 mmol). LCMS: Method A, 2.417 min, MS: ES+ 391.5.

Steps c, d.

The title compound was synthesised from the intermediate above using a procedure similar to that described for steps d and e of Example 1. LCMS: Method D, 4.190 min, MS: ES+ 316.05; $^1$H NMR (400 MHz, DMSO-d6) δ ppm 7.71 (s, 1H), 7.67 (s, 1H), 7.35-7.43 (m, 6H), 6.71 (s, 1H), 6.67 (s, 1H), 4.70 (s, 4H), 3.80 (s, 3H).

Example 6 4-phenylisoindoline-2-carbonitrile

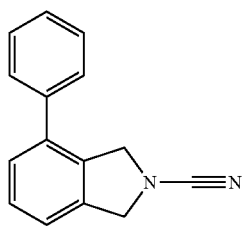 [SMILES: N#CN1Cc2cccc(-c3ccccc3)c2C1]

Step a

To a stirred solution of 4-bromoisoindoline hydrochloride (CAS Number 923590-95-8; 0.1 g, 0.426 mmol) in 1,4-dioxane:water (5:1; 6 ml) were added phenylboronic acid (0.078 g, 0.64 mmol) and K$_2$CO$_3$ (0.176 g, 1.279 mmol) at rt. The reaction mixture was degassed with nitrogen for 10 min. Pd(PPh$_3$)$_4$ (0.024 g, 0.021 mmol) was added to the reaction and reaction mixture was heated at 100° C. for 16 h. The resulting reaction mixture was cooled to rt and combined with 2 other batches prepared on the same scale by an identical method. The reaction mixture was poured into water (100 ml) and extracted with EtOAc (2×20 ml). The combined organic phase was separated, dried over Na$_2$SO$_4$, filtered and evaporated to dryness. The residue was re-dissolved in EtOAc (2 ml) and 4M HCl in 1,4-dioxane (0.3 ml) was added at 0° C. The mixture was stirred at rt for 30 min. The excess of solvent was distilled under vacuum and residue was triturated with diethyl ether (10 ml) and EtOAc (10 ml) yielding 4-phenylisoindoline hydrochloride (0.1 g, 0.512 mmol). This material was used for the next step without further purification. LCMS: Method A, 1.731 min, MS: ES+ 196.44; $^1$H NMR (400 MHz, DMSO-d6) δ ppm 9.84 (br, s, 1H), 7.42-7.60 (m, 8H), 4.49-4.63 (m, 4H).

Step b.

To a stirred solution of 4-phenylisoindoline hydrochloride (0.09 g, 0.461 mmol) in THF (5 ml) were added K$_2$CO$_3$ (0.254 g, 1.844 mmol) and cyanogen bromide (0.058 g, 0.553 mmol) at rt. The reaction mixture was stirred at rt for 16 h. The reaction mixture was filtered through celite bed and filtrate was evaporated to dryness. The resulting crude material was purified by flash chromatography (20% EtOAc in hexane) yielding 4-phenylisoindoline-2-carbonitrile (0.02 g, 0.091 mmol). LCMS: Method C, 7.083 min, MS: ES+ 221.10; $^1$H NMR (400 MHz, DMSO-d6) δ ppm 7.41-7.55 (m, 6H), 7.31-7.39 (m, 2H), 4.86 (d, J=12.8 Hz, 4H).

Scheme C

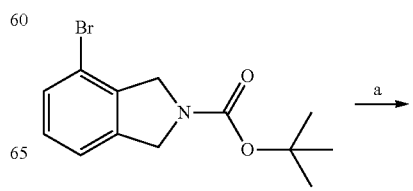

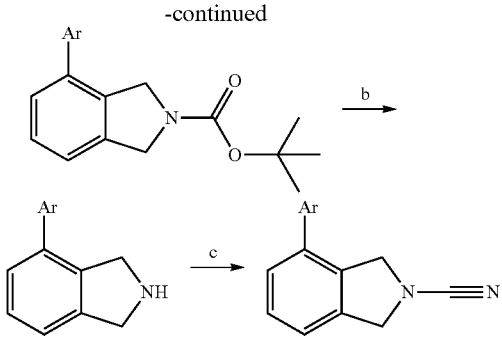

Reagents and conditions: a) ArB(OH)₂, Cs₂CO₃, Pd(PPh₃)₄, 1,4-dioxane, water; b) TFA, DCM; c) BrCN, K₂CO₃, THF Example 7 4-(1-methyl-1H-pyrazol-4-yl)isoindoline-2-carbonitrile

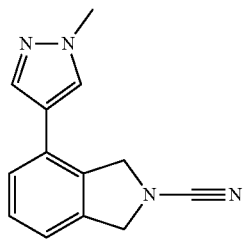 [SMILES: Cn1cc(-c2cccc3c2CN(C#N)C3)cn1]

Step a.

To a stirred solution of tert-butyl 4-bromoisoindoline-2-carboxylate (Intermediate 1, 0.2 g, 0.671 mmol) in 1,4-dioxane:water (4.1; 5 ml) were added Cs₂CO₃ (0.44 g, 1.342 mmol) and 1-methyl-1H-pyrazole-4-boronic acid pinacol ester (CAS Number 761446-44-0; available from Combi Blocks) (0.17 g, 0.805 mmol) at rt. The reaction mixture was degassed for 20 min. Pd(PPh₃)₄ (0.077 g, 0.067 mmol) was added to the reaction mixture at rt. The reaction mixture was heated at 85° C. for 30 min. The resulting reaction mixture was cooled to rt, diluted with water (100 ml) and extracted with EtOAc (3×80 ml). The combined organic phase was separated, dried over Na₂SO₄, filtered and concentrated under reduced pressure. The resulting crude material was purified by flash chromatography (30% EtOAc in hexane) yielding tert-butyl 4-(1-methyl-1H-pyrazol-4-yl)isoindoline-2-carboxylate (0.121 g, 0.404 mmol). LCMS: Method A, 2.335 min, MS: ES+ 300.53; ¹H NMR (400 MHz, DMSO-d6) δ ppm 8.03 (d, J=11.2 Hz, 1H), 7.78 (d, J=20.4 Hz, 1H), 7.43-7.49 (m, 1H), 7.31 (t, J=7.2 Hz, 1H), 7.19 (t, J=7.6 Hz, 1H), 4.69 (s, 2H), 4.62 (d, J=11.2 Hz, 2H), 3.90 (s, 3H), 1.48 (s, 9H).

Steps b, c.

The title compound was synthesised from the intermediate above using a procedure similar to that described for steps d and e of Example 1. LCMS: Method B, 5.102 min, MS: ES+ 225.05; ¹H NMR (400 MHz, DMSO-d6) δ ppm 8.06 (s, 1H), 7.81 (s, 1H), 7.50 (d, J=7.6 Hz, 1H), 7.32 (t, J=7.6 Hz, 1H), 7.15 (J=7.6 Hz, 1H), 4.89 (s, 2H), 4.79 (2H), 3.86 (s, 3H).

Compounds in Table 2 were synthesised using a procedure similar to that described for Example 7

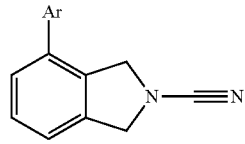

TABLE 2

| Ex | Ar— | Name | Aryl boronic acid/ester CAS Number | LCMS method | LCMS RT | MS ES+ |
| --- | --- | --- | --- | --- | --- | --- |
| Example 8 | quinolin-3-yl | 4-(quinolin-3-yl)isoindoline-2-carbonitrile | 191162-39-7 | E | 3.821 | 272.23 |
| Example 9 | 1H-pyrrolo[2,3-b]pyridin-5-yl | 4-(1H-pyrrolo[2,3-b]pyridin-5-yl)isoindoline-2-carbonitrile | 754214-56-7 | E | 3.529 | 261.18 |
| Example 10 | 1-methyl-1,2,3,6-tetrahydropyridin-4-yl | 4-(1-methyl-1,2,3,6-tetrahydropyridin-4-yl)isoindoline-2-carbonitrile | 454482-11-2 | D | 3.961 | 240.07 |
| Example 11 | 2-methyl-2H-indazol-5-yl | 4-(2-methyl-2H-indazol-5-yl)isoindoline-2-carbonitrile | 952319-71-0 | G | 2.644 | 275 |
| Example 12 | o-tolyl | 4-(o-tolyl)isoindoline-2-carbonitrile | 16419-60-6 | G | 3.199 | 235 |

TABLE 2-continued

| Ex | Ar— | Name | Aryl boronic acid/ester CAS Number | LCMS method | LCMS RT | MS ES+ |
|---|---|---|---|---|---|---|
| Example 13 | NC-C6H4- | 4-(4-cyanophenyl)isoindoline-2-carbonitrile | 126747-14-6 | G | 2.797 | 246 |
| Example 157 | 2-H2NCO-C6H4- | 2-(2-cyanoisoindolin-4-yl)benzamide | 380430-54-6 | D | 3.346 | 263.97 |
| Example 158 | 3-F-2-H2NCO-C6H3- | 2-(2-cyanoisoindolin-4-yl)-5-fluorobenzamide | 1217500-90-7 | D | 3.512 | 281.99 |
| Example 159 | 2-CH3CO-C6H4- | 4-(2-acetylphenyl)isoindoline-2-carbonitrile | 308103-40-4 | D | 4.406 | 263.04 |
| Example 160 | 2-MeNHSO2-C6H4- | 2-(2-cyanoisoindolin-4-yl)-N-methylbenzenesulfonamide | 956283-09-3 | A | 2.084 | ES– 312.33 |
| Example 161 | 2-H2NSO2-C6H4- | 2-(2-cyanoisoindolin-4-yl)benzenesulfonamide | 193753-37-6 | J | 3.63 | 300 |
| Example 162 | 2-MeSO2-C6H4- | 4-(2-(methylsulfonyl)phenyl)isoindoline-2-carbonitrile | 330804-03-0 | Q | 3.42 | 299 |

Example 14 4-(1-methylpiperidin-4-yl)isoindoline-2-carbonitrile

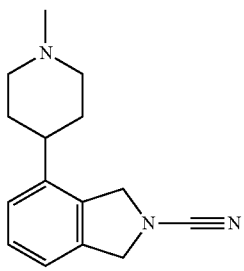 [SMILES: CN1CCC(c2cccc3c2CN(C#N)C3)CC1]

Step a. was carried out using a procedure similar to that described for step a of Example 7 to give tert-butyl 4-(1-methyl-1,2,3,6-tetrahydropyridin-4-yl)isoindoline-2-carboxylate.

Step b. To a solution of tert-butyl 4-(1-methyl-1,2,3,6-tetrahydropyridin-4-yl)isoindoline-2-carboxylate (0.35 g, 1.111 mmol) in MeOH (20 ml) was added 10% dry Pd/C (0.18 g) at rt. The reaction mixture was purged with hydrogen gas at rt for 7 h. The resulting reaction mixture was carefully filtered through celite hyflow and the celite bed was washed with MeOH (20 ml). The resulting filtrate was concentrated under reduced pressure. The resulting residue was purified by flash chromatography (2% MeOH in DCM) yielding tert-butyl 4-(1-methylpiperidin-4-yl)isoindoline-2-carboxylate (0.29 g, 0.917 mmol). LCMS: Method A, 1.816 min, MS: ES+ 317.37.

Steps c, d. The title compound was synthesised from the intermediate above using a procedure similar to that described for steps d and e of Example 1. LCMS: Method D, 3.883 min, MS: ES+ 242.06

Example 15 N-benzyl-3-(6-cyano-6,7-dihydro-5H-pyrrolo[3,4-b]pyridin-4-yl)benzamide

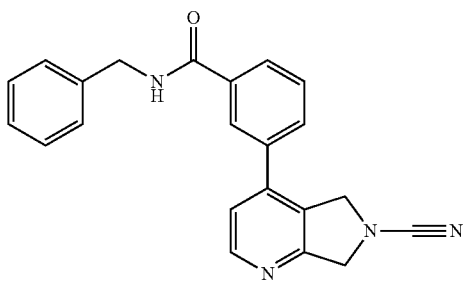 [SMILES: N#CN1Cc2nccc(-c3cccc(C(=O)NCc4ccccc4)c3)c2C1]

Step a.

To a stirred solution of 6-(methylsulfonyl)-6,7-dihydro-5H-pyrrolo[3,4-b]pyridine 1-oxide (Intermediate 5, 0.9 g, 4.2 mmol) in DMF (80 ml) was added oxalyl chloride (1.06 g, 8.399 mmol) drop wise at 0° C. The reaction mixture was stirred at rt for 48 h. The reaction mixture was combined with 1 other batch prepared on the same scale by an identical method. The resulting reaction mixture was poured into water (50 ml) and extracted with DCM (3×100 ml). The combined organic phase was washed with cold water (3×100 ml). The organic phase was separated, dried over $Na_2SO_4$, filtered and concentrated under reduced pressure to yield a regio-isomeric mixture of 4-chloro-6-(methylsulfonyl)-6,7-dihydro-5H-pyrrolo[3,4-b]pyridine and 2-chloro-6-(methylsulfonyl)-6,7-dihydro-5H-pyrrolo[3,4-b]pyridine. The resulting residue was purified by flash chromatography (16.5% EtOAc in hexane) yielding the desired 4-chloro-6-(methylsulfonyl)-6,7-dihydro-5H-pyrrolo[3,4-b]pyridine (0.6 g, 2.586 mmol). LCMS: Method A, 1.664 min, MS: ES+ 233.18; $^1$H NMR (400 MHz, $CDCl_3$) δ ppm 8.45 (d, J=5.2 Hz, 1H), 7.28 (s, 1H), 4.81 (s, 4H), 2.98 (s, 3H).

Step b.

To a stirred solution of 4-chloro-6-(methylsulfonyl)-6,7-dihydro-5H-pyrrolo[3,4-b]pyridine (0.15 g, 0.646 mmol) in 1,4-dioxane:water (4:1; 5 ml) was added $Cs_2CO_3$ (0.42 g, 1.292 mmol) at rt. The reaction mixture was degassed with nitrogen for 10 min. $Pd(PPh_3)_4$ (0.07 g, 0.064 mmol) and 3-(N-benzylaminocarbonyl)phenylboronic acid (CAS Number 625470-96-4; available from Combi Blocks) (0.25 g, 0.969 mmol) were added to the reaction mixture at rt. The reaction mixture was heated at 90° C. for 18 h. The resulting reaction mixture was cooled to rt, poured into water (5 ml) and extracted with EtOAc (3×20 ml). The combined organic phase was separated, dried over $Na_2SO_4$, filtered and concentrated under reduced pressure. The resulting residue was purified by flash chromatography (1.8% MeOH in DCM) yielding N-benzyl-3-(6-(methylsulfonyl)-6,7-dihydro-5H-pyrrolo[3,4-b]pyridin-4-yl)benzamide (0.13 g, 0.319 mmol). LCMS: Method A, 1.893 min, MS: ES+ 408.28; $^1$H NMR (400 MHz, DMSO-d6) δ ppm 9.21 (t, J=6.4 Hz, 1H), 8.61 (d, J=5.2 Hz, 1H), 8.12 (s, 1H), 8.02 (d, J=8.0 Hz, 1H), 7.83 (d, J=7.6 Hz, 1H), 7.66 (t, J=7.6 Hz, 1H), 7.52 (d, J=3.9 Hz, 1H), 7.34-7.35 (m, 4H), 7.23-7.27 (m, 1H), 4.877 (s, 2H), 4.71 (s, 2H), 4.53 (d, J=6.0 Hz, 2H), 3.08 (s, 3H).

Step c.

To a stirred solution of N-benzyl-3-(6-(methylsulfonyl)-6,7-dihydro-5H-pyrrolo[3,4-b]pyridin-4-yl)benzamide (0.12 g, 0.295 mmol) in AcOH (1 ml) was slowly added HBr in AcOH (1 ml) at rt. The reaction mixture was heated at 90° C. for 18 h. The reaction mixture was cooled to rt, poured into water (10 ml) and extracted with EtOAc (3×10 ml). The aqueous phase was basified with saturated $NaHCO_3$ solution and re-extracted with EtOAc (3×50 ml). The combined organic phase was washed with brine (20 ml), separated, dried over $Na_2SO_4$ and filtered. 4M HCl in 1,4-dioxane (1 ml) was added to the filtrate at rt and stirred for 10 min. The filtrate was concentrated under reduced pressure yielding N-benzyl-3-(6,7-dihydro-5H-pyrrolo[3,4-b]pyridin-4-yl)benzamide hydrochloride (0.07 g, 0.192 mmol). LCMS: Method A, 1560 min, MS: ES+ 330.6; $^1$H NMR (400 MHz, DMSO-d6) δ ppm 10.07 (br s, 1H), 9.30 (t, J=6.0 Hz, 1H), 8.65 (d, J=5.2 Hz, 1H), 8.12 (s, 1H), 8.05 (d, J=8.0 Hz, 1H), 7.78 (d, J=8.0 Hz, 1H), 7.68 (t, J=7.6 Hz, 1H), 7.63 (d, J=5.2 Hz, 1H), 7 32-7.35 (m, 3H), 7.25-7.29 (m, 1H), 4.78 (t, J=5.2 Hz, 2H), 4.57 (t, J=5.6 Hz, 2H), 4.53 (d, J=6.0 Hz, 2H).

Step d.

To a stirred solution of N-benzyl-3-(6,7-dihydro-5H-pyrrolo[3,4-b]pyridin-4-yl)benzamide hydrochloride (0.06 g, 0.016 mmol) in THF: DMF (5:1; 6 ml) was added $K_2CO_3$ (0.068 g, 0.049 mmol) at rt. Cyanogen bromide (0.026 g, 0.0246 mmol) was added to the reaction mixture at rt. The reaction mixture was stirred at rt for 4 h. The resulting reaction mixture was poured into water (5 ml) and extracted with EtOAc (3×10 ml). The combined organic phase was washed with cold water (2×10 ml) and brine (10 ml). The organic phase was separated, dried over $Na_2SO_4$, filtered and concentrated under reduced pressure. The resulting residue was purified by flash chromatography (1.5% MeOH in DCM) yielding N-benzyl-3-(6-cyano-6,7-dihydro-5H-pyrrolo[3,4-b]pyridin-4-yl)benzamide (0.02 g, 0.056 mmol). LCMS: Method D, 3.405 min, MS: ES+ 355.49; $^1$H NMR (400 MHz, DMSO-d6) δ ppm 9.20 (t, J=6.0 Hz, 1H), 8.60 (d, J=5.2 Hz, 1H), 8.09 (s, 1H), 8.02 (d, J=7.6 Hz, 1H), 7.79 (d, J=8.0 Hz, 1H), 7.65 (t, J=7.6 Hz, 1H), 7.53 (d, J=5.2 Hz, 1H), 7.34-7.35 (m, 4H), 7.23-7.30 (m, 1H), 5.06 (s, 2H), 4.85 (s, 2H), 4.53 (d, J=5.6 Hz, 2H).

Example 16 4-(4-chlorophenyl)-5,7-dihydro-6H-pyrrolo[3,4-b]pyridine-6-carbonitrile

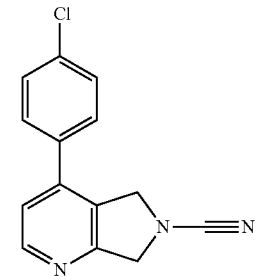 [SMILES: N#CN1Cc2nccc(-c3ccc(Cl)cc3)c2C1]

Step a.

To a stirred solution of 6-(methylsulfonyl)-6,7-dihydro-5H-pyrrolo[3,4-b]pyridine 1-oxide (Intermediate 5, 0.5 g, 2.336 mmol) in DMF (7 ml) was added oxalyl chloride (1 ml) at rt. The reaction mixture was stirred at rt for 15 h. The reaction mixture was combined with 4 other batches prepared on the same scale by an identical method. The resulting reaction mixture was poured into cold saturated NaHCO₃ solution (100 ml) and extracted with EtOAc (5×20 ml). The combined organic phase was washed with brine (2×40 ml). The organic phase was separated, dried over Na₂SO₄, filtered and concentrated under reduced pressure yielding a mixture of 4-chloro-6-(methylsulfonyl)-6,7-dihydro-5H-pyrrolo[3,4-b]pyridine and 2-chloro-6-(methylsulfonyl)-6,7-dihydro-5H-pyrrolo[3,4-b]pyridine (1.6 g, 6.896 mmol). LCMS: Method A, 1.786 min, MS: ES+ 233.35; 1.825 min, MS: ES+ 233.35. This material was directly used for the next step without any purification.

Step b.

To a stirred solution of a mixture of 4-chloro-6-(methylsulfonyl)-6,7-dihydro-5H-pyrrolo[3,4-b]pyridine and 2-chloro-6-(methylsulfonyl)-6,7-dihydro-5H-pyrrolo[3,4-b]pyridine (0.4 g, 1.724 mmol) in 1,4-dioxane:water (9:1; 18 ml) were added 4-chlorophenylboronic acid (0.35 g, 2.586 mmol) and K₂CO₃ (0.713 g, 5.172 mmol) at rt. The reaction mixture was degassed with nitrogen for 30 min before addition of Pd(PPh₃)₄ (0.199 g, 0.172 mmol). The reaction mixture was heated at 100° C. for 6 h. The resulting reaction mixture was cooled to rt, poured into water (40 ml) and extracted with EtOAc (3×15 ml). The combined organic phase was separated, washed with brine (2×20 ml), dried over Na₂SO₄, filtered and concentrated under reduced pressure. The resulting residue was purified by flash chromatography (2% MeOH in DCM) first yielding 4-(4-chlorophenyl)-6-(methylsulfonyl)-6,7-dihydro-5H-pyrrolo[3,4-b]pyridine (0.1 g, 0.324 mmol) LCMS: Method A, 2.173 min, MS: ES+ 309.58; ¹H NMR (400 MHz, DMSO-d6) δ ppm 8.58 (d, J=5.2 Hz, 1H), 7.58-7.68 (m, 4H), 7.46 (d, J=5.2 Hz, 1H), 4.84 (d, 2H), 4.69 (d, 2H), 3.08 (s, 3H).

Step c.

To a solution of 4-(4-chlorophenyl)-6-(methylsulfonyl)-6,7-dihydro-5H-pyrrolo[3,4-b]pyridine (0.1 g, 0.324 mmol) in AcOH (5 ml) was slowly added HBr in AcOH (3 ml) at rt. The reaction mixture was heated at 90° C. for 4 h. The resulting reaction mixture was concentrated under reduced pressure. The obtained residue was azeotropically distilled with a with MeOH (4×30 ml) and dried under high vacuum yielding 4-(4-chlorophenyl)-6,7-dihydro-5H-pyrrolo[3,4-b]pyridine HBr salt (0.12 g, quantitative). LCMS: Method A, 1.678 min, MS: ES+ 231.3.

Step d.

To a stirred solution of 4-(4-chlorophenyl)-6,7-dihydro-5H-pyrrolo[3,4-b]pyridine HBr salt (0.12 g, 0.387 mmol) in THF (15 ml) was added K₂CO₃ (0.16 g, 1.161 mmol) at rt. Cyanogen bromide (0.049 g, 0.464 mmol) was added to the reaction mixture at rt. The reaction mixture was stirred at rt for 30 min. The resulting reaction mixture was poured into saturated NaHCO₃ solution (30 ml) and extracted with EtOAc (3×15 ml). The combined organic phase was washed with brine (2×20 ml), dried over Na₂SO₄, filtered and concentrated under reduced pressure. The resulting residue was purified by flash chromatography (55-60% EtOAc in n-hexane) yielding 4-(4-chlorophenyl)-5,7-dihydro-6H-pyrrolo[3,4-b]pyridine-6-carbonitrile. LCMS: Method D, 4.288 min, MS: ES+ 255.99; ¹H NMR (400 MHz, DMSO-d6) δ ppm 8.57 (d, J=5.2 Hz, 1H), 7.58-7.66 (m, 4H), 7.46 (d, J=5.2 Hz, 1H), 5.09 (s, 2H), 4.83 (s, 2H).

Compounds in Table 3 were synthesised using a procedure similar to that described for Example 16.

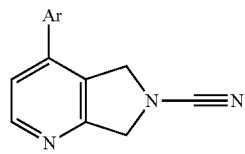

TABLE 3

| Ex | Ar— | Name | Aryl boronic acid/ester CAS Number | LCMS method | LCMS RT/ min | MS ES+ |
|---|---|---|---|---|---|---|
| Example 17 | MeO—⌬— | 4-(4-methoxyphenyl)-5,7-dihydro-6H-pyrrolo[3,4-b]pyridine-6-carbonitrile | 5720-07-0 | D | 3.904 | 252.00 |
| Example 18 | Cl-⌬— | 4-(3-chlorophenyl)-5,7-dihydro-6H-pyrrolo[3,4-b]pyridine-6-carbonitrile | 63503-60-6 | D | 4.238 | 255.92 |

Example 19 4-phenyl-1,3-dihydro-2H-pyrrolo[3,4-c]pyridine-2-carbonitrile

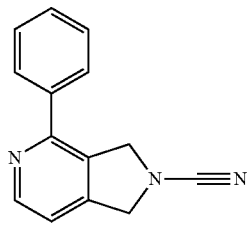 [SMILES: N#CN1Cc2ccnc(-c3ccccc3)c2C1]

Step a.

To a stirred solution of 4,6-dichloropyrimidine-5-carboxylic acid (CAS Number 87600-98-4; available from Combi Blocks) (2.0 g, 10.36 mmol) in DCM (10 ml) was added DMF (0.2 ml) at rt. Oxalyl chloride (2.63 g, 20.72 mmol) was added dropwise to the reaction mixture at 0° C. under nitrogen. The reaction mixture was stirred at rt for 1 h. The reaction mixture was added drop wise to the previously stirred solution of propargyl amine (0.57 g, 10.362 mmol) and TEA (5.23 g, 51.813 mmol) in DCM (10 ml) at −78° C.

under nitrogen. The reaction mixture was stirred at −78° C. for 1 h. The resulting reaction mixture was poured into water (50 ml) and extracted with DCM (4×30 ml). The combined organic phase was separated, dried over $Na_2SO_4$, filtered and concentrated under reduced pressure. The resulting residue was purified by flash chromatography (25% EtOAc in hexane) yielding 4,6-dichloro-N-(prop-2-yn-1-yl)pyrimidine-5-carboxamide (1.55 g, 6.768 mmol). LCMS: Method A, 1.689 min, MS: ES+ 229.98; $^1$H NMR (400 MHz, DMSO-d6) δ ppm 9.31 (t, J=5.2 Hz, 1H), 9.02 (s, 1H), 4.11 (dd, J=2.8 Hz, 5.6 Hz, 2H), 3.27 (t, J=2.4 Hz, 1H).

Step b.

A solution of 4,6-dichloro-N-(prop-2-yn-1-yl)pyrimidine-5-carboxamide (0.5 g, 2.183 mmol) in nitrobenzene (5 ml) was degassed at rt for 30 min. The reaction mixture was heated at 250° C. in a microwave for 2.5 min. The resulting reaction mixture was cooled to rt and combined with 2 other batches on the same scale prepared by an identical method. The reaction mixture was poured onto neutral silica and subjected to flash chromatography (3% MeOH in DCM) to yield 4-chloro-1,2-dihydro-3H-pyrrolo[3,4-c]pyridin-3-one (0.4 g, 2.381 mmol). LCMS: Method A, 1.086 min, MS: ES+ 169.03

Step c.

To a stirred solution of 4-chloro-1,2-dihydro-3H-pyrrolo[3,4-c]pyridin-3-one (0.39 g, 2.321 mmol) in DMF:water (2:1; 12 ml) were added phenylboronic acid (0.34 g, 2.786 mmol) and $Na_2CO_3$ (0.62 g, 5.803 mmol) at rt. The reaction mixture was degassed for 30 min. Pd(dppf)Cl$_2$ (0.17 g, 0.232 mmol) was added to the reaction mixture at rt. The reaction mixture was heated at 120° C. for 3 h. The resulting reaction mixture was cooled to rt, poured into a mixture of water:EtOAc (1:1; 60 ml) and filtered through celite bed. The filtrate was extracted with EtOAc (3×30 ml) and then with 10% MeOH in DCM (2×50 ml). The combined organic phase was separated, dried over $Na_2SO_4$, filtered and concentrated under reduced pressure. The resulting residue was purified by flash chromatography (neutral silica; 1% MeOH in DCM) yielding 4-phenyl-1,2-dihydro-3H-pyrrolo[3,4-c]pyridin-3-one (0.27 g, 1.286 mmol). LCMS: Method A, 1.564 min, MS: ES+ 211.13

Step d.

To a stirred solution of 4-phenyl-1,2-dihydro-3H-pyrrolo[3,4-c]pyridin-3-one (0.086 g, 0.409 mmol) in THF (5 ml) was added sodium borohydride (0.16 g, 4.279 mmol) portion wise at rt. Boron trifluoride etherate (0.68 g, 4.775 mmol) was added drop wise to the reaction mixture at −10° C. The reaction mixture was heated at 70° C. for 1 h. The resulting reaction mixture was cooled to rt and combined with another batch prepared on a 0.05 g scale by an identical method. The reaction mixture was quenched into MeOH (5 ml) and evaporated to dryness under vacuum. The residue was diluted with water (20 ml) and extracted with EtOAc (2×20 ml). The aqueous phase was treated with aqueous NaOH solution to adjust the pH 10 and re-extracted with EtOAc (2×20 ml). The combined organic phase was separated, dried over $Na_2SO_4$, filtered and concentrated under reduced pressure yielding 4-phenyl-2,3-dihydro-1H-pyrrolo[3,4-c]pyridine (0.075 g, 0.383 mmol). This material was used for the next step without further purification. LCMS: Method D, 3.549 min, MS: ES+ 197.03; $^1$H NMR (400 MHz, DMSO-d6) δ ppm 8.50 (s, 1H), 7.78 (d, J=5.6 Hz, 2H), 7.45-7.50 (m, 3H), 7.25-7.33 (m, 2H), 4.27 (s, 2H), 4.11 (m, 2H).

Step e.

To a stirred solution of 4-phenyl-2,3-dihydro-1H-pyrrolo[3,4-c]pyridine (0.073 g, 0.372 mmol) in THF (3 ml) was added $K_2CO_3$ (0.26 g, 1.862 mmol) at rt. Cyanogen bromide (0.04 g, 0.372 mmol) was added to the reaction mixture at rt. The reaction mixture was stirred at rt for 5 min. The resulting reaction mixture was poured into water (10 ml) and extracted with EtOAc (2×10 ml). The combined organic phase was separated, dried over $Na_2SO_4$, filtered and concentrated under reduced pressure. The resulting residue was purified by flash chromatography (18-20% EtOAc in hexane) yielding 4-phenyl-1,3-dihydro-2H-pyrrolo[3,4-c]pyridine-2-carbonitrile (0.008 g, 0.036 mmol). LCMS: Method E, 3.129 min, MS: ES+ 222.30; $^1$H NMR (400 MHz, DMSO-d6) δ ppm 8.64 (d, J=4.8 Hz, 1H), 7.80 (d, J=6.8 Hz, 2H), 7.47-7.53 (m, 3H), 7.40 (d, J=4.8 Hz, 1H), 5.07 (s, 2H), 4.88 (s, 2H).

Example 20 6-(5-methyl-1,2,4-oxadiazol-3-yl)-4-phenylisoindoline-2-carbonitrile

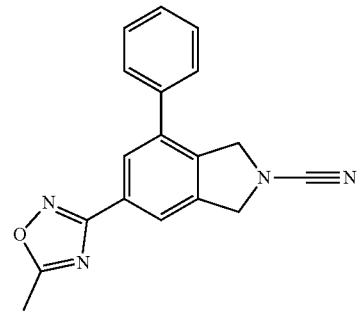 [SMILES: Cc1nc(-c2cc3c(c(-c4ccccc4)c2)CN(C#N)C3)no1]

Step a.

A mixture of 3,4-dimethylbenzoic acid (5.0 g, 33.29 mmol) and AlCl$_3$ (11.1 g, 83.23 mmol) in DCM (90 ml) was stirred at 0° C. for 30 min. A solution of bromine (5.85 g, 36.623 mmol) in DCM (10 ml) was slowly added to the reaction mixture at 0° C. over a period of 10 min. The reaction mixture was stirred at rt for 4 h. The resulting reaction mixture was carefully quenched into saturated sodium thiosulphate solution (500 ml) and extracted with DCM (2×500 ml). The combined organic phase was separated, dried over $Na_2SO_4$, filtered and concentrated under reduced pressure yielding 3-bromo-4,5-dimethylbenzoic acid (9.0 g, quantitative). This material was used for the next step without further purification. LCMS: Method A, 2.259 min, MS: ES+ 227.1, 229.0

Step b.

To a stirred solution of 3-bromo-4,5-dimethylbenzoic acid (9.0 g, 39.30 mmol) in DMF (70 ml) were added EDC HCl (8.26 g, 43.23 mmol) and HOBt (3.0 g, 19.65 mmol) at rt. The reaction mixture was stirred at rt for 20 min. Ammonium chloride (4.24 g, 78.602 mmol) was added to the reaction mixture at rt and stirred for 5 h. The resulting reaction mixture was poured into saturated NaHCO$_3$ solution (500 ml) and extracted with EtOAc (2×400 ml). The combined organic phase was separated, dried over $Na_2SO_4$, filtered and concentrated under reduced pressure. The resulting residue was purified by column chromatography (40% EtOAc in hexane) yielding 3-bromo-4,5-dimethylbenzamide (2.6 g, 11.45 mmol). LCMS: Method A, 1.982 min, MS: ES+ 228.1, 230.1; $^1$H NMR (400 MHz, DMSO-d6) δ ppm 7.98 (br s, 1H), 7.93 (d, J=1.6 Hz, 1H), 7.69 (d, J=1.6 Hz, 1H), 7.39 (br s, 1H), 2.35 (s, 6H).

Step c.

To a stirred solution of 3-bromo-4,5-dimethylbenzamide (2.5 g, 11.013 mmol) in 1,4-dioxane:water (4:1, 25 ml) were added Cs$_2$CO$_3$ (7.18 g, 22.026 mmol) and phenylboronic acid (1.61 g, 13.216 mmol) at rt. The reaction mixture was degassed with nitrogen for 10 min. Pd(PPh$_3$)$_4$ (0.63 g, 0.551 mmol) was added to the reaction mixture at rt. The reaction mixture was heated at 80° C. for 16 h. The resulting reaction mixture was cooled to rt, poured into water (500 ml) and extracted with EtOAc (2×200 ml). The combined organic phase was separated, dried over Na$_2$SO$_4$, filtered and concentrated under reduced pressure. The resulting residue was purified by column chromatography (25% EtOAc in hexane) yielding 5,6-dimethyl-[1,1'-biphenyl]-3-carboxamide (2.5 g, quantitative). LCMS: Method A, 2.031 min, MS: ES+ 226.19.

Step d.

To a stirred solution of 5,6-dimethyl-[1,1'-biphenyl]-3-carboxamide (2.5 g, 11.11 mmol) in THF (30 ml) was added thionyl chloride (1.98 g, 16.67 mmol) at 0° C. The reaction mixture was heated at 80° C. for 16 h. The resulting reaction mixture was cooled to rt, poured into water (500 ml), basified with solid NaHCO$_3$, and extracted with EtOAc (2×300 ml). The combined organic phase was separated, dried over Na$_2$SO$_4$, filtered and concentrated under reduced pressure yielding 5,6-dimethyl-[1,1'-biphenyl]-3-carbonitrile (2.9 g, quantitative). This material was used for the next step without further purification. MS: ES+ 208.3

Step e.

A mixture of 5,6-dimethyl-[1,1'-biphenyl]-3-carbonitrile (0.5 g, 2.40 mmol), AIBN (0.02 g, 0.12 mmol) and NBS (1.7 g, 9.61 mmol) in CCl$_4$ (6 ml) was heated at 80° C. for 16 h. The resulting reaction mixture was cooled to rt and filtered. The filtrate was evaporated to dryness to yield 5,6-bis(bromomethyl)-[1,1'-biphenyl]-3-carbonitrile (0.77 g, 2.13 mmol). This material was used for the next step without further purification.

Step f.

To a stirred solution of 5,6-bis(bromomethyl)[1,1'-biphenyl]-3-carbonitrile (0.77 g, 2.13 mmol) in THF (6 ml) was added TEA (0.47 g, 4.68 mmol) at 0° C. The reaction mixture was stirred at 0° C. for 5 min. Benzylamine (0.25 g, 2.34 mmol) was added to the reaction mixture at 0° C. The reaction mixture was stirred at rt for 16 h. The reaction mixture poured into water (170 ml) and extracted with EtOAc (2×100 ml). The combined organic phase was separated, dried over Na$_2$SO$_4$, filtered and concentrated under reduced pressure yielding 2-benzyl-7-phenylisoindoline-5-carbonitrile (0.7 g, quantitative). This material was used for the next step without further purification. LCMS: Method A, 1.974 min, MS: ES+ 311.3.

Step g.

To a stirred solution of 2-benzyl-7-phenylisoindoline-5-carbonitrile (0.5 g, 1.61 mmol) in MeOH (7 ml) were added hydroxylamine hydrochloride (0.13 g, 1.93 mmol) and DIPEA (0.31 g, 2.42 mmol) at rt. The reaction mixture was heated at 80° C. for 16 h. The resulting reaction was poured into water (150 ml), acidified by solid citric acid, extracted with EtOAc (100 ml). The aqueous phase was separated, basified using saturated NaHCO$_3$ solution and re-extracted with EtOAc (2×100 ml). The combined organic phase was separated, dried over Na$_2$SO$_4$, filtered and concentrated under reduced pressure yielding 2-benzyl-N'-hydroxy-7-phenylisoindoline-5-carboximidamide (0.36 g, 1.06 mmol). This material was used for the next step without further purification. LCMS: Method A, 1.635 min, 1.645 min, MS: ES+ 344.3.

Step h.

A mixture of 2-benzyl-N'-hydroxy-7-phenylisoindoline-5-carboximidamide (0.05 g, 0.145 mmol) and acetic anhydride (1 ml) in AcOH (2 ml) was heated at 80° C. for 12 h. The reaction mixture was cooled to rt and combined with 3 other batches prepared on the same scale by an identical method. The resulting reaction mixture was poured into water (70 ml), basified using solid NaHCO$_3$ and extracted with EtOAc (2×70 ml). The combined organic phase was separated, dried over Na$_2$SO$_4$, filtered and concentrated under reduced pressure. The resulting residue was purified by flash chromatography (20% EtOAc in hexane) yielding 3-(2-benzyl-7-phenylisoindolin-5-yl)-5-methyl-1,2,4-oxadiazole (0.04 g, 0.109 mmol). LCMS: Method A, 1.948 min, MS: ES+ 368.35; $^1$H NMR (400 MHz, DMSO-d6) δ ppm 7.88 (s, 2H), 7.48 (d, J=4.4 Hz, 4H), 7.31-7.44 (m, 5H), 7.23-7.27 (m, 1H), 3.98 (d, J=2.0 Hz, 4H), 3.91 (s, 2H), 2.67 (s, 3H).

Step i.

To a stirred solution of 3-(2-benzyl-7-phenylisoindolin-5-yl)-5-methyl-1,2,4-oxadiazole (0.04 g, 0.109 mmol) in THF (5 ml) was added K$_2$CO$_3$ (0.022 g, 0.163 mmol) at rt. Reaction mixture was stirred at rt for 5 min. Cyanogen bromide (0.014 g, 0.131 mmol) in THF was added dropwise to the reaction mixture at 0° C. The reaction mixture was stirred at rt for 4 h. The resulting reaction mixture was filtered and evaporated to dryness. The resulting residue was purified by preparative TLC (30% EtOAc in hexane) yielding 6-(5-methyl-1,2,4-oxadiazol-3-yl)-4-phenylisoindoline-2-carbonitrile (0.014 g, 0.046 mmol). LCMS: Method C, 7.242 min, MS: ES+ 303.15; $^1$H NMR (400 MHz, DMSO-d6) δ ppm 7.97 (s, 1H), 7.93 (s, 1H), 7.46-7.58 (m, 5H), 4.94 (d, J=10.8 Hz, 4H), 2.68 (s, 3H).

Example 21

4-(quinazolin-2-ylamino)isoindoline-2-carbonitrile

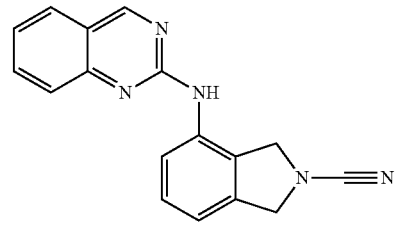 [SMILES: N#CN1Cc2cccc(Nc3ncc4ccccc4n3)c2C1]

Step a.

To a stirred solution of tert-butyl 4-aminoisoindoline-2-carboxylate (CAS Number 871013-98-8, 0.1 g, 0.427 mmol) in n-butanol (5 ml) were added catalytic TFA and 2-chloroquinazoline (CAS Number 6141-13-5; 0.07 g, 0.427 mmol) at rt. The reaction mixture was heated at 120° C. for 4 h. The reaction mixture was cooled to rt and excess of solvent was distilled off. The residue was purified by flash chromatography (15-18% EtOAc in hexane) yielding tert-butyl 4-(quinazolin-2-ylamino)-isoindoline-2-carboxylate (0.108 g, 0.298 mmol). LCMS: Method A, 2.699 min, MS: ES+ 363.60; $^1$H NMR (400 MHz, DMSO-d6) δ ppm 10.76 (s, 1H), 8.88 (s, 1H), 8.26 (t, J=8.8 Hz, 1H), 7.28-7.34 (m, 3H), 7.00 (d, J=5.2 Hz, 2H), 6.94 (t, J=7.6 Hz, 1H), 4.62 (d, J=8.4 Hz, 4H), 1.48 (s, 9H).

Step b.

To a stirred solution of tert-butyl 4-(quinazolin-2-ylamino)isoindoline-2-carboxylate (0.1 g, 0.276 mmol) in DCM (5 ml) was added TFA (2 ml) at 0° C. The reaction mixture was heated at 40° C. for 30 min. The reaction mixture was cooled to rt and evaporated to dryness under vacuum. The resulting residue was azeotroped with DCM (3×10 ml) yielding N-(isoindolin-4-yl)quinazolin-2-amine TFA salt (0.115 g, 0.306 mmol). LCMS: Method A, 1.647 min, MS: ES+ 263.36.

Step c.

To a stirred solution of N-(isoindolin-4-yl)quinazolin-2-amine TFA salt (0.11 g, 0.292 mmol) in THF (5 ml) were added TEA (0.12 g, 1.17 mmol) and cyanogen bromide (0.031 g, 0.292 mmol) at −78° C. The reaction mixture was stirred at −78° C. for 0.5 h. The resulting reaction mixture was diluted with a mixture of EtOAc:water (1:3; 40 ml) and extracted with EtOAc (3×20 ml). The combined organic phase was separated, dried over $Na_2SO_4$, filtered and concentrated under reduced pressure. The obtained crude material was subjected for preparative HPLC purification; mobile phase: (A) 10 mM ammonium acetate in water (B) 100% MeCN, column: Phenomenex Luna C8 (250*21.2) mm, 5 micron, flow rate 15.0 ml/min which yielded 4-(quinazolin-2-ylamino)isoindoline-2-carbonitrile (0.017 g, 0.059 mmol). LCMS: Method E, 4.051 min, MS: ES+ 288.44; $^1$H NMR (400 MHz, DMSO-d6) δ ppm 9.45 (s, 1H), 9.33 (s, 1H), 7.93 (d, J=8.0 Hz, 1H), 7.78-7.86 (m, 2H), 7.60 (d, J=8.4 Hz, 1H), 7.33-7.41 (m, 2H), 7.06 (d, J=7.6 Hz, 1H), 4.83 (s, 4H).

Example 22 34(2-cyanoisoindolin-4-yl)amino)-N-methylisoquinoline-6-carboxamide

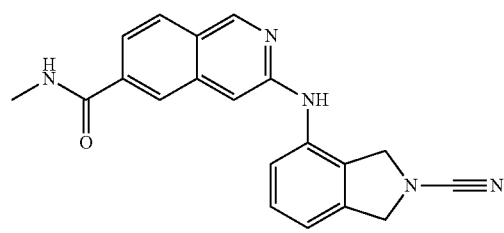 [SMILES: CNC(=O)c1ccc2cnc(Nc3cccc4c3CN(C#N)C4)cc2c1]

Step a.

A suspension of 3-amino-N-methylisoquinoline-6-carboxamide TFA salt (Intermediate 6, 0.40 g, 1.262 mmol), tert-butyl 4-bromoisoindoline-2-carboxylate (Intermediate 1, 0.15 g, 0.505 mmol), and potassium tert-butoxide (0.28 g, 2.525 mmol) in toluene (10 ml) was degassed with nitrogen for 10 min at rt. BINAP (0.047 g, 0.050 mmol) and $Pd_2(dba)_3$ (0.032 g, 0.050 mmol) were added to the reaction mixture at rt. The reaction mixture was heated at 105° C. for 2 h. The resulting reaction mixture was cooled to rt, poured into water (20 ml) and extracted with EtOAc (2×40 ml). The combined organic phase was dried over $Na_2SO_4$, filtered and concentrated under reduced pressure. The resulting residue was purified by flash chromatography (4% MeOH in DCM) yielding tert-butyl 4-((6-(methylcarbamoyl)isoquinolin-3-yl)amino)isoindoline-2-carboxylate (0.135 g, 0.322 mmol). LCMS: Method A, 2.278 min, MS: ES+ 419.5.

Steps b, c.

The title compound was synthesised from the intermediate above using a procedure similar to that described for steps d and e of Example 1. LCMS: Method E, 3.469 min, MS: ES+ 344.43.

Scheme D

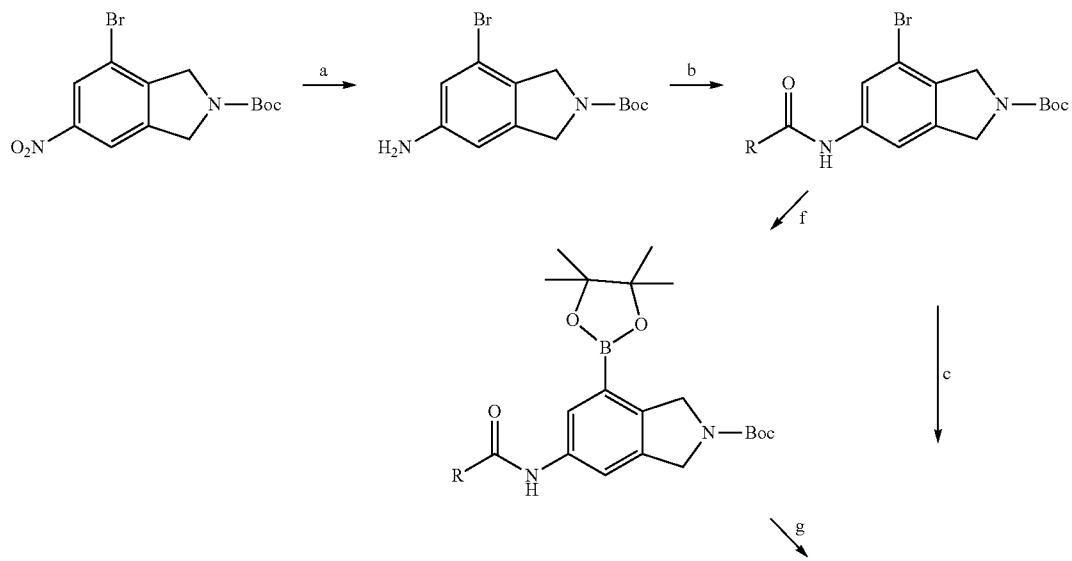

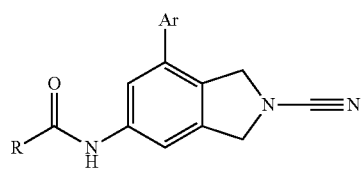 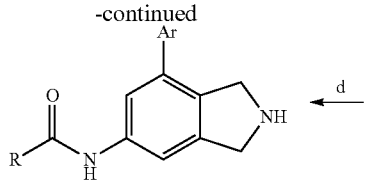

Reagents and conditions: a) Fe, NH₄Cl, THF/water; b) HATU, DIPEA, DMF, RCO₂H; c) ArB(OH)₂, Cs₂CO₃, Pd(PPh₃)₄, 1,4-dioxane, water; d) TFA, DCM; e) BrCN, K₂CO₃, THF; f) bis(pinacolato)diboron, Pd(dppf)Cl₂·CH₂Cl₂; g) Ar—Br, Cs₂CO₃, Pd(PPh₃)₄, 1,4-dioxane, water

Example 23
N-(2-cyano-7-phenylisoindolin-5-yl)nicotinamide

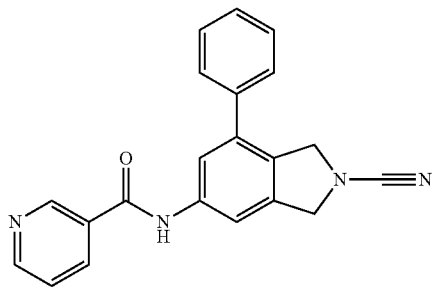 [SMILES: N#CN1Cc2cc(NC(=O)c3cccnc3)cc(-c3ccccc3)c2C1]

Step a.

To a stirred solution of tert-butyl 4-bromo-6-nitroisoindoline-2-carboxylate (Intermediate 3, 0.15 g, 0.437 mmol) in THF and water (1:1; 4 ml) were added Fe powder (0.12 g, 2.185 mmol) and ammonium chloride (0.12 g, 2.185 mmol) at rt. The reaction mixture was heated at 90° C. for 18 h. The reactions mixture was cooled to rt, filtered through celite hyflow, washed with EtOAc (15 ml) and evaporated to dryness. The resulting residue was re-dissolved in EtOAc (100 ml) and washed with water (20 ml), brine (20 ml), dried over Na₂SO₄, filtered and concentrated under reduced pressure yielding tert-butyl 6-amino-4-bromoisoindoline-2-carboxylate (0.15 g, quantitative). LCMS: Method A, 2.351 min, MS: ES+ 313.2, 315.2.

Step b.

To a stirred solution of pyridine-3-carboxylic acid (0.07 g, 0.574) in DMF (3 ml) was added DIPEA (0.1 g, 0.766 mmol) and HATU (0.22 g, 0.574 mmol) at rt. The reaction mixture was stirred at rt for 10 min. A solution of tert-butyl 6-amino-4-bromoisoindoline-2-carboxylate (0.12 g, 0.383 mmol) in DMF was added to the reaction mixture. The reaction mixture was stirred at rt for 2 h. The resulting reaction mixture was poured into water (10 ml) and extracted with EtOAc (3×30 ml). The combined organic phase was washed with brine (50 ml). The organic phase was separated, dried over Na₂SO₄, filtered and concentrated under reduced pressure. The resulting crude material was purified by flash chromatography (1.5% MeOH in DCM) yielding tert-butyl 4-bromo-6-(nicotinamido)isoindoline-2-carboxylate (0.135 g, 0.322 mmol). LCMS: Method A, 2.375 min, MS: ES+ 418.6, 420.6; ¹H NMR (400 MHz, DMSO-d6) δ ppm 10.62 (d, J=4.8 Hz, 1H), 9.10 (d, J=2.4 Hz, 1H), 8.78 (dd, J=2.0 Hz, 5.2 Hz, 1H), 8.28-8.32 (m, 1H), 7.98 (s, 1H), 7.75 (d, J=18.0 Hz, 1H), 7.59 (dd, J=5.2 Hz, 8.0 Hz, 1H), 4.72 (d, 8.8 Hz, 2H), 4.51 (d, J=9.6 Hz, 2H), 1.47 (s, 9H).

Step c.

A solution of tert-butyl 4-bromo-6-(nicotinamido)isoindoline-2-carboxylate (0.12 g, 0.787 mmol), Cs₂CO₃ (0.14 g, 0.43 mmol) in 1,4-dioxane:water (4:1; 10 ml) was stirred at rt. The reaction mixture was degassed using nitrogen for 15 min before addition of Pd(PPh₃)₄ (0.033 g, 0.0.29 mmol) and phenylboronic acid (0.052 g, 0.43 mmol). The resulting reaction mixture was heated at 90° C. for 8 h. The resulting reaction mixture was cooled to rt and poured into water (20 ml) and extracted with EtOAc (3×20 ml). The combined organic phase was washed with brine (20 ml) and dried over Na₂SO₄, filtered and concentrated under reduced pressure. The residue was purified by flash chromatography (2% MeOH in DCM) yielding tert-butyl 6-(nicotinamido)-4-phenylisoindoline-2-carboxylate (0.11 g, 0.265 mmol). LCMS: Method A, 2.785 min, ES– 414.5; ¹H NMR (400 MHz, DMSO-d6) δ ppm 10.56 (d, J=3.6 Hz, 1H), 9.13 (d, J=1.6 Hz, 1H), 8.77 (dd, J=1.6 Hz, 4.8 Hz, 1H), 8.30-8.33 (m, 1H), 7.82 (d, J=18.4 Hz, 1H), 7.73 (d, J=14.4 Hz, 1H), 7.57-7.61 (m, 1H), 7.50-7.52 (m, 4H), 7.43-7.45 (m, 1H), 4.63-4.69 (m, 4H), 1.45 (d, J=13.6 Hz, 9H).

Step d.

To a stirred solution of tert-butyl 6-(nicotinamido)-4-phenylisoindoline-2-carboxylate (0.1 g, 0.241 mmol) in DCM (5 ml) was added TFA (0.2 ml) at rt. The reaction mixture was stirred at rt for 4 h. The reaction mixture was evaporated to dryness. The residue was azeotropically distilled with DCM (2×10 ml), diethyl ether (20 ml) and dried under vacuum to yield N-(7-phenylisoindolin-5-yl)nicotinamide TFA salt (0.165 g, quantitative). LCMS: Method A, 1.453 min, MS: ES+ 336.59.

Step e.

To a stirred solution of N-(7-phenylisoindolin-5-yl)nicotinamide TFA salt (0.15 g, 0.349 mmol) in THF (5 ml) were added K₂CO₃ (0.14 g, 1.048 mmol) and cyanogen bromide (0.05 g, 0.524 mmol) at rt. The reaction mixture was stirred at rt for 30 min. The resulting reaction mixture was filtered and evaporated to dryness. The resulting residue was purified by flash chromatography (2.1% MeOH in DCM) yielding N-(2-cyano-7-phenylisoindolin-5-yl)nicotinamide (g, mmol). LCMS: Method D, 4.028 min, ES+ 340.99; ¹H NMR (400 MHz, DMSO-d6) δ ppm 10.62 (s, 1H), 9.13 (s, 1H), 8.77 (d, J=3.6 Hz, 1H), 8.31 (d, J=7.6 Hz, 1H), 7.85 (s, 1H), 7.76 (s, 1H), 7.59 (dd, J=4.8 Hz, 8.0 Hz, 1H), 7.48-7.52 (m, 4H), 7.43-7.44 (m, 1H), 4.87 (s, 4H).

Example 24
2-(6-acetamido-2-cyanoisoindolin-4-yl)benzamide

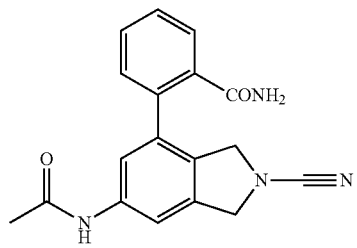 [SMILES: CC(=O)Nc1cc2c(c(-c3ccccc3C(N)=O)c1)CN(C#N)C2]

This was synthesised using a procedure similar to that described for Example 23 using 2-(aminocarbonyl)phenyl-boronic acid (CAS Number 380430-54-6). LCMS: Method D, 2.916 min, MS: ES+ 320.97.

Compounds in Table 4 were synthesised using a procedure similar to that described for Example 23 using (R)-1-methylpiperidine-3-carboxylic acid (CAS Number 952480-19-2) in step b.

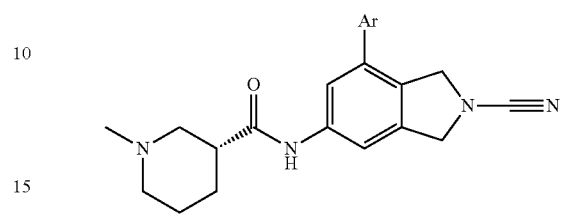

TABLE 4

| Ex | Ar— | Name | Aryl boronic acid CAS Number | LCMS method | LCMS RT/ min | MS ES+ |
|---|---|---|---|---|---|---|
| Example 25 | 3-fluorophenyl | (R)-N-(2-cyano-7-(3-fluorophenyl)isoindolin-5-yl)-1-methylpiperidine-3-carboxamide | 768-35-4 | I | 3.2 | 379 |
| Example 26 | 4-cyanophenyl | (R)-N-(2-cyano-7-(4-cyanophenyl)isoindolin-5-yl)-1-methylpiperidine-3-carboxamide | 126747-14-6 | I | 3.29 | 386 |
| Example 27 | 3-cyanophenyl | (R)-N-(2-cyano-7-(3-cyanophenyl)isoindolin-5-yl)-1-methylpiperidine-3-carboxamide | 150255-96-2 | I | 3.32 | 386 |
| Example 28 | 4-fluorophenyl | (R)-N-(2-cyano-7-(4-fluorophenyl)isoindolin-5-yl)-1-methylpiperidine-3-carboxamide | 1765-93-1 | I | 3.29 | 379 |
| Example 29 | 4-(methylcarbamoyl)phenyl | (R)-N-(2-cyano-7-(4-(methylcarbamoyl)phenyl)isoindolin-5-yl)-1-methylpiperidine-3-carboxamide | 121177-82-0 | K | 3.44 | 418 |
| Example 30 | 3-(methylcarbamoyl)phenyl | (R)-N-(2-cyano-7-(3-methylcarbamoyl)phenyl)isoindolin-5-yl)-1-methylpiperidine-3-carboxamide | 1197171-76-8 | K | 3.51 | 418 |
| Example 31 | 3-methoxyphenyl | (R)-N-(2-cyano-7-(3-methoxyphenyl)isoindolin-5-yl)-1-methylpiperidine-3-carboxamide | 10365-98-7 | K | 4.06 | 391 |
| Example 32 | 4-methoxyphenyl | (R)-N-(2-cyano-7-(4-methoxyphenyl)isoindolin-5-yl)-1-methylpiperidine-3-carboxamide | 5720-07-0 | I | 3.38 | 391 |

TABLE 4-continued

| Ex | Ar— | Name | Aryl boronic acid CAS Number | LCMS method | LCMS RT/ min | MS ES+ |
|---|---|---|---|---|---|---|
| Example 33 | Cl-C6H4- (4-chlorophenyl) | (R)-N-(7-(4-chlorophenyl)-2-cyanoisoindolin-5-yl)-1-methylpiperidine-3-carboxamide | 1679-18-1 | M | 3.85 | 395, 397 |
| Example 34 | 3-chlorophenyl | (R)-N-(7-(3-chlorophenyl)-2-cyanoisoindolin-5-yl)-1-methylpiperidine-3-carboxamide | 63503-60-6 | I | 3.64 | 395, 397 |
| Example 35 | 2-methylbenzo[d]oxazol-6-yl | (R)-N-(2-cyano-7-(2-methylbenzo[d]oxazol-6-yl)isoindolin-5-yl)-1-methylpiperidine-3-carboxamide | 866332-15-2 | L | 2.13 | 416 |

Compounds in Table 4a were synthesised according to Scheme D using a procedure similar to that described for Example 23 using (R)-1-methylpiperidine-3-carboxylic acid (CAS Number 952480-19-2) in step b. In place of step c, reaction with bis(pinacolato)diboron was carried out by a method similar to that described for Intermediate 2, followed by reaction with an aryl bromide by a method similar to step a of Example 1.

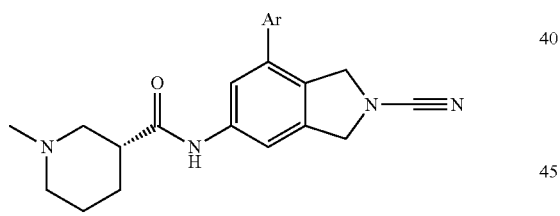

TABLE 4a

| Ex | Ar— | Name | Aryl bromide CAS Number | LCMS method | LCMS RT/min | MS ES+ |
|---|---|---|---|---|---|---|
| Example 163 | pyridin-4-yl | (R)-N-(2-cyano-7-(pyridin-4-yl)isoindolin-5-yl)-1-methylpiperidine-3-carboxamide | 19524-06-2 | M | 0.6 | 362 |
| Example 164 | pyridin-3-yl | (R)-N-(2-cyano-7-(pyridin-3-yl)isoindolin-5-yl)-1-methylpiperidine-3-carboxamide | 626-55-1 | M | 0.55 | 362 |

Scheme E

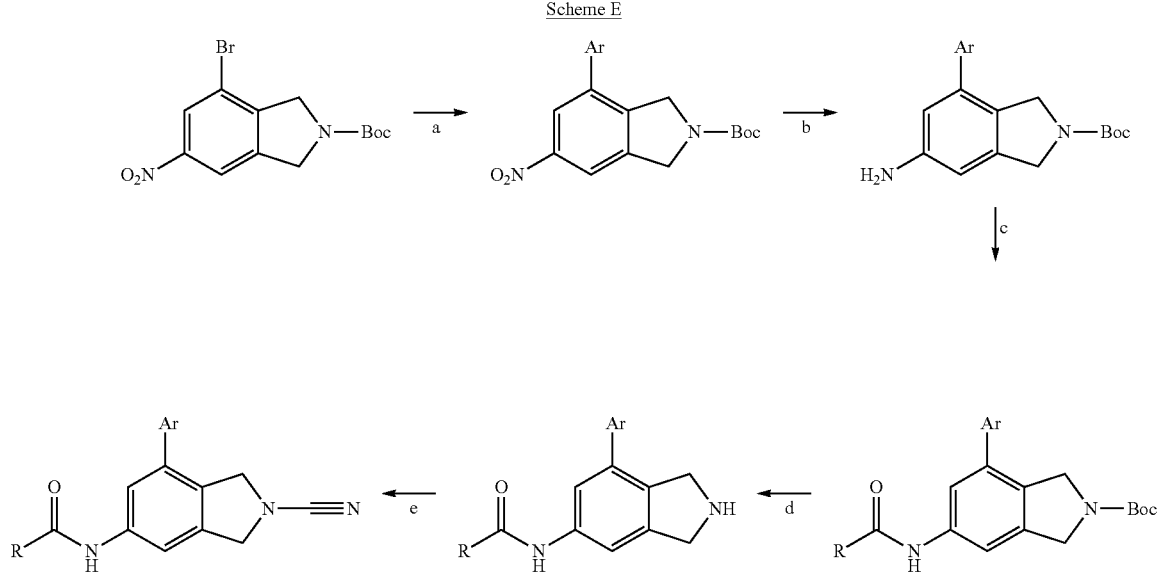

Reagents and conditions: a) ArB(OH)$_2$, Pd(PPh$_3$)$_4$, Cs$_2$CO$_3$, 1,4-dioxane, water; b) Fe, NH$_4$Cl, THF, water; b) c) RCO$_2$H, HATU, DIPEA, THF; or RCOCl, TEA, DCM; d) TFA, DCM; e) BrCN, K$_2$CO$_3$, THF.

Example 36 N-(2-cyano-7-phenylisoindolin-5-yl)-1-methylpiperidine-3-carboxamide

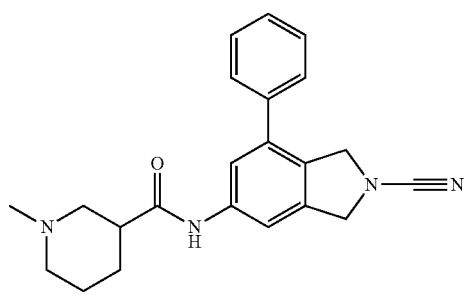

Steps a, b.
Carried out as described in steps a-b of Intermediate 4.

Step c.
To a stirred solution of 1-methylpiperidine-3-carboxylic acid (CAS Number 5657-70-5; available from Apollo Scientific) (0.069 g, 0.483 mmol) in THF (5 ml) were added DIPEA (0.083 g, 0.644 mmol) and HATU (0.18 g, 0.0483 mmol) at rt. The reaction mixture was stirred at rt for 30 min. Tert-butyl 6-amino-4-phenylisoindoline-2-carboxylate (Intermediate 4, 0.1 g, 0.322 mmol) was added to the reaction mixture at rt. The reaction mixture was stirred at rt for 18 h and then heated at 80° C. for 1 h. The resulting reaction mixture was cooled to rt and combined with 1 other batch prepared on the same scale by an identical method. The reaction mixture was poured into water (20 ml) and extracted with EtOAc (2×30 ml). The combined organic phase was washed with brine (20 ml). The organic phase was separated, dried over Na$_2$SO$_4$, filtered and concentrated under reduced pressure. The resulting residue was purified by flash chromatography (20% EtOAc in hexane) yielding tert-butyl 6-(1-methylpiperidine-3-carboxamido)-4-phenylisoindoline-2-carboxylate (0.11 g, 0.252 mmol). LCMS: Method A, 2.024 min, MS: ES+ 436.8; $^1$H NMR (400 MHz, DMSO-d6) δ ppm 10.31 (s, 1H), 7.56-7.62 (m, 2H), 7.39-7.49 (m, 5H), 4.63 (d, J=7.6 Hz, 2H), 4.59 (s, 2H), 3.38-3.41 (m, 4H), 2.79-2.85 (m, 2H), 2.74 (s, 3H), 1.95-2.03 (m, 1H), 1.71-1.78 (m, 1H), 1.62-1.75 (m, 1H), 1.43 (d, J=14.4 Hz, 9H).

Step d.
To a stirred solution of tert-butyl 6-(1-methylpiperidine-3-carboxamido)-4-phenylisoindoline-2-carboxylate (0.09 g, 0.206 mmol) in DCM (5 ml) was added TFA (0.45 ml) at rt. The reaction mixture was stirred at rt for 3 h. The reaction mixture was evaporated to dryness and the residue was azeotropically distilled with DCM (3×10 ml). The resulting residue was triturated with diethyl ether (20 ml) and dried under vacuum to yield 1-methyl-N-(7-phenylisoindolin-5-yl)piperidine-3-carboxamide TFA salt (0.13 g, quantitative). LCMS: Method A, 1.453 min, MS: ES+ 336.59.

Step e.
To a stirred solution of 1-methyl-N-(7-phenylisoindolin-5-yl)piperidine-3-carboxamide TFA salt (0.1 g, 0.222 mmol) in THF:DMF (1:0.1, 5.5 ml) were added TEA (0.07 g, 0.668 mmol) and cyanogen bromide (0.026 g, 0.244 mmol) at −78° C. The reaction mixture was stirred at −78° C. for 10 min. The reaction mixture was quenched with water (10 ml) at −78° C. and warmed to rt. The reaction mixture was extracted with EtOAc (3×20 ml). The combined organic phase was washed with brine (20 ml). The organic phase was separated, dried over Na$_2$SO$_4$, filtered and concentrated under reduced pressure. The resulting residue was purified by flash chromatography (neutral silica; 2% MeOH in DCM) yielding N-(2-cyano-7-phenylisoindolin-5-yl)-1-methylpiperidine-3-carboxamide (0.03 g, 0.083 mmol). LCMS: Method D, 4.282 min, MS: ES+ 361.09; $^1$H NMR (400 MHz, DMSO-d6) δ ppm 10.14 (s, 1H), 7.64 (d, 1.6 Hz, 1H), 7.55 (d, J=2.0 Hz, 1H), 7.45-7.48 (m, 4H), 7.39-7.43 (m, 1H), 4.81 (s, 4H), 2.84 (d, J=10.4 Hz, 1H), 2.68-2.71 (m, 1H), 2.56-2.61 (m, 1H), 2.18 (s, 3H), 2.01 (t, J=10.8 Hz, 1H), 1.79-1.88 (m, 2H), 1.65-1.68 (m, 1H), 1.36-1.51 (m, 2H).

Example 37 (S)—N-(2-cyano-7-phenylisoindolin-5-yl)-1-methylpiperidine-3-carboxamide

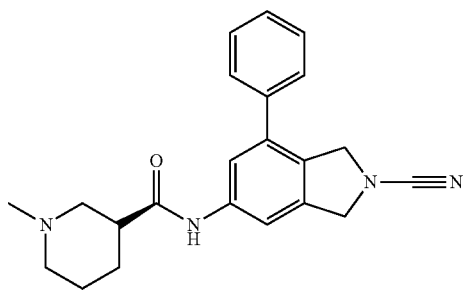

The racemic Example 36 was subjected for enantiomeric separation via SFC; mobile phase: (A) Liquid carbon dioxide and (B) 0.1% ammonia in IPA, column: CHIRALCEL OJ-H 250×21.0 mm, 5 micron, column flow was 70.0 ml/min. After evaporation of the product fractions the title compound was obtained along with Example 39. Stereochemistry was confirmed by X-Ray crystallography. LCMS: Method D, 4.260 min, MS: ES+ 361.09; Chiral HPLC Method T RT 3.92 min; $^1$H NMR (400 MHz, DMSO-d6) δ ppm 10.15 (s, 1H), 7.64 (d, J=1.6 Hz, 1H), 7.54 (d, J=1.6 Hz, 1H), 7.45-7.50 (m, 4H), 7.39-7.43 (m, 1H), 4.81 (s, 4H), 2.87 (d, J=8.8 Hz, 1H), 2.72 (d, J=10.8 Hz, 1H), 2.60-2.63 (m, 1H), 2.10 (s, 3H), 2.00-2.09 (m, 1H), 1.85-1.89 (m, 1H), 1.79-1.83 (m, 1H), 1.67-1.70 (m, 1H), 1.49-1.53 (m, 1H), 1.41-1.44 (m, 1H).

Example 38 (R)—N-(2-cyano-7-phenylisoindolin-5-yl)-1-methylpiperidine-3-carboxamide

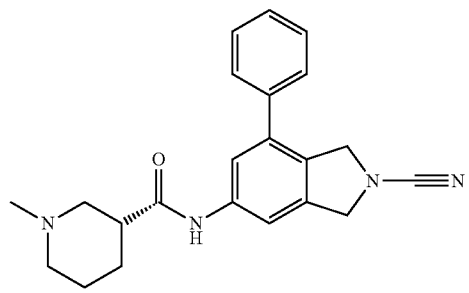

This was prepared as described for Example 37. LCMS: Method D, 4.241 min, MS: ES+ 361.09; Chiral HPLC Method T RT 4.37 min; $^1$H NMR (400 MHz, DMSO-d6) δ ppm 10.18 (s, 1H), 7.64 (d, J=1.6 Hz, 1H), 7.54 (d, J=1.6 Hz, 1H), 7.45-7.50 (m, 4H), 7.40-7.43 (m, 1H), 4.81 (s, 4H), 2.78-2.79 (m, 1H), 2.67-2.68 (m, 1H), 2.55-2.63 (m, 1H), 2.70 (br s, 3H), 1.96-2.03 (m, 1H), 1.80-1.94 (m, 1H), 1.65-1.73 (m, 1H), 1.49-1.55 (m, 2H), 1.40-1.43 (m, 1H).

Compounds in Table 5 were synthesised using a procedure similar to that described for Example 36

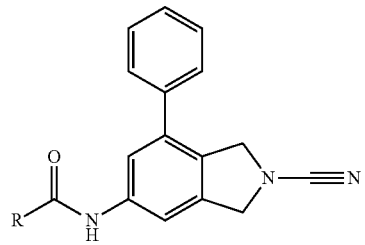

TABLE 5

| Ex | R— | Name | Acid CAS Number | LCMS method | LCMS RT/ min | MS ES+ |
|---|---|---|---|---|---|---|
| Example 39 | | N-(2-cyano-7-phenylisoindolin-5-yl)-1-methyl-1H-pyrazole-5-carboxamide | 16034-46-1 | E | 4.020 | 344.98 |
| Example 40 | | 4-benzyl-N-(2-cyano-7-phenylisoindolin-5-yl)morpholine-2-carboxamide | 769087-80-1 | E | 3.882 | 439.38 |
| Example 41 | | N-(2-cyano-7-phenylisoindolin-5-yl)-3-(pyridin-3-yl)propanamide | 3724-19-4 | A | 1.807 | 369.70 |

TABLE 5-continued

| Ex | R— | Name | Acid CAS Number | LCMS method | LCMS RT/min | MS ES+ |
|---|---|---|---|---|---|---|
| Example 42 | 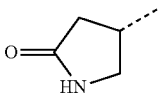 | N-(2-cyano-7-phenylisoindolin-5-yl)-5-oxopyrrolidine-3-carboxamide | 7268-43-1 | E | 3.434 | 347.67 |
| Example 43 | 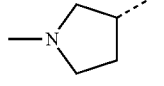 | N-(2-cyano-7-phenyl-isoindolin-5-yl)-1-methylpyrrolidine-3-carboxamide | 412281-11-9 | A | 1.749 | 347.69 |
| Example 44 | 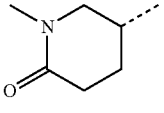 | N-(2-cyano-7-phenylisoindolin-5-yl)-1-methyl-6-oxopiperidine-3-carboxamide | 22540-51-8 | D | 3.734 | 375.06 |
| Example 45 | 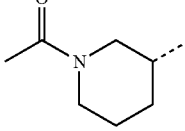 | 1-acetyl-N-(2-cyano-7-phenylisoindolin-5-yl)piperidine-3-carboxamide | 2637-76-5 | D | 3.903 | 389.10 |
| Example 46 | 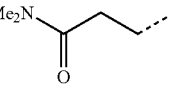 | N1-(2-cyano-7-phenylisoindolin-5-yl)-N4,N4-dimethylsuccinamide | 2564-95-6 | I | 3.22 | 363 |
| Example 47 | 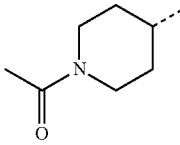 | 1-acetyl-N-(2-cyano-7-phenylisoindolin-5-yl)piperidine-4-carboxamide | 25503-90-6 | I | 3.28 | 389 |
| Example 48 | 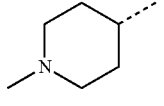 | N-(2-cyano-7-phenylisoindolin-5-yl)-1-methylpiperidine-4-carboxamide | 68947-43-3 | I | 3.26 | 361 |
| Example 49 | 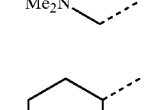 | N-2-cyano-7-phenylisoindolin-5-yl)-2-(dimethylamino)acetamide | 1118-68-9 | I | 2.94 | 321 |
| Example 50 | 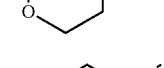 | N-(2-cyano-7-phenylisoindolin-5-yl)tetrahydro-2H-pyran-4-carboxamide | 5337-03-1 | I | 3.89 | 348 |
| Example 51 | 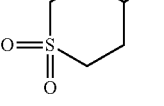 | N-(2-cyano-7-phenylisoindoin-5-yl)tetrahydro-2H-thiopyran-4-carboxamide 1,1-dioxide | 55112-42-0 | I | 3.89 | 348 |
| Example 52 | 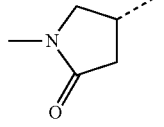 | N-(2-cyano-7-phenylisoindolin-5-yl)-1-methyl-5-oxopyrrolidine-3-carboxamide | 42346-68-9 | D | 3.658 | 361.09 |
| Example 53 | 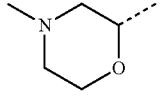 | N-(2-cyano-7-phenylisoindolin-5-yl)-4-methylmorpholine-2-carboxamide | 42949-48-8 | E | 3.152 | 363.30 |
| Example 54 | 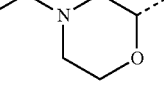 | N-(2-cyano-7-phenylisoindolin-5-yl)-4-ethylmorpholine-2-carboxamide | 939979-52-9 | D | 4.351 | 376.98 |

TABLE 5-continued

| Ex | R— | Name | Acid CAS Number | LCMS method | LCMS RT/min | MS ES+ |
|---|---|---|---|---|---|---|
| Example 55 | 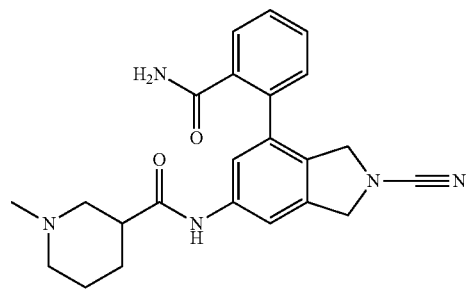 | N-(2-cyano-7-phenylisoindolin-5-yl)-4-isopropylmorpholine-2-carboxamide | 1250219-33-0 | D | 4.608 | 390.95 |

Example 56 N-(7-(2-carbamoylphenyl)-2-cyanoisoindolin-5-yl)-1-methylpiperidine-3-carboxamide

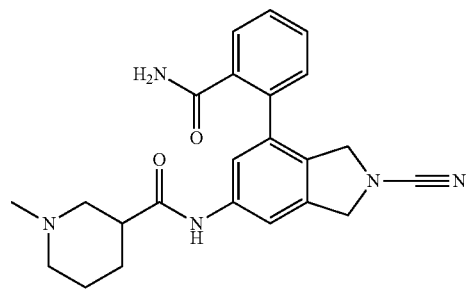 [SMILES: CN1CCCC(C(=O)Nc2cc3c(c(-c4ccccc4C(N)=O)c2)CN(C#N)C3)C1]

This was synthesised using a procedure similar to that described for Example 36, using 2-(aminocarbonyl)phenylboronic acid (CAS Number 380430-54-6) in step a. LCMS: Method E, 2.520 min, MS: ES+ 404.45

Example 57 Methyl 2-cyano-7-phenylisoindoline-5-carboxylate

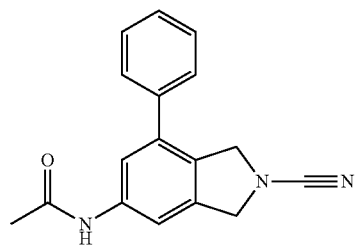 [SMILES: CC(=O)Nc1cc2c(c(-c3ccccc3)c1)CN(C#N)C2]

Step a.

To a solution of tert-butyl 6-amino-4-phenylisoindoline-2-carboxylate (Intermediate 4, 0.055 g, 0.177 mmol) in DCM (2 ml) was added TEA (0.049 ml, 0.354 mmol) at 0° C. Acetyl chloride (0.016 ml, 0.224 mmol) was added to the reaction mixture at 0° C. The reaction mixture was stirred at 0° C. for 30 min. The resulting reaction mixture was poured into water (5 ml) and extracted with DCM (2×5 ml). The combined organic phase was dried over $Na_2SO_4$, filtered and concentrated under reduced pressure yielding tert-butyl 6-acetamido-4-phenylisoindoline-2-carboxylate (0.040 g, 0.113 mmol). This material was used directly for the next step without further purification. LCMS: Method A, 2.307 min, MS: ES+ 297.33 (M−56).

Steps b, c.

The title compound was synthesised from the intermediate above using a procedure similar to that described for steps d and e of Example 36. LCMS: Method C, 6.498 min, MS: ES− 276.15; NMR (400 MHz, DMSO-d6) δ ppm 10.13 (s, 1H), 7.18-7.47 (m, 7H), 4.81 (s, 4H), 2.06 (s, 3H).

Example 58 N-(2-cyano-7-phenylisoindolin-5-yl)-N-methylacetamide

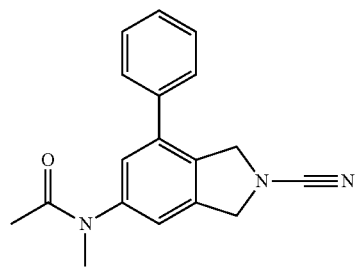 [SMILES: CC(=O)N(C)c1cc2c(c(-c3ccccc3)c1)CN(C#N)C2]

Step a.

Tert-butyl 6-acetamido-4-phenylisoindoline-2-carboxylate was prepared as described in step a of Example 57.

Step b.

NaH (60% dispersion in mineral oil, 17 mg, 0.43 mmol) was added to a solution of a tert-butyl 6-acetamido-4-phenylisoindoline-2-carboxylate (100 mg, 0.28 mmol) in dry THF (5 ml) under $N_2$ at 0° C. and the mixture stirred at this temperature for 30 min. Methyl iodide (20 µl, 0.31 mmol) was added dropwise and warmed to rt. The reaction mixture was stirred at rt for 18 h. After the reaction was completed, the reaction mixture was poured into water (10 ml) and extracted with EtOAc (2×20 ml). The organic layers were collected and washed with brine (20 ml), dried over $Na_2SO_4$, and concentrated under reduced pressure. The residue (145 mg) was dissolved in DCM and purified by flash chromatography on a 12 g Telos silica column using a gradient of DCM/MeOH (100:0) to (94:6) to give tert-butyl 6-(N-methylacetamido)-4-phenylisoindoline-2-carboxylate (95 mg, 92%) as a yellow solid. LCMS: Method I, 3.5 min, MS: ES+ 367; $^1$H NMR (400 MHz, $CDCl_3$) δ ppm 7.39-7.48 (m, 5H), 7.04-7.12 (m, 2H), 4.70-4.76 (m, 4H), 3.30 (s, 3H), 1.94 (s, 3H), 1.50 (s, 9H).

Steps c, d.

The title compound was synthesised from the intermediate above using a procedure similar to that described for steps d and e of Example 36. LCMS: Method I, 3.29 min, ES+ 292.

Example 59 N-(2-cyano-7-phenylisoindolin-5-yl)-N,1-dimethylpiperidine-3-carboxamide

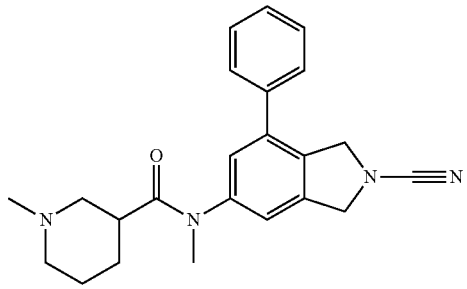

Step a.

This was carried out in a similar way to Example 36 using 1-methylpiperidine-3-carboxylic acid (CAS Number 5657-70-5)

Steps b-d.

Carried out in a similar way to steps b-d of Example 58. LCMS: Method I, 2.97 min, MS: ES+ 375.

Example 60 N-(2-cyano-7-phenylisoindolin-5-yl)-4-methylpiperazine-1-carboxamide

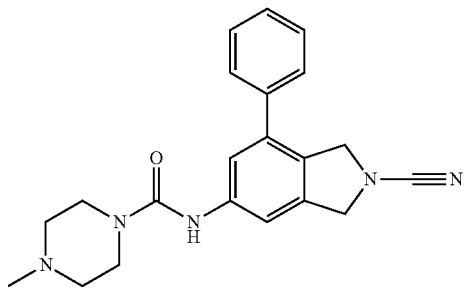 [SMILES: CN1CCN(C(=O)Nc2cc3c(c(-c4ccccc4)c2)CN(C#N)C3)CC1]

Step a.

To a stirred solution of tert-butyl 6-amino-4-phenylisoindoline-2-carboxylate (Intermediate 4, 65 mg, 0.21 mmol) in pyridine (5 ml), was added 4-methylpiperazine-1-carbonyl chloride (CAS Number 55112-42-0, 42 mg, 0.21 mmol). The reaction mixture was stirred at rt for 1 h after which 4-methylpiperazine-1-carbonyl chloride (84 mg, 0.42 mmol) was added to the reaction and stirred at rt for 18 h. DMAP (26 mg, 0.21 mmol) and 4-methylpiperazine-1-carbonyl chloride (84 mg, 0.42 mmol) were then added to the reaction and this stirred at rt for 48 h. The solvent was then removed, water (20 ml) added to the residue and the mixture then extracted with DCM (3×20 ml). The combined organic extracts were washed with brine (30 ml), dried over Na$_2$SO$_4$, and evaporated under reduced pressure. The residue was dissolved in DCM and purified by flash chromatography on a 12 g Telos silica column using a gradient of DCM/MeOH (100:0) to (80:20) to give tert-butyl 6-(4-methylpiperazine-1-carboxamido)-4-phenylisoindoline-2-carboxylate (45 mg, 50%) as a yellow oil. LCMS: Method I, 3.67 min, MS: ES+ 437.

Steps b, c.

Carried out in a similar way to steps d and e of Example 36. LCMS: Method I, 3.52 min, MS: ES+ 362.

Example 61 N-(2-cyano-7-phenylisoindolin-5-yl)methanesulfonamide

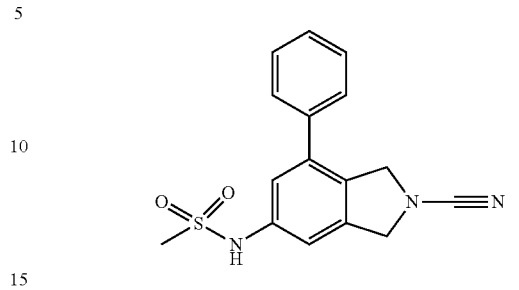

Step a.

To a stirred solution of tert-butyl 6-amino-4-phenylisoindoline-2-carboxylate (Intermediate 4, 100 mg, 0.323 mmol) and pyridine (39 μl, 0.484 mmol) in DCM (5 ml), at 0° C. under nitrogen, was added methanesulfonyl chloride (25 μl, 0.323 mmol) slowly. The reaction solution was stirred at 0° C. for 1 h, then warmed to rt. The reaction was poured into water (10 ml) and extracted with DCM (3×20 ml). The combined organic extracts were washed with brine (10 ml), dried over Na$_2$SO$_4$, filtered and evaporated under reduced pressure. The residue (132 mg) was dissolved in DCM and purified by flash chromatography on a 12 g Telos silica column using a gradient of DCM/MeOH (100:0) to (95:5) to give tert-butyl 6-(methylsulfonamido)-4-phenylisoindoline-2-carboxylate (106 mg, 85%) as a yellow oil. LCMS: Method I, 3.42 min, MS: ES+ 389.

Steps b, c.

The title compound was synthesised from the intermediate above using a procedure similar to that described for steps d and e of Example 36. LCMS: Method I, 3.66 min, MS: ES+ 314.

Example 62 N-(2-cyano-7-phenylisoindolin-5-yl)piperidine-3-carboxamide

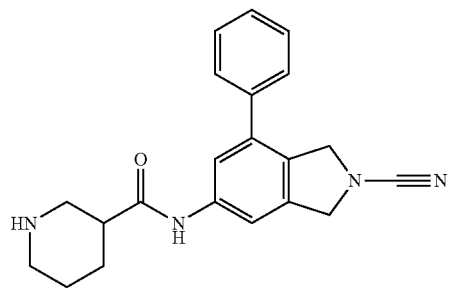 [SMILES: N#CN1Cc2cc(NC(=O)C3CCCNC3)cc(-c3ccccc3)c2C1]

Steps a-c.

These were carried out according to scheme E using a procedure similar to that described for Example 36, using 1-(((9H-fluoren-9-yl)methoxy)carbonyl)piperidine-3-carboxylic acid (CAS Number 158922-07-7; available from Combi Block) in step c to give (9H-fluoren-9-yl)methyl 3-((2-cyano-7-phenylisoindolin-5-yl)carbamoyl)piperidine-1-carboxylate.

Step d.

To a stirred solution of (9H-fluoren-9-yl)methyl 3-((2-cyano-7-phenylisoindolin-5-yl)carbamoyl)piperidine-1-carboxylate (0.21 g, 0.369 mmol) in DMF (10 ml) was added piperidine (0.094 g, 1.107 mmol) at 0° C. The reaction mixture was stirred at 0° C. for 1 h. The reaction mixture was poured into ice cold water (150 ml) and extracted with EtOAc (3×70 ml). The combined organic phase was separated, dried over $Na_2SO_4$, filtered and concentrated under reduced pressure. The resulting crude material was purified by flash chromatography (13% MeOH in DCM). The obtained material was subjected for preparative HPLC purification; mobile phase: (A) 0.1% formic acid in water (B) MeCN:MeOH (1:1; v/v), column: Phenomenex Luna C8 (250×21.2) mm, 5 μm, flow rate 10.0 ml/min which yielded N-(2-cyano-7-phenylisoindolin-5-yl)piperidine-3-carboxamide (0.02 g, 0.058 mmol). LCMS: Method D, 4.252 min, MS: ES+ 347.11; $^1$H NMR (400 MHz, DMSO-d6) δ ppm 10.27 (s, 1H), 7.64 (s, 1H), 7.56 (d, J=1.6 Hz, 1H), 7.46-7.50 (m, 4H), 7.40-7.43 (m, 1H), 4.81 (s, 4H), 3.45-3.50 (m, 1H), 3.16 (d, J=12.0 Hz, 1H), 3.01 (d, J=12.4, 1H), 2.77-2.83 (m, 1H), 2.64-2.67 (m, 2H), 1.95 (d, J=12.0 Hz, 1H), 1.70-1.73 (m, 1H), 1.51-1.65 (m, 2H).

Example 63 N-(2-cyano-7-phenylisoindolin-5-yl) piperidine-4-carboxamide

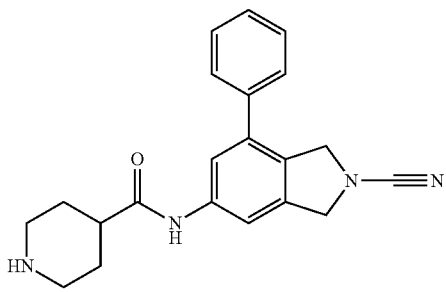 [SMILES: N#CN1Cc2cc(NC(=O)C3CCNCC3)cc(-c3ccccc3)c2C1]

This was synthesised using 1-Fmoc-piperidine-4-carboxylic acid (CAS Number 148928-15-8) using a procedure similar to that described for Example 62. LCMS: Method I, 3.09 min, MS: ES+ 347.

Example 64 6-(((1-methylpiperidin-3-yl)methyl) amino)-4-phenylisoindoline-2-carbonitrile

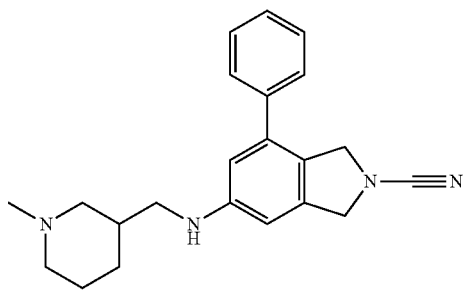 [SMILES: CN1CCCC(CNc2cc3c(c(-c4ccccc4)c2)CN(C#N)C3)C1]

Step a.

To a stirred solution of (1-methylpiperidin-3-yl)methanol (CAS Number 7583-53-1; available from Ark Pharm) (0.5 g, 3.876 mmol) in DCM (10 ml) was added TEA (0.78 g, 7.752 mmol) and methanesulfonyl chloride (0.66 g, 5.804 mmol) at 0° C. The reaction mixture was stirred at rt for 5 h. The reaction mixture was poured into water (20 ml) and saturated $NaHCO_3$ solution (10 ml) and extracted with EtOAc (3×50 ml). The combined organic phase was washed with brine solution (20 ml), dried over $Na_2SO_4$, filtered and concentrated under reduced pressure. The resulting residue was purified by flash chromatography (5% MeOH in DCM) yielding (1-methylpiperidin-3-yl)methyl methanesulfonate (0.65 g, 3.136 mmol); $^1$H NMR (400 MHz, DMSO-d6) δ ppm 4.04-4.13 (m, 2H), 3.17 (s, 3H), 2.68 (d, J=8.8 Hz, 1H), 2.57 (d, J=10.4 Hz, 1H), 2.15 (s, 3H), 1.87-1.92 (m, 2H), 1.76 (t, J=10 Hz, 1H), 1.59-1.63 (m, 2H), 1.41-1.50 (m, 1H), 0.97-1.05 (m, 1H).

Step b.

To a stirred solution of tert-butyl 6-amino-4-phenylisoindoline-2-carboxylate (Intermediate 4, 0.18 g, 0.58 mmol) in toluene (3 ml) was added (1-methylpiperidin-3-yl)methyl methanesulfonate (0.42 g, 2.029 mmol) at rt. The reaction mixture was heated at 160° C. for 48 h. The reaction mixture was cooled to rt and evaporated to dryness. The resulting residue was purified by flash chromatography using (5.5% MeOH in DCM) yielding tert-butyl 6-(((1-methylpiperidin-3-yl)methyl)amino)-4-phenylisoindoline-2-carboxylate (0.05 g, 0.118 mmol). LCMS: Method A, 2.146 min, ES+ 422.63.

Step c.

To a stirred solution of tert-butyl 6-(((1-methylpiperidin-3-yl)methyl)amino)-4-phenylisoindoline-2-carboxylate (0.045 g, 0.107 mmol) in DCM (3 ml) was added 4 M HCl in 1,4-dioxane (0.23 ml) drop wise at 0° C. The reaction mixture was stirred at rt for 3 h. The solvent was distilled under vacuum and the resulting residue was washed with n-pentane (10 ml) and finally dried under vacuum yielding N-((1-methylpiperidin-3-yl)methyl)-7-phenylisoindolin-5-amine HCl (0.037 g, 0.103 mmol). LCMS: Method A, 1.444 min, ES+ 322.5.

Step d.

To a stirred solution of N-((1-methylpiperidin-3-yl) methyl)-7-phenylisoindolin-5-amine hydrochloride (0.035 g, 0.097 mmol) in THF:DMF (2:0.5, 2.5 ml) was added TEA (0.029 g, 0.29 mmol) at −40° C. The reaction mixture stirred at −40° C. for 10 min. Cyanogen bromide (0.012 g, 0.117 mmol) was added to the reaction mixture at −40° C. and stirred for 30 min. The resulting reaction mixture was poured into water (20 ml) and extracted with 10% DCM in MeOH (3×30 ml). The combined organic phase was washed with brine (10 ml). The organic phase was separated, dried over $Na_2SO_4$, filtered and concentrated under reduced pressure. The resulting residue was purified by column chromatography (5% MeOH in DCM). The obtained material was repurified by preparative TLC using 13% MeOH in DCM as mobile phase yielding 6-(((1-methylpiperidin-3-yl)methyl) amino)-4-phenylisoindoline-2-carbonitrile (0.002.4 g, mmol). LCMS: Method E, 3.444 min, ES+ 347.31, $^1$H NMR (400 MHz, DMSO-d6) δ ppm 7.35-7.47 (m, 5H), 6.55 (s, 1H), 6.49 (s, 1H), 5.93-5.96 (m, 1H), 4.69 (d, J=5.6 Hz, 4H), 2.88-2.93 (m, 3H), 2.69-2.78 (m, 1H), 2.18-2.28 (m, 3H), 1.94-2.13 (m, 1H), 1.80-1.94 (m, 2H), 1.65-1.76 (m, 2H), 1.48-1.55 (m, 1H), 0.96-0.98 (m, 1H).

Scheme F

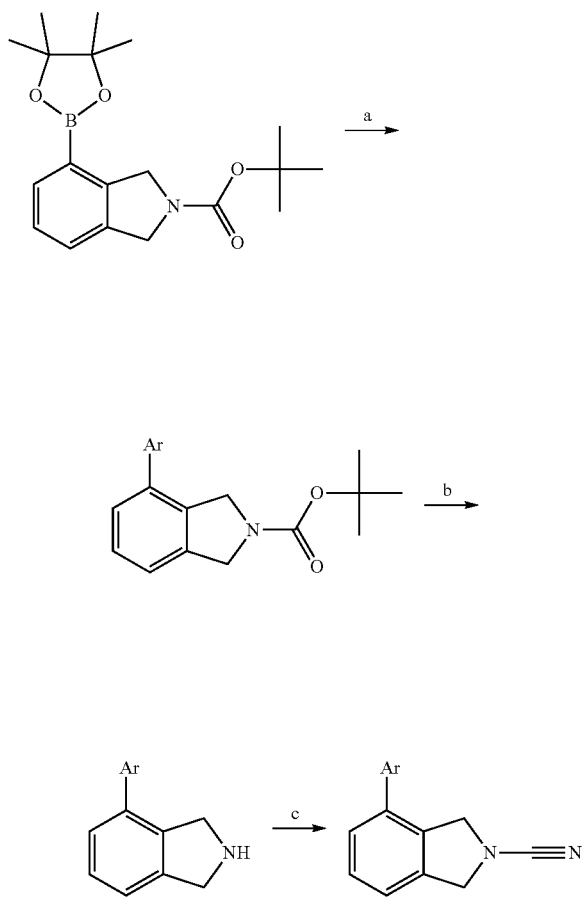

Reagents and conditions: a) ArBr or ArOTf; K₂CO₃, Pd(PPh₃)₄, 1,4-dioxane, water; b) TFA, DCM; c) BrCN, TEA, THF.

Example 65 4-(2-chloro-4-cyanophenyl)isoindoline-2-carbonitrile

Prepared According to Scheme F

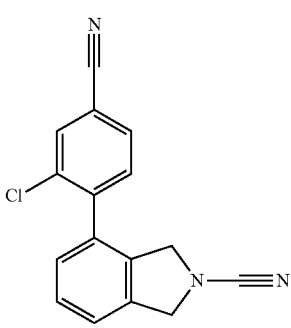 [SMILES: N#Cc1ccc(-c2cccc3c2CN(C#N)C3)c(Cl)c1]

Step a.

A mixture of 4-bromo-3-chlorobenzonitrile (150 mg, 0.69 mmol), tert-butyl 4-(4,4,5,5-tetramethyl-1,3,2-dioxaborolan-2-yl)isoindoline-2-carboxylate (Intermediate 2, 287 mg, 0.83 mmol) and K₂CO₃ (238 mg, 1.73 mmol) in 1,4-dioxane (5.4 ml) and water (0.6 ml) was degassed by nitrogen bubbling for 5 min. Pd(PPh₃)₄ (79 mg, 0.069 mmol) was then added. The mixture was heated at reflux for 18 h and then cooled to rt. The mixture was filtered on a silica pad and washed with EtOAc (200 ml). The filtrate was evaporated under reduced pressure. The residue (500 mg) was dissolved in DCM and purified by flash chromatography on silica gel using hexane/EtOAc (90:10) to give tert-butyl 4-(2-chloro-4-cyanophenyl)isoindoline-2-carboxylate (242 mg, 99%) as a bright yellow solid. LCMS: Method I, 3.66 min, MS: ES+ 355, 357; ¹H NMR (400 MHz, CDCl₃) δ ppm 7.80 (m, 1H), 7.63 (m, 1H), 7.33-7.41 (m, 3H), 7.14 (m, 1H), 4.77 (m, 2H), 4.56 (m, 2H), 1.49 (m, 9H).

Step b.

TFA (1 ml) was added to a solution of tert-butyl 4-(2-chloro-4-cyanophenyl)isoindoline-2-carboxylate (232 mg, 0.65 mmol) in DCM (9 ml) and the resulting solution was stirred at rt for 18 h. The mixture was evaporated under reduced pressure and azeotroped consecutively with toluene (20 ml) and MeCN (2×20 ml) to give 3-chloro-4-(isoindolin-4-yl)benzonitrile TFA salt (260 mg, 0.40 mmol, quantitative) as a dark yellow gum. LCMS: Method I, 2.81 min, MS: ES+ 255, 257; NMR (400 MHz, MeOD) δ ppm 8.02 (d, J=1.6 Hz, 1H), 7.81 (dd, J=7.9, 1.6 Hz, 1H), 7.53-7.58 (m, 3H), 7.32-7.36 (m, 1H), 4.72 (s, 2H), 4.46 (s, 2H).

Step c.

A solution of 3-chloro-4-(isoindolin-4-yl)benzonitrile TFA salt (252 mg, 0.65 mmol) and TEA (0.30 ml, 2.13 mmol) in THF (7 ml) was cooled to 0° C. under a nitrogen atmosphere and then cyanogen bromide (5M in MeCN, 0.19 ml, 0.93 mmol) was added. The mixture was stirred at 0° C. for 2 h. The mixture was poured into water (40 ml) and extracted with EtOAc (3×40 ml). The combined organic extracts were dried on Na₂SO₄, filtered and evaporated under reduced pressure. The residue was dissolved in DCM and purified by flash chromatography on a 12 g Telos silica column using a gradient of hexane/EtOAc (90:10) to (60:40) to give 4-(2-chloro-4-cyanophenyl)isoindoline-2-carbonitrile (140 mg, 77% over 2 steps) as a white solid. LCMS: Method J, 4.17 min, MS: ES+ 280, 282; ¹H NMR (400 MHz, CDCl₃) δ ppm 7.81 (d, J=1.6 Hz, 1H), 7.65 (dd, J=7.8, 1.6 Hz, 1H), 7.45 (t, J=7.6 Hz, 1H), 7.38 (J=7.8 Hz, 1H), 7.35 (dd, J=7.6, 0.8 Hz, 1H), 7.19 (dd, J=7.6, 0.8 Hz, 1H) 4.88 (s, 2H), 4.60 (br s, 2H).

Compounds in Table 6 were synthesised according to Scheme F using a procedure similar to that described for Example 65.

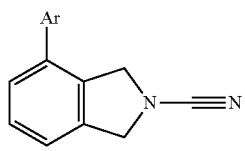

TABLE 6

| Ex | Ar— | Name | Aryl halide or triflate CAS Number | LCMS method | LCMS RT/ min | MS ES+ |
|---|---|---|---|---|---|---|
| Example 66 | 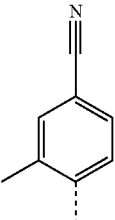 | 4-(4-cyano-2-methylphenyl)isoindoline-2-carbonitrile | 41963-20-6 | J | 4.09 | 260 |
| Example 67 | 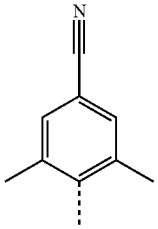 | 4-(4-cyano-2,6-dimethylphenyl)isoindoline-2-carbonitrile | 75344-77-3 | D | 5.030 | 273.97 |
| Example 68 | 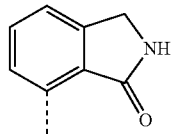 | 3-oxo-[4,4'-biisoindoline]-2'-carbonitrile | 200049-46-3 | J | 3.5 | 276 |
| Example 69 | 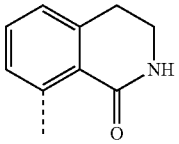 | 4-(1-oxo-1,2,3,4-tetrahydroisoquinolin-8-yl)isoindoline-2-carbonitrile | 1159811-99-0 | J | 3.82 | 290 |
| Example 70 | 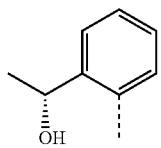 | (R)-4-(2-(1-hydroxyethyl)phenyl)isoindoline-2-carbonitrile | 76116-20-6 | J | 4.23 | 247 (−H$_2$O) |
| Example 71 | 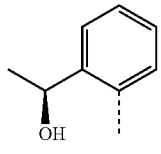 | (S)-4-(2-(1-hydroxyethyl)phenyl)isoindoline-2-carbonitrile | 114446-55-8 | J | 4.76 | 247 (−H$_2$O) |
| Example 72 | 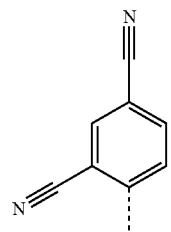 | 4-(2-cyanoisoindolin-4-yl)isophthalonitrile | 22433-89-2 (prepared according to procedure described in WO 2013/142266) | J | 4.38 | 271 |
| Example 165 | 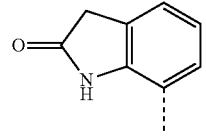 | 4-(2-oxoindolin-7-yl)isoindoline-2-carbonitrile | 320734-35-8 | D | 3.773 | 276.07 |

TABLE 6-continued

| Ex | Ar— | Name | Aryl halide or triflate CAS Number | LCMS method | LCMS RT/ min | MS ES+ |
|---|---|---|---|---|---|---|
| Example 166 | 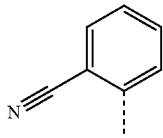 | 4-(2-cyanophenyl)isoindoline-2-carbonitrile | 2042-37-7 | D | 4.294 | 245.99 |
| Example 167 | 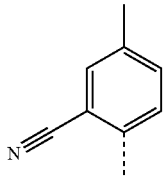 | 4-(2-cyano-4-fluorophenyl)isoindoline-2-carbonitrile | 57381-39-2 | E | 4.134 | 264.38 |
| Example 168 | 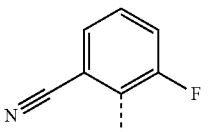 | 4-(2-cyano-6-fluorophenyl)isoindoline-2-carbonitrile | 425379-16-4 | D | 4.34 | 264 |
| Example 169 | 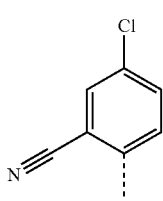 | 4-(4-chloro-2-cyanophenyl)isoindoline-2-carbonitrile | 57381-37-0 | D | 4.74 | 280.02 |
| Example 170 | 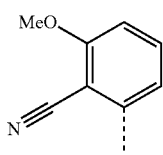 | 4-(2-cyano-3-methoxyphenyl)isoindoline-2-carbonitrile | 1245647-50-0 | D | 4.62 | 276.03 |
| Example 171 | 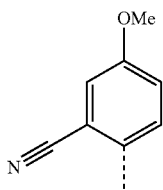 | 4-(2-cyano-4-methoxyphenyl)isoindoline-2-carbonitrile | 138642-47-4 | D | 4.75 | 275.96 |
| Example 172 | 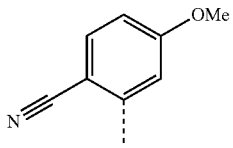 | 4-(2-cyano-5-methoxyphenyl)isoindoline-2-carbonitrile | 140860-51-1 | D | 4.681 | 275.96 |
| Example 173 | 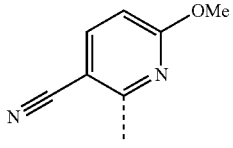 | 4-(3-cyano-6-methoxypyridin-2-yl)isoindoline-2-carbonitrile | 121643-47-8 | I | 2.32 | 277 |
| Example 174 | 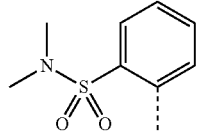 | 2-(2-cyanoisoindolin-4-yl)-N,N-dimethylbenzenesulfonamide | 65000-13-7 | Q | 3.51 | 328 |

TABLE 6-continued

| Ex | Ar— | Name | Aryl halide or triflate CAS Number | LCMS method | LCMS RT/ min | MS ES+ |
|---|---|---|---|---|---|---|
| Example 175 | | 2-(2-cyanoisoindolin-4-yl)-N-ethylbenzenesulfonamide | 169189-80-4 | Q | 3.47 | 328 |
| Example 176 | | 4-(7-cyano-3-oxo-2,3-dihydro-1H-inden-4-yl)isoindoline-2-carbonitrile | Intermediate 8 | J | 4.22 | 300 |
| Example 177 | | 4-(4-cyano-2-(trifluoromethyl)phenyl)isoindoline-2-carbonitrile | 1735-53-1 | Q | 3.64 | 314 |
| Example 178 | | 4-(2-(azetidin-1-ylsulfonyl)phenyl)isoindoline-2-carbonitrile | 1359705-87-5 | Q | 3.52 | 340 |
| Example 179 | | 2-(2-cyanoisoindolin-4-yl)-N-(2-hydroxyethyl)benzenesulfonamide | 1156254-91-9 | Q | 3.34 | 344 |
| Example 180 | | 2-(2-cyanoisoindolin-4-yl)-N-(2-(6-oxopyrimidin-1(6H)-yl)ethyl)benzamide | Intermediate 9 | K | 4.18 | 386 |
| Example 181 | | 4-(2-cyano-4-(1H-imidazol-1-yl)phenyl)isoindoline-2-carbonitrile | Intermediate 10 | R | 2.14 | 312 |

Scheme G

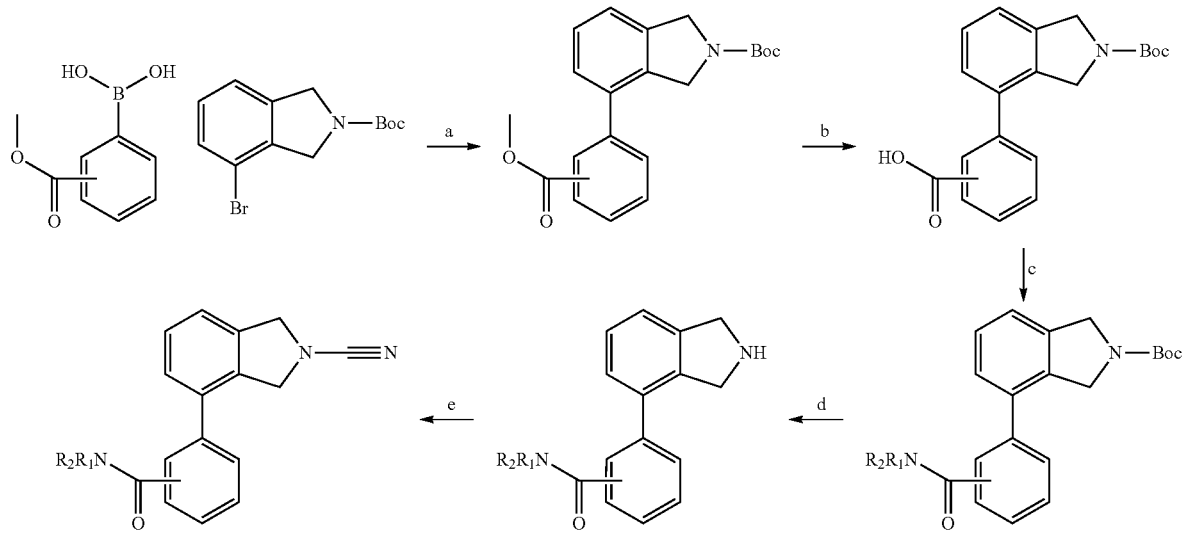

Reagents and conditions: a) Pd(PPh₃)₄, Cs₂CO₃, 1,4-dioxane, water; b) NaOH, THF, water; c) R₁R₂NH, EDC, HOBt, THF; d) TFA, DCM; e) BrCN, K₂CO₃, THF Example 73
N-benzyl-3-(2-cyanoisoindolin-4-yl)benzamide

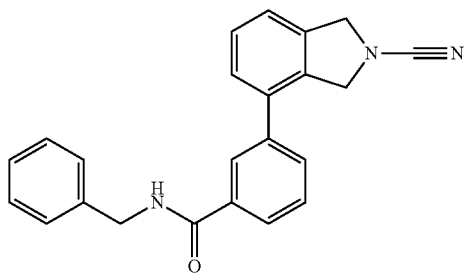 [SMILES: N#CN1Cc2cccc(-c3cccc(C(=O)NCc4ccccc4)c3)c2C1]

Step a.

To a stirred solution of tert-butyl 4-bromoisoindoline-2-carboxylate (Intermediate 1, 0.35 g, 1.185 mmol) in 1,4-dioxane:water (4:1; 20 ml) was added Cs₂CO₃ (0.77 g, 2.371 mmol) at rt under nitrogen. The reaction was purged with nitrogen for 15 min. Pd(PPh₃)₄ (0.14 g, 0.118 mmol) was added to the reaction mixture and purged with nitrogen for 10 min. 3-(Methoxycarbonyl)phenylboronic acid (CAS Number 99769-19-4; available from Combi Blocks) (0.26 g, 1.422 mmol) was added to the reaction mixture. The reaction mixture was heated at 80° C. for 24 h. The resulting reaction mixture was cooled to rt, poured into water (20 ml) and extracted with EtOAc (3×50). The combined organic phase was washed with brine (80 ml). The organic phase was separated, dried over Na₂SO₄, filtered and concentrated under reduced pressure. The resulting crude material was purified by flash chromatography (5% EtOAc in hexane) yielding tert-butyl 4-(3-(methoxycarbonyl)phenyl)isoindoline-2-carboxylate (0.33 g, 0.932 mmol). LCMS: Method A, 2.782 min, MS: ES+ 298.4 (M−56); ¹H NMR (400 MHz, CDCl₃) δ ppm 8.04-8.11 (m, 2H), 7.62 (d, J=7.2 Hz, 1H), 7.49-7.58 (m, 2H), 7.40 (t, J=7.2 Hz, 1H), 7.31-7.33 (m, 1H), 4.69-4.79 (m, 4H), 3.95 (s, 3H), 1.53 (s, 9H).

Step b.

To a stirred solution of tert-butyl 4-(3-(methoxycarbonyl)phenyl)isoindoline-2-carboxylate (0.32 g, 0.903 mmol) in THF:water (4:1; 10 ml) was added NaOH (0.072 g, 1.806 mmol) at rt. The reaction mixture was heated at 80° C. for 18 h. The resulting reaction mixture was cooled to rt and extracted with EtOAc (50 ml). The aqueous phase was acidified using 1M HCl and re-extracted with EtOAc (3×50 ml). The combined organic phase was separated and washed with brine (20 ml). The organic phase was separated, dried over Na₂SO₄, filtered and concentrated under reduced pressure yielding 3-(2-(tert-butoxycarbonyl)isoindolin-4-yl)benzoic acid (0.25 g, 0.737 mmol). This material was used for the next step without further purification. LCMS: Method A, 2.413 min, MS: ES− 338.58; ¹H NMR (400 MHz, DMSO-d6) δ ppm 13.09 (br s 1H), 7.98 (t, J=7.2 Hz, 2H), 7.77-7.64 (m, 1H), 7.62 (t, J=8.0 Hz, 1H), 7.33-7.46 (m, 3H), 4.66 (d, J=10.8 Hz, 4H), 1.43 (d, J=15.2 Hz, 9H).

Step c.

To a stirred solution of 3-(2-(tert-butoxycarbonyl)isoindolin-4-yl)benzoic acid (0.1 g, 0.295 mmol) in THF (5 ml) were added EDC.HCl (0.113 g, 0.589 mmol), HOBt (0.054 g, 0.353 mmol) and benzylamine (0.038 g, 0.353 mmol) at rt. The reaction mixture was stirred at rt for 4 h. The resulting reaction mixture was poured into water (10 ml) and extracted with EtOAc (3×20 ml). The combined organic layer was separated, washed with saturated NaHCO₃ solution (5 ml) and brine (5 ml). The organic phase was separated, dried over Na₂SO₄, filtered and concentrated under reduced pressure. The resulting crude material was purified by flash chromatography (35% EtOAc in hexane) yielding tert-butyl 4-(3-(benzylcarbamoyl)phenyl)isoindoline-2-carboxylate (0.11 g, 0.257 mmol). LCMS: Method A, 2.664 min, MS: ES+ 373.58 (M−56); ¹H NMR (400 MHz, DMSO-d6) δ ppm 9.13-9.18 (m, 1H), 8.01 (d, J=4.4 Hz, 1H), 7.94 (d, J=7.6 Hz, 1H), 7.69 (t, J=7.2 Hz, 1H), 7.59 (t, J=7.6 Hz, 1H), 7.37-7.41 (m, 3H), 7.33-7.34 (m, 4H), 7.24-7.27 (m, 1H), 4.67 (d, J=8.0 Hz, 4H), 4.51 (d, J=5.6 Hz, 2H), 1.43 (d, J=18.0 Hz, 9H).

Steps d, e.

The title compound was synthesised from the intermediate above using a procedure similar to that described for steps d and e of Example 1. LCMS: Method A, 3.977 min, MS: ES+ 354.53; $^1$H NMR (400 MHz, DMSO-d6) δ ppm 9.15 (t, 4.8 Hz, 1H), 7.98 (s, 1H), 7.93 (d, J=7.6 Hz, 1H), 7.68 (d, J=7.2 Hz, 1H), 7.58 (t, J=7.6 Hz, 1H), 7.44-7.49 (m, 2H), 7.33-7.42 (m, 5H), 7.25-7.27 (m, 1H), 4.88 (d, J=18.0 Hz, 4H), 4.51 (d, J=5.6 Hz, 2H).

Compounds in Table 7 were synthesised using a procedure similar to that described for Example 73

Steps a-f.

Carried out using a procedure similar to that described for Example 73, using 2-(ethoxycarbonyl)phenylboronic acid (CAS Number 380430-53-5) in step a and N-[(9-fluorenyl)-methoxycarbonyl]-1,2-ethylenediamine (CAS Number 166410-32-8) in step d.

Step g.

To a stirred solution of (9H-fluoren-9-yl)methyl (2-(2-(2-cyanoisoindolin-4-yl)-benzamido)ethyl)carbamate (0.08 g, 0.515 mmol) in THF (6 ml) was added piperidine (0.039 g, 0.454 mmol) at 0° C. The reaction mixture was stirred at rt for 16 h. The resulting reaction mixture was poured into water (70 ml) and extracted with DCM (2×50 ml). The resulting crude material was purified by flash chromatography (neutral aluminium oxide; 15% MeOH in DCM) to

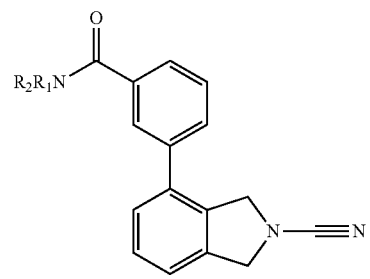

TABLE 7

| Ex | $R_1R_2N—$ | Name | Amine CAS Number | LCMS method | LCMS RT/ min | MS ES+ |
|---|---|---|---|---|---|---|
| Example 74 | | 3-(2-cyanoisoindolin-4-yl)-N-(1-phenylethyl)benzamide | 618-36-0 | B | 6.382 | 368.00 |
| Example 75 | | 3-(2-cyanoisoindolin-4-yl)-N-phenylbenzamide | 62-53-3 | B | 6.352 | 339.98 |
| Example 76 | | (R)-3-(2-cyanoisoindolin-4-yl)-N-(1-phenylethyl)benzamide | 3886-69-9 | D | 4.750 | 368.00 |

Example 77 N-(2-aminoethyl)-2-(2-cyanoisoindolin-4-yl)benzamide

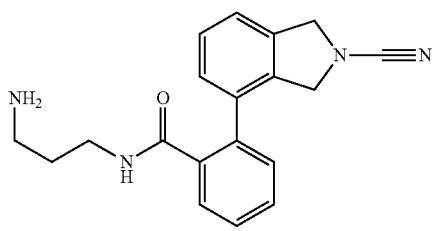 [SMILES: N#CN1Cc2cccc(-c3ccccc3C(=O)NCCCN)c2C1]

yield crude N-(2-aminoethyl)-2-(2-cyanoisoindolin-4-yl)benzamide (0.04 g, 0.131 mmol). The obtained material was further purified by preparative HPLC; mobile phase: (A) 10 mM ammonium bicarbonate (B) 100% MeCN, column: Phenomenex Gemini C18I (250×21.2) mm, 15.0 μm, flow rate 15.0 ml/min to yield N-(2-aminoethyl)-2-(2-cyanoisoindolin-4-yl)benzamide (0.02 g, 0.065 mmol). The obtained material was suspended in DCM (5 ml) and the DCM layer was carefully decanted, this process was repeated twice. The combined DCM phase was filtered and evaporated under vacuum yielded N-(2-aminoethyl)-2-(2-cyanoisoindolin-4-yl)benzamide (0.0018 g, 0.0058 mmol). LCMS: Method D, 3.225 min, MS: ES+ 307.03.

Example 78 4-(2-(piperazine-1-carbonyl)phenyl) isoindoline-2-carbonitrile

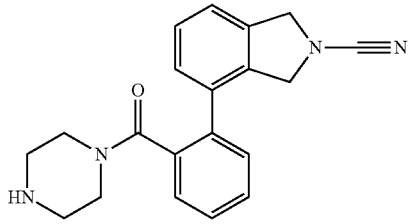 [SMILES: N#CN1Cc2cccc(-c3ccccc3C(=O)N3CCNCC3)c2C1]

This was synthesised using a procedure similar to that described for Example 77, using 1-Fmoc-piperazine (CAS Number 219312-89-7). LCMS: Method D, 3.240, MS: ES+ 333.14.

Example 79 N-benzyl-4-(2-cyanoisoindolin-4-yl)picolinamide

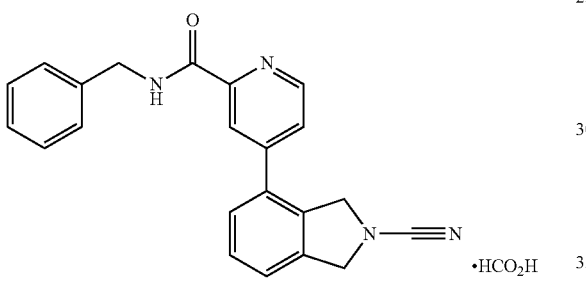

Step a.

To a stirred solution of tert-butyl 4-(4,4,5,5-tetramethyl-1,3,2-dioxaborolan-2-yl)isoindoline-2-carboxylate (Intermediate 2, 0.3 g, 0.804 mmol) in DMF (3 ml) was added $Cs_2CO_3$ (0.52 g, 1.608 mmol) at rt. The reaction mixture was degassed for 10 min. $Pd(PPh_3)_4$ (0.018 g, 0.016 mmol) and methyl 4-bromopicolinate (CAS Number 29681-42-3; 0.17 g, 0.804 mmol) was added to the reaction mixture at rt. The reaction mixture was degassed for additional 5 min. The reaction mixture was heated at 120° C. for 8 h. The resulting reaction mixture was cooled to rt, diluted with water (100 ml) and extracted with EtOAc (2×100 ml). The combined organic phase was separated, dried over $Na_2SO_4$, filtered and concentrated under reduced pressure yielding tert-butyl 4-(2-(methoxycarbonyl)pyridin-4-yl)isoindoline-2-carboxylate (0.45 g, quantitative). This material was used for the next step without further purification LCMS: Method A, 2.234 min, MS: ES+ 355.28.

Step b.

To a stirred solution of tert-butyl 4-(2-(methoxycarbonyl)pyridin-4-yl)isoindoline-2-carboxylate (0.43 g, 1.215 mmol) in THF (2 ml) was added DIPEA (0.08 g, 0.607 mmol) and trimethylaluminum solution (2M in toluene) (3.03 ml, 6.073 mmol) at rt. Benzylamine (0.16 g, 1.458 mmol) was added to the reaction mixture at rt. The reaction mixture was heated at 80° C. for 1 h. The resulting reaction mixture was cooled to rt, diluted with water (100 ml) and extracted with EtOAc (2×100 ml). The combined organic phase was separated, dried over $Na_2SO_4$, filtered and concentrated under reduced pressure yielding tert-butyl 4-(2-(benzylcarbamoyl)pyridin-4-yl)isoindoline-2-carboxylate (0.47 g, 1.095 mmol). This material was used for the next step without further purification LCMS: Method A, 2.600 min, MS: ES+ 430.33.

Steps c, d.

The title compound was synthesised from the intermediate above using a procedure similar to that described for steps d and e of Example 1. The obtained crude material was subjected for preparative HPLC purification; mobile phase: (A) 0.1% formic acid in water (B) 0.1% formic acid in MeCN, column: Phenomenex Luna C8 (250×21.2) mm, 5 μm, flow rate 20.0 ml/min which yielded N-benzyl-4-(2-cyanoisoindolin-4-yl)picolinamide. LCMS: Method E, 4.307 min, MS: ES+ 355.28; $^1$H NMR (400 MHz, DMSO-d6) δ ppm 9.46 (t, J=6.8 Hz, 1H), 8.73 (d, J=3.9 Hz, 1H), 8.09 (d, J=1.2 Hz, 1H), 7.78 (dd, J=1.6 Hz, 4.8 Hz, 1H), 7.52-7.55 (m, 2H), 7.44-7.47 (m, 1H), 7.31-7.37 (m, 4H), 7.23-7.26 (m, 1H), 4.95 (s, 2H), 4.86 (s, 2H), 4.52 (d, J=6.4 Hz, 2H).

Scheme H

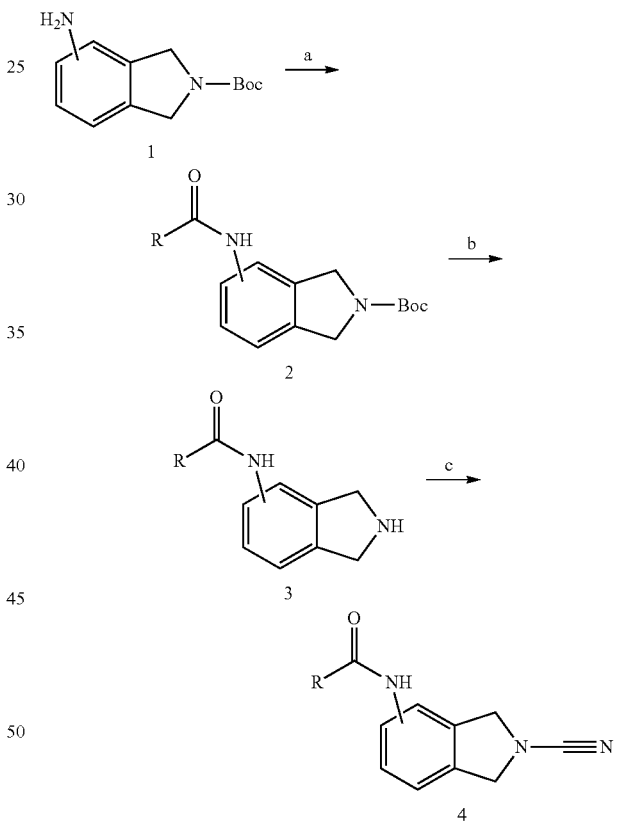

Reagents and conditions: a) HATU, DIPEA, DCM; b) HCl/EtOAc; c) cyanogen bromide, $NaHCO_3$, EtOH.

Step a.

To a solution of compound 1 (0.2 mmol) in DCM (1 ml) was added HATU (0.2 mmol). The reaction mixture was stirred at 0° C. for 20 min. Tert-butyl 4-aminoisoindoline-2-carboxylate (CAS Number 871013-98-8) (0.2 mmol) and DIPEA (0.6 mmol) were added to the reaction mixture at rt. The reaction mixture was stirred at rt for 16 h. The resulting mixture was concentrated under reduced pressure. The resulting residue was purified by prep-TLC (PE/EtOAc=1:1) yielding compound 2.

Step b.

To a solution of compound 2 in EtOAc (1 ml) was added HCl/EtOAc (4 M, 1 ml). The reaction mixture was stirred at rt for 2 h. The resulting mixture was concentrated under reduced pressure. The residue 3 was used for next step directly without further purification.

Step c.

To a solution of compound 3 in EtOH (2 ml) was added cyanogen bromide (0.2 mmol) and NaHCO$_3$ (0.6 mmol). The reaction mixture was stirred at rt for 16 h. The resulting mixture was concentrated under reduced pressure. The crude was purified by preparative reverse phase HPLC (A: 0.078% CH$_3$COONH$_4$ in water, B: MeCN) to provide compound 4.

Compounds in Table 8 were synthesised according to Scheme H using 4-amino-1,3-dihydroisoindole-2-carboxylic acid tert-butyl ester (CAS Number 871013-98-8) in step a.

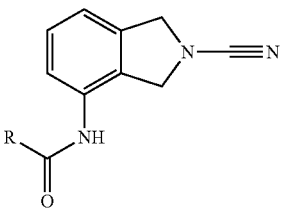

TABLE 8

| Ex | R— | Name | Acid CAS Number | LCMS method | LCMS RT/min | MS ES+ |
|---|---|---|---|---|---|---|
| Example 80 | | N-(2-cyanoisoindolin-4-yl)-3-(cyclopropanecarboxamido)benzamide | 54057-68-0 | H | 2.388 | 347 |
| Example 81 | | N-(2-cyanoisoindolin-4-yl)-4-(pyridin-3-yl)benzamide | 4385-75-5 | F | 3.148 | 341 |
| Example 82 | | N-(2-cyanoisoindolin-4-yl)-4-(pyridin-4-yl)benzamide | 4385-76-6 | F | 3.116 | 341 |
| Example 83 | | N-(2-cyanoisoindolin-4-yl)-3-(o-tolyl)-1H-pyrazole-5-carboxamide | 1140528-29-5 | G | 3.212 | 344 |
| Example 84 | | N-(2-cyanoisoindolin-4-yl)-2-phenylthiazole-4-carboxamide | 1904-28-5 | G | 3.438 | 347 |
| Example 85 | | N-(2-cyanoisoindolin-4-yl)-5-methoxy-1H-pyrrolo[2,3-c]pyridine-2-carboxamide | 17288-36-7 | G | 1.976 | 334 |
| Example 86 | | N-(2-cyanoisoindolin-4-yl)-5-(pyrazin-2-yl)-1H-pyrazole-3-carboxamide | 1029108-75-5 | G | 2.311 | 332 |
| Example 87 | | 1-benzyl-N-(2-cyanoisoindolin-4-yl)-6-oxo-1,6-dihydropyridine-3-carboxamide | 4332-79-0 | F | 3.086 | 371 |

TABLE 8-continued

| Ex | R— | Name | Acid CAS Number | LCMS method | LCMS RT/ min | MS ES+ |
|---|---|---|---|---|---|---|
| Example 88 | MeO-CH2-C6H4- | N-(2-cyanoisoindolin-4-yl)-4-(methoxymethyl)benzamide | 67003-50-3 | F | 3.077 | 308 |
| Example 89 | MeO-C(O)-NH-C6H4- | methyl (3-((2-cyanoisoindolin-4-yl)carbamoyl)phenyl)carbamate | 209551-66-6 | H | 2.328 | 337 |
| Example 90 | Ph-C(O)-NH-C6H4- | 3-benzamido-N-(2-cyanoisoindolin-4-yl)benzamide | 587-54-2 | F | 2.714 | 383 |
| Example 91 | BnO-C(O)-NH-CH2-C6H4- | benzyl (4-((2-cyanoisoindolin-4-yl)carbamoyl)benzyl)carbamate | 58933-52-1 | G | 2.858 | 427 |
| Example 92 | Ph-NH-SO2-C6H4- | N-(2-cyanoisoindolin-4-yl)-4-(N-phenylsulfamoyl)benzamide | 6314-72-3 | H | 1.982 | 419 |
| Example 93 | morpholino-thiophene | N-(2-cyanoisoindolin-4-yl)-5-morpholinothiophene-2-carboxamide | 332345-27-4 | F | 3.087 | 355 |

Example 94 N-(2-cyanoisoindolin-5-yl)-1-methyl-pyrrolidine-3-carboxamide

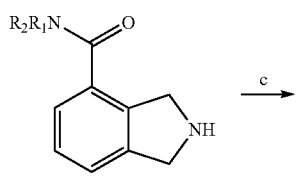

This was synthesised according to scheme H using 4-amino-1,3-dihydroisoindole-2-carboxylic acid tert-butyl ester (CAS Number 871013-98-8) and 1-methyl-2-oxo-4-pyrrolidinecarboxylic acid (CAS Number 42346-68-9) in step a. LCMS: Method D, 3.022 min, MS: ES+ 270.98.

Scheme I

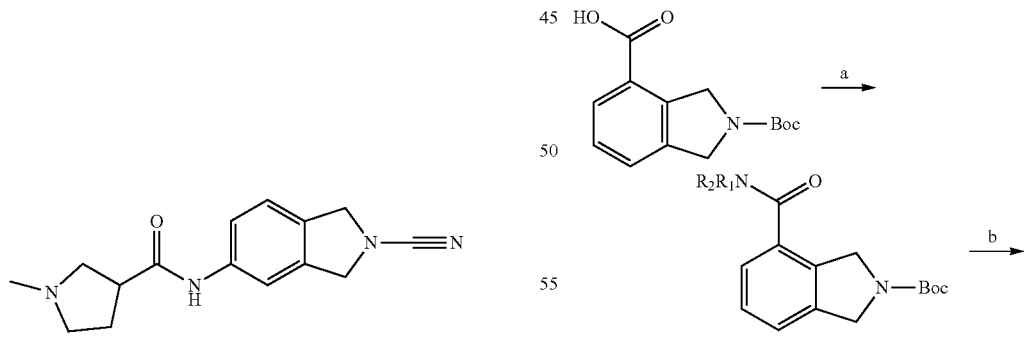

-continued

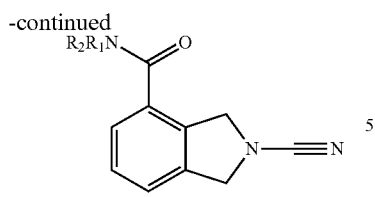

Reagents and conditions: a) R₁R₂NH, EDC, HOBt, THF; b) TFA, EtOAc; c) CNBr, K₂CO₃, THF

Example 95
N-benzyl-2-cyanoisoindoline-4-carboxamide

Prepared According to Scheme I

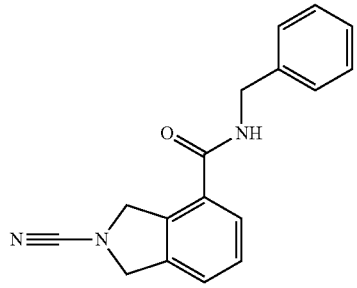 [SMILES: N#CN1Cc2cccc(C(=O)NCc3ccccc3)c2C1]

Step a.

To a solution of 2-(tert-butoxycarbonyl) isoindoline-4-carboxylic acid (Intermediate 7, 0.3 g, 1.14 mmol) in THF (3 ml) were added EDC (0.12 g, 1.254 mmol) and HOBt (0.088 g, 0.57 mmol) at rt under nitrogen atmosphere. Benzylamine (0.11 g, 1.02 mmol) was added and the reaction mixture was stirred at rt for 40 min. The resulting reaction mixture was poured into water (100 ml) and basified with solid NaHCO₃. The resulting mixture was extracted with EtOAc (2×100 ml). The combined organic phase was dried over Na₂SO₄, filtered and concentrated under reduced pressure to yield tert-butyl 4-(benzylcarbamoyl) isoindoline-2-carboxylate (0.4 g, 1.13 mmol). LCMS: Method A, 2.340 min, MS: ES+ 370.48 (M+18).

Step b.

To a solution of tert-butyl 4-(benzylcarbamoyl)isoindoline-2-carboxylate (0.4 g, 1.13 mmol) in EtOAc (5 ml) was added TFA (1 ml, 11.36 mmol) at 0° C. The reaction mixture was stirred at 80° C. for 3 h. The reaction mixture was cooled to rt and concentrated under reduced pressure to yield N-benzylisoindoline-4-carboxamide TFA salt (0.513 g, 1.40 mmol). LCMS: Method A, 1.583 min, MS: ES+ 253.43.

Step c.

To a solution of N-benzylisoindoline-4-carboxamide TFA salt (0.513 g, 1.39 mmol) in THF (3 ml) was added K₂CO₃ (0.55 g, 4.02 mmol) at rt and stirred for 5 min. Cyanogen bromide (0.23 g, 2.21 mmol) was added and the reaction mixture was stirred at rt for 1 hr. The resulting reaction mixture was filtered under vacuum and concentrated under reduced pressure. The resulting residue was purified by column chromatography (70% EtOAc in hexane) to yield N-benzyl-2-cyanoisoindoline-4-carboxamide (0.114 g, 0.41 mmol). LCMS: Method B, 5.531 min, MS: ES+ 278.1; NMR (400 MHz, DMSO-d₆) δ ppm 9.12 (t, J=4 Hz, 1H), 7.81 (d, J=7.2 Hz, 1H), 7.44-7.55 (m, 2H), 7.30-7.40 (m, 4H), 7.23-7.28 (m, 1H), 4.99 (s, 2H), 4.78 (s, 2H), 4.47 (d, J=6 Hz, 2H).

Example 96
N-(2-cyano-4-phenylisoindolin-5-yl)acetamide

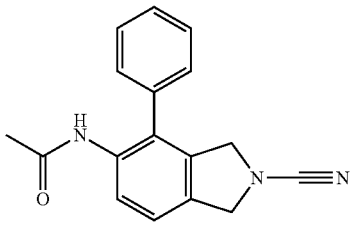 [SMILES: CC(=O)Nc1ccc2c(c1-c1ccccc1)CN(C#N)C2]

Step a.

To a solution of 2,3-dimethyl-6-nitroaniline (CAS Number 59146-96-2, available from Alfa aesar) (4.5 g, 27.1 mmol) in MeCN (120 ml) was added tert-butyl nitrite (4.96 ml, 40.6 mmol) drop wise at 0° C. The reaction mixture was stirred at 0° C. for 45 min. Copper(II)bromide (4.23 g, 10.83 mmol) was added portion wise to the reaction mixture at 0° C. The reaction mixture was warmed to rt and stirred for 20 h. The resulting reaction mixture was combined with 1 other batch prepared on the same scale by an identical method. The reaction mixture was poured into saturated NaHCO₃ solution (250 ml). The resulting reaction mixture was extracted with EtOAc (3×70 ml). The combined organic phase was washed with brine (2×50 ml) and dried over Na₂SO₄, filtered and concentrated under reduced pressure. The resulting residue was purified by column chromatography (2.4% EtOAc in hexane) yielding 2-bromo-3,4-dimethyl-1-nitrobenzene (10.5 g, 45.857 mmol). ¹H NMR (400 MHz, DMSO-d6) δ ppm 7.68 (d, J=8.4 Hz, 1H), 7.41 (d, J=8.4 Hz, 1H), 2.47 (s, 6H).

Step b.

To a mixture of water (132 ml) and pyridine (52.5 ml) was added 2-bromo-3,4-dimethyl-1-nitrobenzene (5.25 g, 22.83 mmol) at rt. The reaction mixture was heated at 60° C. KMnO₄ (56.49 g, 376.6 mmol) was added portion wise over a period of 15 min to the reaction mixture at 60° C. The reaction mixture was heated at 90° C. for 4 h. The resulting reaction mixture was cooled to rt and was combined with 1 other batch prepared on the same scale by an identical method. The reaction mixture was filtered through celite bed and washed with hot water (50 ml). The resulting filtrate cooled to 0° C. and acidified to pH 4 using 1M HCl. The resulting mixture was extracted with diethyl ether (3×50 ml). The combined organic phase was washed with brine (2×50 ml), dried over Na₂SO₄, filtered and concentrated under reduced pressure yielding 3-bromo-4-nitrophthalic acid (7.2 g, 24.920 mmol). LCMS: Method A, 1.577 min, MS: ES– 288.

Step c.

To a solution of 3-bromo-5-nitrophthalic acid (7.2 g, 24.920 mmol) in o-xylene (50 ml) was added urea (4.48 g, 74.76 mmol) at rt. The reaction mixture was heated at 150° C. for 8 h. The reaction mixture was cooled to rt. The resulting reaction mixture was poured into water (70 ml) and extracted with EtOAc (3×35 ml). The combined organic phase was washed with brine (2×40 ml). The organic phase was separated, dried over Na₂SO₄, filtered and concentrated under reduced pressure. The resulting residue was purified by column chromatography (20-25% EtOAc in Hexane) yielding 4-bromo-5-nitroisoindoline-1,3-dione (3.5 g, 12.962 mmol). LCMS: Method A, 1.832 min, MS: ES– 269;

¹H NMR (400 MHz, DMSO-d₆) δ ppm 11.88 (s, 1H), 8.34 (d, J=8.0 Hz, 1H) 8.01 (d, J=8.0 Hz, 1H).

Step d.

To a solution of 4-bromo-6-nitroisoindoline-1,3-dione (0.15 g, 0.555 mmol) in THF (5 ml) was added NaBH₄ (0.314 g, 8.332 mmol) at rt. BF₃.Et₂O (1.03 ml, 8.332 mmol) was drop wise added to the reaction mixture at 0° C. The reaction mixture was stirred at 0° C. for 20 min. The reaction mixture was then heated at 70° C. for 70 h. The resulting reaction mixture was cooled to rt. Additional BF₃.Et₂O (0.35 ml, 2.775 mmol) was added to the reaction mixture at 0° C. The reaction mixture was then heated at 70° C. for 16 h. The reaction mixture was cooled to rt and combined with 19 other batches prepared on the same scale by an identical method. The reaction mixture was poured into 1M HCl (40 ml) and heated at 100° C. for 30 min. The resulting reaction mixture was cooled to rt and basify using saturated NaOH solution (250 ml). The combined organic phase was washed with brine (2×70 ml) and dried over Na₂SO₄, filtered and concentrated under reduced pressure yielding 4-bromoisoindolin-5-amine (1.0 g, 4.716 mmol). This material was used for the next step without further purification. LCMS: Method I, 3.240 min, MS: ES+ 212.85, 214.8; ¹H NMR (400 MHz, DMSO-d6) δ ppm 6.93 (d, J=8 6.93 Hz, 1H), 6.65 (d, J=8 Hz, 1H), 5.18 (br s, 2H), 4.09 (s, 2H), 4.01 (s, 2H).

Step e.

To a solution of 4-bromoisoindolin-5-amine (1.0 g, 4.716 mmol) in THF (20 ml) was added TEA (1.9 ml, 14.148 mmol) at 0° C. Boc anhydride (0.82 g, 3.772 mmol) was added to the reaction mixture at 0° C. The reaction mixture was stirred at rt for 1 h. The resulting reaction mixture was poured into water (50 ml) and extracted with EtOAc (3×30 ml). The combined organic phase was washed with brine (2×50 ml) and dried over Na₂SO₄, filtered and concentrated under reduced pressure. The resulting residue was purified by flash chromatography (30% EtOAc in hexane) yielding tert-butyl 5-amino-4-bromoisoindoline-2-carboxylate (0.5 g, 1.602 mmol). LCMS: Method A, 2.337 min, MS: ES+ 313.1, 315.1; ¹H NMR (400 MHz, DMSO-d6) δ ppm 7.00 (t, J=7.6 Hz, 1H), 6.72 (d, J=8.4 Hz, 1H), 5.30 (br s, 2H), 4.53 (d, J=10.4 Hz, 2H), 4.43 (d, J=10.4 Hz, 2H), 1.45 (d, J=4 Hz, 9H).

Step f.

To a solution of tert-butyl 5-amino-4-bromoisoindoline-2-carboxylate (0.2 g, 0.641 mmol) in THF (15 ml) was added K₂CO₃ (0.26 g, 1.923 mmol) at 0° C. Acetyl chloride (0.05 ml, 0.769 mmol) was added dropwise to the reaction mixture at 0° C. The reaction mixture was stirred at rt for 2 h. The resulting reaction mixture was poured into saturated NaHCO₃ solution (30 ml) and extracted with EtOAc (3×10 ml). The combined organic phase was washed with brine (2×15 ml), dried over Na₂SO₄, filtered and concentrated under reduced pressure yielding tert-butyl 5-acetamido-4-bromoisoindoline-2-carboxylate (0.14 g, 0.395 mmol). LCMS: Method A, 2.132 min, MS ES– 353.09.

Step g.

A mixture of tert-butyl 5-acetamido-4-bromoisoindoline-2-carboxylate (0.14 g, 0.395 mmol), phenyl boronic acid (0.096 g, 0.790 mmol) and Na₂CO₃ (0.083 g, 0.790 mmol) in 1,4-dioxane:water (8:2) (15 ml) was degassed for 30 min at rt. PdCl₂(dppf) (0.029 g, 0.039 mmol) was added to the reaction mixture at rt. The reaction mixture was heated at 80° C. for 4 h. The resulting reaction mixture was cooled to rt. The obtained reaction mixture was poured into saturated NaHCO₃ solution (30 ml) and extracted with EtOAc (3×10 ml). The combined organic phase was washed with brine (2×15 ml) and dried over Na₂SO₄, filtered and concentrated under reduced pressure. The resulting residue was purified by flash chromatography (25-30% EtOAc in hexane) yielding tert-butyl 5-acetamido-4-phenylisoindoline-2-carboxylate (0.11 g, 0.312 mmol). LCMS: Method A, 2.275 min, MS: ES+ 353.3

Step h.

To a solution of tert-butyl 5-acetamido-4-phenylisoindoline-2-carboxylate (0.1 g, 0.273 mmol) in DCM (20 ml) was added TFA (0.7 ml) at rt. The reaction mixture was stirred at rt for 1 h. The resulting reaction mixture was concentrated under reduced pressure. The obtained residue was azeotropically distilled with DCM (3×25 ml) and finally dried under high vacuum to yield N-(4-phenylisoindolin-5-yl)acetamide TFA salt (0.12 g, 0.327 mmol). LCMS: Method I, 2.550 min, MS: ES+ 252.96. This material was used directly for the next step without further purification.

Step i.

To a solution of N-(4-phenylisoindolin-5-yl)acetamide TFA salt (0.12 g, 0.327 mmol) in THF (20 ml) was added K₂CO₃ (0.145 g, 0.983 mmol) at rt. Cyanogen bromide (0.04 g, 0.393 mmol) was added to the reaction mixture at rt. The reaction mixture was stirred at rt for 10 min. The resulting reaction mixture was poured into saturated NaHCO₃ solution (30 ml) and extracted with EtOAc (3×10 ml). The combined organic phase was washed with brine (2×50 ml) and dried over Na₂SO₄, filtered and concentrated under reduced pressure. The resulting residue was purified by flash chromatography (2% MeOH in DCM) yielding the title compound (0.05 g, 0.180 mmol). LCMS: Method D, 3.585 min, MS: ES+ 277.89; ¹H NMR (400 MHz, DMSO-d6) δ ppm 9.10 (s, 1H), 7.32-7.46 (m, 4H), 7.27-7.29 (m, 3H), 4.82 (s, 2H), 4.56 (s, 2H), 1.80 (s, 3H).

Example 97 1-(1-methyl-1H-pyrazol-4-yl)-4-phenyl-5,7-dihydro-6H-pyrrolo[3,4-c]pyridazine-6-carbonitrile

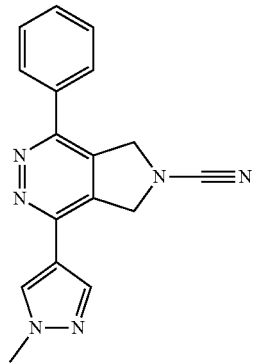 [SMILES: Cn1cc(-c2nnc(-c3ccccc3)c3c2CN(C#N)C3)cn1]

Step a.

To a solution of 3,6-dichloro-4,5-dimethylpyridazine (CAS Number 34584-69-5, available from Accela chembio) (6 g, 33.9 mmol) in CCl₄ (150 ml) were added NBS (18.08 g, 101.6 mmol) and AIBN (0.055 g, 0.33 mmol) at rt. The reaction mixture was heated at 80° C. for 16 h. The resulting reaction mixture was filtered and evaporated to yield 4,5-bis(bromomethyl)-3,6-dichloropyridazine (11 g, 32.8 mmol), LCMS: Method A, 2.102 min, MS: ES+ 335.18.

Step b.

To a solution of tritylamine (CAS Number 5824-40-8; 8.5 g, 32.93 mmol) in DMF was added DIPEA (17.6 ml, 98.8 mmol) at rt. 4,5-Bis(bromomethyl)-3,6-dichloropyridazine (11 g, 32.85 mmol) was added to the reaction mixture at rt. The reaction mixture was stirred at 60° C. for 2 h. The resulting mixture was poured into water (300 ml) and extracted with EtOAc (2×200 ml). The combined organic phase was dried over $Na_2SO_4$, filtered and concentrated under reduced pressure. The obtained crude material was purified by column chromatography (2% EtOAc in hexane) to yield 1,4-dichloro-6-trityl-6,7-dihydro-5H-pyrrolo[3,4-d]pyridazine (1.5 g, 3.46 mmol) LCMS: Method A, 3.023 min, MS: ES+ 243.33.

Step c.

To a solution of 1,4-dichloro-6-trityl-6,7-dihydro-5H-pyrrolo[3,4-d]pyridazine (1.4 g, 3.24 mmol) in 1,4-dioxane (14 ml) was added phenylboronic acid (0.395 g, 3.24 mmol) at rt. A solution of $Na_2CO_3$ (1.05 g, 9.721 mmol) in water (0.5 ml) was added to the reaction mixture at rt. The reaction mixture was degassed with $N_2$ for 15 min. $Pd(PPh_3)_4$ (0.375 g, 0.324 mmol) was added to the reaction mixture at rt. The reaction mixture was heated at 80° C. for 4 h. The resulting mixture was cooled to rt and poured into water (25 ml). The resulting mixture was extracted with EtOAc (3×15 ml). The combined organic phase was dried over $Na_2SO_4$, filtered and concentrated under reduced pressure. The crude was purified by column chromatography (5% EtOAc in hexane) to yield 1-chloro-4-phenyl-6-trityl-6,7-dihydro-5H-pyrrolo[3,4-d]pyridazine (0.38 g, 0.80 mmol), LCMS: Method A, 3.076 min, MS: ES+ 474.5.

Step d.

To a solution of 1-chloro-4-phenyl-6-trityl-6,7-dihydro-5H-pyrrolo[3,4-d]pyridazine (0.3 g, 0.63 mmol) in DMF (8 ml) were added 1-methyl-1H-pyrazole-4-boronic acid pinacol ester (CAS Number 761446-44-0) (0.131 g, 0.634 mmol) and $K_2CO_3$ (0.262 g, 1.902 mmol) at rt. The reaction mixture was degassed with $N_2$ for 15 min. $Pd(PPh_3)_4$ (0.073 g, 0.063 mmol) was added to the reaction mixture at rt. The reaction mixture was heated at 110° C. in a microwave for 30 min. The resulting mixture was poured into water (30 ml) and extracted with EtOAc (3×10 ml). The combined organic phase was dried over $Na_2SO_4$, filtered and concentrated under reduced pressure to yield 1-(1-methyl-1H-pyrazol-4-yl)-4-phenyl-6-trityl-6,7-dihydro-5H-pyrrolo[3,4-d]pyridazine (0.4 g, 0.77 mmol), LCMS: Method A, 2.742 min, MS: ES+ 520.58.

Step e.

To a solution of 1-(1-methyl-1H-pyrazol-4-yl)-4-phenyl-6-trityl-6,7-dihydro-5H-pyrrolo[3,4-d]pyridazine (0.35 g, 0.674 mmol) in DCM (5 ml) was added TFA (0.153 g, 1.34 mmol) at 0° C. The reaction mixture was stirred rt for 1 h. The resulting reaction mixture was concentrated under reduced pressure to yield 1-(1-methyl-1H-pyrazol-4-yl)-4-phenyl-6,7-dihydro-5H-pyrrolo[3,4-d]pyridazine TFA salt (0.3 g, 0.562 mmol). LCMS: Method A, 1.401 min, MS: ES+ 278.53.

Step f.

To a solution of 1-(1-methyl-1H-pyrazol-4-yl)-4-phenyl-6,7-dihydro-5H-pyrrolo[3,4-d]pyridazine TFA salt (0.3 g, 0.562 mmol) in THF (6 ml) was added $K_2CO_3$ (0.44 g, 3.18 mmol) at rt and stirred for 10 min. Cyanogen bromide (0.11 g, 1.08 mmol) was added to the reaction mixture at rt and stirred for 1 h. The reaction mixture was poured into water (10 ml) and extracted with EtOAc (3×5 ml). The combined organic phase was dried over $Na_2SO_4$, filtered and concentrated under reduced pressure. The obtained crude material was purified by Prep HPLC using a Waters Sunfire C18 (250×19) mm, 5 µm column eluting with 35 to 100% MeCN/water as mobile phase at a flow rate of 16.0 ml/min to yield 1-(1-methyl-1H-pyrazol-4-yl)-4-phenyl-5,7-dihydro-6H-pyrrolo[3,4-d]pyridazine-6-carbonitrile (0.016 g, 0.052 mmol). LCMS: Method E, 3.302 min, MS: ES+ 373.53; $^1$H NMR (400 MHz, DMSO-d6) δ ppm 8.45 (s, 1H), 8.14 (s, 1H), 7.89 (dd, J=1.6, 7.6 Hz, 2H), 7.54-7.60 (m, 3H), 5.18 (s, 2H), 5.12 (s, 2H), 3.96 (s, 3H).

Example 182 1-(3-methoxyphenyl)-4-(1-methyl-1H-pyrazol-4-yl)-5,7-dihydro-6H-pyrrolo[3,4-d]pyridazine-6-carbonitrile

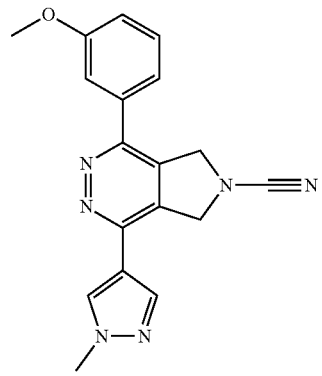 [SMILES: COc1cccc(-c2nnc(-c3cnn(C)c3)c3c2CN(C#N)C3)c1]

Synthesised using a procedure similar to that described for Example 97 using 3-methoxyphenylboronic acid in step c. LCMS: Method H, RT 2.331 min, MS: ES+ 333.1

Example 98 methyl 2-cyano-7-phenylisoindoline-5-carboxylate

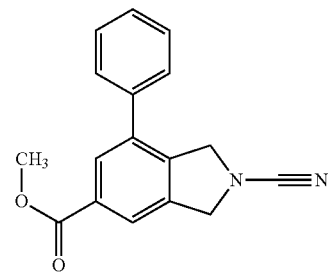 [SMILES: COC(=O)c1cc2c(c(-c3ccccc3)c1)CN(C#N)C2]

Step a.

To a solution of 3,4-dimethylbenzoic acid (5.000 g, 33.3 mmol) in DCM (30 ml) was added $AlCl_3$ (6.6 g, 49.624 mmol) at 0° C. The reaction mixture was stirred at rt for 30 min. A solution of bromine (3.500 g, 22.01 mmol) in DCM (10 ml) was added and the reaction mixture was stirred at rt for 1 h. The resulting reaction mixture was combined with 2 other batches prepared on the same scale by an identical method and evaporated under reduced pressure. The resulting mixture was poured into ice cold water (120 ml) and extracted with EtOAc (2×200 ml). The combined organic phase was dried over $Na_2SO_4$, filtered and concentrated under reduced pressure yielding 3-bromo-4,5-dimethylbenzoic acid (22.00 g, 96.49 mmol). This material was used directly for the next step without further purification. LCMS: Method E, 4.151 min, MS: ES+ 229.03.

Step b.

To a solution of 3-bromo-4,5-dimethylbenzoic acid (22.00 g, 96.49 mmol) in MeOH (200 ml) was added concentrated H$_2$SO$_4$ (5 ml) at rt. The reaction mixture was refluxed for 12 h. The resulting reaction mixture was cooled to rt and concentrated under reduced pressure. The obtained mixture was poured into water (300 ml) and extracted with EtOAc (3×200 ml). The combined organic phase was dried over Na$_2$SO$_4$, filtered and concentrated under reduced pressure yielding methyl 3-bromo-4,5-dimethylbenzoate (15.00 g, 61.73 mmol). This material was used directly for the next step without further purification. $^1$H NMR (400 MHz, DMSO-d6) δ ppm 7.92 (d, J=1.6 Hz, 1H), 7.75 (d, J=1.6 Hz, 1H), 3.84 (s, 3H), 2.37 (s, 6H).

Step c.

To a solution of 3-bromo-4,5-dimethylbenzoate (25.00 g, 102.88 mmol) in CCl$_4$ (250 ml) was added NBS (36.6 g, 205.62 mmol) at rt. The resulting reaction mixture was exposed to a UV light source which increased the temperature, in this manner the reaction mixture was heated at 80° C. for 15 min. The resulting reaction mixture was cooled to rt. The resulting reaction mixture was filtered through celite bed, washed with CCl$_4$ (2×50 ml). The combine filtrate was concentrated under reduced pressure yielding methyl 3-bromo-4,5-bis(bromomethyl)benzoate (46.0 g, quantitative). LCMS: Method E, 5.174 min; $^1$H NMR (400 MHz, DMSO-d6) δ ppm 7.83-8.11 (m, 2H), 4.79-4.95 (m, 2H), 3.86-3.88 (m, 2H), 2.57 (s, 3H). This material was used directly for the next step without further purification.

Step d.

To a solution of methyl 3-bromo-4, 5-bis(bromomethyl) benzoate (46.00 g, 114.71 mmol) in THF (200 ml) was added TEA (24.2 ml, 174.2 mmol) at 0° C. Benzylamine (12.40 g, 115.9 mmol) was added to the reaction mixture at 0° C. The resulting reaction mixture was stirred at rt for 5 h. The resulting reaction mixture was poured into water (200 ml) and extracted with EtOAc (2×300 ml). The combined organic phase was dried over Na$_2$SO$_4$, filtered and concentrated under reduced pressure. The resulting residue was purified by column chromatography (20% EtOAc in Hexane) yielding methyl 2-benzyl-7-bromoisoindoline-5-carboxylate (6.00 g, 17.34 mmol). LCMS: Method E, 3.337 min, MS: ES+ 346.02.

Step e.

To a solution of 2-benzyl-7-bromoisoindoline-5-carboxylate (2.000 g, 5.797 mmol) in chlorobenzene (12.4 ml) was added 4 Å molecular sieves (1.1 g) at rt. The resulting reaction mixture was stirred at rt for 30 min. 1-Chloroethyl chloroformate (1.650 g, 11.546 mmol) was added to the reaction mixture at rt. The reaction mixture was heated at 90° C. for 2 h. The resulting reaction mixture was filtered through celite bed, washed with chlorobenzene:MeOH (1:1, 10 ml). The combined filtrate was heated at 70° C. for 2 h. The resulting reaction mixture was stirred at rt for 12 h. The resulting precipitates were filtered off under vacuum, washed with n-hexane (30 ml) and dried under vacuum yielding methyl 7-bromoisoindoline-5-carboxylate HCl salt (1.500 g, 5.128 mmol). LCMS: Method A, 1.432 min, MS: ES+ 256.18.

Step f.

To a solution of methyl 7-bromoisoindoline-5-carboxylate HCl salt (1.500 g, 5.128 mmol) in in DMF (30 ml) was added TEA (0.710 g, 7.029 mmol) at 0° C. Boc anhydride (1.270 g, 5.825 mmol) was added to the reaction at 0° C. The reaction mixture was stirred at rt for 3 h. The resulting reaction mixture was poured into ice-cold water (100 ml) and extracted with EtOAc (3×80 ml). The combined organic layer was dried over Na$_2$SO$_4$, filtered and concentrated under reduced pressure. The resulting residue was triturated with n-hexane (2×5 ml) yielding 2-(tert-butyl) 5-methyl 7-bromoisoindoline-2,5-dicarboxylate (1.700 g, 4.775 mmol). LCMS: Method C, 8.421 min, MS: ES+ 300 (M−56); $^1$H NMR (400 MHz, DMSO-d6) δ ppm 7.99 (s, 1H), 7.93 (d, J=9.2 Hz, 1H), 4.74 (d, J=9.6 Hz, 2H), 4.58 (d, J=9.2 Hz, 2H), 3.87 (s, 3H), 1.46 (s, 9H).

Step g.

To a solution of 2-(tert-butyl) 5-methyl 7-bromoisoindoline-2,5-dicarboxylate (0.250 g, 0.702 mmol) in 1,4-dioxane:water (2:1, 10 ml) prepared in microwave tube was added phenylboronic acid (0.101 g, 0.843 mmol) at rt. The resulting reaction mixture was degassed for 15 min. To the reaction mixture was added Na$_2$CO$_3$ (0.221 g, 2.100 mmol) and Pd(PPh$_3$)$_4$ (0.040 g, 0.034 mmol). The reaction mixture was sealed and heated in a microwave at 80° C. for 3 h. The resulting mixture was poured into water (30 ml) and extracted with EtOAc (3×20 ml). The combined organic phase was dried over Na$_2$SO$_4$, filtered and concentrated under reduced pressure. The resulting residue was purified by flash chromatography (15% EtOAc in hexane) yielding 2-(tert-butyl) 5-methyl 7-phenylisoindoline-2,5-dicarboxylate (0.190 g, 0.538 mmol). LCMS: Method E, 5.371 min, MS: ES+ 339.28 (M−15); $^1$H NMR (400 MHz, DMSO-d6) δ ppm 7.95 (d, J=10.0 Hz, 1H), 7.85 (d, J=11.2 Hz, 1H), 7.51-7.54 (m, 5H), 4.70-4.72 (m, 4H), 3.88 (s, 3H), 1.44 (d, J=15.2 Hz, 9H).

Step h.

To a solution of 2-(tert-butyl) 5-methyl 7-phenylisoindoline-2,5-dicarboxylate (0.185 g, 0.524 mmol) in DCM (10 ml) was added TFA (1 ml) at 0° C. The reaction mixture was heated at 40° C. for 1 h. The resulting reaction mixture was cooled to rt and evaporated under reduced pressure. The resulting residue was co-evaporated with DCM (2×10 ml). The obtained residue was triturated with diethyl ether (2×10 ml) and dried under vacuum yielding methyl 7-phenylisoindoline-5-carboxylate TFA salt (0.148 g, quantitative). LCMS: Method E, 2.944 min, MS: ES+ 254.17; $^1$H NMR (400 MHz, DMSO-d6) δ ppm 9.49 (br s, 1H), 8.05 (s, 1H), 7.97 (s, 1H), 7.49-7.55 (m, 5H), 4.64-4.67 (m, 4H), 3.90 (s, 3H). This material was used directly for the next step without further purification.

Step i.

To a solution of methyl 7-phenylisoindoline-5-carboxylate TFA salt (0.140 g, 0.550 mmol) in THF (10 ml) was added K$_2$CO$_3$ (0.229 g, 1.659 mmol) at 0° C. Cyanogen bromide (0.070 g, 0.663 mmol) was added to the reaction mixture at 0° C. The reaction mixture was stirred at 0° C. for 1 h. The resulting reaction mixture was poured into water (20 ml) and extracted with EtOAc (2×20 ml). The combined organic phase was dried over Na$_2$SO$_4$, filtered and concentrated under reduced pressure. The resulting residue was purified by column chromatography (1% MeOH in DCM) yielding the title compound (0.052 g, 0.187 mmol). LCMS: Method E, 4.384 min, MS: ES+ 279.33; $^1$H NMR (400 MHz, DMSO-d6) δ ppm 7.93 (s, 1H), 7.89 (s, 1H), 7.43-7.55 (m, 5H), 4.95 (s, 2H), 4.90 (s, 2H), 3.88 (s, 3H).

Scheme J

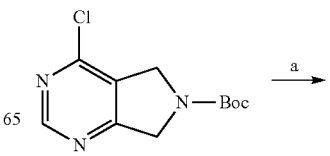

-continued

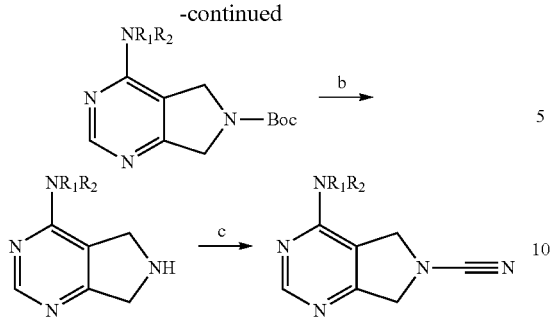

Reagents and conditions: a) DIPEA, IPA, or TEA, MeCN; b) HCl/EtOAc or TFA, DCM 2 h; c) BrCN, NaHCO₃, EtOH or BrCN, K₂CO₃, THF Example 99 4-(4-(2,4-difluorophenyl)piperazin-1-yl)-5H-pyrrolo[3,4-d]pyrimidine-6(7H)-carbonitrile

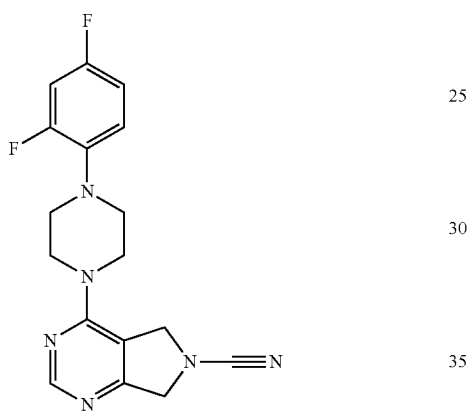

Step a.

To a solution of tert-butyl 4-chloro-5H-pyrrolo[3,4-d]pyrimidine-6(7H)-carboxylate (0.2 mmol) and 1-(2,4-difluorophenyl)piperazine (0.6 mmol) in IPA (1 ml) was added DIPEA (0.6 mmol). The reaction mixture was stirred at 100° C. for 16 h. The resulting mixture was concentrated under reduced pressure. The resulting residue was purified by prep-TLC (PE/EtOAc=1:2) yielding tert-butyl tert-butyl 4-(4-(2,4-difluorophenyl)piperazin-1-yl)-5H-pyrrolo[3,4-d]pyrimidine-6(7H)-carboxylate MS: ES+ 418.4.

Step b.

To a solution of tert-butyl 4-(4-(2,4-difluorophenyl)piperazin-1-yl)-5H-pyrrolo[3,4-d]pyrimidine-6(7H)-carboxylate in EtOAc (1 ml) was added HCl/EtOAc (4 M, 1 ml). The reaction mixture was stirred at rt for 2 h. The resulting mixture was concentrated under reduced pressure. The residue 4-(4-(2,4-difluorophenyl)piperazin-1-yl)-6,7-dihydro-5H-pyrrolo[3,4-d]pyrimidine was used for next step directly without further purification. MS: ES+ 318.3.

Step c.

To a solution of 4-(4-(2,4-difluorophenyl)piperazin-1-yl)-6,7-dihydro-5H-pyrrolo[3,4-d]pyrimidine in EtOH (2 ml) was added cyanogen bromide (0.2 mmol) and NaHCO₃ (0.6 mmol). The reaction mixture was stirred at rt for 16 h. The resulting mixture was concentrated under reduced pressure. The crude was purified by preparative reverse phase HPLC (A: 0.078% CH₃COONH₄ in water, B: MeCN) yielding (17.3 mg, 0.050 mmol). LCMS: Method G, 2.307 min, MS: ES+ 343.0.

Example 100 4-(isoindolin-2-yl)-5,7-dihydro-6H-pyrrolo[3,4-c]pyrimidine-6-carbonitrile

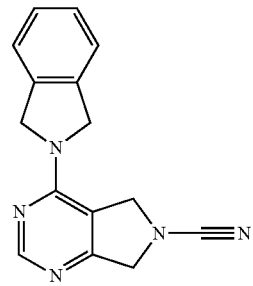 [SMILES: N#CN1Cc2ncnc(N3Cc4ccccc4C3)c2C1]

Synthesised using a procedure similar to that described for Example 99 using isoindoline hydrochloride in step a. LCMS: Method D, 3.718 min, MS: ES+ 264.57

Example 183 4-(3,4-dihydroisoquinolin-2(1H)-yl)-5,7-dihydro-6H-pyrrolo[3,4-c]pyrimidine-6-carbonitrile

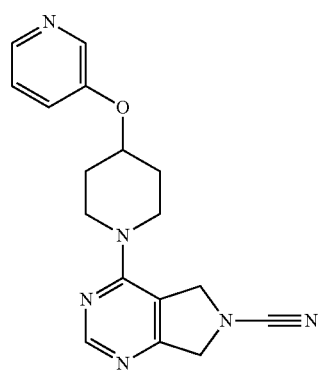 [SMILES: N#CN1Cc2ncnc(N3CCC(Oc4cccnc4)CC3)c2C1]

Synthesised using a procedure similar to that described for Example 99 using 1,2,3,4-tetrahydro isoquinoline in step a. LCMS: Method D, 4.058 min, MS: ES+ 278.1

Example 101 4-(4-(pyridin-3-yloxy)piperidin-1-yl)-5,7-dihydro-6H-pyrrolo[3,4-c]pyrimidine-6-carbonitrile Step a.

To a solution of 6-Boc-4-chloro-6,7-dihydro-5H-pyrrolo[3,4-d]pyrimidine (CAS Number 1053657-15-0 available from Advanced ChemBlocks) (0.300 g, 1.173 mmol) in DCM (6 ml) was added TFA (1.5 ml) at rt. The resulting reaction mixture was stirred at rt for 4 h. The resulting reaction mixture was evaporated under reduced pressure. The obtained residue was co-evaporated with diethyl ether (2×5 ml) and dried under vacuum yielding 4-chloro-6,7-dihydro-5H-pyrrolo[3,4-d]pyrimidine TFA Salt (0.330 g, quantitative). LCMS: Method I, 2.211 min, MS: ES+ 155.90. This material was used for next step without any further purification.

Step b.

To a solution 4-chloro-6,7-dihydro-5H-pyrrolo[3,4-d]pyrimidine TFA salt (0.330 g, 1.226 mmol) in THF (10 ml) was added $K_2CO_3$ (0.680 g, 4.927 mmol) at rt. Cyanogen bromide (0.160 g, 1.510 mmol) was added to the reaction mixture at rt. The resulting reaction mixture was stirred at rt for 30 min. The resulting reaction mixture was poured in to water (50 ml) and extracted with EtOAc (3×25 ml). The combined organic phase was washed with brine solution (25 ml), dried over $Na_2SO_4$, filtered and concentrated under vacuum yielding 4-chloro-5,7-dihydro-6H-pyrrolo[3,4-d]pyrimidine-6-carbonitrile (0.180 g, 0.001 mmol). LCMS: Method A, 1.579 min, MS: ES+ 180.80; $^1$H NMR (400 MHz, DMSO-d6) δ ppm 9.01 (s, 1H), 4.91 (s, 4H). This material was used for next step without any further purification.

Step c.

To a solution of 4-chloro-5,7-dihydro-6H-pyrrolo[3,4-d]pyrimidine-6-carbonitrile (0.050 g, 0.277 mmol) in MeCN (2 ml) was added TEA (0.2 ml, 1.437 mmol) at 0° C. The reaction mixture was stirred at rt for 5 min. 3-(Piperidin-4-yloxy)pyridine dihydrochloride (CAS Number 310880-81-0 available from Chembridge) (0.049 g, 0.197 mmol). The reaction mixture was stirred at rt for 16 h. The reaction mixture was poured into water (10 ml) and extracted with EtOAc (3×10 ml). The combined organic phase were washed with brine solution (25 ml), dried over $Na_2SO_4$, filtered and concentrated under reduced pressure. The resulting residue was purified by flash chromatography (40-50% EtOAc in hexane) yielding 4-(4-(pyridin-3-yloxy)piperidin-1-yl)-5,7-dihydro-6H-pyrrolo[3,4-d]pyrimidine-6-carbonitrile (0.025 g, 0.077 mmol). LCMS: Method D, 3.981 min, MS: ES+ 322.96; $^1$H NMR (400 MHz, DMSO-d6) δ ppm 8.44 (s, 1H), 8.33 (d, J=2.8 Hz, 1H), 8.18 (dd, J=4.8, 1.2 Hz, 1H), 7.46-7.48 (m, 1H), 7.32-7.35 (m, 1H), 4.99 (s, 2H), 4.77-4.80 (m, 1H), 4.59 (s, 2H), 3.94-3.97 (m, 2H), 3.47-3.51 (m, 2H), 2.01-2.04 (m, 2H), 1.61-1.69 (m, 2H).

Compounds in Table 9 were prepared in a manner similar to Example 101.

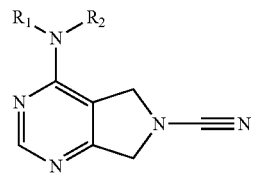

TABLE 9

| Ex | $R_1R_2NH$— | Name | Amine CAS Number | LCMS method | LCMS RT/ min | MS ES+ |
|---|---|---|---|---|---|---|
| Example 102 | (3-methoxyphenoxy piperidine structure) | 4-(4-(3-methoxyphenoxy)piperidin-1-yl)-5,7-dihydro-6H-pyrrolo[3,4-d]pyrimidine-6-carbonitrile | 162402-37-1 | D | 4.340 | 352.10 |
| Example 103 | (2-carbamoylphenoxy piperidine structure) | 2-((1-(6-cyano-6,7-dihydro-5H-pyrrolo[3,4-d]pyrimidin-4-yl)piperidin-4-yl)oxy)benzamide | 907159-01-7 | D | 3.294 | 365.01 |
| Example 184 | (o-tolyloxy piperidine structure) | 4-(4-(o-tolyloxy)piperidin-1-yl)-5,7-dihydro-6H-pyrrolo[3,4-d]pyrimidine-6-carbonitrile | 63843-42-5 | D | 4.729 | 336.07 |
| Example 185 | (benzyloxy piperidine structure) | 4-(4-(benzyloxy)piperidin-1-yl)-5,7-dihydro-6H-pyrrolo[3,4-d]pyriimidine-6-carbonitrile | 76716-51-3 | D | 5.117 | 336 |
| Example 186 | (2-methoxyphenoxy piperidine structure) | 4-(4-(2-methoxyphenoxy)piperidin-1-yl)-5,7-dihydro-6H-pyrrolo[3,4-d]pyrimidine-6-carbonitrile | 28033-32-1 | D | 4.094 | 352.1 |

Scheme K

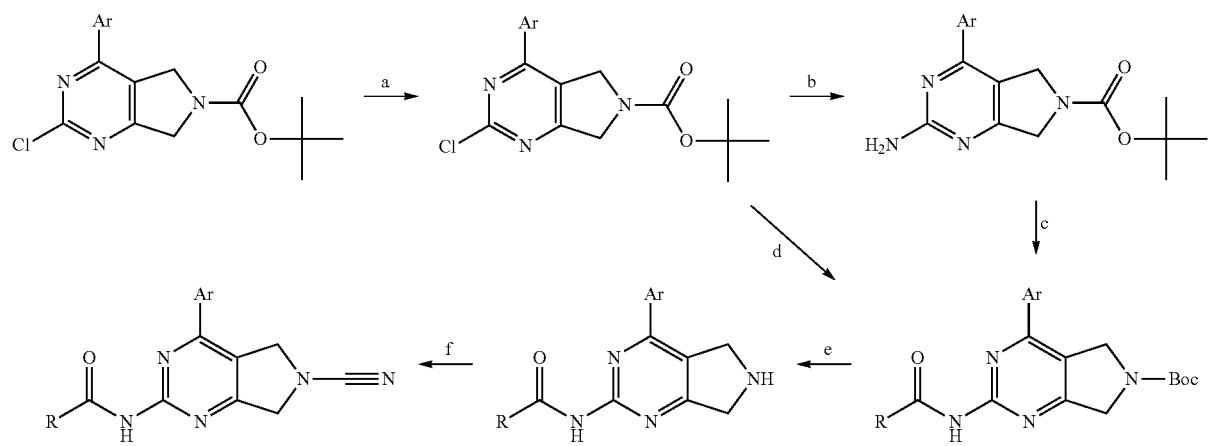

Reagents and conditions: a) Na₂CO₃, PdCl₂(dppf), ArB(OH)₂, 1,4-dioxane, water; b) ammonia, 100 psi, THF; c) (RCO)₂O, DMAP, TEA; d) RCONH₂, xantphos, Pd₂(dba)₃, K₂CO₃, 1,4-dioxane; e) TFA, DCM; f) BrCN, K₂CO₃, THF Example 104 N-(6-cyano-4-phenyl-6,7-dihydro-5H-pyrrolo[3,4-c]pyrimidin-2-yl)acetamide (Prepared According to Scheme K)

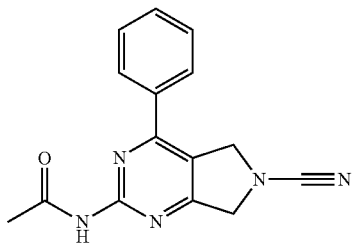 [SMILES: CC(=O)Nc1nc2c(c(-c3ccccc3)n1)CN(C#N)C2]

Step a.

A solution of tert-butyl 2,4-dichloro-5H-pyrrolo[3,4-d]pyrimidine-6(7H)-carboxylate (CAS Number 903129-71-5, available from Advance chem block) (0.4 g, 1.378 mmol) and phenylboronic acid (0.17 g, 1.378 mmol) in 1,4-dioxane (13.5 ml) was prepared at rt. A solution of Na₂CO₃ (0.29 g, 2.757 mmol) in water (1.5 ml) was added to the reaction mixture at rt. The reaction mixture was degassed with nitrogen for 15 min at rt. PdCl₂(dppf) (0.10 g, 0.137 mmol) was added to the reaction mixture at rt. The reaction mixture was heated at 90° C. for 2 h. The resulting reaction mixture was cooled to rt, poured into water (30 ml) and extracted with DCM (3×30 ml). The combined organic phase was dried over Na₂SO₄, filtered and concentrated under reduced pressure. The resulting residue was purified by flash chromatography (10% EtOAc in hexane) yielding tert-butyl 2-chloro-4-phenyl-5,7-dihydro-6H-pyrrolo[3,4-d]pyrimidine-6-carboxylate (0.35 g, 1.057 mmol). LCMS: Method A, 2.767 min, MS: ES+ 332.59; ¹H NMR (400 MHz, DMSO-d6) δ ppm 7.91-7.97 (m, 2H), 7.59-7.63 (m, 3H), 4.91 (s, 2H), 4.64 (d, J=8 Hz, 2H), 1.47 (s, 9H).

Step b.

To a solution of tert-butyl 2-chloro-4-phenyl-5,7-dihydro-6H-pyrrolo[3,4-d]pyrimidine-6-carboxylate (0.35 g, 1.057 mmol) in THF (20 ml) in an autoclave was purged with ammonia gas at −78° C. for 5 minutes. The reaction mixture was sealed, 100 psi ammonia gas pressure was applied and the reaction mixture was heated at 50° C. for 15 h. The reaction mixture was cooled to rt and the pressure was carefully released. The resulting reaction mixture was concentrated under reduced pressure and the obtained residue was purified by flash chromatography (20-40% EtOAc in n-hexane) yielding tert-butyl 2-amino-4-phenyl-5,7-dihydro-6H-pyrrolo[3,4-d]pyrimidine-6-carboxylate (0.091 g, 0.292 mmol). LCMS: Method A, 2.168 min, MS: ES+ 313.58.

Step c.

To a solution of tert-butyl 2-amino-4-phenyl-5,7-dihydro-6H-pyrrolo[3,4-d]pyrimidine-6-carboxylate (0.08 g, 0.256 mmol) in AC₂O (2 ml) were added TEA (0.05 g, 0.512 mmol) and DMAP (0.015 g, 0.128 mmol) at rt. The reaction mixture was heated at 70° C. for 1 h. The resulting reaction mixture was cooled to rt and diluted with cold water (30 ml). The pH of the obtained mixture was adjusted at 9 by slow addition of solid Na₂CO₃ under continuous stirring. The resulting mixture was extracted with EtOAc (2×30 ml). The combined organic phase was dried over Na₂SO₄, filtered and concentrated under reduced pressure. The resulting residue was purified by flash chromatography (72% EtOAc in hexane) yielding tert-butyl 2-acetamido-4-phenyl-5,7-dihydro-6H-pyrrolo[3,4-d]pyrimidine-6-carboxylate (0.07 g, 0.197 mmol). LCMS: Method A, 2.218 min, MS: ES+ 355.65; ¹H NMR (400 MHz, DMSO-d6) δ ppm 10.67 (d, J=6 Hz, 1H), 7.93-7.99 (m, 2H), 7.57-7.59 (m, 3H), 4.86 (s, 2H), 4.56 (d, J=8.4 Hz, 2H), 2.24 (s, 3H), 1.47 (s, 9H).

Steps e, f.

The title compound was synthesised from the intermediate above using a procedure similar to that described for steps d and e of Example 1. LCMS: Method D, 3.322 min, MS: ES+ 280.0; ¹H NMR (400 MHz, DMSO-d6) δ ppm 10.72 (s, 1H), 7.95-7.97 (m, 2H), 7.56-7.60 (m, 3H), 5.13 (s, 2H), 4.78 (s, 2H), 2.24 (s, 3H).

Example 187 N-(6-cyano-4-(4-fluorophenyl)-6,7-dihydro-5H-pyrrolo[3,4-c]pyrimidin-2-yl)acetamide

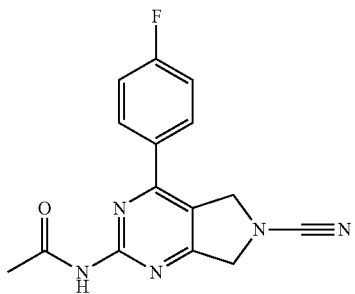 [SMILES: CC(=O)Nc1nc2c(c(-c3ccc(F)cc3)n1)CN(C#N)C2]

Synthesised using a procedure similar to that described for Example 104, using (4-fluorophenyl)boronic acid (CAS number 1765-93-1) in step a. LCMS: Method I, 2.36 min, MS: ES+298

Example 105 N-(6-cyano-4-(3-cyanophenyl)-6,7-dihydro-5H-pyrrolo[3,4-c]pyrimidin-2-yl)acetamide (Prepared According to Scheme K Steps a, d, e, f)

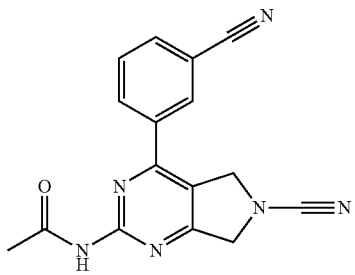 [SMILES: CC(=O)Nc1nc2c(c(-c3cccc(C#N)c3)n1)CN(C#N)C2]

Step a.
Carried out as described in step a of Example 104.

Step d.
To a solution of tert-butyl 2-chloro-4-(3-cyanophenyl)-5,7-dihydro-6H-pyrrolo[3,4-d]pyrimidine-6-carboxylate (0.350 g, 0.983 mmol) in 1,4-dioxane (5 ml) was added acetamide (0.069 g, 1.169 mmol) at rt. $K_2CO_3$ (0.271 g, 1.963 mmol) was added to the reaction mixture at rt. The resulting reaction mixture was degassed for 15 min. Xantphos (0.056 g, 0.096 mmol) was added to the reaction mixture at rt. $Pd_2(dba)_3$ (0.089 g, 0.098 mmol) was added to reaction mixture at rt. The reaction mixture was heated at 100° C. for 1 h. The resulting reaction mixture was cooled to rt and poured into ice cold water (50 ml). The obtained mixture was extracted with EtOAc (3×40 ml). The combined organic phase was dried over $Na_2SO_4$, filtered and concentrated under reduced pressure. The resulting residue was purified by flash chromatography (55% EtOAc in hexane) yielding tert-butyl 2-acetamido-4-(3-cyanophenyl)-5,7-dihydro-6H-pyrrolo[3,4-d]pyrimidine-6-carboxylate (0.300 g, 0.791 mmol). LCMS: Method A, 2.036 min, MS: ES+ 380.44; $^1$H NMR (400 MHz, DMSO-d6) δ ppm 10.76 (d, J=5.6 Hz, 1H), 8.38 (d, J=8.4 Hz, 1H), 8.23 (dd, J=8.0, 3.6 Hz, 1H), 8.05 (d, J=8.0 Hz, 1H), 7.90-7.83 (m, 1H), 4.91 (s, 2H), 4.58 (d, J=8.4 Hz, 2H), 2.22 (s, 3H), 2.47 (s, 9H).

Steps e, f.
Carried out using a similar procedure as that described in for steps d and e of Example 1. LCMS: Method D, 3.261 min, MS: ES+ 305.00; $^1$H NMR (400 MHz, DMSO-d6) δ ppm 10.82 (s, 1H), 8.36 (s, 1H), 8.24 (d, J=8.0 Hz, 1H), 8.06 (d, J=8.0 Hz, 1H), 7.79 (t, J=8.0 Hz, 1H), 5.18 (s, 2H), 4.81 (s, 2H), 2.22 (s, 3H).

Compounds in Table 10 were synthesised using a procedure similar to that described for Example 105.

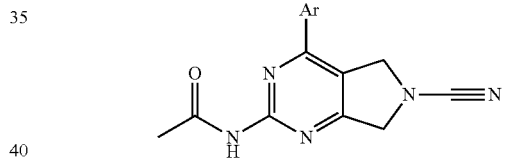

TABLE 10

| Ex | Ar— | Name | Boronic Acid CAS Number | LCMS method | LCMS RT/min | MS ES+ |
|---|---|---|---|---|---|---|
| Example 106 | ![] OCF3 | N-(6-cyano-4-(3-(trifluoromethoxy)phenyl)-6,7-dihydro-5H-pyrrolo[3,4-d]pyrimidin-2-yl)acetamide | 179113-90-7 | D | 4.150 | 363.95 |
| Example 107 | ![] pyrazole | N-(6-cyano-4-(1-methyl-1H-pyrazol-4-yl)-6,7-dihydro-5H-pyrrolo[3,4-d]pyrimidin-2-yl)acetamide | 761446-44-0 | D | 2.527 | 283.99 |
| Example 108 | ![] NHAc | N-(3-(2-acetamido-6-cyano-6,7-dihydro-5H-pyrrolo[3,4-d]pyrimidin-4-yl)phenyl)acetamide | 78887-39-5 | D | 2.851 | 336.94 |

TABLE 10-continued

| Ex | Ar— | Name | Boronic Acid CAS Number | LCMS method | LCMS RT/ min | MS ES+ |
|---|---|---|---|---|---|---|
| Example 109 | | N-(6-cyano-4-(3-(methylsulfonamido)phenyl)-6,7-dihydro-5H-pyrrolo[3,4-d]pyrimidin-2-yl)acetamide | 148355-75-3 | D | 2.078 | 372.92 |

Scheme L

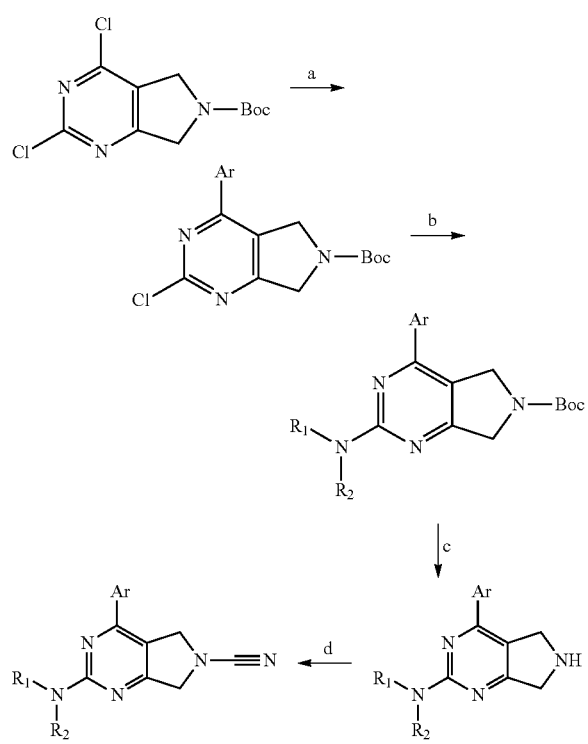

Reagents and conditions: a) ArB(OH)$_2$, Na$_2$CO$_3$, PdCl$_2$(dppf), 1,4-dioxane, water; OR K$_2$CO$_3$, Pd(PPh$_3$)$_4$, 1,4-dioxane, water; b) R$_1$R$_2$NH, THF, or R$_1$R$_2$NH, DIPEA, IPA; c) TFA, DCM OR HCl/EtOAc; d) BrCN, K$_2$CO$_3$ or BrCN, NaHCO$_3$, EtOH.

Example 110 2-(((1R,4R)-4-hydroxycyclohexyl)amino)-4-phenyl-5H-pyrrolo[3,4-d]pyrimidine-6(7H)-carbonitrile (Prepared According to Scheme L)

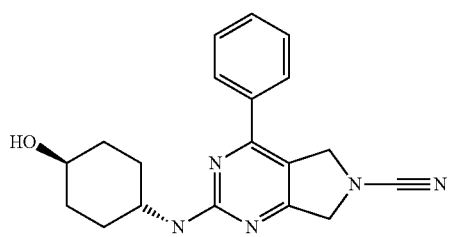

Step a.

A mixture of tert-butyl 2,4-dichloro-5,7-dihydropyrrolo[3,4-d]pyrimidine-6-carboxylate (20 g, 68.9 mmol), phenylboronic acid (8.40 g, 68.9 mmol), K$_2$CO$_3$ (28.58 g, 206.8 mmol) and Pd(PPh$_3$)$_4$ (7.97 g, 6.89 mmol) in 1,4-dioxane (250 ml) and water (50 ml) was degassed and purged with N$_2$ 3 times, and then the mixture was stirred at 105° C. for 16 h under N$_2$ atmosphere. The reaction mixture was concentrated under reduced pressure to remove 1,4-dioxane. The residue was diluted with water (400 ml) and extracted with DCM (300 ml×3). The combined organic layers were washed with brine (600 ml), dried over Na$_2$SO$_4$, filtered and concentrated under reduced pressure to give a residue. The residue was purified by silica gel chromatography (PE/EtOAc=14/1 to 12/1). Tert-butyl 2-chloro-4-phenyl-5H-pyrrolo[3,4-d]pyrimidine-6(7H)-carboxylate (14 g, 80% purity) was obtained as a colourless oil used in the next step directly.

Step b.

To a solution of tert-butyl 2-chloro-4-phenyl-5H-pyrrolo[3,4-d]pyrimidine-6(7H)-carboxylate (0.2 mmol) and (1R,4R)-4-aminocyclohexanol (0.6 mmol) in IPA (1 ml) was added DIPEA (0.6 mmol). The reaction mixture was stirred at 100° C. for 16 h. The resulting mixture was concentrated under reduced pressure. The residue was purified by prep-TLC (PE/EtOAc=1:2) yielding tert-butyl tert-butyl 2-(((1R,4R)-4-hydroxycyclohexyl)amino)-4-phenyl-5H-pyrrolo[3,4-d]pyrimidine-6(7H)-carboxylate. MS: ES+ 411.5.

Step c.

To a solution of tert-butyl 2-4(1r,4r)-4-hydroxycyclohexyl)amino)-4-phenyl-5H-pyrrolo[3,4-d]pyrimidine-6(7H)-carboxylate in EtOAc (1 ml) was added HCl/EtOAc (4 M, 1 ml). The reaction mixture was stirred at rt for 2 h. The resulting mixture was concentrated under reduced pressure. The residue (1R,4R)-4-((4-phenyl-6,7-dihydro-5H-pyrrolo[3,4-d]pyrimidin-2-yl)amino)cyclohexanol was used for next step directly without further purification. MS: ES+ 311.3.

Step d.

To a solution of (1R,4R)-4-((4-phenyl-6,7-dihydro-5H-pyrrolo[3,4-d]pyrimidin-2-yl)amino)cyclohexanol in EtOH (2 ml) was added cyanogen bromide (0.2 mmol) and NaHCO$_3$ (0.6 mmol). The reaction mixture was stirred at rt for 16 h. The resulting mixture was concentrated under reduced pressure. The crude was purified by preparative reverse phase HPLC (A: 0.078% CH$_3$COONH$_4$ in water, B: MeCN) yielding (49.4 mg, 0.146 mmol). LCMS: Method G, 2.786 min, MS: ES+ 336.1.

Compounds in Table 11 were prepared in a manner similar to Example 110 according to Scheme L.

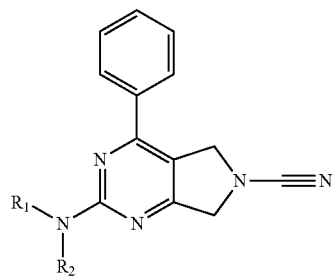

TABLE 11

| Ex | R₁R₂NH— | Name | Amine CAS Number | LCMS method | LCMS RT/ min | MS ES+ |
|---|---|---|---|---|---|---|
| Example 111 | | 4-phenyl-2-(((tetrahydro-2H-pyran-4-yl)methyl)amino)-5,7-dihydro-6H-pyrrolo[3,4-d]pyrimidine-6-carbonitrile | 130290-79-8 | G | 2.61 | 336 |
| Example 112 | | 2-((1-methyl-1H-pyrazol-4-yl)amino)-4-phenyl-5,7-dihydro-6H-pyrrolo[3,4-d]pyrimidine-6-carbonitrile | 1063734-49-5 | G | 2.823 | 318 |
| Example 113 | | 4-phenyl-2-((pyrimidin-2-ylmethyl)amino)-5,7-dihydro-6H-pyrrolo[3,4-d]pyrimidine-6-carbonitrile | 60348-81-4 | H | 2.607 | 330 |
| Example 114 | | 4-phenyl-2-((2-(pyridin-2-yl)ethyl)amino)-5,7-dihydro-6H-pyrrolo[3,4-d]pyrimidine-6-carbonitrile | 2706-56-1 | G | 2.509 | 343 |
| Example 115 | | 4-phenyl-2-((1,2,3,4-tetrahydronaphthalen-1-yl)amino)-5,7-dihydro-6H-pyrrolo[3,4-d]pyrimidine-6-carbonitrile | 2217-40-5 | N | 3.174 | 368 |
| Example 116 | | 4-phenyl-2-(phenylamino)-5,7-dihydro-6H-pyrrolo[3,4-d]pyrimidine-6-carbonitrile | 62-53-3 | N | 2.969 | 314 |
| Example 117 | | 4-phenyl-2-((pyridin-2-ylmethyl)amino)-5,7-dihydro-6H-pyrrolo[3,4-d]pyrimidine-6-carbonitrile | 3731-51-9 | G | 2.494 | 329 |
| Example 118 | | 4-phenyl-2-((pyridin-3-ylmethyl)amino)-5,7-dihydro-6H-pyrrolo[3,4-d]pyrimidine-6-carbonitrile | 3731-52-0 | G | 2.51 | 329 |
| Example 119 | | 4-phenyl-2-((thiazol-5-ylmethyl)amino)-5,7-dihydro-6H-pyrrolo[3,4-d]pyrimidine-6-carbonitrile | 131052-46-5 | G | 2.825 | 335 |

TABLE 11-continued

| Ex | R₁R₂NH— | Name | Amine CAS Number | LCMS method | LCMS RT/min | MS ES+ |
|---|---|---|---|---|---|---|
| Example 120 | HO-CH₂CH₂-NH- | 2-((2-hydroxyethyl)amino)-4-phenyl-5,7-dihydro-6H-pyrrolo[3,4-d]pyrimidine-6-carbonitrile | 141-43-5 | H | 2.521 | 282 |
| Example 121 | furan-CH₂-NH- | 2-((furan-2-ylmethyl)amino)-4-phenyl-5,7-dihydro-6H-pyrrolo[3,4-d]pyrimidine-6-carbonitrile | 617-89-0 | G | 3.011 | 318 |
| Example 122 | imidazolyl-propyl-NH- | 2-((3-(1H-imidazol-1-yl)propyl)amino)-4-phenyl-5,7-dihydro-6H-pyrrolo[3,4-d]pyrimidine-6-carbonitrile | 5036-48-6 | G | 2.272 | 346 |
| Example 188 | CH₃SO₂-CH₂CH₂-NH- | 2-((2-(methylsulfonyl)ethyl)amino)-4-phenyl-5,7-dihydro-6H-pyrrolo[3,4-d]pyrimidine-6-carbonitrile | 104458-24-4 | I | 2.43 | 344 |
| Example 189 | tetrahydropyran-4-yl-NH- | 4-phenyl-2-((tetrahydro-2H-pyran-4-yl)amino)-5,7-dihydro-6H-pyrrolo[3,4-d]pyrimidine-6-carbonitrile | 38041-19-9 | I | 2.54 | 322 |
| Example 190 | HO-CH₂CH₂-N(CH₃)- | 2-((2-hydroxyethyl)(methyl)amino)-4-phenyl-5,7-dihydro-6H-pyrrolo[3,4-d]pyrimidine-6-carbonitrile | 109-83-1 | D | 3.96 | 296.04 |
| Example 191 | 4-methylmorpholin-2-yl-CH₂-N(CH₃)- | 2-(methyl((4-methylmorpholin-2-yl)methyl)amino)-4-phenyl-5,7-dihydro-6H-pyrrolo[3,4-d]pyrimidine-6-carbonitrile | 933752-31-9 | D | 4.453 | 365.08 |

Compounds in Table 11a were prepared in a manner similar to Example 110 according to Scheme L, using 4-methyl-2-morpholinemethanamine in step b.

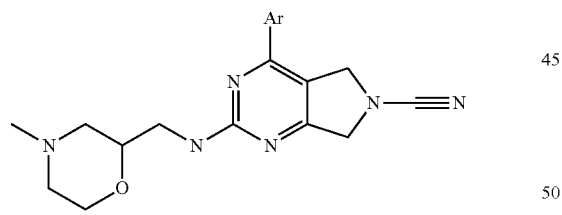

TABLE 11a

| Ex | Ar— | Name | Aryl boronic acid CAS number | LCMS method | LCMS RT/min | MS ES+ |
|---|---|---|---|---|---|---|
| Example 192 | pyridin-3-yl | 2-(((4-methylmorpholin-2-yl)methyl)amino)-4-(pyridin-3-yl)-5,7-dihydro-6H-pyrrolo[3,4-d]pyrimidine-6-carbonitrile | 1692-25-7 | J | 1.13 | 352 |

TABLE 11a-continued

| Ex | Ar— | Name | Aryl boronic acid CAS number | LCMS method | LCMS RT/ min | MS ES+ |
|---|---|---|---|---|---|---|
| Example 193 | 3-fluorophenyl | 4-(3-fluorophenyl)-2-(((4-methylmorpholin-2-yl)methyl)amino)-5,7-dihydro-6H-pyrrolo[3,4-d]pyrimidine-6-carbonitrile | 768-35-4 | J | 2.61 | 369 |
| Example 194 | 4-fluorophenyl | 4-(4-fluorophenyl)-2-(((4-methylmorpholin-2-yl)methyl)amino)-5,7-dihydro-6H-pyrrolo[3,4-d]pyrimidine-6-carbonitrile | 1765-93-1 | J | 2.63 | 369 |
| Example 195 | 3-acetamidophenyl | N-(3-(6-cyano-2-(((4-methylmorpholin-2-yl)methyl)amino)-6,7-dihydro-5H-pyrrolo[3,4-d]pyrimidin-4-yl)phenyl)acetamide | 78887-39-5 | E | 3.219 | 408 |

Example 123 2-(6-cyano-2-(ethylamino)-6,7-dihydro-5H-pyrrolo[3,4-c]pyrimidin-4-yl)benzamide

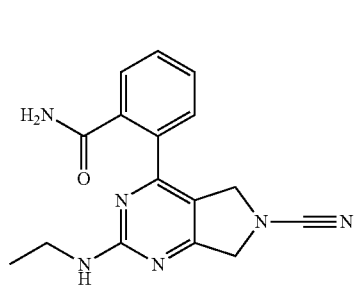 [SMILES: CCNc1nc2c(c(-c3ccccc3C(N)=O)n1)CN(C#N)C2]

Synthesised using a procedure similar to that described for Example 110, using 2-(aminocarbonyl)phenylboronic acid (CAS Number 380430-54-6) in step a and ethylamine (2M in THF) in step b. LCMS: Method A, 1.592 min, MS: ES+ 309.39.

Example 124 2-(((4-methylmorpholin-2-yl)methyl)amino)-4-phenyl-5,7-dihydro-6H-pyrrolo[3,4-d]pyrimidine-6-carbonitrile (Prepared According to Scheme L)

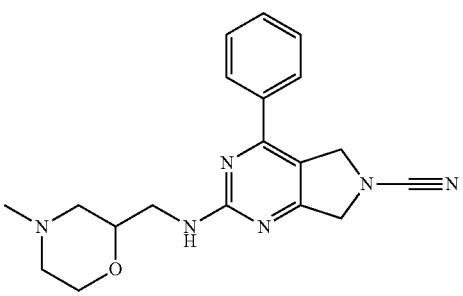 [SMILES: CN1CCOC(CNc2nc3c(c(-c4ccccc4)n2)CN(C#N)C3)C1]

Step a.

To a solution of tert-butyl 2-chloro-4-phenyl-5,7-dihydro-6H-pyrrolo[3,4-d]pyrimidine-6-carboxylate (described in step a of Example 104) (0.3 g, 0.906 mmol) in THF (10 ml) was added (4-methylmorpholin-2-yl)methanamine (CAS Number 141814-57-5, available from Enamine) (0.16 g, 1.177 mmol) at rt. The reaction mixture was heated at 100° C. for 15 h. The resulting reaction mixture was cooled to rt, poured into water (50 ml) and extracted with EtOAc (3×25 ml). The combined organic phase was dried over Na₂SO₄, filtered and concentrated under reduced pressure. The resulting residue was purified by flash chromatography (7% MeOH in DCM) yielding tert-butyl 24((4-methylmorpholin-2-yl)methyl)amino)-4-phenyl-5,7-dihydro-6H-pyrrolo[3,4-d]pyrimidine-6-carboxylate (0.29 g, 0.698 mmol). LCMS: Method A, 1.890 min, MS: ES+ 426.67; ¹H NMR (400 MHz, DMSO-d6) δ ppm 7.83-7.92 (m, 2H), 7.52-7.55 (m, 3H), 7.27-7.30 (m, 1H), 4.71 (s, 2H), 4.40 (d, J=10.8 Hz, 2H), 3.77 (d, J=11.2 Hz, 1H), 3.65-3.66 (m, 1H), 3.41-3.50 (m, 3H), 2.74 (d, J=11.2 HZ, 1H), 2.51-2.57 (m, 1H), 2.15 (s, 3H), 1.93-1.99 (m, 1H), 1.74 (t, J=10 Hz, 1H), 1.46 (s, 9H).

Steps b, c.

The title compound was synthesised from the intermediate above using a procedure similar to that described for steps d and e of Example 1. LCMS: Method D, 3.764 min, MS: ES+ 352.10.

Compounds in Table 12 were synthesised according to Scheme L using a procedure similar to that described for Example 124

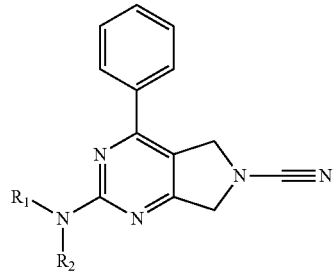

Example 128 N-(6-cyano-4-(3,4-dihydroisoquinolin-2(1H)-yl)-6,7-dihydro-5H-pyrrolo[3,4-d]pyrimidin-2-yl)acetamide

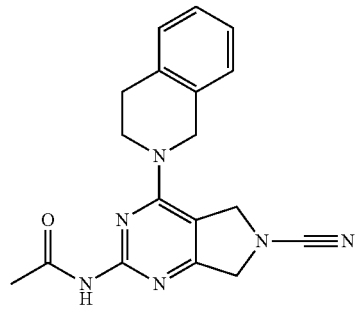 [SMILES: CC(=O)Nc1nc2c(c(N3CCc4ccccc4C3)n1)CN(C#N)C2]

Step a.

To a solution of tert-butyl 2,4-dichloro-5,7-dihydro-6H-pyrrolo[3,4-d]pyrimidine-6-carboxylate (CAS Number 903129-71-5, available from Advanced Chem-blocks) (2.000 g, 6.896 mmol) in MeCN (20 ml) was added 1,2,3,4-tetrahydroisoquinoline (CAS Number 91-21-4, available from Alfa Aesar) (0.917 g, 6.895 mmol) at 0° C. TEA (2.94 ml, 21.25 mmol) was added to reaction mixture at 0° C. The reaction mixture was stirred at rt for 1 h. The resulting reaction mixture was poured into water (100 ml) and extracted with EtOAc (4×20 ml). The combined organic phase was dried over Na₂SO₄, filtered and concentrated under reduced pressure. The resulting residue was purified by column chromatography (20% EtOAc in hexane) yielding tert-butyl 2-chloro-4-(3,4-dihydroisoquinolin-2(1H)-yl)-5,7-dihydro-6H-pyrrolo[3,4-d]pyrimidine-6-carboxylate

TABLE 12

| Ex | R₁R₂N— | Name | Aryl halide CAS Number | LCMS method | LCMS RT/min | MS ES+ |
|---|---|---|---|---|---|---|
| Example 125 | (1-methylpiperidin-3-yl)methylamino | 2-(((1-methylpiperidin-3-yl)methyl)amino)-4-phenyl-5,7-dihydro-6H-pyrrolo[3,4-d]pyrimidine-6-carbonitrile | 14613-37-7 | D | 4.646 | 349.11 |
| Example 126 | (1-methyl-1H-pyrazol-5-yl)methylamino | 2-(((1-methyl-1H-pyrazol-5-yl)methyl)amino)-4-phenyl-5,7-dihydro-6H-pyrrolo[3,4-d]pyrimidine-6-carbonitrile | 863548-52-1 | D | 3.868 | 332.14 |
| Example 127 | (1-methylpyrrolidin-3-yl)methylamino | 2-(((1-methylpyrrolidin-3-yl)methyl)amino)-4-phenyl-5,7-dihydro-6H-pyrrolo[3,4-d]pyrimidine-6-carbonitrile | 13005-11-3 | D | 4.328 | 335.47 |

(2.300 g, 5.96 mmol). LCMS: Method A, 2.674 min, MS: ES+ 387.54; $^1$H NMR (400 MHz, DMSO-d6) δ ppm 7.21-7.28 (m, 4H), 4.82-4.86 (m, 4H), 4.36-4.38 (m, 2H), 3.82-3.87 (m, 2H), 2.92-2.95 (m, 2H), 1.46-1.47 (m, 9H).

Steps b-d.

These were carried out using a procedure similar to that described for steps d-f of Example 105. LCMS: Method E, 3.315 min, ES+ 335.17.

Example 129 N-(6-cyano-4-phenyl-6,7-dihydro-5H-pyrrolo[3,4-c]pyrimidin-2-yl)-5-oxopyrrolidine-3-carboxamide

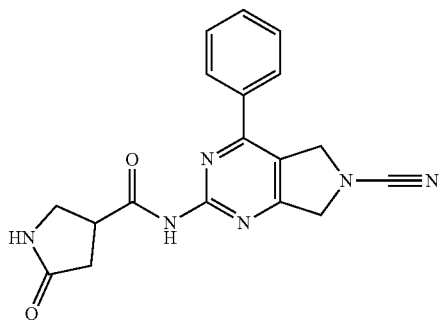 [SMILES: N#CN1Cc2nc(NC(=O)C3CNC(=O)C3)nc(-c3ccccc3)c2C1]

Step a.

To a solution of tert-butyl 2-amino-4-phenyl-5,7-dihydro-6H-pyrrolo[3,4-d]pyrimidine-6-carboxylate (prepared as in steps a and b of Example 104, 0.05 g, 0.160 mmol) and 5-oxopyrrolidine-3-carboxylic acid (CAS Number 7268-43-1, available from Enamine) (0.022 g, 0.176 mmol) in DCM (5 ml) was added pyridine (0.14 g, 1.762 mmol) at 0° C. Phosphorous oxychloride (0.24 g, 1.602 mmol) was added to reaction mixture at 0° C. The resulting reaction mixture was stirred at 0° C. for 30 min. The resulting reaction mixture was poured into water (20 ml) and pH of the resulting mixture was adjusted to 7 by slow addition of solid Na$_2$CO$_3$. The resulting mixture was extracted with EtOAc (3×30 ml). The combined organic phase was collected, dried over Na$_2$SO$_4$, filtered and concentrated under reduced pressure. The resulting residue was purified by flash chromatography (3% MeOH in DCM) yielding tert-butyl 2-(5-oxopyrrolidine-3-carboxamido)-4-phenyl-5,7-dihydro-6H-pyrrolo[3,4-d]pyrimidine-6-carboxylate (0.095 g, 0.224 mmol). LCMS: Method A, 2.009 min, MS: ES+ 424.7.

Steps b, c.

The title compound was synthesised from the intermediate above using a procedure similar to that described for steps d and e of Example 1. LCMS: Method E, 2.993 min, MS: ES+ 349.52.

Scheme M

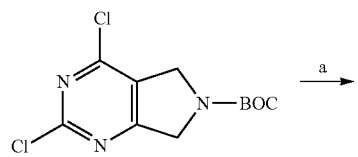

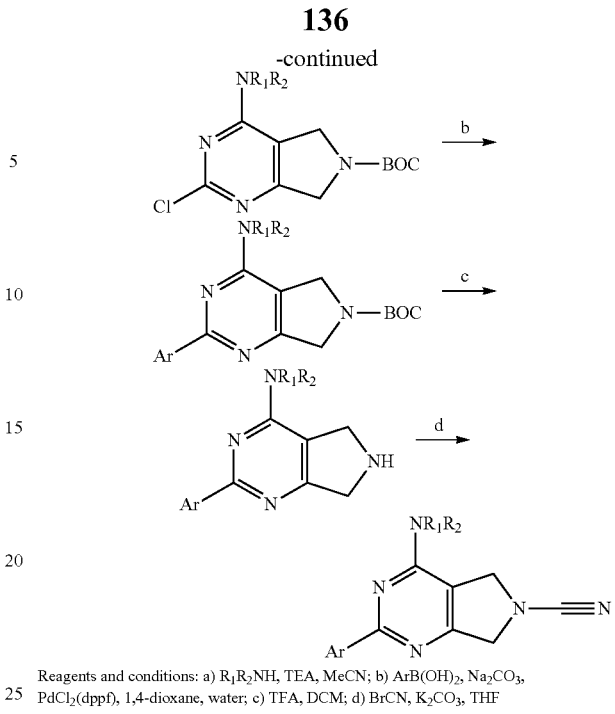

Reagents and conditions: a) R$_1$R$_2$NH, TEA, MeCN; b) ArB(OH)$_2$, Na$_2$CO$_3$, PdCl$_2$(dppf), 1,4-dioxane, water; c) TFA, DCM; d) BrCN, K$_2$CO$_3$, THF Example 130 2-(4-methoxyphenyl)-4-(pyrrolidin-1-yl)-5,7-dihydro-6H-pyrrolo[3,4-c]pyrimidine-6-carbonitrile

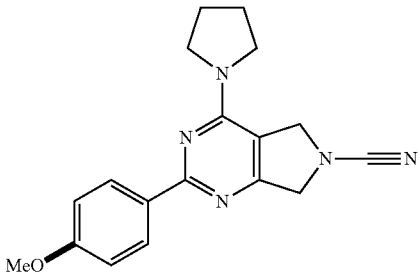

Step a.

To a solution of tert-butyl 2,4-dichloro-5H-pyrrolo[3,4-d]pyrimidine-6(7H)-carboxylate (CAS Number 903129-71-5, available from Advance chem block) (0.5 g, 1.723 mmol) in MeCN (15 ml) was added TEA (0.36 ml, 2.58 mmol) at 0° C. Pyrrolidine (0.11 g, 1.55 mmol) was added at 0° C. The reaction mixture was stirred at rt for 1.5 h. The reaction mixture was concentrated under reduced pressure and poured into water (70 ml). The residue was extracted with EtOAc (3×30 ml). The combined organic phase was washed with brine (30 ml), dried over Na$_2$SO$_4$, filtered and concentrated under reduced pressure yielding tert-butyl 2-chloro-4-(pyrrolidin-1-yl)-5,7-dihydro-6H-pyrrolo[3,4-d]pyrimidine-6-carboxylate (0.6 g, 1.851 mmol). LCMS: Method A, 2.346 min, MS: ES+ 325.59.

Step b.

To a solution of tert-butyl 2-chloro-4-(pyrrolidin-1-yl)-5,7-dihydro-6H-pyrrolo[3,4-d]pyrimidine-6-carboxylate (0.100 g, 0.308 mmol) in 1,4-dioxane:water (9:1, 10 ml) was added 4-methoxyphenylboronic acid (0.056 g, 0.368 mmol) at rt. Sodium carbonate (0.065 g, 0.613 mmol) was added to the reaction mixture at rt. The resulting reaction mixture was degassed for 15 min. Pd(PPh$_3$)$_4$ (0.035 g, 0.026 mmol) was added to reaction mixture at rt. The resulting reaction mixture was heated at 130° C. for 16 h. The reaction mixture was cooled to rt and poured into water (20 ml). The resulting mixture was extracted using EtOAc (3×10 ml). The combined organic phase was washed with brines solution (2×10 ml), dried over Na$_2$SO$_4$, filtered and concentrated under reduced pressure. The residue was purified by flash chromatography (25% EtOAc in hexane) yielding tert-butyl 2-(4-methoxyphenyl)-4-(pyrrolidin-1-yl)-5,7-dihydro-6H-pyrrolo[3,4-d]pyrimidine-6-carboxylate (0.048 g, 0.121 mmol). LCMS: Method A, 2.446 min, MS: ES+ 397.38.

Steps c, d.

The title compound was synthesised from the intermediate above using a procedure similar to that described for steps d and e of Example 1. LCMS: Method D, 2.202 min, MS: ES+ 322.00; $^1$H NMR (400 MHz, DMSO-d6) δ ppm 8.31-8.35 (m, 2H), 6.95-6.98 (m, 2H), 5.05 (t, J=2.8 Hz, 2H), 4.66 (t, J=2.4 Hz, 2H), 3.88 (s, 3H), 3.71-3.75 (m, 4H), 2.03-2.06 (m, 4H).

Compounds in Table 13 were synthesised using a procedure similar to that described for Example 130

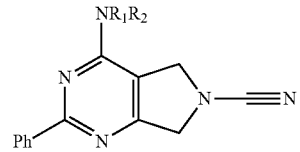

TABLE 13

| Ex | R$_1$R$_2$N— | Name | Amine CAS Number | LCMS method | LCMS RT/min | MS ES+ |
|---|---|---|---|---|---|---|
| Example 131 | H$_2$NOC-[pyrrolidinyl] | 1-(6-cyano-2-phenyl-6,7-dihydro-5H-pyrrolo[3,4-d]pyrimidin-4-yl)pyrrolidine-2-carboxamide | 115630-49-4 | E | 3.159 | 335.54 |
| Example 132 | H$_2$NOC-NH | 2-((6-cyano-2-phenyl-6,7-dihydro-5H-pyrrolo[3,4-d]pyrimidin-4-yl)amino)acetamide | 1668-10-6 | D | 3.132 | 295.03 |
| Example 133 | MeHNOC-[pyrrolidinyl] | 1-(6-cyano-2-phenyl-6,7-dihydro-5H-pyrrolo[3,4-d]pyrimidin-4-yl)-N-methylpyrrolidine-2-carboxamide | 137693-34-6 | D | 3.502 | 349.51 |

Compounds in Table 14 were synthesised using a procedure similar to that described for Example 130 using pyrrolidine in step a.

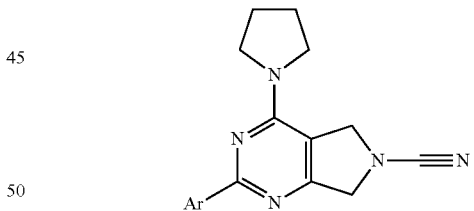

TABLE 14

| Ex | Ar— | Name | Aryl boronic acid/ester CAS Number | LCMS method | LCMS RT/min | MS ES+ |
|---|---|---|---|---|---|---|
| Example 134 | [5-methyl-1H-pyrazol-4-yl] | 2-(5-methyl-1H-pyrazol-4-yl)-4-(pyrrolidin-1-yl)-5,7-dihydro-6H-pyrrolo[3,4-d]pyrimidine-6-carbonitrile | 936250-20-3 | B | 3.422 | 295.96 |

TABLE 14-continued

| Ex | Ar— | Name | Aryl boronic acid/ester CAS Number | LCMS method | LCMS RT/min | MS ES+ |
|---|---|---|---|---|---|---|
| Example 135 | 2-OMe-phenyl | 2-(2-methoxyphenyl)-4-(pyrrolidin-1-yl)-5,7-dihydro-6H-pyrrolo[3,4-d]pyrimidine-6-carbonitrile | 5720-06-9 | A | 1.844 | 322.23 |
| Example 136 | 3-MeO-phenyl | 2-(3-methoxyphenyl)-4-(pyrrolidin-1-yl)-5,7-dihydro-6H-pyrrolo[3,4-d]pyrimidine-6-carbonitrile | 10365-98-7 | A | 2.361 | 322.00 |
| Example 137 | pyridin-3-yl | 2-(pyridin-3-yl)-4-(pyrrolidin-1-yl)-5,7-dihydro-6H-pyrrolo[3,4-d]pyrimidine-6-carbonitrile | 1692-25-7 | D | 3.783 | 293.03 |

Compounds in Table 15 were synthesised using a procedure similar to that described for Example 130 using 1,2,3,4-tetrahydroisoquinoline (CAS Number 91-21-4) in step a.

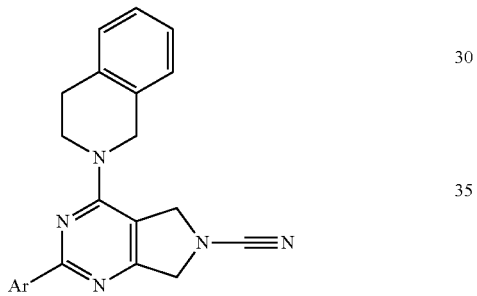

TABLE 15

| Ex | Ar— | Name | Aryl boronic acid/ester CAS Number | LCMS method | LCMS RT/min | MS ES+ |
|---|---|---|---|---|---|---|
| Example 138 | 2-CONH$_2$-phenyl | 2-(6-cyano-4-(3,4-dihydroisoquinolin-2(1H)-yl)-6,7-dihydro-5H-pyrrolo[3,4-d]pyrimidin-2-yl)benzamide | 380430-54-6 | A | 2.008 | 397.23 |
| Example 139 | 5-methyl-1H-pyrazol-4-yl | 4-(3,4-dihydroisoquinolin-2(1H)-yl)-2-(5-methyl-1H-pyrazol-4-yl)-5,7-dihydro-6H-pyrrolo[3,4-d]pyrimidine-6-carbonitrile | 936250-20-3 | D | 4.016 | 358.16 |
| Example 140 | 2-OMe-phenyl | 4-(3,4-dihydroisoquinolin-2(1H)-yl)-2-(2-methoxyphenyl)-5,7-dihydro-6H-pyrrolo[3,4-d]pyrimidine-6-carbonitrile | 5720-06-9 | D | 4.958 | 384.11 |

TABLE 15-continued

| Ex | Ar— | Name | Aryl boronic acid/ester CAS Number | LCMS method | LCMS RT/min | MS ES+ |
|---|---|---|---|---|---|---|
| Example 141 | N≡C—⟨phenyl⟩ | 2-(3-cyanophenyl)-4-(3,4-dihydroisoquinolin-2(1H)-yl)-5,7-dihydro-6H-pyrrolo[3,4-d]pyrimidine-6-carbonitrile | 150255-96-2 | D | 5.313 | 379.12 |
| Example 142 | 1-methylpyrazol-4-yl | 4-(3,4-dihydroisoquinolin-2(1H)-yl)-2-(1-methyl-1H-pyrazol-4-yl)-5,7-dihydro-6H-pyrrolo[3,4-d]pyrimidine-6-carbonitrile | 847818-55-7 | D | 4.151 | 358.09 |

Compounds in Table 16 were synthesised using a procedure similar to that described for Example 130 using 2-pyrrolidinecarboxamide hydrochloride (CAS Number 115630-49-4) in step a.

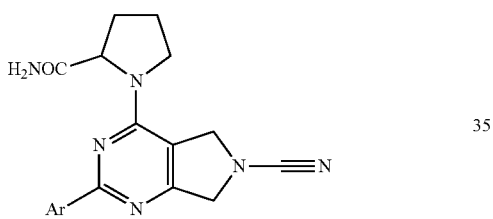

TABLE 16

| Ex | Ar— | Name | Aryl boronic acid/ester CAS Number | LCMS method | LCMS RT/min | MS ES+ |
|---|---|---|---|---|---|---|
| Example 143 | o-tolyl | 1-(6-cyano-2-(o-tolyl)-6,7-dihydro-5H-pyrrolo[3,4-d]pyrimidin-4-yl)pyrrolidine-2-carboxamide | 16419-60-6 | D | 3.328 | 348.98 |
| Example 144 | 5-methyl-1H-pyrazol-4-yl | 1-(6-cyano-2-(5-methyl-1H-pyrazol-4-yl)-6,7-dihydro-5H-pyrrolo[3,4-d]pyrimidin-4-yl)pyrrolidine-2-carboxamide | 936250-20-3 | D | 2.552 | 339.20 |

Example 145 4-(3,4-dihydroisoquinolin-2(1H)-yl)-2-(1H-pyrazol-4-yl)-5,7-dihydro-6H-pyrrolo[3,4-d]pyrimidine-6-carbonitrile

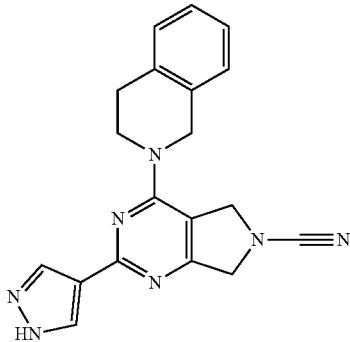 [SMILES: N#CN1Cc2nc(-c3cn[nH]c3)nc(N3CCc4ccccc4C3)c2C1]

Step a.

To a solution of tert-butyl 2,4-dichloro-5,7-dihydro-6H-pyrrolo[3,4-d]pyrimidine-6-carboxylate (CAS Number 903129-71-5, available from Advanced Chem-blocks) (2.000 g, 6.896 mmol) in MeCN (20 ml) was added 1,2,3,4-tetrahydroisoquinoline (CAS Number 91-21-4, available from Alfa Aesar) (0.917 g, 6.895 mmol) and TEA (2.94 ml, 21.25 mmol) at 0° C. The reaction mixture was stirred at rt for 1 h. The resulting reaction mixture was poured into water (100 ml) and extracted with EtOAc (4×20 ml). The combined organic phase was dried over Na₂SO₄, filtered and concentrated under reduced pressure. The resulting residue was purified by column chromatography (20% EtOAc in hexane) yielding tert-butyl 2-chloro-4-(3,4-dihydroisoquinolin-2(1H)-yl)-5,7-dihydro-6H-pyrrolo[3,4-d]pyrimidine-6-carboxylate (2.300 g, 5.958 mmol). LCMS: Method A, 2.674 min, MS: ES+ 387.54; ¹H NMR (400 MHz, DMSO-d6) δ ppm 7.21-7.28 (m, 4H), 4.82-4.86 (m, 4H), 4.36-4.38 (m, 2H), 3.82-3.87 (m, 2H), 2.92-2.95 (m, 2H), 1.46-1.47 (m, 9H).

Step b.

To a solution of tert-butyl 2-chloro-4-(3,4-dihydroisoquinolin-2(1H)-yl)-5,7-dihydro-6H-pyrrolo[3,4-d]pyrimidine-6-carboxylate (0.300 g, 0.777 mmol) in DMF:water (9:1, 5 ml) prepared in a microwave tube were added pyrazole-4-boronic acid pinacol ester (CAS Number 269410-08-4; 0.176 g, 0.926 mmol) and Na₂CO₃ (0.164 g, 1.547 mmol) at rt. The resulting reaction mixture was degassed for 15 min before addition of PdCl₂(dppf) DCM complex (0.063 g, 0.077 mmol). The reaction mixture was sealed and heated in a microwave at 140° C. for 40 min. The reaction mixture was cooled to rt. The resulting reaction mixture was poured into water (20 ml) and extracted with EtOAc (3×10 ml). The combined organic phase was washed with brine solution (10 ml), dried over Na₂SO₄, filtered and concentrated under reduced pressure. The resulting residue was purified by flash chromatography (8% MeOH in DCM) yielding tert-butyl 4-(3,4-dihydroisoquinolin-2(1H)-yl)-2-(1H-pyrazol-4-yl)-5,7-dihydro-6H-pyrrolo[3,4-d]pyrimidine-6-carboxylate (0.182 g, 0.434 mmol). LCMS: Method A, 2.220 min, MS: ES+ 419.38; ¹H NMR (400 MHz, DMSO-d6) δ ppm 13.07 (s, 1H), 8.32 (s, 1H), 8.04 (s, 1H), 7.19-7.24 (m, 4H), 4.93 (s, 2H), 4.85 (s, 2H), 4.38-4.41 (m, 2H), 3.90-3.94 (m, 2H), 2.93-2.96 (m, 2H), 1.47-1.49 (m, 9H).

Step c.

To a solution of tert-butyl 4-(3,4-dihydroisoquinolin-2(1H)-yl)-2-(1H-pyrazol-4-yl)-5,7-dihydro-6H-pyrrolo[3,4-d]pyrimidine-6-carboxylate (0.122 g, 0.291 mmol) in DCM (10 ml) was added TFA (1.0 ml) at 0° C. The resulting reaction mixture was stirred at 0° C. for 0.5 h and then at rt for 1 h. The resulting reaction mixture was evaporated under reduced pressure. The resulting residue was triturated with n-pentane (2×2 ml), diethyl ether (2×2 ml) and dried under vacuum yielding 2-(2-(1H-pyrazol-4-yl)-6,7-dihydro-5H-pyrrolo[3,4-d]pyrimidin-4-yl)-1,2,3,4-tetrahydroisoquinoline TFA salt (0.125 g, quantitative). LCMS: Method A, 1.680 min, MS: ES+ 319.18. This material was used directly for the next step without further purification.

Step d.

To a solution of 2-(2-(1H-pyrazol-4-yl)-6,7-dihydro-5H-pyrrolo[3,4-d]pyrimidin-4-yl)-1,2,3,4-tetrahydroisoquinoline TFA salt (0.125 g, 0.300 mmol) in THF (2 ml) was added K₂CO₃ (0.083 g, 0.601 mmol) at 0° C. Cyanogen bromide (0.035 g, 0.331 mmol) was added to the reaction mixture at 0° C. The resulting reaction mixture was stirred at 0° C. for 0.5 h. The resulting reaction mixture was poured into water (20 ml) and extracted with EtOAc (3×10 ml). The combined organic phase was washed with brine solution (20 ml). The combined organic phase was dried over Na₂SO₄, filtered and concentrated under reduced pressure. The resulting residue was purified by Preparative TLC (5% MeOH in DCM) yielding the title compound (0.021 g, 0.061 mmol). LCMS: Method A, 1.989 min, MS: ES+ 344.13; ¹H NMR (400 MHz, DMSO-d6) δ ppm 13.12 (s, 1H), 8.33 (s, 1H), 8.06 (s, 1H), 7.33 (d, J=5.6 Hz, 1H), 7.20-7.24 (m, 3H), 5.11 (s, 2H), 4.90 (s, 2H), 4.62 (s, 2H), 3.90 (t, J=6 Hz, 2H) 2.93 (t, J=5.6 Hz, 2H).

Example 146 4-(3,4-dihydroisoquinolin-2(1H)-yl)-2-(1H-pyrazol-4-yl)-5,7-dihydro-6H-pyrrolo[3,4-d]pyrimidine-6-carbonitrile

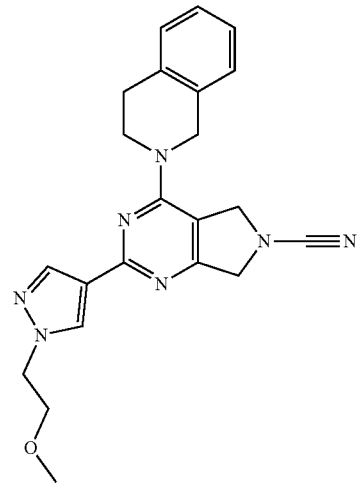 [SMILES: COCCn1cc(-c2nc3c(c(N4CCc5ccccc5C4)n2)CN(C#N)C3)cn1]

Steps a, b.

Carried out as described in steps a, b of Example 145.

Step c.

To a solution of tert-butyl 4-(3,4-dihydroisoquinolin-2(1H)-yl)-2-(1H-pyrazol-4-yl)-5,7-dihydro-6H-pyrrolo[3,4-d]pyrimidine-6-carboxylate (0.100 g, 0.238 mmol) in DMF (2 ml) was added K₂CO₃ (0.131 g, 0.949 mmol) at rt. The reaction mixture was stirred at rt for 15 min before addition of 1-bromo-2-methoxyethane (CAS Number 6482-24-2; 0.066 g, 0.474 mmol). The reaction mixture was heated to 80° C. for 16 h. The resulting reaction mixture was poured into water (20 ml) and extracted with EtOAc (2×10 ml). The combined organic layer was washed with brine solution (10 ml), dried over Na$_2$SO$_4$, filtered and concentrated under reduced pressure. The residue was purified by flash chromatography (10% MeOH in DCM) yielding tert-butyl 4-(3,4-dihydroisoquinolin-2(1H)-yl)-2-(1-(2-methoxyethyl)-1H-pyrazol-4-yl)-5,7-dihydro-6H-pyrrolo[3,4-d]pyrimidine-6-carboxylate (0.058 g, 0.121 mmol). LCMS: Method A, 2.444 min, MS: ES+ 477.23.

Steps d, e.

The title compound was synthesised from the intermediate above using a procedure similar to that described for steps c and d of Example 145. LCMS: Method A, 2.131 min, MS: ES+ 402.23; $^1$H NMR (400 MHz, DMSO-d6) δ ppm 8.32 (s, 1H), 8.01 (s, 1H), 7.32 (d, J=5.6 Hz, 1H), 7.20-7.23 (m, 3H), 5.11 (s, 2H), 4.89 (s, 2H), 4.61 (s, 2H), 4.31 (t, J=5.6 Hz, 2H), 3.90 (t, J=5.6 Hz, 2H), 3.72 (t, J=5.2 Hz, 2H), 3.24 (s, 3H), 2.93 (t, J=6 Hz, 2H).

Example 147 4-(5,8-dihydro-1,7-naphthyridin-7(6H)-yl)-2-(5-methyl-1H-pyrazol-4-yl)-5,7-dihydro-6H-pyrrolo[3,4-d]pyrimidine-6-carbonitrile

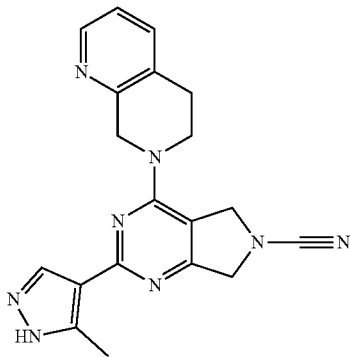 [SMILES: Cc1[nH]ncc1-c1nc2c(c(N3CCc4cccnc4C3)n1)CN(C#N)C2]

Synthesised using a procedure similar to that described for Example 130 using 5,6,7,8-tetrahydro-1,7-naphthyridine hydrochloride (CAS Number 1338707-67-7) and (3-methyl-1H-pyrazol-4-yl)boronic acid pinacol ester (CAS Number 936250-20-3). LCMS: Method A, 1.656 min, MS: ES+ 359.28.

Example 148 N-(6-cyano-4-(pyrrolidin-1-yl)-6,7-dihydro-5H-pyrrolo[3,4-d]pyrimidin-2-yl)acetamide

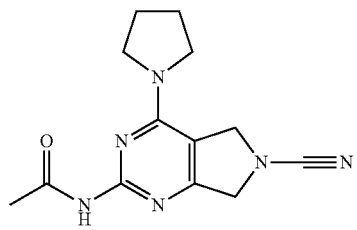 [SMILES: CC(=O)Nc1nc2c(c(N3CCCC3)n1)CN(C#N)C2]

Step a.

A suspension of tert-butyl 2-chloro-4-(pyrrolidin-1-yl)-5,7-dihydro-6H-pyrrolo[3,4-d]pyrimidine-6-carboxylate (prepared as described in step a of Example 130 (0.2 g, 0.616 mmol), K$_2$CO$_3$ (0.17 g, 1.233 mmol) and DMAP (0.15 g, 1.233 mmol) in 2,4-dimethoxybenzylamine (2 ml) was heated at 130° C. for 2.5 h in microwave. The resulting reaction mixture was cooled to rt and was combined with 1 other batch prepared on the same scale by an identical method. The resulting reaction mixture was poured in to 10% citric acid solution (50 ml) and extracted with EtOAc (3×40 ml). The combined organic phase was washed with brine (30 ml), dried over Na$_2$SO$_4$, filtered and concentrated under reduced pressure. The resulting residue was purified by flash chromatography (4% MeOH in DCM). The obtained material was triturated with diethyl ether (5 ml) then n-pentane (10 ml) and dried well yielding the title compound yielding tert-butyl 2-((2,4-dimethoxybenzyl)amino)-4-(pyrrolidin-1-yl)-5,7-dihydro-6H-pyrrolo[3,4-d]pyrimidine-6-carboxylate (0.35 g, 0.768 mmol). LCMS: Method A, 2.190 min, MS: ES+ 456.95; $^1$H NMR (400 MHz, DMSO-d6) δ ppm 7.65 (br s, 1H), 7.12 (d, J=6.8 Hz, 1H), 6.54 (d, J=2 Hz, 1H), 6.47 (dd, J=2 Hz, 8.4 Hz, 1H), 4.67 (s, 2H), 4.38 (s, 2H), 4.32 (s, 2H), 3.79 (s, 3H), 3.73 (s, 3H), 3.51 (s, 4H), 1.87 (s, 4H), 1.44 (s, 9H).

Step b.

TFA (1 ml) was added to tert-butyl 2-((2,4-dimethoxybenzyl)amino)-4-(pyrrolidin-1-yl)-5,7-dihydro-6H-pyrrolo[3,4-d]pyrimidine-6-carboxylate (0.19 g, 0.417 mmol) at 0° C. The resulting reaction mixture was stirred at rt for 30 min. The resulting reaction mixture was concentrated under reduced pressure. The obtained residue was azeotropically distilled with a with DCM (2×10 ml) and triturated with diethyl ether (2×7 ml) yielding 4-(pyrrolidin-1-yl)-6,7-dihydro-5H-pyrrolo[3,4-d]pyrimidin-2-amine TFA salt (0.17 g, 0.392 mmol). LCMS: Method D, 2.564 min, MS: ES+ 206.07.

Step c.

To a solution of 4-(pyrrolidin-1-yl)-6,7-dihydro-5H-pyrrolo[3,4-d]pyrimidin-2-amine TFA salt (0.18 g, 0.415 mmol) in DCM (5 ml) was added TEA (0.11 ml, 0.830 mmol) at 0° C. The resulting reaction mixture was stirred at 0° C. for 5 min. Boc anhydride (0.1 g, 0.456 mmol) was added to the reaction mixture at 0° C. The reaction mixture was stirred at rt for 30 min. The resulting reaction mixture was combined with another batch which was ran at 0.07 g scale by an identical method. The resulting reaction mixture was poured into water (30 ml) and extracted with EtOAc (3×20 ml). The combined organic phase was dried over Na$_2$SO$_4$, filtered and concentrated under reduced pressure. The residue was triturated with the diethyl ether (5 ml) and dried under vacuum to yielding tert-butyl 2-amino-4-(pyrrolidin-1-yl)-5,7-dihydro-6H-pyrrolo[3,4-d]pyrimidine-6-carboxylate (0.14 g, 0.458 mmol). LCMS: Method A, 1.772 min, MS: ES+ 306.68; $^1$H NMR (400 MHz, DMSO-d6) δ ppm 6.87 (br s, 2H), 4.68 (s, 2H), 4.28 (d, J=8.8 Hz, 2H), 3.74 (s, 4H), 1.91 (s, 4H), 1.47 (s, 9H).

Step d.

To a solution of tert-butyl 2-amino-4-(pyrrolidin-1-yl)-5,7-dihydro-6H-pyrrolo[3,4-d]pyrimidine-6-carboxylate (0.13 g, 0.425 mmol) in AC$_2$O (1 ml) was added DMAP (0.0025 g, 0.021 mmol) and TEA (0.12 ml, 0.850 mmol) at 0° C. The reaction mixture was heated at 50° C. for 2 h. The resulting reaction mixture was poured into water (20 ml) and basified by addition of solid $Na_2CO_3$. The obtained basic mixture was extracted with EtOAc (3×20 ml). The combined organic phase was washed with brine (30 ml), dried over $Na_2SO_4$, filtered and concentrated under reduced pressure. The resulting residue was purified by flash chromatography (3.6% MeOH in DCM). The obtained material was triturated with diethylether (3 ml) and dried well yielding tert-butyl 2-acetamido-4-(pyrrolidin-1-yl)-5,7-dihydro-6H-pyrrolo[3,4-d]pyrimidine-6-carboxylate (0.06 g, 0.172 mmol). LCMS: Method A, 1.681 min, MS: ES+ 348.45.

Step e.

To a solution of tert-butyl 2-acetamido-4-(pyrrolidin-1-yl)-5,7-dihydro-6H-pyrrolo[3,4-d]pyrimidine-6-carboxylate (0.06 g, 0.172 mmol) in DCM (3 ml) was added TFA (0.6 ml) at 0° C. The reaction mixture was heated at 40° C. for 3 h. The resulting reaction mixture was concentrated under reduced pressure. The obtained residue was azeotropically distilled with DCM (2×10 ml) and finally dried under high vacuum yielding N-(4-(pyrrolidin-1-yl)-6,7-dihydro-5H-pyrrolo[3,4-d]pyrimidin-2-yl)acetamide TFA salt (0.06 g, 0.165 mmol). MS: ES+ 248.27.

Step f.

To a solution of N-(4-(pyrrolidin-1-yl)-6,7-dihydro-5H-pyrrolo[3,4-d]pyrimidin-2-yl)acetamide TFA salt (0.06 g, 0.165 mmol) in THF (3 ml) was added $K_2CO_3$ (0.09 g, 0.663 mmol) at 0° C. The reaction mixture was stirred for 5 min. Cyanogen bromide (0.021 g, 0.199 mmol) was added to the reaction mixture at 0° C. The reaction mixture was stirred at rt for 1 h. The resulting reaction mixture was poured into water (20 ml) and extracted with EtOAc (3×10 ml). The combined organic phase was dried over $Na_2SO_4$, filtered and concentrated under reduced pressure. The resulting residue was purified by flash chromatography (4% MeOH in DCM). The obtained material was triturated with diethylether (2 ml) and dried well yielding the title compound (0.012 g, 0.044 mmol). LCMS: Method D, 2.930 min, MS: ES+ 273.01; $^1$H NMR (400 MHz, DMSO-d6) δ ppm 9.96 (s, 1H), 5.01 (s, 2H), 4.51 (s, 2H), 3.57 (s, 4H), 2.24 (s, 3H), 1.87 (s, 4H).

Compounds in Table 17 were synthesised using a procedure similar to that described for Example 105, omitting step d.

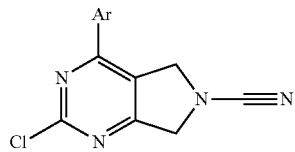

TABLE 17

| Ex | Ar— | Name | Aryl boronic acid/ester CAS Number | LCMS method | LCMS RT/min | MS ES+ |
|---|---|---|---|---|---|---|
| Example 149 | F (4-fluorophenyl) | 2-chloro-4-(4-fluorophenyl)-5,7-dihydro-6H-pyrrolo[3,4-d]pyrimidine-6-carbonitrile | 1765-93-1 | C | 6.679 | ES− 273.10 |
| Example 150 | F (2-fluorophenyl) | 2-chloro-4-(2-fluorophenyl)-5,7-dihydro-6H-pyrrolo[3,4-d]pyrimidine-6-carbonitrile | 1993-03-9 | D | 4.263 | 275.01 |

Example 151 4-(4-fluorophenyl)-2-methyl-5,7-dihydro-6H-pyrrolo[3,4-d]pyrimidine-6-carbonitrile

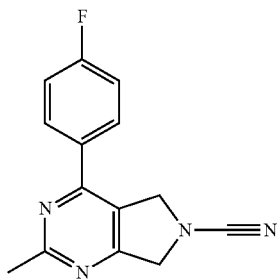 [SMILES: Cc1nc2c(c(-c3ccc(F)cc3)n1)CN(C#N)C2]

Step a.
To a solution of tert-butyl 3-cyano-4-oxopyrrolidine-1-carboxylate (CAS Number 175463-32-8; 10.0 g, 47.59 mmol) in EtOH (150 ml) was added ammonium formate (4.42 g, 71.29 mmol) at rt. The reaction mixture was heated at 70° C. for 16 h. The resulting reaction mixture was cooled to rt and concentrated under reduced pressure. The residue was extracted with EtOAc (3×150 ml). The combined organic phase was washed with brine (100 ml), dried over $Na_2SO_4$, filtered and concentrated under reduced pressure. The residue was purified by trituration using solvent n-hexane to yield tert-butyl 3-amino-4-cyano-2,5-dihydro-1H-pyrrole-1-carboxylate (9.0 g, 43.06 mmol). LCMS: Method E, 3.464 min, MS: ES− 208.3.

Step b.
To a solution of tert-butyl 3-amino-4-cyano-2,5-dihydro-1H-pyrrole-1-carboxylate (1.3 g, 7.17 mmol) in 1-butanol (15 ml) was added acetamide HCl (5.00 g, 52.88 mmol) at rt. The reaction mixture was heated at 100° C. for 96 h. The resulting reaction mixture was cooled to rt and concentrated under reduced pressure. The resulting residue was poured in water (40 ml) and extracted with EtOAc (3×40 ml). The combined organic phase was dried over $Na_2SO_4$, filtered and concentrated under reduced pressure. The obtained crude material was purified by column chromatography (6% MeOH in DCM) to yield tert-butyl 4-amino-2-methyl-5,7-dihydro-6H-pyrrolo [3,4-d]pyrimidine-6-carboxylate (1.30 g, 5.20 mmol). This material was used directly for the next step without further purification.

Step c.
To a solution of tert-butyl 4-amino-2-methyl-5,7-dihydro-6H-pyrrolo[3,4-d]pyrimidine-6-carboxylate (1.3 g, 5.20 mmol) in MeCN (20 ml) was added copper (II) bromide (2.32 g, 10.4 mmol) at 0° C. and stirred for 15 min. Tert-Butyl nitrite (0.804 g, 7.8 mmol) was added to the reaction mixture at 0° C. The reaction mixture was stirred at rt for 16 h. The resulting reaction mixture was poured into water (100 ml) and extracted with EtOAc (3×50 ml). The combined organic phase was dried over $Na_2SO_4$, filtered and concentrated under reduced pressure. The residue was purified by column chromatography (3% MeOH in DCM) to yield tert-butyl 4-bromo-2-methyl-5,7-dihydro-6H-pyrrolo[3,4-d]pyrimidine-6-carboxylate (0.088 g, 0.28 mmol). LCMS: Method A, 2.146 min, MS: ES+ 314, 316

Step d.
To a solution of tert-butyl 4-bromo-2-methyl-5,7-dihydro-6H-pyrrolo[3,4-d]pyrimidine-6-carboxylate (0.08 g, 0.254 mmol) in toluene:EtOH (9:1, 20 ml) were added 4-fluorophenylboronic acid (0.042 g, 0.305 mmol) and $K_2CO_3$ (0.087 g, 0.636 mmol) at rt. The reaction mixture was degassed for 15 min. $Pd(PPh_3)_4$ (0.029 g, 0.025 mmol) was added to the reaction mixture and stirred at 110° C. for 2 h. The resulting reaction mixture was cooled to rt and poured into water (50 ml). The resulting mixture was extracted with EtOAc (2×50 ml). The combined organic phase was dried over $Na_2SO_4$, filtered and concentrated under reduced pressure to yield crude material. The crude material was purified by flash chromatography (20% in EtOAc in n-hexane) to yield tert-butyl 4-(4-fluorophenyl)-2-methyl-5,7-dihydro-6H-pyrrolo[3,4-d]pyrimidine-6-carboxylate (1.67 g, 6.34 mmol). This material was used directly for the next step without further purification.

Steps e, f.
The title compound was synthesised from the intermediate above using a procedure similar to that described for steps e and f of Example 97. LCMS: Method E, 3.662 min, MS: ES+ 255.28, NMR (400 MHz, DMSO-d6) δ ppm 8.00-8.036 (m, 2H), 7.383-7.427 (m, 2H), 5.164 (s, 2H), 4.815 (s, 2H), 2.69 (s, 3H).

Example 152 2-(((4-methylmorpholin-2-yl)methyl)amino)-4-phenyl-5,7-dihydro-6H-pyrrolo[3,4-d]pyrimidine-6-carbonitrile: Enantiomer 1

Example 153 2-(((4-methylmorpholin-2-yl)methyl)amino)-4-phenyl-5,7-dihydro-6H-pyrrolo[3,4-d]pyrimidine-6-carbonitrile: Enantiomer 2

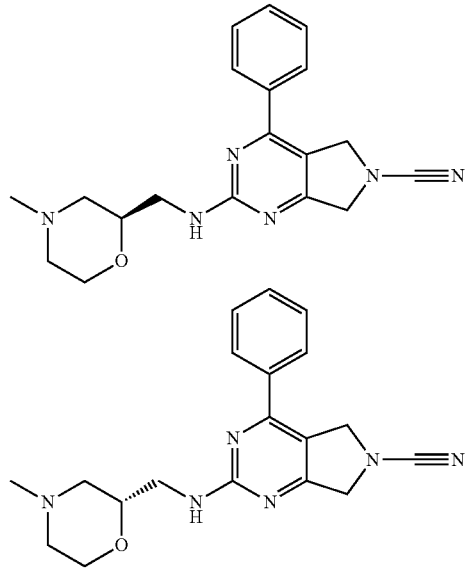

Example 124 was subjected for further enantiomeric separation by Chiral HPLC; mobile phase: (A) 0.3% diethylamine in hexane (B) 0.3% diethylamine in IPA, column: CHIRALPAK AD-H 250×21.0 mm, 5 μm, column flow was 15.0 ml/min which yielded both enantiomers. Absolute stereochemistry was not determined.

Example 152: LCMS: Method D, 3.769 min, MS: ES+ 351.11; NMR (400 MHz, DMSO-d6) δ ppm 7.82-7.91 (m, 2H), 7.52-7.57 (m, 3H), 7.41 (br s, 1H), 4.96 (s, 2H), 4.62 (s, 2H), 3.78 (d, J=10.4 Hz, 1H), 3.61-3.69 (m, 1H), 3.38-3.50 (m, 3H), 2.75 (d, J=10.8 Hz, 1H), 2.51-2.60 (m, 1H), 2.17 (s, 3H), 1.94-2.06 (m, 1H), 1.72-1.81 (m, 1H).

Example 153: LCMS: Method D, 3.761 min, MS: ES+ 351.11; NMR (400 MHz, DMSO-d6) δ ppm 7.82-7.91 (m, 2H), 7.52-7.57 (m, 3H), 7.41 (br s, 1H), 4.96 (s, 2H), 4.62 (s, 2H), 3.78 (d, J=10.4 Hz, 1H), 3.61-3.69 (m, 1H), 3.38-3.50 (m, 3H), 2.74 (d, J=10.8 Hz, 1H), 2.51-2.60 (m, 1H), 2.16 (s, 3H), 1.94-2.06 (m, 1H), 1.72-1.81 (m, 1H).

Scheme N

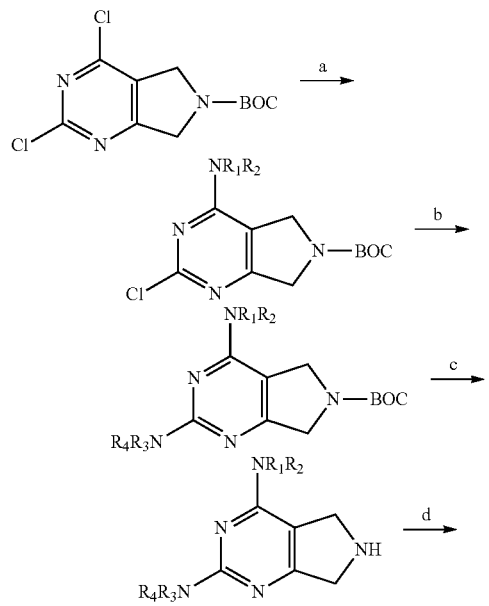

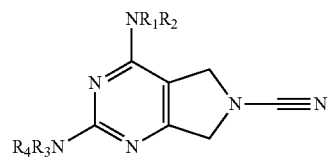

Reagents and conditions: a) R₁R₂NH, TEA, MeCN; b) R₃R₄NH THF; c) TFA, DCM; d) BrCN, K₂CO₃, THF Compounds in Table 18 were prepared according to Scheme N. Step a was carried out by a method similar to step a of example 145, and steps b-d were carried out by a method similar to steps a-c of Example 124

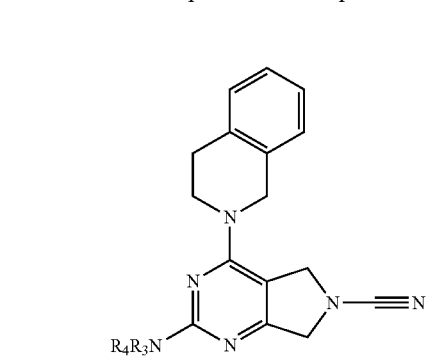

TABLE 18

| Ex | R₃R₄N— | Name | Amine CAS Number | LCMS method | LCMS RT/min | MS ES+ |
|---|---|---|---|---|---|---|
| Example 196 | (1-methylpiperidin-3-yl)methylamine | 4-(3,4-dihydroisoquinolin-2(1H)-yl)-2-(((1-methylpiperidin-3-yl)methyl)amino)-5,7-dihydro-6H-pyrrolo[3,4-d]pyrimidine-6-carbonitrile | 14613-37-7 | I | 2.23 | 404 |
| Example 197 | (4-methylmorpholin-2-yl)methylamine | 4-(3,4-dihydroisoquinolin-2(1H)-yl)-2-(((4-methylmorpholin-2-yl)methyl)amino)-5,7-dihydro-6H-pyrrolo[3,4-d]pyrimidine-6-carbonitrile | 141814-57-5 | I | 2.21 | 406 |
| Example 198 | (1-methyl-1H-pyrazol-5-yl)methylamine | 4-(3,4-dihydroisoquinolin-2(1H)-yl)-2-(((1-methyl-1H-pyrazol-5-yl)methyl)amino)-5,7-dihydro-6H-pyrrolo[3,4-d]pyrimidine-6-carbonitrile | 863548-52-1 | I | 2.29 | 387 |
| Example 199 | trans-4-hydroxycyclohexylamine | 4-(3,4-dihydroisoquinolin-2(1H)-yl)-2-((trans)-4-hydroxycyclohexyl)amino)-5,7-dihydro-6H-pyrrolo[3,4-d]pyrimidine-6-carbonitrile | 50910-54-8 | I | 2.37 | 391 |
| Example 200 | (tetrahydro-2H-pyran-4-yl)methylamine | 4-(3,4-dihydroisoquinolin-2(1H)-yl)-2-(((tetrahydro-2H-pyran-4-yl)methyl)amino)-5,7-dihydro-6H-pyrrolo[3,4-d]pyrimidine-6-carbonitrile | 130290-79-8 | S | 2.44 | 391 |
| Example 201 | (1-methyl-1H-pyrazol-4-yl)methylamine | 4-(3,4-dihydroisoquinolin-2(1H)-yl)-2-(((1-methyl-1H-pyrazol-4-yl)methyl)amino)-5,7-dihydro-6H-pyrrolo[3,4-d]pyrimidine-6-carbonitrile | 400877-05-6 | I | 2.4 | 387 |
| Example 202 | 2-hydroxyethylamine | 4-(3,4-dihydroisoquinolin-2(1H)-yl)-2-((2-hydroxyethyl)amino)-5,7-dihydro-6H-pyrrolo[3,4-d]pyrimidine-6-carbonitrile | 141-43-5 | I | 2.32 | 337 |

TABLE 18-continued

| Ex | R₃R₄N— | Name | Amine CAS Number | LCMS method | LCMS RT/min | MS ES+ |
|---|---|---|---|---|---|---|
| Example 203 | 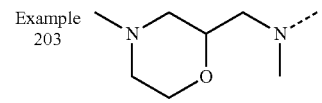 | 4-(3,4-dihydroisoquinolin-2(1H)-yl)-2-(methyl((4-methylmorpholin-2-yl)methyl)amino)-5,7-dihydro-6H-pyrrolo[3,4-d]pyrimidine-6-carbonitrile | 933752-31-9 | D | 4.78 | 420.16 |

Compounds in Table 19 were prepared according to Scheme N. Step a was carried out by a method similar to step a of example 145, and steps b-d were carried out by a method similar to steps a-c of Example 124, using 4-phenoxypiperidine in step a

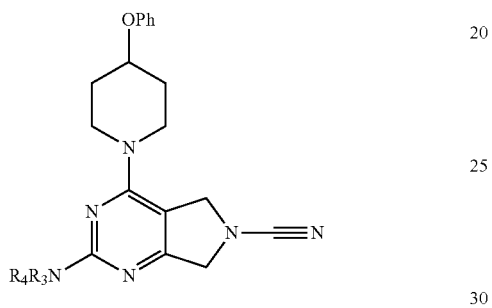

TABLE 19

| Ex | R₃R₄N— | Name | Amine name or CAS Number | LCMS method | LCMS RT/min | MS ES+ |
|---|---|---|---|---|---|---|
| Example 204 | Me-NH- | 2-(methylamino)-4-(4-phenoxypiperidin-1-yl)-5,7-dihydro-6H-pyrrolo[3,4-d]pyrimidine-6-carbonitrile | methylamine | D | 4.709 | 351.04 |
| Example 205 | Me-N(Me)- | 2-(dimethylamino)-4-(4-phenoxy-piperidin-1-yl)-5,7-dihydro-6H-pyrrolo[3,4-d]pyrimidine-6-carbonitrile | Dimethyl-amine | D | 5.393 | 365.01 |
| Example 206 | HO-CH₂CH₂-NH- | 2-((2-hydroxyethyl)amino)-4-(4-phenoxypiperidin-1-yl)-5,7-dihydro-6H-pyrrolo[3,4-d]pyrimidine-6-carbonitrile | 141-43-5 | D | 4.174 | 381.04 |
| Example 207 | H₂N- | 2-amino-4-(4-phenoxypiperidin-1-yl)-5,7-dihydro-6H-pyrrolo[3,4-d]pyrimidine-6-carbonitrile | ammonia | D | 3.912 | 337.2 |

Compounds in Table 20 were prepared according to Scheme L by a method similar to Example 110, using 2-ethanolamine in step b

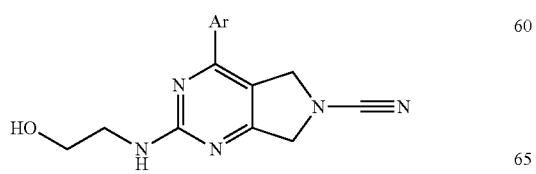

TABLE 20

| Ex | Ar— | Name | Aryl boronic acid CAS Number | LCMS method | LCMS RT/min | MS ES+ |
|---|---|---|---|---|---|---|
| Example 208 | NC-phenyl | 4-(4-cyanophenyl)-2-((2-hydroxyethyl)amino)-5,7-dihydro-6H-pyrrolo[3,4-d]pyrimidine-6-carbonitrile | 126747-14-6 | I | 2.34 | 307 |
| Example 209 | 3,4-difluorophenyl | 4-(3,4-difluorophenyl)-2-((2-hydroxyethyl)amino)-5,7-dihydro-6H-pyrrolo[3,4-d]pyrimidine-6-carbonitrile | 168267-41-2 | J | 2.95 | 318 |
| Example 210 | 3-acetamidophenyl | N-(3-(6-cyano-2-((2-hydroxyethyl)amino)-6,7-dihydro-5H-pyrrolo[3,4-d]pyrimidin-4-yl)phenyl)acetamide | 78887-39-5 | J | 2.58 | 339 |
| Example 211 | MeO-phenyl | 2-((2-hydroxyethyl)amino)-4-(4-methoxyphenyl)-5,7-dihydro-6H-pyrrolo[3,4-d]pyrimidine-6-carbonitrile | 5720-07-0 | I | 2.4 | 312 |
| Example 212 | 4-(4-methylpiperazin-1-yl)phenyl | 2-((2-hydroxyethyl)amino)-4-(4-(4-methylpiperazin-1-yl)phenyl)-5,7-dihydro-6H-pyrrolo[3,4-d]pyrimidine-6-carbonitrile | 229009-40-9 | D | 3.228 | 380.1 |

Example 213 6-((dimethylamino)methyl)-4-phenylisoindoline-2-carbonitrile

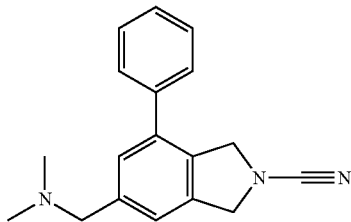 [SMILES: CN(C)Cc1cc2c(c(-c3ccccc3)c1)CN(C#N)C2]

Step a. To a stirred solution of methyl 7-bromoisoindoline-5-carboxylate HCl salt (prepared as in step e of Example 98, 4.200 g, 14.35 mmol) in 1,4-dioxane (150 ml) was added K₂CO₃ (5.600 g, 40.539 mmol) at 0° C. Benzyl chloroformate (3.60 g, 21.2 mmol) was dropwise added to the reaction mixture at 0° C. The reaction mixture was stirred at rt for 3 h. The resulting mixture was evaporated under reduced pressure, diluted with ice cold water (150 ml) and extracted with EtOAc (3×200 ml). The combined organic layer was dried over Na₂SO₄, filtered and concentrated under reduced pressure. The residue was triturated with diethyl ether:hexane (7:3, 4×50 ml) and obtained solid material was dried under high vacuum yielding 2-benzyl 5-methyl 7-bromoisoindoline-2, 5-dicarboxylate (4.80 g, 12.31 mmol). This material was use directly for next step without further purification. LCMS: Method A, 2.753 min, MS: ES+ 390.00; 392.00

Step b. A stirred solution of 2-benzyl 5-methyl 7-bromoisoindoline-2,5-dicarboxylate (4.000 g, 10.28 mmol) in THF (100 ml) was added lithium aluminium hydride (1M in THF) (24 ml, 24 mmol) at −78° C. The reaction mixture was stirred at −78° C. for 4 h. The resulting reaction mixture was quenched with saturated NH₄Cl solution (100 ml) and extracted in EtOAc (3×80 ml). The combined organic layer was dried over Na₂SO₄, filtered and concentrated under reduced pressure. The obtained residue was triturate using n-Hexane (2×15 ml) and dried under high vacuum yielding benzyl 4-bromo-6-(hydroxymethyl) isoindoline-2-carboxylate (3.600 g, 9.972 mmol). This material was use directly for next step without further purification. LCMS: Method A, 2.205 min, MS: ES+ 362.25; 364.25

Step c. To a solution of benzyl 4-bromo-6-(hydroxymethyl) isoindoline-2-carboxylate (3.600 g, 9.972 mmol) in DCM (60 ml) was added Dess Martin periodinane (5.500 g, 12.94 mmol) at 0° C. The reaction mixture was stirred at 0° C. to 10° C. for 60 min. The resulting mixture was poured into saturated NaHCO₃ solution (150 ml) and extracted with EtOAc (3×150 ml). The combined organic phase was dried over Na₂SO₄, filtered and concentrated under reduced pressure. The residue was purified by flash column chromatography (15% EtOAc in hexane) yielding benzyl 4-bromo-6-formyl-isoindoline-2-carboxylate (3.150 g, 8.750 mmol). LCMS: Method A, 2.38 min, MS: ES+ 360.13; 362.00

Step d. To a stirred solution of benzyl 4-bromo-6-formylisoindoline-2-carboxylate (3.100 g, 8.635 mmol) in 1,4-dioxane:water (9:1, 50 ml) were added K₃PO₄ (3.66 g, 17.26 mmol) and phenylboronic acid (1.580 g, 12.95 mmol) at rt. The reaction mixture was degassed with N₂ gas for 15 min before addition of PdCl₂(dppf) (0.630 g, 0.864 mmol). The resulting reaction mixture was heated at 75° C. for 6 h. The reaction mixture was cooled to rt, poured into water (100 ml) and extracted with EtOAc (3×100 ml). The combined organic phase was dried over Na₂SO₄, filtered and concentrated under reduced pressure. The residue was purified by flash column chromatography (15% EtOAc in hexane) yielding title compound benzyl 6-formyl-4-phenylisoindoline-2-carboxylate (2.600 g, 7.262 mmol). LCMS: Method A, 2.54 min, MS: ES+ 358.34

Step e. To a stirred solution of benzyl 6-formyl-4-phenylisoindoline-2-carboxylate (0.200 g, 0.560 mmol) in MeOH (10 ml) was added dimethyl amine (40% aqueous solution) (2 ml, 3.36 mmol) at rt. The reaction mixture was stirred at rt for 2 h. Then reaction mixture was cooled to 0° C. and AcOH (0.4 ml, 5.60 mmol) was added. The reaction mixture was stirred at 0° C. for 5 min. NaCNBH$_3$ (0.065 g, 0.840 mmol) was added to the reaction mixture at 0° C. The resulting reaction mixture was stirred at 0° C. for 2 h. The resulting reaction mixture was combined with one other batch prepared on the same scale by an identical method. The reaction mixture was evaporated under reduced pressure, poured into saturated NaHCO$_3$ (60 ml) and extracted with EtOAc (3×60 ml). The combined organic phase was dried over Na$_2$SO$_4$, filtered and concentrated under reduced pressure. The residue was purified by flash column chromatography (3% MeOH in DCM) yielding benzyl 6-((dimethylamino)methyl)-4-phenylisoindoline-2-carboxylate (0.4 g, 1.033 mmol). LCMS: Method A, 1.982 min, MS: ES+ 387.51

Step f. To a solution of benzyl 6-((dimethylamino) methyl)-4-phenylisoindoline-2-carboxylate (0.400 g, 1.033 mmol) in AcOH (10 ml) was added 10% dry Pd/C (0.2 g) at RT. The reaction mixture was purged with hydrogen gas at atmospheric pressure for 4 h. The resulting reaction mixture was filtered through celite pad and washed with AcOH (2×10 ml) and DCM (20 ml). The combined filtrate was evaporated under high vacuum and triturated with hexane: diethyl ether (1:1, 2×10 ml). The obtained residue was dried under high vacuum yielding N,N-dimethyl-1-(7-phenylisoindolin-5-yl)methanamine acetate salt (0.300 g). This material was use directly for next step without further purification. LCMS: Method D, 4.192 min, MS: ES+ 253.10

Step g was carried out in a similar manner to step e of Example 1. LCMS: Method D, 4.683 min, MS: ES+ 278.09; 1H NMR (400 MHz, DMSO-d6) δ ppm: 7.40-7.48 (m, 5H), 7.26 (s, 2H), 4.82-4.85 (m, 4H), 3.45 (s, 2H), 2.16 (s, 6H).

Example 214 N-((2-cyano-7-phenylisoindolin-5-yl) methyl)acetamide

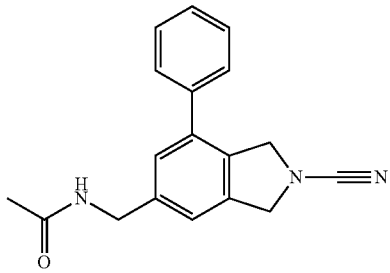 [SMILES: CC(=O)NCc1cc2c(c(-c3ccccc3)c1)CN(C#N)C2]

Step a. To a stirred solution of benzyl 6-formyl-4-phenylisoindoline-2-carboxylate (prepared as in step d of Example 213, 0.500 g, 1.400 mmol) in MeOH (10 ml) was added NH$_2$OH.HCl (0.485 g, 7.00 mmol) at rt. The reaction mixture was stirred at rt for 4 h. The reaction mixture was evaporated under reduced pressure, poured into saturated NaHCO$_3$ (70 ml) and extracted with EtOAc (3×70 ml). The combined organic phase was dried over Na$_2$SO$_4$, filtered and concentrated under reduced pressure. Then obtained residue was dissolved in AcOH (5 ml) and cooled to 0° C. Zinc dust (0.448 g, 7.00 mmol) was added to the reaction mixture at 0° C. The reaction mixture was stirred at rt for 40 h. The resulting mixture was filtered through celite pad and washed with AcOH (2×10 ml) and DCM (20 ml). The combined filtrate was evaporated under high vacuum and triturated with diethyl ether (2×15 ml) to yield benzyl 6-(aminomethyl)-4-phenylisoindoline-2-carboxylate (0.400 g). This material was used is directly for the next step without further purification. LCMS: Method A, 1.925 min, MS: ES+ 359.23

Step b. To a stirred solution of benzyl 6-(aminomethyl)-4-phenylisoindoline-2-carboxylate (0.400 g, 1.12 mmol) in THF (10 ml) were added K$_2$CO$_3$ (0.463 g, 3.356 mmol) followed by acetyl chloride (0.17 ml, 2.24 mmol) at 0° C. The reaction mixture was stirred at rt for 4 h. The resulting mixture was poured into water (50 ml) and extracted with EtOAc (3×40 ml). The combined organic phase was dried over Na$_2$SO$_4$, filtered and concentrated under reduced pressure. The resulting residue was purified by flash column chromatography (2% MeOH in DCM) yielding benzyl 6-(acetamidomethyl)-4-phenylisoindoline-2-carboxylate (0.160 g, 0.400 mmol). LCMS: Method A, 2.236 min, MS: ES+ 401.32

Steps c and d were carried out in a similar manner to steps f and g of Example 213. LCMS: Method D, 3.769 min, MS: ES+ 291.99; 1H NMR (400 MHz, DMSO-d6) δ ppm: 8.39 (s, 1H), 7.38-7.48 (m, 5H), 7.20-7.25 (m, 2H), 4.82-4.84 (m, 4H), 4.30-4.31 (d, J=6.0 Hz, 2H), 1.87 (s, 3H).

Example 215 6-(2-methoxyethyl)-4-phenylisoindoline-2-carbonitrile

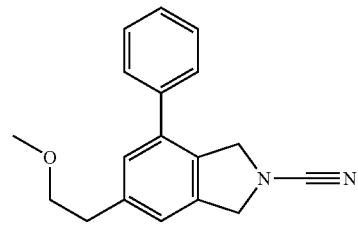 [SMILES: COCCc1cc2c(c(-c3ccccc3)c1)CN(C#N)C2]

Step a. To a solution of methoxymethyl triphenylphosphonium chloride (9.592 g, 27.98 mmol) in THF (30 ml) was added NaHMDS (1M in THF) (28 ml, 28 mmol) at −78° C. drop wise. The reaction mixture was stirred at −78° C. for 45 min. A solution of benzyl 6-formyl-4-phenylisoindoline-2-carboxylate (prepared as in step d of Example 213, 2.5 g, 7.0 mmol) in THF (20 ml) was added drop wise to the reaction mixture at −78° C. The resulting reaction mixture was stirred at 0° C. for 1 h. The resulting reaction mixture was combined with 1 other batch prepared on the same scale by an identical method. The resulting mixture was quenched with water (250 ml) and extracted with EtOAc (3×100 ml). The combined organic phase was washed with brine (40 ml), dried over Na$_2$SO$_4$, filtered and concentrated under reduced pressure. The obtained residue was purified by flash column chromatography (18% EtOAc in Hexane) yielding benzyl 6-(2-methoxyvinyl)-4-phenylisoindoline-2-carboxylate (0.750 g 1.948 mmol). LCMS: Method E, 5.657+5.694 min, MS: ES+ 386.31.

Steps b and c were carried out in a similar manner to steps c and d of Example 214. LCMS: Method D, 4.960 min, MS: ES+ 278.96; 1H NMR (400 MHz, DMSO-d6) δ ppm:

7.37-7.49 (m, 5H), 7.19 (s, 1H), 7.23 (s, 1H), 4.80-4.83 (m, 4H), 3.56 (t, J=6.4 Hz, 2H), 3.23 (s, 3H), 2.87 (t, J=6.0 Hz, 2H).

Example 216 4-(4-cyanophenyl)-6-((methylsulfonyl)methyl)isoindoline-2-carbonitrile

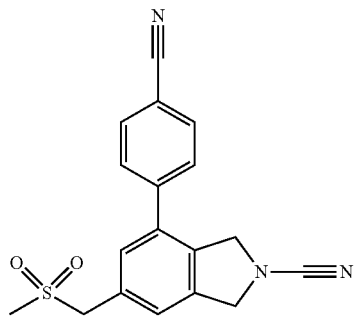 [SMILES: CS(=O)(=O)Cc1cc2c(c(-c3ccc(C#N)cc3)c1)CN(C#N)C2]

Step a. To a stirred solution of Intermediate 13 (2.000 g, 5.633 mmol) in THF (30 ml) was added lithium aluminium hydride (1M in THF) (16.9 ml, 16.9 mmol) at −78° C. The reaction mixture was stirred at −78° C. for 4 h. The resulting reaction mixture was quenched with saturated NH$_4$Cl solution (50 ml) and extracted in EtOAc (3×40 ml). The combined organic layer was dried over Na$_2$SO$_4$, filtered and concentrated under reduced pressure. The obtained residue was triturate with n-hexane (2×15 ml) and dried under high vacuum yielding tert-butyl 4-bromo-6-(hydroxymethyl)isoindoline-2-carboxylate (1.700 g, 5.197 mmol). This material was use directly for next step without further purification. LCMS: Method A, 2.058 min, MS: ES+ 272.29, 274.29 [M−56]; $^1$H NMR (400 MHz, DMSO-d6) δ ppm 7.42 (s, 1H), 7.25-7.28 (m, 1H), 5.34 (t, J=6.4 Hz, 1H), 4.66-4.68 (d, J=8.4 Hz, 2H), 4.48-4.51 (m, 4H), 1.46 (s, 9H).

Step b. To a stirred solution of tert-butyl 4-bromo-6-(hydroxymethyl)isoindoline-2-carboxylate (1.000 g, 3.058 mmol) in 1,4-dioxane:water (9:1, 10 ml) were added K$_3$PO$_4$ (1.29 g, 6.12 mmol) and 4-cyanophenylboronic acid (0.673 g, 4.59 mmol) at rt. The reaction mixture was degassed with N$_2$ gas for 30 min before addition of PdCl$_2$(dppf) (0.220 g, 0.305 mmol). The resulting reaction mixture was heated at 80° C. for 8 h. The reaction mixture was cooled to rt, poured into water (50 ml) and extracted with EtOAc (3×50 ml). The combined organic phase was dried over Na$_2$SO$_4$, filtered and concentrated under reduced pressure. The residue was purified by flash column chromatography (30% EtOAc in hexane) yielding tert-butyl 4-(4-cyanophenyl)-6-(hydroxymethyl)-isoindoline-2-carboxylate (0.850 g, 2.428 mmol). LCMS: Method A, 2.111 min, MS: ES+ 336.38 [M−15]

Step c. To a stirred solution of tert-butyl 4-(4-cyanophenyl)-6-(hydroxymethyl)isoindoline-2-carboxylate (0.300 g, 0.854 mmol) in toluene (10 ml) was added PBr$_3$ (0.341 g, 1.282 mmol) at 0° C. The reaction mixture was stirred at 0° C. for 4 h. Then reaction mixture was evaporated under reduced pressure and yielding 4-(6-(bromomethyl)isoindolin-4-yl)benzonitrile hydrobromide (0.255 g, Quantitative). This material was used directly for next step without further purification. LCMS: Method A, 1.90 min, MS: ES+ 313.00

Step d. To a solution of 4-(6-(bromomethyl)isoindolin-4-yl)benzonitrile hydrobromide (0.250 g, 0.639 mmol) in THF (10 ml) was added K$_2$CO$_3$ (0.176 g, 1.278 mmol) at 0° C. Boc anhydride (0.557 g, 2.556 mmol) was added to the reaction mixture at 0° C. The reaction mixture was stirred at rt for 4 h. The resulting mixture was poured into ice-cold water (30 ml) and extracted with EtOAc (3×30 ml). The combined organic layer was dried over Na$_2$SO$_4$, filtered and concentrated under reduced pressure yielding tert-butyl 6-(bromomethyl)-4-(4-cyanophenyl)isoindoline-2-carboxylate (0.300 g, 0.726 mmol). This material was use directly for next step without further purification. LCMS: Method A, 2.625 min, MS: ES+ 398.54 (M−15)

Step e. To a solution of tert-butyl 6-(bromomethyl)-4-(4-cyanophenyl)isoindoline-2-carboxylate (0.300 g, 0.726 mmol) in THF (10 ml) was added sodium thiomethoxide (0.076 g, 1.098 mmol) at 0° C. The reaction mixture was stirred at rt for 5 h. The resulting mixture was poured in to ice-cold water (30 ml) and extracted with EtOAc (3×30 ml). The combined organic layer was dried over Na$_2$SO$_4$, filtered and concentrated under reduced pressure yielding tert-butyl 4-(4-cyanophenyl)-6-((methylthio)methyl)isoindoline-2-carboxylate (0.220 g, 0.579 mmol). This material was use directly for next step without further purification. LCMS: Method A, 2.66 min, MS: ES+ 366.40 [M−15]

Step f. To a solution of tert-butyl 4-(4-cyanophenyl)-6-((methylthio)methyl)isoindoline-2-carboxylate (0.210 g, 0.552 mmol) in DCM (5 ml) was added m-CPBA (0.190 g, 1.105 mmol) at 0° C. The reaction mixture was stirred at rt for 4 h. The resulting mixture was poured into saturated NaHCO$_3$ (20 ml) and extracted with EtOAc (3×20 ml). The combined organic layer was dried over Na$_2$SO$_4$, filtered and concentrated under reduced pressure yielding tert-butyl 4-(4-cyanophenyl)-6-((methylsulfonyl)methyl)isoindoline-2-carboxylate (0.125 g, 0.303 mmol). This material was use directly for next step without further purification. LCMS: Method A, 2.034 min, MS: ES− 411.59

Steps g and h were carried out in a similar manner to steps d and e of Example 1. LCMS: Method D, 5.149 min, MS: ES− 336.00; $^1$H NMR (400 MHz, DMSO-d6) δ ppm 7.97 (d, J=8.4 Hz, 2H), 7.71 (d, J=8.0 Hz, 2H), 7.47 (s, 1H), 7.43 (s, 1H), 4.92 (s, 2H), 4.87 (s, 2H), 4.59 (s, 2H), 2.95 (s, 3H).

Example 217 N-((2-cyano-7-(4-cyanophenyl)isoindolin-5-yl)methyl)acetamide

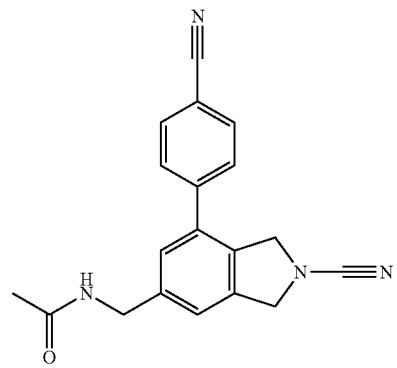 [SMILES: CC(=O)NCc1cc2c(c(-c3ccc(C#N)cc3)c1)CN(C#N)C2]

Step a. Carried out in a similar manner as step b of Example 214 using Intermediate 12.

Steps b and c were carried out in a similar manner to steps d and e of Example 1. LCMS: Method D, 3.528 min, MS: ES+ 317.09; $^1$H NMR (400 MHz, DMSO-d6) δ ppm 8.41 (t, J=5.6 Hz, 1H), 7.95 (d, J=8.4 Hz, 2H), 7.69 (d, J=8.0 Hz, 2H), 7.30 (s, 1H), 7.26 (s, 1H), 4.87 (s, 2H), 4.82 (s, 2H), 4.31 (d, J=6.0 Hz, 2H), 1.86 (s, 3H).

Example 218 N-((2-cyano-7-(4-cyanophenyl)isoindolin-5-yl)methyl)-N-methylacetamide

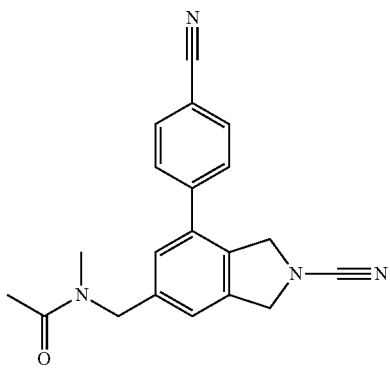 [SMILES: CC(=O)N(C)Cc1cc2c(c(-c3ccc(C#N)cc3)c1)CN(C#N)C2]

Step a. To a solution of tert-butyl 6-(acetamidomethyl)-4-(4-cyanophenyl)isoindoline-2-carboxylate (Prepared as in step a of Example 217), 0.250 g, 0.639 mmol) in DMF (5 ml) was added NaH (60% in oil) (0.076 g, 1.917 mmol) at 0° C. The reaction mixture was stirred at 0° C. for 30 min. CH$_3$I (0.050 ml, 0.767 mmol) was added to the reaction mixture at 0° C. The reaction mixture was stirred at rt for 2 h. The reaction mixture was poured into cold water (50 ml) and extracted with EtOAc (3×20 ml). The combined organic phase was dried over Na$_2$SO$_4$, filtered and concentrated under reduced pressure. The resulting residue was purified by flash column chromatography (22% EtOAc in Hexane) to yield tert-butyl 4-(4-cyanophenyl)-6-4N-methylacetamido)methyl)isoindoline-2-carboxylate (0.200 g, 0.493 mmol). LCMS: Method A, 2.039 min, MS: ES+ 406.53

Steps b and c were carried out in a similar manner to steps d and e of Example 1. LCMS: Method D, 3.757 min, MS: ES+ 331.20; $^1$H NMR (400 MHz, DMSO-d6) δ ppm 7.94-7.96 (m, 2H), 7.69-7.73 (m, 2H), 7.28 (s, 1H), 7.25 (s, 1H), 4.87 (s, 2H), 4.82 (s, 2H), 4.55-4.63 (m, 2H), 2.81-2.94 (m, 3H), 2.08 (s, 3H).

Example 219 N-((2-cyano-7-(4-cyanophenyl)isoindolin-5-yl)methyl)tetrahydro-2H-pyran-4-carboxamide

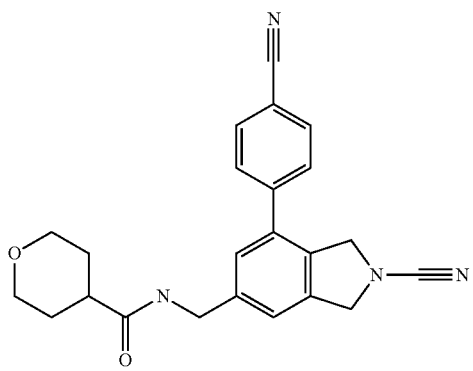 [SMILES: N#Cc1ccc(-c2cc(CNC(=O)C3CCOCC3)cc3c2CN(C#N)C3)cc1]

Step a.

To a solution of tetrahydropyran-4-yl-carboxylic acid (CAS Number 5337-03-1; 0.071 g, 0.554 mmol) in THF (5 ml) were added DIPEA (0.150 ml, 0.916 mmol) and HATU (0.260 g, 0.687 mmol) at rt. The reaction mixture was stirred at rt for 30 min. Intermediate 12 (0.160 g, 0.458 mmol) was added to the reaction mixture at 0° C. The reaction mixture was stirred at rt for 6 h. The resulting mixture was poured into water (30 ml) and extracted with EtOAc (3×30 ml). The combined organic phase was collected, washed with brine (20 ml), dried over Na$_2$SO$_4$, filtered and concentrated under reduced pressure. The residue was purified by column chromatography (80% EtOAc in hexane) yielding tert-butyl 4-(4-cyanophenyl)-6-((tetrahydro-2H-pyran-4-carboxamido)methyl)-isoindoline-2-carboxylate (0.100 g, 0.216 mmol). LCMS: Method A, 2.022 min, MS: ES+ 406.58 [M−56]

Steps b and c.

Carried out in a similar manner to steps d and e of Example 1. LCMS: Method D, 3.602 min, MS: ES+ 386.96; $^1$H NMR (400 MHz, DMSO-d6) δ ppm 8.40 (t, J=5.6 Hz, 1H), 7.96 (d, J=8 Hz, 2H), 7.69 (d, J=8.0 Hz, 2H), 7.25 (s, 1H), 7.29 (s, 1H), 4.83-4.87 (m, 4H), 4.32-4.34 (d, J=5.6 Hz, 2H), 3.84-3.87 (m, 2H), 3.26-3.30 (m, 2H), 3.38-3.46 (m, 1H), 1.56-1.62 (m, 4H).

Example 220 N-((2-cyano-7-(4-cyanophenyl)isoindolin-5-yl)methyl)tetrahydro-2H-thiopyran-4-carboxamide 1,1-dioxide

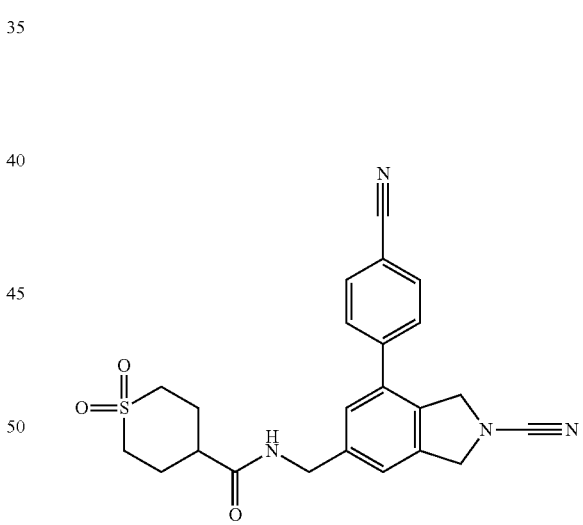

This was made by using tetrahydro-2H-thiopyran-4-carboxylic acid 1,1-dioxide (CAS Number 64096-87-3) using a similar method to Example 219. LCMS: Method D, 3.350 min, MS: ES+ 435.00; $^1$H NMR (400 MHz, DMSO-d6) δ ppm 8.54 (t, J=6.4 Hz, 1H), 7.95 (d, J=7.6 Hz, 2H), 7.68 (d, J=8.0 Hz, 2H), 7.29 (s, 1H), 7.25 (s, 1H), 4.86 (s, 2H), 4.82 (s, 2H), 4.32-4.33 (m, 2H), 3.07-3.15 (m, 4H), 2.48-2.50 (m, 1H), 2.00-2.07 (m, 4H).

Example 221 N-((2-cyano-7-(4-cyanophenyl)isoindolin-5-yl)methyl)-1-methyl-1H-pyrazole-4-carboxamide

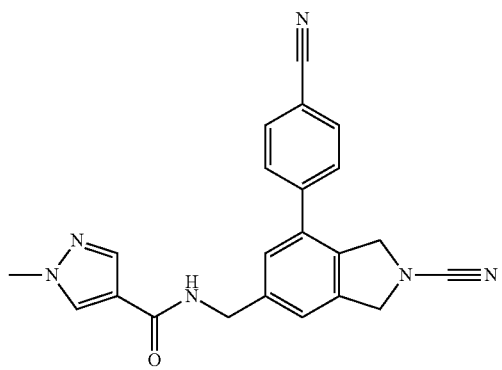 [SMILES: Cn1cc(C(=O)NCc2cc3c(c(-c4ccc(C#N)cc4)c2)CN(C#N)C3)cn1]

Prepared using 1-methyl-1H-pyrazole-4-carboxylic acid (CAS Number 5952-92-1) using a similar method to Example 219. LCMS: Method D, 3.34 min, MS: ES+ 383.04; $^1$H NMR (400 MHz, DMSO-d6) δ ppm 8.65 (t, J=5.6 Hz, 1H), 8.13 (s, 1H), 7.94 (d, J=8.0 Hz, 2H), 7.85 (s, 1H), 7.69 (d, J=8.0 Hz, 2H), 7.30 (s, 1H), 7.35 (S, 1H), 4.82-4.87 (m, 4H), 4.47 (d, J=5.6 Hz, 2H), 3.84 (s, 3H).

Example 222 N-((2-cyano-7-(4-cyanophenyl)isoindolin-5-yl)methyl)methanesulfonamide

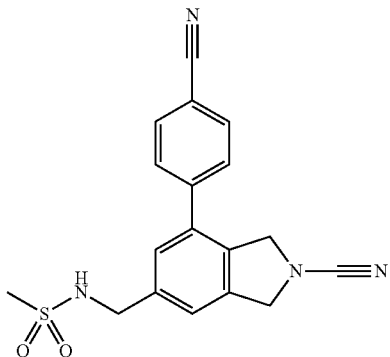 [SMILES: CS(=O)(=O)NCc1cc2c(c(-c3ccc(C#N)cc3)c1)CN(C#N)C2]

Step a. To a stirred solution of Intermediate 12 (0.150 g, 0.429 mmol) in THF (25 ml) was added K$_2$CO$_3$ (0.177 g, 1.29 mmol) at 0° C. Mesyl chloride (0.059 g, 0.515 mmol) was added to the reaction mixture at 0° C. The reaction mixture was stirred at rt for 2 h. The reaction mixture was poured into saturated NaHCO$_3$ solution (50 ml) and extracted with EtOAc (3×20 ml). The combined organic phase was dried over Na$_2$SO$_4$, filtered and concentrated under reduced pressure. The resulting residue was purified by flash column chromatography (30% EtOAc in hexane) to yielding tert-butyl 6-(acetamidomethyl)-4-(4-cyanophenyl)isoindoline-2-carboxylate (0.100 g, 0.234 mmol). LCMS: Method A, 2.103 min, MS: ES– 426.00

Steps b and c were carried out in a similar manner to steps d and e of Example 1. LCMS: Method E, 3.617 min, MS: ES– 351.43; $^1$H NMR (400 MHz, DMSO-d6) δ ppm 7.96 (d, J=8.4 Hz, 2H), 7.72 (d, J=8.4 Hz, 2H), 7.64 (t, J=6.4 Hz, 1H), 7.40 (s, 1H), 7.38 (s, 1H), 4.89 (s, 2H), 4.85 (s, 2H), 4.24 (d, J=6.4 Hz, 2H), 2.91 (s, 3H).

Example 223 3-((2-cyano-7-(4-cyanophenyl)isoindolin-5-yl)methyl)-1,1-dimethylurea

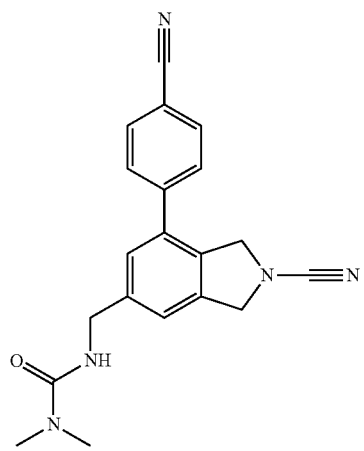 [SMILES: CN(C)C(=O)NCc1cc2c(c(-c3ccc(C#N)cc3)c1)CN(C#N)C2]

Step a. To a stirred solution of Intermediate 12 (0.160 g, 0.458 mmol) in THF (5 ml) was added K$_2$CO$_3$ (0.189 g, 1.38 mmol) at 0° C. Dimethylcarbamoyl chloride (0.058 g, 0.556 mmol) was added to the reaction mixture at 0° C. The reaction mixture was stirred at rt for 6 h. The reaction mixture was poured into water (30 ml) and extracted with EtOAc (2×30 ml). The combined organic phase was dried over Na$_2$SO$_4$, filtered and concentrated under reduced pressure. The resulting residue was purified by flash column chromatography (3% MeOH in DCM) yielding tert-butyl 4-(4-cyanophenyl)-6-((3,3-dimethylureido)methyl)isoindoline-2-carboxylate (0.120 g, 0.285 mmol). LCMS: Method A, 2.412 min, MS: ES+ 365.22 [M–56].

Steps b and c were carried out in a similar manner to steps d and e of Example 1. LCMS: Method D, 3.610 min, MS: ES+ 346.05; $^1$H NMR (400 MHz, DMSO-d6) δ ppm 7.95 (d, J=8.4 Hz, 2H), 7.68 (d, J=8.4 Hz, 2H), 7.27 (s, 1H), 7.31 (s, 1H), 6.92 (t, J=6.0 Hz, 1H), 4.82-4.86 (m, 4H), 4.28 (d, J=5.6 Hz, 2H), 2.80 (s, 6H).

Example 224 isopropyl ((2-cyano-7-(4-cyanophenyl)isoindolin-5-yl)methyl)carbamate

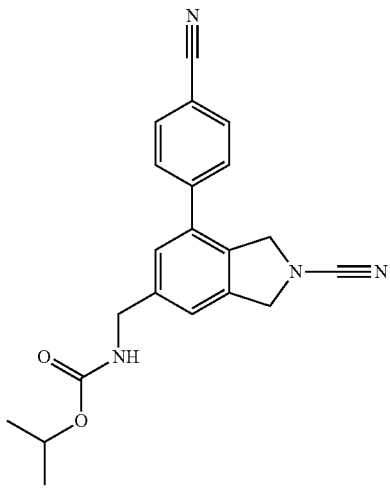 [SMILES: CC(C)OC(=O)NCc1cc2c(c(-c3ccc(C#N)cc3)c1)CN(C#N)C2]

Steps a-c.

Carried out using a similar method to Example 223 using isopropyl chloroformate 1 M solution in toluene (CAS Number 108-23-6) in step a. LCMS: Method D, 4.218 min, MS: ES+ 361.13; $^1$H NMR (400 MHz, DMSO-d6) δ ppm 7.95 (d, J=8.0 Hz, 2H), 7.70 (d, J=8.4 Hz, 2H), 7.65 (t, J=6.0 Hz, 1H), 7.30 (s, 1H), 7.26 (s, 1H), 4.87 (s, 2H), 4.83 (s, 2H), 4.74-4.78 (m, 1H), 4.24 (d, J=6.4 Hz, 2H), 1.16 (d, J=6.4 Hz, 6H).

Example 225 N-((2-cyano-7-(2-cyanophenyl)isoindolin-5-yl)methyl)acetamide

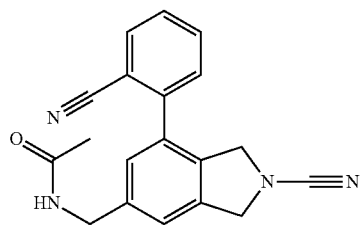 [SMILES: CC(=O)NCc1cc2c(c(-c3ccccc3C#N)c1)CN(C#N)C2]

Step a. To a stirred solution of Intermediate 11 (2.450 g, 7.515 mmol) in MeOH (30 ml) was added NH$_2$OH.HCl (6.260 g, 90.2 mmol) at rt. The reaction mixture was stirred at rt for 2 h. The reaction mixture was evaporated under reduced pressure. The obtained residue was dissolved in AcOH (24.5 ml) and zinc dust (3.430 g, 52.6 mmol) was added at rt. The reaction mixture was stirred at rt for 4 h. The reaction mixture was diluted with saturated NaHCO$_3$ solution (150 ml). The resulting mixture was extracted with EtOAc (3×50 ml). The combined organic phase was dried over Na$_2$SO$_4$, filtered and concentrated under reduced pressure yielding tert-butyl 6-(aminomethyl)-4-bromoisoindoline-2-carboxylate (1.2 g, 3.680 mmol). LCMS: Method A, 1.521 min, MS: ES+ 327.20, 329.20

Step b. To a stirred solution of tert-butyl 6-(aminomethyl)-4-bromoisoindoline-2-carboxylate (1.200 g, 3.67 mmol) in THF (12 ml) was added K$_2$CO$_3$ (1.510 g, 11.01 mmol) at 0° C. Acetyl chloride (0.31 ml, 4.40 mmol) was added to the reaction at 0° C. The reaction mixture was stirred at rt for 16 h. The reaction mixture was poured into saturated NaHCO$_3$ solution (50 ml) and extracted with EtOAc (3×50 ml). The combined organic phase was dried over Na$_2$SO$_4$, filtered and concentrated under reduced pressure. The resulting residue was purified by flash column chromatography (3% MeOH in DCM) yielding tert-butyl 6-(acetamidomethyl)-4-bromoisoindoline-2-carboxylate (0.900 g, 2.445 mmol). LCMS: Method A, 1.872 min, MS: ES+ 369.03, 371.04

Step c. To a stirred solution of tert-butyl 6-(acetamidomethyl)-4-bromoisoindoline-2-carboxylate (0.300 g, 0.813 mmol) in 1,4-dioxane:water (9:1, 5.5 ml) were added K$_2$CO$_3$ (0.223 g, 1.626 mmol) and 2-cyanophenylboronic acid (0.179 g, 1.219 mmol) at rt. The reaction mixture was degassed for 20 min before addition of PdCl$_2$(dppf) (0.089 g, 0.081 mmol). The resulting reaction mixture was heated at 85° C. for 16 h. The reaction mixture was cooled to rt, poured into water (25 ml) and extracted with EtOAc (3×25 ml). The combined organic phase dried over Na$_2$SO$_4$, filtered and concentrated under reduced pressure. The residue was purified by flash column chromatography (70% EtOAc in hexane) yielding tert-butyl 6-(acetamidomethyl)-4-(2-cyanophenyl)-isoindoline-2-carboxylate (0.110 g 0.281 mmol). LCMS: Method A, 1.879 min, MS: ES+ 409.80 [M+18].

Steps d and e were carried out in a similar manner to steps d and e of Example 1. LCMS: Method D, 3.426 min, MS: ES+ 317.50; $^1$H NMR (400 MHz, DMSO-d6, High temperature) δ ppm 8.46-8.41 (m, 1H), 7.99 (d, J=6.8 Hz, 1H), 7.81-7.77 (m, 1H), 7.65-7.59 (m, 1H), 7.40-7.18 (m, 3H), 4.87 (s, 2H), 4.74-4.68 (m, 2H), 4.32 (d, J=6.0 Hz, 1H), 4.24 (d, J=5.6 Hz, 1H), 1.87 (s, 3H).

Example 226 N-((2-cyano-7-(2,4-dicyanophenyl)isoindolin-5-yl)methyl)acetamide

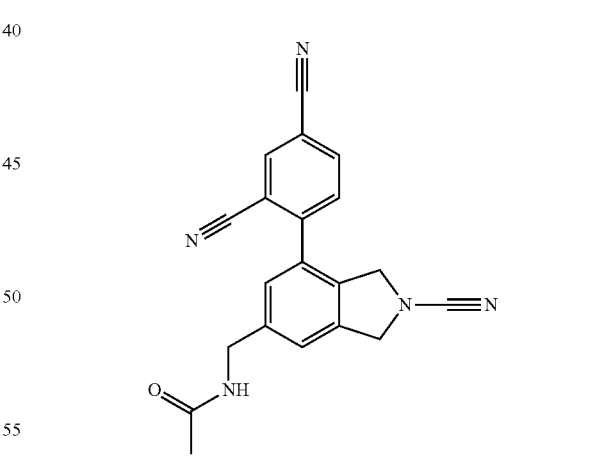

Step a. To a stirred solution of tert-butyl 6-(acetamidomethyl)-4-bromoisoindoline-2-carboxylate (prepared as in step b of Example 225, 0.600 g, 1.626 mmol) in 1,4-dioxane (10 ml) were added KOAc (0.313 g, 3.252 mmol) and bispinacolatodiboron (0.495 g, 1.95 mmol) at rt. The reaction mixture was degassed with N$_2$ gas for 20 min before addition of PdCl$_2$(dppf) (0.117 g, 0.162 mmol). The resulting reaction mixture was heated at 85° C. for 4 h. The reaction mixture was cooled to rt, filtered through celite bed and washed with EtOAc (3×50 ml). The combined filtrate was concentrated under reduced pressure. The obtained residue was triturated with hexane (50 ml) and dried under high vacuum yielding tert-butyl 6-(acetamidomethyl)-4-(4,4,5,5-tetramethyl-1,3,2-dioxaborolan-2-yl)isoindoline-2-carboxylate (0.850 g). This material was directly used for next step without any further purification. LCMS: Method A, 2.132 min, MS: ES+ 361.80 [M−56].

Step b. To a stirred solution of tert-butyl 6-(acetamidomethyl)-4-(4,4,5,5-tetramethyl-1,3,2-dioxaborolan-2-yl)isoindoline-2-carboxylate (1.000 g, 2.415 mmol) in 1,4-dioxane: water (9:1, 4.4 ml) were added $K_2CO_3$ (0.330 g, 2.40 mmol) and 4-bromoisophthalonitrile (CAS Number 22433-89-2; 0.250 g, 1.208 mmol) at rt. The reaction mixture was degassed for 20 min before addition of $PdCl_2(dppf)$ (0.080 g, 0.120 mmol). The resulting reaction mixture was heated at 85° C. for 4 h. The reaction mixture was cooled to rt, poured into water (100 ml) and extracted with EtOAc (3×100 ml). The combined organic phase dried over $Na_2SO_4$, filtered and concentrated under reduced pressure. The residue was purified by flash column chromatography (70% EtOAc in hexane) yielding tert-butyl 6-(acetamidomethyl)-4-(2,4-dicyanophenyl)isoindoline-2-carboxylate (0.120 g, 0.288 mmol). LCMS: Method A, 1.853 min, MS: ES+ 361.58 [M−56].

Steps c and d were carried out in a similar manner to steps d and e of Example 1. LCMS: Method D, 3.234 min, MS: ES+ 359.15; $^1$H NMR (400 MHz, DMSO-d6) δ ppm 8.46-8.41 (m, 1H), 7.99 (d, J=6.8 Hz, 1H), 7.81-7.77 (m, 1H), 7.65-7.59 (m, 1H), 7.40-7.18 (m, 3H), 4.87 (s, 2H), 4.74-4.68 (m, 2H), 4.31 (d, J=6.0 Hz, 1H), 4.24 (d, J=5.6 Hz, 1H), 1.87 (s, 3H).

Example 227 1-((2-cyano-7-(4-cyanophenyl)isoindolin-5-yl)methyl)-3-methylurea

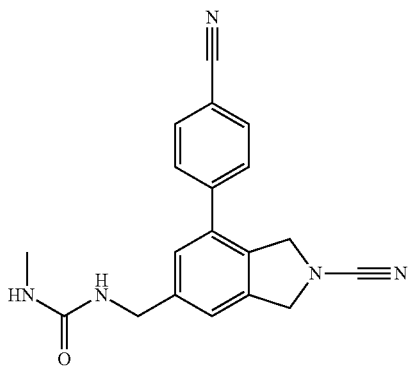 [SMILES: CNC(=O)NCc1cc2c(c(-c3ccc(C#N)cc3)c1)CN(C#N)C2]

Step a. To a stirred solution of Intermediate 12 (0.900 g, 2.58 mmol) in THF (10 ml) were added TEA (0.43 ml, 3.09 mmol) and CDI (0.627 g, 3.87 mmol) at 0° C. The reaction mixture was stirred at 0° C. for 30 min. Methylamine (2 M in THF) (3.86 ml, 7.72 mmol) was added to the reaction mixture at 0° C. The reaction mixture was stirred at rt for 15 h. The resulting mixture was poured into water (100 ml) and extracted with EtOAc (2×100 ml). The combined organic phase was dried over $Na_2SO_4$, filtered and concentrated under reduced pressure. The residue was purified by flash column chromatography (21% EtOAc in hexane) yielding tert-butyl 4-(4-cyanophenyl)-6-((3-methylureido)-methyl)isoindoline-2-carboxylate (0.270 g, 4.70 mmol). LCMS: Method A, 1.908 min, MS: ES+ 407.60; $^1$H NMR (400 MHz, DMSO-d6) δ ppm 7.97-7.94 (m, 2H), 7.69 (t, J=7.6 Hz, 2H), 7.28-7.22 (m, 2H), 6.49 (t, J=5.6 Hz, 1H), 5.85-5.81 (m, 2H), 4.62 (s, 4H), 4.26 (d, J=6.0 Hz, 2H), 2.56 (d, J=4.8 Hz, 3H), 1.44 (d, J=12.4 Hz, 9H).

Steps b and c were carried out in a similar manner to steps d and e of Example 1. LCMS: Method A, 1.567 min, MS: ES+ 332.48; $^1$H NMR (400 MHz, DMSO-d6) δ ppm 7.92 (d, J=8.0 Hz, 2H), 7.66 (d, J=8.0 Hz, 2H), 7.27 (s, 1H), 7.24 (s, 1H), 6.45 (t, J=5.6 Hz, 1H), 5.82 (d, J=4.4 Hz, 1H), 4.84 (s, 2H), 4.80 (s, 2H), 4.23 (d, J=6.0 Hz, 2H), 2.52 (d, J=4.8 Hz, 3H).

Example 228 1-((2-cyano-7-(2,4-dicyanophenyl)isoindolin-5-yl)methyl)-3-methylurea

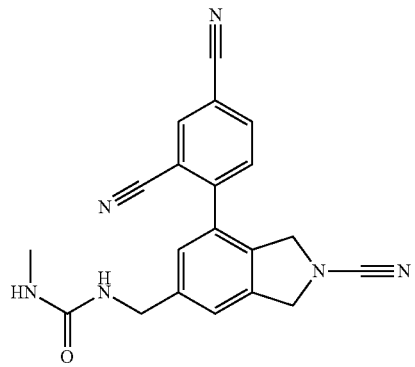 [SMILES: CNC(=O)NCc1cc2c(c(-c3ccc(C#N)cc3C#N)c1)CN(C#N)C2]

Step a. To a stirred solution of Intermediate 11 (2.500 g, 7.668 mmol) in MeOH (10 ml) was added $NH_2OH.HCl$ (5.99 g, 92.0 mmol) at rt. The reaction mixture was stirred at rt for 8 h. The reaction mixture was evaporated under reduced pressure, poured into water (100 ml) and extracted with EtOAc (2×100 ml). The combined organic phase was dried over $Na_2SO_4$, filtered and concentrated under reduced pressure. Then obtained residue was dissolved in AcOH (35 ml) at rt. Zinc dust (0.460 g, 7.19 mmol) was added to the reaction mixture at rt. The reaction mixture was stirred at rt for 24 h. The resulting reaction mixture was diluted with saturated $NaHCO_3$ solution (150 ml) and extracted with EtOAc (3×200 ml). The combined organic phase was dried over $Na_2SO_4$, filtered and concentrated under reduced pressure yielding tert-butyl 6-(aminomethyl)-4-bromoisoindoline-2-carboxylate (2.500 g). This material was directly used for next step without any further purification. LCMS: Method A, 1.527 min, MS: ES+ 327.43, 329.43

Step b. To a stirred solution of tert-butyl 6-(aminomethyl)-4-bromoisoindoline-2-carboxylate (2.500 g, 7.69 mmol) in THF (25 ml) was added TEA (1.28 ml, 9.23 mmol) and CDI (1.870 g, 11.538 mmol) at 0° C. The reaction mixture was stirred at 0° C. for 30 min. Methylamine (2M in THF) (11.5 ml, 23 mmol) was added at 0° C. The reaction mixture was stirred at rt for 15 h. The reaction mixture was poured into water (100 ml) and extracted with EtOAc (2×100 ml). The combined organic phase was dried over $Na_2SO_4$, filtered and concentrated under reduced pressure. The obtained residue was purified by flash column chromatography (21% EtOAc in hexane) yielding tert-butyl 4-bromo-6-((3-methylureido)methyl)isoindoline-2-carboxylate (1.80 g 4.70 mmol). LCMS: Method A, 1.923 min, MS: ES+ 328.33, 330.33 [M−56]; $^1$H NMR (400 MHz, DMSO-d6) δ ppm 7.35 (s, 1H), 7.19 (d, J=8.0 Hz, 1H), 6.46 (t, J=6.0 Hz, 1H), 5.86-5.85 (m, 1H), 4.66 (d, J=8.8 Hz, 2H), 4.66 (d, J=8.8 Hz, 2H), 4.49 (d, J=8.8 Hz, 2H), 4.19 (d, J=10.4 Hz, 2H), 1.46 (s, 9H).

Steps c-f were carried out in a similar manner to steps a-d of Example 226. LCMS: Method D, 2.790 min, MS: ES+ 357.10; ¹H NMR (400 MHz, DMSO-d6) δ ppm 8.64 (d, J=1.2 Hz, 1H), 8.27-8.24 (m, 1H), 7.82 (d, J=8.4 Hz, 1H), 7.35 (s, 1H), 7.28 (s, 1H), 6.50 (t, J=6.0 Hz 1H), 5.87 (d, J=4.4 Hz, 1H), 4.87 (s, 2H), 4.69 (s, 2H), 4.27 (d, J=6 Hz, 2H), 2.55 (d, J=4.8 Hz, 3H).

Example 229 1-((2-cyano-7-(2-cyanophenyl)isoindolin-5-yl)methyl)-3-methylurea

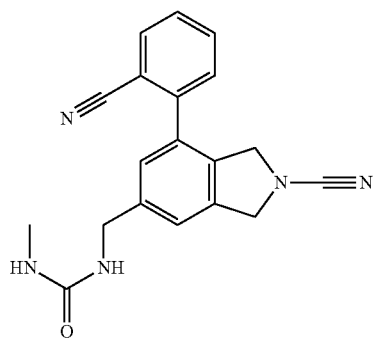 [SMILES: CNC(=O)NCc1cc2c(c(-c3ccccc3C#N)c1)CN(C#N)C2]

The title compound was synthesised using a procedure similar to that described for Example 228, using 2-bromobenzonitrile (CAS Number 2042-37-7). LCMS: Method V, 25.215 min, MS: ES+ 332.02; ¹H NMR (400 MHz, DMSO-d6) δ ppm 7.98 (d, J=7.6 Hz, 1H), 7.79 (t, J=7.6 Hz, 1H), 7.64-7.58 (m, 2H), 7.30 (s, 1H), 7.23 (s, 1H), 6.48 (t, J=6.0 Hz, 1H), 5.84-5.83 (m, 1H), 4.87 (s, 2H), 4.67 (s, 2H), 4.28 (d, J=6.0 Hz, 2H), 2.55 (d, J=4.4 Hz, 3H).

Example 230 6-(((1H-pyrazol-5-yl)amino)methyl)-4-(4-cyanophenyl)isoindoline-2-carbonitrile

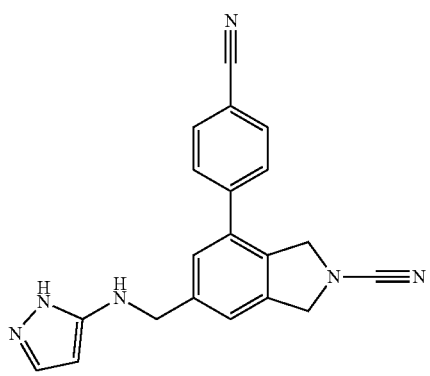 [SMILES: N#Cc1ccc(-c2cc(CNc3ccn[nH]3)cc3c2CN(C#N)C3)cc1]

Step a. To a mixture of tert-butyl 6-(bromomethyl)-4-(4-cyanophenyl)isoindoline-2-carboxylate (Prepared as in step d of Example 216, 0.255 g, 0.833 mmol) and 1H-pyrazol-5-amine (0.345 g, 0.833 mmol) in IPA (5 ml) was added K₂CO₃ (0.459 g, 3.333 mmol) at rt. The reaction mixture was heated at 100° C. for 16 h. The reaction mixture was concentrated under reduced pressure. The obtained crude material was poured into water (50 ml) and extracted with EtOAc (3×50 ml). The combined organic phase was dried over Na₂SO₄, filtered and concentrated under reduced pressure. The resulting residue was purified by flash column chromatography (4% MeOH in DCM) yielding tert-butyl 6-(((1H-pyrazol-5-yl)amino)methyl)-4-(4-cyanophenyl)isoindoline-2-carboxylate (0.100 g, 0.240 mmol). LCMS: Method A, 1.913 min, MS: ES+ 416.57.

Steps b and c were carried out in a similar manner to steps d and e of Example 1. LCMS: Method D, 3.408 min, MS: ES+ 341.15. ¹H NMR (400 MHz, DMSO-d6) δ ppm 11.53 (s, 1H), 7.94 (d, J=8.0 Hz, 2H), 7.69 (d, J=8.4 Hz, 2H), 7.42 (s, 1H), 7.37 (s, 1H), 7.31 (s, 1H), 5.80 (s, 1H), 5.44 (s, 1H), 4.86 (s, 2H), 4.73 (s, 2H), 4.29 (d, J=6.0 Hz, 2H).

Example 231 2-(2,6-dicyanoisoindolin-4-yl)benzamide

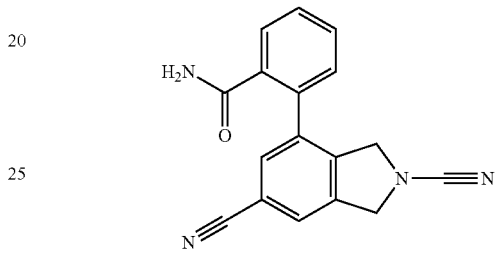

Step a. To a solution of Intermediate 13 (4.000 g, 11.33 mmol) in THF:water:MeOH (1:1:0.1, 16.5 ml) was added LiOH.H₂O (1.40 g, 34.0 mmol) at rt. The reaction mixture was stirred at rt for 16 hr. The resulting reaction mixture was diluted by water (35 ml) and acidified by 1N HCl (40 ml). The resulting precipitates were collected by filtration. The solid material was washed with hexane (2×15 ml) and dried under high vacuum yielding 7-bromo-2-(tert-butoxycarbonyl)isoindoline-5-carboxylic acid (3.500 g, 10.26 mmol). LCMS: Method A, 2.063 min, MS: ES− 340.53, 342.50; ¹H NMR (400 MHz, DMSO-d6) δ ppm 13.42 (br s, 1H), 7.96 (s, 1H), 7.89 (d, J=8.4 Hz, 1H), 4.73 (d, J=8.8 Hz, 2H), 4.57 (d, J=9.2 Hz, 2H), 1.47 (d, 9H).

Step b. To a solution of 7-bromo-2-(tert-butoxycarbonyl)isoindoline-5-carboxylic acid (1.500 g, 4.397 mmol) in THF (15 ml) were added EDC.HCl (1.680 g, 8.795 mmol), HOBT (0.810 g, 5.28 mmol) and DIPEA (2.25 ml, 13.19 mmol) at rt. The reaction mixture was stirred for 30 min before addition of NH₄Br (2.150 g, 21.99 mmol). The reaction mixture was stirred at rt for 1 h. The resulting mixture was poured into water (70 ml) and extracted with EtOAc (3×25 ml). The combined organic phase was washed with saturated NaHCO₃ solution (2×50 ml), dried over Na₂SO₄, filtered and concentrated under reduced pressure. The residue was purified by flash chromatography (3.4% MeOH in DCM) yielding tert-butyl 4-bromo-6-carbamoylisoindoline-2-carboxylate (1.100 g, 3.235 mmol). LCMS: Method A, 1.811 min, MS: ES+ 341.40, 343.40; ¹H NMR (400 MHz, DMSO-d6) δ ppm 8.08 (s, 1H), 7.99 (s, 1H), 7.82 (d, J=14.8 Hz, 1H), 7.52 (s, 1H), 4.72 (d, J=6.4 Hz, 2H), 4.56 (d, J=10.4 Hz, 2H), 1.47 (s, 9H).

Step c. To a mixture of tert-butyl 4-bromo-6-carbamoylisoindoline-2-carboxylate (0.500 g, 1.470 mmol) in DMF (5 ml) was added POCl₃ (0.134 ml, 1.47 mmol) at 0° C. The reaction mixture was stirred at 0° C. for 30 min. The resulting mixture was poured into ice cooled water (50 ml) and extracted with diethyl ether (2×40 ml). The combined organic phase was dried over Na₂SO₄, filtered and concentrated under reduced pressure and dried under high vacuum yielding tert-butyl 4-bromo-6-cyanoisoindoline-2-carboxylate (0.500 g). LCMS: Method A, 2.307 min, MS: ES+ 267.24, 269.24 [M−56]; $^1$H NMR (400 MHz, DMSO-d6) δ ppm 8.11 (s, 1H), 7.87 (d, J=6.4 Hz, 1H), 4.72 (d, J=9.6 Hz, 2H), 4.59 (d, J=9.2 Hz, 2H), 1.46 (s, 9H).

Step d. To a stirred solution of tert-butyl 4-bromo-6-cyanoisoindoline-2-carboxylate (0.500 g, 1.552 mmol) in 1,4-dioxane:water (9:1, 5 ml) were added K$_2$CO$_3$ (0.430 g, 3.105 mmol) and 2-aminocarbonylphenylboronic acid (CAS Number 380430-54-6; 1.020 g, 6.211 mmol) at rt. The reaction mixture was degassed for 20 min before addition of PdCl$_2$(dppf) (0.110 g, 0.155 mmol). The resulting reaction mixture was heated at 90° C. for 15 h. The reaction mixture was cooled to rt, poured into water (50 ml) and extracted with EtOAc (2×50 ml). The combined organic phase washed with brine (40 ml), dried over Na$_2$SO$_4$, filtered and concentrated under reduced pressure. The obtained residue was purified by flash column chromatography (35-40% EtOAc in hexane) yielding tert-butyl 4-(2-carbamoylphenyl)-6-cyanoisoindoline-2-carboxylate (0.150 g, 0.413 mmol). LCMS: Method A, 1.875 min, MS: ES+ 364.70; $^1$H NMR (400 MHz, DMSO-d6) δ ppm 7.82 (d, J=6.0 Hz, 1H), 7.71 (d, J=5.2 Hz, 1H), 7.58-7.49 (m, 4H), 7.39-7.30 (m, 2H), 4.69 (d, J=8.8 Hz, 2H), 4.48 (d, J=16.0 Hz, 2H), 1.42 (d, J=16.4 Hz, 9H).

Steps e and f were carried out in a similar manner to steps d and e of Example 1. LCMS: Method D, 3.207 min, MS: ES− 287.0; $^1$H NMR (400 MHz, DMSO-d6) δ ppm 7.82 (s, 1H), 7.70 (s, 1H), 7.58-7.48 (m, 4H), 7.37-7.35 (m, 2H), 4.89 (s, 2H), 4.69 (s, 2H).

Example 232 2-cyano-7-(4-cyanophenyl)-N,N-dimethylisoindoline-5-carboxamide

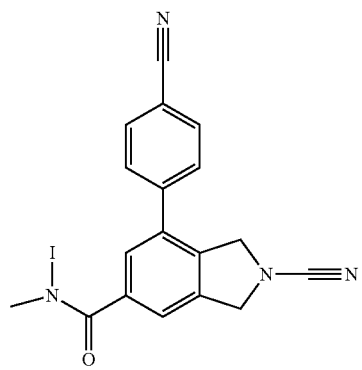 [SMILES: CN(I)C(=O)c1cc2c(c(-c3ccc(C#N)cc3)c1)CN(C#N)C2]

Step a. To a stirred solution of Intermediate 13 (0.900 g, 2.535 mmol) in DMF:water (9:1, 10 ml) were added NaHCO$_3$ (0.638 g, 7.60 mmol) and 4-cyanophenylboronic acid (0.447 g, 3.04 mmol) at rt. The reaction mixture was degassed for 20 min before addition of PdCl$_2$(dppf) (0.185 g, 0.253 mmol). The resulting reaction mixture was heated at 100° C. for 15 h. The reaction mixture was cooled to rt, poured into water (100 ml) and extracted with EtOAc (2×100 ml). The combined organic phase dried over Na$_2$SO$_4$, filtered and concentrated under reduced pressure. The obtained residue was purified by flash column chromatography (10% EtOAc in hexane) yielding 2-(tert-butyl) 5-methyl 7-(4-cyanophenyl)isoindoline-2,5-dicarboxylate (0.840 g, 2.222 mmol). LCMS: Method A, 2.511 min, MS: ES+ 364.38 [M−15].

Step b. To a solution of 2-(tert-butyl) 5-methyl 7-(4-cyanophenyl)isoindoline-2,5-dicarboxylate (0.800 g, 2.115 mmol) in THF:water (1:1, 10 ml) was added LiOH.H$_2$O (0.266 g, 6.345 mmol) at rt. The reaction mixture was stirred at rt for 6 h. The resulting reaction mixture was diluted by saturated NaHCO$_3$ solution (90 ml) and extracted with EtOAc (100 ml). The resulting aqueous layer was acidified by 1M HCl (50 ml) and extracted with EtOAc (2×100 ml). The combined organic phase was dried over Na$_2$SO$_4$, filtered and concentrated under reduced pressure yielding 2-(tert-butoxycarbonyl)-7-(4-cyanophenyl)isoindoline-5-carboxylic acid (0.400 g, 1.098 mmol). This material was use directly for next step without further purification. LCMS: Method A, 2.130 min, MS: ES− 363.38.

Step c. To a solution of 2-(tert-butoxycarbonyl)-7-(4-cyanophenyl)isoindoline-5-carboxylic acid (0.150 g, 0.411 mmol) in THF (7 ml) were added DIPEA (0.211 ml, 1.233 mmol) and HATU (0.234 g, 0.616 mmol) at rt. The reaction mixture was stirred at rt for 15 min. Dimethylamine (2M solution in THF) (0.31 ml, 0.62 mmol) was added to the reaction mixture at 0° C. The reaction mixture was stirred at rt for 15 h. The resulting mixture was poured into saturated NaHCO$_3$ (50 ml) and extracted with EtOAc (2×50 ml). The combined organic phase was collected, dried over Na$_2$SO$_4$, filtered and concentrated under reduced pressure. The resulting residue was purified by column chromatography (3% MeOH in MDC) yielding tert-butyl 4-(4-cyanophenyl)-6-(dimethylcarbamoyl)isoindoline-2-carboxylate (0.110 g, 0.281 mmol). LCMS: Method A, 2.006 min, MS: ES+ 392.51

Steps d and e were carried out in a similar manner to steps d and e of Example 1. LCMS: Method D, 3.653 min, MS: ES+ 316.96; $^1$H NMR (400 MHz, DMSO-d6) δ ppm 7.94 (d, J=8.0 Hz, 2H), 7.74 (d, J=8.4 Hz, 2H), 7.44 (d, J=4.8 Hz, 2H), 4.92 (s, 2H), 4.86 (s, 2H), 2.96 (d, J=19.2 Hz, 6H).

Compounds in Table 21 were prepared using a procedure similar to that described for Example 232

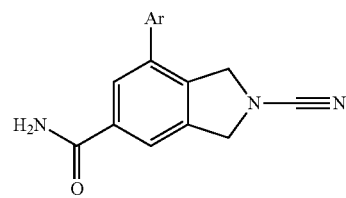

TABLE 21

| Ex | Ar— | Name | Aryl halide CAS Number | LCMS method | LCMS RT/min | MS ES+ |
|---|---|---|---|---|---|---|
| Example 233 | (2,4-dicyanophenyl) | 2-cyano-7-(2,4-dicyanophenyl)isoindoline-5-carboxamide | 22433-89-2 | D | 3.186 min, | ES+ 314.06 |
| Example 234 | (2-cyano-5-methoxyphenyl) | 2-cyano-7-(2-cyano-5-methoxyphenyl)isoindoline-5-carboxamide | 140860-51-1 | E | 3.2 | 319.48 |
| Example 235 | (2-cyano-4-fluorophenyl) | 2-cyano-7-(2-cyano-4-fluorophenyl)isoindoline-5-carboxamide | 57381-39-2 | D | 2.986 | ES− 305.05 |

Compounds in Table 22 were prepared using a procedure similar to that described for Example 232.

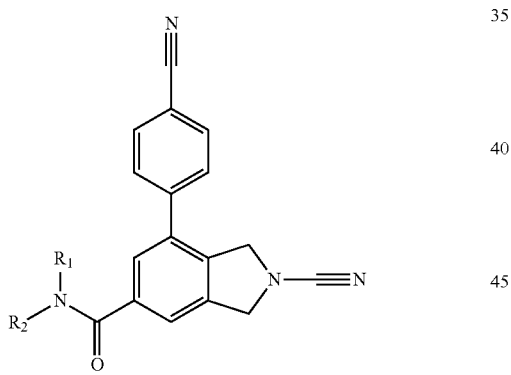

TABLE 22

| Ex | R₁R₂N— | Name | Amine CAS Number | LCMS method | LCMS RT/min | MS ES+ |
|---|---|---|---|---|---|---|
| Example 236 | 1,1-dioxidothiomorpholin-4-yl | 4-(4-cyanophenyl)-6-(1,1-dioxidothiomorpholine-4-carbonyl)isoindoline-2-carbonitrile | 39093-93-1 | E | 3.482 min | ES− 405.43 |
| Example 237 | methylamino | 2-cyano-7-(4-cyanophenyl)-N-methylisoindoline-5-carboxamide | Methyl amine (2M in THF) | E | 3.412 min | ES− 301.30 |

TABLE 22-continued

| Ex | R₁R₂N— | Name | Amine CAS Number | LCMS method | LCMS RT/min | MS ES+ |
|---|---|---|---|---|---|---|
| Example 238 | 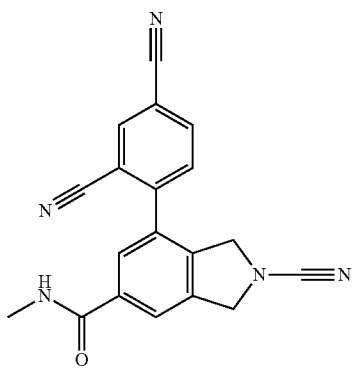 | 2-cyano-7-(4-cyanophenyl)-N-(tetrahydro-2H-pyran-4-yl)isoindoline-5-carboxamide | 38041-19-9 | C | 5.115 min | ES+ 373.10 |

Example 239 2-cyano-7-(2,4-dicyanophenyl)-N-methylisoindoline-5-carboxamide

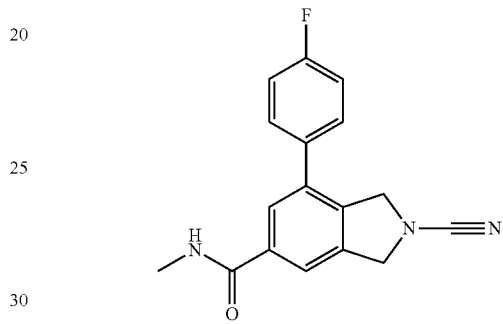

Step a. Carried out in a similar method to Example 226 step a using Intermediate 13.

Step b. To a stirred solution of 2-(tert-butyl) 5-methyl 7-(4,4,5,5-tetramethyl-1,3,2-dioxaborolan-2-yl)isoindoline-2,5-dicarboxylate (0.500 g, 1.240 mmol) in DMF:water (9:1, 15 ml) were added NaHCO₃ (0.260 g, 3.10 mmol) and 4-bromoisophthalonitrile (CAS Number 22433-89-2; 0.214 g, 1.003 mmol) at rt. The reaction mixture was degassed for 20 min before addition of PdCl₂(dppf) (0.075 g, 0.124 mmol). The resulting reaction mixture was heated at 90° C. for 4 h. The reaction mixture was cooled to rt, poured into water (50 ml) and extracted with EtOAc (3×15 ml). The combined organic phase dried over Na₂SO₄, filtered and concentrated under reduced pressure. The residue was purified by flash column chromatography (40% EtOAc in hexane) yielding 2-(tert-butyl) 5-methyl 7-(2,4-dicyanophenyl)isoindoline-2,5-dicarboxylate (0.350 g, 0.868 mmol). LCMS: Method A, 2.299 min, MS: ES+ 421.70 [M+18].

Steps c and d were carried out in a similar manner to Example 232 steps b and c using methylamine in step d Steps e and f were carried out in a similar manner to steps d and e of Example 1 LCMS: Method D, 3.447 min, MS: ES+ 328.09; ¹H NMR (400 MHz, DMSO-d6) δ ppm 8.67 (d, J=1.6 Hz, 1H), 8.59 (d, J=4.08 Hz, 1H), 8.29 (dd, J=8.0, 1.6 Hz, 1H), 7.95 (s, 1H), 7.88-7.90 (m, 2H), 4.93 (s, 2H), 4.77 (s, 2H), 2.80 (s, 3H).

Example 240 2-cyano-7-(4-fluorophenyl)-N-methyl-isoindoline-5-carboxamide

Step a. Carried out in a similar manner to Example 232 step b using methylamine (2M solution in THF).

Step b. Carried out in a similar manner to Example 73 step a using 4-fluorophenylboronic acid.

Steps c and d were carried out in a similar manner to steps d and e of Example 1. LCMS: Method D, 3.724 min, MS: ES+ 296.04; ¹H NMR (400 MHz, DMSO-d6) δ ppm 8.58 (d, J=4.4 Hz, 1H), 7.81 (s, 1H), 7.78 (s, 1H), 7.59-7.63 (m, 2H), 7.31-7.35 (m, 2H), 4.91 (s, 2H), 4.88 (s, 2H), 2.79 (d, J=4.4 Hz, 3H).

Example 241 2-cyano-7-(2-cyanophenyl)isoindoline-5-carboxamide

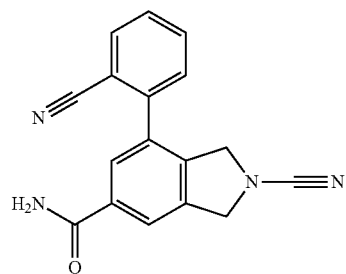 [SMILES: N#Cc1ccccc1-c1cc(C(N)=O)cc2c1CN(C#N)C2]

Step a. Carried out in a similar method to Example 226 step a using tert-butyl 4-bromo-6-carbamoylisoindoline-2-carboxylate (prepared as in step b of Example 231) yielding tert-butyl 6-carbamoyl-4-(4,4,5,5-tetramethyl-1,3,2-dioxaborolan-2-yl)isoindoline-2-carboxylate LCMS: Method A, 2.072 min, MS: ES+ 389.70.

Step b. To a stirred solution of tert-butyl 6-carbamoyl-4-(4,4,5,5-tetramethyl-1,3,2-dioxaborolan-2-yl)isoindoline-2- carboxylate (0.383 g, 0.987 mmol) in DMF:water (9:1, 5 ml) were added K₂CO₃ (0.227 g, 1.65 mmol) and 2-bromobenzonitrile (0.150 g, 0.824 mmol) at rt. The reaction mixture was degassed for 20 min before addition of PdCl₂(dppf) (0.060 g, 0.082 mmol). The resulting reaction mixture was heated at 95° C. for 6 h. The reaction mixture was cooled to rt, poured into water (80 ml) and extracted with EtOAc (3×80 ml). The combined organic phase dried over Na₂SO₄, filtered and concentrated under reduced pressure. The residue was purified by flash column chromatography (2.3% MeOH in DCM) yielding tert-butyl 6-carbamoyl-4-(2-cyanophenyl)isoindoline-2-carboxylate (0.188 g, 0.518 mmol). LCMS: Method A, 1.818 min, MS: ES+ 381.78 [M+18].

Steps c and d were carried out in a similar manner to steps d and e of Example 1 LCMS: Method D, 2.860 min, MS: ES− 287.10; ¹H NMR (400 MHz, DMSO-d6) δ ppm 8.08 (s, 1H), 8.02 (d, J=8.0 Hz, 1H), 7.95 (s, 1H), 7.90 (s, 1H), 7.80-7.84 (m, 1H), 7.64-7.68 (m, 2H), 7.51 (s, 1H), 4.93 (s, 2H), 4.76 (s, 2H).

Example 242 N-(2-cyano-7-(2-cyanophenyl)isoindolin-5-yl)methanesulfonamide

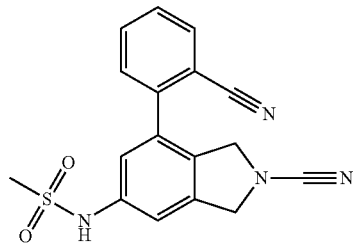 [SMILES: CS(=O)(=O)Nc1cc2c(c(-c3ccccc3C#N)c1)CN(C#N)C2]

Step a. To a solution of tert-butyl 6-amino-4-bromoisoindoline-2-carboxylate (prepared as in step a of Example 23, 0.900 g, 2.884 mmol) in DCM (9 ml) were added pyridine (9.000 ml) and mesyl chloride (0.650 g, 5.77 mmol) at 0° C. The reaction mixture was stirred at rt for 2 h. The resulting mixture was poured into saturated citric acid solution (50 ml) and extracted with EtOAc (2×50 ml). The combined organic phase was dried over Na₂SO₄, filtered and concentrated under reduced pressure. The resulting residue was purified by flash column chromatography (35% EtOAc in Hexane) yielding tert-butyl 4-bromo-6-(methylsulfonamido) isoindoline-2-carboxylate (0.800 g, 2.051 mmol). LCMS: Method A, 2.128 min, MS: ES+ 376.33, 378.33 [M−15]

Step b was carried out in a similar method to Example 226 step a yielding tert-butyl 6-(methylsulfonamido)-4-(4,4,5,5-tetramethyl-1,3,2-dioxaborolan-2-yl)isoindoline-2-carboxylate (0.800 g, 1.825 mmol). LCMS: Method A, 2.353 min, MS: ES− 437.58

Step c. To a stirred solution of tert-butyl 6-(methylsulfonamido)-4-(4,4,5,5-tetramethyl-1,3,2-dioxaborolan-2-yl) isoindoline-2-carboxylate (0.360 g, 0.821 mmol) in 1,4-dioxane:water (9:1, 10 ml) were added K₂CO₃ (0.220 g, 1.640 mmol) and 2-bromobenzonitrile (0.150 g, 8.82 mmol) at rt. The reaction mixture was degassed for 20 min before addition of PdCl₂(dppf) (0.060 g, 0.082 mmol). The resulting reaction mixture was heated at 80° C. for 2 h. The reaction mixture was cooled to rt, poured into water (30 ml) and extracted with EtOAc (2×30 ml). The combined organic phase dried over Na₂SO₄, filtered and concentrated under reduced pressure. The residue was purified by flash column chromatography (22% EtOAc in hexane) yielding tert-butyl 4-(2-cyanophenyl)-6-(methylsulfonamido)isoindoline-2-carboxylate (0.150 g 0.363 mmol). LCMS: Method A, 2.037 min, MS: ES+ 431.48 [M+18].

Steps d and e were carried out in a similar manner to steps d and e of Example 1. LCMS: Method E, 3.542 min, MS: ES+ 339.38; ¹H NMR (400 MHz, DMSO-d6) δ ppm 10.10 (s, 1H), 8.00 (d, J=7.2 Hz, 1H), 7.78-7.81 (m, 1H), 7.62-7.66 (m, 2H), 7.25 (s, 1H), 7.20 (s, 1H), 4.87 (s, 2H), 4.66 (s, 2H), 3.06 (s, 3H).

Example 243 N-(2-cyano-7-(2,4-dicyanophenyl)isoindolin-5-yl)methanesulfonamide

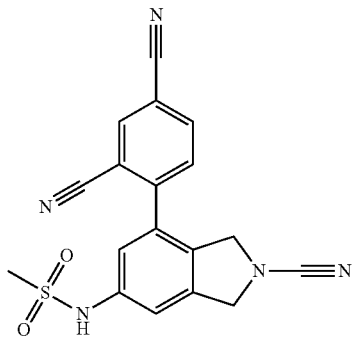 [SMILES: CS(=O)(=O)Nc1cc2c(c(-c3ccc(C#N)cc3C#N)c1)CN(C#N)C2]

The title compound was synthesised using a procedure similar to that described for Example 242 using 4-bromoisophthalonitrile (CAS Number 22433-89-2) in step c. LCMS: Method E, 3.509 min, MS: ES+ 364.38; ¹H NMR (400 MHz, DMSO-d6) δ ppm 10.16 (s, 1H), 8.65 (s, 1H), 8.27 (dd, J=8.0, 1.6 Hz, 1H), 7.89 (d, J=8.4 Hz, 1H), 7.29 (s, 1H), 7.24 (s, 1H), 4.87 (s, 2H), 4.69 (s, 2H), 3.07 (s, 3H).

Example 244 N-(2-cyano-7-(4-cyanophenyl)isoindolin-5-yl)methanesulfonamide

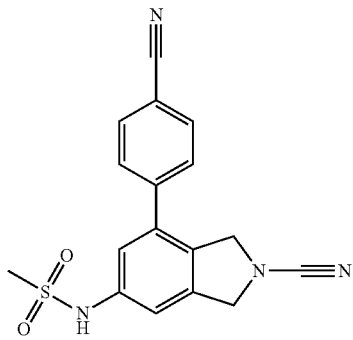 [SMILES: CS(=O)(=O)Nc1cc2c(c(-c3ccc(C#N)cc3)c1)CN(C#N)C2]

Step a was carried out using a procedure similar to that described for Example 242.

Step b was carried out using a method similar to step b of Example 216.

Steps c and d were carried out using a method similar to steps d and e of Example 242. LCMS: Method A, 1.729 min, MS: ES+ 339.53; 1H NMR (400 MHz, DMSO-d6) δ ppm: 10.01 (s, 1H), 7.96 (d, J=8.4 Hz, 2H), 7.69 (d, J=8.4 Hz, 2H), 7.24 (d, J=2.4 Hz, 1H), 7.20 (d, J=1.6 Hz, 1H), 4.83 (s, 4H), 3.05 (s, 3H).

Example 245 N-(2-cyano-7-(2-cyano-5-methoxyphenyl)isoindolin-5-yl)methanesulfonamide

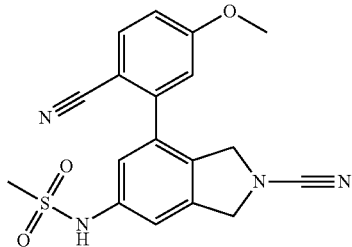 [SMILES: COc1ccc(C#N)c(-c2cc(NS(C)(=O)=O)cc3c2CN(C#N)C3)c1]

Step a was carried out in a similar method to Example 226 step a using tert-butyl 4-bromo-6-(methylsulfonamido)isoindoline-2-carboxylate prepared as in step a of Example 242 yielding tert-butyl 6-(methylsulfonamido)-4-(4,4,5,5-tetramethyl-1,3,2-dioxaborolan-2-yl)isoindoline-2-carboxylate. This material was directly used for next step without any further purification. LCMS: Method A, 2.344 min, MS: ES+ 383.70 [M−56].

Step b. To a stirred solution of tert-butyl 6-(methylsulfonamido)-4-(4,4,5,5-tetramethyl-1,3,2-dioxaborolan-2-yl)isoindoline-2-carboxylate (1.030 g, 2.37 mmol) in 1,4-dioxane:water (9:1, 5 ml) were added $K_2CO_3$ (0.300 g, 2.37 mmol) and 2-bromo-4-methoxybenzonitrile (CAS Number 140860-51-1; 0.250 g, 1.185 mmol) at rt. The reaction mixture was degassed for 20 min before addition of $PdCl_2$(dppf) (0.087 g, 0.118 mmol). The resulting reaction mixture was heated at 90° C. for 2 h. The reaction mixture was cooled to rt, poured into water (50 ml) and extracted with EtOAc (2×50 ml). The combined organic phase washed with brine (40 ml), dried over $Na_2SO_4$, filtered and concentrated under reduced pressure. The residue was purified by flash column chromatography (8% EtOAc in hexane) yielding tert-butyl 4-(2-cyano-5-methoxyphenyl)-6-(methylsulfonamido)isoindoline-2-carboxylate (0.150 g, 0.338 mmol). LCMS: Method A, 2.038 min, MS: ES+ 444.6; $^1$H NMR (400 MHz, DMSO-d6) δ ppm 9.99 (s, 1H), 7.89 (t, J=6.0 Hz, 1H), 7.23-7.10 (m, 4H), 4.64 (d, J=11.2, 2H), 4.42 (d, J=10.4, 2H), 3.85 (s, 3H), 3.02 (s, 3H), 1.40 (d, J=15.6 Hz, 9H).

Steps c and d were carried out in a similar manner to steps d and e of Example 1. LCMS: Method D, 3.819 min, MS: ES+ 369.0; $^1$H NMR (400 MHz, DMSO-d6) δ ppm 10.06 (s, 1H), 7.88 (d, J=9.2 Hz, 1H), 7.22 (s, 1H), 7.14 (d, J=7.6, 3H), 4.84 (s, 2H), 4.66 (s, 2H), 3.86 (s, 3H), 3.03 (s, 3H).

Example 246 4-(4-fluorophenyl)-2-(((tetrahydro-2H-pyran-4-yl)methyl)amino)-5,7-dihydro-6H-pyrrolo[3,4-b]pyridine-6-carbonitrile

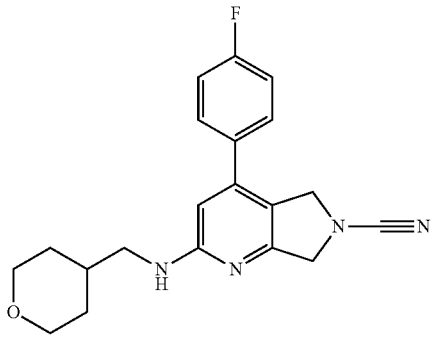 [SMILES: N#CN1Cc2nc(NCC3CCOCC3)cc(-c3ccc(F)cc3)c2C1]

Step a.
To a stirred solution of 6,7-dihydro-5H-pyrrolo[3,4-b]pyridine 2 HCl (CAS Number 147740-02-1; 10.0 g, 51.8 mmol) in DCM (120 ml) was added DIPEA (26.0 ml, 155.4 mmol) at 0° C. The resulting reaction mixture was stirred at 0° C. for 5 min. Mesyl chloride (4.89 ml, 62.2 mmol) was added drop wise to the reaction mixture at 0° C. The resulting reaction mixture was stirred at rt for 6 h. The reaction mixture was cooled to rt, poured into saturated $NaHCO_3$ solution (150 ml) and extracted with EtOAc (3×50 ml). The combined organic phase was washed with brine (2×100 ml) and dried over $Na_2SO_4$, filtered and concentrated under reduced pressure yielding 6-(methylsulfonyl)-6,7-dihydro-5H-pyrrolo[3,4-b]pyridine (8.000 g, 40.404 mmol). This material was directly used for next step without any further purification. LCMS: Method A, 1.332 min, MS: ES+ 199.19.

Step b.
To a stirred solution of 6-(methylsulfonyl)-6,7-dihydro-5H-pyrrolo[3,4-b]pyridine (8.000 g, 40.404 mmol) in DCM (200 ml) was portion wise added m-CPBA (10.00 g, 60.61 mmol) at rt. The reaction mixture was stirred at rt for 2 h. The resulting mixture was concentrated under reduced pressure. The obtained crude was triturated with methyl tert-butyl ether (3×100 ml) and diethyl ether (2×50 ml). The resulting solid was dried under high vacuum yielding 6-(methylsulfonyl)-6,7-dihydro-5H-pyrrolo[3,4-b]pyridine 1-oxide (8.500 g, 39.719 mmol). MS: ES+ 215.02; $^1$H NMR (400 MHz, DMSO-d6) δ ppm 8.21 (d, J=6.4 Hz, 1H), 7.55 (t, J=8.0 Hz, 1H), 7.33 (d, J=7.6 Hz, 1H), 4.75 (d, J=1.2 Hz, 2H), 4.67 (d, J=1.2 Hz, 2H), 3.09 (s, 3H).

Step c.
To a stirred solution of 6-(methylsulfonyl)-6,7-dihydro-5H-pyrrolo[3,4-b]pyridine 1-oxide (0.500 g, 2.336 mmol) in DMF (10 ml) was added $(COCl)_2$ (2 vol, 1.000 ml) at rt. The resulting reaction mixture was stirred at rt for 15 h. The resulting reaction mixture was combined with 16 other batches on the same scale prepared by an identical method. The resulting residue was poured into saturated $NaHCO_3$ solution (400 ml) and extracted with EtOAc (5×70 ml). The combined organic phase was washed with brine (2×150 ml), dried over $Na_2SO_4$, filtered and concentrated under reduced pressure yielding a mixture of 4-chloro-6-(methylsulfonyl)-6,7-dihydro-5H-pyrrolo[3,4-b]pyridine and 2-chloro-6-(methylsulfonyl)-6,7-dihydro-5H-pyrrolo[3,4-b]pyridine (7.500 g, 32.327 mmol). The crude material was used in next step without further purification. LCMS: Method A, 1.529, 1.563 min, MS: ES+ 233.28.

Step d.

To a solution of 4-chloro-6-(methylsulfonyl)-6,7-dihydro-5H-pyrrolo[3,4-b]pyridine and 2-chloro-6-(methylsulfonyl)-6,7-dihydro-5H-pyrrolo[3,4-b]pyridine (7.000 g, 30.172 mmol) in 1,4-dioxane:water (9:1, 70 ml) were added $K_2CO_3$ (12.50 g, 90.52 mmol) and 4-fluorophenylboronic acid (5.070 g, 36.21 mmol) at rt. The reaction mixture was degassed for 30 min before addition of $PdCl_2(dppf)$ (2.200 g, 3.017 mmol). The resulting reaction mixture was heated at 100° C. for 4 h. The reaction mixture was cooled to rt and poured into saturated $NaHCO_3$ solution (200 ml). The resulting mixture was extracted with EtOAc (3×40 ml). The combined organic phase was washed with brine (2×100 ml) and dried over $Na_2SO_4$, filtered and concentrated under reduced pressure. The obtained residue was purified by column chromatography (40-55% EtOAc in n-hexane) yielding 4-(4-fluorophenyl)-6-(methylsulfonyl)-6,7-dihydro-5H-pyrrolo[3,4-b]pyridine (3.00 g, 10.3 mmol). LCMS: Method A, 2.139 min, MS: ES+ 293.10; $^1$H NMR (400 MHz, DMSO-d6) δ ppm 8.57 (d, J=4.8 Hz, 1H), 7.73-7.70 (m, 2H), 7.45-7.36 (m, 3H), 4.83 (s, 2H), 4.69 (s, 2H), 3.08 (s, 3H).

Step e.

To a solution of 4-(4-fluorophenyl)-6-(methylsulfonyl)-6,7-dihydro-5H-pyrrolo[3,4-b]pyridine (0.500 g, 1.712 mmol) in MeCN (20 ml) was added Urea-hydrogen peroxide (0.643 g, 6.848 mmol) at 0° C. The reaction mixture was stirred at rt for 5 min. TFAA (0.5 ml, 1 vol) was added to the reaction mixture at 0° C. The reaction mixture was stirred at rt for 2 h. The resulting reaction mixture was combined with 5 other batches prepared on the same scale by an identical method. The reaction mixture was cooled to rt, poured into water (200 ml) and extracted with EtOAc (3×50 ml). The combined organic phase was washed with brine (2×50 ml) and dried over $Na_2SO_4$, filtered and concentrated under reduced pressure. The residue was purified by flash column chromatography (3-5% MeOH in DCM) yielding 4-(4-fluorophenyl)-6-(methylsulfonyl)-6,7-dihydro-5H-pyrrolo[3,4-b]pyridine-1-oxide (1.600 g, 5.194 mmol). LCMS: Method A, 1.498 min, MS: ES+ 309.44.

Step f.

To a stirred solution of 4-(4-fluorophenyl)-6-(methylsulfonyl)-6,7-dihydro-5H-pyrrolo[3,4-b]pyridine 1-oxide (0.400 g, 1.298 mmol) in DMF (8 ml) was added $(COCl)_2$ (0.80 ml, 2 vol) at rt. The resulting reaction mixture was stirred at rt for 24 h. The resulting reaction mixture was added $(COCl)_2$ (0.40 ml, 1 vol) at rt. The resulting reaction mixture was again stirred at rt for 24 h. The resulting reaction mixture was combined with 3 other batches prepared on the same scale by an identical method. The resulting mixture was poured into saturated $NaHCO_3$ solution (200 ml) and extracted with EtOAc (3×50 ml). The combined organic phase was washed with brine (2×30 ml) and dried over $Na_2SO_4$, filtered and concentrated under reduced pressure. The resulting residue was purified by flash column chromatography (30-40% EtOAc in n-hexane) yielding 2-chloro-4-(4-fluorophenyl)-6-(methylsulfonyl)-6,7-dihydro-5H-pyrrolo[3,4-b]pyridine (0.600 g, 1.840 mmol). LCMS: Method A, 2.018 min, MS: ES+ 327.28.

Step g.

To a mixture of 2-chloro-4-(4-fluorophenyl)-6-(methylsulfonyl)-6,7-dihydro-5H-pyrrolo[3,4-b]pyridine (0.200 g, 0.613 mmol) in 1,4-dioxane (15 ml) were added $Cs_2CO_3$ (0.598 g, 1.840 mmol) and 4-aminomethyltetrahydropyran (CAS Number 130290-79-8; 0.084 g, 0.736 mmol) at rt. The reaction mixture was degassed for 30 min before addition of $Pd_2(dba)_3$ (0.112 g, 0.122 mmol) and Xanthphos (0.070 g, 0.122 mmol). The resulting reaction mixture was heated at 100° C. for 3 h. The reaction mixture was cooled to rt, poured into saturated $NaHCO_3$ solution (30 ml) and extracted with EtOAc (3×15 ml). The combined organic phase was washed with brine (2×20 ml), dried over $Na_2SO_4$, filtered and concentrated under reduced pressure. The obtained residue was purified by column chromatography (40-50% EtOAc in n-hexane) yielding 4-(4-fluorophenyl)-6-(methylsulfonyl)-N-((tetrahydro-2H-pyran-4-yl)methyl)-6,7-dihydro-5H-pyrrolo[3,4-b]pyridin-2-amine (0.140 g 0.345 mmol). LCMS: Method A, 1.767 min, MS: ES+ 406.53.

Step h.

To a mixture of 4-(4-fluorophenyl)-6-(methylsulfonyl)-N-((tetrahydro-2H-pyran-4-yl)methyl)-6,7-dihydro-5H-pyrrolo[3,4-b]pyridin-2-amine (0.140 g, 0.345 mmol) in AcOH (10 ml) was added 33% HBr in AcOH (1.4 ml) at rt. The resulting reaction mixture was heated at 100° C. for 2 h. The reaction mixture was cooled to rt and concentrated under reduced pressure. The obtained crude material was azeotropically distilled with DCM (3×20 ml) followed by MeOH (2×10 ml). The resulting residue was purified by crystallization in MeOH:diethyl ether. The obtained solid was triturated with diethyl ether (3×20 ml) and dried under high vacuum yielding 4-(4-fluorophenyl)-N-((tetrahydro-2H-pyran-4-yl)methyl)-6,7-dihydro-5H-pyrrolo[3,4-b]pyridin-2-amine HBr salt (0.080 g, 0.196 mmol). LCMS: Method A, 1.428 min, MS: ES+ 328.48. This material was used directly next step without further purification.

Step d was carried out in a similar manner to step e of Example 1. LCMS: Method D, 4.253 min, MS: ES+ 353.04; $^1$H NMR (400 MHz, DMSO-d6) δ ppm 7.54-7.57 (m, 2H), 7.29-7.34 (m, 2H), 6.86 (t, J=5.2 Hz, 1H), 6.46 (s, 1H), 4.76 (s, 2H), 4.59 (s, 2H), 3.84-3.86 (m, 2H), 3.23-3.29 (m, 2H), 3.14-3.18 (m, 2H), 1.77-1.80 (m, 1H), 1.61-1.64 (m, 2H), 1.15-1.24 (m, 2H).

Compounds in Table 23 were prepared in a manner similar to Example 246.

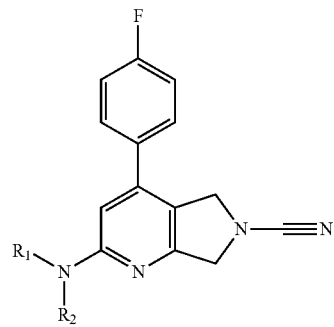

TABLE 23

| Ex | Name | R₁R₂NH— | Amine CAS Number | LCMS method | LCMS RT/min | MS ES+ |
|---|---|---|---|---|---|---|
| Example 247 | 4-(4-fluorophenyl)-2-((pyridin-2-ylmethyl)amino)-5,7-dihydro-6H-pyrrolo[3,4-b]pyridine-6-carbonitrile | 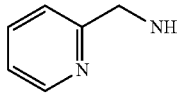 | 3731-51-9 | D | 4.936 | 345.99 |
| Example 248 | 4-(4-fluorophenyl)-2-(((1-methyl-1H-pyrazol-5-yl)methyl)amino)-5,7-dihydro-6H-pyrrolo[3,4-b]pyridine-6-carbonitrile | 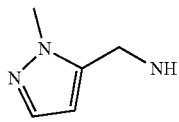 | 863548-52-1 | D | 3.894 | 349.11 |

Example 249 N-(6-cyano-4-(4-fluorophenyl)-6,7-dihydro-5H-pyrrolo[3,4-b]pyridin-2-yl)acetamide

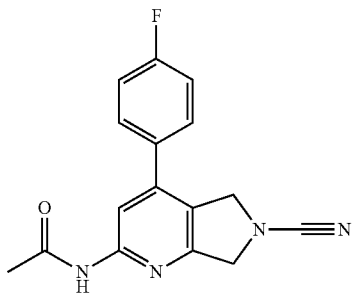 [SMILES: CC(=O)Nc1cc(-c2ccc(F)cc2)c2c(n1)CN(C#N)C2]

Step a was carried out in a similar manner to step h of Example 246 yielding 2-bromo-4-(4-fluorophenyl)-6,7-dihydro-5H-pyrrolo[3,4-b]pyridine HBr salt (0.160 g, 0.430 mmol). LCMS: Method A, 1.454 min, MS: ES+ 293.33, 295.33.

Step b. To a stirred solution of 2-bromo-4-(4-fluorophenyl)-6,7-dihydro-5H-pyrrolo[3,4-b]pyridine HBr salt (0.160 g 0.430 mmol) in THF (20 ml) was added K$_2$CO$_3$ (0.178 g, 1.290 mmol) at rt. Boc-anhydride (0.187 g, 0.860 mmol) was added in to the reaction mixture at 0° C. The reaction mixture was stirred at rt for 2 h. The reaction was poured into saturated NaHCO$_3$ solution (30 ml) and extracted with EtOAc (3×20 ml). The combined organic phase was washed with brine (2×15 ml), dried over Na$_2$SO$_4$, filtered and concentrated under reduced pressure. The residue was purified by column chromatography (2-3% MeOH in DCM) yielding tert-butyl 2-bromo-4-(4-fluorophenyl)-5,7-dihydro-6H-pyrrolo[3,4-b]pyridine-6-carboxylate (0.130 g, 0.331 mmol). LCMS: Method A, 2.586 min, MS: ES+ 393.28, 395.28.

Step c. To a mixture of tert-butyl 2-bromo-4-(4-fluorophenyl)-5,7-dihydro-6H-pyrrolo[3,4-b]pyridine-6-carboxylate (0.130 g, 0.331 mmol) in 1,4-dioxane (15 ml) were added Cs$_2$CO$_3$ (0.323 g, 0.994 mmol) and CH$_3$CONH$_2$ (0.039 g, 0.663 mmol) at rt. The reaction mixture was degassed for 30 min before addition of Pd$_2$(dba)$_3$ (0.060 g, 0.066 mmol) and Xantphos (0.038 g, 0.066 mmol). The resulting reaction mixture was heated at 100° C. for 3 h. The reaction was cooled to rt and poured into saturated NaHCO$_3$ solution (25 ml). The resulting mixture was extracted with EtOAc (3×10 ml). The combined organic phase was washed with brine (2×10 ml), dried over Na$_2$SO$_4$, filtered and concentrated under reduced pressure. The residue was purified by column chromatography (30-40% EtOAc in n-hexane) yielding tert-butyl 2-acetamido-4-(4-fluorophenyl)-5,7-dihydro-6H-pyrrolo[3,4-b]pyridine-6-carboxylate (0.060 g 0.161 mmol). LCMS: Method A, 2.083 min, MS: ES+ 372.68; $^1$H NMR (400 MHz, CDCl$_3$) δ ppm 8.19 (d, J=8.8 Hz, 1H), 7.95-7.87 (m, 1H), 7.49-7.46 (m, 2H), 7.20-7.11 (m, 2H), 4.75-4.59 (m, 4H), 2.22 (s, 3H), 1.50 (d, J=5.6 Hz, 9H).

Steps d and e were carried out in a similar manner to steps d and e of Example 1. LCMS: Method D, 3.492 min, MS: ES+ 297.04; $^1$H NMR (400 MHz, DMSO-d6) δ ppm 10.71 (s, 1H), 8.11 (s, 1H), 7.58-7.61 (m, 2H), 7.32-7.37 (m, 2H), 4.91 (s, 2H), 4.74 (s, 2H), 2.08 (m, 3H).

Example 250 2-((2,3-dihydroxypropyl)amino)-4-(4-fluorophenyl)-5,7-dihydro-6H-pyrrolo[3,4-b]pyridine-6-carbonitrile

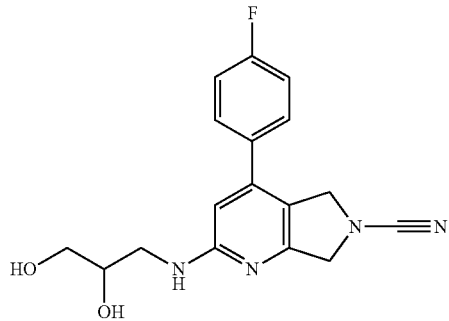 [SMILES: N#CN1Cc2nc(NCC(O)CO)cc(-c3ccc(F)cc3)c2C1]

Step a. To a mixture of 2-chloro-4-(4-fluorophenyl)-6-(methylsulfonyl)-6,7-dihydro-5H-pyrrolo[3,4-b]pyridine (prepared as in step f of Example 246, (0.400 g, 1.226 mmol) in DMSO:water (1:1, 5 ml) was added 3-amino-1,2-propanediol (CAS Number 616-30-8; 2.23 g, 24.5 mmol) at rt. The resulting reaction mixture was heated at 140° C. for 16 h. The reaction mixture was cooled to rt and concentrated under reduced pressure. The resulting mixture was cooled to rt, poured into water (30 ml) and extracted with EtOAc (3×15 ml). The combined organic phase was washed with brine (2×20 ml), dried over Na$_2$SO$_4$, filtered and concentrated under reduced pressure. The obtained residue was purified by column chromatography (2-4% MeOH in DCM) yielding 3-((4-(4-fluorophenyl)-6-(methylsulfonyl)-6,7-dihydro-5H-pyrrolo[3,4-b]pyridin-2-yl)-amino)propane-1,2-diol (0.200 g 0.524 mmol). LCMS: Method A, 1.522 min, MS: ES+ 382.43.

Steps b and c were carried out using a similar method to the final 2 steps of Example 246. LCMS: Method D, 3.425 min, MS: ES+ 329.03; ¹H NMR (400 MHz, DMSO-d6) δ ppm 7.54-7.60 (m, 2H), 7.30-7.34 (m, 2H), 6.71 (t, J=6.0 Hz, 1H), 6.54 (s, 1H), 4.82-4.83 (m, 1H), 4.76 (s, 2H), 4.60-4.62 (m, 3H), 3.60-3.64 (m, 1H), 3.34-3.50 (m, 3H).

Example 251 2-(2-cyano-7-phenylisoindolin-5-yl)-N,N-dimethylacetamide

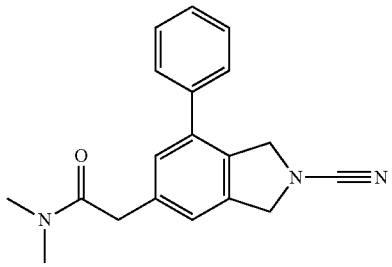 [SMILES: CN(C)C(=O)Cc1cc2c(c(-c3ccccc3)c1)CN(C#N)C2]

Step a. To a mixture of (methoxymethyl)triphenylphosphonium chloride (CAS Number 4009-98-7; 2.88 g, 8.40 mmol) in THF (5 ml) was dropwise added NaHMDS (1M in THF) (8.4 ml, 8.4 mmol) at −78° C. The reaction mixture was stirred at −78° C. for 45 min. A solution of benzyl 6-formyl-4-phenylisoindoline-2-carboxylate (prepared as in step d of Example 213, 0.750 g, 2.100 mmol) in THF (5 ml) was drop wise added to the reaction mixture at −78° C. The resulting reaction mixture was stirred at −78° C. to 0° C. for 1 h. The resulting reaction mixture was combined with 1 other batch on the same scale prepared by an identical method. The resulting mixture was poured into water (100 ml) and extracted with EtOAc (2×100 ml). The combined organic phase washed with brine (40 ml), dried over Na₂SO₄, filtered and concentrated under reduced pressure. The residue was purified by flash column chromatography (20-25% EtOAc in hexane) yielding benzyl 6-(2-methoxyvinyl)-4-phenylisoindoline-2-carboxylate (0.750 g 1.95 mmol). LCMS: Method E, 5.381, 5.417 min, MS: ES+ 386.40.

Step b. To a solution of benzyl 6-(2-methoxyvinyl)-4-phenylisoindoline-2-carboxylate (0.750 g, 1.948 mmol) in THF (5 ml) was added 6M HCl (5 ml) at rt. The resulting reaction mixture was stirred at rt for 8 h. The resulting precipitates were collected by filtration. The obtained residue was dried under high vacuum yielding benzyl 6-(2-oxoethyl)-4-phenylisoindoline-2-carboxylate (0.700 g, 1.886 mmol). This material was use directly for next step without further purification. LCMS: Method A, 2.688 min, MS: ES+ 372.30; ¹H NMR (400 MHz, DMSO-d₆) δ ppm 9.72 (s, 1H), 7.52-7.21 (m, 12H), 5.14 (d, J=6.4 Hz, 2H), 4.76 (s, 2H), 4.71 (s, 2H), 3.85 (s, 2H).

Step c. CrO₃ (1 g) was dissolved in water (3 ml) at 5° C. to 10° C. Concentrated H₂SO₄ (1 ml) was added dropwise at 0° C. to 10° C. to give Jone's reagent. To a solution of benzyl 6-(2-oxoethyl)-4-phenylisoindoline-2-carboxylate (0.700 g, 1.89 mmol) in acetone (7 ml) was added this Jone's reagent (1 ml). The resulting mixture was stirred at 0° C. to 10° C. for 1 h. The resulting mixture was poured into water (60 ml) and extracted with EtOAc (2×70 ml). The combined organic phase washed with brine (60 ml), dried over Na₂SO₄, filtered and concentrated under reduced pressure. The residue was triturated with diethyl ether (2×4 ml) and dried under high vacuum yielding 2-(2-((benzyloxy)carbonyl)-7-phenylisoindolin-5-yl)acetic acid (0.450 g, 1.162 mmol). This material was use directly for next step without further purification. LCMS: Method A, 2.406 min, MS: ES+ 388.12.

Step d. To a solution of 2-(2-((benzyloxy)carbonyl)-7-phenylisoindolin-5-yl)acetic acid (0.450 g, 1.162 mmol) in THF (5 ml) were added HATU (0.660 g, 1.743 mmol) and DIPEA (0.400 ml, 2.324 mmol) at rt. The reaction mixture was stirred at rt for 25 min. Dimethylamine (2M in THF) (0.87 ml, 1.74 mmol) was added to the reaction mixture at rt. The reaction mixture was stirred at rt for 15 h. The resulting reaction mixture was poured into water (80 ml) and extracted with EtOAc (2×80 ml). The combined organic phase was washed with brine (80 ml), dried over Na₂SO₄, filtered and concentrated under reduced pressure. The resulting residue was purified by flash chromatography (3% MeOH in DCM) yielding benzyl 6-(2-(dimethylamino)-2-oxoethyl)-4-phenylisoindoline-2-carboxylate (0.250 g, 0.603 mmol). LCMS: Method A, 2.336 min, MS: ES+ 415.50.

Steps e and f were carried out in a similar manner to steps f and g of Example 213. LCMS: Method D, 3.986 min, MS: ES+ 306.02; ¹H NMR (400 MHz, DMSO-d6) δ ppm 7.48-7.38 (m, 5H), 7.23 (s, 1H), 7.18 (s, 1H), 4.85 (s, 2H), 4.81 (s, 2H), 3.76 (s, 2H), 3.03 (s, 3H), 2.83 (s, 3H).

Example 252 6-(2-(methylsulfonyl)ethyl)-4-phenylisoindoline-2-carbonitrile

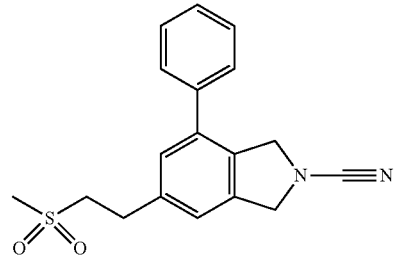 [SMILES: CS(=O)(=O)CCc1cc2c(c(-c3ccccc3)c1)CN(C#N)C2]

Step a. To a solution of benzyl 6-(2-oxoethyl)-4-phenylisoindoline-2-carboxylate (prepared as in step b of Example 251 (0.800 g, 2.156 mmol) in THF:MeOH (1:1, 10 ml) was portion wise added NaBH₄ (0.244 g, 6.469 mmol) at 0° C. The resulting reaction mixture was stirred at rt for 2 h. The resulting mixture was poured into water (100 ml) and extracted with EtOAc (2×100 ml). The combined organic phase was dried over Na₂SO₄, filtered and concentrated under reduced pressure yielding benzyl 6-(2-hydroxyethyl)-4-phenylisoindoline-2-carboxylate (0.800 g, 2.144 mmol). This material was used in next step without further purification. LCMS: Method A, 2.417 min, MS: ES+ 374.44.

Step b. To a solution of benzyl 6-(2-hydroxyethyl)-4-phenylisoindoline-2-carboxylate (0.270 g, 0.723 mmol) in DCM (10 ml) were added pyridine (0.291 ml, 3.619 mmol) followed by p-toluenesulfonyl chloride (0.344 g, 1.81 mmol) at 0° C. The reaction mixture was stirred at rt for 36 h. The resulting reaction mixture was poured into saturated citric acid solution (75 ml) and extracted with EtOAc (2×75 ml). The combined organic phase was dried over Na₂SO₄, filtered and concentrated under reduced pressure. The resulting residue was purified by flash chromatography (21% EtOAc in hexane) yielding benzyl 4-phenyl-6-(2-(tosyloxy)

ethyl)isoindoline-2-carboxylate (0.200 g, 0.379 mmol). LCMS: Method A, 2.851 min, MS: ES+ 545.50 [M+18].

Step c. A stirred solution of benzyl 4-phenyl-6-(2-(tosyloxy)ethyl)isoindoline-2-carboxylate (0.200 g, 0.379 mmol) in THF (2 ml) were added NMP (1 ml) followed by sodium methane thiolate (0.053 g, 0.758 mmol) at rt. The reaction mixture was heated at 70° C. for 15 h. The reaction mixture was poured into saturated NaHCO$_3$ solution (100 ml) and extracted with EtOAc (2×100 ml). The combined organic phase was dried over Na$_2$SO$_4$, filtered and concentrated under reduced pressure. The residue was purified by flash chromatography (23% EtOAc in hexane) yielding benzyl 6-(2-(methylthio)-ethyl)-4-phenylisoindoline-2-carboxylate (0.100 g, 0.248 mmol). LCMS: Method A, 2.926 min, MS: ES+ 404.40

Step d. To a solution of benzyl 6-(2-(methylthio)ethyl)-4-phenylisoindoline-2-carboxylate (0.100 g, 0.248 mmol) in DCM (5 ml) was portion wise added m-CPBA (0.120 g, 0.744 mmol) at 0° C. The reaction mixture was stirred at rt for 5 h. The resulting mixture was poured into saturated NaHCO$_3$ solution (100 ml) and extracted with EtOAc (2×100 ml). The combined organic phase was dried over Na$_2$SO$_4$, filtered and concentrated under reduced pressure yielding benzyl 6-(2-(methylsulfonyl)-ethyl)-4-phenylisoindoline-2-carboxylate (0.100 g, 0.229 mmol). This material was used in next step without further purification. LCMS: Method A, 2.334 min, MS: ES+ 453.38 [M+18].

Steps e and f were carried out in a similar manner to steps f and g of Example 213. LCMS: Method D, 4.312 min, MS: ES+ 326.96; $^1$H NMR (400 MHz, DMSO-d6) δ ppm 7.40-7.52 (m, 5H), 7.33 (s, 1H), 7.27 (s, 1H), 4.84 (s, 2H), 4.81 (s, 2H), 3.45-3.49 (m, 2H), 3.05-3.09 (m, 2H), 2.99 (s, 3H).

Example 253 6-((methylsulfonyl)methyl)-4-phenylisoindoline-2-carbonitrile

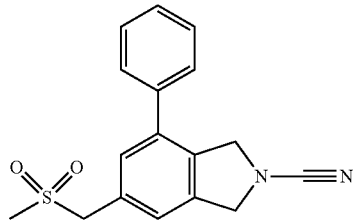 [SMILES: CS(=O)(=O)Cc1cc2c(c(-c3ccccc3)c1)CN(C#N)C2]

Step a. To a solution of benzyl 6-formyl-4-phenylisoindoline-2-carboxylate (prepared as in step d of Example 213, 1.200 g, 3.361 mmol) in THF (22 ml) were portion wise added NaBH$_4$ (0.380 g, 10.08 mmol) followed by MeOH (2 ml) at rt. The resulting reaction mixture was stirred at rt for 1 h. The resulting mixture was poured into water (75 ml) and extracted with EtOAc (2×100 ml). The combined organic phase was dried over Na$_2$SO$_4$, filtered and concentrated under reduced pressure yielding benzyl 6-(hydroxymethyl)-4-phenylisoindoline-2-carboxylate (1.200 g, 3.342 mmol). This material was used in next step without further purification. LCMS: Method A, 2.476 min, MS: ES+ 360.30.

Step b. To a solution of benzyl 6-(hydroxymethyl)-4-phenylisoindoline-2-carboxylate (1.000 g, 2.785 mmol) in DCM (20 ml) were drop wise added TEA (0.194 ml, 1.392 mmol) and PBr$_3$ (0.753 g, 2.785 mmol) at −78° C. sequentially. The reaction mixture was stirred at −78° C. to rt for 1 h. The resulting reaction mixture was poured into saturated NaHCO$_3$ solution (100 ml) and extracted with EtOAc (2×100 ml). The combined organic phase was dried over Na$_2$SO$_4$, filtered and concentrated under reduced pressure yielding benzyl 6-(bromomethyl)-4-phenylisoindoline-2-carboxylate (0.700 g, 1.662 mmol). This material was used in next step without further purification. LCMS: Method A, 3.023 min, MS: ES+ 422.28, 424.28.

Step c. A stirred solution of benzyl 6-(bromomethyl)-4-phenylisoindoline-2-carboxylate (0.700 g, 1.662 mmol) in MeOH: DCM (1:1, 15 ml) was drop wise added sodium methane thiolate (0.116 g, 1.662 mmol) at 0° C. The reaction mixture was stirred at rt for 5 h. The resulting mixture was concentrated under reduced pressure yielding benzyl 6-((methylthio)methyl)-4-phenylisoindoline-2-carboxylate (0.700 g). This material was used in next step without further purification. LCMS: Method A, 3.042 min, MS: ES+ 390.33.

Steps d-f were carried out in a similar manner to steps d-f of Example 252. LCMS: Method D, 4.032 min, MS: ES+ 312.93; $^1$H NMR (400 MHz, DMSO-d6) δ ppm 7.49-7.50 (m, 4H), 7.43-7.44 (m, 1H), 7.42 (s, 1H), 7.36 (s, 1H), 4.89 (s, 2H), 4.86 (s, 2H), 4.57 (s, 2H), 2.94 (s, 3H).

Example 254 4-(4-cyanophenyl)-6-(2-methoxyethyl)isoindoline-2-carbonitrile

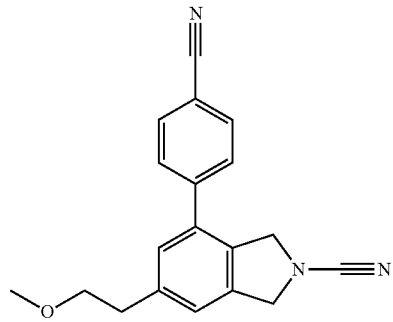 [SMILES: COCCc1cc2c(c(-c3ccc(C#N)cc3)c1)CN(C#N)C2]

Step a. To a mixture of (Methoxymethyl)triphenylphosphonium chloride (CAS Number 4009-98-7; 67.50 g, 196.9 mmol) in THF (320 ml) was dropwise added NaHMDS (1M in THF) (197 ml, 197 mmol) at −78° C. The reaction mixture was stirred at −78° C. for 45 min. A solution of Intermediate 11 (16.0 g, 49.23 mmol) in THF (50 mL) was added drop wise to the reaction mixture at −78° C. The resulting reaction mixture was stirred at −78° C. to 0° C. for 1 h. The resulting mixture was poured into water (250 ml) and extracted with EtOAc (2×250 ml). The combined organic phase was dried over Na$_2$SO$_4$, filtered and concentrated under reduced pressure. The residue was purified by flash column chromatography (15% EtOAc in hexane) yielding tert-butyl 4-bromo-6-(2-methoxyvinyl)isoindoline-2-carboxylate (10.0 g, 28.2 mmol). LCMS: Method A, 2.611+2.647 min, MS: ES+ 298.40, 300.40 [M−56].

Step b. A stirred solution of tert-butyl 4-bromo-6-(2-methoxyvinyl)isoindoline-2-carboxylate (5.000 g, 14.03 mmol) in EtOH (100 ml) was added Wilkinson's catalyst RhCl(PPh$_3$)$_3$ (3.930 g, 4.21 mmol) at rt. The resulting reaction mixture was purged with H$_2$ gas and heated at 60° C. for 6 h. The resulting reaction mixture was combined with 1 other batch on the same scale prepared by an identical method. The reaction mixture was filtered through celite pad and washed with MeOH (3×250 ml). The combined filtrate was concentrated under reduced pressure. The residue was purified by flash column chromatography (16.3% EtOAc in hexane) yielding tert-butyl 4-bromo-6-(2-methoxyethyl)-isoindoline-2-carboxylate (7.600 g, 21.41 mmol). LCMS: Method A, 2.487 min, MS: ES+ 356.40, 358.40; $^1$H NMR (400 MHz, DMSO-d$_6$) δ ppm 7.38 (s, 1H), 7.21 (s, 1H), 4.65 (d, J=5.2 Hz, 2H), 4.48 (d, J=6.0 Hz, 2H), 3.52 (t, J=6.0 Hz, 2H), 3.22 (s, 3H), 2.81 (t, J=6.0 Hz, 2H), 1.46 (s, 9H).

Step c. To a stirred solution of tert-butyl 4-bromo-6-(2-methoxyethyl)isoindoline-2-carboxylate (0.250 g, 0.704 mmol) in 1,4-dioxane (5 ml) were added K$_2$CO$_3$ (0.194 g, 1.41 mmol) and 4-cyanophenylboronic acid (0.114 g, 0.774 mmol) at rt. The reaction mixture was degassed for 30 min before addition of PdCl$_2$(dppf) (0.052 g, 0.070 mmol). The resulting reaction mixture was heated at 80° C. for 2 h. The reaction mixture was cooled to rt and poured into water (20 ml). The resulting mixture was extracted with EtOAc (3×20 ml). The combined organic phase was dried over Na$_2$SO$_4$, filtered and concentrated under reduced pressure. The residue was purified by flash column chromatography (50% EtOAc in n-hexane) yielding tert-butyl 4-(4-cyanophenyl)-6-(2-methoxyethyl)isoindoline-2-carboxylate (0.170 g, 0.449 mmol). LCMS: Method A, 2.415 min, MS: ES+ 323.47 [M−56].

Steps d and e were carried out in a similar manner to steps d and e of Example 1. LCMS: Method E, 4.121 min, MS: ES+ 304.53; $^1$H NMR (400 MHz, DMSO-d6) δ ppm 7.94 (d, J=8.0 Hz, 2H), 7.71 (d, J=7.06 Hz, 2H), 7.30 (s, 1H), 7.27 (s, 1H), 4.86 (s, 2H), 4.81 (s, 2H), 3.57 (t, J=6.8 Hz, 2H), 3.23 (s, 3H), 2.88 (t, J=6.4 Hz, 2H).

Example 255 2-(2-cyano-6-(2-methoxyethyl)isoindolin-4-yl)benzamide

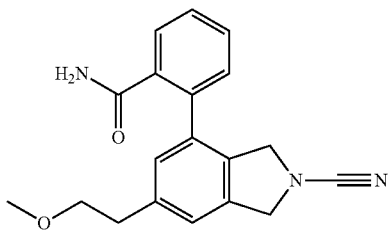 [SMILES: COCCc1cc2c(c(-c3ccccc3C(N)=O)c1)CN(C#N)C2]

Step a. To a stirred solution of tert-butyl 4-bromo-6-(2-methoxyethyl)isoindoline-2-carboxylate (prepared as in step b of Example 254, 0.500 g, 1.41 mmol) in DMF:water (9:1, 5 ml) were added NaHCO$_3$ (0.355 g, 4.225 mmol) and 2-ethoxycarbonylphenylboronic acid (CAS Number 380430-53-5; 0.328 g, 1.686 mmol) at rt. The reaction mixture was degassed for 30 min before addition of PdCl$_2$ (dppf) (0.103 g, 0.140 mmol). The resulting reaction mixture was heated at 100° C. for 6 h. The reaction mixture was cooled to rt and poured into water (20 ml). The resulting mixture was extracted with EtOAc (3×20 ml). The combined organic phase was dried over Na$_2$SO$_4$, filtered and concentrated under reduced pressure. The residue was purified by flash column chromatography (2.5% MeOH in DCM) yielding tert-butyl 4-(2-(ethoxycarbonyl)phenyl)-6-(2-methoxyethyl)-isoindoline-2-carboxylate (0.500 g, 1.176 mmol). LCMS: Method A, 2.527 min, MS: ES+ 426.70.

Step b. To a solution of tert-butyl 4-(2-(ethoxycarbonyl)phenyl)-6-(2-methoxyethyl)isoindoline-2-carboxylate (0.500 g, 1.176 mmol) in THF:water (1:1, 10 ml) was added NaOH (0.141 g, 3.53 mmol) at rt. The reaction mixture was heated at 70° C. for 1 h. The resulting mixture was diluted by 1M HCl solution (10 ml) and extracted with EtOAc (4×10 ml). The combined organic phase was dried over Na$_2$SO$_4$, filtered and concentrated under reduced pressure yielding 2-(2-(tert-butoxycarbonyl)-6-(2-methoxyethyl)isoindolin-4-yl)benzoic acid (0.400 g, 1.007 mmol). This material was directly used for next step without any further purification. LCMS: Method A, 2.118 min, MS: ES− 396.76.

Step c. To a solution of 2-(2-(tert-butoxycarbonyl)-6-(2-methoxyethyl)isoindolin-4-yl)benzoic acid (0.400 g, 1.007 mmol) in THF (4 ml) were added EDC.HCl (0.386 g, 2.015 mmol), HOBt (0.185 g, 1.209 mmol) and DIPEA (0.390 g, 3.022 mmol) at rt. The reaction mixture was stirred for 10 min before addition of NH$_4$Br (0.493 g, 5.037 mmol). The resulting reaction mixture was stirred at rt for 16 h. The reaction mixture was poured into water (20 ml) and extracted with EtOAc (4×20 ml). The combined organic phase was dried over Na$_2$SO$_4$, filtered and concentrated under reduced pressure. The residue was purified by flash chromatography (2.1% MeOH in DCM) yielding tert-butyl 4-(2-carbamoylphenyl)-6-(2-methoxyethyl)isoindoline-2-carboxylate (0.287 g, 0.724 mmol). LCMS: Method A, 1.927 min, MS: ES+ 341.63 [M−56].

Steps d and e were carried out using a similar method to the final two steps of Example 1. LCMS: Method D, 2.954 min, MS: ES− 320.15; 1H NMR (400 MHz, DMSO-d6) δ ppm: 7.43-7.50 (m, 4H), 7.29-7.31 (m, 1H), 7.21 (s, 1H), 7.16 (s, 1H), 7.04 (s, 1H), 4.80 (s, 2H), 4.62 (s, 2H), 3.53 (t, J=6.4 Hz, 2H), 3.24 (s, 3H), 2.81 (t, J=6.8 Hz, 2H).

Example 256 4-(4-cyanophenyl)-6-(2-(pyridin-3-yl)ethyl)isoindoline-2-carbonitrile

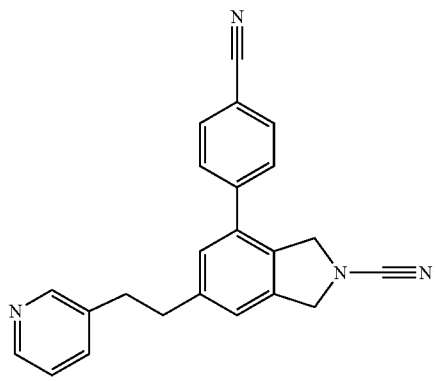 [SMILES: N#Cc1ccc(-c2cc(CCc3cccnc3)cc3c2CN(C#N)C3)cc1]

Step a. To a mixture of triphenyl(pyridin-3-ylmethyl)phosphonium chloride (CAS Number 79296-92-7, 1.341 g, 3.447 mmol) in THF (5 ml) was dropwise added NaHMDS (1M in THF) (3.45 ml, 3.45 mmol) at −78° C. The reaction mixture was stirred at −78° C. for 45 min. A solution of tert-butyl 4-(4-cyanophenyl)-6-formylisoindoline-2-carboxylate (prepared as in step a of Intermediate 12, 0.300 g, 0.861 mmol) in THF (5 ml) was added dropwise added to the reaction mixture at −78° C. The resulting reaction mixture was stirred at 0° C. to rt for 1 h. The resulting mixture was poured into water (50 ml) and extracted with EtOAc (2×30 ml). The combined organic phase dried over Na$_2$SO$_4$, filtered and concentrated under reduced pressure. The residue was purified by flash column chromatography (25% EtOAc in hexane) yielding tert-butyl 4-(4-cyanophenyl)-6-(2-(pyridin-3-yl)-vinyl)isoindoline-2-carboxylate (0.29 g, 0.68 mmol). LCMS: Method A, 2.312 min, MS: ES+ 424.63.

Step b. A stirred solution of tert-butyl 4-(4-cyanophenyl)-6-(2-(pyridin-3-yl)vinyl)isoindoline-2-carboxylate (0.250 g, 0.590 mmol) in MeOH (10 ml) was added 20% Pd(OH)$_2$ (0.090 g, 0.36 w/v) at rt. The resulting reaction mixture was purged with H$_2$ gas at rt for 30 min. The reaction mixture was filtered through celite bed and washed with MeOH (2×10 ml). The combined filtrate was concentrated under reduced pressure. The residue was purified by flash column chromatography (35% EtOAc in hexane) yielding tert-butyl 4-(4-cyanophenyl)-6-(2-(pyridin-3-yl)ethyl)isoindoline-2-carboxylate (0.115 g, 0.270 mmol). LCMS: Method A, 2.001 min, MS: ES+ 426.83.

Steps c and d were carried out using a similar method to the final 2 steps of Example 1. LCMS: Method D, 4.451 min, MS: ES+ 351.32; $^1$H NMR (400 MHz, DMSO-d6) δ ppm 8.44 (d, J=2.0 Hz, 1H), 8.40 (d, J=4.8, 1.06 Hz, 1H), 7.93 (d, J=8.0 Hz, 2H), 7.66-7.68 (m, 3H), 7.28-7.32 (m, 3H), 4.85 (s, 2H), 4.81 (s, 2H), 2.92-2.99 (m, 4H).

Example 257 6-(2-(1-acetylpiperidin-4-yl)ethyl)-4-(4-cyanophenyl)isoindoline-2-carbonitrile

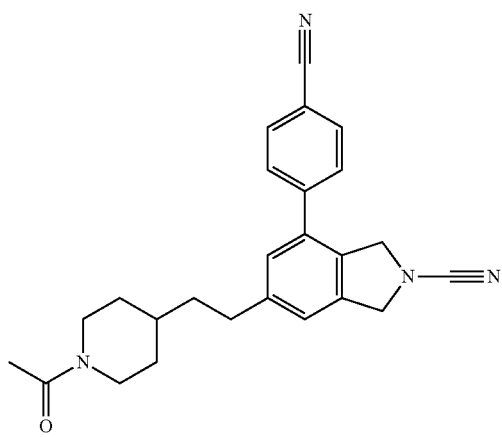 [SMILES: CC(=O)N1CCC(CCc2cc3c(c(-c4ccc(C#N)cc4)c2)CN(C#N)C3)CC1]

Step a. To a solution of 1-(4-(iodomethyl)piperidin-1-yl)ethan-1-one (CAS Number 1353954-96-7; 1.500 g, 5.62 mmol) in MeCN (25 ml) was added triphenylphosphine (1.910 g, 7.30 mmol) at rt. The reaction mixture was heated at 100° C. for 48 h. The mixture was cooled to rt and concentrated under reduced pressure. The residue was triturated with 30% DCM in diethyl ether (10 ml) and dried under high vacuum yielding ((1-acetylpiperidin-4-yl)methyl)triphenylphosphonium iodide (2.000 g, 3.78 mmol). The material used in next step without further purification. LCMS: Method A, 1.517 min, MS: ES+ 402.58.

Step b. To a mixture of ((1-acetylpiperidin-4-yl)methyl) triphenyl phosphonium iodide (0.606 g, 1.146 mmol) in THF (2 ml) was dropwise added n-BuLi (15% solution in hexane) (1.00 ml, 2.3 mmol) at −0° C. The reaction mixture was stirred at 0° C. for 45 min. A solution of tert-butyl 4-(4-cyanophenyl)-6-formylisoindoline-2-carboxylate (prepared as in step a of Intermediate 12, 0.100 g, 0.286 mmol) in THF (1 ml) was drop wise added to the reaction mixture at 0° C. The resulting reaction mixture was stirred at 0° C. for 1.5 h. The resulting reaction mixture was combined with 2 other batches prepared on the same scale by an identical method. The resulting mixture was quenched with saturated NH$_4$Cl solution (200 ml) and extracted with EtOAc (3×50 ml). The combined organic phase washed with brine (2×50 ml), dried over Na$_2$SO$_4$, filtered and concentrated under reduced pressure. The obtained residue was purified by flash column chromatography (70% EtOAc in hexane) yielding tert-butyl 6-(2-(1-acetylpiperidin-4-yl)vinyl)-4-(4-cyanophenyl)isoindoline-2-carboxylate (0.200 g, 0.424 mmol). LCMS: Method A, 2.392 min, MS: ES+ 472.83.

Steps c-e were carried out using a similar method to steps b-d of Example 256. LCMS: Method D, 4.408 min, MS: ES+ 399.20; $^1$H NMR (400 MHz, DMSO-d6) δ ppm 7.93 (d, J=8.0 Hz, 2H), 7.71 (d, J=8.4 Hz, 2H), 7.27 (s, 1H), 7.25 (s, 1H), 4.86 (s, 2H), 4.81 (s, 2H), 4.32-4.35 (m, 1H), 3.75-3.79 (m, 1H), 2.92-2.99 (m, 1H), 2.66-2.70 (m, 2H), 2.43-2.47 (m, 2H), 1.99 (s, 3H), 1.69-1.75 (m, 2H), 1.47-1.57 (m, 4H).

Example 258 5-chloro-2-(2-cyano-1-methylisoindolin-4-yl)benzamide Single Unknown Enantiomer

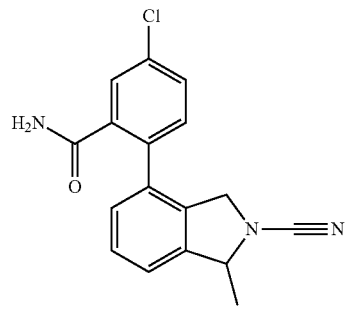 [SMILES: CC1c2cccc(-c3ccc(Cl)cc3C(N)=O)c2CN1C#N]

Step a. To a solution of 4-bromoisoindoline-1,3-dione (CAS Number 70478-63-6, 15.00 g, 66.4 mmol) in DCM (150 ml) was dropwise added methyl magnesium bromide (1 M in THF) (199 ml, 199 mmol) at 0° C. under N$_2$ atmosphere. The reaction mixture was stirred at rt for 2 h. The reaction mixture was combined with three other batches prepared on the same scale by an identical method. The resulting reaction mixture was poured in to NH$_4$Cl solution (500 ml) and extracted with the DCM (3×1 L). The combined organic phases was dried over Na$_2$SO$_4$, filtered and concentrated under reduced pressure. The crude material was purified by column chromatography (30-32% EtOAc in hexane) yielding a mixture of 7-bromo-3-hydroxy-3-methylisoindolin-1-one and 4-bromo-3-hydroxy-3-methylisoindolin-1-one (37.00 g, 153.6 mmol). LCMS: Method A, 1.435 min, MS: ES+ 242.33, 244.33.

Step b. A mixture of 7-bromo-3-hydroxy-3-methylisoindolin-1-one and 4-bromo-3-hydroxy-3-methyl isoindolin-1-one (12.00 g, 49.8 mmol) in DCM (100 ml) was cooled to −40° C. Triethylsilane (80.4 ml, 498 mmol) was added to the reaction mixture at −40° C. under N$_2$ atmosphere. Boron trifluoride diethyletherate (18.7 ml, 149.4 mmol) was added to the reaction mixture at −40° C. under N$_2$ atmosphere. The reaction mixture was stirred at 0° C. for 1 h. The resulting reaction mixture was combined with two other batches prepared on the same scale by an identical method. The resulting reaction mixture was poured into NaHCO$_3$ solution (500 ml) and extracted with the DCM (3×1000 ml). The combined organic phase was dried over Na$_2$SO$_4$, filtered and concentrated under reduced pressure. The crude material obtained was purified by column chromatography (3% EtOAc in DCM) yielding 7-bromo-3-methylisoindolin-1-one (9.200 g, 40.9 mmol). LCMS: Method A, 1.521 min, MS: ES+ 226.11, 228.11; $^1$H NMR (400 MHz, CDCl$_3$) δ ppm 7.61 (dd, J=7.2, 1.2 Hz, 1H), 7.43-7.38 (m, 3H), 7.68-7.63 (m, 1H), 1.52 (d, J=6.8 Hz, 3H).

Step c. To a solution of sodium borohydride (0.672 g, 17.8 mmol) in dry THF (10 ml) was added iodine (3.380 g, 13.3 mmol) at 0° C. under N₂ atmosphere. The reaction mixture was stirred at 0° C. for 30 min under N₂ atmosphere. A solution of 7-bromo-3-methyl isoindolin-1-one (1.0 g, 4.444 mmol) in dry THF (2 ml) was added to the reaction mixture at 0° C. The reaction mixture was stirred at rt for 2 h and at reflux for a further 2 h. The resulting reaction mixture was combined with 8 other batches prepared on the same scale by an identical method. The reaction mixture was poured into 1 M HCl solution (200 ml) and extracted with EtOAc (2×250 ml). The aqueous layer was neutralised with Na₂CO₃ up to pH 8 and further extracted with EtOAc (2×500 ml). The organic phases was collected, dried over Na₂SO₄, filtered and concentrated under reduced pressure to yielding 4-bromo-1-methylisoindoline (5.89 g, 27.91 mmol). This material was directly used for next step without any further purification. LCMS: Method A, 1.387 min, MS: ES+ 212.13, 214.13.

Step d. To a solution of 4-bromo-1-methylisoindoline (5.89 g, 27.914 mmol) in THF (50 ml) were added TEA (7.800 ml, 55.828 mmol) and Boc-anhydride (7.260 g, 93.04 mmol) at 0° C. The reaction mixture was stirred at rt for 1 h. The reaction mixture was poured into water (250 ml) and extracted with EtOAc (3×250 ml). The combined organic phases was dried over Na₂SO₄, filtered and concentrated under reduced pressure. The crude material was purified by column chromatography (5% EtOAc in hexane) yielding tert-butyl 4-bromo-1-methylisoindoline-2-carboxylate (5.4 g, 17.307 mmol). LCMS: Method A, 2.631 min, MS: ES+ 256.28, 258.28 [M−56].

Step e was carried out in a similar method to Example 226 yielding tert-butyl 1-methyl-4-(4,4,5,5-tetramethyl-1,3,2-dioxaborolan-2-yl)isoindoline-2-carboxylate. LCMS: Method A, 2.920 min, MS: ES+ 304.56 [M−56].

Step f. To a stirred solution of tert-butyl 1-methyl-4-(4,4,5,5-tetramethyl-1,3,2-dioxaborolan-2-yl)isoindoline-2-carboxylate (1.430 g, 4.01 mmol) in 1,4-dioxane:water (9:1, 8.8 ml) were added K₂CO₃ (1.100 g, 8.016 mmol) and methyl 2-bromo-5-chlorobenzoate (CAS Number 27007-53-0; 1.00 g, 4.01 mmol) at rt. The reaction mixture was degassed for 15 min before addition of PdCl₂(dppf) DCM complex (0.327 g, 0.040 mmol). The resulting reaction mixture was heated at 90° C. for 1 h. The reaction mixture was cooled to rt and poured into water (100 ml). The resulting mixture was extracted with EtOAc (3×100 ml). The combined organic phase was dried over Na₂SO₄, filtered and concentrated under reduced pressure. The residue was purified by flash column chromatography (5% EtOAc in n-hexane) yielding tert-butyl 4-(4-chloro-2-(methoxycarbonyl)phenyl)-1-methylisoindoline-2-carboxylate (0.890 g, 2.215 mmol). LCMS: Method A, 2.854 min, MS: ES+ 402.50

Step g. To a solution of tert-butyl 4-(4-chloro-2-(methoxycarbonyl)phenyl)-1-methylisoindoline-2-carboxylate (0.890 g, 2.215 mmol) in THF:water (1:1, 10 ml) was added LiOH.H₂O (0.278 g, 6.645 mmol) at rt. The reaction mixture was stirred at 70° C. for 3 hr. The resulting reaction mixture was diluted by water (100 ml) and extracted with DCM (50 ml). The resulting aqueous layer was acidified by 1N HCl (50 ml) and extracted with EtOAc (3×50 ml). The combined organic phase was dried over Na₂SO₄, filtered and concentrated under reduced pressure yielding 2-(2-(tert-butoxycarbonyl)-1-methylisoindolin-4-yl)-5-chlorobenzoic acid (0.601 g, 1.552 mmol). This material was directly used for next step without any further purification. LCMS: Method A, 2.473 min, MS: ES+ 332.38 [M−56].

Step h. To a solution of 2-(2-(tert-butoxycarbonyl)-1-methylisoindolin-4-yl)-5-chlorobenzoic acid (0.300 g, 0.775 mmol) in THF (5 ml) were added EDC.HCl (0.296 g, 1.550 mmol), HOBt (0.118 g, 0.775 mmol) and DIPEA (0.299 ml, 2.325 mmol) at rt. The reaction mixture was stirred at rt for 20 min. NH₄Cl (0.207 g, 23.560 mmol) was added to the reaction mixture at rt. The reaction mixture was stirred at rt for 3 h. The resulting reaction mixture was poured into saturated NaHCO₃ solution (100 ml) and extracted with EtOAc (3×100 ml). The combined organic phase was dried over Na₂SO₄, filtered and concentrated under reduced pressure. The resulting residue was purified by flash chromatography (0.1% MeOH in DCM) yielding tert-butyl 4-(2-carbamoyl-4-chlorophenyl)-1-methylisoindoline-2-carboxylate (0.230 g, 0.595 mmol). LCMS: Method A, 2.248 min, MS: ES+ 387.50.

Steps i and j were carried out in a similar manner to steps d and e of Example 1. LCMS: Method D, 3.994 min, MS: ES+ 312.10; ¹H NMR (400 MHz, DMSO-d6) δ ppm 7.69 (m, 1H), 7.54-7.52 (m, 2H), 7.38-7.35 (m, 3H), 7.31 (d, J=7.6 Hz, 1H), 7.15 (d, J=7.2 Hz, 1H), 5.07-5.05 (m, 1H), 4.63 (s, 2H), 1.52 (d, J=6.4 Hz, 3H). Enantiomers were separated by SFC purification (Waters SFC 200 and UV detector; Chiralcel OXH 250×21.0 mm column, 5 micron, column flow 80.0 ml/min; ABPR 90 bar; isocratic solvent ratio of 30% IPA in liquid CO₂). Chiral SFC: Method U, RT=6.13 min, LCMS: Method D, 3.920 min, MS: ES+ 311.90; ¹H NMR (400 MHz, DMSO-d6) δ ppm 7.70 (m, 1H), 7.53-7.55 (m, 2H), 7.36-7.40 (m, 3H), 7.32 (d, J=7.2 Hz, 1H), 7.16 (d, J=7.26 Hz, 1H), 5.06-5.08 (m, 1H), 4.64 (s, 2H), 1.53 (d, J=6.4 Hz, 3H). Absolute stereochemistry was not determined.

Example 259 5-cyano-2-(2-cyano-1-methylisoindolin-4-yl)benzamide Single Unknown Enantiomer

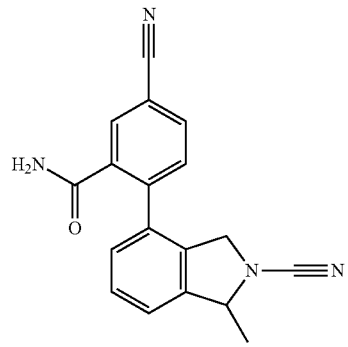 [SMILES: CC1c2cccc(-c3ccc(C#N)cc3C(N)=O)c2CN1C#N]

This was synthesised using a procedure similar to that described for Example 258 (using methyl 2-bromo-5-cyanobenzoate (CAS Number 1031927-03-3) in step f. LCMS: Method D, 3.521 min, MS: ES+ 303.05; Chiral SFC: (column CHIRALCEL OX-H 250 mm×4.6 mm, 5μm, flow rate 3.0 ml/min, isocratic solvent ratio of 25% IPA in liquid CO₂) RT 12.05 min; NMR (400 MHz, DMSO-d6) δ ppm 7.98 (d, J=1.6 Hz, 1H), 7.94 (dd, J=8.0, 1.6 Hz, 1H), 7.76 (s, 1H), 7.57 (d, J=8.0 Hz, 1H), 7.45 (s, 1H), 7.35-7.42 (m, 2H), 7.18 (d, J=8.0 Hz, 1H), 5.07 (d, J=6.4 Hz, 1H), 4.64 (s, 2H), 1.53 (d, J=6.4 Hz, 3H).

Example 260 5-cyano-2-(2-cyano-5-fluoroisoindolin-4-yl)benzamide

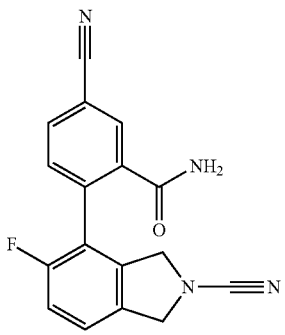 [SMILES: N#Cc1ccc(-c2c(F)ccc3c2CN(C#N)C3)c(C(N)=O)c1]

Step a. To a stirred solution of 5-fluoro-2-methylbenzoic acid (CAS Number 33184-16-6; 19.2 g, 124.675 mmol) in DMF (225 ml) were added N-iodosuccinimide (30.86 g, 137.1 mmol) and palladium(II) acetate (2.8 g, 12.5 mmol) at rt. The resulting reaction mixture was heated at 110° C. for 15 h. The reaction mixture was cooled to rt and poured into water (500 ml). The resulting mixture was extracted with EtOAc (2×200 ml). The combined organic phase was washed with brine (150 ml), dried over $Na_2SO_4$, filtered and concentrated under reduced pressure yielding 3-fluoro-2-iodo-6-methylbenzoic acid (25.0 g, 89.285 mmol). This material was directly used for next step without any further purification. LCMS: Method A, 1.779 min, MS: ES− 279.12.

Step b. To a stirred solution of 3-fluoro-2-iodo-6-methylbenzoic acid (25.0 g, 89.285 mmol) in DMF (50 ml) was added $K_2CO_3$ (24.65 g, 178.570 mmol) at rt. The reaction mixture was stirred at rt for 20 min before addition of ethyl iodide (10.9 g, 133.9 mmol). The reaction mixture was stirred at rt for 2 h. The resulting mixture was poured into water (350 ml) and extracted with EtOAc (3×200 ml). The combined organic phase was washed with brine (150 ml) and dried over $Na_2SO_4$, filtered and concentrated under reduced pressure. The residue was purified by column chromatography (2.5% MeOH in DCM) yielding ethyl 3-fluoro-2-iodo-6-methylbenzoate (27.0 g, 87.662 mmol). LCMS: Method A, 2.330 min, MS: ES+ 309.20

Step c. To a stirred solution of ethyl 3-fluoro-2-iodo-6-methylbenzoate (27.00 g, 87.66 mmol) in $CCl_4$ (270 ml) were added NBS (23.4 g, 131.5 mmol) and AIBN (1.44 g, 8.77 mmol) at rt. The resulting reaction mixture was heated at 90° C. for 15 h. The reaction mixture was cooled to 10° C. The reaction mixture was filtered and washed with $CCl_4$ (20 ml). The resulting filtrate was concentrated under reduced pressure. The residue was purified by flash column chromatography (23% EtOAc in n-hexane) yielding ethyl 6-(bromomethyl)-3-fluoro-2-iodobenzoate (31.000 g, 80.310 mmol). $^1$H NMR (400 MHz, DMSO-d6) δ ppm 7.68-7.59 (m, 1H), 7.39 (d, J=8.0 Hz, 1H), 4.65 (s, 2H), 4.35-4.46 (m, 2H), 1.32-1.38 (m, 3H).

Step d. To a solution of ethyl 6-(bromomethyl)-3-fluoro-2-iodobenzoate (31.000 g, 80.310 mmol) in EtOH (210 ml) was added $K_2CO_3$ (44.330 g, 321.240 mmol) and 4-methoxybenzyl amine (13.20 g, 96.4 mmol) at rt. The reaction mixture was heated at 80° C. for 15 h. The reaction mixture was cooled to rt and concentrated under reduced pressure. The reaction mixture was poured into saturated $NaHCO_3$ solution (200 ml) and extracted with EtOAc (3×100 ml). The combined organic phase was dried over $Na_2SO_4$, filtered and concentrated under reduced pressure. The residue was purified by flash column chromatography (35% EtOAc in n-hexane) yielding 6-fluoro-7-iodo-2-(4-methoxybenzyl)isoindolin-1-one (22.0 g, 55.4 mmol). LCMS: Method A, 2.082 min, MS: ES+ 398.48; $^1$H NMR (400 MHz, DMSO-d6) δ ppm 7.56-7.52 (m, 1H), 7.45 (t, J=8.4 Hz, 1H), 7.23 (d, J=8.4 Hz, 2H), 6.91 (d, J=8.4 Hz, 2H), 4.64 (s, 2H), 4.23 (s, 2H), 3.73 (s, 3H).

Step e. To a solution of 6-fluoro-7-iodo-2-(4-methoxybenzyl)isoindolin-1-one (22.0 g, 55.4 mmol) in THF (220 ml) was drop wise added $BH_3$-DMS (42.060 ml, 443.320 mmol) at 0° C. The reaction mixture was stirred at rt for 15 h and then reaction mixture was stirred at 75° C. for 24 h. The reaction mixture was again cooled to 0° C. Second lot of $BH_3$-DMS (42.060 ml, 443.320 mmol) was added to the reaction mixture at 0° C. The reaction mixture was again stirred at rt for 15 h and then heated at 75° C. for 24 h. The reaction mixture was cooled to 0° C. and quenched with slow addition of MeOH (50 ml). The resulting mixture was heated at 75° C. for 2 h. The resulting reaction mixture was cooled to rt and concentrated under reduced pressure. The residue was purified by flash column chromatography (2% MeOH in DCM) yielding 5-fluoro-4-iodo-2-(4-methoxybenzyl)isoindoline (15.00 g, 39.16 mmol). LCMS: Method A, 1.509 min, MS: ES+ 384.38.

Step f. To a solution of 5-fluoro-4-iodo-2-(4-methoxybenzyl)isoindoline (10.00 g, 26.11 mmol) in chlorobenzene (80 ml) was added 4 Å molecular sieves (5 g) at rt. The resulting reaction mixture was stirred at rt for 30 min. 1-Chloroethyl chloroformate (7.500 g, 52.22 mmol) was added to the reaction mixture at 0° C. The resulting reaction mixture was stirred at rt for 15 min and then heated at 90° C. for 5 h. The resulting mixture was filtered through celite bed and washed with MeOH (35 ml). The combined filtrate was heated at 90° C. for 2 h. The reaction mixture was cooled to 0° C. and slowly diluted with n-hexane (40 ml). The resulting mixture was stirred at 0° C. for 30 min. The resulting precipitates were filtered off under vacuum, washed with n-hexane (20 ml) and dried under vacuum yielding 5-fluoro-4-iodoisoindoline HCl salt (6.000 g, 20.03 mmol). The material was used as such in next step without further purification. LCMS: Method A, 1.325 min, MS: ES+ 264.29; $^1$H NMR (400 MHz, DMSO-d6) δ ppm 10.14 (s, 2H), 7.44-7.40 (m, 1H), 7.24 (t, J=8.4 Hz, 1H), 4.62 (s, 2H), 4.42 (s, 2H).

Step g. To a solution of 5-fluoro-4-iodoisoindoline HCl salt (6.000 g, 20.03 mmol) in THF (60 ml) was added TEA (7.0 ml, 50.1 mmol) at rt. The reaction mixture was stirred at rt for 10 min. Boc anhydride (8.730 g, 40.07 mmol) was added to the reaction mixture at rt. The reaction mixture was stirred at rt for 3 h. The reaction mixture was poured into water (200 ml) and extracted with EtOAc (2×150 ml). The combined organic phase was dried over $Na_2SO_4$, filtered and concentrated under reduced pressure. The residue was purified by flash column chromatography (10% EtOAc in n-hexane) yielding tert-butyl 5-fluoro-4-iodoisoindoline-2-carboxylate (6.000 g, 16.53 mmol). LCMS: Method A, 2.653 min, MS: ES+ 308.10 [M−56]; $^1$H NMR (400 MHz, DMSO-d6) δ ppm 7.36-7.32 (m, 1H), 7.16 (t, J=8.4 Hz, 1H), 4.69 (d, J=10.8 Hz, 2H), 4.46 (d, J=8.8 Hz, 2H), 1.47 (d, J=5.2 Hz, 9H)

Step h was carried out in a similar method to Example 226 step a yielding tert-butyl 5-fluoro-4-(4,4,5,5-tetramethyl-1,3,2-dioxaborolan-2-yl)isoindoline-2-carboxylate LCMS: Method A, 2.721 min, MS: ES+ 308.10 [M−56].

Step i. To a stirred solution of tert-butyl 5-fluoro-4-(4,4,5,5-tetramethyl-1,3,2-dioxaborolan-2-yl)isoindoline-2-carboxylate (3.630 g, 10.00 mmol) in 1,4-dioxane:water (9:1, 20 ml) were added K₂CO₃ (2.300 g, 16.67 mmol) and methyl 2-bromo-5-cyanobenzoate (CAS Number 1031927-03-3; 2.00 g, 8.33 mmol) at rt. The reaction mixture was degassed for 20 min before addition of PdCl₂(dppf) (0.610 g, 0.833 mmol). The reaction mixture was heated at 110° C. for 15 h. The reaction mixture was cooled to rt and poured into water (100 ml). The resulting mixture was extracted with EtOAc (2×100 ml). The combined organic phase was washed with brine (100 ml), dried over Na₂SO₄, filtered and concentrated under reduced pressure. The residue was purified by flash column chromatography (25% EtOAc in n-hexane) yielding tert-butyl 4-(4-cyano-2-(methoxycarbonyl)-phenyl)-5-fluoroisoindoline-2-carboxylate (2.20 g, 5.55 mmol). LCMS: Method A, 2.539 min, MS: ES+ 341.27 [M−56].

Step j. To a solution of tert-butyl 4-(4-cyano-2-(methoxycarbonyl)phenyl)-5-fluoroisoindoline-2-carboxylate (2.200 g, 5.555 mmol) in THF:water (1:1, 30 ml) was added LiOH.H₂O (0.710 g, 16.725 mmol) at rt. The reaction mixture was stirred at rt for 15 h. The resulting reaction mixture was diluted by saturated NaHCO₃ solution (30 ml) and extracted with EtOAc (30 ml) to separate undesired impurities. The resulting aqueous layer was acidified by 1M HCl (50 ml) and extracted with EtOAc (3×50 ml). The combined organic phase was dried over Na₂SO₄, filtered and concentrated under reduced pressure yielding 2-(2-(tert-butoxycarbonyl)-5-fluoroisoindolin-4-yl)-5-cyanobenzoic acid (1.800 g, 4.71 mmol). This material was directly used for next step without any further purification. LCMS: Method A, 2.018 min, MS: ES− 381.60.

Step k. To a solution of 2-(2-(tert-butoxycarbonyl)-5-fluoroisoindolin-4-yl)-5-cyanobenzoic acid (1.800 g, 4.712 mmol) in THF (20 ml) were added EDC.HCl (1.360 g, 7.068 mmol), HOBt (0.870 g, 5.654 mmol) and DIPEA (1.62 ml, 9.424 mmol) at rt. The reaction mixture was stirred for 20 min before addition of NH₄Br (2.300 g, 23.56 mmol). The reaction mixture was stirred at rt for 3 h. Extra NH₄Br (2.300 g, 23.56 mmol) was added to the reaction mixture and stirred for a further 15 h. The resulting reaction mixture was poured into water (100 ml) and extracted with EtOAc (2×80 ml). The combined organic phase was washed with brine (50 ml), dried over Na₂SO₄, filtered and concentrated under reduced pressure. The residue was purified by flash chromatography (2.3% MeOH in DCM) yielding tert-butyl 4-(2-carbamoyl-4-cyanophenyl)-5-fluoroisoindoline-2-carboxylate (0.500 g, 1.312 mmol). LCMS: Method A, 1.889 min, MS: ES+ 382.50.

Steps l and m were carried out in a similar manner to the last 2 steps of Example 258. LCMS: Method D, 2.931 min, MS: ES+ 324.10 [M+18]; ¹H NMR (400 MHz, DMSO-d6) δ ppm 8.07 (s, 1H), 8.02 (d, J=8.0 Hz, 1H), 7.90 (br s, 1H), 7.60 (d, J=8.0 Hz, 1H), 7.46 (br s, 1H), 7.38-7.35 (m, 1H), 7.23 (t, J=9.2 Hz, 1H), 4.82 (br s, 2H), 4.67 (d, J=9.2 Hz, 1H), 4.46 (d, J=9.2 Hz, 1H).

Example 261 5-cyano-2-(2-cyano-7-fluoroisoindolin-4-yl)benzamide

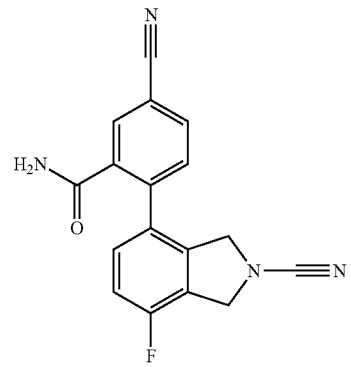 [SMILES: N#Cc1ccc(-c2ccc(F)c3c2CN(C#N)C3)c(C(N)=O)c1]

Step a. To a solution of 3-bromo-6-fluoro-o-xylene (CAS Number 52548-00-2; 3.00 g, 14.8 mmol) in CCl₄ (45 ml) was added NBS (5.780 g, 32.51 mmol) at rt. The reaction mixture was exposed to a UV light source which increased the temperature, in this manner the reaction mixture was heated at 85° C. for 2 h. The reaction mixture was cooled to rt and poured into saturated NaHCO₃ solution (100 ml). The resulting mixture was extracted with EtOAc (3×100 ml). The combined organic phase was washed with brine (100 ml), dried over Na₂SO₄, filtered and concentrated under reduced pressure yielding 1-bromo-2,3-bis(bromomethyl)-4-fluorobenzene (5.80 g, 16.25 mmol). This material was directly used for next step without any further purification. LCMS: Method A, 2.489 min.

Step b. To a solution of 1-bromo-2,3-bis(bromomethyl)-4-fluorobenzene (5.00 g, 13.97 mmol) in EtOH (50 ml) were added K₂CO₃ (7.71 g, 55.9 mmol) and 4-methoxybenzylamine (2.300 g, 16.77 mmol) at rt. The reaction mixture was heated at 80° C. for 2 h. The reaction mixture was poured into saturated NaHCO₃ solution (200 ml) and extracted with EtOAc (3×150 ml). The combined organic phase was washed with brine (200 ml), dried over Na₂SO₄, filtered and concentrated under reduced pressure. The residue was purified by column chromatography (2% EtOAc in n-hexane) yielding 4-bromo-7-fluoro-2-(4-methoxybenzyl)isoindoline (1.60 g, 4.77 mmol). LCMS: Method A, 1.600 min, MS: ES+ 336.40, 338.38; ¹H NMR (400 MHz, DMSO-d6) δ ppm 7.46-7.43 (m, 1H), 7.30-7.27 (m, 2H), 7.06 (t, J=8.8 Hz, 1H), 6.93-6.90 (m, 2H), 4.01 (s, 2H), 3.82 (s, 4H), 3.75 (s, 3H).

Step c. To a solution of 4-bromo-7-fluoro-2-(4-methoxybenzyl)isoindoline (1.60 g, 4.77 mmol) in chlorobenzene (15 ml) was added 4 Å molecular sieves (0.800 g) at rt. 1-Chloroethyl chloroformate (1.550 g, 14.33 mmol) was added to the reaction mixture at rt and the reaction was heated at 110° C. for 3 h. The reaction mixture was filtered through celite bed and washed with MeOH:DCM (1:1, 35 ml). The combined filtrate was concentrated under reduced pressure. The crude product was triturated with n-hexane (2×10 ml) and dried under vacuum yielding 4-bromo-7-fluoroisoindoline HCl salt (0.800 g, 3.19 mmol). This material was directly used for next step without any further purification. LCMS: Method A, 1.277 min, MS: ES+ 216.23, 218.23.

Step d. To a solution of 4-bromo-7-fluoroisoindoline HCl salt (0.800 g, 3.19 mmol) in THF (10 ml) was added TEA (0.86 ml, 6.37 mmol) and Boc anhydride (0.830 g, 3.824 mmol) at 0° C. The reaction mixture was stirred at rt for 1 h. The resulting reaction mixture was poured into water (50 ml) and extracted with EtOAc (2×50 ml). The combined organic phase was dried over Na$_2$SO$_4$, filtered and concentrated under reduced pressure. The residue was purified by flash column chromatography (1% MeOH in DCM) yielding tert-butyl 4-bromo-7-fluoroisoindoline-2-carboxylate (0.600 g, 1.90 mmol). LCMS: Method A, 2.652 min, MS: ES+ 316.38, 318.38.

Step e was carried out in a similar method to Example 226 step a yielding tert-butyl 4-fluoro-7-(4,4,5,5-tetramethyl-1,3,2-dioxaborolan-2-yl)isoindoline-2-carboxylate. LCMS: Method A, 2.928 min, MS: ES+ 308.27 [M−56].

Step f. To a stirred solution of tert-butyl 4-fluoro-7-(4,4,5,5-tetramethyl-1,3,2-dioxaborolan-2-yl)isoindoline-2-carboxylate (0.246 g, 0.677 mmol) in 1,4-dioxane:water (9:1, 5 ml) were added K$_2$CO$_3$ (0.189 g, 1.375 mmol) and methyl 2-bromo-5-cyanobenzoate (CAS Number 1031927-03-3; 0.165 g, 0.687 mmol) at rt. The reaction mixture was degassed for 20 min before addition of PdCl$_2$(dppf) (0.050 g, 0.068 mmol). The resulting reaction mixture was heated at 90° C. for 15 h. The reaction mixture was cooled to rt and poured into water (50 ml). The resulting mixture was extracted with EtOAc (2×50 ml). The combined organic phase was dried over Na$_2$SO$_4$, filtered and concentrated under reduced pressure. The residue was purified by flash column chromatography (14% EtOAc in n-hexane) yielding tert-butyl 4-(4-cyano-2-(methoxycarbonyl)phenyl)-7-fluoroisoindoline-2-carboxylate (0.200 g 0.505 mmol). LCMS: Method A, 2.419 min, MS: ES+ 341.32 [M−56]

Step g. To a solution of tert-butyl 4-(4-cyano-2-(methoxycarbonyl)phenyl)-7-fluoroisoindoline-2-carboxylate (0.200 g, 0.505 mmol) in THF:water:MeOH (1:1:0.1, 6.3 ml) was added LiOH.H$_2$O (0.063 g, 1.515 mmol) at 0° C. The reaction mixture was stirred at rt for 2 h. The resulting reaction mixture was acidified with 1M HCl (15 ml) and extracted with EtOAc (3×20 ml). The combined organic phase was dried over Na$_2$SO$_4$, filtered and concentrated under reduced pressure yielding 2-(2-(tert-butoxycarbonyl)-7-fluoroisoindolin-4-yl)-5-cyanobenzoic acid (0.160 g, 0.418 mmol). This material was directly used for next step without any further purification. LCMS: Method A, 2.116 min, MS: ES+ 327.40 [M−56].

Steps h-j were carried out in a similar manner to the last 3 steps of Example 260. LCMS: Method D, 3.572 min, MS: ES+ 307.08; $^1$H NMR (400 MHz, DMSO-d6) δ ppm 7.94-8.03 (m, 2H), 7.80 (s, 1H), 7.56 (d, J=8.0 Hz, 1H), 7.47 (s, 1H), 7.22-7.28 (m, 2H), 4.94 (s, 2H), 4.70 (s, 2H).

Example 262 6-(1-methyl-6-oxopiperidin-3-yl)-4-phenylisoindoline-2-carbonitrile

Step a. To a stirred solution of tert-butyl 6-bromo-4-phenylisoindoline-2-carboxylate (prepared as in step a of Example 5, 0.200 g, 0.536 mmol) in 1,4-dioxane:water (9:1, 5 ml) were added Na$_2$CO$_3$ (0.113 g, 1.072 mmol) and 1-methyl-5-(4,4,5,5-tetramethyl-1,3,2-dioxaborolan-2-yl)pyridin-2 (1H)-one (CAS Number 1002309-52-5; 0.189 g) at rt in a microwave tube. The reaction mixture was degassed for 30 min before addition of PdCl$_2$(dppf) (0.039 g, 0.053 mmol). The resulting reaction mixture was heated at 120° C. for 2 h in Microwave. The reaction mixture was cooled to rt and poured into water (30 ml). The resulting mixture was extracted with EtOAc (3×10 ml). The combined organic phase dried over Na$_2$SO$_4$, filtered and concentrated under reduced pressure. The obtained residue was purified by flash-column chromatography (3.1% MeOH in DCM) yielding tert-butyl 6-(1-methyl-6-oxo-1,6-dihydropyridin-3-yl)-4-phenylisoindoline-2-carboxylate (0.070 g, 0.173 mmol). LCMS: Method A, 2.505 min, MS: ES+ 403.4 [M+H].

Step b. A stirred solution of tert-butyl 6-(1-methyl-6-oxo-1,6-dihydropyridin-3-yl)-4-phenyl-isoindoline-2-carboxylate (0.07 g, 0.173 mmol) in MeOH (10 ml) was added 10% Pd/C (100% dry) (0.050 g) at rt in autoclave. The resulting reaction mixture was pressurized with H$_2$ gas up to 20 kg atmosphere and heated at 80° C. for 72 h. The reaction mixture was filtered through celite bed and washed with MeOH (30 ml). The resulting filtrate was concentrated under reduced pressure yielding a mixture of tert-butyl 6-(1-methyl-6-oxopiperidin-3-yl)-4-phenylisoindoline-2-carboxylate and tert-butyl 6-(1-methyl-6-oxo-1,6-dihydropyridin-3-yl)-4-phenylisoindoline-2-carboxylate (80:20). (0.077 g). This material was directly used for next step without any further purification. LCMS: Method A, 2.378 min, MS: ES+ 407.47 and Method A, 2.349 min, MS: ES+ 403.41.

Steps c and d were carried out in a similar manner to steps d and e of Example 1 yielding desired 6-(1-methyl-6-oxopiperidin-3-yl)-4-phenylisoindoline-2-carbonitrile and a byproduct from incomplete reduction in step b 6-(1-methyl-6-oxo-1,6-dihydropyridin-3-yl)-4-phenylisoindoline-2-carbonitrile LCMS: Method D, 3.974 min, MS: ES+ 332.20.

Example 263 6-(1-methyl-6-oxo-1,6-dihydropyridin-3-yl)-4-phenylisoindoline-2-carbonitrile

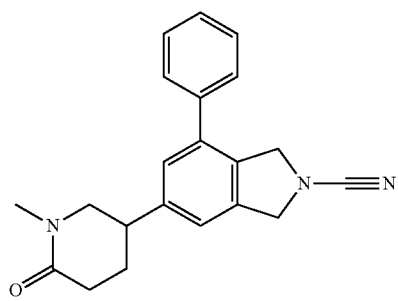 [SMILES: CN1CC(c2cc3c(c(-c4ccccc4)c2)CN(C#N)C3)CCC1=O]

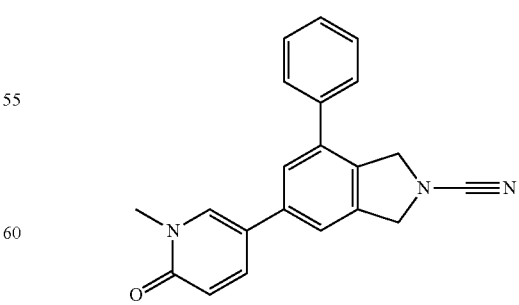

This was prepared as described in the preparation of Example 262 above. LCMS: Method D, 3.929 min, MS: ES+ 328.20

Example 264 N-(2-cyano-7-(4-cyanophenyl)isoindolin-5-yl)tetrahydro-2H-pyran-4-carboxamide

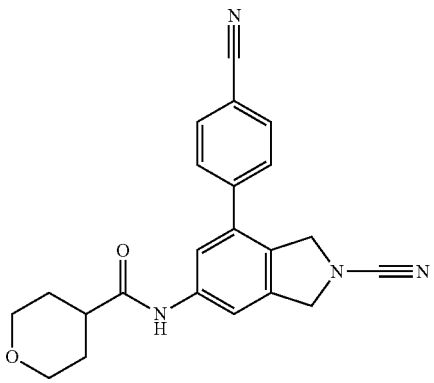 [SMILES: N#Cc1ccc(-c2cc(NC(=O)C3CCOCC3)cc3c2CN(C#N)C3)cc1]

Step a. Nitrogen was bubbled through a solution of tert-butyl 4-bromo-6-nitroisoindoline-2-carboxylate (Intermediate 3, 1.0 g, 2.90 mmol), 4-cyanophenylboronic acid (630 mg, 4.30 mmol) and cesium carbonate (1.9 g, 5.80 mmol) in a 4:1 (v/v) mixture of 1,4-dioxane and water (25 ml) for 15 min. Pd(Ph$_3$P)$_4$ (340 mg, 0.29 mmol) was added and the resulting mixture was heated at 90° C. and monitored by LCMS. After 1 h, the reaction mixture was cooled to rt, poured into water and extracted with EtOAc (3×20 ml). The combined organic extracts were washed with brine (10 ml), dried over Na$_2$SO$_4$, filtered and evaporated. The residue was triturated with Et$_2$O (20 ml), then with hexane (30 ml) and dried. Tert-butyl 4-(4-cyanophenyl)-6-nitroisoindoline-2-carboxylate (857 mg, 81%) was obtained as a light brown solid. LCMS (Method I): rt 2.82 min, m/z 266 [M+H-Boc]$^+$; $^1$H NMR (400 MHz, CDCl$_3$) δ ppm 8.33 (m, 1H), 8.16 (m, 1H), 8.04-7.97 (m, 2H), 7.86-7.79 (m, 2H), 4.80-4.72 (m, 4H), 1.44 (d, 9H).

Step b. A mixture of tert-butyl 4-(4-cyanophenyl)-6-nitroisoindoline-2-carboxylate (857 mg, 2.35 mmol), iron powder (655 mg, 11.72 mmol), NH$_4$Cl (627 mg, 11.72 mmol), THF (12 ml) and water (12 ml) was heated at 90° C. for 18 h. The reaction mixture was cooled to rt and filtered through a pad of Celite®, which was subsequently washed with EtOAc (3×25 ml). The combined filtrate was washed with brine (25 ml), dried over Na$_2$SO$_4$, filtered and evaporated to give tert-butyl 6-amino-4-(4-cyanophenyl)isoindoline-2-carboxylate as a brown solid (590 mg, 75%). LCMS (Method I): rt 2.63 min, m/z 336 [M+H]$^+$; $^1$H NMR (400 MHz, DMSO-d6) δ ppm 8.06-7.50 (m, 6H), 6.55 (m, 1H), 5.29 (s, 1H), 4.81-4.42 (m, 4H), 1.49-1.38 (m, 9H).

Step c. To a solution of tetrahydro-2H-pyran-4-carboxylic acid (80 mg, 0.60 mmol) in THF (8 ml) was added DIPEA (0.13 mL, 0.80 mmol) and HATU (228 mg, 0.60 mmol) at rt, and the resulting mixture was stirred for 30 min. tert-Butyl 6-amino-4-(4-cyanophenyl)isoindoline-2-carboxylate (126 mg, 0.37 mmol) was then added to the reaction, and the resulting mixture was stirred for 18 h. The reaction mixture was poured into water (40 ml) and extracted with EtOAc (3×30 ml). The combined organic extracts were washed with brine (20 ml), dried over Na$_2$SO$_4$, filtered and evaporated to give a brown oil (270 mg), which was purified by reverse phase HPLC (Agilent pursuit 5 C18 with UV detection at 254 nm) eluting with a gradient 50-95% MeCN in water+ 0.1% formic acid to give tert-butyl 4-(4-cyanophenyl)-6-(tetrahydro-2H-pyran-4-carboxamido)isoindoline-2-carboxylate as a white solid (62 mg, 38%). LCMS (Method I): rt 2.65 min, m/z 392 [M-t-Bu+H]$^+$. $^1$H NMR (400 MHz, DMSO-d6) δ ppm 10.09 (bs, 1H), 7.96 (m, 2H), 7.75-7.54 (m, 4H), 4.70-4.56 (m, 4H), 3.91 (m, 2H), 2.65-2.54 (m, 1H), 1.78-1.58 (m, 4H), 1.44 (d, 9H).

Steps d and e were carried out in a similar manner to steps d and e of Example 1. LCMS (Method I): rt 2.51 min, m/z 373 [M+H]$^+$; $^1$H NMR (400 MHz, DMSO-d$_6$) δ ppm 10.13 (brs, 1H), 7.97-7.92 (m, 2H), 7.71-7.61 (m, 4H), 4.83 (m, 4H), 3.91 (m, 2H), 2.61 (m, 1H), 1.76-1.58 (m, 5H), 2.08 (m, 1H).

Compounds in Table 24 were prepared in a manner similar to Example 264.

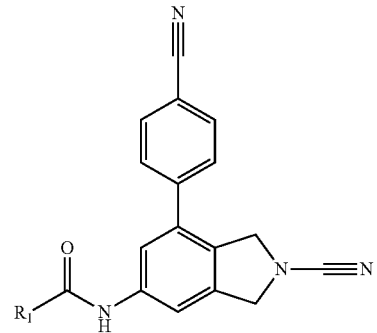

TABLE 24

| Ex | Name | R$_1$— | Alkylating Agent CAS Number | LCMS method | LCMS RT/min | MS ES+ |
|---|---|---|---|---|---|---|
| Example 265 | N-(2-cyano-7-(4-cyanophenyl)isoindolin-5-yl)-1-methyl-5-oxopyrrolidine-3-carboxamide | | 42346-68-9 | I | 0.61 | 386 |
| Example 266 | N-(2-cyano-7-(4-cyanophenyl)isoindolin-5-yl)-1-methyl-6-oxopiperidine-3-carboxamide | | 22540-51-8 | I | 0.56 | 400 |

TABLE 24-continued

| Ex | Name | R₁— | Alkylating Agent CAS Number | LCMS method | LCMS RT/min | MS ES+ |
|---|---|---|---|---|---|---|
| Example 267 | N-(2-cyano-7-(4-cyano-phenyl)isoindolin-5-yl)-2-(dimethylamino)acetamide | 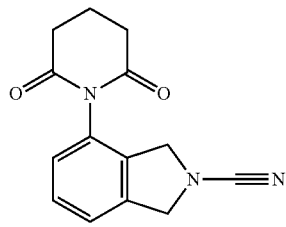 | 1118-68-9 | I | 2.28 | 346 |

Example 268 4-(2,6-dioxopiperidin-1-yl)isoindoline-2-carbonitrile

Example 269 4-(4-cyanophenyl)-6-(methylamino)isoindoline-2-carbonitrile

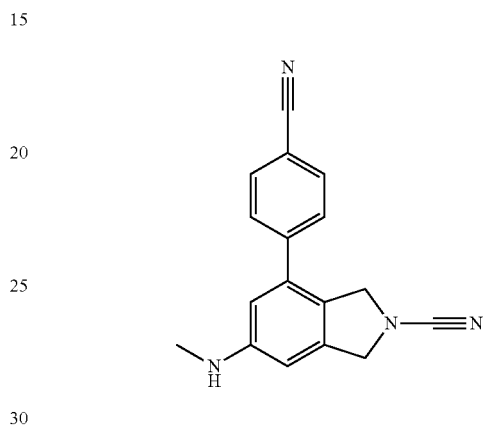

Step a. A Reacti-Vial™ was charged with tert-butyl 4-(4,4,5,5-tetramethyl-1,3,2-dioxaborolan-2-yl)isoindoline-2-carboxylate (Intermediate 2, 200 mg, 0.58 mmol), glutarimide (60 mg, 0.53 mmol), copper(II) acetate monohydrate (43 mg, 0.21 mmol), DMF (0.6 ml) and pyridine (0.18 ml, 2.16 mmol), and the resulting mixture was stirred at 90° C. for 8 h. The mixture was cooled to rt and partitioned between EtOAc (15 ml) and water (5 ml). The aqueous phase was extracted with EtOAc (10 ml) and the combined organic extracts were washed with brine (10 ml), dried over Na₂SO₄, filtered and evaporated under vacuum. The residue was purified by flash column chromatography (0-5% MeOH in DCM) to give an oily solid (150 mg), which was triturated in diethyl ether to give tert-butyl 4-(2,6-dioxopiperidin-1-yl)isoindoline-2-carboxylate as a solid (120 mg, 62%). LCMS (Method I): rt 2.57 min, m/z 275 (-tBu)/231(-Boc) [M+H]⁺; ¹H NMR (400 MHz, CDCl₃) δ ppm 7.36-7.28 (m, 1H), 7.15-7.09 (m, 1H), 7.01-6.94 (m, 1H), 4.71 (s, 2H), 4.46 (d, 2H), 2.89 (m, 4H), 1.51 (d, 11H).

Steps b and c were carried out in a similar manner to steps b and c of Example 21. LCMS (Method I): rt 2.32 min, m/z 256 [M+H]⁺; ¹H NMR (400 MHz, CDCl₃) δ ppm 7.46-7.37 (m, 1H), 7.31-7.26 (m, 1H), 7.08-6.99 (m, 1H), 4.84 (s, 2H), 4.55 (s, 2H), 2.90-2.75 (m, 4H), 2.19-2.03 (m, 2H).

Step a. TFAA (0.07 mL, 0.48 mmol) was added dropwise to a stirred solution of tert-butyl 6-amino-4-(4-cyanophenyl)isoindoline-2-carboxylate (prepared as in step b of Example 264, 80 mg, 0.24 mmol) and TEA (0.1 ml, 0.72 mmol) in DCM (5 ml) at rt, and the resulting mixture was stirred for 30 min. The reaction mixture was evaporated to dryness under vacuum to give a residue, which was partitioned between DCM (10 ml) and a saturated solution of NaHCO₃ (10 ml). The organic phase was collected, dried over Na₂SO₄, filtered and concentrated to dryness under vacuum to give tert-butyl 4-(4-cyanophenyl)-6-(2,2,2-trifluoroacetamido)isoindoline-2-carboxylate as a brown solid (90 mg, 100%). LCMS (Method I): rt 2.81 min, m/z 376 [M+H-tBu]⁺

Step b. Methyl iodide (22 µL 0.36 mmol) was added to a stirred suspension of potassium carbonate (66 mg, 0.48 mmol) and tert-butyl 4-(4-cyanophenyl)-6-(2,2,2-trifluoroacetamido)isoindoline-2-carboxylate (90 mg, 0.21 mmol) in MeCN (5 ml), and the resulting mixture was heated at 40° C. in a sealed tube for 18 h. The reaction mixture was cooled to rt and poured into water (20 ml), before being extracted with DCM (2×20 ml). The combined organic extracts were washed with water (20 ml), dried over Na₂SO₄ and evaporated to dryness under vacuum to give tert-butyl 4-(4-cyanophenyl)-6-(2,2,2-trifluoro-N-methylacetamido)isoindoline-2-carboxylate as a brown oil (74 mg, 80%). LCMS (Method I): rt 2.76 min, m/z 350 [M+H—CF₃CO]⁺; ¹H NMR (400 MHz, CDCl₃) δ ppm 7.67-7.61 (m, 2H), 7.38-7.36 (m, 2H), 7.12-7.02 (m, 2H), 4.66-4.54 (m, 4H), 3.27 (s, 3H), 1.37 (s, 9H).

Steps c and d were carried out in a similar manner to steps b and c of Example 21 to give N-(2-cyano-7-(4-cyanophenyl)isoindolin-5-yl)-2,2,2-trifluoro-N-methylacetamide as a white solid. LCMS (Method I): rt 2.60 min, m/z 371 [M+H]⁺

Step e. A solution of N-(2-cyano-7-(4-cyanophenyl)isoindolin-5-yl)-2,2,2-trifluoro-N-methylacetamide (44 mg, 0.12 mmol) and ammonium hydroxide (35%, 2 ml) in a 1:4 (v/v)

mixture of MeOH and DCM (5 ml) was stirred at rt for 5 h. The reaction mixture was evaporated to dryness under vacuum to give a residue, which was purified by reverse phase HPLC over an Agilent Pursuit 5 C18 column, eluting with a gradient (60-66%) of MeCN in water+0.1% formic acid with detection at 254 nm to give a solid. The solid material was recrystallized from DCM and hexane to give 4-(4-cyanophenyl)-6-(methylamino)isoindoline-2-carbonitrile was obtained as an off-white solid (14 mg, 83%). LCMS (Method I): rt 2.54 min, m/z 275 [M+H]$^+$; $^1$H NMR (400 MHz, CDCl$_3$) δ ppm 7.70 (d, 2H), 7.45 (d, 2H), 6.48 (m, 2H), 4.74 (m, 2H), 4.66 (m, 2H), 2.86 (s, 3H).

Example 270 4-(4-cyanophenyl)-6-(dimethylamino)isoindoline-2-carbonitrile

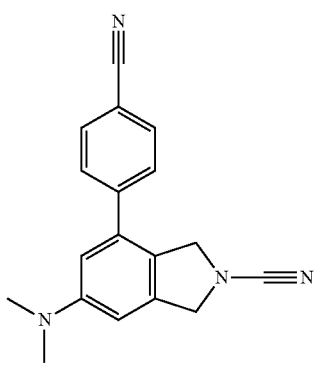 [SMILES: CN(C)c1cc2c(c(-c3ccc(C#N)cc3)c1)CN(C#N)C2]

Step a. A solution of tert-butyl 6-amino-4-(4-cyanophenyl)isoindoline-2-carboxylate (prepared as in step b of Example 264, 160 mg, 0.48 mmol), paraformaldehyde (29 mg, 0.96 mmol), AcOH (83 μl, 1.44 mmol) and sodium triacetoxyborohydride (254 mg, 1.2 mmol) in MeCN (3 ml) was heated at 110° C. for 18 h. The reaction mixture was cooled to rt, poured into saturated NaHCO$_3$ and extracted with EtOAc (3×25 ml). The combined organic extracts were washed with brine, dried over Na$_2$SO$_4$, filtered and evaporated. The residue was purified by flash column chromatography (0-40% EtOAc in hexane) to give tert-butyl 4-(4-cyanophenyl)-6-(dimethylamino)-isoindoline-2-carboxylate as a yellow solid (87 mg, 53%). LCMS (Method I): rt 2.62 min, m/z 364 [M+H]$^+$ Steps b and c were carried out in a similar manner to the final two steps of Example 21. LCMS (Method I): rt 2.64 min, m/z 289 [M+H]$^+$; $^1$H NMR (400 MHz, DMSO-d6) δ ppm 7.92 (d, 2H), 7.72 (d, 2H), 6.74 (d, 1H), 6.69 (d, 1H), 4.76 (s, 4H), 2.95 (s, 6H).

Example 271 4-(4-cyanophenyl)-6-((2-hydroxyethyl)amino)isoindoline-2-carbonitrile

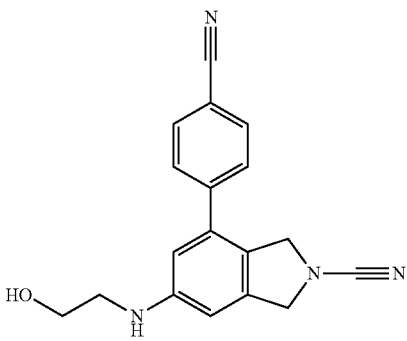 [SMILES: N#Cc1ccc(-c2cc(NCCO)cc3c2CN(C#N)C3)cc1]

Step a. A solution of tert-butyl 6-amino-4-(4-cyanophenyl)isoindoline-2-carboxylate (prepared as in step b of Example 264, 155 mg, 0.46 mmol), 2-((tert-butyldimethylsilyl)oxy)-acetaldehyde (98 mg, 0.51 mmol), AcOH (40 μl, 0.69 mmol) and sodium triacetoxyborohydride (196 mg, 0.93 mmol) in DCE (6 ml) was stirred for 18 h, at rt. The reaction mixture was poured into saturated NaHCO$_3$ and extracted with DCM (3×50 ml). The combined organic extracts were washed with brine, dried over Na$_2$SO$_4$, filtered and evaporated. The residue was purified by flash column chromatography (0-25% EtOAc in hexane) to give tert-butyl 6-42-((tert-butyldimethylsilyl)-oxy)ethyl)amino)-4-(4-cyanophenyl)-isoindoline-2-carboxylate as a yellow solid (110 mg, 49%). LCMS (Method I): rt 3.37 min, m/z 494 [M+H]$^+$; $^1$H NMR (400 MHz, CDCl$_3$) δ ppm 7.62 (dd, 2H), 7.44 (d, 2H), 6.40-6.50 (m, 2H), 4.40-4.60 (m, 4H), 4.78 (s, 2H), 3.76 (t, 2H), 3.16 (t, 2H), 1.41 (d, 9H), 0.83 (s, 9H), 0.00 (s, 6H).

Step b. A solution of tert-butyl 6-42-((tert-butyldimethylsilyl)oxy)ethyl)amino)-4-(4-cyanophenyl)isoindoline-2-carboxylate (110 mg, 0.22 mmol) and HCl (4 M in 1,4-dioxane, 2.2 ml, 8.8 mmol) in 1,4-dioxane (2 ml) was stirred at rt for 3 h. Further HCl (4 M in 1,4-dioxane, 2.0 ml) was added and stirred at rt for a further 2 h The mixture was evaporated to give a residue, which was azeotroped with toluene/MeCN [1:1] (3×15 ml) and dried to give 4-(6-((2-hydroxyethyl)amino)-isoindolin-4-yl)benzonitrile bis HCl salt as a yellow solid (105 mg). LCMS (Method I): rt 1.08 min, m/z 280 [M+H]$^+$. $^1$H NMR (400 MHz, CD$_3$OD) δ ppm 7.90 (d, 2H), 7.72 (d, 2H), 7.60 (d, 1H), 7.54 (d, 1H), 4.78 (s, 2H), 4.74 (s, 2H), 3.80 (t, 2H), 3.56 (t, 2H).

Step c was carried out in a similar manner to the final step of Example 21. LCMS (Method J): rt 2.94 min, m/z 305 [M+H]$^+$. $^1$H NMR (400 MHz, CD$_3$OD) δ ppm 7.79 (d, 2H), 7.60 (d, 2H), 6.65 (d, 1H), 6.62 (d, 1H), 4.74 (d, 2H), 4.71 (d, 2H), 3.73 (t, 2H), 3.26 (t, 2H).

Example 272 4-(4-cyanophenyl)-6-(isopropylamino)isoindoline-2-carbonitrile

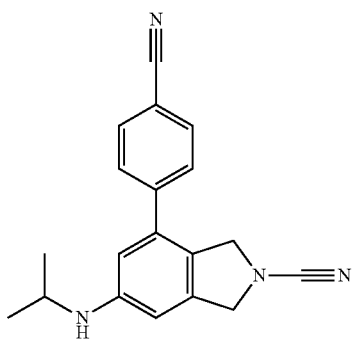 [SMILES: CC(C)Nc1cc2c(c(-c3ccc(C#N)cc3)c1)CN(C#N)C2]

Step a. A solution of tert-butyl 6-amino-4-(4-cyanophenyl)isoindoline-2-carboxylate (80 mg, 0.24 mmol), acetone (20 μl, 0.26 mmol), AcOH (16 μl, 0.28 mmol) and sodium triacetoxyborohydride (80 mg, 0.36 mmol) in THF (1 ml) was heated for 3 days, at 70° C. The reaction mixture was cooled to rt, poured into saturated NaHCO$_3$ and extracted with diethyl ether. The organic extract was dried over Na$_2$SO$_4$, filtered and evaporated to give a residue, which was purified by trituration with MeOH/diethyl ether and subsequently with EtOAc/hexane to give tert-butyl 4-(4-cyanophenyl)-6-(isopropylamino)-isoindoline-2-carboxylate (78 mg, 86%). LCMS (Method I): rt 2.77 min, m/z 378 [M+H]$^+$.

Steps b and c were carried out in a similar manner to the final two steps of Example 21. LCMS (Method I): rt 2.57 min, m/z 303 [M+H]$^+$; $^1$H NMR (400 MHz, DMSO-d6) δ ppm 7.91 (d, 2H), 7.64 (d, 2H), 6.58 (d, 1H), 6.54 (d, 1H), 5.71 (1H, d), 4.70 (s, 4H), 3.50-3.70 (m, 1H), 1.13 (d, 6H).

Compounds in Table 25 were prepared in a manner similar to Example 272.

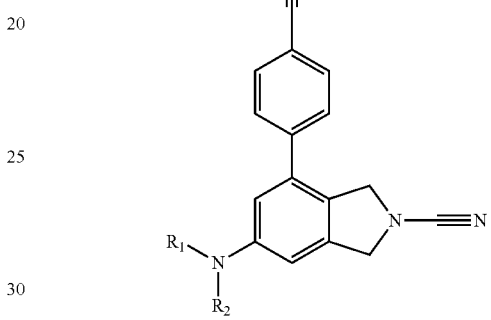

TABLE 25

| Ex | Name | R$_1$R$_2$NH— | Aldehyde/ketone CAS Number | LCMS method | LCMS RT/min | MS ES+ |
|---|---|---|---|---|---|---|
| Example 273 | 4-(4-cyanophenyl)-6-((1,1-dioxidotetrahydro-2H-thiopyran-4-yl)amino)isoindoline-2-carbonitrile | | 17396-35-9 | I | 2.5 | 393 |
| Example 274 | 4-(4-cyanophenyl)-6-((tetrahydro-2H-pyran-4-yl)amino)isoindoline-2-carbonitrile | | 29943-42-8 | I | 2.53 | 345 |
| Example 275 | 4-(4-cyanophenyl)-6-(((tetrahydro-2H-pyran-4-yl)methyl)amino)isoindoline-2-carbonitrile | | 50675-18-8 | I | 2.62 | 359 |
| Example 276 | 4-(4-cyanophenyl)-6-(((1-methyl-1H-pyrazol-5-yl)methyl)amino)isoindoline-2-carbonitrile | | 27258-33-9 | J | 3.13 | 355 |
| Example 277 | 4-(4-cyanophenyl)-6-(ethylamino)isoindoline-2-carbonitrile | | 75-07-0 | J | 3.13 | 289 |

Example 278 4-(4-cyanophenyl)-6-(1,1-dioxidothiomorpholino)isoindoline-2-carbonitrile

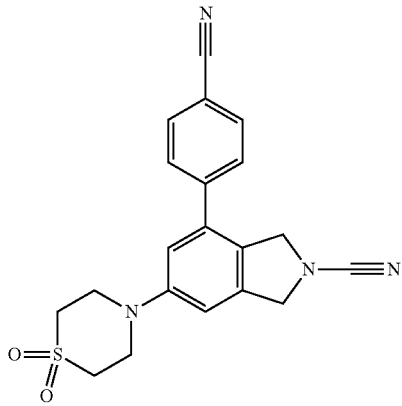 [SMILES: N#Cc1ccc(-c2cc(N3CCS(=O)(=O)CC3)cc3c2CN(C#N)C3)cc1]

Step a. A solution of tert-butyl 6-amino-4-(4-cyanophenyl)isoindoline-2-carboxylate (prepared as in step b of Example 264, 100 mg, 0.30 mmol), 1-bromo-2-(2-bromoethanesulfonyl)ethane (84 mg, 0.30 mmol) and TEA (1.66 ml, 1.2 mmol) in DMF (3 ml) was heated at 100° C. for 24 h. An additional charge of 1-bromo-2-(2-bromoethanesulfonyl)ethane (170 mg, 0.60 mmol) was added to the reaction, and the resulting mixture was heated at 100° C. for 24 h. The reaction mixture was cooled to rt and partitioned between saturated aqueous NaHCO$_3$ solution (10 ml) and EtOAc (10 ml). The organic phase was separated, dried over Na$_2$SO$_4$, filtered and evaporated to dryness under vacuum to give a residue. The crude residue (180 mg) was purified by reverse phase HPLC over an Agilent Pursuit 5 C18 column, eluting with a gradient (50-70%) of MeCN in water+0.1% formic acid with detection at 254 nm to give tert-butyl 4-(4-cyanophenyl)-6-(1,1-dioxidothiomorpholino)isoindoline-2-carboxylate as a pale-yellow solid (21 mg, 15%). LCMS (Method I): rt 2.70 min, m/z 454 [M+H]$^+$ Steps b and c were carried out in a similar manner to steps b and c of Example 21. LCMS (Method I): rt 2.51 min, m/z 379 [M+H]$^+$; $^1$H NMR (400 MHz, CDCl$_3$) δ ppm 7.72-7.66 (m, 2H), 7.41-7.35 (m, 2H), 6.79-6.72 (m, 2H), 4.76-4.60 (m, 4H), 3.85-3.77 (m, 4H), 3.11-2.97 (m, 4H).

Example 279 4-(4-Cyanophenyl)-6-(diethylamino)isoindoline-2-carbonitrile

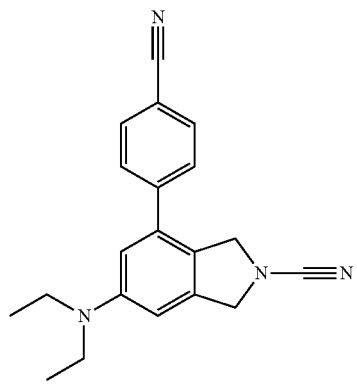 [SMILES: CCN(CC)c1cc2c(c(-c3ccc(C#N)cc3)c1)CN(C#N)C2]

Step a. To a solution of tert-butyl 6-amino-4-(4-cyanophenyl)isoindoline-2-carboxylate (Prepared as in step b of Example 264, 150 mg, 0.45 mmol), AcOH (0.04 ml), acetaldehyde (5 M in MeCN, 0.11 ml, 0.54 mmol) in DCE (4.5 ml) was added NaBH(OAc)$_3$ (191 mg, 0.90 mmol) and the resulting mixture was stirred at rt for 12 h. The reaction mixture was poured into a saturated aqueous NaHCO$_3$ solution (20 ml) and extracted with DCM (3×20 ml). The combined extracts were washed with brine, dried over Na$_2$SO$_4$, filtered and evaporated to dryness under vacuum. The crude residue was purified by flash column chromatography (10-50% EtOAc in hexane, followed by 5% MeOH in EtOAc) to give tert-butyl 4-(4-cyanophenyl)-6-(diethylamino)isoindoline-2-carboxylate as a yellow solid (50 mg, 28%). LCMS (Method I): rt 2.68 min, m/z 392 [M+H]$^+$; $^1$H NMR (400 MHz, CDCl$_3$) δ ppm 7.77-7.66 (m, 2H), 7.53 (d, 2H), 6.64-6.50 (m, 2H), 4.67 (d, 2H), 4.63-4.51 (d, 2H), 3.39 (q, J=7.1 Hz, 4H), 1.50 (s, 9H), 1.19 (t, J=7.1 Hz, 6H).

Steps b and c were carried out in a similar manner to steps b and c of Example 21. LCMS (Method J): rt 3.01 min, m/z 317 [M+H]$^+$; $^1$H NMR (400 MHz, CDCl$_3$) δ ppm 7.76-7.71 (m, 2H), 7.51-7.45 (m, 2H), 6.55 (s, 2H), 4.77 (m, 2H), 4.68 (m, 2H), 3.39 (q, J=6.9 Hz, 4H), 1.19 (t, J=6.9 Hz, 6H).

Example 280 4-(4-Cyanophenyl)-6-((2,3-dihydroxypropyl)amino)isoindoline-2-carbonitrile

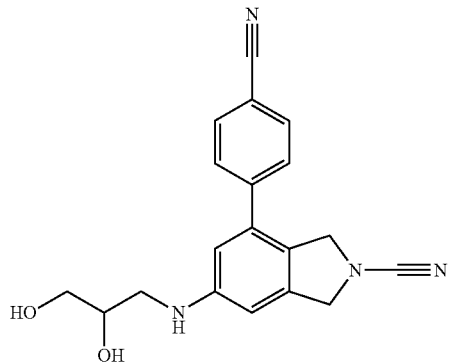 [SMILES: N#Cc1ccc(-c2cc(NCC(O)CO)cc3c2CN(C#N)C3)cc1]

Step a. To a suspension of tert-butyl 6-amino-4-(4-cyanophenyl)isoindoline-2-carboxylate (Prepared as in step b of Example 264, 150 mg, 0.45 mmol), AcOH (0.04 ml), (S)-2,2-dimethyl-1,3-dioxolane-4-carboxaldehyde (70 mg, 0.27 mmol) and (R)-2,2-dimethyl-1,3-dioxolane-4-carboxaldehyde (70 mg, 0.27 mmol) in DCE (4.5 ml) at 0° C. was added NaBH(OAc)$_3$ (191 mg, 0.90 mmol), and the resulting mixture was stirred for 1 h at 0° C., followed by 16 h at rt. The reaction mixture was poured into a saturated aqueous solution of NaHCO$_3$ and extracted with DCM (3×20 ml). The combined DCM extracts were washed with brine, dried over Na$_2$SO$_4$, filtered and evaporated to dryness under vacuum. The crude residue was purified by flash column chromatography (20-50% EtOAc in hexane) to give tert-butyl 4-(4-cyanophenyl)-6-4(2,2-dimethyl-1,3-dioxolan-4-yl)methyl)amino)-isoindoline-2-carboxylate as a light brown solid (171 mg, 85%). LCMS (Method I): rt 2.86 min, m/z 450 [M+H]$^+$; $^1$H NMR (400 MHz, CDCl$_3$) δ ppm 7.77-7.66 (m, 2H), 7.51 (d, 2H), 6.62-6.50 (m, 2H), 4.70-4.51 (m, 4H), 4.44-4.35 (m, 1H), 4.12 (dd, J=8.2, 6.4 Hz, 1H), 3.79 (dd, J=8.2 Hz, 1H), 3.39-3.31 (m, 1H), 3.26-3.18 (m, 1H), 1.50 (d, 9H), 1.47 (s, 3H), 1.39 (s, 3H).

Step b. A solution of tert-butyl 4-(4-cyanophenyl)-6-4(2,2-dimethyl-1,3-dioxolan-4-yl)methyl)-amino)isoindoline-2-carboxylate (170 mg, 0.38 mmol) in MeOH (4 mL) was treated with a 4 M solution of HCl in 1,4-dioxane (2 ml, 8 mmol), and the resulting mixture was stirred at rt for 16 h. The mixture was evaporated to dryness under vacuum to give 4-(6-((2,3-dihydroxypropyl)-amino)isoindolin-4-yl) benzonitrile HCl as a green solid (158 mg). LCMS (Method I): rt 0.55 min, m/z 310 [M+H]$^+$; $^1$H NMR (400 MHz, DMSO-d$_6$) δ ppm 9.70 (m, 2H), 7.99-7.92 (m, 2H), 7.68-7.48 (m, 2H), 6.86-6.75 (m, 2H), 4.48-4.38 (m, 4H), 3.42-3.35 (m, 3H), 3.26-3.20 (m, 1H), 3.04-2.94 (m, 1H).

Step c was carried out in a similar manner to the final step of Example 36. LCMS (Method J): rt 3.01 min, m/z 335 [M+H]$^+$; $^1$H NMR (400 MHz, DMSO-d$_6$) δ ppm 7.89 (d, J=8.0 Hz, 2H), 7.64 (d, J=8.0 Hz, 2H), 6.67-6.55 (m, 2H), 5.84-5.72 (m, 1H), 4.79 (d, J=5.0 Hz, 1H), 4.70 (s, 4H), 4.61 (m, 1H), 3.63 (m, 1H), 3.24-3.14 (m, 1H), 2.99-2.89 (m, 1H).

Example 281 5-Cyano-2-(2-cyano-6-(((tetrahydro-2H-pyran-4-yl)methyl)amino)isoindolin-4-yl)benzamide

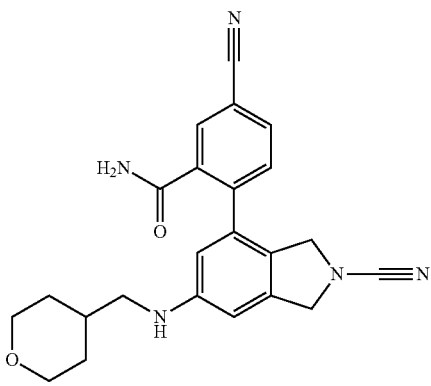 [SMILES: N#Cc1ccc(-c2cc(NCC3CCOCC3)cc3c2CN(C#N)C3)c(C(N)=O)c1]

Step a. A mixture of tert-butyl 4-bromo-6-nitroisoindoline-2-carboxylate (Intermediate 3, 1.0 g, 2.91 mmol), bis(pinacolato)diboron (886 mg, 3.49 mmol) and potassium acetate (858 mg, 8.74 mmol) in 1,4-dioxane (5 ml) was degassed with nitrogen for 10 min. Pd(dppf)Cl$_2$.DCM (236 mg, 0.29 mmol) was added and the resulting mixture was heated at reflux for 18 h. The reaction mixture was cooled to rt and filtered through a pad of Celite®, which was subsequently washed with Et$_2$O (50 ml) followed by EtOAc (50 ml). The filtrate was evaporated to dryness under vacuum to give a black residue, which was purified by flash column chromatography (0-10% EtOAc in hexane). The resulting solid was triturated with a 1:1 (v/v) mixture of EtOAc and Et$_2$O to afford tert-butyl 6-nitro-4-(4,4,5,5-tetramethyl-1,3,2-dioxaborolan-2-yl)isoindoline-2-carboxylate as a yellow solid (878 mg, 77%). LCMS (Method I): rt 3.11 min, m/z 335 [M+H-tBu]$^+$; $^1$H NMR (400 MHz, DMSO-d$_6$) δ ppm 8.37-8.28 (m, 2H), 4.78-4.63 (m, 4H), 1.47 (s, 9H), 1.33 (m, 12H).

Step b. A solution of tert-butyl 6-nitro-4-(4,4,5,5-tetramethyl-1,3,2-dioxaborolan-2-yl)isoindoline-2-carboxylate (830 mg, 2.13 mmol), methyl-2-bromo-5-cyanobenzoate (425 mg, 1.77 mmol) and potassium carbonate (740 mg, 5.31 mmol) in a 9:1 (v/v) mixture of 1,4-dioxane and water (9:1, 5 ml) was degassed with nitrogen for 10 min. Pd(dppf) Cl$_2$.DCM (140 mg, 0.17 mmol) was added to the solution and the resulting mixture was heated at 100° C. for 1 h. The reaction mixture was cooled to rt and filtered through a pad of Celite®, which was washed with EtOAc (50 ml) and Et$_2$O (50 ml). The filtrate was evaporated to dryness under vacuum. The crude product was purified by flash column chromatography (0-10% EtOAc in hexane) to give tert-butyl 4-(4-cyano-2-(methoxycarbonyl)-phenyl)-6-nitroisoindoline-2-carboxylate as a white solid (373 mg, 42%). LCMS (Method I): rt 2.78 min, m/z 324 [M+H-Boc]$^+$; $^1$H NMR (400 MHz, DMSO-d$_6$) δ ppm 8.41 (d, J=1.6 Hz, 1H), 8.32-8.27 (m, 1H), 8.21-8.16 (m, 1H), 7.99-7.93 (dd, J=9.5, 1.6 Hz, 1H), 7.71-7.65 (t, J=7.9 Hz, 1H), 4.75 (m, 2H), 4.40-4.28 (m, 2H), 3.63 (s, 3H), 1.40 (d, 9H).

Step c. A mixture of tert-butyl 4-(4-cyano-2-(methoxycarbonyl)phenyl)-6-nitroisoindoline-2-carboxylate (373 mg, 0.88 mmol), iron powder (246 mg, 4.4 mmol) and NH$_4$Cl (235 mg, 4.4 mmol) in THF (5 ml) and water (5 ml) was heated at 90° C. for 18 h. The mixture was cooled to rt filtered through a pad of Celite®, which was washed with EtOAc (3×10 ml). The filtrate was collected and washed with brine (10 ml), before being dried over Na$_2$SO$_4$, filtered and evaporated to give tert-butyl 6-amino-4-(4-cyano-2-(methoxycarbonyl)phenyl)isoindoline-2-carboxylate as a yellow solid (375 mg, 34%). LCMS (Method I): rt 2.56 min, m/z 294 [M+H-Boc]$^+$; $^1$H NMR (400 MHz, DMSO-d6) δ ppm 8.21 (m, 1H), 8.08-8.02 (m, 1H), 7.60-7.54 (m, 1H), 6.52-6.47 (m, 1H), 6.27-6.22 (m, 1H), 5.21 (bs, 2H), 4.52 (m, 2H), 4.19-4.10 (m, 2H), 3.63 (d, 3H), 1.40 (d, 9H).

Step d. A suspension of tert-butyl 6-amino-4-(4-cyano-2-(methoxycarbonyl)phenyl)isoindoline-2-carboxylate (187 mg, 0.47 mmol), AcOH (0.08 mL), tetrahydropyrancarboxyldehyde (43 mg, 0.38 mmol) and NaBH(OAc)$_3$ (250 mg, 1.17 mmol) in MeCN (3 ml) was stirred for 1 h at 110° C. The mixture was cooled to rt and poured into a saturated aqueous solution of NaHCO$_3$ (20 ml), before being extracted with EtOAc (3×20 ml). The combined extracts were washed with brine (25 mL), dried over Na$_2$SO$_4$, filtered and evaporated to give a residue. Purification by reverse phase HPLC over an Agilent Pursuit 5 C18 column eluting with a gradient (50-95%) MeCN in water+0.1% formic acid with detection at 254 nM gave tert-butyl 4-(4-cyano-2-(methoxycarbonyl) phenyl)-6-(((tetrahydro-2H-pyran-4-yl)methyl)amino)isoindoline-2-carboxylate as a yellow solid (56 mg, 25%). LCMS (Method I): rt 2.67 min, m/z 492 [M+H]$^+$; $^1$H NMR (400 MHz, DMSO-d$_6$) δ ppm: 8.23 (d, J=1.7 Hz, 1H), 8.09-8.04 (dt, J=8.0, 2.0 Hz, 1H), 7.63-7.58 (d, J=8.0, 4.7 Hz, 1H), 6.54 (m, 1H), 6.23 (m, 1H), 5.88-5.82 (m, 1H), 4.57-4.50 (m, 2H), 4.23-4.13 (m, 2H), 3.89-3.81 (m, 2H), 3.64 (d, 3H), 3.30-3.21 (m, 2H), 2.88 (m, 2H), 1.85-1.72 (m, 1H), 1.69-1.601 (m, 2H), 1.41 (d, 9H), 1.26-1.13 (m, 2H).

Step e. A solution of tert-butyl 4-(4-cyano-2-(methoxycarbonyl)phenyl)-6-(((tetrahydro-2H-pyran-4-yl)methyl) amino)isoindoline-2-carboxylate (79 mg, 0.16 mmol) in THF (0.6 mL) was treated with a solution of LiOH (34 mg, 0.80 mmol) in water (0.4 mL) at rt, and the resulting mixture was stirred for 36 h. The reaction was concentrated under vacuum to remove the THF, and the resulting residue was diluted with water (20 mL). The reaction mixture was acidified (pH 1) with 1 M HCl and extracted with EtOAc (3×20 mL). The combined organic extracts were washed with brine (25 mL), dried over Na$_2$SO$_4$ and evaporated to dryness under vacuum to give 2-(2-(tert-butoxycarbonyl)-6-(((tetrahydro-2H-pyran-4-yl)methyl)amino)isoindolin-4-yl)-5-cyano benzoic acid as a brown solid (60 mg, 79%). LCMS (Method I): rt 2.55 min, m/z 478 [M+H]$^+$ Step f. A solution of 2-(2-(tert-butoxycarbonyl)-6-(((tetrahydro-2H-pyran-4-yl)methyl)amino)-isoindolin-4-yl)-5-cyanobenzoic acid (60 mg, 0.125 mmol) in THF (3 ml) was treated with TEA (0.02 ml, 0.15 mmol) and HATU (58 mg, 0.15 mmol) at rt under nitrogen, and the resulting mixture was stirred for 30 min. A 0.5 M solution of ammonia in 1,4-dioxane (0.5 ml, 0.25 mmol) was added to the reaction, and the resulting mixture was stirred for 18 h. The reaction mixture was poured into water (10 ml) and extracted with EtOAc (3×5 ml). The combined organic extracts were washed with brine (10 ml), dried over $Na_2SO_4$, filtered and evaporated to dryness under vacuum to give tert-butyl 4-(2-carbamoyl-4-cyanophenyl)-6-(((tetrahydro-2H-pyran-4-yl)methyl)amino)-isoindoline-2-carboxylate as a brown solid (41 mg, 70%). LCMS (Method I): rt 2.44 min, m/z 477 $[M+H]^+$ Steps g and h were carried out in a similar manner to steps b and c of Example 21. LCMS (Method I): rt 2.03 min, m/z 400 $[M+H]^-$. $^1H$ NMR (400 MHz, $CDCl_3$) δ ppm 8.15 (d, J=1.6 Hz, 1H), 7.80-7.74 (dd, J=7.8, 1.7 Hz, 1H), 7.36 (d, J=7.8. Hz, 1H), 6.51-6.40 (m, 2H), 5.88 (s, 1H), 5.61 (s, 1H), 4.72 (s, 2H), 4.43 (s, 2H), 4.02-3.94 (m, 2H), 3.44-3.33 (m, 2H), 3.01 (d, 2H), 1.91-1.75 (m, 2H), 1.73-1.64 (m, 2H), 1.43-1.30 (m, 2H).

Example 282 (S)-6((2,3-dihydroxypropyl)amino)-4-(4-fluorophenyl)isoindoline-2-carbonitrile

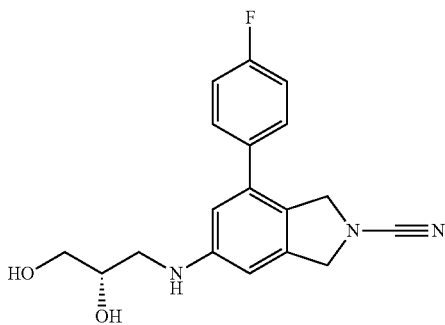 [SMILES: N#CN1Cc2cc(NC[C@H](O)CO)cc(-c3ccc(F)cc3)c2C1]

Step a.

A solution of tert-butyl 4-bromo-6-nitroisoindoline-2-carboxylate (Intermediate 3, 300 mg, 0.87 mmol), 4-fluorophenylboronic acid (145 mg, 1.04 mmol) and caesium carbonate (850 mg, 2.61 mmol) in a 4:1 (v/v) mixture of 1,4-dioxane and water (5 ml) was degassed with nitrogen for 15 min. $Pd(Ph_3P)_4$ (104 mg, 0.09 mmol) was added, and the resulting mixture was heated at 110° C. for 3 h. The reaction mixture was cooled to rt and poured into water (20 mL). The mixture was extracted with EtOAc (2×20 ml) and the combined organic extracts were dried over $Na_2SO_4$, filtered and evaporated to dryness under vacuum. The residue was purified by flash column chromatography (0-70% EtOAc in hexane) to give tert-butyl 4-(4-fluorophenyl)-6-nitroisoindoline-2-carboxylate as an off-white solid (331 mg). LCMS (Method I): rt 2.86 min, m/z 303 $[M+H-Boc]^+$ Step b.

A mixture of tert-butyl 4-(4-fluorophenyl)-6-nitroisoindoline-2-carboxylate (331 mg, 0.92 mmol) and Pd/C (10%, 33 mg) in EtOH (10 ml) was stirred at rt under hydrogen (balloon) for 18 h. The reaction mixture was filtered through a pad of Celite®, which was subsequently washed with EtOH and the filtrate was evaporated to dryness under vacuum to give tert-butyl 6-amino-4-(4-fluorophenyl)isoindoline-2-carboxylate as a yellow oil (269 mg, 90%). LCMS (Method I): rt 2.63 min, m/z 329 $[M+H]^+$ Step c.

A suspension of tert-butyl 6-amino-4-(4-fluorophenyl)isoindoline-2-carboxylate (269 mg, 0.82 mmol), AcOH (0.07 ml), (R)-(+)-2,2-dimethyl-1,3-dioxolane-4-carboxaldehyde (50% DCM, 234 mg, 0.9 mmol) and $NaBH(OAc)_3$ (348 mg, 1.64 mmol) in DCE (10 ml) was stirred for 16 h at rt. The reaction mixture was poured into a saturated aqueous solution of $NaHCO_3$ (20 ml) and extracted with DCM (2×20 ml). The combined extracts were dried over $Na_2SO_4$, filtered and evaporated to dryness under vacuum. The crude product was purified by flash column chromatography (0-25% EtOAc in hexane) to give tert-butyl (S)-6-(((2,2-dimethyl-1,3-dioxolan-4-yl)methyl)amino)-4-(4-fluorophenyl)-isoindoline-2-carboxylate as a yellow oil (280 mg, 77%). LCMS (Method I): rt 2.77 min, m/z 443 $[M+H]^+$ Step e.

A solution of tert-butyl (S)-6-(((2,2-dimethyl-1,3-dioxolan-4-yl)methyl)amino)-4-(4-fluorophenyl)isoindoline-2-carboxylate (280 mg, 0.63 mmol) in MeOH (1 ml) and water (0.5 ml) was treated with a 4 M solution of HCl in 1,4-dioxane (4 ml), and the resulting mixture was stirred at rt for 2 h. The mixture was evaporated to dryness under vacuum to give (S)-3-((7-(4-fluorophenyl)-isoindolin-5-yl)amino)propane-1,2-diol hydrogen chloride as a white solid (157 mg, 100%). LCMS (Method I): rt 0.30 min, m/z 303 $[M+H]^+$ Step f.

A solution of (S)-3-((7-(4-fluorophenyl)isoindolin-5-yl)amino)propane-1,2-diol hydrogen chloride (140 mg, 0.62 mmol) and TEA (0.26 ml) in DCM (5 ml) was cooled to 0° C. under nitrogen. The cooled solution was treated with a 3.0 M solution of cyanogen bromide in DCM (0.19 ml) and the resulting suspension was stirred at 0° C. for 1 h. The reaction mixture was partitioned between water (20 ml) and DCM (20 ml). The DCM layer was collected and the aqueous phase was extracted with DCM (20 ml). The combined organic extracts were dried over $Na_2SO_4$, filtered and evaporated to dryness under vacuum. The crude was purified by HPLC over an Agilent Pursuit 5 C18 column eluting with a gradient (35-60%) of MeCN in water+0.1% formic acid with detection at 254 nM to give (S)-6-((2,3-dihydroxypropyl)amino)-4-(4-fluorophenyl)isoindoline-2-carbonitrile as a grey solid (75 mg, 37%). LCMS (Method I): rt 1.37 min, m/z 328 $[M+H]^+$; $^1H$ NMR (400 MHz, $CD_3OD$) δ ppm 7.43-7.41 (m, 2H), 7.18-7.13 (m, 2H), 6.62 (m, 1H), 6.59-6.58 (m, 1H), 4.74 (m, 2H), 4.69 (m, 2H), 3.86-3.80 (m, 1H), 3.60-3.57 (m, 2H), 3.33-3.29 (m, 1H), 3.13-3.08 (m, 1H).

Example 283 (S)-4-(2-cyanophenyl)-6-((2,3-dihydroxypropyl)amino)isoindoline-2-carbonitrile

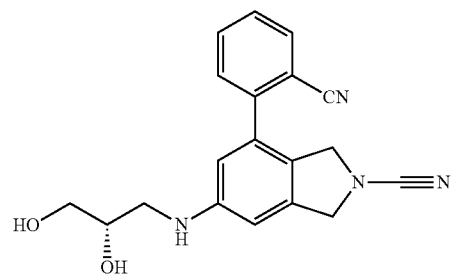 [SMILES: N#Cc1ccccc1-c1cc(NC[C@H](O)CO)cc2c1CN(C#N)C2]

The title compound was synthesised using a procedure similar to that described for Example 282 using 4-cyanophenylboronic acid in step a. LCMS: Method I, rt 0.48 min, m/z 335 [M+H]⁺.

Example 284 4-(4-Cyanophenyl)-6-((3-hydroxy-2-methoxypropyl)amino)isoindoline-2-carbonitrile

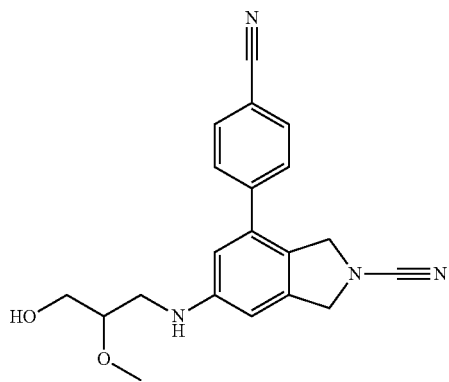 [SMILES: COC(CO)CNc1cc2c(c(-c3ccc(C#N)cc3)c1)CN(C#N)C2]

Step a. A mixture of tert-butyl 6-amino-4-bromoisoindoline-2-carboxylate (prepared as in step a of Example 23, 640 mg, 2.0 mmol), 2,3-dimethoxy-3-oxopropanoic acid (680 mg, 4.6 mmol), HATU (935 mg, 2.4 mmol) and TEA (1.1 ml) in DCM (60 ml) was stirred at rt for 24 h. The reaction mixture was evaporated to dryness under vacuum to give a residue, which was dissolved in EtOAc and washed sequentially with water, saturated NaHCO₃ and brine. The organic phase was dried over Na₂SO₄, filtered and evaporated. The residue was purified by flash column chromatography (20-100% EtOAc in hexane) to give tert-butyl 4-bromo-6-(2,3-dimethoxy-3-oxopropanamido)isoindoline-2-carboxylate as an off white foam (850 mg, 96%). LCMS (Method I): rt 2.29 min, m/z 387/389 [M+H]⁺.

Step b. Lithium borohydride (247 mg, 11.2 mmol) was added to a solution of tert-butyl 4-bromo-6-(2,3-dimethoxy-3-oxopropanamido)isoindoline-2-carboxylate (800 mg, 1.8 mmol) in THF (22 ml), and the resulting mixture was heated at 60° C. for 1 h. The mixture was cooled to rt and quenched by the addition of water, followed by MeOH. The reaction mixture was partitioned between EtOAc (10 ml) and saturated NaHCO₃ solution (10 ml). The organic phase was collected and washed sequentially with saturated NaHCO₃ and brine, before being dried over Na₂SO₄, filtered and evaporated to dryness under vacuum to give a residue. The crude product was purified by flash column chromatography (40-100% EtOAc in hexane) to give tert-butyl 4-bromo-6-((3-hydroxy-2-methoxypropyl)amino)-isoindoline-2-carboxylate as a white solid (250 mg, 34%). LCMS (Method I): rt 2.55 min, m/z 401/403 [M+H]⁺; ¹H NMR (400 MHz, CDCl₃) δ ppm 6.72 (d, 1H), 6.46 (d, 1H), 4.52-4.75 (4s, 4H), 4.10 (bs, 1H), 3.77 (ABq, 2H), 3.55 (quin, 1H), 3.49 (s, 3H), 3.25 (ABq, 2H), 1.88 (bs, 1H), 1.54 (d, 9H).

Step c. A mixture of tert-butyl 4-bromo-6-((3-hydroxy-2-methoxypropyl)amino)isoindoline-2-carboxylate (250 mg, 0.62 mmol), 4-cyanophenylboronic acid (100 mg, 0.68 mmol) and potassium carbonate (200 mg, 1.56 mmol) in a 9:1 (v/v) mixture of 1,4-dioxane and water (11 ml) was degassed with nitrogen for 10 min. Pd(PPh₃)₄ (100 mg, 0.09 mmol) was added, and the resulting mixture was heated at reflux for 18 h. The reaction was cooled to rt and diluted with EtOAc, before being dried over Na₂SO₄, filtered and evaporated to dryness under vacuum. The crude product was purified by flash column chromatography (50-100% EtOAc in hexane) to give tert-butyl 4-(4-cyanophenyl)-6-((3-hydroxy-2-methoxypropyl)amino)isoindoline-2-carboxylate as a brown oil gum (270 mg, 100%). LCMS (Method I): rt 2.40 min, m/z 424 [M+H]⁺; ¹H NMR (400 MHz, CDCl₃) δ ppm 7.75 (d, 1H), 7.71 (d, 1H), 7.53 (d, 2H), 6.55-6.65 (m, 2H), 4.50-4.70 (m, 4H), 3.80 (ABq, 2H), 3.58 (quin, 1H), 3.50 (s, 3H), 3.35 (ABq, 2H), 1.51 (d, 9H).

Steps d and e were carried out in a similar manner to steps b and c of Example 21. LCMS (Method I): rt 0.59 min, m/z 349 [M+H]⁺; ¹H NMR (400 MHz, CDCl₃) δ ppm 7.75 (d, 2H), 7.48 (d, 2H), 6.58 (s, 1H), 6.56 (s, 1H), 4.77 (s, 2H), 4.70 (s, 2H), 3.83 (dd, 1H), 3.73 (dd, 1H), 3.57 (quin, 1H), 3.50 (s, 3H), 3.42 (dd, 1H), 3.28 (dd, 1H).

Example 285 5-Cyano-2-(2-cyano-6-(dimethylamino)isoindolin-4-yl)benzamide

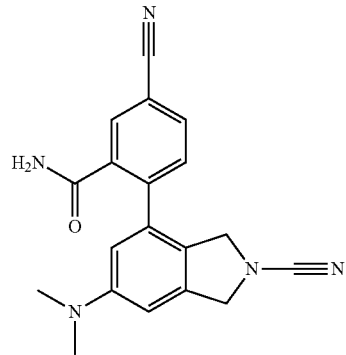 [SMILES: CN(C)c1cc2c(c(-c3ccc(C#N)cc3C(N)=O)c1)CN(C#N)C2]

Step a. A suspension of tert-butyl 6-amino-4-bromoisoindoline-2-carboxylate (prepared as in step a of Example 23, 300 mg, 0.96 mmol), AcOH (0.14 ml), paraformaldehyde (60 mg, 2.0 mmol) and NaBH(OAc)₃ (509 mg, 2.4 mmol) in DCE (10 ml) was stirred for 16 h at rt. The reaction mixture was then heated at 80° C. for 20 h. Additional charges of paraformaldehyde (30 mg) and NaBH(OAc)₃ (250 mg) were added to the reaction, and the resulting mixture was heated for 4 h at 80° C. The reaction mixture was cooled to rt, poured into water (30 ml) and extracted with DCM (2×30 ml). The combined extracts were dried over Na₂SO₄, filtered and evaporated to dryness under vacuum. The crude product was purified by flash column chromatography (0-20% EtOAc in hexane) to give tert-butyl 4-bromo-6-(dimethylamino)isoindoline-2-carboxylate as a yellow solid (406 mg, 100%). LCMS (Method I): rt 2.81 min, m/z 341/343 [M+H]⁺

Step b. A mixture of tert-butyl 4-bromo-6-(dimethylamino)isoindoline-2-carboxylate (320 mg, 0.96 mmol), bis(pinacolato)diboron (292 mg, 1.15 mmol) and potassium acetate (284 mg, 2.9 mmol) in 1,4-dioxane (5 ml) was degassed with nitrogen for 10 min. Pd(dppf)Cl₂ (73 mg, 0.1 mmol) was added and the resulting mixture was heated at 100° C. for 18 h. The mixture was then cooled to rt and filtered through a pad of Celite®, washing with EtOAc (20 ml). The filtrate was evaporated to give a residue, which was purified by flash column chromatography (0-20% EtOAc in hexane) to give tert-butyl 6-(dimethylamino)-4-(4,4,5,5-tetramethyl-1,3,2-dioxaborolan-2-yl)isoindoline-2-carboxylate as a yellow solid (299 mg, 80%). LCMS (Method I): rt 2.74 min, m/z 389 [M+H]⁺

Step c. TEA (1.7 ml, 12.3 mmol) and HATU (3.7 g, 9.8 mmol) were added sequentially to a solution of 2-bromo-5-cyanobenzamide (CAS Number 1261670-21-6, 1.85 g, 8.19 mmol) in THF (75 mL) under nitrogen at rt, and the resulting mixture was stirred for 2 h. A 0.5 M solution of ammonia in 1,4-dioxane (82 ml, 41 mmol) was added to the reaction, resulting in a thick suspension, which was stirred for 72 h. The reaction mixture was evaporated to dryness under vacuum to give a residue, which was taken into water (50 ml) and extracted sequentially with EtOAc (2×100 ml) and DCM (2×100 ml). The combined organic extracts were dried over $Na_2SO_4$, filtered and evaporated to dryness under reduced pressure. The crude product was purified by flash column chromatography (20-100% EtOAc in hexane) to give a solid, which was triturated with $Et_2O$ (2×20 ml) to give 2-bromo-5-cyanobenzamide as a white solid (575 mg, 31%). LCMS (Method I): rt 0.87 min, m/z 225/227 $[M+H]^+$; $^1$H NMR (400 MHz, DMSO-$d_6$) δ ppm 8.02 (brs, 1H), 7.93 (dd, J=2.0 and 0.3 Hz, 1H), 7.91-7.87 (dd, J=8.3 and 0.3 Hz, 1H), 7.82-7.79 (dd, J=8.3 and 2.0 Hz, 1H), 7.78 (brs, 1H).

Step d. A suspension of 2-bromo-5-cyanobenzamide (189 mg, 0.84 mmol), tert-butyl 6-(dimethylamino)-4-(4,4,5,5-tetramethyl-1,3,2-dioxaborolan-2-yl)isoindoline-2-carboxylate (299 mg, 0.77 mmol) and caesium carbonate (752 mg, 2.31 mmol) in a (4:1 v/v) mixture of 1,4-dioxane and water (5 mL) was degassed with nitrogen (bubbling) for 10 min. $Pd(PPh_3)_4$ (92 mg, 0.08 mmol) was added to the degassed solution, and the resulting mixture was heated at reflux for 16 h. The mixture was then cooled to rt and partitioned between water (20 mL) and EtOAc (20 mL). The organic phase was collected and washed with water (20 mL). The combined aqueous phases were extracted with EtOAc (20 mL). The combined organic extracts were dried over $Na_2SO_4$, filtered and evaporated to give a residue, which was purified by flash column chromatography (5-20% EtOAc in hexane) to give tert-butyl 4-(2-carbamoyl-4-cyanophenyl)-6-(dimethylamino)isoindoline-2-carboxylate as a yellow solid (260 mg, 83%). LCMS (Method I): rt 1.15 min, m/z 407 $[M+H]^+$ Steps e and f were carried out in a similar manner to steps b and c of Example 21. LCMS (Method I): rt 0.55 min, m/z 332 $[M+H]^+$; $^1$H NMR (400 MHz, $CD_3OD+CDCl_3$) δ ppm 7.96 (m, 1H), 7.85-7.82 (m, 1H), 7.51-7.49 (m, 1H), 6.66-6.65 (m, 1H), 6.63-6.62 (m, 1H), 4.80 (bs, 2H), 4.59 (bs, 2H), 3.00 (s, 6H).

Example 286 4-(4-Cyanophenyl)-6-((2-hydroxypropyl)amino)isoindoline-2-carbonitrile Step a. Propylene oxide (0.05 mL, 0.71 mmol) and $LiClO_4$ (76 mg, 0.71 mmol) were added sequentially to a solution of tert-butyl 6-amino-4-(4-cyanophenyl)isoindoline-2-carboxylate (prepared as in step b of Example 264, 200 mg, 0.59 mmol) in diethyl ether (5 ml), and the reaction mixture was stirred at rt for 16 h. The reaction mixture was diluted with EtOAc (30 ml) and washed sequentially with water (30 ml) and brine (30 ml), before being dried over $Na_2SO_4$, filtered and evaporated to dryness under vacuum to give a residue. The crude product was purified by flash column chromatography (0-70% EtOAc in hexane) to give tert-butyl 4-(4-cyanophenyl)-6-((2-hydroxypropyl)amino)isoindoline-2-carboxylate as a yellow solid (84 mg, 36%). LCMS (Method I): rt 2.52 min, m/z 394 $[M+H]^+$ Step b. A 4 M solution of HCl in 1,4-dioxane (2 ml) was added to a solution of tert-butyl 4-(4-cyanophenyl)-6-((2-hydroxypropyl)amino)isoindoline-2-carboxylate (84 mg, 0.21 mmol) in 1,4-dioxane (2 ml), and the resulting solution was stirred at rt for 4 h. The mixture was evaporated to dryness under vacuum to give 4-(6-((2-hydroxypropyl)amino)isoindolin-4-yl)benzonitrile HCl as an off white solid (69 mg, 100%). LCMS (Method I): rt 0.39 min, m/z 294 $[M+H]^+$ Step c was carried out in a similar manner to the final step of Example 21. LCMS (Method I): rt 2.19 min, m/z 319 $[M+H]^+$; $^1$H NMR (400 MHz, DMSO-d6) δ ppm 7.91 (m, 2H), 7.65 (m, 2H), 6.61 (m, 2H), 5.85 (t, J=5.5 Hz, 1H), 4.71 (m, 5H), 3.80 (m, 1H), 2.99 (m, 2H), 1.11 (d, J=6.0 Hz, 3H).

Compounds in Table 26 were prepared in a manner similar to Example 286.

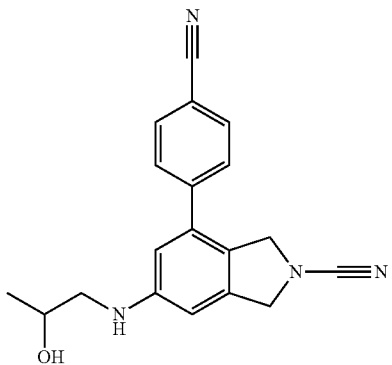 [SMILES: CC(O)CNc1cc2c(c(-c3ccc(C#N)cc3)c1)CN(C#N)C2]

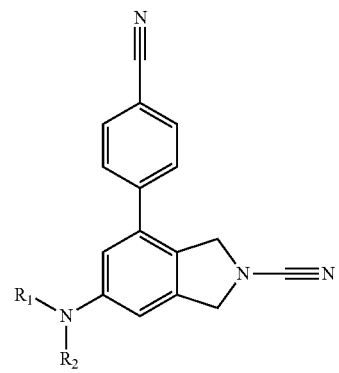

TABLE 26

| Ex | Name | R₁R₂NH— | Epoxide CAS Number | LCMS method | LCMS RT/min | MS ES+ |
|---|---|---|---|---|---|---|
| Example 287 | 4-(4-cyanophenyl)-6-((2-hydroxy-2-methylpropyl)amino)iso-indoline-2-carbonitrile | 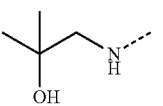 | 558-30-5 | I | 2.2 | 333 |
| Example 288 | 4-(4-cyanophenyl)-6-((2-hydroxy-2-methoxypropyl)amino)iso-indoline-2-carbonitrile | 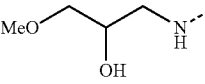 | 930-37-0 | I | 2.21 | 349 |

Example 289 2-methyl-4-(3-(2-oxopyrrolidin-1-yl)phenyl)-5,7-dihydro-6H-pyrrolo[3,4-d]pyrimidine-6-carbonitrile

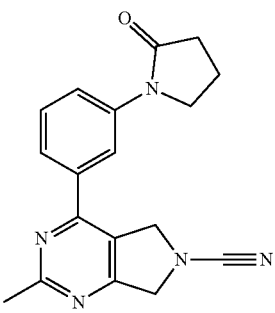 [SMILES: Cc1nc2c(c(-c3cccc(N4CCCC4=O)c3)n1)CN(C#N)C2]

Step a.

To a stirred solution of 1-(3-(4,4,5,5-tetramethyl-1,3,2-dioxaborolan-2-yl)phenyl)pyrrolidin-2-one (CAS Number 1185265-61-5; 0.595 g, 2.07 mmol) in 1,4-dioxane:water (9:1, 10 ml) were added K₂CO₃ (0.713 g, 5.17 mmol) and 6-Boc-2,4-dichloro-5,7-dihydropyrrolo[3,4-d]pyrimidine (CAS Number 903129-71-5; 0.500 g, 1.724 mmol) at rt. The reaction mixture was degassed for 10 min before addition of PdCl₂(dppf) (0.126 g, 0.172 mmol). The reaction mixture was heated at 90° C. for 4 h. The resulting reaction mixture was combined with 3 other batches prepared on the same scale by an identical method. The reaction mixture was cooled to rt and poured into water (60 ml). The resulting mixture was extracted with EtOAc (3×30 ml). The combined organic phase was dried over Na₂SO₄, filtered and concentrated under reduced pressure. The residue was purified by flash column chromatography (44% EtOAc in hexane) to yielding tert-butyl 2-chloro-4-(3-(2-oxopyrrolidin-1-yl)phenyl)-5,7-dihydro-6H-pyrrolo[3,4-d]pyrimidine-6-carboxylate (1.300 g, 3.140 mmol). LCMS: Method A, 2.306 min, MS: ES+ 415.30.

Step b.

To a stirred solution of tert-butyl 2-chloro-4-(3-(2-oxopyrrolidin-1-yl)phenyl)-5,7-dihydro-6H-pyrrolo[3,4-d]pyrimidine-6-carboxylate (0.300 g, 0.724 mmol) in toluene:EtOH:water (1:1:1, 8 ml) were added NaHCO₃ (0.182 g, 2.168 mmol) and methylboronic acid (CAS Number 13061-96-6; 0.065 g, 1.086 mmol) at rt. The reaction mixture was degassed for 10 min before addition of Pd(PPh₃)₄ (0.083 g, 0.072 mmol). The reaction mixture was heated at 100° C. for 16 h. The resulting mixture was cooled to rt and poured into water (30 ml). The resulting mixture was extracted with EtOAc (3×20 ml). The combined organic phase was dried over Na₂SO₄, filtered and concentrated under reduced pressure. The residue was purified by flash column chromatography (60% EtOAc in n-hexane) to yield tert-butyl 2-methyl-4-(3-(2-oxopyrrolidin-1-yl)phenyl)-5,7-dihydro-6H-pyrrolo[3,4-d]pyrimidine-6-carboxylate (0.130 g, 0.329 mmol). LCMS: Method A, 1.919 min, MS: ES+ 395.40.

Steps c, d.

The title compound was synthesised from the intermediate above using a procedure similar to that described for steps d and e of Example 1. LCMS: Method D, 2.786 min, MS: ES+ 320.15; ¹H NMR (400 MHz, DMSO-d6) δ ppm: 8.24 (s, 1H), 7.75 (d, J=8.0 Hz, 1H), 7.69 (d, J=7.6 Hz, 1H), 7.54 (t, J=16.0 Hz, 1H), 5.12 (s, 2H), 4.79 (s, 2H), 3.89 (t, J=6.8 Hz, 2H), 2.67 (s, 3H), 2.52 (t, J=8.0 Hz, 2H), 2.11-2.06 (m, 2H)

Example 290 2-(((1-methyl-1H-pyrazol-5-yl)methyl)amino)-4-(3-(2-oxopyrrolidin-1-yl)phenyl)-5,7-dihydro-6H-pyrrolo[3,4-d]pyrimidine-6-carbonitrile

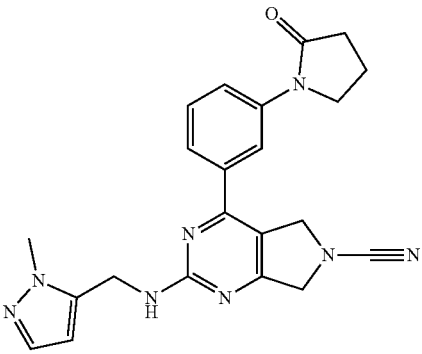 [SMILES: Cn1nccc1CNc1nc2c(c(-c3cccc(N4CCCC4=O)c3)n1)CN(C#N)C2]

Step a.

To a mixture of tert-butyl 2-chloro-4-(3-(2-oxopyrrolidin-1-yl)phenyl)-5,7-dihydro-6H-pyrrolo[3,4-d]pyrimidine-6-carboxylate (prepared as in step a of Example 289, 0.450 g, 1.086 mmol) and 1-methyl-1H-pyrazol-5-yl)methylamine (CAS Number 863548-52-1; 0.180 g, 1.629 mmol) in 1,4-dioxane (100 ml) was added K₂CO₃ (0.450 g, 3.258 mmol) at rt. The reaction mixture was degassed for 10 min before addition of Pd₂(dba)₃ (0.099 g, 0.108 mmol) and Xanthphos (0.062 g, 0.108 mmol). The reaction mixture was heated at 90° C. for 16 h. The resulting mixture was cooled to rt, poured into water (20 ml) and extracted with EtOAc (3×30 ml). The combined organic phase was dried over Na₂SO₄, filtered and concentrated under reduced pressure. The residue was purified by flash column chromatography (3.2% MeOH in DCM) yielding tert-butyl 2-(((1-methyl-1H-pyrazol-5-yl)methyl)amino)-4-(3-(2-oxopyrrolidin-1-yl)phenyl)-5,7-dihydro-6H-pyrrolo[3,4-d]pyrimidine-6-carboxylate (0.250 g, 0.511 mmol). LCMS: Method A, 1.858 min, MS: ES+ 490.41.

Steps b, c.

The title compound was synthesised from the intermediate above using a procedure similar to that described for steps d and e of Example 1. LCMS: Method D, 2.927 min, MS: ES+ 415.20; $^1$H NMR (400 MHz, DMSO-d6) δ ppm 8.17 (br s, 1H), 7.99-7.91 (m, 1H), 7.74 (d, J=8.0 Hz, 1H), 7.60 (d, J=7.6 Hz, 1H), 7.50 (t, J=8.0 Hz, 1H), 7.24 (d, J=1.6 Hz, 1H), 6.15 (s, 1H), 4.93 (s, 2H), 4.50-4.62 (m, 4H), 3.87 (t, J=7.2 Hz, 2H), 3.81 (s, 3H), 2.51 (t, J=8.0 Hz, 2H), 2.11-2.03 (m, 2H).

Example 291 2-((2-hydroxyethyl)amino)-4-(3-(2-oxopyrrolidin-1-yl)phenyl)-5,7-dihydro-6H-pyrrolo[3,4-d]pyrimidine-6-carbonitrile

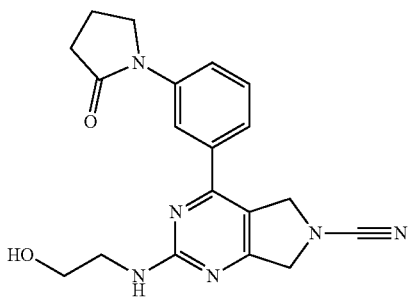 [SMILES: N#CN1Cc2nc(NCCO)nc(-c3cccc(N4CCCC4=O)c3)c2C1]

Step a.

To a solution of tert-butyl 2-chloro-4-(3-(2-oxopyrrolidin-1-yl)phenyl)-5,7-dihydro-6H-pyrrolo[3,4-d]pyrimidine-6-carboxylate (prepared as in step a of Example 289, 0.450 g, 1.086 mmol) in THF (2 ml) was added ethanolamine (2 ml) at rt. The reaction mixture was heated at 90° C. for 1 h. The reaction mixture was cooled to rt and poured into water (10 ml). The resulting precipitates were collected by filtration and washed with n-hexane (5 ml). The resulting solid was triturated with n-pentane (3×10 ml) and dried under high vacuum to yield tert-butyl 2-((2-hydroxyethyl)amino)-4-(3-(2-oxopyrrolidin-1-yl)phenyl)-5,7-dihydro-6H-pyrrolo[3,4-d]pyrimidine-6-carboxylate (0.160 g, 0.364 mmol). LCMS: Method A, 1.150 min, MS: ES+ 440.42.

Steps b, c.

The title compound was synthesised from the intermediate above using a procedure similar to that described for steps d and e of Example 1. LCMS: Method D, 2.590 min, MS: ES+ 365.15; $^1$H NMR (400 MHz, DMSO-d6) δ ppm: 8.19 (br s, 1H), 7.75 (d, J=8.0 Hz, 1H), 7.63 (br s, 1H), 7.52 (t, J=7.6 Hz, 1H), 7.32 (br s, 2H), 4.94 (s, 2H), 4.70 (t, J=5.6 Hz, 1H), 4.62 (s, 2H), 3.90 (t, J=7.2 Hz, 2H), 3.54-3.41 (m, 4H), 2.54 (t, J=8.0 Hz, 2H), 2.13-2.05 (m, 2H).

Example 292 2-((2-hydroxyethyl)amino)-4-(3-(2-oxooxazolidin-3-yl)phenyl)-5,7-dihydro-6H-pyrrolo[3,4-d]pyrimidine-6-carbonitrile

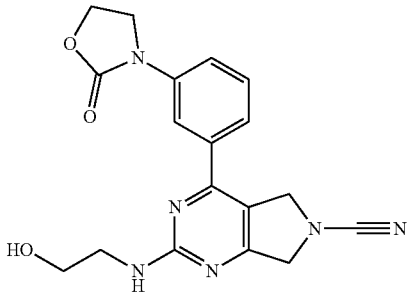

The title compound was synthesised using a procedure similar to that described for Example 291 using Intermediate 14. LCMS: Method D, 2.617 min, MS: ES+ 367.10; $^1$H NMR (400 MHz, DMSO-d6) δ ppm 8.05 (br s, 1H), 7.69 (d, J=7.6 Hz, 1H), 7.56-7.52 (m, 2H), 7.34 (br s, 1H), 4.94 (s, 2H), 4.70 (s, 1H), 4.62 (s, 2H), 4.48 (t, J=7.6 Hz, 2H), 4.14 (t, J=8.0 Hz, 2H), 3.54 (br s, 2H), 3.40-3.35 (m, 2H)

Example 293 2-cyano-7-(2-cyano-5-methoxypyridin-3-yl)-N-methylisoindoline-5-carboxamide

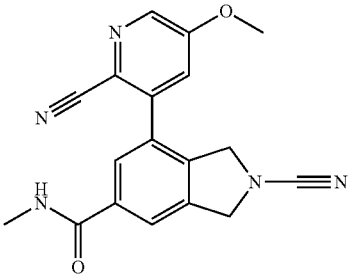 [SMILES: CNC(=O)c1cc2c(c(-c3cc(OC)cnc3C#N)c1)CN(C#N)C2]

Step a.

Carried out in a similar method to Example 226 step a using tert-butyl 4-bromo-6-(methylcarbamoyl)isoindoline-2-carboxylate (prepared as in step a of Example 240) yielding tert-butyl 6-(methylcarbamoyl)-4-(4,4,5,5-tetramethyl-1,3,2-dioxaborolan-2-yl)isoindoline-2-carboxylate. LCMS: Method A, 2.193 min, MS: ES+ 403.56.

Step b.

To a stirred solution of tert-butyl 6-(methylcarbamoyl)-4-(4,4,5,5-tetramethyl-1,3,2-dioxaborolan-2-yl)isoindoline-2-carboxylate (0.540 g, 1.351 mmol) in 1,4-dioxane:water (9:1, 5 ml) were added K$_2$CO$_3$ (0.240 g, 1.802 mmol) and 3-bromo-5-methoxypicolinonitrile (CAS Number 717843-46-4; 0.200 g, 0.901 mmol) at rt. The reaction mixture was degassed for 15 min before addition of PdCl$_2$(dppf) (0.060 g, 0.090 mmol). The reaction mixture was heated at 100° C. for 2.5 h. The reaction mixture was cooled to rt, poured into water (30 ml) and extracted with EtOAc (3×10 ml). The combined organic phase was dried over Na$_2$SO$_4$, filtered and concentrated under reduced pressure. The residue was purified by flash column chromatography (3% MeOH in DCM) yielding tert-butyl 4-(2-cyano-5-methoxypyridin-3-yl)-6-(methylcarbamoyl)-isoindoline-2-carboxylate (0.210 g, 0.514 mmol). LCMS: Method A, 2.024 min, MS: ES+ 409.40.

Steps c, d.

The title compound was synthesised from the intermediate above using a procedure similar to that described for steps d and e of Example 1. LCMS: Method D, 2.775 min, MS: ES− 332.10; $^1$H NMR (400 MHz, DMSO-d6) δ ppm 8.59 (d, J=4.4 Hz, 1H), 8.53 (d, J=2.8 Hz, 1H), 7.96 (s, 1H), 7.92 (s, 1H), 7.72 (d, J=2.8 Hz, 1H), 4.95 (s, 2H), 4.82 (s, 2H), 3.97 (s, 3H), 2.81 (d, J=4.4 Hz, 3H).

Example 294 4-(2-cyano-4-(1H-pyrazol-4-yl)phenyl)isoindoline-2-carbonitrile

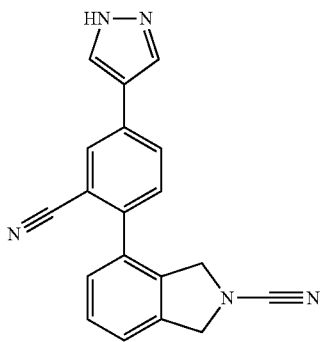 [SMILES: N#Cc1cc(-c2cn[nH]c2)ccc1-c1cccc2c1CN(C#N)C2]

Step a.

To a stirred solution of tert-butyl 4-(4,4,5,5-tetramethyl-1,3,2-dioxaborolan-2-yl)isoindoline-2-carboxylate (Intermediate 2, 0.620 g, 1.786 mmol) in 1,4-dioxane:water (9:1, 6 ml) were added K$_2$CO$_3$ (0.680 g, 4.871 mmol) and 5-bromo-2-iodobenzonitrile (CAS Number 121554-10-7; 0.500 g, 1.623 mmol) at rt. The reaction mixture was degassed for 15 min before addition of PdCl$_2$(dppf) (0.120 g, 0.162 mmol). The reaction mixture was heated at 80° C. for 6 h. The resulting reaction mixture was combined with one other batch prepared on the same scale by an identical method. The reaction mixture was cooled to rt and poured into water (100 ml). The resulting mixture was extracted with EtOAc (2×70 ml). The combined organic phase was dried over Na$_2$SO$_4$, filtered and concentrated under reduced pressure. The residue was purified by flash column chromatography (6% EtOAc in n-hexane) yielding tert-butyl 4-(4-bromo-2-cyanophenyl)isoindoline-2-carboxylate (0.620 g, 1.56 mmol). LCMS: Method A, 2.512 min, MS: ES+ 343.38, 345.38 [M−56].

Step b.

To a stirred solution of tert-butyl 4-(4-bromo-2-cyanophenyl)isoindoline-2-carboxylate (0.310 g, 0.778 mmol) in DMF:water (9:1, 5 ml) were added NaHCO$_3$ (0.196 g, 2.336 mmol) and pyrazole-4-boronic acid pinacol ester (CAS Number 269410-08-4; 0.302 g, 1.557 mmol) at rt. The reaction mixture was degassed for 15 min before addition of PdCl$_2$(dppf) (0.060 g, 0.077 mmol). The reaction mixture was heated at 130° C. for 3 h. The reaction mixture was cooled to rt and poured into water (80 ml). The resulting mixture was extracted with EtOAc (3×50 ml). The combined organic phase was dried over Na$_2$SO$_4$, filtered and concentrated under reduced pressure. The residue was purified by flash column chromatography (40% EtOAc in hexane) yielding tert-butyl 4-(2-cyano-4-(1H-pyrazol-4-yl)phenyl)isoindoline-2-carboxylate (0.130 g, 0.336 mmol). LCMS: Method A, 2.067 min, MS: ES+ 387.40

Steps c, d.

The title compound was synthesised from the intermediate above using a procedure similar to that described for steps d and e of Example 1. LCMS: Method D, 3.412 min, MS: ES− 310.10; $^1$H NMR (400 MHz, DMSO) δ ppm 13.08 (s, 1H), 8.40 (s, 1H), 8.23 (s, 1H), 8.10 (s, 1H), 7.98 (d, J=8.0 Hz, 1H), 7.58 (d, J=8.0 Hz, 1H), 7.49-7.36 (m, 3H), 4.86 (s, 2H), 4.73 (s, 2H).

Example 295 4-(5,8-dihydro-1,7-naphthyridin-7(6H)-yl)-2-(methyl((1-methylpiperidin-3-yl)methyl)amino)-5,7-dihydro-6H-pyrrolo[3,4-d]pyrimidine-6-carbonitrile

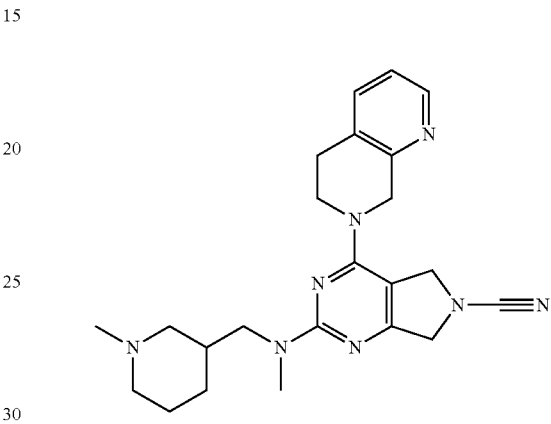

Step a.

A stirred solution of 6-Boc-2,4-dichloro-5,7-dihydropyrrolo[3,4-d]pyrimidine (CAS Number 903129-71-5; 0.420 g, 1.448 mmol) in MeCN (10 ml) was added TEA (0.40 ml, 2.86 mmol) at 0° C. The reaction mixture was stirred at 0° C. for 30 min before addition of 5,6,7,8-tetrahydro-1,7-naphthyridine dihydrochloride (CAS Number 351038-62-5; 0.300 g, 1.448 mmol). The reaction mixture was stirred at rt for 16 h. The resulting mixture was poured into water (50 ml) and extracted with EtOAc (3×30 ml). The combined organic phase was dried over Na$_2$SO$_4$, filtered and concentrated under reduced pressure. The residue was purified by flash column chromatography (40% EtOAc in hexane) yielding tert-butyl 2-chloro-4-(5,8-dihydro-1,7-naphthyridin-7(6H)-yl)-5,7-dihydro-6H-pyrrolo[3,4-d]pyrimidine-6-carboxylate (0.350 g, 0.904 mmol). LCMS: Method A, 1.866 min, MS: ES+ 388.56.

Step b.

To a solution of tert-butyl 2-chloro-4-(5,8-dihydro-1,7-naphthyridin-7(6H)-yl)-5,7-dihydro-6H-pyrrolo[3,4-d]pyrimidine-6-carboxylate (0.350 g, 0.904 mmol) in NMP (5 ml) was added DIPEA (0.350 g, 2.713 mmol) at rt. N-Methyl-1-(1-methylpiperidin-3-yl)methanamine (CAS Number 639078-61-8; 0.155 g, 1.084 mmol) was added to the reaction mixture at rt. The reaction mixture was heated at 90° C. for 16 h. The resulting reaction mixture was cooled to rt, poured into water (30 ml) and extracted with EtOAc (3×25 ml). The combined organic phase was dried over Na$_2$SO$_4$, filtered and concentrated under reduced pressure. The residue was purified by flash column chromatography (12% MeOH in DCM) yielding tert-butyl 4-(5,8-dihydro-1,7-naphthyridin-7(6H)-yl)-2-(methyl((1-methylpiperidin-3-yl)methyl)amino)-5,7-dihydro-6H-pyrrolo[3,4-d]pyrimidine-6-carboxylate (0.160 g, 0.904 mmol). LCMS: Method A, 1.442 min, MS: ES+ 494.75.

Steps c, d.

The title compound was synthesised from the intermediate above using a procedure similar to that described for steps d and e of Example 1. LCMS: Method D, 2.919 min, MS: ES+ 419.25; $^1$H NMR (400 MHz, DMSO-d6) δ ppm 8.39 (d, J=4.4 Hz, 1H), 8.14 (s, 1H), 7.60 (d, J=7.6 Hz, 1H), 7.25-7.21 (m, 1H), 4.93 (s, 2H), 4.82 (s, 2H), 4.43 (s, 2H), 3.80 (t, J=5.6 Hz, 2H), 3.46 (s, 2H), 3.05 (s, 3H), 2.90 (s, 3H), 2.50-2.33 (m, 4H), 2.24-2.02 (m, 2H), 1.70-1.51 (m, 5H).

Example 296
2-(2,6-dicyanoisoindolin-4-yl)-5-fluorobenzamide

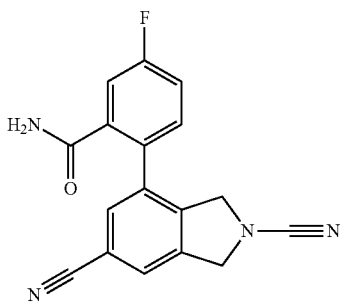 [SMILES: N#Cc1cc2c(c(-c3ccc(F)cc3C(N)=O)c1)CN(C#N)C2]

Step a.

To a stirred solution of tert-butyl 6-carbamoyl-4-(4,4,5,5-tetramethyl-1,3,2-dioxaborolan-2-yl)isoindoline-2-carboxylate (prepared as in step a of Example 241, 1.298 g, 3.347 mmol) in DMF:water (9:1, 8 ml) were added $K_2CO_3$ (0.769 g, 5.579 mmol) and methyl 2-bromo-5-fluorobenzoate (CAS Number 6942-39-8; 0.650 g, 2.79 mmol) at rt. The reaction mixture was degassed for 20 min before addition of $PdCl_2$(dppf) (0.203 g, 0.278 mmol). The reaction mixture was heated at 95° C. for 4 h. The reaction mixture was cooled to rt and poured into water (100 ml). The resulting mixture was extracted with EtOAc (3×100 ml). The combined organic phase was washed with brine (100 ml), dried over $Na_2SO_4$, filtered and concentrated under reduced pressure. The obtained residue was purified by flash column chromatography (2.3% MeOH in DCM) yielding tert-butyl 6-carbamoyl-4-(4-fluoro-2-(methoxycarbonyl)phenyl)isoindoline-2-carboxylate (0.605 g, 1.461 mmol). LCMS: Method A, 1.959 min, MS: ES+ 341.27 [M−56].

Step b.

To a solution of tert-butyl 6-carbamoyl-4-(4-fluoro-2-(methoxycarbonyl)phenyl)isoindoline-2-carboxylate (0.605 g, 1.461 mmol) in DCM (7 ml) was added TEA (0.147 g, 1.461 mmol) at 0° C. The reaction mixture was stirred for 5 min at 0° C. before addition of TFAA (0.613 g, 2.92 mmol). The reaction mixture was stirred at rt for 8 h. The resulting reaction mixture was poured into water (80 ml) and extracted with EtOAc (3×80 ml). The combined organic phase was washed with brine (100 ml), dried over $Na_2SO_4$, filtered and concentrated under reduced pressure. The residue was purified by flash chromatography (0.1% MeOH in DCM) yielding tert-butyl 6-cyano-4-(4-fluoro-2-(methoxycarbonyl)phenyl)isoindoline-2-carboxylate (0.455 g, 1.148 mmol). LCMS: Method A, 2.458 min, MS: ES+ 341.27 [M−56].

Step c.

To a solution of tert-butyl 6-cyano-4-(4-fluoro-2-(methoxycarbonyl)phenyl)isoindoline-2-carboxylate (0.427 g, 1.078 mmol) in THF:water (8:2, 6 ml) was added $LiOH.H_2O$ (0.135 g, 3.23 mmol) at rt. The reaction mixture was stirred at rt for 8 h. The resulting reaction mixture was diluted with water (30 ml), acidified using 1M HCl (50 ml) and extracted with EtOAc (3×60 ml). The combined organic phase was dried over $Na_2SO_4$, filtered and concentrated under reduced pressure to yield 2-(2-(tert-butoxycarbonyl)-6-cyanoisoindolin-4-yl)-5-fluorobenzoic acid (0.372 g, 0.973 mmol). This material was directly used for next step without any further purification. LCMS: Method A, 2.151 min, MS: ES− 381.38.

Step d.

To a solution of 2-(2-(tert-butoxycarbonyl)-6-cyanoisoindolin-4-yl)-5-fluorobenzoic acid (0.357 g, 0.934 mmol) in DMF (5 ml) were added EDC.HCl (0.358 g, 1.869 mmol), HOBt (0.171 g, 1.121 mmol) and DIPEA (0.364 g, 2.803 mmol) at rt. The reaction mixture was stirred at rt for 30 min before addition of $NH_4Br$ (0.457 g, 4.67 mmol). The reaction mixture was stirred at rt for 7 h. The resulting reaction mixture was poured into saturated $NaHCO_3$ solution (60 ml) and extracted with EtOAc (3×80 ml). The combined organic phase was dried over $Na_2SO_4$, filtered and concentrated under reduced pressure. The residue was purified by flash chromatography (2.7% MeOH in DCM) yielding tert-butyl 4-(2-carbamoyl-4-fluorophenyl)-6-cyanoisoindoline-2-carboxylate (0.235 g, 0.616 mmol). LCMS: Method A, 2.005 min, MS: ES+ 326.27 [M−56]; $^1$H NMR (400 MHz, DMSO-d6) δ ppm 7.83-7.79 (m, 2H), 7.52 (d, J=8.8 Hz, 1H), 7.46-7.39 (m, 4H), 4.69 (d, J=8.8 Hz, 2H), 4.48 (d, J=14.8 Hz, 2H), 1.43 (d, J=15.2 Hz, 9H).

Steps e, f.

The title compound was synthesised from the intermediate above using a procedure similar to that described for steps d and e of Example 1. LCMS: Method D, 2.943 min, MS: ES− 305.05; $^1$H NMR (400 MHz, DMSO-d6) δ ppm 7.82 (s, 1H), 7.77 (s, 1H), 7.56 (s, 1H), 7.47-7.36 (m, 4H), 4.89 (s, 2H), 4.68 (s, 2H).

Example 297 5-cyano-2-(2,6-dicyanoisoindolin-4-yl)-3-fluorobenzamide

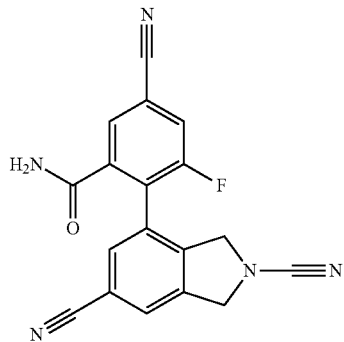 [SMILES: N#Cc1cc(F)c(-c2cc(C#N)cc3c2CN(C#N)C3)c(C(N)=O)c1]

The title compound was synthesised using a procedure similar to that described for Example 296 using methyl 2-bromo-5-cyano-3-fluorobenzoate (CAS Number 1807215-21-9). LCMS: Method E, 3.346 min, MS: ES− 330.23; $^1$H NMR (400 MHz, DMSO-d6) δ ppm 8.15 (d, J=9.2 Hz, 1H), 7.97-7.92 (m, 3H), 7.71 (s, 1H), 7.61 (s, 1H), 4.92 (s, 2H), 4.62 (s, 2H).

Example 298 4-(2-cyano-5-(2-oxooxazolidin-3-yl)phenyl)isoindoline-2-carbonitrile

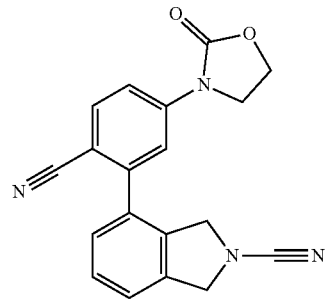 [SMILES: N#Cc1ccc(N2CCOC2=O)cc1-c1cccc2c1CN(C#N)C2]

Step a.

To a stirred solution of tert-butyl 4-(4,4,5,5-tetramethyl-1,3,2-dioxaborolan-2-yl)isoindoline-2-carboxylate (Intermediate 2, 1.434 g, 4.157 mmol) in 1,4-dioxane:water (9:1, 10 ml) were added K$_2$CO$_3$ (0.956 g, 6.93 mmol) and 2-bromo-4-chlorobenzonitrile (CAS Number 57381-49-4; 0.750 g, 3.46 mmol) at rt. The reaction mixture was degassed for 15 min before addition of PdCl$_2$(dppf) (0.253 g, 0.346 mmol). The reaction mixture was heated at 90° C. for 2 h. The resulting reaction mixture was combined with one other batch prepared on the same scale by an identical method. The reaction mixture was cooled to rt and poured into water (100 ml). The resulting mixture was extracted with EtOAc (2×100 ml). The combined organic phase was dried over Na$_2$SO$_4$, filtered and concentrated under reduced pressure. The residue was purified by flash column chromatography (49% EtOAc in n-hexane) yielding tert-butyl 4-(5-chloro-2-cyanophenyl) isoindoline-2-carboxylate (1.600 g, 4.52 mmol). LCMS: Method A, 2.462 min, MS: ES+ 299.20 [M−56].

Step b.

To a stirred solution of tert-butyl 4-(5-chloro-2-cyanophenyl)isoindoline-2-carboxylate (0.500 g, 1.412 mmol) in 1,4-dioxane (10 ml) were added K$_2$CO$_3$ (0.584 g, 4.237 mmol) and 1,3-oxazolidin-2-one (CAS Number 497-25-6; 0.246 g, 2.82 mmol) at rt in microwave tube. The reaction mixture was degassed for 20 min before addition of Pd$_2$(dba)$_3$ (0.129 g, 0.141 mmol) and Xanthphos (0.080 g, 0.141 mmol). The reaction mixture was heated at 120° C. for 2 h under microwave irritation. The reaction mixture was cooled to rt and poured into water (100 ml). The resulting mixture was extracted with EtOAc (3×100 ml). The combined organic phase was dried over Na$_2$SO$_4$, filtered and concentrated under reduced pressure. The residue was purified by flash column chromatography (43% EtOAc in hexane) yielding tert-butyl 4-(2-cyano-5-(2-oxooxazolidin-3-yl)phenyl)isoindoline-2-carboxylate (0.380 g, 0.938 mmol). LCMS: Method A, 2.144 min, MS: ES+ 350.20 [M−56].

Steps c, d.

The title compound was synthesised from the intermediate above using a procedure similar to that described for steps d and e of Example 1. LCMS: Method E, 3.664 min, MS: ES+ 331.22; $^1$H NMR (400 MHz, DMSO-d6) δ ppm 8.00 (d, J=8.8 Hz, 1H), 7.84-7.89 (m, 1H), 7.68 (d, J=2.0 Hz, 1H), 7.54-7.46 (m, 2H), 7.39 (d, J=7.2 Hz, 1H), 4.90 (s, 2H), 4.73 (s, 2H), 4.49 (t, J=7.2 Hz, 2H), 4.14 (t, J=8.4 Hz, 2H).

Example 299 4-(2-cyano-5-(2-oxopyrrolidin-1-yl)phenyl)isoindoline-2-carbonitrile

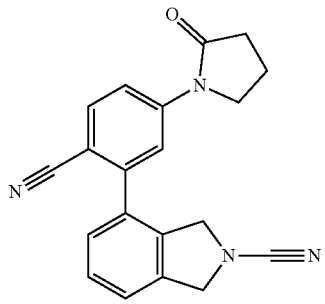 [SMILES: N#Cc1ccc(N2CCCC2=O)cc1-c1cccc2c1CN(C#N)C2]

The title compound was synthesised using a procedure similar to that described for Example 298 using 2-pyrrolidinone (CAS Number 616-45-5). LCMS: Method E, 3.737 min, MS: ES+ 329.22; $^1$H NMR (400 MHz, DMSO-d6) δ ppm 7.96 (t, J=9.2 Hz, 2H), 7.82 (s, 1H), 7.53-7.45 (m, 2H), 7.38 (d, J=7.2 Hz, 1H), 4.90 (s, 2H), 4.73 (s, 2H), 3.91 (t, J=6.8 Hz, 2H), 2.56 (t, J=8.4 Hz, 2H), 2.11-2.04 (m, 2H).

Example 300 4-(3-(2-oxoimidazolidin-1-yl)phenyl)-5,7-dihydro-6H-pyrrolo[3,4-c]pyrimidine-6-carbonitrile Step a was carried out in a similar method to Example 226 step a using 1-(3-bromophenyl)imidazolidin-2-one (CAS Number 14088-96-1) yielding 1-(3-(4,4,5,5-tetramethyl-1,3,2-dioxaborolan-2-yl)phenyl)-imidazolidin-2-one. LCMS: Method A, 1.819 min, MS: ES+ 289.28.

Step b. To a stirred solution of 1-(3-(4,4,5,5-tetramethyl-1,3,2-dioxaborolan-2-yl)phenyl)imidazolidin-2-one (0.397 g, 1.378 mmol) in 1,4-dioxane:water (9:1, 10 ml) were added K$_2$CO$_3$ (0.570 g, 4.135 mmol) and 6-Boc-2,4-dichloro-5,7-dihydropyrrolo[3,4-d]pyrimidine (CAS Number 903129-71-5; 0.400 g, 1.378 mmol) at rt. The reaction mixture was degassed for 10 min before addition of PdCl$_2$(dppf) (0.100 g, 0.137 mmol). The resulting reaction mixture was heated at 80° C. for 2 h. The reaction mixture was cooled to rt and poured into water (30 ml). The resulting mixture was extracted with EtOAc (3×25 ml). The combined organic phase was dried over Na$_2$SO$_4$, filtered and concentrated under reduced pressure. The residue was purified by flash column chromatography (30% EtOAc in n-hexane) to yielding tert-butyl 2-chloro-4-(3-(2-oxoimidazolidin-1-yl)phenyl)-5,7-dihydro-6H-pyrrolo[3,4-d]pyrimidine-6-carboxylate (0.350 g, 0.843 mmol). LCMS: Method A, 2.043 min, MS: ES+ 360.27 [M−56]; $^1$H NMR (400 MHz, DMSO-d6) δ ppm 8.27 (s, 1H), 7.66 (t, J=8.0 Hz, 1H), 7.60-7.50 (m, 2H), 7.11 (s, 1H), 4.90 (d, J=14.0 Hz, 2H), 4.63 (d, J=8.4 Hz, 2H), 3.92 (t, J=7.2 Hz, 2H), 3.50-3.41 (m, 2H), 1.47 (s, 9H).

Step c. A stirred solution of tert-butyl 2-chloro-4-(3-(2-oxoimidazolidin-1-yl)phenyl)-5,7-dihydro-6H-pyrrolo[3,4-d]pyrimidine-6-carboxylate (0.325 g, 0.783 mmol) in MeOH: DCM (1:1.15 ml) was added TEA (0.540 ml, 3.915 mmol) at rt, followed by 10% Pd/C (0.033 g). The reaction mixture was purged with H$_2$ gas at rt for 5 h. The resulting reaction mixture was filtered through celite bed and washed with DCM: MeOH (1:1, 30 ml). The combined filtrate was concentrated under reduced pressure. The residue was purified by flash column chromatography (40% EtOAc in n-hexane) yielding tert-butyl 4-(3-(2-oxoimidazolidin-1-yl)phenyl)-5,7-dihydro-6H-pyrrolo[3,4-d]pyrimidine-6-carboxylate (0.220 g, 0.577 mmol). LCMS: Method A, 1.739 min, MS: ES+ 382.40.

Steps d, e. The title compound was synthesised from the intermediate above using a procedure similar to that described for steps d and e of Example 1. LCMS: Method D, 2.495 min, MS: ES+ 307.15; $^1$H NMR (400 MHz, DMSO-d6) δ ppm 9.20 (s, 1H), 8.21 (s, 1H), 7.69 (d, J=7.6 Hz, 1H), 7.58-7.48 (m, 2H), 7.11 (s, 1H), 5.19 (s, 2H), 4.86 (s, 2H), 3.93 (t, J=7.6 Hz, 2H), 3.44 (t, J=7.6 Hz, 2H).

Example 301 5-cyano-2-(2-cyanoisoindolin-4-yl)-3-fluorobenzamide

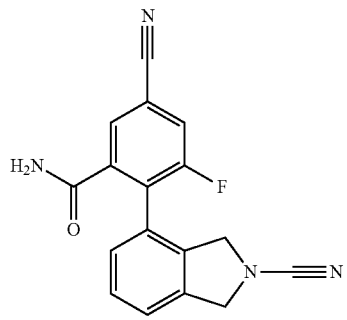 [SMILES: N#Cc1cc(F)c(-c2cccc3c2CN(C#N)C3)c(C(N)=O)c1]

Step a. NBS (114.8 g, 645 mmol) was added in a portion wise manner over 1 h to a stirred orange/brown suspension of 2-amino-3-fluorobenzoic acid (100 g, 645 mmol) in DCM (1000 ml) at rt, and the resulting mixture was stirred at rt for 2 h. The mixture was then filtered and the resulting solid was washed sequentially with DCM (2×250 ml) and water (3×400 ml) before being dried under vacuum at 55° C. for 7 h to give the desired product as a beige solid (121.4 g, 80%). LCMS (Method S): rt 2.93 min, m/z 232/234 [M−H]$^−$; $^1$H NMR (400 MHz, DMSO-d$_6$) δ ppm 7.64 (m, 1H), 7.52 (dd, J=10.9, 2.3 Hz, 1H)

Step b. Concentrated H$_2$SO$_4$ (42 ml, 775 mmol) was added in a dropwise manner over 40 min to a stirred suspension of 2-amino-5-bromo-3-fluorobenzoic acid (120.9 g, 517 mmol) in MeOH (700 ml), and the resulting dark brown solution was heated at reflux for 18 h. The mixture was cooled to rt and evaporated to dryness under vacuum to give a brown oily solid, which was partitioned between water (50 ml) and EtOAc (800 ml). The biphasic mixture was then treated with a saturated aqueous solution of NaHCO$_3$ (around 1 L) until the aqueous phase became neutral (pH 7-8). The aqueous phase was collected and extracted with EtOAc (800 ml), and the combined organic extracts were dried over Na$_2$SO$_4$ and evaporated to dryness under vacuum to give the crude product as a brown solid (116 g). The crude solid was suspended in a 20:1 (v/v) mixture of PE and EtOAc (400 mL), and the resulting mixture was stirred for 1 h before being filtered. The filter-cake was then washed with PE (400 ml) to remove any residual starting material and dried under vacuum at rt to give the desired product as a light tan solid (96.6 g, 75%). LCMS (Method L): rt 2.77 min, m/z 248/250 [M+H]$^+$; NMR (400 MHz, DMSO-d6) δ ppm 7.67-7.64 (dd, J=2.2, 1.6 Hz, 1H), 7.59-7.54 (dd, J=11.9, 2.3 Hz, 1H), 6.71 (bs, 2H), 3.83 (s, 3H)

Step c. To a solution of methyl 2-amino-5-bromo-3-fluorobenzoate (100 g, 400 mmol) in DMF (1 L) was added zinc(II) cyanide (28 g, 240 mmol), and the resulting mixture was degassed with nitrogen for 20 min. The reaction mixture was treated with Pd(PPh$_3$)$_4$ and was heated under an atmosphere of nitrogen for 6 h at 100° C. Upon completion of the reaction, as determined by LCMS, the mixture was cooled to rt and poured into water (2 L). The resulting aqueous mixture was extracted with EtOAc (3×1 L) and the combined organics were washed with brine (500 ml) before being evaporated to dryness under vacuum to give a solid. The crude solid was passed through a pad of silica eluting with DCM (5 L). Fractions containing the desired product were combined and evaporated to dryness under vacuum to give the crude product as a solid, which was triturated successively with hexane (200 ml) and in a 1:1 (v/v) mixture of hexane and Et$_2$O (2×130 ml). The solid was then dried under vacuum at rt to give the desired product as a pale coloured solid (44 g, 56%). LCMS (Method R): rt 2.44 min, m/z 195 [M+H]$^+$; $^1$H NMR (400 MHz, DMSO-d6) δ ppm 7.95-7.91 (m, 1H), 7.81-7.75 (dd, J=11.5, 1.9 Hz, 1H), 7.43 (bs, 2H), 3.84 (s, 3H).

Step d. CuBr$_2$ (46.9 g, 210 mmol) was added to a stirred suspension of methyl 2-amino-5-cyano-3-fluorobenzoate (31.4 g, 162 mmol) in MeCN (550 ml) to give dark brown suspension, which was stirred at rt for 5 min. A solution of tBuNO$_2$ (25.6 ml, 194 mmol) in MeCN (50 ml) was then added to the reaction mixture in a dropwise manner over 50 min (resulting in gentle gas evolution and temperature increase from 20 to 30° C.), and the resulting black suspension was stirred at rt for 4 h. Upon completion of the reaction, as determined by LCMS, the mixture was diluted with water (400 ml), resulting in the formation of a thick precipitate. EtOAc (500 ml) was added to give a biphasic mixture, which was stirred at rt for 12 h. The mixture was allowed to settle and the aqueous layer was collected and extracted with EtOAc (2×500 ml). The combined organic layers were dried over Na$_2$SO$_4$, filtered and concentrated to dryness under vacuum to give a solid (41.4 g). This crude solid was dissolved in DCM (100 ml) and passed through a pad of silica eluting with DCM to give the desired product as an off white solid (37 g, 88%). LCMS (Method R): rt 2.57 min, m/z 258 [M+H]$^−$; $^1$H NMR (400 MHz, DMSO-d6) δ ppm 8.27-8.22 (dd, J=8.5, 1.9 Hz, 1H), 8.12-8.10 (dd, J=1.9, 1.2 Hz, 1H), 3.90 (s, 3H).

Step e. TEA (126 ml, 903 mmol) was added drop-wise over 5 min to a stirred suspension of 4-bromoisoindoline HCl (100 g, 430 mmol) in THF (700 ml) and the mixture was cooled to 10° C. The cooled mixture was then treated with a solution of di-tert-butyl dicarbonate (122 g, 559 mmol) in THF (300 ml) over 15 min whilst maintaining the temperature below 20° C., and the resulting mixture was stirred at rt for 12 h. The reaction was concentrated under vacuum to give an oil, which was partitioned between EtOAc (600 ml) and water (600 ml). The aqueous phase was collected and extracted with EtOAc (2×500 ml), and the combined organic extracts were washed with brine, dried over $Na_2SO_4$, filtered and evaporated to dryness under vacuum to give the crude product as a solid (161 g). The crude solid was slurried in hexane (150 ml), filtered and the resulting solid washed with hexane (60 ml) before being dried under vacuum at rt to give the desired product as a solid (95.7 g, 75%). LCMS (Method R): rt 3.02 min, m/z 242 (-tBu)/198(-Boc) [M+H]$^-$; $^1$H NMR (400 MHz, DMSO-d6) δ ppm 7.51-7.46 (dd, J=7.8, 0.6 Hz, 1H), 7.38-730 (m, 1H), 7.29-7.21 (m, 1H), 4.73-4.63 (d, 2H), 4.56-4.47 (d, 2H), 1.50-1.42 (d, 9H).

Step f. Bis(pinacolato)diboron (87.5 g, 344 mmol) was added to a solution of tert-butyl 4-bromoisoindoline-2-carboxylate (85.6 g, 287 mmol) in 1,4-dioxane (850 ml), followed by potassium acetate (56.2 g, 574 mmol), and the resulting mixture was degassed with nitrogen for 15 min. Pd(dppf)Cl$_2$ (21 g, 28.7 mmol) was added to the reaction flask and the resulting mixture was heated at 100° C. for 6 h. Upon completion of the reaction, as determined by LCMS, the mixture was cooled to rt and filtered through a pad of Celite®, washing with EtOAc (2×50 ml). The filtrate was evaporated to dryness under vacuum to give a black oily residue, which was dissolved in DCM and passed through a silica pad, eluting with DCM. The solvent was subsequently removed under vacuum to give a solid, which was triturated with hexane (200 ml) and dried under vacuum at rt to give the desired product as a white solid (88 g, 89%). LCMS (Method R): rt 3.36 min, m/z 346, 290 (-tBu), 246 (-Boc) [M+H]$^+$; $^1$H NMR (400 MHz, DMSO-d6) δ ppm 7.62-7.54 (m, 1H), 7.48-7.41 (m, 1H), 7.33-7.25 (m, 1H), 4.70-4.62 (m, 2H), 4.60-4.53 (m, 2H), 1.49-1.43 (m, 9H), 1.33-1.27 (m, 12H).

Step g. A stirred suspension of methyl 2-bromo-5-cyano-3-fluorobenzoate (70 g, 271 mmol), tert-butyl 4-(4,4,5,5-tetramethyl-1,3,2-dioxaborolan-2-yl)isoindoline-2-carboxylate (Intermediate 2, 103 g, 298 mmol) and K$_2$CO$_3$ (75 g, 542 mmol) in a 9:1 (v/v) mixture of 1,4-dioxane and water (1 L) was degassed with nitrogen for 20 min. Pd(dppf)Cl$_2$ (19.8 g, 27 mmol) was added to the reaction flask, and the resulting mixture was degassed with nitrogen for 20 min. The mixture was then heated at 100° C. for 6 h under an atmosphere of nitrogen, before being cooled to rt with stirring for 12 h. Water (500 ml) was added to the reaction, forming a thick suspension, which was filtered through a pad of Celite®, washing with EtOAc (1 L). The biphasic filtrate was separated and the aqueous layer was extracted with EtOAc (2×800 ml). The combined organic layers were washed with brine (500 ml), dried over Na$_2$SO$_4$ and evaporated to dryness under vacuum to give the crude product as a viscous brown oil (180 g). The crude product was purified by flash column chromatography (0-20% EtOAc in hexane). Fractions containing the desired product were combined and evaporated to dryness under vacuum to give an oil, which was triturated with MeCN (500 mL) to the desired product as an off-white solid (87.8 g, 82%). LCMS (Method R): rt 2.81 min, m/z 397/341 (-tBu)/297 (-Boc) [M+H]$^-$; $^1$H NMR (400 MHz, DMSO-d6) δ ppm 8.32-8.24 (m, 1H), 8.23-8.19 (m, 1H), 7.47-7.34 (m, 2H), 7.15-7.06 (m, 1H), 4.74-4.63 (m, 2H), 4.37-4.15 (m, 2H), 3.60 (s, 3H), 1.47-1.36 (d, 9H).

Step h. To a cloudy solution of tert-butyl 4-(4-cyano-2-fluoro-6-(methoxycarbonyl)phenyl)-isoindoline-2-carboxylate (80 g, 202 mmol) in a 1:1 (v/v) mixture of THF and water (800 ml) was added LiOH.H$_2$O (8.64 g, 206 mmol) in a single portion and stirred at rt for 4.5 h. The reaction mixture was diluted with water (400 ml) and evaporated under vacuum at 20° C. to remove the THF. The remaining aqueous solution was washed with hexane (3×400 ml) and acidified to pH 4-5 by the careful addition of a 1 M aqueous HCl solution. The acidified mixture was extracted with DCM (3×400 ml) and the combined organic extracts were dried over Na$_2$SO$_4$ and evaporated to dryness under vacuum to give the desired product as yellow foam (88.4 g, 100%). LCMS (Method R): rt 2.61 min, m/z 383/327 (-tBu)/283 (-Boc) [M+H]$^+$; $^1$H NMR (400 MHz, DMSO-d6) δ ppm 8.23-8.12 (m, 2H), 7.46-7.33 (m, 2H), 7.19-7.08 (m, 1H), 4.72-4.63 (m, 2H), 4.36-4.23 (m, 2H), 1.48-1.36 (d, 9H).

Step i. TEA (56.3 ml, 404 mmol) was added dropwise over 15 min to a stirred yellow suspension of 2-(2-(tert-butoxycarbonyl)isoindolin-4-yl)-5-cyano-3-fluorobenzoic acid (78 g, 202 mmol), HATU (92.2 g, 242 mmol) and NH$_4$Cl (54 g, 1 mol) in THF (880 ml), and the resulting mixture was stirred at rt for 24 h. The reaction was then treated with water (1 L), and the resulting mixture was extracted with EtOAc (1 L). The organic layer was washed with a saturated aqueous solution of NaHCO$_3$ (250 ml), dried over Na$_2$SO$_4$, filtered and evaporated to dryness under vacuum to give a yellow solid, which was triturated in Et$_2$O (700 ml). The triturated solid was dissolved in DCM and purified by flash column chromatography (0-80% EtOAc in hexane). Fractions containing the desired product were evaporated to give a yellow foam, which was azeotroped from MeCN (2×100 ml) to give the desired product as a pale yellow solid (68.6 g, 87%). LCMS (Method R): rt 2.54 min, m/z 382/326 (-tBu)/282 (-Boc) [M+H]$^+$; $^1$H NMR (400 MHz, DMSO-d6) δ ppm 8.11-8.02 (m, 1H), 7.93-7.79 (m, 2H), 7.54-7.44 (m, 1H), 7.43-7.33 (m, 2H), 7.21-7.11 (m, 1H), 4.74-4.59 (m, 2H), 4.52-4.21 (m, 2H), 1.47-1.38 (m, 9H).

Steps j and k were carried out in a similar manner to steps b and c of Example 21. LCMS (Method K): rt 4.36 min, m/z 307 [M+H]$^+$; $^1$H NMR (400 MHz, DMSO-d6) δ ppm 8.10-8.03 (dd, J=9.2, 1.5 Hz, 1H), 7.89 (d, J=1.3 Hz, 1H), 7.84 (bs, 1H), 7.50 (bs, 1H), 7.45-7.37 (m, 2H), 7.22-7.17 (dd, J=6.7, 1.9 Hz, 1H), 4.93-4.81 (m, 2H), 4.66-4.58 (m, 1H), 4.55-4.47 (m, 1H); $^{19}$F NMR (400 MHz, DMSO-d6, proton coupled) δ ppm: 111.25/−111.27.

Biological Activity of Compounds of the Invention
Abbreviations:
TAMRA carboxytetramethylrhodamine
PCR polymerase chain reaction
PBS phosphate buffered saline
EDTA ethylenediaminetetraacetic acid
Tris 2-amino-2-(hydroxymethyl)-1,3-propanediol
NP40 Nonidet P-40, octylphenoxypolyethoxyethanol
BSA bovine serum albumin
In Vitro USP7 Inhibition Assay
Expression and Purification of USP7

The USP7 construct was PCR amplified and cloned into a pFLAG-CMV-6a vector (Sigma-Aldrich) with an N-terminal FLAG tag. HEK293T cells were transfected with FLAG-USP7 using TransIT-LT1 transfection reagent (Mirus) according to the manufacturer's instructions. Cells were harvested 40 hours after transfection. Cells were washed once with PBS and scraped in lysis buffer (50 mM Tris, pH 7.5, 150 mM NaCl, 3 mM EDTA, 0.5% NP40, 10% glycerol, 5 mM beta-mercaptoethanol, protease inhibitors (complete mini, Roche) and phosphatase inhibitors (PhosSTOP mini, Roche). Lysates were incubated for 30 min on ice and centrifuged at 4000 rpm for 10 min at 4° C. Soluble supernatant was added to FLAG affinity resin (EZview Rad ANTI-FLAG M2 affinity gel, Sigma-Aldrich) equilibrated in low salt buffer (20 mM Tris, pH 7.5, 150 mM NaCl, 0.5 mM EDTA, 5 mM beta-mercaptoethanol) and incubated at 4° C. for 3 hours rotating. The resin was spun at 2000 rpm for 2 min and the supernatant was removed. The resin was washed two times with low salt buffer plus protease inhibitors (complete mini, Roche) and phosphatase inhibitors (PhosSTOP mini, Roche) and one time with high salt buffer (20 mM Tris, pH 7.5, 500 mM NaCl, 0.5 mM EDTA, 5 mM beta-mercaptoethanol, protease inhibitors (complete mini, Roche) and phosphatase inhibitors (PhosSTOP mini, Roche). To elute the bound USP7, elution buffer (10 mM Tris, pH 7.5, 150 mM NaCl, 0.5 mM EDTA, 10% glycerol, 0.5% NP40, 5 mM beta-mercaptoethanol, 0.15 mg/ml 3×FLAG peptide (Sigma-Aldrich)) was added to the resin and incubated at 4° C. for 2.5 hours rotating. The resin was centrifuged at 4000 rpm for 30 seconds, and the supernatant containing purified FLAG-USP7 was removed and stored at −80° C.

USP7 Biochemical Kinetic Assay

Reactions were performed in duplicate in black 384 well plates (small volume, Greiner 784076) in a final reaction volume of 21 μl. USP7 was diluted in reaction buffer (20 mM Tris, pH 7.5, 100 mM NaCl, 0.05% Tween 20, 0.5 mg/ml BSA, 5 mM—beta mercaptoethanol) to the equivalent of 0, 0.0005, 0.001, 0.0025, and 0.005 μl/well. Buffer was optimised for optimal temperature, pH, reducing agent, salts, time of incubation, and detergent. Reactions were initiated by the addition of 50 nM of TAMRA labelled peptide linked to ubiquitin via an iso-peptide bond as fluorescence polarisation substrate. Reactions were incubated at room temperature and read every 2 min for 120 min. Readings were performed on a Pherastar Plus (BMG Labtech). Excitation 540 nm; Emission 590 nm.

USP7 Biochemical IC$_{50}$ Assay

Dilution plates were prepared at 21 times the final concentration (2100 μM for a final concentration of 100 μM) in 50% DMSO in a 96-well polypropylene V-bottom plate (Greiner #651201). A typical 8-point dilution series would be 100, 30, 10, 3, 1, 0.3, 0.1, 0.03 μM final. Reactions were performed in duplicate in black 384 well plates (small volume, Greiner 784076) in a final reaction volume of 21 μl. Either 1 μl of 50% DMSO or diluted compound was added to the plate. USP7 was diluted in reaction buffer (20 mM Tris, pH 7.5, 100 mM NaCl, 0.05% Tween 20, 0.5 mg/ml BSA, 5 mM—beta mercaptoethanol) to the equivalent of 0.0025 μl/well and 10 μl of diluted USP7 was added to the compound. Enzyme and compound were incubated for 30 min at room temp. Reactions were initiated by the addition of 50 nM of TAMRA labelled peptide linked to ubiquitin via an iso-peptide bond as fluorescence polarisation substrate. Reactions were read immediately after addition of substrate and following a 2 hr incubation at room temperature. Readings were performed on a Pherastar Plus (BMG Labtech). λ Excitation 540 nm; λ Emission 590 nm.

Activity of Exemplary Compounds in USP7 Biochemical IC50 Assay

Ranges:
A<1 μM;
1 μM<B<10 μM;
10 μM<C<30 μM;
30 μM<C<100 μM;

| Example | IC50 range |
|---|---|
| 1 | B |
| 2 | B |
| 3 | B |
| 4 | B |
| 5 | A |
| 6 | B |
| 7 | B |
| 8 | B |
| 9 | B |
| 10 | B |
| 11 | B |
| 12 | B |
| 13 | B |
| 14 | D |
| 15 | C |
| 16 | B |
| 17 | B |
| 18 | B |
| 19 | B |
| 20 | B |
| 21 | B |
| 22 | B |
| 23 | D |
| 24 | B |
| 25 | A |
| 26 | A |
| 27 | A |
| 28 | A |
| 29 | A |
| 30 | B |
| 31 | B |
| 32 | A |
| 33 | A |
| 34 | B |
| 35 | A |
| 36 | A |
| 37 | A |
| 38 | A |
| 39 | B |
| 40 | B |
| 41 | B |
| 42 | A |
| 43 | D |
| 44 | A |
| 45 | B |
| 46 | B |
| 47 | A |
| 48 | A |
| 49 | A |
| 50 | A |
| 51 | B |
| 52 | A |
| 53 | A |
| 54 | A |
| 55 | A |
| 56 | B |
| 57 | B |
| 58 | B |
| 59 | B |
| 60 | A |
| 61 | B |
| 62 | A |
| 63 | B |
| 64 | A |
| 65 | B |
| 66 | B |
| 67 | B |
| 68 | B |
| 69 | B |
| 70 | B |
| 71 | B |
| 72 | A |
| 73 | B |
| 74 | B |
| 75 | B |
| 76 | B |
| 77 | B |
| 78 | B |
| 79 | B |
| 80 | B |
| 81 | B |

| Example | IC50 range |
|---|---|
| 82 | B |
| 83 | C |
| 84 | C |
| 85 | B |
| 86 | B |
| 87 | B |
| 88 | C |
| 89 | B |
| 90 | B |
| 91 | B |
| 92 | B |
| 93 | B |
| 94 | B |
| 95 | C |
| 96 | B |
| 97 | C |
| 98 | B |
| 99 | C |
| 100 | B |
| 101 | C |
| 102 | B |
| 103 | C |
| 104 | B |
| 105 | B |
| 106 | B |
| 107 | C |
| 108 | B |
| 109 | B |
| 110 | B |
| 111 | B |
| 112 | B |
| 113 | B |
| 114 | B |
| 115 | C |
| 116 | B |
| 117 | B |
| 118 | B |
| 119 | B |
| 120 | B |
| 121 | C |
| 122 | B |
| 123 | C |
| 124 | B |
| 125 | B |
| 126 | B |
| 127 | B |
| 128 | B |
| 129 | C |
| 130 | C |
| 131 | C |
| 132 | C |
| 133 | C |
| 134 | C |
| 135 | B |
| 136 | D |
| 137 | B |
| 138 | B |
| 139 | B |
| 140 | B |
| 141 | B |
| 142 | B |
| 143 | C |
| 144 | C |
| 145 | B |
| 146 | A |
| 147 | B |
| 148 | C |
| 149 | C |
| 150 | D |
| 151 | B |
| 152 | B |
| 153 | A |
| 154 | B |
| 155 | C |
| 156 | B |
| 157 | B |
| 158 | B |
| 159 | B |
| 160 | B |
| 161 | B |
| 162 | B |
| 163 | B |
| 164 | B |
| 165 | B |
| 166 | B |
| 167 | B |
| 168 | B |
| 169 | B |
| 170 | B |
| 171 | B |
| 172 | B |
| 173 | C |
| 174 | B |
| 175 | B |
| 176 | B |
| 177 | B |
| 178 | B |
| 179 | B |
| 180 | B |
| 181 | B |
| 182 | B |
| 183 | B |
| 184 | B |
| 185 | C |
| 186 | B |
| 187 | B |
| 188 | B |
| 189 | C |
| 190 | B |
| 191 | B |
| 192 | B |
| 193 | B |
| 194 | B |
| 195 | B |
| 196 | B |
| 197 | B |
| 198 | B |
| 199 | B |
| 200 | B |
| 201 | B |
| 202 | B |
| 203 | B |
| 204 | B |
| 205 | B |
| 206 | B |
| 207 | C |
| 208 | C |
| 209 | B |
| 210 | B |
| 211 | A |
| 212 | B |
| 213 | B |
| 214 | B |
| 215 | B |
| 216 | B |
| 217 | B |
| 218 | B |
| 219 | B |
| 220 | B |
| 221 | A |
| 222 | B |
| 223 | B |
| 224 | B |
| 225 | B |
| 226 | B |
| 227 | A |
| 228 | B |
| 229 | B |
| 230 | A |
| 231 | B |
| 232 | B |
| 233 | B |
| 234 | B |
| 235 | B |

-continued

| Example | IC50 range |
|---------|------------|
| 236 | B |
| 237 | B |
| 238 | B |
| 239 | B |
| 240 | A |
| 241 | B |
| 242 | B |
| 243 | B |
| 244 | B |
| 245 | B |
| 246 | B |
| 247 | B |
| 248 | A |
| 249 | B |
| 250 | B |
| 251 | B |
| 252 | B |
| 253 | B |
| 254 | B |
| 255 | B |
| 256 | B |
| 257 | B |
| 258 | C |
| 259 | B |
| 260 | B |
| 261 | B |
| 262 | B |
| 263 | B |
| 264 | B |
| 265 | B |
| 266 | B |
| 267 | A |
| 268 | C |
| 269 | B |
| 270 | A |
| 271 | B |
| 272 | B |
| 273 | B |
| 274 | B |
| 275 | A |
| 276 | B |
| 277 | B |
| 278 | B |
| 279 | B |
| 280 | B |
| 281 | B |
| 282 | B |
| 283 | A |
| 284 | B |
| 285 | B |
| 286 | B |
| 287 | B |
| 288 | B |
| 289 | B |
| 290 | B |
| 291 | A |
| 292 | A |
| 293 | B |
| 294 | B |
| 295 | B |
| 296 | B |
| 297 | B |
| 298 | B |
| 299 | B |
| 300 | B |
| 301 | B |

The invention claimed is:

1. A compound of formula I

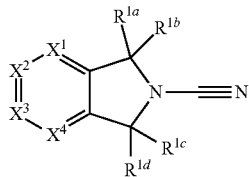

(I)

a tautomer thereof, or a pharmaceutically acceptable salt of said compound or tautomer, wherein:

$R^{1a}$, $R^{1b}$, $R^{1c}$ and $R^{1d}$ each independently represent hydrogen or $C_1$-$C_6$ alkyl, which is optionally substituted with halogen, hydroxyl or cyano;

$X^1$, $X^3$ and $X^4$ each independently represent N, C-$Q^1$-$R^2$ or C-$Q^2$-$(R^6)_n$ and $X^2$ represents N or CH, wherein one of $X^1$, $X^3$ and $X^4$ represents C-$Q^1$-$R^2$ and no more than two of $X^1$, $X^2$, $X^3$ and $X^4$ represent N;

$Q^1$ represents a covalent bond, an oxygen atom, a sulphur atom, —$OR^5$—, —SO—, —$SO_2$—, —CO—, —C(O)O—, —$C_0$-$C_3$ alkylene-$CONR^3$—$C_0$-$C_3$ alkylene-, —$C_0$-$C_3$ alkylene-$NR^3$—$C_0$-$C_3$ alkylene, —$C_0$-$C_3$ alkylene-$NR^3$CO—$C_0$-$C_3$ alkylene, —$NR^3CONR^4$—, —$SO_2NR^3$—, $NR^3SO_2$—, —$NR^3SO_2NR^4$—, —$NR^3C(O)O$—, —$NR^3C(O)OR^5$—, optionally substituted —$C_1$-$C_6$ alkylene or optionally substituted —$C_2$-$C_6$ alkenylene;

wherein for $Q^1$ the optional substituents for $C_1$-$C_6$ alkylene and —$C_2$-$C_6$ alkenylene are selected from halogen, oxo, hydroxyl, thiol, cyano, amino, amido nitro and $SF_5$;

$R^2$ is an optionally substituted, 3 to 10-membered, monocyclic or bicyclic, heteroaryl, aryl or heterocyclyl ring;

$R^3$ and $R^4$ each independently represent hydrogen or optionally substituted $C_1$-$C_6$ alkyl;

$R^5$ represents optionally substituted $C_1$-$C_6$ alkylene;

n is 0 or 1;

wherein for $R^3$, $R^4$ and $R^5$ the optional substituents for $C_1$-$C_6$ alkyl and $C_1$-$C_6$ alkylene are selected from halogen, oxo, hydroxyl, thiol, cyano, amino, amido, nitro and $SF_5$;

$R^2$ is unsubstituted or substituted with one or more substituents selected from halogen, cyano, oxo, nitro, hydroxyl, —$CF_3$, —$SR^{10}$, —$C_1$-$C_6$ alkyl, —$C_1$-$C_6$ alkoxy, —$C_2$-$C_6$ alkenyl, —$C_2$-$C_6$ alkynyl, -$Q^{3a}$-$R^{12}$, -$Q^{3a}$-O-$Q^{3b}$-$R^{12}$, -$Q^{3a}$-S-$Q^{3b}$-$R^{12}$, -$Q^{3a}$-SO-$Q^{3b}$-$R^{12}$, -$Q^{3a}$-$NR^{10}CONR^{11}R^{11a}$, -$Q^{3a}$-$NR^{10}CONR^{11}$-$Q^{3b}$-$R^{12}$, -$Q^{3a}$-$NR^{10}R^{11}$, -$Q^{3a}$-$NR^{10}$-$Q^{3b}$-$R^{12}$, -$Q^{3a}$-$COR^{10}$, -$Q^{3a}$-CO-$Q^{3b}$-$R^{12}$, -$Q^{3a}$-$NR^{10}COR^{11}$-$Q^{3a}$-$NR^{10}CO$-$Q^{3b}$-$R^{12}$, -$Q^{3a}$-$NR^{10}C(O)OR^{11}$, -$Q^{3a}$-$NR^{10}C(O)O$-$Q^{3a}$-$R^{12}$, -$Q^{3a}$-$SO_2R^{10}$, -$Q^{3a}$-$SO_2$-$Q^{3b}$-$R^{12}$, -$Q^{3a}$-$CONR^{10}R^{11}$, -$Q^{3a}$-$CONR^{10}$-$Q^{3b}$-$R^{12}$, -$Q^{3a}$-$CO_2R^{10}$, -$Q^{3a}$-$CO_2$-$Q^{3c}$-$R^{12}$, -$Q^{3a}$-$SO_2NR^{10}R^{11}$, -$Q^{3a}$-$SO_2NR^{10}$-$Q^{3b}$-$R^{12}$, -$Q^{3a}$-$NR^{10}SO_2R^{11}$, -$Q^{3a}$-$NR^{10}SO_2$-$Q^{3b}$-$R^{12}$, -$Q^{3a}$-$NR^{10}SO_2NR^{11}R^{11a}$, and -$Q^{3a}$-$NR^{10}SO_2NR^{11}$-$Q^{3b}$-$R^{12}$; wherein $Q^{3a}$ and $Q^{3b}$ independently represent a covalent bond optionally substituted $C_1$-$C_6$ alkylene or optionally substituted $C_2$-$C_6$ alkenylene;

$R^{10}$, $R^{11}$ and $R^{11a}$ each independently represent hydrogen or optionally substituted $C_1$-$C_6$ alkyl; and $R^{12}$ represents a 3 to 10-membered, optionally substituted heterocyclyl, optionally substituted heteroaryl, optionally substituted aryl, or an optionally substituted cycloalkyl;

$Q^2$ represents hydrogen, halogen, cyano, nitro, hydroxyl, —$SR^7$, —$NR^7R^8$, —$CONR^7R^8$, —$NR^7COR^8$, —$NR^7CONR^8R^{8a}$, —$COR^7$, —$C(O)OR^7$, —$SO_2R^7$, —$SO_2NR^7R^8$, —$NR^7SO_2R^8$, —$NR^7SO_2NR^8R^{8a}$, —$NR^7C(O)OR^8$, optionally substituted —$C_1$-$C_6$ alkyl, optionally substituted —$C_1$-$C_6$ alkoxy, optionally substituted —$C_2$-$C_6$ alkenyl, —$C_0$-$C_3$ alkylene-$NR^7CONR^8R^{8a}$, —$C_0$-$C_3$ alkylene-$NR^7C(O)OR^{8a}$, a covalent bond, an oxygen atom, a sulphur atom, —$OR^9$—, —SO—, —$SO_2$—, —CO—, —$C(O)O$—, —$C_0$-$C_3$ alkylene-$CONR^7$—$C_0$-$C_3$ alkylene, —$C_0$-$C_3$ alkylene-$NR^1$—$C_0$-$C_3$ alkylene, —$C_0$-$C_3$ alkylene-$NR^7CO$—$C_0$—$C_3$ alkylene, —$NR^7CONR^8$—, —$SO_2NR^7$—, $NR^7SO_2$—, —$NR^7SO_2NR^8$—, —$NR^7C(O)O$—, —$NR^7C(O)OR^9$—, optionally substituted $C_1$-$C_6$ alkylene, or optionally substituted —$C_2$-$C_6$ alkenylene;

wherein for $Q^2$ the optional substituents for —$C_1$-$C_6$ alkyl, —$C_1$-$C_6$ alkoxy, $C_2$-$C_6$ alkenyl, —$C_1$-$C_6$ alkylene and —$C_2$-$C_6$ alkenylene are selected from halogen, hydroxyl, thiol, cyano, amino, amido, nitro, $SF_5$, —$NHC(O)C_1$-$C_6$ alkyl, —$C_1$-$C_6$ alkoxy, —$SO_2C_1$-$C_6$ alkyl, —$N(C_1$-$C_6$ alkyl)$C(O)$ $C_1$-$C_6$ alkyl, —$NHSO_2C_1$-$C_6$ alkyl, and —$C(O)N(C_1$-$C_6$ alkyl)$_2$;

$R^6$ is an optionally substituted, 3 to 10-membered, monocyclic or bicyclic, heteroaryl, aryl, heterocyclyl or cycloalkyl ring;

$R^7$, $R^8$ and $R^{8a}$ each independently represent hydrogen or optionally substituted $C_1$-$C_6$ alkyl;

$R^9$ represents optionally substituted $C_1$-$C_6$ alkylene;

wherein for $R^7$, $R^8$ and $R^9$ the optional substituents for $C_1$-$C_6$ alkyl and $C_1$-$C_6$ alkylene are selected from halogen, oxo, hydroxyl, thiol, cyano, amino, amido, nitro, $SF_5$, —$SO_2C_1$-$C_6$ alkyl, and —$C_1$-$C_6$ alkoxy;

$R^6$ is unsubstituted or substituted with one or more substituents selected from halogen, cyano, oxo, nitro, hydroxyl, —$SR^{13}$, —$C_1$-$C_6$ alkyl, —$C_1$-$C_6$ alkoxy, —$C_2$-$C_6$ alkenyl, —$C_2$-$C_6$ alkynyl, -$Q^{4a}$-$R^{15}$, -$Q^{4a}$-O-$Q^{4b}$-$R^{15}$, -$Q^{4a}$-S-$Q^{4b}$-$R^{15}$-$Q^{4a}$-SO-$Q^{4b}$-$R^{15}$-$Q^{4a}$-$NR^{13}CONR^{14}R^{14b}$-$Q^{4a}$-$NR^{13}CONR^{14}$-$Q^{4b}$-$R^{15}$, -$Q^{4a}$-$NR^{13}R^{14}$-$Q^{4a}$-$NR^{13}$-$Q^{4b}$-$R^{15}$-$Q^{4a}$-$COR^{13}$, -$Q^{4a}$-$CO$-$Q^{4b}$-$R^{15}$—, -$Q^{4a}$-$NR^{13}COR^{14}$, -$Q^{4a}$-$NR^{13}CO$-$Q^{4b}$-$R^{15}$, -$Q^{4a}$-$NR^{13}C(O)OR^{14}$, -$Q^{4a}$-$NR^{13}C(O)O$-$Q^{4b}$-$R^{14}$-$Q^{4a}$-$SO_2R^{13}$, -$Q^{4a}$-$SO_2$-$Q^{4b}$-$R^{15}$, -$Q^{4a}$-$CONR^{13}R^{14}$-$Q^{4a}$-$CONR^{13}$-$Q^{4b}$-$R^{15}$-$Q^{4a}$-$CO_2R^{13}$, -$Q^{4a}$-$CO_2$-$Q^{4b}$-$R^{15}$, -$Q^{4a}$-$SO_2NR^{13}R^{14}$, -$Q^{4a}$-$SO_2NR^{13}$-$Q^{4b}$-$R^{15}$, $Q^{4a}$-$NR^{13}SO_2R^{14}$, $Q^{4a}$-$NR^{13}SO_2$-$Q^{4b}$-$R^{15}$, $Q^{4a}$-$NR^{13}SO_2NR^{14}R^{14b}$ and -$Q^{4a}$-$NR^{13}SO_2NR^{14}$-$Q^{4b}$-$R^{15}$;

$Q^{4a}$ and $Q^{4b}$ independently represent a covalent bond optionally substituted $C_1$-$C_6$ alkylene or optionally substituted $C_2$-$C_6$ alkenylene;

$R^{13}$, $R^{14}$ and $R^{14a}$ each independently represent hydrogen or optionally substituted $C_1$-$C_6$ alkyl;

$R^{15}$ represents a 3 to 10-membered, optionally substituted heterocyclyl, optionally substituted heteroaryl, optionally substituted aryl, or an optionally substituted cycloalkyl;

wherein for $Q^{3a}$, $Q^{3b}$, $Q^{4a}$, $Q^{4b}$, $R^5$, $R^{8a}$, $R^{10}$, $R^{11}$, $R^{11a}$, $R^{13}$, $R^{14}$ and $R^{14a}$, the optional substituents for $C_1$-$C_6$ alkyl, $C_1$-$C_6$ alkylene, $C_2$-$C_6$ alkenylene and $C_3$-$C_4$ cycloalkylene are selected from halogen, hydroxyl, thiol, cyano, amino, amido, nitro and $SF_5$;

wherein the optional substituents for the heterocyclyl, heteroaryl, aryl and cycloalkyl within the definitions of $R^{12}$ and $R^{15}$ are selected from halogen, cyano, oxo, nitro, amino, hydroxy, amido, $C_1$-$C_6$ alkyl and $C_1$-$C_6$ alkoxy.

2. The compound according to claim 1, wherein $X^4$ is N or CH.

3. The compound according to claim 1, wherein $X^1$ represents C-$Q^1$-$R^2$, $X^3$ represents C-$Q^2$-$(R^6)_n$ and $X^2$ and $X^4$ are either both N or both CH.

4. The compound according to claim 1, wherein $Q^1$ is selected from a covalent bond, —$C_0$-$C_3$ alkylene-$CONR^3$—$C_0$-$C_3$ alkylene, —$C_0$-$C_3$ alkylene-$NR^3C(O)$—$C_0$-$C_3$ alkylene, $C_0$-$C_3$ alkylene-$NR^3$—$C_0$-$C_3$ alkylene, and —$NR^3C(O)R^5$—, wherein $R^3$ and $R^4$ are each independently selected from hydrogen and $C_1$-$C_3$ alkyl, and $R^5$ represents $C_1$-$C_3$ alkylene or $C_3$-$C_4$ cycloalkyl.

5. The compound according to claim 4, wherein $Q^1$ is a covalent bond.

6. The compound according to claim 1, wherein each occurrence of $Q^2$ is independently selected from halogen, optionally substituted —$C_1$-$C_6$ alkyl, —$C(O)OR^7$, —$NR^7COR^8$, —$NR^7SO_2R^8$, —$NR^7R^8$, a covalent bond, —$C_0$-$C_3$ alkylene-$NR^7$—$C_0$-$C_3$ alkylene, —$C_0$-$C_3$ alkylene-$NR^7CO$—$C_0$-$C_3$ alkylene, —$C_0$-$C_3$ alkylene-$NR^7CONR^8R^{8a}$, and —$C_0$-$C_3$ alkylene-$NR^7C(O)OR^{8a}$, wherein $R^7$ and $R^8$ each independently represent hydrogen or optionally substituted $C_1$-$C_6$ alkyl.

7. The compound according to claim 1, wherein $R^1$ is selected from optionally substituted, pyrrolidinyl, phenyl, quinazolinyl, pyrazolyl, quinolinyl, pyrrolopyridinyl, oxadiazolyl, isoquinolinyl, dihydroisoquinolinyl, tetrahydroisoquinolinyl, pyridinyl, pyrimidinyl, isoxazolyl, indazolyl, thiazolyl, dihydronaphthyridinyl, thiophenyl, piperazinyl, isoindolyl, tetrahydronaphthalenyl, benzoxazolyl, morpholinyl, tetrahydropyranyl, furanyl, imidazolyl, piperidinyl, indolinyl, dihydroindenyl, tetrahydroisoquinolinyl, and tetrahydronaphthyridinyl.

8. The compound according to claim 1, wherein $R^{12}$ is selected from optionally substituted, phenyl, pyrazinyl, pyridinyl, cyclopropyl, piperazinyl, azetidinyl, morpholinyl, pyrimidinyl, imidazolyl, pyrrolidinyl, oxazolidinyl, pyrazoyl, and imidazolidinyl.

9. The compound according to claim 1, wherein each occurrence of $R^6$ is independently selected from optionally substituted, phenyl, oxadiazolyl, pyrazolyl, piperidinyl, morpholinyl, pyridinyl, pyrrolidinyl, tetrahydropyranyl, thiophenyl, tetrahydroisoquinolinyl, dihydronaphthyridinyl, isoxazolyl, isoquinolinyl, pyrimidinyl, tetrahydronaphthalenyl, thiazolyl, cyclohexyl, furanyl, imidazolyl, tetrahydrothiopyranyl, thiomorpholinyl, and dihydropyridinyl.

10. The compound according to claim 1, wherein $R^6$ is optionally substituted with one or more substituents selected from halogen, cyano, oxo, hydroxyl, $C_1$-$C_6$ alkyl, $C_1$-$C_6$ alkoxy, -$Q^{4a}$-$CONR^{13}R^{14}$, -$Q^{4a}$-$COR^{13}$ and -$Q^{4a}$-$R^{15}$; wherein $Q^{4a}$ is a covalent bond;

$R^{13}$ and $R^{14}$ each independently represent hydrogen or $C_1$-$C_3$ alkyl; and $R^{15}$ is phenyl.

11. The compound according to claim 1, wherein $R^{1a}$, $R^{1b}$, $R^{1c}$ and $R^{1d}$ each independently represent hydrogen or $C_1$-$C_6$ alkyl.

12. The compound according to claim 1, wherein $R^{1a}$, $R^{1b}$, $R^{1c}$ and $R^{1d}$ each represent hydrogen.

13. The compound according to claim 1, wherein X$^1$ represents C-Q$^1$-R$^2$, wherein Q$^1$ represents a covalent bond and R$^2$ is an optionally substituted phenyl, and wherein X$^2$, X$^3$ and X$^4$ are not N.

14. The compound of formula I as defined in claim 1, selected from the group consisting of:

5-cyano-2-(2-cyanoisoindolin-4-yl)benzamide;
5-chloro-2-(2-cyanoisoindolin-4-yl)benzamide;
2-(2-cyanoisoindolin-4-yl)-5-methylbenzamide;
4-(2-(azetidine-1-carbonyl)-4-cyanophenyl)isoindoline-2-carbonitrile;
6-((1-methyl-1H-pyrazol-4-yl)amino)-4-phenylisoindoline-2-carbonitrile;
4-phenylisoindoline-2-carbonitrile;
4-(1-methyl-1H-pyrazol-4-yl)isoindoline-2-carbonitrile;
4-(quinolin-3-yl)isoindoline-2-carbonitrile;
4-(1H-pyrrolo[2,3-b]pyridin-5-yl)isoindoline-2-carbonitrile;
4-(1-methyl-1,2,3,6-tetrahydropyridin-4-yl)isoindoline-2-carbonitrile;
4-(2-methyl-2H-indazol-5-yl)isoindoline-2-carbonitrile;
4-(o-tolyl)isoindoline-2-carbonitrile;
4-(4-cyanophenyl)isoindoline-2-carbonitrile;
4-(1-methylpiperidin-4-yl)isoindoline-2-carbonitrile;
N-benzyl-3-(6-cyano-6,7-dihydro-5H-pyrrolo[3,4-b]pyridin-4-yl)benzamide;
4-(4-chlorophenyl)-5,7-dihydro-6H-pyrrolo[3,4-b]pyridine-6-carbonitrile;
4-(4-methoxyphenyl)-5,7-dihydro-6H-pyrrolo[3,4-b]pyridine-6-carbonitrile;
4-(3-chlorophenyl)-5,7-dihydro-6H-pyrrolo[3,4-b]pyridine-6-carbonitrile;
4-phenyl-1,3-dihydro-2H-pyrrolo[3,4-c]pyridine-2-carbonitrile;
6-(5-methyl-1,2,4-oxadiazol-3-yl)-4-phenylisoindoline-2-carbonitrile;
4-(quinazolin-2-ylamino)isoindoline-2-carbonitrile;
3-((2-cyanoisoindolin-4-yl)amino)-N-methylisoquinoline-6-carboxamide;
N-(2-cyano-7-phenylisoindolin-5-yl)nicotinamide;
2-(6-acetamido-2-cyanoisoindolin-4-yl)benzamide;
(R)—N-(2-cyano-7-(3-fluorophenyl)isoindolin-5-yl)-1-methylpiperidine-3-carboxamide;
(R)—N-(2-cyano-7-(4-cyanophenyl)isoindolin-5-yl)-1-methylpiperidine-3-carboxamide;
(R)—N-(2-cyano-7-(3-cyanophenyl)isoindolin-5-yl)-1-methylpiperidine-3-carboxamide;
(R)—N-(2-cyano-7-(4-fluorophenyl)isoindolin-5-yl)-1-methylpiperidine-3-carboxamide;
(R)—N-(2-cyano-7-(4-(methylcarbamoyl)phenyl)isoindolin-5-yl)-1-methylpiperidine-3-carboxamide;
(R)—N-(2-cyano-7-(3-(methylcarbamoyl)phenyl)isoindolin-5-yl)-1-methylpiperidine-3-carboxamide;
(R)—N-(2-cyano-7-(3-methoxyphenyl)isoindolin-5-yl)-1-methylpiperidine-3-carboxamide;
(R)—N-(2-cyano-7-(4-methoxyphenyl)isoindolin-5-yl)-1-methylpiperidine-3-carboxamide;
(R)—N-(7-(4-chlorophenyl)-2-cyanoisoindolin-5-yl)-1-methylpiperidine-3-carboxamide;
(R)—N-(7-(3-chlorophenyl)-2-cyanoisoindolin-5-yl)-1-methylpiperidine-3-carboxamide;
(R)—N-(2-cyano-7-(2-methylbenzo[d]oxazol-6-yl)isoindolin-5-yl)-1-methylpiperidine-3-carboxamide;
N-(2-cyano-7-phenylisoindolin-5-yl)-1-methylpiperidine-3-carboxamide;
(S)—N-(2-cyano-7-phenylisoindolin-5-yl)-1-methylpiperidine-3-carboxamide;
(R)—N-(2-cyano-7-phenylisoindolin-5-yl)-1-methylpiperidine-3-carboxamide;
N-(2-cyano-7-phenylisoindolin-5-yl)-1-methyl-1H-pyrazole-5-carboxamide;
4-benzyl-N-(2-cyano-7-phenylisoindolin-5-yl)morpholine-2-carboxamide;
N-(2-cyano-7-phenylisoindolin-5-yl)-3-(pyridin-3-yl)propanamide;
N-(2-cyano-7-phenylisoindolin-5-yl)-5-oxopyrrolidine-3-carboxamide;
N-(2-cyano-7-phenylisoindolin-5-yl)-1-methylpyrrolidine-3-carboxamide;
N-(2-cyano-7-phenylisoindolin-5-yl)-1-methyl-6-oxopiperidine-3-carboxamide;
1-acetyl-N-(2-cyano-7-phenylisoindolin-5-yl)piperidine-3-carboxamide;
N1-(2-cyano-7-phenylisoindolin-5-yl)-N4,N4-dimethylsuccinamide;
1-acetyl-N-(2-cyano-7-phenylisoindolin-5-yl)piperidine-4-carboxamide;
N-(2-cyano-7-phenylisoindolin-5-yl)-1-methylpiperidine-4-carboxamide;
N-(2-cyano-7-phenylisoindolin-5-yl)-2-(dimethylamino)acetamide;
N-(2-cyano-7-phenylisoindolin-5-yl)tetrahydro-2H-pyran-4-carboxamide;
N-(2-cyano-7-phenylisoindolin-5-yl)tetrahydro-2H-thiopyran-4-carboxamide 1,1-dioxide;
N-(2-cyano-7-phenylisoindolin-5-yl)-1-methyl-5-oxopyrrolidine-3-carboxamide;
N-(2-cyano-7-phenylisoindolin-5-yl)-4-methylmorpholine-2-carboxamide;
N-(2-cyano-7-phenylisoindolin-5-yl)-4-ethylmorpholine-2-carboxamide;
N-(2-cyano-7-phenylisoindolin-5-yl)-4-isopropylmorpholine-2-carboxamide;
N-(7-(2-carbamoylphenyl)-2-cyanoisoindolin-5-yl)-1-methylpiperidine-3-carboxamide;
N-(2-cyano-7-phenylisoindolin-5-yl)acetamide;
N-(2-cyano-7-phenylisoindolin-5-yl)-N-methylacetamide;
N-(2-cyano-7-phenylisoindolin-5-yl)-N, 1-dimethylpiperidine-3-carboxamide;
N-(2-cyano-7-phenylisoindolin-5-yl)-4-methylpiperazine-1-carboxamide;
N-(2-cyano-7-phenylisoindolin-5-yl)methanesulfonamide;
N-(2-cyano-7-phenylisoindolin-5-yl)piperidine-3-carboxamide;
N-(2-cyano-7-phenylisoindolin-5-yl)piperidine-4-carboxamide;
6-(((1-methylpiperidin-3-yl)methyl)amino)-4-phenylisoindoline-2-carbonitrile;
4-(2-chloro-4-cyanophenyl)isoindoline-2-carbonitrile;
4-(4-cyano-2-methylphenyl)isoindoline-2-carbonitrile;
4-(4-cyano-2,6-dimethylphenyl)isoindoline-2-carbonitrile;
3-oxo-[4,4'-biisoindoline]-2'-carbonitrile;
4-(1-oxo-1,2,3,4-tetrahydroisoquinolin-8-yl)isoindoline-2-carbonitrile;
(R)-4-(2-(1-hydroxyethyl)phenyl)isoindoline-2-carbonitrile;
(S)-4-(2-(1-hydroxyethyl)phenyl)isoindoline-2-carbonitrile;
4-(2-cyanoisoindolin-4-yl)isophthalonitrile;
N-benzyl-3-(2-cyanoisoindolin-4-yl)benzamide;
3-(2-cyanoisoindolin-4-yl)-N-(1-phenylethyl)benzamide;

3-(2-cyanoisoindolin-4-yl)-N-phenylbenzamide;
(R)-3-(2-cyanoisoindolin-4-yl)-N-(1-phenylethyl)benzamide;
N-(2-aminoethyl)-2-(2-cyanoisoindolin-4-yl)benzamide;
4-(2-(piperazine-1-carbonyl)phenyl)isoindoline-2-carbonitrile;
N-benzyl-4-(2-cyanoisoindolin-4-yl)picolinamide;
N-(2-cyanoisoindolin-4-yl)-3-(cyclopropanecarboxamido)benzamide;
N-(2-cyanoisoindolin-4-yl)-4-(pyridin-3-yl)benzamide;
N-(2-cyanoisoindolin-4-yl)-4-(pyridin-4-yl)benzamide;
N-(2-cyanoisoindolin-4-yl)-3-(o-tolyl)-1H-pyrazole-5-carboxamide;
N-(2-cyanoisoindolin-4-yl)-2-phenylthiazole-4-carboxamide;
N-(2-cyanoisoindolin-4-yl)-5-methoxy-1H-pyrrolo[2,3-c]pyridine-2-carboxamide;
N-(2-cyanoisoindolin-4-yl)-5-(pyrazin-2-yl)-1H-pyrazole-3-carboxamide;
1-benzyl-N-(2-cyanoisoindolin-4-yl)-6-oxo-1,6-dihydropyridine-3-carboxamide;
N-(2-cyanoisoindolin-4-yl)-4-(methoxymethyl)benzamide;
methyl (3-((2-cyanoisoindolin-4-yl)carbamoyl)phenyl) carbamate;
3-benzamido-N-(2-cyanoisoindolin-4-yl)benzamide;
benzyl (4-((2-cyanoisoindolin-4-yl)carbamoyl)benzyl) carbamate;
N-(2-cyanoisoindolin-4-yl)-4-(N-phenylsulfamoyl)benzamide;
N-(2-cyanoisoindolin-4-yl)-5-morpholinothiophene-2-carboxamide;
N-(2-cyanoisoindolin-5-yl)-1-methylpyrrolidine-3-carboxamide;
N-benzyl-2-cyanoisoindoline-4-carboxamide;
N-(2-cyano-4-phenylisoindolin-5-yl)acetamide;
1-(1-methyl-1H-pyrazol-4-yl)-4-phenyl-5,7-dihydro-6H-pyrrolo[3,4-d]pyridazine-6-carbonitrile methyl 2-cyano-7-phenylisoindoline-5-carboxylate;
4-(4-(2,4-difluorophenyl)piperazin-1-yl)-5,7-dihydro-6H-pyrrolo[3,4-d]pyrimidine-6-carbonitrile;
4-(isoindolin-2-yl)-5,7-dihydro-6H-pyrrolo[3,4-d]pyrimidine-6-carbonitrile;
4-(4-(pyridin-3-yloxy)piperidin-1-yl)-5,7-dihydro-6H-pyrrolo[3,4-d]pyrimidine-6-carbonitrile;
4-(4-(3-methoxyphenoxy)piperidin-1-yl)-5,7-dihydro-6H-pyrrolo[3,4-d]pyrimidine-6-carbonitrile;
2-((1-(6-cyano-6,7-dihydro-5H-pyrrolo[3,4-d]pyrimidin-4-yl)piperidin-4-yl)oxy)benzamide;
N-(6-cyano-4-phenyl-6,7-dihydro-5H-pyrrolo[3,4-d]pyrimidin-2-yl)acetamide;
N-(6-cyano-4-(3-cyanophenyl)-6,7-dihydro-5H-pyrrolo[3,4-d]pyrimidin-2-yl)acetamide;
N-(6-cyano-4-(3-(trifluoromethoxy)phenyl)-6,7-dihydro-5H-pyrrolo[3,4-d]pyrimidin-2-yl)acetamide;
N-(6-cyano-4-(1-methyl-1H-pyrazol-4-yl)-6,7-dihydro-5H-pyrrolo[3,4-d]pyrimidin-2-yl)acetamide;
N-(3-(2-acetamido-6-cyano-6,7-dihydro-5H-pyrrolo[3,4-d]pyrimidin-4-yl)phenyl)acetamide;
N-(6-cyano-4-(3-(methylsulfonamido)phenyl)-6,7-dihydro-5H-pyrrolo[3,4-d]pyrimidin-2-yl)acetamide;
2-(((1r,4r)-4-hydroxycyclohexyl)amino)-4-phenyl-5,7-dihydro-6H-pyrrolo[3,4-d]pyrimidine-6-carbonitrile;
4-phenyl-2-(((tetrahydro-2H-pyran-4-yl)methyl)amino)-5,7-dihydro-6H-pyrrolo[3,4-d]pyrimidine-6-carbonitrile;
24(1-methyl-1H-pyrazol-4-yl)amino)-4-phenyl-5,7-dihydro-6H-pyrrolo[3,4-d]pyrimidine-6-carbonitrile;
4-phenyl-2-((pyrimidin-2-ylmethyl)amino)-5,7-dihydro-6H-pyrrolo[3,4-d]pyrimidine-6-carbonitrile;
4-phenyl-2-((2-(pyridin-2-yl)ethyl)amino)-5,7-dihydro-6H-pyrrolo[3,4-d]pyrimidine-6-carbonitrile;
4-phenyl-2-((1,2,3,4-tetrahydronaphthalen-1-yl)amino)-5,7-dihydro-6H-pyrrolo[3,4-d]pyrimidine-6-carbonitrile;
4-phenyl-2-(phenylamino)-5,7-dihydro-6H-pyrrolo[3,4-d]pyrimidine-6-carbonitrile;
4-phenyl-2-((pyridin-2-ylmethyl)amino)-5,7-dihydro-6H-pyrrolo[3,4-d]pyrimidine-6-carbonitrile;
4-phenyl-2-((pyridin-3-ylmethyl)amino)-5,7-dihydro-6H-pyrrolo[3,4-d]pyrimidine-6-carbonitrile;
4-phenyl-2-((thiazol-5-ylmethyl)amino)-5,7-dihydro-6H-pyrrolo[3,4-d]pyrimidine-6-carbonitrile;
2-((2-hydroxyethyl)amino)-4-phenyl-5,7-dihydro-6H-pyrrolo[3,4-d]pyrimidine-6-carbonitrile;
2-((furan-2-ylmethyl)amino)-4-phenyl-5,7-dihydro-6H-pyrrolo[3,4-d]pyrimidine-6-carbonitrile;
24(3-(1H-imidazol-1-yl)propyl)amino)-4-phenyl-5,7-dihydro-6H-pyrrolo[3,4-d]pyrimidine-6-carbonitrile;
2-(6-cyano-2-(ethylamino)-6,7-dihydro-5H-pyrrolo[3,4-d]pyrimidin-4-yl)benzamide;
2-(((4-methylmorpholin-2-yl)methyl)amino)-4-phenyl-5,7-dihydro-6H-pyrrolo[3,4-d]pyrimidine-6-carbonitrile;
2-(((1-methylpiperidin-3-yl)methyl)amino)-4-phenyl-5,7-dihydro-6H-pyrrolo[3,4-d]pyrimidine-6-carbonitrile;
2-(((1-methyl-1H-pyrazol-5-yl)methyl)amino)-4-phenyl-5,7-dihydro-6H-pyrrolo[3,4-d]pyrimidine-6-carbonitrile;
2-(((1-methylpyrrolidin-3-yl)methyl)amino)-4-phenyl-5,7-dihydro-6H-pyrrolo[3,4-d]pyrimidine-6-carbonitrile;
N-(6-cyano-4-(3,4-dihydroisoquinolin-2(1H)-yl)-6,7-dihydro-5H-pyrrolo[3,4-d]pyrimidin-2-yl)acetamide;
N-(6-cyano-4-phenyl-6,7-dihydro-5H-pyrrolo[3,4-d]pyrimidin-2-yl)-5-oxopyrrolidine-3-carboxamide;
2-(4-methoxyphenyl)-4-(pyrrolidin-1-yl)-5,7-dihydro-6H-pyrrolo[3,4-d]pyrimidine-6-carbonitrile;
1-(6-cyano-2-phenyl-6,7-dihydro-5H-pyrrolo[3,4-d]pyrimidin-4-yl)pyrrolidine-2-carboxamide;
2-((6-cyano-2-phenyl-6,7-dihydro-5H-pyrrolo[3,4-d]pyrimidin-4-yl)amino)acetamide;
1-(6-cyano-2-phenyl-6,7-dihydro-5H-pyrrolo[3,4-d]pyrimidin-4-yl)-N-methylpyrrolidine-2-carboxamide;
2-(5-methyl-1H-pyrazol-4-yl)-4-(pyrrolidin-1-yl)-5,7-dihydro-6H-pyrrolo[3,4-d]pyrimidine-6-carbonitrile;
2-(2-methoxyphenyl)-4-(pyrrolidin-1-yl)-5,7-dihydro-6H-pyrrolo[3,4-d]pyrimidine-6-carbonitrile;
2-(3-methoxyphenyl)-4-(pyrrolidin-1-yl)-5,7-dihydro-6H-pyrrolo[3,4-d]pyrimidine-6-carbonitrile;
2-(pyridin-3-yl)-4-(pyrrolidin-1-yl)-5,7-dihydro-6H-pyrrolo[3,4-d]pyrimidine-6-carbonitrile;
2-(6-cyano-4-(3,4-dihydroisoquinolin-2(1H)-yl)-6,7-dihydro-5H-pyrrolo[3,4-d]pyrimidin-2-yl)benzamide;
4-(3,4-dihydroisoquinolin-2(1H)-yl)-2-(5-methyl-1H-pyrazol-4-yl)-5,7-dihydro-6H-pyrrolo[3,4-d]pyrimidine-6-carbonitrile;
4-(3,4-dihydroisoquinolin-2(1H)-yl)-2-(2-methoxyphenyl)-5,7-dihydro-6H-pyrrolo[3,4-d]pyrimidine-6-carbonitrile;
2-(3-cyanophenyl)-4-(3,4-dihydroisoquinolin-2(1H)-yl)-5,7-dihydro-6H-pyrrolo[3,4-d]pyrimidine-6-carbonitrile;

4-(3,4-dihydroisoquinolin-2(1H)-yl)-2-(1-methyl-1H-pyrazol-4-yl)-5,7-dihydro-6H-pyrrolo[3,4-d]pyrimidine-6-carbonitrile;
1-(6-cyano-2-(o-tolyl)-6,7-dihydro-5H-pyrrolo[3,4-d]pyrimidin-4-yl)pyrrolidine-2-carboxamide;
1-(6-cyano-2-(5-methyl-1H-pyrazol-4-yl)-6,7-dihydro-5H-pyrrolo[3,4-d]pyrimidin-4-yl)pyrrolidine-2-carboxamide;
4-(3,4-dihydroisoquinolin-2(1H)-yl)-2-(1H-pyrazol-4-yl)-5,7-dihydro-6H-pyrrolo[3,4-d]pyrimidine-6-carbonitrile;
4-(3,4-dihydroisoquinolin-2(1H)-yl)-2-(1-(2-methoxyethyl)-1H-pyrazol-4-yl)-5,7-dihydro-6H-pyrrolo[3,4-d]pyrimidine-6-carbonitrile;
4-(5,8-dihydro-1,7-naphthyridin-7(6H)-yl)-2-(5-methyl-1H-pyrazol-4-yl)-5,7-dihydro-6H-pyrrolo[3,4-d]pyrimidine-6-carbonitrile;
N-(6-cyano-4-(pyrrolidin-1-yl)-6,7-dihydro-5H-pyrrolo[3,4-d]pyrimidin-2-yl)acetamide;
2-chloro-4-(4-fluorophenyl)-5,7-dihydro-6H-pyrrolo[3,4-d]pyrimidine-6-carbonitrile;
2-chloro-4-(2-fluorophenyl)-5,7-dihydro-6H-pyrrolo[3,4-d]pyrimidine-6-carbonitrile;
4-(4-fluorophenyl)-2-methyl-5,7-dihydro-6H-pyrrolo[3,4-d]pyrimidine-6-carbonitrile;
(R)-2-(((4-methylmorpholin-2-yl)methyl)amino)-4-phenyl-5,7-dihydro-6H-pyrrolo[3,4-d]pyrimidine-6-carbonitrile;
(S)-2-(((4-methylmorpholin-2-yl)methyl)amino)-4-phenyl-5,7-dihydro-6H-pyrrolo[3,4-d]pyrimidine-6-carbonitrile;
2-chloro-6-(2-cyanoisoindolin-4-yl)benzamide;
4-(2-(pyrrolidine-1-carbonyl)phenyl)isoindoline-2-carbonitrile;
5-cyano-2-(2-cyanoisoindolin-4-yl)-4-methylbenzamide;
2-(2-cyanoisoindolin-4-yl)benzamide;
2-(2-cyanoisoindolin-4-yl)-5-fluorobenzamide;
4-(2-acetylphenyl)isoindoline-2-carbonitrile;
2-(2-cyanoisoindolin-4-yl)-N-methylbenzenesulfonamide;
2-(2-cyanoisoindolin-4-yl)benzenesulfonamide;
4-(2-(methylsulfonyl)phenyl)isoindoline-2-carbonitrile;
(R)—N-(2-cyano-7-(pyridin-4-yl)isoindolin-5-yl)-1-methylpiperidine-3-carboxamide;
(R)—N-(2-cyano-7-(pyridin-3-yl)isoindolin-5-yl)-1-methylpiperidine-3-carboxamide;
4-(2-oxoindolin-7-yl)isoindoline-2-carbonitrile;
4-(2-cyanophenyl)isoindoline-2-carbonitrile;
4-(2-cyano-4-fluorophenyl)isoindoline-2-carbonitrile;
4-(2-cyano-6-fluorophenyl)isoindoline-2-carbonitrile;
4-(4-chloro-2-cyanophenyl)isoindoline-2-carbonitrile;
4-(2-cyano-3-methoxyphenyl)isoindoline-2-carbonitrile;
4-(2-cyano-4-methoxyphenyl)isoindoline-2-carbonitrile;
4-(2-cyano-5-methoxyphenyl)isoindoline-2-carbonitrile;
4-(3-cyano-6-methoxypyridin-2-yl)isoindoline-2-carbonitrile;
2-(2-cyanoisoindolin-4-yl)-N,N-dimethylbenzenesulfonamide;
2-(2-cyanoisoindolin-4-yl)-N-ethylbenzenesulfonamide;
4-(7-cyano-3-oxo-2,3-dihydro-1H-inden-4-yl)isoindoline-2-carbonitrile;
4-(4-cyano-2-(trifluoromethyl)phenyl)isoindoline-2-carbonitrile;
4-(2-(azetidin-1-ylsulfonyl)phenyl)isoindoline-2-carbonitrile;
2-(2-cyanoisoindolin-4-yl)-N-(2-hydroxyethyl)benzenesulfonamide;
2-(2-cyanoisoindolin-4-yl)-N-(2-(6-oxopyrimidin-1(6H)-yl)ethyl)benzamide;
4-(2-cyano-4-(1H-imidazol-1-yl)phenyl)isoindoline-2-carbonitrile;
1-(3-methoxyphenyl)-4-(1-methyl-1H-pyrazol-4-yl)-5,7-dihydro-6H-pyrrolo[3,4-d]pyridazine-6-carbonitrile;
4-(3,4-dihydroisoquinolin-2(1H)-yl)-5,7-dihydro-6H-pyrrolo[3,4-d]pyrimidine-6-carbonitrile;
4-(4-(o-tolyloxy)piperidin-1-yl)-5,7-dihydro-6H-pyrrolo[3,4-d]pyrimidine-6-carbonitrile;
4-(4-(benzyloxy)piperidin-1-yl)-5,7-dihydro-6H-pyrrolo[3,4-d]pyrimidine-6-carbonitrile;
4-(4-(2-methoxyphenoxy)piperidin-1-yl)-5,7-dihydro-6H-pyrrolo[3,4-d]pyrimidine-6-carbonitrile;
N-(6-cyano-4-(4-fluorophenyl)-6,7-dihydro-5H-pyrrolo[3,4-d]pyrimidin-2-yl)acetamide;
2-((2-(methyl sulfonyl)ethyl)amino)-4-phenyl-5,7-dihydro-6H-pyrrolo[3,4-d]pyrimidine-6-carbonitrile;
4-phenyl-2-((tetrahydro-2H-pyran-4-yl)amino)-5,7-dihydro-6H-pyrrolo[3,4-d]pyrimidine-6-carbonitrile;
2-((2-hydroxyethyl)(methyl)amino)-4-phenyl-5,7-dihydro-6H-pyrrolo[3,4-d]pyrimidine-6-carbonitrile;
2-(methyl((4-methylmorpholin-2-yl)methyl)amino)-4-phenyl-5,7-dihydro-6H-pyrrolo[3,4-d]pyrimidine-6-carbonitrile;
2-(((4-methylmorpholin-2-yl)methyl)amino)-4-(pyridin-3-yl)-5,7-dihydro-6H-pyrrolo[3,4-d]pyrimidine-6-carbonitrile;
4-(3-fluorophenyl)-2-((4-methylmorpholin-2-yl)methyl)amino)-5,7-dihydro-6H-pyrrolo[3,4-d]pyrimidine-6-carbonitrile;
4-(4-fluorophenyl)-2-((4-methylmorpholin-2-yl)methyl)amino)-5,7-dihydro-6H-pyrrolo[3,4-d]pyrimidine-6-carbonitrile;
N-(3-(6-cyano-2-(((4-methylmorpholin-2-yl)methyl)amino)-6,7-dihydro-5H-pyrrolo[3,4-d]pyrimidin-4-yl)phenyl)acetamide;
4-(3,4-dihydroisoquinolin-2(1H)-yl)-2-(((1-methylpiperidin-3-yl)methyl)amino)-5,7-dihydro-6H-pyrrolo[3,4-d]pyrimidine-6-carbonitrile;
4-(3,4-dihydroisoquinolin-2(1H)-yl)-2-(((4-methylmorpholin-2-yl)methyl)amino)-5,7-dihydro-6H-pyrrolo[3,4-d]pyrimidine-6-carbonitrile;
4-(3,4-dihydroisoquinolin-2(1H)-yl)-2-(((1-methyl-1H-pyrazol-5-yl)methyl)amino)-5,7-dihydro-6H-pyrrolo[3,4-d]pyrimidine-6-carbonitrile;
4-(3,4-dihydroisoquinolin-2(1H)-yl)-2-((trans)-4-hydroxycyclohexyl)amino)-5,7-dihydro-6H-pyrrolo[3,4-d]pyrimidine-6-carbonitrile;
4-(3,4-dihydroisoquinolin-2(1H)-yl)-2-(((tetrahydro-2H-pyran-4-yl)methyl)amino)-5,7-dihydro-6H-pyrrolo[3,4-d]pyrimidine-6-carbonitrile;
4-(3,4-dihydroisoquinolin-2(1H)-yl)-2-(((1-methyl-1H-pyrazol-4-yl)methyl)amino)-5,7-dihydro-6H-pyrrolo[3,4-d]pyrimidine-6-carbonitrile;
4-(3,4-dihydroisoquinolin-2(1H)-yl)-2-((2-hydroxyethyl)amino)-5,7-dihydro-6H-pyrrolo[3,4-d]pyrimidine-6-carbonitrile;
4-(3,4-dihydroisoquinolin-2(1H)-yl)-2-(methyl((4-methylmorpholin-2-yl)methyl)amino)-5,7-dihydro-6H-pyrrolo[3,4-d]pyrimidine-6-carbonitrile;
2-(methylamino)-4-(4-phenoxypiperidin-1-yl)-5,7-dihydro-6H-pyrrolo[3,4-d]pyrimidine-6-carbonitrile;
2-(dimethylamino)-4-(4-phenoxypiperidin-1-yl)-5,7-dihydro-6H-pyrrolo[3,4-d]pyrimidine-6-carb e;

2-((2-hydroxyethyl)amino)-4-(4-phenoxypiperidin-1-yl)-5,7-dihydro-6H-pyrrolo[3,4-d]pyrimidine-6-carbonitrile;
2-amino-4-(4-phenoxypiperidin-1-yl)-5,7-dihydro-6H-pyrrolo[3,4-d]pyrimidine-6-carbonitrile;
4-(4-cyanophenyl)-2-((2-hydroxyethyl)amino)-5,7-dihydro-6H-pyrrolo[3,4-d]pyrimidine-6-carbonitrile;
4-(3,4-difluorophenyl)-2-((2-hydroxyethyl)amino)-5,7-dihydro-6H-pyrrolo[3,4-d]pyrimidine-6-carb e;
N-(3-(6-cyano-2-((2-hydroxyethyl)amino)-6,7-dihydro-5H-pyrrolo[3,4-d]pyrimidin-4-yl)phenyl)acetamide;
2-((2-hydroxyethyl)amino)-4-(4-methoxyphenyl)-5,7-dihydro-6H-pyrrolo[3,4-d]pyrimidine-6-carb e;
2-((2-hydroxyethyl)amino)-4-(4-(4-methylpiperazin-1-yl)phenyl)-5,7-dihydro-6H-pyrrolo[3,4-d]pyrimidine-6-carbonitrile;
6-((dimethylamino)methyl)-4-phenylisoindoline-2-carbonitrile;
N-((2-cyano-7-phenylisoindolin-5-yl)methyl)acetamide;
6-(2-methoxyethyl)-4-phenylisoindoline-2-carbonitrile;
4-(4-cyanophenyl)-6-((methylsulfonyl)methyl)isoindoline-2-carbonitrile;
N-((2-cyano-7-(4-cyanophenyl)isoindolin-5-yl)methyl)acetamide;
N-((2-cyano-7-(4-cyanophenyl)isoindolin-5-yl)methyl)-N-methylacetamide;
N-((2-cyano-7-(4-cyanophenyl)isoindolin-5-yl)methyl)tetrahydro-2H-pyran-4-carboxamide;
N-((2-cyano-7-(4-cyanophenyl)isoindolin-5-yl)methyl)tetrahydro-2H-thiopyran-4-carboxamide-1,1-dioxide;
N-((2-cyano-7-(4-cyanophenyl)isoindolin-5-yl)methyl)-1-methyl-1H-pyrazole-4-carboxamide;
N-((2-cyano-7-(4-cyanophenyl)isoindolin-5-yl)methyl)methanesulfonamide;
3-((2-cyano-7-(4-cyanophenyl)isoindolin-5-yl)methyl)-1,1-dimethylurea;
isopropyl ((2-cyano-7-(4-cyanophenyl)isoindolin-5-yl)methyl)carbamate;
N-((2-cyano-7-(2-cyanophenyl)isoindolin-5-yl)methyl)acetamide;
N-((2-cyano-7-(2,4-dicyanophenyl)isoindolin-5-yl)methyl)acetamide;
1-((2-cyano-7-(4-cyanophenyl)isoindolin-5-yl)methyl)-3-methylurea;
1-((2-cyano-7-(2,4-dicyanophenyl)isoindolin-5-yl)methyl)-3-methylurea;
1-((2-cyano-7-(2-cyanophenyl)isoindolin-5-yl)methyl)-3-methylurea;
6-(((1H-pyrazol-5-yl)amino)methyl)-4-(4-cyanophenyl)isoindoline-2-carbonitrile;
2-(2,6-dicyanoisoindolin-4-yl)benzamide;
2-cyano-7-(4-cyanophenyl)-N,N-dimethylisoindoline-5-carboxamide;
2-cyano-7-(2,4-dicyanophenyl)isoindoline-5-carboxamide;
2-cyano-7-(2-cyano-5-methoxyphenyl)isoindoline-5-carboxamide;
2-cyano-7-(2-cyano-4-fluorophenyl)isoindoline-5-carboxamide;
4-(4-cyanophenyl)-6-(1,1-dioxidothiomorpholine-4-carbonyl)isoindoline-2-carbonitrile;
2-cyano-7-(4-cyanophenyl)-N-methylisoindoline-5-carboxamide;
2-cyano-7-(4-cyanophenyl)-N-(tetrahydro-2H-pyran-4-yl)isoindoline-5-carboxamide;
2-cyano-7-(2,4-dicyanophenyl)-N-methylisoindoline-5-carboxamide;
2-cyano-7-(4-fluorophenyl)-N-methylisoindoline-5-carboxamide;
2-cyano-7-(2-cyanophenyl)isoindoline-5-carboxamide;
N-(2-cyano-7-(2-cyanophenyl)isoindolin-5-yl)methanesulfonamide;
N-(2-cyano-7-(2,4-dicyanophenyl)isoindolin-5-yl)methanesulfonamide;
N-(2-cyano-7-(4-cyanophenyl)isoindolin-5-yl)methanesulfonamide;
N-(2-cyano-7-(2-cyano-5-methoxyphenyl)isoindolin-5-yl)methanesulfonamide;
4-(4-fluorophenyl)-2-(((tetrahydro-2H-pyran-4-yl)methyl)amino)-5,7-dihydro-6H-pyrrolo[3,4-b]pyridine-6-carbonitrile;
4-(4-fluorophenyl)-2-((pyridin-2-ylmethyl)amino)-5,7-dihydro-6H-pyrrolo[3,4-b]pyridine-6-carbonitrile;
4-(4-fluorophenyl)-2-(((1-methyl-1H-pyrazol-5-yl)methyl)amino)-5,7-dihydro-6H-pyrrolo[3,4-b]pyridine-6-carbonitrile;
N-(6-cyano-4-(4-fluorophenyl)-6,7-dihydro-5H-pyrrolo[3,4-b]pyridin-2-yl)acetamide;
2-((2,3-dihydroxypropyl)amino)-4-(4-fluorophenyl)-5,7-dihydro-6H-pyrrolo[3,4-b]pyridine-6-carbonitrile;
2-(2-cyano-7-phenylisoindolin-5-yl)-N,N-dimethylacetamide;
6-(2-(methylsulfonyl)ethyl)-4-phenylisoindoline-2-carbonitrile;
6-((methylsulfonyl)methyl)-4-phenylisoindoline-2-carbonitrile;
4-(4-cyanophenyl)-6-(2-methoxyethyl)isoindoline-2-carbonitrile;
2-(2-cyano-6-(2-methoxyethyl)isoindolin-4-yl)benzamide;
4-(4-cyanophenyl)-6-(2-(pyridin-3-yl)ethyl)isoindoline-2-carbonitrile;
6-(2-(1-acetylpiperidin-4-yl)ethyl)-4-(4-cyanophenyl)isoindoline-2-carbonitrile;
5-chloro-2-(2-cyano-1-methylisoindolin-4-yl)benzamide;
5-cyano-2-(2-cyano-1-methylisoindolin-4-yl)benzamide;
5-cyano-2-(2-cyano-5-fluoroisoindolin-4-yl)benzamide;
5-cyano-2-(2-cyano-7-fluoroisoindolin-4-yl)benzamide;
6-(1-methyl-6-oxopiperidin-3-yl)-4-phenylisoindoline-2-carbonitrile;
6-(1-methyl-6-oxo-1,6-dihydropyridin-3-yl)-4-phenylisoindoline-2-carbonitrile;
N-(2-cyano-7-(4-cyanophenyl)isoindolin-5-yl)tetrahydro-2H-pyran-4-carboxamide;
N-(2-cyano-7-(4-cyanophenyl)isoindolin-5-yl)-1-methyl-5-oxopyrrolidine-3-carboxamide;
N-(2-cyano-7-(4-cyanophenyl)isoindolin-5-yl)-1-methyl-6-oxopiperidine-3-carboxamide;
N-(2-cyano-7-(4-cyanophenyl)isoindolin-5-yl)-2-(dimethylamino)acetamide;
4-(2,6-dioxopiperidin-1-yl)isoindoline-2-carbonitrile;
4-(4-cyanophenyl)-6-(methylamino)isoindoline-2-carbonitrile;
4-(4-cyanophenyl)-6-(dimethylamino)isoindoline-2-carbonitrile;
4-(4-cyanophenyl)-6-((2-hydroxyethyl)amino)isoindoline-2-carbonitrile;
4-(4-cyanophenyl)-6-(isopropylamino)isoindoline-2-carbonitrile;
4-(4-cyanophenyl)-6-((1,1-dioxidotetrahydro-2H-thiopyran-4-yl)amino)isoindoline-2-carbonitrile;
4-(4-cyanophenyl)-6-((tetrahydro-2H-pyran-4-yl)amino)isoindoline-2-carbonitrile;

4-(4-cyanophenyl)-6-(((tetrahydro-2H-pyran-4-yl)methyl)amino)isoindoline-2-carbonitrile;
4-(4-cyanophenyl)-6-(((1-methyl-1H-pyrazol-5-yl)methyl)amino)isoindoline-2-carbonitrile;
4-(4-cyanophenyl)-6-(ethylamino)isoindoline-2-carbonitrile;
4-(4-cyanophenyl)-6-(1,1-dioxidothiomorpholino)isoindoline-2-carbonitrile;
4-(4-cyanophenyl)-6-(diethylamino)isoindoline-2-carbonitrile;
4-(4-cyanophenyl)-6-((2,3-dihydroxypropyl)amino)isoindoline-2-carbonitrile;
5-cyano-2-(2-cyano-6-(((tetrahydro-2H-pyran-4-yl)methyl)amino)isoindolin-4-yl)benzamide;
(S)-6-((2,3-dihydroxypropyl)amino)-4-(4-fluorophenyl)isoindoline-2-carbonitrile;
(S)-4-(2-cyanophenyl)-6-((2,3-dihydroxypropyl)amino)isoindoline-2-carbonitrile;
4-(4-cyanophenyl)-6-((3-hydroxy-2-methoxypropyl)amino)isoindoline-2-carbonitrile;
5-cyano-2-(2-cyano-6-(dimethylamino)isoindolin-4-yl)benzamide;
4-(4-cyanophenyl)-6-((2-hydroxypropyl)amino)isoindoline-2-carbonitrile;
4-(4-cyanophenyl)-6-((2-hydroxy-2-methylpropyl)amino)isoindoline-2-carbonitrile;
4-(4-cyanophenyl)-6-((2-hydroxy-3-methoxypropyl)amino)isoindoline-2-carbonitrile;
2-methyl-4-(3-(2-oxopyrrolidin-1-yl)phenyl)-5,7-dihydro-6H-pyrrolo[3,4-d]pyrimidine-6-carbonitrile;
2-(((1-methyl-1H-pyrazol-5-yl)methyl)amino)-4-(3-(2-oxopyrrolidin-1-yl)phenyl)-5,7-dihydro-6H-pyrrolo[3,4-d]pyrimidine-6-carbonitrile;
2-((2-hydroxyethyl)amino)-4-(3-(2-oxopyrrolidin-1-yl)phenyl)-5,7-dihydro-6H-pyrrolo[3,4-d]pyrimidine-6-carbonitrile;
2-((2-hydroxyethyl)amino)-4-(3-(2-oxooxazolidin-3-yl)phenyl)-5,7-dihydro-6H-pyrrolo[3,4-d]pyrimidine-6-carbonitrile;
2-cyano-7-(2-cyano-5-methoxypyridin-3-yl)-N-methylisoindoline-5-carboxamide;
4-(2-cyano-4-(1H-pyrazol-4-yl)phenyl)isoindoline-2-carbonitrile;
4-(5,8-dihydro-1,7-naphthyridin-7(6H)-yl)-2-(methyl((1-methylpiperidin-3-yl)methyl)amino)-5,7-dihydro-6H-pyrrolo[3,4-d]pyrimidine-6-carbonitrile;
2-(2,6-dicyanoisoindolin-4-yl)-5-fluorobenzamide;
5-cyano-2-(2,6-di cyanoisoindolin-4-yl)-3-fluorobenzamide;
4-(2-cyano-5-(2-oxooxazolidin-3-yl)phenyl)isoindoline-2-carbonitrile;
4-(2-cyano-5-(2-oxopyrrolidin-1-yl)phenyl)isoindoline-2-carbonitrile;
4-(3-(2-oxoimidazolidin-1-yl)phenyl)-5,7-dihydro-6H-pyrrolo[3,4-d]pyrimidine-6-carbonitrile; and
5-cyano-2-(2-cyanoisoindolin-4-yl)-3-fluorobenzamide;
a tautomer thereof, or a pharmaceutically acceptable salt of said compound or tautomer.

15. A pharmaceutical composition comprising a compound of formula (I) as defined in claim 1, a tautomer thereof, or a pharmaceutically acceptable salt of said compound or tautomer, together with one or more pharmaceutically acceptable excipients.

\* \* \* \* \*

UNITED STATES PATENT AND TRADEMARK OFFICE
CERTIFICATE OF CORRECTION

PATENT NO. : 10,683,269 B2  
APPLICATION NO. : 16/080506  
DATED : June 16, 2020  
INVENTOR(S) : Karl Richard Gibson et al.

Page 1 of 1

It is certified that error appears in the above-identified patent and that said Letters Patent is hereby corrected as shown below:

On the Title Page

Item (72), the name of the 7th inventor should read "Michael David Woodrow" instead of "Michael D Woodrow."

Signed and Sealed this
Eighteenth Day of May, 2021

Drew Hirshfeld
*Performing the Functions and Duties of the
Under Secretary of Commerce for Intellectual Property and
Director of the United States Patent and Trademark Office*